US011567478B2

(12) United States Patent
Cella et al.

(10) Patent No.: US 11,567,478 B2
(45) Date of Patent: Jan. 31, 2023

(54) SELECTION AND CONFIGURATION OF AN AUTOMATED ROBOTIC PROCESS

(71) Applicant: Strong Force TX Portfolio 2018, LLC, Fort Lauderdale, FL (US)

(72) Inventors: Charles Howard Cella, Pembroke, MA (US); Jenna Lynn Parenti, Boulder, CO (US); Taylor D. Charon, Troy, MI (US)

(73) Assignee: Strong Force TX Portfolio 2018, LLC, Fort Lauderdale, FL (US)

( * ) Notice: Subject to any disclaimer, the term of this patent is extended or adjusted under 35 U.S.C. 154(b) by 0 days.

(21) Appl. No.: 17/333,491

(22) Filed: May 28, 2021

(65) Prior Publication Data

US 2021/0356941 A1 Nov. 18, 2021

Related U.S. Application Data

(63) Continuation of application No. 17/332,700, filed on May 27, 2021, which is a continuation of application
(Continued)

(51) Int. Cl.
*G05B 19/41* (2006.01)
*G05B 19/4155* (2006.01)
(Continued)

(52) U.S. Cl.
CPC .......... *G05B 19/4155* (2013.01); *B25J 9/161* (2013.01); *B25J 9/163* (2013.01); *B25J 9/1656* (2013.01);
(Continued)

(58) Field of Classification Search
CPC ........ G05B 19/4155; B25J 9/163; G06N 5/04
See application file for complete search history.

(56) References Cited

U.S. PATENT DOCUMENTS 5,126,028 A 6/1992 Hurwitt et al.
5,812,422 A 9/1998 Lyons
(Continued)

FOREIGN PATENT DOCUMENTS

AU 2017352545 A1 8/2018
CA 3064604 A1 * 12/2018 ............... G06N 5/04
(Continued)

OTHER PUBLICATIONS

U.S. Appl. No. 17/332,700, filed May 27, 2021, Pending, Charles Howard Cella.
(Continued)

*Primary Examiner* — Scott C Anderson
(74) *Attorney, Agent, or Firm* — GTC Law Group PC & Affiliates

(57) ABSTRACT

A method for selection and configuration of an automated robotic process includes receiving a temporal biometric measurement of a worker performing a task, receiving a spatial-temporal environmental input provided to the worker, identifying a type of reasoning used when performing the task partially based on the temporal biometric measurement of the worker, selecting a component of an AI solution to replicate the type of reasoning, and configuring the component of the AI solution based on the spatial-temporal environmental input. The temporal biometric measurement includes a set of spatial-temporal imaging data of a brain of the worker and identifying the type of reasoning includes identifying a set of spatial-temporal neocortical activity patterns of the worker, identifying an active area of a neocortex of the worker; and selecting the component of the AI solution partially based on the identified active area of the neocortex.

16 Claims, 106 Drawing Sheets

Related U.S. Application Data

No. PCT/US2021/016473, filed on Feb. 3, 2021, which is a continuation-in-part of application No. 16/780,519, filed on Feb. 3, 2020.

(60) Provisional application No. 63/127,980, filed on Dec. 18, 2020, provisional application No. 63/069,542, filed on Aug. 24, 2020, provisional application No. 62/994,581, filed on Mar. 25, 2020.

(51) Int. Cl.

| | | |
|---|---|---|
| *G06N 5/04* | (2006.01) | |
| *B25J 9/16* | (2006.01) | |
| *G06N 20/00* | (2019.01) | |
| *G05B 13/02* | (2006.01) | |
| *B25J 13/00* | (2006.01) | |
| *G05B 19/18* | (2006.01) | |
| *G06F 3/01* | (2006.01) | |
| *G06N 3/04* | (2006.01) | |
| *G06F 16/27* | (2019.01) | |
| *G06F 16/23* | (2019.01) | |
| *G16Y 10/50* | (2020.01) | |
| *G16Y 40/10* | (2020.01) | |
| *G06F 9/46* | (2006.01) | |
| *G06F 9/54* | (2006.01) | |
| *G06K 9/62* | (2022.01) | |
| *G06N 3/08* | (2006.01) | |
| *G06Q 10/06* | (2012.01) | |
| *G06Q 10/10* | (2012.01) | |
| *G06Q 20/40* | (2012.01) | |
| *G06Q 30/00* | (2012.01) | |
| *G06Q 30/02* | (2012.01) | |
| *G06Q 40/02* | (2012.01) | |
| *G06Q 40/08* | (2012.01) | |
| *G06Q 50/00* | (2012.01) | |
| *G06Q 50/18* | (2012.01) | |
| *G06Q 50/26* | (2012.01) | |
| *H04L 9/06* | (2006.01) | |
| *G06Q 40/04* | (2012.01) | |

(52) U.S. Cl.
CPC ............ *B25J 13/00* (2013.01); *G05B 13/027* (2013.01); *G05B 19/18* (2013.01); *G06F 3/015* (2013.01); *G06F 9/466* (2013.01); *G06F 9/543* (2013.01); *G06F 16/2379* (2019.01); *G06F 16/27* (2019.01); *G06K 9/6215* (2013.01); *G06K 9/6218* (2013.01); *G06K 9/6268* (2013.01); *G06N 3/0427* (2013.01); *G06N 3/0454* (2013.01); *G06N 3/08* (2013.01); *G06N 5/04* (2013.01); *G06N 20/00* (2019.01); *G06Q 10/0639* (2013.01); *G06Q 10/10* (2013.01); *G06Q 20/405* (2013.01); *G06Q 30/018* (2013.01); *G06Q 30/0201* (2013.01); *G06Q 30/0206* (2013.01); *G06Q 30/0208* (2013.01); *G06Q 30/0215* (2013.01); *G06Q 30/0278* (2013.01); *G06Q 40/025* (2013.01); *G06Q 40/08* (2013.01); *G06Q 50/01* (2013.01); *G06Q 50/18* (2013.01); *G06Q 50/188* (2013.01); *G06Q 50/26* (2013.01); *G16Y 10/50* (2020.01); *G16Y 40/10* (2020.01); *H04L 9/0637* (2013.01); *G05B 2219/39292* (2013.01); *G05B 2219/50391* (2013.01); *G06Q 40/04* (2013.01); *G06Q 2220/18* (2013.01)

(56) References Cited

U.S. PATENT DOCUMENTS

| | | |
|---|---|---|
| 6,289,488 B1 | 9/2001 | Dave et al. |
| 6,519,574 B1 | 2/2003 | Wilton et al. |
| 6,589,447 B1 | 7/2003 | Ishizaki et al. |
| 6,785,592 B1 | 8/2004 | Smith et al. |
| 6,810,817 B1 | 11/2004 | James |
| 7,272,572 B1 | 9/2007 | Pienkos |
| 7,289,965 B1 | 10/2007 | Bradley et al. |
| 7,343,360 B1 | 3/2008 | Ristanovic et al. |
| 7,447,659 B2 | 11/2008 | Parthasarathy |
| 7,653,551 B2 | 1/2010 | Poltorak |
| 7,752,124 B2 | 7/2010 | Green et al. |
| 7,797,217 B2 | 9/2010 | Rosen et al. |
| 7,856,141 B2 | 12/2010 | Li |
| 7,856,414 B2 | 12/2010 | Zee |
| 7,860,767 B1 | 12/2010 | Vinci et al. |
| 7,904,381 B1 | 3/2011 | Tatang et al. |
| 8,024,262 B2 | 9/2011 | Tai et al. |
| 3,156,022 A1 | 4/2012 | Fell et al. |
| 8,160,952 B1 | 4/2012 | Fell et al. |
| 8,199,768 B1 | 6/2012 | Gossett et al. |
| 8,412,613 B2 | 4/2013 | Prager et al. |
| 8,472,447 B2 | 6/2013 | Humphries |
| 8,489,499 B2 | 7/2013 | Yan et al. |
| 8,504,463 B2 | 8/2013 | Johnson et al. |
| 8,538,848 B1 | 9/2013 | Jung et al. |
| 8,600,571 B2 | 12/2013 | Dillon et al. |
| 8,639,392 B2 | 1/2014 | Chassin |
| 8,660,943 B1 | 2/2014 | Chirehdast |
| 8,762,246 B2 | 6/2014 | Blank et al. |
| 8,848,640 B2 | 9/2014 | Reznik et al. |
| 9,240,026 B2 | 1/2016 | Chassin et al. |
| 9,425,620 B2 | 8/2016 | Chassin et al. |
| 9,454,646 B2 * | 9/2016 | Siefert ................. A61B 5/0205 |
| 9,589,297 B2 | 3/2017 | Fuller et al. |
| 9,595,070 B2 | 3/2017 | Matsuoka et al. |
| 9,697,544 B1 | 7/2017 | Bayer et al. |
| 9,762,060 B2 | 9/2017 | Kalsi et al. |
| 9,800,052 B2 | 10/2017 | Li et al. |
| 9,811,847 B2 | 11/2017 | Berger et al. |
| 9,983,670 B2 | 5/2018 | Coleman et al. |
| 10,013,654 B1 | 7/2018 | Levy et al. |
| 10,025,941 B1 | 7/2018 | Griffin et al. |
| 10,075,987 B2 | 9/2018 | Teyeb et al. |
| 10,157,407 B2 | 12/2018 | Jung et al. |
| 10,168,675 B2 | 1/2019 | Hashimoto et al. |
| 10,234,835 B2 | 3/2019 | Liu et al. |
| 10,243,743 B1 | 3/2019 | Madisetti et al. |
| 10,311,371 B1 | 6/2019 | Hotchkies et al. |
| 10,318,896 B1 | 6/2019 | Sarkar et al. |
| 10,320,569 B1 | 6/2019 | Wentz et al. |
| 10,353,745 B1 | 7/2019 | Sait |
| 10,396,919 B1 | 8/2019 | O'Shea et al. |
| 10,521,780 B1 | 12/2019 | Hopkins et al. |
| 10,642,967 B2 | 5/2020 | Balaraman et al. |
| 10,657,457 B1 | 5/2020 | Jeffery et al. |
| 10,841,236 B1 | 11/2020 | Jin et al. |
| 10,880,313 B2 | 12/2020 | Manna et al. |
| 10,884,810 B1 | 1/2021 | Verma et al. |
| 10,949,777 B2 | 3/2021 | Elbsat et al. |
| 10,963,231 B1 | 3/2021 | Singh |
| 10,970,742 B1 | 4/2021 | Knijnik et al. |
| 11,068,978 B1 | 7/2021 | Ferreira |
| 11,074,648 B1 | 7/2021 | Duccini et al. |
| 2001/0027949 A1 | 10/2001 | Safir et al. |
| 2001/0034701 A1 | 10/2001 | Fox et al. |
| 2001/0044766 A1 | 11/2001 | Keyes |
| 2002/0019758 A1 | 2/2002 | Scarpelli |
| 2002/0019802 A1 | 2/2002 | Malme et al. |
| 2002/0038279 A1 | 3/2002 | Samuelson et al. |
| 2002/0087234 A1 | 7/2002 | Lof et al. |
| 2002/0103745 A1 | 8/2002 | Lof et al. |
| 2002/0144255 A1 | 10/2002 | Anderson |
| 2002/0147670 A1 | 10/2002 | Lange |
| 2002/0161624 A1 | 10/2002 | Bradlee |
| 2002/0198805 A1 | 12/2002 | Burkhardt |

(56) References Cited

U.S. PATENT DOCUMENTS

| | | |
|---|---|---|
| 2003/0033242 A1 | 2/2003 | Lynch et al. |
| 2003/0055677 A1 | 3/2003 | Brown et al. |
| 2003/0055776 A1 | 3/2003 | Samuelson |
| 2003/0101123 A1 | 5/2003 | Alvarado et al. |
| 2003/0212572 A1 | 11/2003 | Poltorak |
| 2003/0212643 A1 | 11/2003 | Steele et al. |
| 2003/0229582 A1 | 12/2003 | Sherman et al. |
| 2003/0233278 A1 | 12/2003 | Marshall |
| 2004/0044442 A1 | 3/2004 | Bayoumi et al. |
| 2004/0230512 A1 | 11/2004 | Gulati |
| 2005/0004858 A1 | 1/2005 | Foster et al. |
| 2005/0004862 A1 | 1/2005 | Kirkland et al. |
| 2005/0065871 A1 | 3/2005 | Gerhart et al. |
| 2005/0125329 A1 | 6/2005 | Gerhart et al. |
| 2005/0125701 A1 | 6/2005 | Hensbergen et al. |
| 2005/0149401 A1 | 7/2005 | Ratcliffe et al. |
| 2005/0257079 A1 | 11/2005 | Arcangeli |
| 2005/0267837 A1 | 12/2005 | White |
| 2006/0020526 A1 | 1/2006 | Viner |
| 2006/0036530 A1 | 2/2006 | Shkedy |
| 2006/0069640 A1 | 3/2006 | Fitzgerald et al. |
| 2006/0069786 A1 | 3/2006 | Mogul et al. |
| 2006/0155423 A1 | 7/2006 | Budike |
| 2006/0195715 A1 | 8/2006 | Herington |
| 2006/0235788 A1 | 10/2006 | Guyton |
| 2006/0293985 A1 | 12/2006 | Lederman et al. |
| 2007/0011083 A1 | 1/2007 | Bird et al. |
| 2007/0016518 A1 | 1/2007 | Atkinson et al. |
| 2007/0050286 A1 | 3/2007 | Abrahams et al. |
| 2007/0055579 A1 | 3/2007 | Ha |
| 2007/0073625 A1 | 3/2007 | Shelton |
| 2007/0179855 A1 | 8/2007 | Rueda et al. |
| 2007/0226139 A1 | 9/2007 | Crumbach et al. |
| 2007/0299683 A1 | 12/2007 | Elliott |
| 2008/0046378 A1 | 2/2008 | Harrison et al. |
| 2008/0103895 A1 | 5/2008 | Burdick et al. |
| 2008/0121690 A1 | 5/2008 | Carani et al. |
| 2008/0133402 A1 | 6/2008 | Kurian et al. |
| 2008/0154784 A1 | 6/2008 | Veeraraghavan |
| 2008/0177423 A1 | 7/2008 | Brickfield et al. |
| 2008/0221951 A1 | 9/2008 | Stanforth et al. |
| 2008/0222021 A1 | 9/2008 | Stan et al. |
| 2008/0275746 A1 | 11/2008 | Musier et al. |
| 2008/0319893 A1 | 12/2008 | Mashinsky et al. |
| 2009/0048901 A1 | 2/2009 | Richard et al. |
| 2009/0049443 A1 | 2/2009 | Powers et al. |
| 2009/0055270 A1 | 2/2009 | Magdon-Ismail et al. |
| 2009/0070273 A1 | 3/2009 | Moryto |
| 2009/0106070 A1 | 4/2009 | Konar |
| 2009/0119172 A1 | 5/2009 | Soloff |
| 2009/0171842 A1 | 7/2009 | Blythe |
| 2009/0240380 A1 | 9/2009 | Shah et al. |
| 2009/0254410 A1 | 10/2009 | Chang et al. |
| 2010/0042534 A1 | 2/2010 | Moran |
| 2010/0050172 A1 | 2/2010 | Ferris |
| 2010/0057582 A1 | 3/2010 | Arfin et al. |
| 2010/0063644 A1 | 3/2010 | Kansal et al. |
| 2010/0076615 A1 | 3/2010 | Daniel et al. |
| 2010/0106332 A1 | 4/2010 | Chassin et al. |
| 2010/0114387 A1 | 5/2010 | Chassin |
| 2010/0153960 A1 | 6/2010 | Youn et al. |
| 2010/0179704 A1 | 7/2010 | Ozog |
| 2010/0179911 A1 | 7/2010 | Gorina et al. |
| 2010/0198743 A1 | 8/2010 | Plunket |
| 2010/0217550 A1 | 8/2010 | Crabtree et al. |
| 2010/0217642 A1 | 8/2010 | Crubtree et al. |
| 2010/0217651 A1 | 8/2010 | Crabtree et al. |
| 2010/0218108 A1 | 8/2010 | Crabtree et al. |
| 2010/0228598 A1 | 9/2010 | Seuken et al. |
| 2010/0332373 A1 | 12/2010 | Crabtree et al. |
| 2011/0004575 A1 | 1/2011 | Yang et al. |
| 2011/0040632 A1 | 2/2011 | Margasahayam et al. |
| 2011/0040666 A1 | 2/2011 | Crabtree et al. |
| 2011/0047056 A1 | 2/2011 | Overman et al. |
| 2011/0071882 A1 | 3/2011 | Jakagnanam et al. |
| 2011/0071934 A1 | 3/2011 | Brown et al. |
| 2011/0087531 A1 | 4/2011 | Winters et al. |
| 2011/0093382 A1 | 4/2011 | Coltrell et al. |
| 2011/0106277 A1 | 5/2011 | Sayyar-Rodsari et al. |
| 2011/0125671 A1 | 5/2011 | Zhang et al. |
| 2011/0178915 A1 | 7/2011 | Vinokour et al. |
| 2011/0231028 A1 | 9/2011 | Ozog |
| 2011/0270779 A1 | 11/2011 | Showalter |
| 2011/0313578 A1 | 12/2011 | Jones et al. |
| 2011/0320342 A1 | 12/2011 | Kremen |
| 2012/0010757 A1 | 1/2012 | Francino et al. |
| 2012/0130556 A1 | 5/2012 | Marhoefer |
| 2012/0131591 A1 | 5/2012 | Moorthi et al. |
| 2012/0150679 A1 | 6/2012 | Lazaris |
| 2012/0158568 A1 | 6/2012 | Ford et al. |
| 2012/0191594 A1 | 7/2012 | Welch et al. |
| 2012/0245752 A1 | 9/2012 | Borrett et al. |
| 2012/0246037 A1 | 9/2012 | Wilmes et al. |
| 2012/0278220 A1 | 11/2012 | Chassin et al. |
| 2012/0283005 A1 | 11/2012 | Van Luchene |
| 2012/0296845 A1 | 11/2012 | Andrews et al. |
| 2012/0310847 A1 | 12/2012 | Tadayon et al. |
| 2012/0316688 A1 | 12/2012 | Boardman et al. |
| 2012/0322387 A1 | 12/2012 | Nicoara et al. |
| 2012/0323758 A1 | 12/2012 | Henning |
| 2012/0323760 A1 | 12/2012 | Lee et al. |
| 2013/0006844 A1 | 1/2013 | Kremen |
| 2013/0006845 A1 | 1/2013 | Kremen |
| 2013/0013520 A1 | 1/2013 | Lee |
| 2013/0035992 A1 | 2/2013 | Silverman |
| 2013/0054036 A1 | 2/2013 | Cherian |
| 2013/0054863 A1 | 2/2013 | Imes et al. |
| 2013/0067074 A1 | 3/2013 | Allen et al. |
| 2013/0072775 A1 | 3/2013 | Rogers et al. |
| 2013/0085614 A1 | 4/2013 | Wenzel et al. |
| 2013/0151383 A1 | 6/2013 | Gancarz et al. |
| 2013/0159163 A1 | 6/2013 | Kayanuma et al. |
| 2013/0159165 A1 | 6/2013 | Marlowe-Noren |
| 2013/0159832 A1 | 6/2013 | Ingargiola et al. |
| 2013/0185722 A1 | 7/2013 | Kruglick |
| 2013/0218743 A1 | 8/2013 | Chassin et al. |
| 2013/0304758 A1 | 11/2013 | Gruber et al. |
| 2013/0311925 A1 | 11/2013 | Denker et al. |
| 2013/0332327 A1 | 12/2013 | Sgouridis et al. |
| 2013/0345884 A1 | 12/2013 | Forbes |
| 2013/0345888 A1 | 12/2013 | Forbes |
| 2013/0346139 A1 | 12/2013 | Steven et al. |
| 2013/0346284 A1 | 12/2013 | Stubbs et al. |
| 2013/0346285 A1 | 12/2013 | Louis |
| 2014/0006329 A1 | 1/2014 | Hu et al. |
| 2014/0012650 A1 | 1/2014 | Patro |
| 2014/0018969 A1 | 1/2014 | Forbes |
| 2014/0039710 A1 | 2/2014 | Carter et al. |
| 2014/0046819 A1 | 2/2014 | Hendrix |
| 2014/0067650 A1 | 3/2014 | Gardiner et al. |
| 2014/0067740 A1 | 3/2014 | Solari |
| 2014/0089163 A1 | 3/2014 | Parsons et al. |
| 2014/0136264 A1 | 5/2014 | Kinsey, II |
| 2014/0164262 A1 | 6/2014 | Graham |
| 2014/0171018 A1 | 6/2014 | Elrefaey et al. |
| 2014/0171136 A1 | 6/2014 | Elrefaey et al. |
| 2014/0172679 A1 | 6/2014 | Shimko |
| 2014/0180907 A1 | 6/2014 | Blank et al. |
| 2014/0201118 A1 | 7/2014 | Cleve et al. |
| 2014/0229394 A1 | 8/2014 | Slutsker et al. |
| 2014/0277797 A1 | 9/2014 | Mokhtari et al. |
| 2014/0297515 A1 | 10/2014 | Fish et al. |
| 2014/0304025 A1 | 10/2014 | Steven et al. |
| 2014/0310072 A1 | 10/2014 | Wojciechowski |
| 2014/0310155 A1 | 10/2014 | Postrel |
| 2014/0315560 A1 | 10/2014 | Smith et al. |
| 2014/0316838 A1 | 10/2014 | Zhou et al. |
| 2014/0331235 A1 | 11/2014 | Lee |
| 2014/0344018 A1 | 11/2014 | Thalken |
| 2014/0344019 A1 | 11/2014 | Thalken |
| 2014/0344189 A1 | 11/2014 | Ienaga et al. |
| 2014/0372150 A1 | 12/2014 | Karle et al. |
| 2015/0019342 A1 | 1/2015 | Gupta |
| 2015/0079578 A1 | 3/2015 | Nardi |

(56) References Cited

U.S. PATENT DOCUMENTS

| | | |
|---|---|---|
| 2015/0094968 A1 | 4/2015 | Jia et al. |
| 2015/0127515 A1 | 5/2015 | Studnitzer et al. |
| 2015/0149249 A1 | 5/2015 | Mansfield |
| 2015/0161736 A1 | 6/2015 | Thomas |
| 2015/0170080 A1 | 6/2015 | Kaushik |
| 2015/0186904 A1 | 7/2015 | Guha et al. |
| 2015/0199774 A1 | 7/2015 | Gottesman et al. |
| 2015/0242747 A1 | 8/2015 | Packes et al. |
| 2015/0248510 A1 | 9/2015 | Meagher et al. |
| 2015/0254566 A1 | 9/2015 | Chandramouli et al. |
| 2015/0269669 A1 | 9/2015 | Gil et al. |
| 2015/0302303 A1 | 10/2015 | Hakim |
| 2015/0310470 A1 | 10/2015 | Mathew et al. |
| 2015/0317558 A1 | 11/2015 | Adachi et al. |
| 2015/0339765 A1 | 11/2015 | Dubey et al. |
| 2015/0339769 A1 | 11/2015 | Deoliveira et al. |
| 2015/0348166 A1 | 12/2015 | Trivedi et al. |
| 2015/0373554 A1 | 12/2015 | Freda et al. |
| 2015/0379439 A1 | 12/2015 | Klein et al. |
| 2016/0033986 A1 | 2/2016 | Kamel et al. |
| 2016/0050168 A1 | 2/2016 | Zutphen |
| 2016/0055507 A1 | 2/2016 | Patil et al. |
| 2016/0063626 A1 | 3/2016 | Axelrod et al. |
| 2016/0092208 A1 | 3/2016 | Nicol et al. |
| 2016/0098770 A1 | 4/2016 | Chang et al. |
| 2016/0117657 A1 | 4/2016 | Forbes et al. |
| 2016/0140521 A1 | 5/2016 | Trivedi et al. |
| 2016/0256690 A1 | 9/2016 | Cecchi et al. |
| 2016/0267587 A1 | 9/2016 | Woltsovitch et al. |
| 2016/0283933 A1 | 9/2016 | Orlando et al. |
| 2016/0300135 A1 | 10/2016 | Moudy et al. |
| 2016/0307272 A1 | 10/2016 | Thalken |
| 2016/0308783 A1 | 10/2016 | Bookman et al. |
| 2016/0314545 A1 | 10/2016 | Jessen |
| 2016/0321115 A1 | 11/2016 | Thorpe et al. |
| 2016/0322835 A1 | 11/2016 | Carlson et al. |
| 2016/0330027 A1 | 11/2016 | Ebrahimi |
| 2016/0350671 A1 | 12/2016 | Morris, et al. |
| 2016/0358099 A1 | 12/2016 | Sturlaugson et al. |
| 2016/0364767 A1 | 12/2016 | Maugans |
| 2016/0364796 A1 | 12/2016 | Rosen et al. |
| 2016/0379165 A1 | 12/2016 | Moakley |
| 2016/0380886 A1 | 12/2016 | Blair et al. |
| 2016/0380911 A1 | 12/2016 | Bhandaru et al. |
| 2017/0004407 A1 | 1/2017 | Benson et al. |
| 2017/0005515 A1 | 1/2017 | Sanders et al. |
| 2017/0019496 A1 | 1/2017 | Orbach |
| 2017/0048216 A1 | 2/2017 | Chow et al. |
| 2017/0053552 A1 | 2/2017 | Zhong et al. |
| 2017/0054608 A1 | 2/2017 | Caputo et al. |
| 2017/0061535 A1 | 3/2017 | Williams |
| 2017/0085545 A1 | 3/2017 | Lohe et al. |
| 2017/0091791 A1 | 3/2017 | Srinivasan et al. |
| 2017/0098291 A1 | 4/2017 | Code et al. |
| 2017/0103385 A1 | 4/2017 | Wilson et al. |
| 2017/0103456 A1 | 4/2017 | Parsells et al. |
| 2017/0111233 A1 | 4/2017 | Kokkula et al. |
| 2017/0124668 A1 | 5/2017 | Okamoto et al. |
| 2017/0132615 A1 | 5/2017 | Castinado et al. |
| 2017/0132625 A1 | 5/2017 | Kennedy |
| 2017/0154374 A1 | 6/2017 | Iglesias et al. |
| 2017/0169331 A1 | 6/2017 | Garner |
| 2017/0193619 A1 | 7/2017 | Rollins et al. |
| 2017/0200260 A1 | 7/2017 | Bhaskar et al. |
| 2017/0206604 A1 | 7/2017 | Al-Masoud |
| 2017/0214522 A1 | 7/2017 | Code et al. |
| 2017/0232300 A1 | 8/2017 | Tran et al. |
| 2017/0236222 A1 | 8/2017 | Chen et al. |
| 2017/0243025 A1 | 8/2017 | Kurian et al. |
| 2017/0243290 A1 | 8/2017 | Brown |
| 2017/0250751 A1 | 8/2017 | Kargieman et al. |
| 2017/0262614 A1 | 9/2017 | Mshnubhatla et al. |
| 2017/0262761 A1 | 9/2017 | Yan et al. |
| 2017/0284691 A1 | 10/2017 | Sinha et al. |
| 2017/0286086 A1 | 10/2017 | Narasimhan et al. |
| 2017/0286572 A1 | 10/2017 | Hershey et al. |
| 2017/0287090 A1 | 10/2017 | Hunn et al. |
| 2017/0288399 A1 | 10/2017 | Fife |
| 2017/0289111 A1 | 10/2017 | Voell et al. |
| 2017/0308802 A1 | 10/2017 | Ramsøy et al. |
| 2017/0308976 A1 | 10/2017 | Eidelman et al. |
| 2017/0322579 A1 | 11/2017 | Goparaju et al. |
| 2017/0325041 A1 | 11/2017 | Kulavik |
| 2017/0330058 A1 | 11/2017 | Silberman et al. |
| 2017/0338967 A1 | 11/2017 | Lewison et al. |
| 2017/0352041 A1 | 12/2017 | Ramamurthy et al. |
| 2017/0357984 A1 | 12/2017 | Takamatsu et al. |
| 2017/0358041 A1 | 12/2017 | Forbes et al. |
| 2017/0372472 A1 | 12/2017 | Takahashi et al. |
| 2018/0004948 A1 | 1/2018 | Martin et al. |
| 2018/0018723 A1 | 1/2018 | Nagla et al. |
| 2018/0025442 A1 | 1/2018 | Isaacson et al. |
| 2018/0039962 A1 | 2/2018 | Ren et al. |
| 2018/0040007 A1 | 2/2018 | Lane et al. |
| 2018/0047111 A1 | 2/2018 | Vieira et al. |
| 2018/0063021 A1 | 3/2018 | Beveridge et al. |
| 2018/0063235 A1 | 3/2018 | Beveridge et al. |
| 2018/0075371 A1 | 3/2018 | Lobachev et al. |
| 2018/0075421 A1 | 3/2018 | Serrano et al. |
| 2018/0075527 A1 | 3/2018 | Nagla et al. |
| 2018/0089758 A1 | 3/2018 | Stradling et al. |
| 2018/0089760 A1 | 3/2018 | Stradling et al. |
| 2018/0091524 A1 | 3/2018 | Setty et al. |
| 2018/0096175 A1 | 4/2018 | Schmeling et al. |
| 2018/0101448 A1 | 4/2018 | Ventura et al. |
| 2018/0113742 A1 | 4/2018 | Chung et al. |
| 2018/0114167 A1 | 4/2018 | Bharti et al. |
| 2018/0114205 A1 | 4/2018 | Thomas et al. |
| 2018/0114267 A1 | 4/2018 | Khatami |
| 2018/0120813 A1 | 5/2018 | Coffman et al. |
| 2018/0121829 A1 | 5/2018 | Chowdhary et al. |
| 2018/0123391 A1 | 5/2018 | Lakamp et al. |
| 2018/0129961 A1 | 5/2018 | Kailas et al. |
| 2018/0136633 A1 | 5/2018 | Small et al. |
| 2018/0137503 A1 | 5/2018 | High et al. |
| 2018/0144355 A1 | 5/2018 | Holman et al. |
| 2018/0144403 A1 | 5/2018 | Heimowitz |
| 2018/0165585 A1 | 6/2018 | Saxena et al. |
| 2018/0165611 A1 | 6/2018 | Saxena et al. |
| 2018/0167198 A1 | 6/2018 | Muller et al. |
| 2018/0173203 A1 | 6/2018 | Freer et al. |
| 2018/0174255 A1 | 6/2018 | Hunn et al. |
| 2018/0182052 A1 | 6/2018 | Panagos |
| 2018/0183606 A1 | 6/2018 | High et al. |
| 2018/0189753 A1 | 7/2018 | Konda et al. |
| 2018/0204111 A1 | 7/2018 | Zadeh et al. |
| 2018/0204213 A1 | 7/2018 | Zappier et al. |
| 2018/0211115 A1 | 7/2018 | Klein |
| 2018/0211313 A1 | 7/2018 | Narahari |
| 2018/0218027 A1 | 8/2018 | Cronie et al. |
| 2018/0218069 A1 | 8/2018 | Rege et al. |
| 2018/0218176 A1 | 8/2018 | Voorhees et al. |
| 2018/0232804 A1 | 8/2018 | Mack |
| 2018/0240187 A1 | 8/2018 | Lee et al. |
| 2018/0246883 A1 | 8/2018 | Wang |
| 2018/0247320 A1 | 8/2018 | Gauld |
| 2018/0253451 A1 | 9/2018 | Callan et al. |
| 2018/0257306 A1 | 9/2018 | Mattingly et al. |
| 2018/0260872 A1 | 9/2018 | Ali |
| 2018/0268337 A1 | 9/2018 | Miller et al. |
| 2018/0276625 A1 | 9/2018 | Saye et al. |
| 2018/0284741 A1 | 10/2018 | Cella et al. |
| 2018/0285810 A1 | 10/2018 | Ramachandran et al. |
| 2018/0285839 A1 | 10/2018 | Yang et al. |
| 2018/0285971 A1 | 10/2018 | Rosenoer |
| 2018/0285996 A1 | 10/2018 | Ma |
| 2018/0288637 A1 | 10/2018 | Laselva et al. |
| 2018/0308184 A1 | 10/2018 | Pankanti et al. |
| 2018/0313798 A1 | 11/2018 | Chokshi et al. |
| 2018/0315056 A1 | 11/2018 | Klavins |
| 2018/0322587 A1 | 11/2018 | Linne |
| 2018/0322588 A1 | 11/2018 | Linne |
| 2018/0322597 A1 | 11/2018 | Sher |
| 2018/0329399 A1 | 11/2018 | Neelakandan et al. |

(56) References Cited

U.S. PATENT DOCUMENTS

| | | |
|---|---|---|
| 2018/0337820 A1 | 11/2018 | Chen et al. |
| 2018/0342171 A1 | 11/2018 | Darnell et al. |
| 2018/0356800 A1 | 12/2018 | Chao et al. |
| 2018/0357162 A1 | 12/2018 | Khandka et al. |
| 2018/0365764 A1 | 12/2018 | Nelson |
| 2019/0005469 A1 | 1/2019 | Dhupkar et al. |
| 2019/0013932 A1 | 1/2019 | Maino et al. |
| 2019/0019249 A1 | 1/2019 | Bhattacharjee et al. |
| 2019/0028278 A1 | 1/2019 | Gilson |
| 2019/0036932 A1 | 1/2019 | Bathen et al. |
| 2019/0057362 A1 | 2/2019 | Wright et al. |
| 2019/0081789 A1 | 3/2019 | Madisetti et al. |
| 2019/0086891 A1 | 3/2019 | Kawamoto et al. |
| 2019/0087893 A1 | 3/2019 | Pellew |
| 2019/0096001 A1 | 3/2019 | Kamrava |
| 2019/0096210 A1 | 3/2019 | Jarvis et al. |
| 2019/0101896 A1 | 4/2019 | Cantrell et al. |
| 2019/0101985 A1 | 4/2019 | Sajda et al. |
| 2019/0102835 A1 | 4/2019 | Bjonerud et al. |
| 2019/0108227 A1 | 4/2019 | Ikezoye et al. |
| 2019/0114706 A1 | 4/2019 | Bell et al. |
| 2019/0129824 A1 | 5/2019 | Radhakrishnan et al. |
| 2019/0130399 A1 | 5/2019 | Wright et al. |
| 2019/0138333 A1 | 5/2019 | Deutsch et al. |
| 2019/0139159 A1 | 5/2019 | Sarker et al. |
| 2019/0147174 A1 | 5/2019 | Narasimhan et al. |
| 2019/0155225 A1 | 5/2019 | Kothandaraman et al. |
| 2019/0155997 A1 | 5/2019 | Vos et al. |
| 2019/0156304 A1 | 5/2019 | Hudson et al. |
| 2019/0156336 A1 | 5/2019 | Kasthuri |
| 2019/0163896 A1 | 5/2019 | Balaraman et al. |
| 2019/0164136 A1 | 5/2019 | Gray |
| 2019/0164221 A1 | 5/2019 | Hill et al. |
| 2019/0165577 A1 | 5/2019 | Carr et al. |
| 2019/0165931 A1 | 5/2019 | Bharti et al. |
| 2019/0171438 A1 | 6/2019 | Franchitti |
| 2019/0173884 A1 | 6/2019 | Vincent |
| 2019/0175763 A1* | 6/2019 | Shapiro ............... A61K 48/0075 |
| 2019/0180266 A1 | 6/2019 | Sidhu et al. |
| 2019/0180358 A1 | 6/2019 | Nandan et al. |
| 2019/0188697 A1 | 6/2019 | Wu et al. |
| 2019/0197404 A1 | 6/2019 | Wang et al. |
| 2019/0197551 A1 | 6/2019 | Dickinson et al. |
| 2019/0197635 A1 | 6/2019 | Kim |
| 2019/0228409 A1 | 7/2019 | Madisetti et al. |
| 2019/0228495 A1 | 7/2019 | Tremblay et al. |
| 2019/0229890 A1 | 7/2019 | Brehmer et al. |
| 2019/0230046 A1 | 7/2019 | Djukic et al. |
| 2019/0237169 A1 | 8/2019 | Culver et al. |
| 2019/0238486 A1 | 8/2019 | Zizka |
| 2019/0238525 A1 | 8/2019 | Padmanabhan et al. |
| 2019/0243631 A1 | 8/2019 | Sharma et al. |
| 2019/0244287 A1 | 8/2019 | Prasad Datta et al. |
| 2019/0247662 A1 | 8/2019 | Poltroak |
| 2019/0251199 A1 | 8/2019 | Klianev |
| 2019/0251295 A1 | 8/2019 | Vieyra |
| 2019/0252880 A1 | 8/2019 | Watanabe et al. |
| 2019/0272591 A1 | 9/2019 | Leonard et al. |
| 2019/0278950 A1 | 9/2019 | Iuzifovich et al. |
| 2019/0287168 A1 | 9/2019 | Williams et al. |
| 2019/0287195 A1 | 9/2019 | Lee et al. |
| 2019/0287283 A1 | 9/2019 | Lin et al. |
| 2019/0289454 A1 | 9/2019 | Inoue |
| 2019/0295163 A1 | 9/2019 | Zurick et al. |
| 2019/0303893 A1 | 10/2019 | Ramasamy et al. |
| 2019/0303926 A1 | 10/2019 | Yantis et al. |
| 2019/0305957 A1 | 10/2019 | Reddy et al. |
| 2019/0311428 A1 | 10/2019 | Adjaoute |
| 2019/0319968 A1 | 10/2019 | Mehta |
| 2019/0324781 A1 | 10/2019 | Ramamurthy et al. |
| 2019/0333142 A1 | 10/2019 | Thomas |
| 2019/0340586 A1 | 11/2019 | Sheng et al. |
| 2019/0340715 A1 | 11/2019 | Cella |
| 2019/0342182 A1 | 11/2019 | Dhanabalan et al. |
| 2019/0356473 A1 | 11/2019 | Rosenoer et al. |
| 2019/0370601 A1 | 12/2019 | Anil Kumar et al. |
| 2019/0372345 A1 | 12/2019 | Bain et al. |
| 2019/0378051 A1 | 12/2019 | Widmann et al. |
| 2019/0384408 A1 | 12/2019 | Iyer et al. |
| 2020/0026560 A1 | 1/2020 | Singh et al. |
| 2020/0027157 A1 | 1/2020 | Xu et al. |
| 2020/0027159 A1 | 1/2020 | Blank et al. |
| 2020/0030608 A1 | 1/2020 | Halpern |
| 2020/0034197 A1 | 1/2020 | Nagpal et al. |
| 2020/0059097 A1 | 2/2020 | Bangalore et al. |
| 2020/0082735 A1 | 3/2020 | Nel et al. |
| 2020/0086127 A1 | 3/2020 | Intrator |
| 2020/0111158 A1 | 4/2020 | Collins et al. |
| 2020/0145210 A1 | 5/2020 | Thekadath et al. |
| 2020/0160465 A1 | 5/2020 | Spangenberg et al. |
| 2020/0179810 A1 | 6/2020 | Cunningham et al. |
| 2020/0184556 A1 | 6/2020 | Cella |
| 2020/0186355 A1 | 6/2020 | Davies |
| 2020/0202038 A1 | 6/2020 | Zhang et al. |
| 2020/0211104 A1 | 7/2020 | Mack |
| 2020/0211109 A1 | 7/2020 | Bean et al. |
| 2020/0218767 A1 | 7/2020 | Ritchey et al. |
| 2020/0219093 A1 | 7/2020 | Malhotra et al. |
| 2020/0234605 A1 | 7/2020 | Shuart |
| 2020/0302523 A1 | 9/2020 | Cella |
| 2020/0320057 A1 | 10/2020 | Van |
| 2020/0379537 A1 | 12/2020 | Henson et al. |
| 2020/0380889 A1 | 12/2020 | Fitzpatrick et al. |
| 2020/0394708 A1 | 12/2020 | Cella |
| 2020/0412731 A1 | 12/2020 | Gulbrandsen |
| 2021/0004923 A1 | 1/2021 | Mackenzie et al. |
| 2021/0082033 A1 | 3/2021 | Yao |
| 2021/0103984 A1 | 4/2021 | Leonard et al. |
| 2021/0118067 A1 | 4/2021 | Muenz et al. |
| 2021/0176638 A1 | 6/2021 | Heldt-Sheller et al. |
| 2021/0224903 A1 | 7/2021 | Mathiesen-Ohman et al. |
| 2021/0248514 A1 | 8/2021 | Cella et al. |
| 2021/0272179 A1 | 9/2021 | Sanjeevaiah Krishnaiah |
| 2021/0294791 A1 | 9/2021 | Narayanaswamy et al. |
| 2021/0342836 A1 | 11/2021 | Cella et al. |
| 2021/0358032 A1 | 11/2021 | Cella et al. |

FOREIGN PATENT DOCUMENTS

| | | |
|---|---|---|
| CN | 108667618 A | 10/2018 |
| JP | 2002233053 A | 8/2002 |
| WO | 9746929 A2 | 12/1997 |
| WO | 2001061579 | 8/2001 |
| WO | 02103879 A1 | 12/2002 |
| WO | 2008109641 A2 | 9/2008 |
| WO | 2009039500 A1 | 3/2009 |
| WO | 2011057173 A2 | 5/2011 |
| WO | 2012027478 A1 | 3/2012 |
| WO | 2013001392 A1 | 1/2013 |
| WO | 2015178609 A1 | 11/2015 |
| WO | 2017007692 A1 | 1/2017 |
| WO | 2017059866 A2 | 4/2017 |
| WO | 2017163090 A1 | 9/2017 |
| WO | 2017187397 A1 | 11/2017 |
| WO | 2018014123 A1 | 1/2018 |
| WO | 2018148732 A2 | 8/2018 |
| WO | 2018152519 A1 | 8/2018 |
| WO | 2018165155 A1 | 9/2018 |
| WO | 2018213630 A1 | 11/2018 |
| WO | 2019021311 A1 | 1/2019 |
| WO | 2019067801 A1 | 4/2019 |
| WO | 2019083974 A1 | 5/2019 |
| WO | 2019122977 A1 | 6/2019 |
| WO | 2019217323 A1 | 11/2019 |
| WO | 2019223373 A1 | 11/2019 |
| WO | 2020006639 A1 | 1/2020 |
| WO | 2020091746 A1 | 5/2020 |
| WO | 2020092426 A2 | 5/2020 |
| WO | 2020092446 A2 | 5/2020 |
| WO | 2020092426 A3 | 8/2020 |
| WO | 2020092446 A3 | 8/2020 |
| WO | 2020178752 A1 | 9/2020 |
| WO | 2021158702 A1 | 8/2021 |
| WO | 2022016102 A1 | 1/2022 |

(56) References Cited

FOREIGN PATENT DOCUMENTS

| WO | 2022133210 A2 | 6/2022 |
|----|---------------|--------|
| WO | 2022133210 A3 | 8/2022 |
| WO | 2022204425 A1 | 9/2022 |

OTHER PUBLICATIONS

PCT/US2021/016473, Feb. 3, 2021, Pending, Charles Howard Cella.
U.S. Appl. No. 17/243,145, filed Apr. 28, 2021, Pending, Charles Howard Cella.
U.S. Appl. No. 17/378,393, filed Jul. 16, 2021, Pending, Charles Howard Cella.
PCT/US2021/042050, Jul. 16, 2021, Pending, Charles Howard Cella.
Neural Networks for Data Processing, Ecole Superieure de Physique et Chimie Industrielles de la Ville, https://cordis.europa.eu/project/id/ST2*0422 (accessed on Feb. 1, 2021), Oct. 2, 1990, 3 pages.
Chance, C. , "Are Smart Contracts Contracts? Talking Tech looks at the Concepts and Realities of Smart Contracts", 2017, 9 pages.
Clark, Birgit , "Blockchain and IP Law: A Match Made in Crypto Heaven", [online], WIPO Magazine, published Feb. 2018, available at: <https://www.wipo.int/wipo_magazine/en/2018/01/article_0005.html>, 2018, 6 pages.
PCT/US19/58647 , "International Application Serial No. PCT/US19/58647, International Preliminary Report on Patentability dated May 14, 2021", Strong Force TX Portfolio 2018, LLC, 21 pages.
PCT/US19/58647 , "International Application Serial No. PCT/US19/58647, International Search Report and Written Opinion dated Jul. 7, 2020", Strong Force TX Portfolio 2018, LLC, 27 pages.
PCT/US19/58647 , "International Application Serial No. PCT/US19/58647, Invitation to Pay Additional Fees and, Where Applicable, Protest Fee mailed Apr. 24, 2020", Strong Force TX Portfolio 2018, LLC, 7 pages.
PCT/US19/58671 , "International Application Serial No. PCT/US19/58671, International Preliminary Report on Patentability dated May 14, 2021", Strong Force TX Portfolio 2018, LLC, 15 pages.
PCT/US19/58671 , "International Application Serial No. PCT/US19/58671, International Search Report and Written Opinion dated Jul. 7, 2020", Strong Force TX Portfolio 2018, LLC, 21 pages.
PCT/US19/58671 , "International Application Serial No. PCT/US19/58671, Invitation to Pay Additional Fees and, Where Applicable, Protest Fee mailed Apr. 24, 2020", 7 pages.
PCT/US2019/030934 , "International Application Serial No. PCT/US2019/030934, International Preliminary Report on Patentability dated Nov. 10, 2020", Strong Force TX Portfolio 2018, LLC, 77 pages.
PCT/US2019/030934 , "International Application Serial No. PCT/US2019/030934, International Search Report and Written Opinion dated Oct. 11, 2019", Strong Force TX Portfolio 2018, LLC, 89 pages.
PCT/US2019/030934 , "International Application Serial No. PCT/US2019/030934, Invitation to Pay Additional Fees mailed Jul. 30, 2019", Strong Force TX Portfolio 2018, LLC, 8 pages.
PCT/US2021/016473 , "International Application Serial No. PCT/US2021/016473, International Search Report and Written Opinion dated May 24, 2021", Strong Force TX Portfolio 2018, LLC, 18 pages.
PCT/US2021/016473 , "International Application Serial No. PCT/US2021/016473, Invitation to Pay Additional Fees mailed Mar. 18, 2021", Strong Force TX Portfolio 2018, LLC, 3 pages.
Puri, Vikram , et al., "A hybrid artificial intelligence and internet of things model for generation of renewable resource of energy", IEEE Access 7 (2019), 2019, p. 111181-111191.
Raza, Muhammad Qamar, et al., "A review on artificial intelligence based load demand forecasting techniques for smart grid and buildings", Renewable and Sustainable Energy Reviews 50 (2015), 2015, pp. 1352-1372.
Riady, Yos , "Smart Contract Extensibilty with Wrapped Tokens", Jul. 13, 2019, 13 pages.
"Scikit-Learn: Machine Learning in Python", from Wayback Machine, http://web.archive.org/web/20210525051513/https://scikit-learn.org/stable/, retrieved from the internet on Jun. 1, 2021, May 25, 2021, 2 pages.
"Scikit-learn: machine learning in Python", from Wayback Machine, http://web.archive.org/web/20190228205841/https://scikit-learn.org/stable/, retrieved from the internet on Aug. 11, 2021, Feb. 28, 2019, 3 pages.
Shields, Ronan , "Media futures trading is one step closer as NIYIAX raises $5.6M", The Drum, Oct. 19, 2017, 6 pages.
Ullah, Qazi Zia, et al., "Adaptive resource utilization prediction system for infrastructure as a service cloud", Computational intelligence and neuroscience 2017, 2017, 13 pages.
"Making sense of IoT", (Internet of Things)—the IoT business guide, May 27, 2015, 61 pages.
19799943.6 , "European Application Serial No. 19799943.6, Partial Supplementary Search Report, Communication Pursuant to Rule 164(1) EPC dated Jan. 21, 2022", Strong Force TX Portfolio 2018, LLC, 13 pages.
Bashir, Imran , "Mastering Blockchain", Packt Publishing, XP055872144JSBN: 978-1-78712-544-5pages ToC, 16-29,358-368, Mar. 17, 2017, 51 pages.
Berka, P. , "Using The LISp-Miner System for Credit Risk Assessment", Neural Network World 26.5: Czech Technical University, Prague., 2016, 22 pages.
Cant, Bart , et al., "Smart Contracts in Financial Services: Getting from Hype to Reality", Capgemini Consulting, 2016, 25 pages.
Capgemini Report , "Smart Contracts in Financial Services: getting from Hype to Reality", 2016, pp. 1-25.
Dineshreddy, Vemula , et al., "Towards on "Internet of Things" Framework for Financial Services Sector", IEEE Xplore, 3rd International Conference on Recent Advances in Information Technology(RAIT-2016)., Jul. 9, 2016, 5 pages.
Dineshreddy, Vemula , et al., "Towards on "Internet of Things" Framework for Financial Services Sector", IEEE Xplore, 3rd International Conference on Recent Advances in Information Technology, 2016, 5 pages.
Eckenrode, Jim , "The derivative effect: How financial services can make IoT technology pay off", Deloitte Insights, Oct. 2015, 12 pages.
Fang, Xuewei, et al., "Study on Metal Deposit in the Fused-coating Based Additive Manufacturing", Procedia CIRP, vol. 55, XP055872287,NL ISSN: 2212-8271, DOI: 10.1016/j.procir.2016.08.034Retrieved from the Internets RL:https://www.sciencedirect.com/science/article/pii/S2212827116309234, Oct. 6, 2016, pp. 115-121.
Holliday, Joanne , et al., "Epidemic algorithms for replicated databases", IEEE Transactions on Knowledge and Data Engineering (vol. 15 Issue 5), 2003, pp. 1218-1238.
Infosys Whitepaper , "Robotic Process Automation (RPA) to Accelerate Mortgage Processing", 2018, pp. 1-8.
Isaja, Mauro , et al., "Distributed ledger technology for decentralization of manufacturing processes", IEEE Industrial Cyber-Physical Systems (ICPS), 2018, pp. 696-701.
Krishnamurthy, Dheepak , et al., "Energy Storage Arbitrage Under Day-Ahead and Real-Time Price Uncertainty", IEEE Transactions on Power Systems, vol. 33, No. 1, Jan. 2008, 10 pages.
Kumar, S.F.P. , et al., "Robotic Process Automation (RPA) to Accelerate Mortgage Processing", Infosys Limited, Bengaluru, India, 2018, 8 pages.
Leber, Jessica , "Can a Credit Score be Crowdsourced?", MIT Technology Review, Jun. 7, 2012, 4 pages.
Lu, Yuan , et al., "ZebraLancer: Private nad Anonymous Crowdsourcing System atop Open Blockchain", New Jersey Institute of Technology, arXiv:1803.01256v1, Mar. 3, 2018, 16 pages.
Memos, Dimitris , "Shaking up the Maritime Industry through Open Data and Crowdsourcing", International Journal of Digital Business, vol. 2017, Issue 1, Apr. 2017, pp. 1-16.
O'Donovan, Caroline , "What If You Could Crowdsource a Loan", BuzzFeed News, Apr. 17, 2015, 5 pages.

(56) References Cited

OTHER PUBLICATIONS

PCT/US2021/042050, "International Application Serial No. PCT/US2021/042050, International Search Report and Written Opinion dated Sep. 24, 2021", Strong Force TX Portfolio 2018, LLC, 18 pages.
Sandner, Philipp, et al., "Application of Blockchain Technology in the Manufacturing Industry", Frankfurt School Blockchain Center Internet Article, XP055872401 .Retrieved from the Internet:URL:http://explore-ip.com/2017_Blockchain-Technology-in-Manufacturing.pdf [retrieved on Dec. 13, 2021], Nov. 18, 2017, 23 pages.
Shah, Agam, "The Chain Gang", XP055872061 Retrieved from the Internets RL:https://asmedigitalcollection.asme.org/memagazineselect/article/140/05/30/369470/The-Chain-GangManufacturing-supply-chains-aremore [retrieved on Dec. 13, 2021], May 1, 2018, 13 pages.
spencepc.com, "Four Types of Intellectual Property for Business", viewed at https://www.spencepc.com/intellectual-property-basics/four-types-of-intellectual-property-for-businesses/, Apr. 4, 2016, 3 pages.
Stocker, Carsten, et al., "Erfahrungsbericht Genesis of Things Project Ansätze und Herausforderungen bei der Integration von Blockchain in der additiven Fertigung und Geschäftsmodelle", www.digitaletechnologien.deInternet Article, XP055872377,Retrieved from the InterneLU RL:https://www.digitaletechnologien.de/DT/Redaktion/DE/Downloads/2018-paice-hmiworkshop-vortrag-Blechschmidt-St°/oC3%B6ckert.pdf? blob=publicationFile&v=2, Apr. 24, 2018, 11 pages.
Szabo, Nick, et al., "Smart Contracts: 12 Use Cases for Business & Beyond", Chamber of Digital Commerce, Dec. 2016, 56 pages.
Taylor, Patrick, "The Robots are coming to Corporate Finance", Forbes Technology Council, May 1, 2018, pp. 1-5.
Trouton, Stuart, et al., "3D opportunity for blockchain", DeloitteInternet Article, XP055539847,Retrieved from the InternetsRL:https://www2.deloitte.com/content/dam/insights/us/articles/3255_3Dopportunity_blockchain/DUP_3D-opportunity_blockchain.pdf [retrieved on Jan. 9, 2019], Nov. 17, 2016, 20 pages.
Wang, Qing, et al., "Dynamic Spectrum Allocation under Cognitive Cell Network for M2M Applications", 2012 Conference Record of the Forty Sixth Asilomar Conference on Signals, Systems and Computers (ASILOMAR), 2012, pp. 596-600.
Zeng, Yaxiong, et al., "Distributed solar renewable generation: Option contracts with renewable energy credit uncertainty", Energy Economics, vol. 48, 2015, pp. 295-305.
19799943.6, "European Application Serial No. 19799943.6, Extended European Search Report dated Apr. 25, 2022", Strong Force TX Portfolio 2018, LLC, 13 pages.
19880153.2, "European Application Serial No. 19880153.2, Extended European Search Report dated May 17, 2022", 10 pages.
Bis, "What is distributed ledger technology", available at: < https://www.bis.org/publ/qtrpdf/r_qt1709y.htm, Sep. 2017, 3 pages.
Chinthalapati, V.L. Raju, et al., "A Simultaneous Deterministic Pertubation Actor-Critic Algorithm with an Application to Optimal Mortgage Refinancing,", 45th IEEE Conference on Decision & Control, Dec. 2006, pp. 4151-4156.
Gupta, Yachna, et al., "A software for insurance consultancy", 2013 International Conference on Advances in Computing, Communications and Informatics (ICACCI), Aug. 22-25, 2013, pp. 1288-1292.
Janiesch, Christian, et al., "The Internet-of-Things Meets Business Process Management: Mutual Benefits and Challenges", retrieved from internet, https://arxiv.org/abs/1709.03628., Sep. 11, 2017, 9 pages.
Jin, Yu, et al., "A Data-Driven Approach to Predict Default Risk of Loan for Online Peer-to-Peer (P2P) Lending", 2015 Fifth International Conference on Communication Systems and Network Technologies, Apr. 4-6, 2015, pp. 609-613.
Kuo, Ping-Huan, et al., "An electricity price forecasting model by hybrid structured deep neural networks", Sustainability 10.4, Apr. 21, 2018, 17 pages.

Luo, Liang, et al., "A resource scheduling algorithm of cloud computing based on energy efficient optimization methods", 2012 International Green Computing Conference (IGCC). IEEE, 2012, 6 pages.
Min, Zaw, et al., "Facilities management added value in closing the energy performance gap", International Journal of Sustainable Built Environment, 2016, 23 pages.
Namvar, Anahita, et al., "Credit risk prediction in an imbalanced social lending environment", retrieved from the Internet, https://doi.org/10.48550/arXiv.1805.00801,2018, pp. 1-11.
Ogiela, Marek R., et al., "Security of Distributed Ledger Solutions Based on Blockchain Technologies", IEEE 32nd International Conference on Advanced Information Networking and Applications (AINA), May 2018, pp. 1089-1095.
PCT/US2021/064029, "International Application Serial No. PCT/US2021/064029, Invitation to Pay Additional Fees and, Where Applicable, Protest Fee dated Mar. 16, 2022", Strong Force TX Portfolio 2018, LLC, 3 pages.
Shakhatreh, Hazim, et al., "Unmanned Aerial Vehicles: A Survey on Civil Applications and Key Research Challenges", Arxiv.org, Cornell University Library, 201 Olin Library Cornell University Ithaca, NY 14853, Apr. 19, 2018, 58 pages.
19878940.6, "European Application Serial No. 19878940.6, Extended European Search Report dated Jun. 14, 2022", Strong Force TX Portfolio 2018, LLC, 7 pages.
Baltaoglu, Sevi, et al., "Algorithmic Bidding for Virtual Trading in Electricity Markets", IEEE Journal of Latex Class Files vol. 14 No. 8, Aug. 2015, 12 pages.
Bashir, Imran, "Mastering Blockchain", Packt Publishing, XP055393678, ISBN: 978-1-78712-544-5, Mar. 17, 2017, 531 pages.
Batra, Gaurav, et al., "Improving the semiconductor industry through advanced analytics", [online] McKinsey and Company, available at: < https://www.mckinsey.com/industries/semiconductors/our-insights/improving-the-semiconductor-industry-through-advanced-analytics, Mar. 11, 2016, 18 pages.
Cain, Collin, et al., "A Common Sense Guide to Wholesale Electric Markets", [online] Published Apr. 2007, available at: < https://www.bateswhite.com/media/publication/55_media.741 .pdf >, 2017, 42 pages.
Crozter, Daniel V., "Energy Storage Myths", Fractal [online], available at: < https://www.energystorageconsultants.com/energy-storage-arbitrage/, Jun. 17, 2016, 6 pages.
Heap, Imogen, "Blockchain could help musicians make money again", https://hbr.org/2017/06/blockchain-could-help-musicians-make-money-again, 2017, 7 pages.
Kelly-Detwiler, Peter, "Stem Adding Artifical Intelligence to Storage and Branching out to New Markets", Forbes.com [online], available at: < https://www.forbes.com/sites/peterdetwiler/2018/01/08/stem-adding-artificial-intelligence-to-storage-and-branching-out-to-new-markets/ (Year: 2018), Jan. 8, 2018, 7 pages.
PCT/US2021/064029, "International Application Serial No. PCT/US2021/064029, International Search Report and Written Opinion dated Jul. 1, 2022", Strong Force TX Portfolio 2018, LLC, 36 pages.
PCT/US2022/021783, "International Application Serial No. PCT/US2022/021783, International Search Report and Written Opinion dated Jul. 7, 2022", Strong Force TX Portfolio 2018, LLC, 13 pages.
Pon, Bruce, "Blockchain will usher in the era of decentralised computing", LSE Business Review, 2016, pp. 1-5.
Rooney, Kate, "Your Guide to Cryptocurrency Regulations Around the World and Where They are Headed", CNBC.com, Mar. 27, 2018, pp. 1-13.
Spector, Julian, "Selling Energy Storage when the Economics Don't Work", [online], available at: <https://www.greentechmedia.com/articles/read/how-to-sell-energystorage-when-the-economics-dont-work >, Sep. 14, 2016, 4 pages.
PCT/US2021/016473, "International Application Serial No. PCT/US2021/016473, International Preliminary Report on Patentability dated Aug. 18, 2022", Strong Force TX Portfolio 2018, LLC, 13 pages.
11202010731V, "Singapore Application Serial No. 11202010731V, Written Opinion dated Aug. 11, 2022", Strong Force TX Portfolio 2018, LLC, 8 pages.

(56) References Cited

OTHER PUBLICATIONS

BITCOINTAXESAPI, "Integrate BitcoinTaxes into wallets or exchanges", available at: < https://web.archive.org/web/20170618155341/https://bitcoin.tax/api >, Jun. 18, 2017, 8 pages.

CME Group, "Trading the Curve in Energies", [online] CME Group, published on Jul. 10, 2017, available at: < https://www.cmegroup.com/education/whitepapers/trading-the-curve-in-energies.html >, Jul. 10, 2017, 4 pages.

Dieterich, Vincent, et al., "Application of Blockchain Technology in the Manufacturing Industry", Frankfurt School Blockchain Center, Germany, Nov. 30, 2017, pp. 1-23.

Malini, A., et al., "Technological innovations in the banking sector in India: An analysis", 2017 International Conference on Technological Advancements in Power and Energy (TAP Energy), 2017, pp. 1-5.

Tso, Fung Po, et al., "Network and server resource management strategies for data centre infrastructures", A survey, Computer Networks, vol. 106, https://www.sciencedirect.com/science/article/pii/S1389128616302298., 2019, pp. 209-222.

\* cited by examiner

SELECTION AND CONFIGURATION OF AN AUTOMATED ROBOTIC PROCESS

CROSS REFERENCE TO RELATED APPLICATIONS

The present application claims the benefit of priority to and is a continuation of U.S. patent application Ser. No. 17/332,700 (SFTX-0013-U01), filed May 27, 2021, entitled "AUTOMATED ROBOTIC PROCESS SELECTION AND CONFIGURATION."

U.S. patent application Ser. No. 17/332,700 (SFTX-0013-U01) claims the benefit of priority of and is a continuation of PCT Application PCT/US2021/016473 (SFTX-0013-WO), filed Feb. 3, 2021, entitled "ARTIFICIAL INTELLIGENCE SELECTION AND CONFIGURATION."

PCT Application PCT/US2021/016473 (SFTX-0013-WO) claims the benefit of priority of and is a continuation-in-part of U.S. patent application Ser. No. 16/780,519, filed Feb. 3, 2020, entitled "ADAPTIVE INTELLIGENCE AND SHARED INFRASTRUCTURE LENDING TRANSACTION ENABLEMENT PLATFORM RESPONSIVE TO CROWD SOURCED INFORMATION."

PCT Application PCT/US2021/016473 (SFTX-0013-WO) also claims priority to the following U.S. Provisional Patent Applications: Ser. No. 63/127,980, filed Dec. 18, 2020, entitled "MARKET ORCHESTRATION SYSTEM FOR FACILITATING ELECTRONIC MARKETPLACE TRANSACTIONS"; Ser. No. 63/069,542, filed Aug. 24, 2020, entitled "INFORMATION TECHNOLOGY SYSTEMS AND METHODS FOR TRANSACTION ARTIFICIAL INTELLIGENCE LEVERAGING DIGITAL TWINS"; and Ser. No. 62/994,581, filed Mar. 25, 2020, entitled "COMPLIANCE SYSTEM FOR FACILITATING LICENSING OF PERSONALITY RIGHTS".

Each of the foregoing applications is incorporated herein by reference in its entirety.

BACKGROUND

Field

This application is related to the field of lending, and more particularly to the field of adaptive intelligent systems used to enable lending transactions.

Description of the Related Art

Lending transactions provide financing for a wide variety of needs, ranging from housing and education to corporate and government projects, among many others, while enabling lenders to earn financial returns. However, lending transactions are plagued by a number of problems, including opacity and asymmetry of information, moral hazard induced by shifting of the consequences of risky or inappropriate behavior, complexity of application and negotiation processes, burdensome regulatory and policy regimes, difficulty in determining the value of property that is used as collateral or backing for obligations, difficulty in determining the reliability or financial health of entities, and others. A need exists for lending systems that address these and other problems of lending transactions and environments.

SUMMARY

Provided herein is a lending transaction enablement platform having a set of data-integrated microservices including data collection and monitoring services, blockchain services, and smart contract services for handling lending entities and transactions. The platform is capable of enabling a wide range of dedicated solutions, which may share data collection and storage infrastructure, and which may share or exchange inputs, events, activities, and outputs, such as to reinforce learning, enable automation, and enable adaptive intelligence across the various solutions.

In embodiments a lending platform is provided having an Internet of Things and sensor platform for monitoring at least one of a set of assets and a set of collateral for a loan, a bond, or a debt transaction.

In embodiments a lending platform is provided having a smart contract and distributed ledger platform for managing at least one of ownership of a set of collateral and a set of events related to a set of collateral.

In embodiments a lending platform is provided having a smart contract system that automatically adjusts an interest rate for a loan based on information collected via at least one of an Internet of Things system, a crowdsourcing system, a set of social network analytic services and a set of data collection and monitoring services.

In embodiments a lending platform is provided having a crowdsourcing system for obtaining information about at least one of a state of a set of collateral for a loan and a state of an entity relevant to a guarantee for a loan.

In embodiments a lending platform is provided having a smart contract that automatically adjusts an interest rate for a loan based on at least one of a regulatory factor and a market factor for a specific jurisdiction.

In embodiments a lending platform is provided having a smart contract that automatically restructures debt based on a monitored condition.

In embodiments a lending platform is provided having a social network monitoring system for validating the reliability of a guarantee for a loan.

In embodiments a lending platform is provided having an Internet of Things data collection and monitoring system for validating reliability of a guarantee for a loan.

In embodiments a lending platform is provided having a robotic process automation system for negotiation of a set of terms and conditions for a loan.

In embodiments a lending platform is provided having a robotic process automation system for loan collection.

In embodiments a lending platform is provided having a robotic process automation system for consolidating a set of loans.

In embodiments a lending platform is provided having a robotic process automation system for managing a factoring loan.

In embodiments a lending platform is provided having a robotic process automation system for brokering a mortgage loan.

In embodiments a lending platform is provided having a crowdsourcing and automated classification system for validating condition of an issuer for a bond.

In embodiments a lending platform is provided having a social network monitoring system with artificial intelligence for classifying a condition about a bond.

In embodiments a lending platform is provided having an Internet of Things data collection and monitoring system with artificial intelligence for classifying a condition about a bond.

In embodiments a lending platform is provided having a system that varies the terms and conditions of a subsidized loan based on a parameter monitored by the IoT.

In embodiments a lending platform is provided having a system that varies the terms and conditions of a subsidized loan based on a parameter monitored in a social network.

In embodiments a lending platform is provided having a system that varies the terms and conditions of a subsidized loan based on a parameter monitored by crowdsourcing.

In embodiments a lending platform is provided having an automated blockchain custody service for managing a set of custodial assets.

In embodiments a lending platform is provided having an underwriting system for a loan with a set of data-integrated microservices including data collection and monitoring services, blockchain services, artificial intelligence services, and smart contract services for underwriting lending entities and transactions.

In embodiments a lending platform is provided having a loan marketing system with a set of data-integrated microservices including data collection and monitoring services, blockchain services, artificial intelligence services and smart contract services for marketing a loan to a set of prospective parties.

In embodiments a lending platform is provided having a rating system with a set of data-integrated microservices including data collection and monitoring services, blockchain services, artificial intelligence services, and smart contract services for rating a set of loan-related entities.

In embodiments a lending platform is provided having a compliance system with a set of data-integrated microservices including data collection and monitoring services, blockchain services, artificial intelligence services, and smart contract services for automatically facilitating compliance with at least one of a law, a regulation and a policy that applies to a lending transaction.

One aspect of the present disclosure relates to a method for electronically facilitating licensing of one or more personality rights of a licensor. The method may include receiving an access request from a licensee to obtain approval to license personality rights from a set of available licensors. The method may include selectively granting access to the licensee based on the access request. The method may include receiving confirmation of a deposit of an amount of funds from the licensee. The method may include issuing an amount of cryptocurrency corresponding to the amount of funds deposited by the licensee to an account of the licensee. The method may include receiving a smart contract request to create a smart contract governing the licensing of the one or more personality rights of the licensor by the licensee. The smart contract request may indicate one or more terms including a consideration amount of cryptocurrency to be paid to the licensor in exchange for one or more obligations on the licensor. The method may include generating the smart contract based on the smart contract request. The method may include escrowing the consideration amount of cryptocurrency from the account of the licensee. The method may include deploying the smart contract to a distributed ledger. The method may include verifying, by the smart contract, that the licensor has performed the one or more obligations. The method may include, in response to receiving verification that the licensor has performed the one or more obligations, releasing at least a portion of the consideration amount of cryptocurrency into a licensor account of the licensor. The method may include outputting a record indicating a completion of a licensing transaction defined by the smart contract to the distributed ledger.

In some implementations of the method, the smart contract may be generated using a smart contract template provided by an interested third party.

In some implementations of the method, the interested third party may be one of a university, a sports team, or a collegiate athletics governance organization.

In some implementations of the method, the distributed ledger may be auditable by a set of third parties, including the interested third party.

In some implementations of the method, the cryptocurrency may be one of Bitcoin, Ethereum, Litecoin, and Ripple.

In some implementations of the method, the cryptocurrency may be a private cryptocurrency.

In some implementations of the method, the cryptocurrency may be pegged to a particular type of real currency.

In some implementations of the method, the distributed ledger may be a public ledger.

In some implementations of the method, the distributed ledger may be a private ledger that is only hosted on computing devices associated with interested third parties.

In some implementations of the method, the distributed ledger may be a blockchain.

In some implementations of the method, verifying that the licensor may have performed the one or more obligations includes receiving location data from a wearable device associated with the licensor. In some implementations of the method, verifying that the licensor may have performed the one or more obligations includes verifying that the licensor has performed the one or more obligations based on the location data.

In some implementations of the method, verifying that the licensor may have performed the one or more obligations includes receiving social media data from a social media website. In some implementations of the method, verifying that the licensor may have performed the one or more obligations includes verifying that the licensor has performed the one or more obligations based on the social media data.

In some implementations of the method, verifying that the licensor may have performed the one or more obligations includes receiving media content from an external data source. In some implementations of the method, verifying that the licensor may have performed the one or more obligations includes verifying that the licensor has performed the one or more obligations based on the media content.

In some implementations of the method, the media content may be one of a video recording, a photograph, or an audio recording.

In some implementations of the method, selectively granting access to the licensor may include receiving a set of affiliations of the licensee. In some implementations of the method, selectively granting access to the licensor may include verifying that the licensee is permitted to engage with a set of licensors including the licensor based on the set of affiliations. In some implementations of the method, selectively granting access to the licensor may include in response to verifying that the licensee is permitted to engage with the set of licensors, granting the licensee approval to engage with the set of licensees.

In some implementations of the method, the set of affiliations of the licensee may include organizations to which the licensee or a principal associated with the licensee donates to or owns.

In some implementations of the method, releasing at least a portion of the consideration amount of cryptocurrency into a licensee account of the licensee may include identifying an allocation smart contract associated with the licensee. In some implementations of the method, the allocation smart contract may define allocation rules governing a manner by which funds resulting from licensing the one or more personality rights are to be distributed amongst the licensor and one or more additional entities. In some implementations of the method, releasing at least a portion of the consideration amount of cryptocurrency into a licensee account of the licensee may include distributing the consideration amount of the cryptocurrency in accordance with the allocation rules.

In some implementations of the method, the additional entities may include one or more of teammates of the licensor, coaches of the licensor, a team of the licensor, a university of the licensee, and the NCAA.

In some implementations of the method, it may include obtaining a set of records indicating completion of a set of respective transactions from the distributed ledger. In some implementations of the method, the set of records may include the record indicating the completion of the transaction defined by the smart contract. In some implementations of the method, it may include determining whether an organization associated with the licensor is likely in violation of one or more regulations based on the set of records and a fraud detection model.

In some implementations of the method, the fraud detection model may be trained using training data that indicates permissible transactions and fraudulent transactions.

Another aspect of the present disclosure relates to a system configured for electronically facilitating licensing of one or more personality rights of a licensor. The system may include one or more hardware processors configured by machine-readable instructions. The processor(s) may be configured to receive an access request from a licensee to obtain approval to license personality rights from a set of available licensors. The processor(s) may be configured to selectively grant access to the licensee based on the access request. The processor(s) may be configured to receive confirmation of a deposit of an amount of funds from the licensee. The processor(s) may be configured to issue an amount of cryptocurrency corresponding to the amount of funds deposited by the licensee to an account of the licensee. The processor(s) may be configured to receive a smart contract request to create a smart contract governing the licensing of the one or more personality rights of the licensor by the licensee. The smart contract request may indicate one or more terms including a consideration amount of cryptocurrency to be paid to the licensor in exchange for one or more obligations on the licensor. The processor(s) may be configured to generate the smart contract based on the smart contract request. The processor(s) may be configured to escrow the consideration amount of cryptocurrency from the account of the licensee. The processor(s) may be configured to deploy the smart contract to a distributed ledger. The processor(s) may be configured to verify, by the smart contract, that the licensor has performed the one or more obligations. The processor(s) may be configured to, in response to receiving verification that the licensor has performed the one or more obligations, release at least a portion of the consideration amount of cryptocurrency into a licensor account of the licensor. The processor(s) may be configured to output a record indicating a completion of a licensing transaction defined by the smart contract to the distributed ledger.

BRIEF DESCRIPTION OF THE FIGURES

FIG. 6 depicts an embodiment of a crowdsourcing workflow enabled by a lending platform.

DETAILED DESCRIPTION

Figure 1:
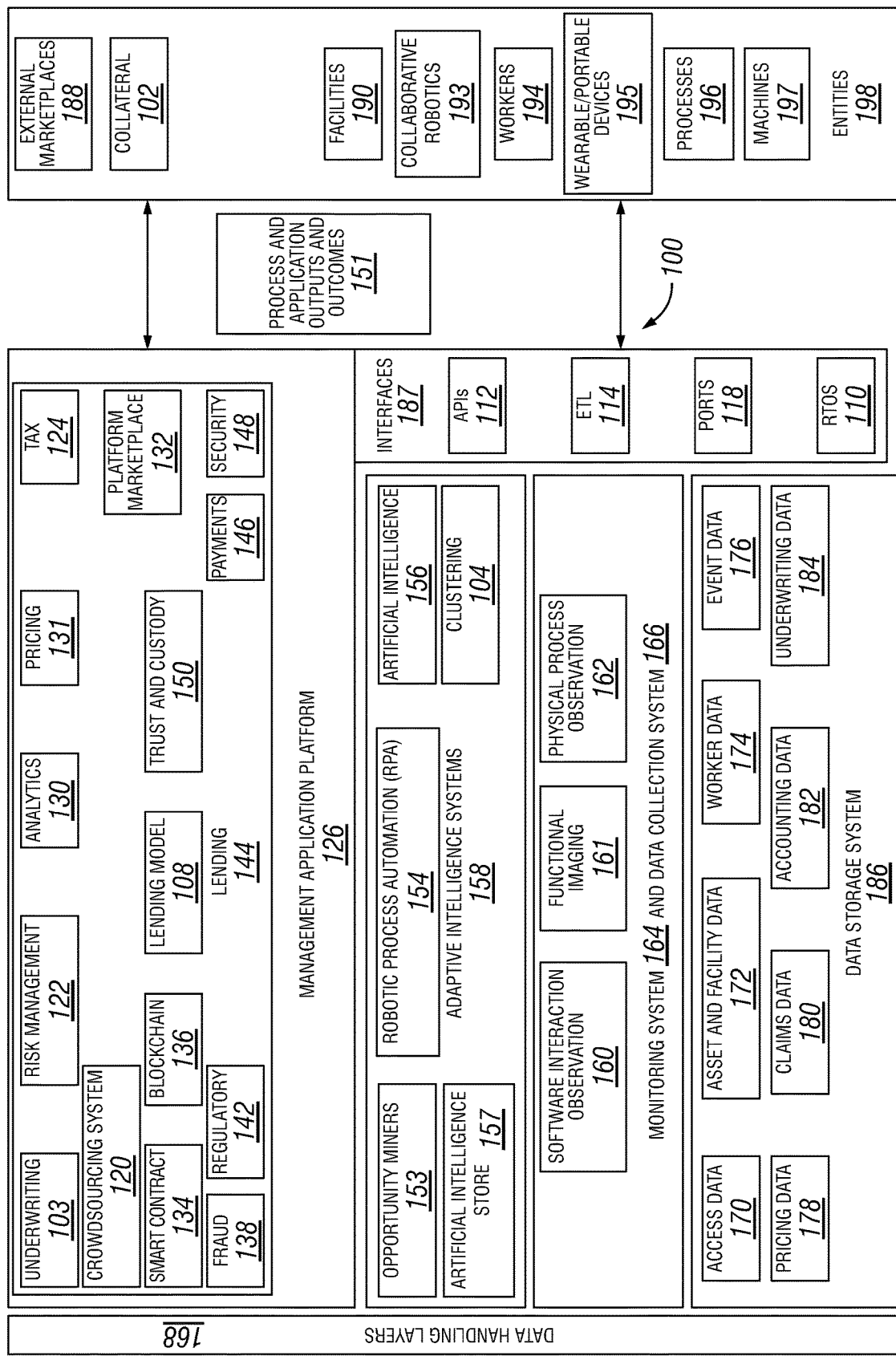
FIG. 1 depicts components and interactions of an embodiment of a lending platform having a set of data-integrated microservices including data collection and monitoring services for handling lending entities and transactions.

The term services/microservices (and similar terms) as utilized herein should be understood broadly. Without limitation to any other aspect or description of the present disclosure, a service/microservice includes any system (or platform) configured to functionally perform the operations of the service, where the system may be data-integrated, including data collection circuits, blockchain circuits, artificial intelligence circuits, and/or smart contract circuits for handling lending entities and transactions. Services/microservices may facilitate data handling and may include facilities for data extraction, transformation and loading; data cleansing and deduplication facilities; data normalization facilities; data synchronization facilities; data security facilities; computational facilities (e.g., for performing pre-defined calculation operations on data streams and providing an output stream); compression and de-compression facilities; analytic facilities (such as providing automated production of data visualizations), data processing facilities, and/or data storage facilities (including storage retention, formatting, compression, migration, etc.), and others.

Services/microservices may include controllers, processors, network infrastructure, input/output devices, servers, client devices (e.g., laptops, desktops, terminals, mobile devices, and/or dedicated devices), sensors (e.g., IoT sensors associated with one or more entities, equipment, and/or collateral), actuators (e.g., automated locks, notification devices, lights, camera controls, etc.), virtualized versions of any one or more of the foregoing (e.g., outsourced computing resources such as a cloud storage, computing operations; virtual sensors; subscribed data to be gathered such as stock or commodity prices, recordal logs, etc.), and/or include components configured as computer readable instructions that, when performed by a processor, cause the processor to perform one or more functions of the service, etc. Services may be distributed across a number of devices, and/or functions of a service may be performed by one or more devices cooperating to perform the given function of the service.

Services/microservices may include application programming interfaces that facilitate connection among the components of the system performing the service (e.g., microservices) and between the system to entities (e.g., programs, web sites, user devices, etc.) that are external to the system. Without limitation to any other aspect of the present disclosure, example microservices that may be present in certain embodiments include (a) a multi-modal set of data collection circuits that collect information about and monitor entities related to a lending transaction; (b) blockchain circuits for maintaining a secure historical ledger of events related to a loan, the blockchain circuits having access control features that govern access by a set of parties involved in a loan; (c) a set of application programming interfaces, data integration services, data processing workflows and user interfaces for handling loan-related events and loan-related activities; and (d) smart contract circuits for specifying terms and conditions of smart contracts that govern at least one of loan terms and conditions, loan-related events and loan-related activities. Any of the services/microservices may be controlled by or have control over a controller. Certain systems may not be considered to be a service/microservice. For example, a point of sale device that simply charges a set cost for a good or service may not be a service. In another example, a service that tracks the cost of a good or service and triggers notifications when the value changes may not be a valuation service itself, but may rely on valuation services, and/or may form a portion of a valuation service in certain embodiments. It can be seen that a given circuit, controller, or device may be a service or a part of a service in certain embodiments, such as when the functions or capabilities of the circuit, controller, or device are configured to support a service or microservice as described herein, but may not be a service or part of a service for other embodiments (e.g., where the functions or capabilities of the circuit, controller, or device are not relevant to a service or microservice as described herein). In another example, a mobile device being operated by a user may form a portion of a service as described herein at a first point in time (e.g., when the user accesses a feature of the service through an application or other communication from the mobile device, and/or when a monitoring function is being performed via the mobile device), but may not form a portion of the service at a second point in time (e.g., after a transaction is completed, after the user un-installs an application, and/or when a monitoring function is stopped and/or passed to another device). Accordingly, the benefits of the present disclosure may be applied in a wide variety of processes or systems, and any such processes or systems may be considered a service (or a part of a service) herein.

One of skill in the art, having the benefit of the disclosure herein and knowledge about a contemplated system ordinarily available to that person, can readily determine which aspects of the present disclosure will benefit a particular system, how to combine processes and systems from the present disclosure to construct, provide performance characteristics (e.g., bandwidth, computing power, time response, etc.), and/or provide operational capabilities (e.g., time between checks, up-time requirements including longitudinal (e.g., continuous operating time) and/or sequential (e.g., time-of-day, calendar time, etc.), resolution and/or accuracy of sensing, data determinations (e.g., accuracy, timing, amount of data), and/or actuator confirmation capability) of components of the service that are sufficient to provide a given embodiment of a service, platform, and/or microservice as described herein. Certain considerations for the person of skill in the art, in determining the configuration of components, circuits, controllers, and/or devices to implement a service, platform, and/or microservice ("service" in the listing following) as described herein include, without limitation: the balance of capital costs versus operating costs in implementing and operating the service; the availability, speed, and/or bandwidth of network services available for system components, service users, and/or other entities that interact with the service; the response time of considerations for the service (e.g., how quickly decisions within the service must be implemented to support the commercial function of the service, the operating time for various artificial intelligence or other high computation operations) and/or the capital or operating cost to support a given response time; the location of interacting components of the service, and the effects of such locations on operations of the service (e.g., data storage locations and relevant regulatory schemes, network communication limitations and/or costs, power costs as a function of the location, support availability for time zones relevant to the service, etc.); the availability of certain sensor types, the related support for those sensors, and the availability of sufficient substitutes (e.g., a camera may require supportive lighting, and/or high network bandwidth or local storage) for the sensing purpose; an aspect of the underlying value of an aspect of the service (e.g., a principal amount of a loan, a value of collateral, a volatility of the collateral value, a net worth or relative net worth of a lender, guarantor, and/or borrower, etc.) including the time sensitivity of the underlying value (e.g., if it changes quickly or slowly relative to the operations of the service or the term of the loan); a trust indicator between parties of a transaction (e.g., history of performance between the parties, a credit rating, social rating, or other external indicator, conformance of activity related to the transaction to an industry standard or other normalized transaction type, etc.); and/or the availability of cost recovery options (e.g., subscriptions, fees, payment for services, etc.) for given configurations and/or capabilities of the service, platform, and/or microservice. Without limitation to any other aspect of the present disclosure, certain operations performed by services herein include: performing real-time alterations to a loan based on tracked data; utilizing data to execute a collateral-backed smart contract; re-evaluating debt transactions in response to a tracked condition or data, and the like. While specific examples of services/microservices and considerations are described herein for purposes of illustration, any system benefitting from the disclosures herein, and any considerations understood to one of skill in the art having the benefit of the disclosures herein, are specifically contemplated within the scope of the present disclosure.

Without limitation, services include a financial service (e.g., a loan transaction service), a data collection service (e.g., a data collection service for collecting and monitoring data), a blockchain service (e.g., a blockchain service to maintain secure data), data integration services (e.g., a data integration service to aggregate data), smart contract services (e.g., a smart contract service to determine aspects of smart contracts), software services (e.g., a software service to extract data related to the entities from publicly available information sites), crowdsourcing services (e.g., a crowdsourcing service to solicit and report information), Internet of Things services (e.g., an Internet of Things service to monitor an environment), publishing services (e.g., a publishing services to publish data), microservices (e.g., having a set of application programming interfaces that facilitate connection among the microservices), valuation services (e.g., that use a valuation model to set a value for collateral based on information), artificial intelligence services, market value data collection services (e.g., that monitor and report on marketplace information), clustering services (e.g., for grouping the collateral items based on similarity of attributes), social networking services (e.g., that enables configuration with respect to parameters of a social network), asset identification services (e.g., for identifying a set of assets for which a financial institution is responsible for taking custody), identity management services (e.g., by which a financial institution verifies identities and credentials), and the like, and/or similar functional terminology. Example services to perform one or more functions herein include computing devices; servers; networked devices; user interfaces; inter-device interfaces such as communication protocols, shared information and/or information storage, and/or application programming interfaces (APIs); sensors (e.g., IoT sensors operationally coupled to monitored components, equipment, locations, or the like); distributed ledgers; circuits; and/or computer readable code configured to cause a processor to execute one or more functions of the service. One or more aspects or components of services herein may be distributed across a number of devices, and/or may consolidated, in whole or part, on a given device. In embodiments, aspects or components of services herein may be implemented at least in part through circuits, such as, in non-limiting examples, a data collection service implemented at least in part as a data collection circuit structed to collect and monitor data, a blockchain service implemented at least in part as a blockchain circuit structured to maintain secure data, data integration services implemented at least in part as a data integration circuit structured to aggregate data, smart contract services implemented at least in part as a smart contract circuit structed to determine aspects of smart contracts, software services implemented at least in part as a software service circuit structured to extract data related to the entities from publicly available information sites, crowdsourcing services implemented at least in part as a crowdsourcing circuit structured to solicit and report information, Internet of Things services implemented at least in part as an Internet of Things circuit structured to monitor an environment, publishing services implemented at least in part as a publishing services circuit structured to publish data, microservice service implemented at least in part as a microservice circuit structured to interconnect a plurality of service circuits, valuation service implemented at least in part as valuation services circuit structured to access a valuation model to set a value for collateral based on data, artificial intelligence service implemented at least in part as an artificial intelligence services circuit, market value data collection service implemented at least in part as market value data collection service circuit structured to monitor and report on marketplace information, clustering service implemented at least in part as a clustering services circuit structured to group collateral items based on similarity of attributes, a social networking service implemented at least in part as a social networking analytic services circuit structured to configure parameters with respect to a social network, asset identification services implemented at least in part as an asset identification service circuit for identifying a set of assets for which a financial institution is responsible for taking custody, identity management services implemented at least in part as an identity management service circuit enabling a financial institution to verify identities and credentials, and the like. Accordingly, the benefits of the present disclosure may be applied in a wide variety of systems, and any such systems may be considered with respect to items and services herein, while in certain embodiments a given system may not be considered with respect to items and services herein. One of skill in the art, having the benefit of the disclosure herein and knowledge about a contemplated system ordinarily available to that person, can readily determine which aspects of the present disclosure will benefit a particular system, and/or how to combine processes and systems from the present disclosure to enhance operations of the contemplated system. Among the considerations that one of skill in the art may contemplate to determine a configuration for a particular service include: the distribution and access devices available to one or more parties to a particular transaction; jurisdictional limitations on the storage, type, and communication of certain types of information; requirements or desired aspects of security and verification of information communication for the service; the response time of information gathering, inter-party communications, and determinations to be made by algorithms, machine learning components, and/or artificial intelligence components of the service; cost considerations of the service, including capital expenses and operating costs, as well as which party or entity will bear the costs and availability to recover costs such as through subscriptions, service fees, or the like; the amount of information to be stored and/or communicated to support the service; and/or the processing or computing power to be utilized to support the service.

The terms items and services (and similar terms) as utilized herein should be understood broadly. Without limitation to any other aspect or description of the present disclosure, items and service includes any items and service, including, without limitation, items and services used as a reward, used as collateral, become the subject of a negotiation, and the like, such as, without limitation, an application for a warranty or guarantee with respect to an item that is the subject of a loan, collateral for a loan, or the like, such as a product, a service, an offering, a solution, a physical product, software, a level of service, quality of service, a financial instrument, a debt, an item of collateral, performance of a service, or other item. Without limitation to any other aspect or description of the present disclosure, items and service includes any items and service, including, without limitation, items and services as applied to physical items (e.g., a vehicle, a ship, a plane, a building, a home, real estate property, undeveloped land, a farm, a crop, a municipal facility, a warehouse, a set of inventory, an antique, a fixture, an item of furniture, an item of equipment, a tool, an item of machinery, and an item of personal property), a financial item (e.g., a commodity, a security, a currency, a token of value, a ticket, a cryptocurrency), a consumable item (e.g., an edible item, a beverage), a highly valued item (e.g., a precious metal, an item of jewelry, a gemstone), an intellectual item (e.g., an item of intellectual property, an intellectual property right, a contractual right), and the like. Accordingly, the benefits of the present disclosure may be applied in a wide variety of systems, and any such systems may be considered with respect to items and services herein, while in certain embodiments a given system may not be considered with respect to items and services herein. One of skill in the art, having the benefit of the disclosure herein and knowledge about a contemplated system ordinarily available to that person, can readily determine which aspects of the present disclosure will benefit a particular system, and/or how to combine processes and systems from the present disclosure to enhance operations of the contemplated system.

The terms agent, automated agent, and similar terms as utilized herein should be understood broadly. Without limitation to any other aspect or description of the present disclosure, an agent or automated agent may process events relevant to at least one of the value, the condition, and the ownership of items of collateral or assets. The agent or automated agent may also undertake an action related to a loan, debt transaction, bond transaction, subsidized loan, or the like to which the collateral or asset is subject, such as in response to the processed events. The agent or automated agent may interact with a marketplace for purposes of collecting data, testing spot market transactions, executing transactions, and the like, where dynamic system behavior involves complex interactions that a user may desire to understand, predict, control, and/or optimize. Certain systems may not be considered an agent or an automated agent. For example, if events are merely collected but not processed, the system may not be an agent or automated agent. In some embodiments, if a loan-related action is undertaken not in response to a processed event, it may not have been undertaken by an agent or automated agent. One of skill in the art, having the benefit of the disclosure herein and knowledge about a contemplated system ordinarily available to that person, can readily determine which aspects of the present disclosure include and/or benefit from agents or automated agent. Certain considerations for the person of skill in the art, or embodiments of the present disclosure with respect to an agent or automated agent include, without limitation: rules that determine when there is a change in a value, condition or ownership of an asset or collateral, and/or rules to determine if a change warrants a further action on a loan or other transaction, and other considerations. While specific examples of market values and marketplace information are described herein for purposes of illustration, any embodiment benefitting from the disclosures herein, and any considerations understood to one of skill in the art having the benefit of the disclosures herein are specifically contemplated within the scope of the present disclosure.

The term marketplace information, market value and similar terms as utilized herein should be understood broadly. Without limitation to any other aspect or description of the present disclosure, marketplace information and market value describes a status or value of an asset, collateral, food, or service at a defined point or period in time. Market value may refer to the expected value placed on an item in a marketplace or auction setting, or pricing or financial data for items that are similar to the item, asset, or collateral in at least one public marketplace. For a company, market value may be the number of its outstanding shares multiplied by the current share price. Valuation services may include market value data collection services that monitor and report on marketplace information relevant to the value (e.g. market value) of collateral, the issuer, a set of bonds, and a set of assets. a set of subsidized loans, a party, and the like. Market values may be dynamic in nature because they depend on an assortment of factors, from physical operating conditions to economic climate to the dynamics of demand and supply. Market value may be affected by, and marketplace information may include, proximity to other assets, inventory or supply of assets, demand for assets, origin of items, history of items, underlying current value of item components, a bankruptcy condition of an entity, a foreclosure status of an entity, a contractual default status of an entity, a regulatory violation status of an entity, a criminal status of an entity, an export controls status of an entity, an embargo status of an entity, a tariff status of an entity, a tax status of an entity, a credit report of an entity, a credit rating of an entity, a web site rating of an entity, a set of customer reviews for a product of an entity, a social network rating of an entity, a set of credentials of an entity, a set of referrals of an entity, a set of testimonials for an entity, a set of behavior of an entity, a location of an entity, and a geolocation of an entity. In certain embodiments, a market value may include information such as a volatility of a value, a sensitivity of a value (e.g., relative to other parameters having an uncertainty associated therewith), and/or a specific value of the valuated object to a particular party (e.g., an object may have more value as possessed by a first party than as possessed by a second party).

Certain information may not be marketplace information or a market value. For example, where variables related to a value are not market-derived, they may be a value-in-use or an investment value. In certain embodiments, an investment value may be considered a market value (e.g., when the valuating party intends to utilize the asset as an investment if acquired), and not a market value in other embodiments (e.g., when the valuating party intends to immediately liquidate the investment if acquired). One of skill in the art, having the benefit of the disclosure herein and knowledge about a contemplated system ordinarily available to that person, can readily determine which aspects of the present disclosure will benefit from marketplace information or a market value. Certain considerations for the person of skill in the art, in determining whether the term market value is referring to an asset, item, collateral, good, or service include: the presence of other similar assets in a marketplace, the change in value depending on location, an opening bid of an item exceeding a list price, and other considerations. While specific examples of market values and marketplace information are described herein for purposes of illustration, any embodiment benefitting from the disclosures herein, and any considerations understood to one of skill in the art having the benefit of the disclosures herein are specifically contemplated within the scope of the present disclosure.

The term apportion value or apportioned value and similar terms as utilized herein should be understood broadly. Without limitation to any other aspect or description of the present disclosure, apportion value describes a proportional distribution or allocation of value proportionally, or a process to divide and assign value according to a rule of proportional distribution. Apportionment of the value may be to several parties (e.g., each of the several parties is a beneficiary of a portion of the value), to several transactions (e.g., each of the transactions utilizes a portion of the value), and/or in a many-to-many relationship (e.g., a group of objects has an aggregate value that is apportioned between a number of parties and/or transactions). In some embodiments, the value may be a net loss and the apportioned value is the allocation of a liability to each entity. In other embodiments, apportioned value may refer to the distribution or allocation of an economic benefit, real estate, collateral, or the like. In certain embodiments, apportionment may include a consideration of the value relative to the parties—for example, a $10 million asset apportioned 50/50 between two parties, where the parties have distinct value considerations for the asset, may result in one party crediting the apportionment differing resulting values from the apportionment. In certain embodiments, apportionment may include a consideration of the value relative to given transactions—for example, a first type of transaction (e.g., a long-term loan) may have a different valuation of a given asset than a second type of transaction (e.g., a short-term line of credit).

Certain conditions or processes may not relate to apportioned value. For example, the total value of an item may provide its inherent worth, but not how much of the value is held by each identified entity. One of skill in the art, having the benefit of the disclosure herein and knowledge about apportioned value, can readily determine which aspects of the present disclosure will benefit a particular application for apportioned value. Certain considerations for the person of skill in the art, or embodiments of the present disclosure with respect to an apportioned value include, without limitation: the currency of the principal sum, the anticipated transaction type (loan, bond or debt), the specific type of collateral, the ratio of the loan to value, the ratio of the collateral to the loan, the gross transaction/loan amount, the amount of the principal sum, the number of entities owed, the value of the collateral, and the like. While specific examples of apportioned values are described herein for purposes of illustration, any embodiment benefitting from the disclosures herein, and any considerations understood to one of skill in the art having the benefit of the disclosures herein are specifically contemplated within the scope of the present disclosure.

The term financial condition and similar terms as utilized herein should be understood broadly. Without limitation to any other aspect or description of the present disclosure, financial condition describes a current status of an entity's assets, liabilities, and equity positions at a defined point or period in time. The financial condition may be memorialized in financial statement. The financial condition may further include an assessment of the ability of the entity to survive future risk scenarios or meet future or maturing obligations. Financial condition may be based on a set of attributes of the entity selected from among a publicly stated valuation of the entity, a set of property owned by the entity as indicated by public records, a valuation of a set of property owned by the entity, a bankruptcy condition of an entity, a foreclosure status of an entity, a contractual default status of an entity, a regulatory violation status of an entity, a criminal status of an entity, an export controls status of an entity, an embargo status of an entity, a tariff status of an entity, a tax status of an entity, a credit report of an entity, a credit rating of an entity, a web site rating of an entity, a set of customer reviews for a product of an entity, a social network rating of an entity, a set of credentials of an entity, a set of referrals of an entity, a set of testimonials for an entity, a set of behavior of an entity, a location of an entity, and a geolocation of an entity. A financial condition may also describe a requirement or threshold for an agreement or loan. For example, conditions for allowing a developer to proceed may be various certifications and their agreement to a financial payout. That is, the developer's ability to proceed is conditioned upon a financial element, among others. Certain conditions may not be a financial condition. For example, a credit card balance alone may be a clue as to the financial condition, but may not be the financial condition on its own. In another example, a payment schedule may determine how long a debt may be on an entity's balance sheet, but in a silo may not accurately provide a financial condition. One of skill in the art, having the benefit of the disclosure herein and knowledge about a contemplated system ordinarily available to that person, can readily determine which aspects of the present disclosure include and/or will benefit from a financial condition. Certain considerations for the person of skill in the art, in determining whether the term financial condition is referring to a current status of an entity's assets, liabilities, and equity positions at a defined point or period in time and/or for a given purpose include: the reporting of more than one financial data point, the ratio of a loan to value of collateral, the ratio of the collateral to the loan, the gross transaction/loan amount, the credit scores of the borrower and the lender, and other considerations. While specific examples of financial conditions are described herein for purposes of illustration, any embodiment benefitting from the disclosures herein, and any considerations understood to one of skill in the art having the benefit of the disclosures herein are specifically contemplated within the scope of the present disclosure.

The term interest rate and similar terms, as utilized herein should be understood broadly. Without limitation to any other aspect or description of the present disclosure, interest rate includes an amount of interest due per period, as a proportion of an amount lent, deposited, or borrowed. The total interest on an amount lent or borrowed may depend on the principal sum, the interest rate, the compounding frequency, and the length of time over which it is lent, deposited, or borrowed. Typically, interest rate is expressed as an annual percentage but can be defined for any time period. The interest rate relates to the amount a bank or other lender charges to borrow its money, or the rate a bank or other entity pays its savers for keeping money in an account. Interest rate may be variable or fixed. For example, an interest rate may vary in accordance with a government or other stakeholder directive, the currency of the principal sum lent or borrowed, the term to maturity of the investment, the perceived default probability of the borrower, supply and demand in the market, the amount of collateral, the status of an economy, or special features like call provisions. In certain embodiments, an interest rate may be a relative rate (e.g., relative to a prime rate, an inflation index, etc.). In certain embodiments, an interest rate may further consider costs or fees applied (e.g., "points") to adjust the interest rate. A nominal interest rate may not be adjusted for inflation while a real interest rate takes inflation into account. Certain examples may not be an interest rate for purposes of particular embodiments. For example, a bank account growing by a fixed dollar amount each year, and/or a fixed fee amount, may not be an example of an interest rate for certain embodiments. One of skill in the art, having the benefit of the disclosure herein and knowledge about interest rates, can readily determine the characteristics of an interest rate for a particular embodiment. Certain considerations for the person of skill in the art, or embodiments of the present disclosure with respect to an interest rate include, without limitation: the currency of the principal sum, variables for setting an interest rate, criteria for modifying an interest rate, the anticipated transaction type (loan, bond or debt), the specific type of collateral, the ratio of the loan to value, the ratio of the collateral to the loan, the gross transaction/loan amount, the amount of the principal sum, the appropriate lifespans of transactions and/or collateral for a particular industry, the likelihood that a lender will sell and/or consolidate a loan before the term, and the like. While specific examples of interest rates are described herein for purposes of illustration, any embodiment benefitting from the disclosures herein, and any considerations understood to one of skill in the art having the benefit of the disclosures herein are specifically contemplated within the scope of the present disclosure.

The term valuation services (and similar terms) as utilized herein should be understood broadly. Without limitation to any other aspect or description of the present disclosure, a valuation service includes any service that sets a value for a good or service. Valuation services may use a valuation model to set a value for collateral based on information from data collection and monitoring services. Smart contract services may process output from the set of valuation services and assign items of collateral sufficient to provide security for a loan and/or apportion value for an item of collateral among a set of lenders and/or transactions. Valuation services may include artificial intelligence services that may iteratively improve the valuation model based on outcome data relating to transactions in collateral. Valuation services may include market value data collection services that may monitor and report on marketplace information relevant to the value of collateral. Certain processes may not be considered to be a valuation service. For example, a point of sale device that simply charges a set cost for a good or service may not be a valuation service. In another example, a service that tracks the cost of a good or service and triggers notifications when the value changes may not be a valuation service itself, but may rely on valuation services and/or form a part of a valuation service. Accordingly, the benefits of the present disclosure may be applied in a wide variety of processes systems, and any such processes or systems may be considered a valuation service herein, while in certain embodiments a given service may not be considered a valuation service herein. One of skill in the art, having the benefit of the disclosure herein and knowledge about a contemplated system ordinarily available to that person, can readily determine which aspects of the present disclosure will benefit a particular system and how to combine processes and systems from the present disclosure to enhance operations of the contemplated system and/or to provide a valuation service. Certain considerations for the person of skill in the art, in determining whether a contemplated system is a valuation service and/or whether aspects of the present disclosure can benefit or enhance the contemplated system include, without limitation: perform real-time alterations to a loan based on a value of a collateral; utilize marketplace data to execute a collateral-backed smart contract; re-evaluate collateral based on a storage condition or geolocation; the tendency of the collateral to have a volatile value, be utilized, and/or be moved; and the like. While specific examples of valuation services and considerations are described herein for purposes of illustration, any system benefitting from the disclosures herein, and any considerations understood to one of skill in the art having the benefit of the disclosures herein, are specifically contemplated within the scope of the present disclosure.

The term collateral attributes (and similar terms) as utilized herein should be understood broadly. Without limitation to any other aspect or description of the present disclosure, collateral attributes include any identification of the durability (ability of the collateral to withstand wear or the useful life of the collateral), value, identification (does the collateral have definite characteristics that make it easy to identify or market), stability of value (does the collateral maintain value over time), standardization, grade, quality, marketability, liquidity, transferability, desirability, trackability, deliverability (ability of the collateral be delivered or transfer without a deterioration in value), market transparency (is the collateral value easily verifiable or widely agreed upon), physical or virtual. Collateral attributes may be measured in absolute or relative terms, and/or may include qualitative (e.g., categorical descriptions) or quantitative descriptions. Collateral attributes may be different for different industries, products, elements, uses, and the like. Collateral attributes may be assigned quantitative or qualitative values. Values associated with collateral attributes may be based on a scale (such as 1-10) or a relative designation (high, low, better, etc.). Collateral may include various components; each component may have collateral attributes. Collateral may, therefore, have multiple values for the same collateral attribute. In some embodiments, multiple values of collateral attributes may be combined to generate one value for each attribute. Some collateral attributes may apply only to specific portions of collateral. Some collateral attributes, even for a given component of the collateral, may have distinct values depending upon the party of interest (e.g., a party that values an aspect of the collateral more highly than another party) and/or depending upon the type of transaction (e.g., the collateral may be more valuable or appropriate for a first type of loan than for a second type of loan). Certain attributes associated with collateral may not be collateral attributes as described herein depending upon the purpose of the collateral attributes herein. For example, a product may be rated as durable relative to similar products; however, if the life of the product is much lower than the term of a particular loan in consideration, the durability of the product may be rated differently (e.g., not durable) or irrelevant (e.g., where the current inventory of the product is attached as the collateral, and is expected to change out during the term of the loan). Accordingly, the benefits of the present disclosure may be applied to a variety of attributes, and any such attributes may be considered collateral attributes herein, while in certain embodiments a given attribute may not be considered a collateral attribute herein. One of skill in the art, having the benefit of the disclosure herein and knowledge about contemplated collateral attributes ordinarily available to that person, can readily determine which aspects of the present disclosure will benefit a particular collateral attribute. Certain considerations for the person of skill in the art, in determining whether a contemplated attribute is a collateral attribute and/or whether aspects of the present disclosure can benefit or enhance the contemplated system include, without limitation: the source of the attribute and the source of the value of the attribute (e.g. does the attribute and attribute value comes from a reputable source), the volatility of the attribute (e.g. does the attribute values for the collateral fluctuate, is the attribute a new attribute for the collateral), relative differences in attribute values for similar collateral, exceptional values for attributes (e.g., some attribute values may be high, such as, in the 98th percentile or very low, such as in the 2nd percentile, compared to similar class of collateral), the fungibility of the collateral, the type of transaction related to the collateral, and/or the purpose of the utilization of collateral for a particular party or transaction. While specific examples of collateral attributes and considerations are described herein for purposes of illustration, any system benefitting from the disclosures herein, and any considerations understood to one of skill in the art having the benefit of the disclosures herein, are specifically contemplated within the scope of the present disclosure.

The term blockchain services (and similar terms) as utilized herein should be understood broadly. Without limitation to any other aspect or description of the present disclosure, blockchain services includes any service related to the processing, recordation, and/or updating of a blockchain, and may include services for processing blocks, computing hash values, generating new blocks in a blockchain, appending a block to the blockchain, creating a fork in the blockchain, merging of forks in the blockchain, verifying previous computations, updating a shared ledger, updating a distributed ledger, generating cryptographic keys, verifying transactions, maintaining a blockchain, updating a blockchain, verifying a blockchain, generating random numbers. The services may be performed by execution of computer readable instructions on local computers and/or by remote servers and computers. Certain services may not be considered blockchain services individually but may be considered blockchain services based on the final use of the service and/or in a particular embodiment—for example, a computing a hash value may be performed in a context outside of a blockchain such in the context of secure communication. Some initial services may be invoked without first being applied to blockchains, but further actions or services in conjunction with the initial services may associate the initial service with aspects of blockchains. For example, a random number may be periodically generated and stored in memory; the random numbers may initially not be generated for blockchain purposes but may be utilized for blockchains. Accordingly, the benefits of the present disclosure may be applied in a wide variety of services, and any such services may be considered blockchain services herein, while in certain embodiments a given service may not be considered a blockchain service herein. One of skill in the art, having the benefit of the disclosure herein and knowledge about a contemplated blockchain service ordinarily available to that person, can readily determine which aspects of the present disclosure can be configured to implement, and/or will benefit, a particular blockchain service. Certain considerations for the person of skill in the art, in determining whether a contemplated service is a blockchain service and/or whether aspects of the present disclosure can benefit or enhance the contemplated system include, without limitation: the application of the service, the source of the service (e.g., if the service is associated with a known or verifiable blockchain service provider), responsiveness of the service (e.g., some blockchain services may have an expected completion time, and/or may be determined through utilization), cost of the service, the amount of data requested for the service, and/or the amount of data generated by the service (blocks of blockchain or keys associated with blockchains may be a specific size or a specific range of sizes). While specific examples of blockchain services and considerations are described herein for purposes of illustration, any system benefitting from the disclosures herein, and any considerations understood to one of skill in the art having the benefit of the disclosures herein, are specifically contemplated within the scope of the present disclosure.

The term blockchain (and variations such as cryptocurrency ledger, and the like) as utilized herein may be understood broadly to describe a cryptocurrency ledger that records, administrates, or otherwise processes online transactions. A blockchain may be public, private, or a combination thereof, without limitation. A blockchain may also be used to represent a set of digital transactions, agreement, terms, or other digital value. Without limitation to any other aspect or description of the present disclosure, in the former case, a blockchain may also be used in conjunction with investment applications, token-trading applications, and/or digital/cryptocurrency based marketplaces. A blockchain can also be associated with rendering consideration, such as providing goods, services, items, fees, access to a restricted area or event, data, or other valuable benefit. Blockchains in various forms may be included where discussing a unit of consideration, collateral, currency, cryptocurrency, or any other form of value. One of skill in the art, having the benefit of the disclosure herein and knowledge ordinarily available about a contemplated system, can readily determine the value symbolized or represented by a blockchain. While specific examples of blockchains are described herein for purposes of illustration, any embodiment benefitting from the disclosures herein, and any considerations understood to one of skill in the art having the benefit of the disclosures herein, are specifically contemplated within the scope of the present disclosure.

The terms ledger and distributed ledger (and similar terms) as utilized herein should be understood broadly. Without limitation to any other aspect or description of the present disclosure, a ledger may be a document, file, computer file, database, book, and the like which maintains a record of transactions. Ledgers may be physical or digital. Ledgers may include records related to sales, accounts, purchases, transactions, assets, liabilities, incomes, expenses, capital, and the like. Ledgers may provide a history of transactions that may be associated with time. Ledgers may be centralized or decentralized/distributed. A centralized ledger may be a document that is controlled, updated, or viewable by one or more selected entities or a clearinghouse and wherein changes or updates to the ledger are governed or controlled by the entity or clearinghouse. A distributed ledger may be a ledger that is distributed across a plurality of entities, participants or regions which may independently, concurrently, or consensually, update, or modify their copies of the ledger. Ledgers and distributed ledgers may include security measures and cryptographic functions for signing, concealing, or verifying content. In the case of distributed ledgers, blockchain technology may be used. In the case of distributed ledgers implemented using blockchain, the ledger may be Merkle trees comprising a linked list of nodes in which each node contains hashed or encrypted transactional data of the previous nodes. Certain records of transactions may not be considered ledgers. A file, computer file, database, or book may or may not be a ledger depending on what data it stores, how the data is organized, maintained, or secured. For example, a list of transactions may not be considered a ledger if it cannot be trusted or verified, and/or if it is based on inconsistent, fraudulent, or incomplete data. Data in ledgers may be organized in any format such as tables, lists, binary streams of data, or the like which may depend on convenience, source of data, type of data, environment, applications, and the like. A ledger that is shared among various entities may not be a distributed ledger, but the distinction of distributed may be based on which entities are authorized to make changes to the ledger and/or how the changes are shared and processed among the different entities. Accordingly, the benefits of the present disclosure may be applied in a wide variety of data, and any such data may be considered ledgers herein, while in certain embodiments a given data may not be considered a ledger herein. One of skill in the art, having the benefit of the disclosure herein and knowledge about contemplated ledgers and distributed ledger ordinarily available to that person, can readily determine which aspects of the present disclosure can be utilized to implement, and/or will benefit a particular ledger. Certain considerations for the person of skill in the art, in determining whether a contemplated data is a ledger and/or whether aspects of the present disclosure can benefit or enhance the contemplated ledger include, without limitation: the security of the data in the ledger (can the data be tampered or modified), the time associated with making changes to the data in the ledger, cost of making changes (computationally and monetarily), detail of data, organization of data (does the data need to be processed for use in an application), who controls the ledger (can the party be trusted or relied to manage the ledger), confidentiality of the data (who can see or track the data in the ledger), size of the infrastructure, communication requirements (distributed ledgers may require a communication interface or specific infrastructure), resiliency. While specific examples of blockchain services and considerations are described herein for purposes of illustration, any system benefitting from the disclosures herein, and any considerations understood to one of skill in the art having the benefit of the disclosures herein, are specifically contemplated within the scope of the present disclosure.

The term loan (and similar terms) as utilized herein should be understood broadly. Without limitation to any other aspect or description of the present disclosure, a loan may be an agreement related to an asset that is borrowed, and that is expected to be returned in kind (e.g., money borrowed and money returned) or as an agreed transaction (e.g., a first good or service is borrowed, and money, a second good or service, or a combination, is returned). Assets may be money, property, time, physical objects, virtual objects, services, a right (e.g., a ticket, a license, or other right), a depreciation amount, a credit (e.g., a tax credit, an emissions credit, etc.), an agreed assumption of a risk or liability, and/or any combination thereof. A loan may be based on a formal or informal agreement between a borrower and a lender wherein a lender may provide an asset to the borrower for a predefined amount of time, a variable period of time, or indefinitely. Lenders and borrowers may be individuals, entities, corporations, governments, groups of people, organizations, and the like. Loan types may include mortgage loans, personal loans, secured loans, unsecured loans, concessional loans, commercial loans, microloans, and the like. The agreement between the borrower and the lender may specify terms of the loan. The borrower may be required to return an asset or repay with a different asset than was borrowed. In some cases, a loan may require interest to be repaid on the borrowed asset. Borrowers and lenders may be intermediaries between other entities and may never possess or use the asset. In some embodiments, a loan may not be associated with direct transfer of goods but may be associated with usage rights or shared usage rights. In certain embodiments, the agreement between the borrower and the lender may be executed between the borrower and the lender, and/or executed between an intermediary (e.g., a beneficiary of a loan right such as through a sale of the loan). In certain embodiment, the agreement between the borrower and the lender may be executed through services herein, such as through a smart contract service that determines at least a portion of the terms and conditions of the loans, and in certain embodiments may commit the borrower and/or the lender to the terms of the agreement, which may be a smart contract. In certain embodiments, the smart contract service may populate the terms of the agreement, and present them to the borrower and/or lender for execution. In certain embodiments, the smart contract service may automatically commit one of the borrower or the lender to the terms (at least as an offer), and may present the offer to the other one of the borrower or the lender for execution. In certain embodiments, a loan agreement may include multiple borrowers and/or multiple lenders, for example where a set of loans includes a number of beneficiaries of payment on the set of loans, and/or a number of borrowers on the set of loans. In certain embodiments, the risks and/or obligations of the set of loans may be individualized (e.g., each borrower and/or lender is related to specific loans of the set of loans), apportioned (e.g., a default on a particular loan has an associated loss apportioned between the lenders), and/or combinations of these (e.g., one or more subsets of the set of loans is treated individually and/or apportioned).

Certain agreements may not be considered a loan. An agreement to transfer or borrow assets may not be a loan depending on what assets are transferred, how the assets were transferred, or the parties involved. For example, in some cases, the transfer of assets may be for an indefinite time and may be considered a sale of the asset or a permanent transfer. Likewise, if an asset is borrowed or transferred without clear or definite terms or lack of consensus between the lender and the borrower it may, in some cases, not be considered a loan. An agreement may be considered a loan even if a formal agreement is not directly codified in a written agreement as long as the parties willingly and knowingly agreed to the arrangement, and/or ordinary practices (e.g., in a particular industry) may treat the transaction as a loan. Accordingly, the benefits of the present disclosure may be applied in a wide variety of agreements, and any such agreement may be considered a loan herein, while in certain embodiments a given agreement may not be considered a loan herein. One of skill in the art, having the benefit of the disclosure herein and knowledge about contemplated loans ordinarily available to that person, can readily determine which aspects of the present disclosure implement a loan, utilize a loan, or benefit a particular loan transaction. Certain considerations for the person of skill in the art, in determining whether a contemplated data is a loan and/or whether aspects of the present disclosure can benefit or enhance the contemplated loan include, without limitation: the value of the assets involved, the ability of the borrower to return or repay the loan, the types of assets involved (e.g., whether the asset is consumed through utilization), the repayment time frame associated with the loan, the interest on the loan, how the agreement of the loan was arranged, formality of the agreement, detail of the agreement, the detail of the agreements of the loan, the collateral attributes associated with the loan, and/or the ordinary business expectations of any of the foregoing in a particular context. While specific examples of loans and considerations are described herein for purposes of illustration, any system benefitting from the disclosures herein, and any considerations understood to one of skill in the art having the benefit of the disclosures herein, are specifically contemplated within the scope of the present disclosure.

The term loan related event(s) (and similar terms, including loan-related events) as utilized herein should be understood broadly. Without limitation to any other aspect or description of the present disclosure, a loan related events may include any event related to terms of the loan or events triggered by the agreement associated with the loan. Loan-related events may include default on loan, breach of contract, fulfillment, repayment, payment, change in interest, late fee assessment, refund assessment, distribution, and the like. Loan-related events may be triggered by explicit agreement terms; for example—an agreement may specify a rise in interest rate after a time period has elapsed from the beginning of the loan; the rise in interest rate triggered by the agreement may be a loan related event. Loan-related events may be triggered implicitly by related loan agreement terms. In certain embodiments, any occurrence that may be considered relevant to assumptions of the loan agreement, and/or expectations of the parties to the loan agreement, may be considered an occurrence of an event. For example, if collateral for a loan is expected to be replaceable (e.g., an inventory as collateral), then a change in inventory levels may be considered an occurrence of a loan related event. In another example, if review and/or confirmation of the collateral is expected, then a lack of access to the collateral, the disablement or failure of a monitoring sensor, etc. may be considered an occurrence of a loan related event. In certain embodiments, circuits, controllers, or other devices described herein may automatically trigger the determination of a loan-related events. In some embodiments, loan-related events may be triggered by entities that manage loans or loan-related contracts. Loan-related events may be conditionally triggered based on one or more conditions in the loan agreement. Loan related events may be related to tasks or requirements that need to be completed by the lender, borrower, or a third party. Certain events may be considered loan-related events in certain embodiments and/or in certain contexts, but may not be considered a loan-related event in another embodiment or context. Many events may be associated with loans but may be caused by external triggers not associated with a loan. However, in certain embodiments, an externally triggered event (e.g., a commodity price change related to a collateral item) may be loan-related events in certain embodiments. For example, renegotiation of loan terms initiated by a lender may not be considered a loan related event if the terms and/or performance of the existing loan agreement did not trigger the renegotiation. Accordingly, the benefits of the present disclosure may be applied in a wide variety of events, and any such event may be considered a loan related event herein, while in certain embodiments given events may not be considered a loan related event herein. One of skill in the art, having the benefit of the disclosure herein and knowledge about a contemplated system ordinarily available to that person, can readily determine which aspects of the present disclosure may be considered a loan-related event for the contemplated system and/or for particular transactions supported by the system. Certain considerations for the person of skill in the art, in determining whether a contemplated data is a loan related event and/or whether aspects of the present disclosure can benefit or enhance the contemplated transaction system include, without limitation: the impact of the related event on the loan (events that cause default or termination of the loan may have higher impact), the cost (capital and/or operating) associated with the event, the cost (capital and/or operating) associated with monitoring for an occurrence of the event, the entities responsible for responding to the event, a time period and/or response time associated with the event (e.g., time required to complete the event and time that is allotted from the time the event is triggered to when processing or detection of the event is desired to occur), the entity responsible for the event, the data required for processing the event (e.g., confidential information may have different safeguards or restrictions), the availability of mitigating actions if an undetected event occurs, and/or the remedies available to an at-risk party if the event occurs without detection. While specific examples of loan-related events and considerations are described herein for purposes of illustration, any system benefitting from the disclosures herein, and any considerations understood to one of skill in the art having the benefit of the disclosures herein, are specifically contemplated within the scope of the present disclosure.

The term loan-related activities (and similar terms) as utilized herein should be understood broadly. Without limitation to any other aspect or description of the present disclosure, a loan related activity may include activities related to the generation, maintenance, termination, collection, enforcement, servicing, billing, marketing, ability to perform, or negotiation of a loan. Loan-related activity may include activities related to the signing of a loan agreement or a promissory note, review of loan documents, processing of payments, evaluation of collateral, evaluation of compliance of the borrower or lender to the loan terms, renegotiation of terms, perfection of security or collateral for the loan, and/or a negation of terms. Loan-related activities may relate to events associated with a loan before formal agreement on the terms, such as activities associated with initial negotiations. Loan-related activities may relate to events during the life of the loan and after the termination of a loan. Loan-related activities may be performed by a lender, borrower, or a third party. Certain activities may not be considered loan related activities services individually but may be considered loan related activities based on the specificity of the activity to the loan lifecycle—for example, billing or invoicing related to outstanding loans may be considered a loan related activity, however when the invoicing or billing of loans is combined with billing or invoicing for non loan-related elements the invoicing may not be considered a loan related activity. Some activities may be performed in relation to an asset regardless if a loan is associated with the asset; in these cases, the activity may not be considered a loan related activity. For example, regular audits related to an asset may occur regardless if the asset is associated with a loan and may not be considered a loan related activity. In another example, a regular audit related to an asset may be required by a loan agreement and would not typically occur but for the association with a loan, in this case, the activity may be considered a loan related activity. In some embodiments, activities may be considered loan-related activities if the activity would otherwise not occur if the loan were not active or present, but may still be considered a loan-related activity in some instances (e.g., if auditing occurs normally, but the lender does not have the ability to enforce or review the audit, then the audit may be considered a loan-related activity even though it already occurs otherwise). Accordingly, the benefits of the present disclosure may be applied in a wide variety of events, and any such event may be considered a loan related event herein, while in certain embodiments given events may not be considered a loan related events herein. One of skill in the art, having the benefit of the disclosure herein and knowledge about a contemplated system ordinarily available to that person, can readily determine a loan related activity for the purposes of the contemplated system. Certain considerations for the person of skill in the art, in determining whether a contemplated data is a loan related activity and/or whether aspects of the present disclosure can benefit or enhance the contemplated loan include, without limitation: the necessity of the activity for the loan (can the loan agreement or terms be satisfied without the activity), the cost of the activity, the specificity of the activity to the loan (is the activity similar or identical to other industries), time involved in the activity, the impact of the activity on a loan life cycle, entity performing the activity, amount of data required for the activity (does the activity require confidential information related to the loan, or personal information related to the entities), and/or the ability of parties to enforce and/or review the activity. While specific examples of loan-related events and considerations are described herein for purposes of illustration, any system benefitting from the disclosures herein, and any considerations understood to one of skill in the art having the benefit of the disclosures herein, are specifically contemplated within the scope of the present disclosure.

The terms loan-terms, loan terms, terms for a loan, terms and conditions, and the like as utilized herein should be understood broadly ("loan terms"). Without limitation to any other aspect or description of the present disclosure, loan terms may relate to conditions, rules, limitations, contract obligations, and the like related to the timing, repayment, origination, and other enforceable conditions agreed to by the borrower and the lender of the loan. Loan terms may be specified in a formal contract between a borrower and the lender. Loan terms may specify aspects of an interest rate, collateral, foreclose conditions, consequence of debt, payment options, payment schedule, a covenant, and the like. Loan terms may be negotiable or may change during the life of a loan. Loan terms may be change or be affected by outside parameters such as market prices, bond prices, conditions associated with a lender or borrower, and the like. Certain aspects of a loan may not be considered loan terms. In certain embodiments, aspects of loan that have not been formally agreed upon between a lender and a borrower, and/or that are not ordinarily understood in the course of business (and/or the particular industry) may not be considered loan terms. Certain aspects of a loan may be preliminary or informal until they have been formally agreed or confirmed in a contract or a formal agreement. Certain aspects of a loan may not be considered loan terms individually but may not be considered loan terms based on the specificity of the aspect to a specific loan. Certain aspects of a loan may not be considered loan terms at a particular time during the loan, but may be considered loan terms at another time during the loan (e.g., obligations and/or waivers that may occur through the performance of the parties, and/or expiration of a loan term). For example, an interest rate may generally not be considered a loan term until it is defined in relation of a loan and defined as to how the interest compounded (annual, monthly), calculated, and the like. An aspect of a loan may not be considered a term if it is indefinite or unenforceable. Some aspects may be manifestations or related to terms of a loan but may themselves not be the terms. For example, a loan term be the repayment period of a loan, such as one year. The term may not specify how the loan is to be repaid in the year. The loan may be repaid with 12 monthly payments or one annual payment. A monthly payment plan in this case may not be considered a loan term as it just one or many options for repayment not directly specified by a loan. Accordingly, the benefits of the present disclosure may be applied in a wide variety of loan aspects, and any such aspect may be considered a loan term herein, while in certain embodiments given aspects may not be considered loan terms herein. One of skill in the art, having the benefit of the disclosure herein and knowledge about a contemplated system ordinarily available to that person, can readily determine which aspects of the present disclosure are loan terms for the contemplated system.

Certain considerations for the person of skill in the art, in determining whether a contemplated data is a loan term and/or whether aspects of the present disclosure can benefit or enhance the contemplated loan include, without limitation: the enforceability of the terms (can the conditions be enforced by the lender or the lender or the borrower), the cost of enforcing the terms (amount of time, or effort required ensure the conditions are being followed), the complexity of the terms (how easily can they be followed or understood by the parties involved, are the terms error prone or easily misunderstood), entities responsible for the terms, fairness of the terms, stability of the terms (how often do they change), observability of the terms (can the terms be verified by a another party), favorability of the terms to one party (do the terms favor the borrower or the lender), risk associated with the loan (terms may depend on the probability that the loan may not be repaid), characteristics of the borrower or lender (their ability to meet the terms), and/or ordinary expectations for the loan and/or related industry.

While specific examples of loan terms are described herein for purposes of illustration, any system benefitting from the disclosures herein, and any considerations understood to one of skill in the art having the benefit of the disclosures herein, are specifically contemplated within the scope of the present disclosure.

The term loan conditions, loan-conditions, conditions for a loan, terms and conditions, and the like as utilized herein should be understood broadly ("loan conditions"). Without limitation to any other aspect or description of the present disclosure, loan conditions may relate to rules, limits, and/or obligations related to a loan. Loan conditions may relate to rules or necessary obligations for obtaining a loan, for maintaining a loan, for applying for a loan, for transferring a loan, and the like. Loan conditions may include principal amount of debt, a balance of debt, a fixed interest rate, a variable interest rate, a payment amount, a payment schedule, a balloon payment schedule, a specification of collateral, a specification of substitutability of collateral, treatment of collateral, access to collateral, a party, a guarantee, a guarantor, a security, a personal guarantee, a lien, a duration, a covenant, a foreclose condition, a default condition, conditions related to other debts of the borrower, and a consequence of default.

Certain aspects of a loan may not be considered loan conditions. Aspects of loan that have not been formally agreed upon between a lender and a borrower, and/or that are not ordinarily understood in the course of business (and/or the particular industry), may not be considered loan conditions. Certain aspects of a loan may be preliminary or informal until they have been formally agreed or confirmed in a contract or a formal agreement. Certain aspects of a loan may not be considered loan conditions individually but may be considered loan conditions based on the specificity of the aspect to a specific loan. Certain aspects of a loan may not be considered loan conditions at a particular time during the loan, but may be considered loan conditions at another time during the loan (e.g., obligations and/or waivers that may occur through the performance of the parties, and/or expiration of a loan condition). Accordingly, the benefits of the present disclosure may be applied in a wide variety of loan aspects, and any such aspect may be considered loan conditions herein, while in certain embodiments given aspects may not be considered loan conditions herein. One of skill in the art, having the benefit of the disclosure herein and knowledge about a contemplated system ordinarily available to that person, can readily determine which aspects of the present disclosure are loan conditions for the contemplated system. Certain considerations for the person of skill in the art, in determining whether a contemplated data is a loan condition and/or whether aspects of the present disclosure can benefit or enhance the contemplated loan include, without limitation: the enforceability of the condition (can the conditions be enforced by the lender or the borrower), the cost of enforcing the condition (amount of time, or effort required ensure the conditions are being followed), the complexity of the condition (how easily can they be followed or understood by the parties involved, are the conditions error prone or easily misunderstood), entities responsible for the conditions, fairness of the conditions, observability of the conditions (can the conditions be verified by a another party), favorability of the conditions to one party (do the conditions favor the borrower or the lender), risk associated with the loan (conditions may depend on the probability that the loan may not be repaid), and/or ordinary expectations for the loan and/or related industry.

While specific examples of loan conditions are described herein for purposes of illustration, any system benefitting from the disclosures herein, and any considerations understood to one of skill in the art having the benefit of the disclosures herein, are specifically contemplated within the scope of the present disclosure.

The term loan collateral, collateral, item of collateral, collateral item, and the like as utilized herein should be understood broadly. Without limitation to any other aspect or description of the present disclosure, a loan collateral may relate to any asset or property that a borrower promises to a lender as backup in exchange for a loan, and/or as security for the loan. Collateral may be any item of value that is accepted as an alternate form of repayment in case of default on a loan. Collateral may include any number of physical or virtual items such as a vehicle, a ship, a plane, a building, a home, real estate property, undeveloped land, a farm, a crop, a municipal facility, a warehouse, a set of inventory, a commodity, a security, a currency, a token of value, a ticket, a cryptocurrency, a consumable item, an edible item, a beverage, a precious metal, an item of jewelry, a gemstone, an item of intellectual property, an intellectual property right, a contractual right, an antique, a fixture, an item of furniture, an item of equipment, a tool, an item of machinery, and an item of personal property. Collateral may include more than one item or types of items.

A collateral item may describe an asset, a property, a value, or other item defined as a security for a loan or a transaction. A set of collateral items may be defined, and within that set substitution, removal or addition of collateral items may be effected. For example, a collateral item may be, without limitation: a vehicle, a ship, a plane, a building, a home, real estate property, undeveloped land, a farm, a crop, a municipal facility, a warehouse, a set of inventory, a commodity, a security, a currency, a token of value, a ticket, a cryptocurrency, a consumable item, an edible item, a beverage, a precious metal, an item of jewelry, a gemstone, an item of intellectual property, an intellectual property right, a contractual right, an antique, a fixture, an item of furniture, an item of equipment, a tool, an item of machinery, or an item of personal property, or the like. If a set or plurality of collateral items is defined, substitution, removal or addition of collateral items may be effected, such as substituting, removing or adding a collateral item to or from a set of collateral items. Without limitation to any other aspect or description of the present disclosure, a collateral item or set of collateral items may also be used in conjunction with other terms to an agreement or loan, such as a representation, a warranty, an indemnity, a covenant, a balance of debt, a fixed interest rate, a variable interest rate, a payment amount, a payment schedule, a balloon payment schedule, a specification of collateral, a specification of substitutability of collateral, a security, a personal guarantee, a lien, a duration, a foreclose condition, a default condition, and a consequence of default. In certain embodiments, a smart contract may calculate whether a borrower has satisfied conditions or covenants and in cases where the borrower has not satisfied such conditions or covenants, may enable automated action or trigger another conditions or terms that may affect the status, ownership or transfer of a collateral item, or initiate the substitution, removal, or addition of collateral items to a set of collateral for a loan. One of skill in the art, having the benefit of the disclosure herein and knowledge about collateral items, can readily determine the purposes and use of collateral items in various embodiments and contexts disclosed herein, including the substitution, removal, and addition thereof.

While specific examples of loan collateral are described herein for purposes of illustration, any system benefitting from the disclosures herein, and any considerations understood to one of skill in the art having the benefit of the disclosures herein, are specifically contemplated within the scope of the present disclosure.

The term smart contract services (and similar terms) as utilized herein should be understood broadly. Without limitation to any other aspect or description of the present disclosure, a smart contract service includes any service or application that manages a smart contract or a smart lending contract. For example, the smart contract service may specify terms and conditions of a smart contract, such as in a rules database, or process output from a set of valuation services and assign items of collateral sufficient to provide security for a loan. Smart contract services may automatically execute a set of rules or conditions that embody the smart contract, wherein the execution may be based on or take advantage of collected data. Smart contract services may automatically initiate a demand for payment of a loan, automatically initiate a foreclosure process, automatically initiate an action to claim substitute or backup collateral or transfer ownership of collateral, automatically initiate an inspection process, automatically change a payment or interest rate term that is based on the collateral, and may also configure smart contracts to automatically undertake a loan-related action. Smart contracts may govern at least one of loan terms and conditions, loan-related events, and loan-related activities. Smart contracts may be agreements that are encoded as computer protocols and may facilitate, verify, or enforce the negotiation or performance of a smart contract. Smart contracts may or may not be one or more of partially or fully self-executing, or partially or fully self-enforcing.

Certain processes may not be considered to be smart-contract related individually, but may be considered smart-contract related in an aggregated system—for example automatically undertaking a loan-related action may not be smart contract-related in one instance, but in another instance, may be governed by terms of a smart contract. Accordingly, the benefits of the present disclosure may be applied in a wide variety of processes systems, and any such processes or systems may be considered a smart contract or smart contract service herein, while in certain embodiments a given service may not be considered a smart contract service herein.

One of skill in the art, having the benefit of the disclosure herein and knowledge about a contemplated system ordinarily available to that person, can readily determine which aspects of the present disclosure will benefit a particular system and how to combine processes and systems from the present disclosure to implement a smart contract service and/or enhance operations of the contemplated system. Certain considerations for the person of skill in the art, in determining whether a contemplated system includes a smart contract service or smart contract and/or whether aspects of the present disclosure can benefit or enhance the contemplated system include, without limitation: ability to transfer ownership of collateral automatically in response to an event; automated actions available upon a finding of covenant compliance (or lack of compliance); the amenity of the collateral to clustering, re-balancing, distribution, addition, substitution, and removal of items from collateral; the modification parameters of an aspect of a loan in response to an event (e.g., timing, complexity, suitability for the loan type, etc.); the complexity of terms and conditions of loans for the system, including benefits from rapid determination and/or predictions of changes to entities (e.g., in the collateral, a financial condition of a party, offset collateral, and/or in an industry related to a party) related to the loan; the suitability of automated generation of terms and conditions and/or execution of terms and conditions for the types of loans, parties, and/or industries contemplated for the system; and the like. While specific examples of smart contract services and considerations are described herein for purposes of illustration, any system benefitting from the disclosures herein, and any considerations understood to one of skill in the art having the benefit of the disclosures herein, are specifically contemplated within the scope of the present disclosure.

The term IoT system (and similar terms) as utilized herein should be understood broadly. Without limitation to any other aspect or description of the present disclosure, an IoT system includes any system of uniquely identified and interrelated computing devices, mechanical and digital machines, sensors, and objects that are able to transfer data over a network without intervention. Certain components may not be considered an IoT system individually, but may be considered an IoT system in an aggregated system—for example, a single networked sensor, smart speaker, and/or medical device may be not an IoT system, but may be a part of a larger system and/or be accumulated with a number of other similar components to be considered an IoT system and/or a part of an IoT system. In certain embodiments, a system may be considered an IoT system for some purposes but not for other purposes—for example, a smart speaker may be considered part of an IoT system for certain operations, such as for providing surround sound, or the like, but not part of an IoT system for other operations such as directly streaming content from a single, locally networked source. Additionally, in certain embodiments, otherwise similar looking systems may be differentiated in determining whether such systems are IoT systems, and/or which type of IoT system. For example, one group of medical devices may not, at a given time, be sharing to an aggregated HER database, while another group of medical devices may be sharing data to an aggregate HER for the purposes of a clinical study, and accordingly one group of medical devices may be an IoT system, while the other is not. Accordingly, the benefits of the present disclosure may be applied in a wide variety of systems, and any such systems may be considered an IoT system herein, while in certain embodiments a given system may not be considered an IoT system herein. One of skill in the art, having the benefit of the disclosure herein and knowledge about a contemplated system ordinarily available to that person, can readily determine which aspects of the present disclosure will benefit a particular system, how to combine processes and systems from the present disclosure to enhance operations of the contemplated system, and which circuits, controllers, and/or devices include an IoT system for the contemplated system. Certain considerations for the person of skill in the art, in determining whether a contemplated system is an IoT system and/or whether aspects of the present disclosure can benefit or enhance the contemplated system include, without limitation: the transmission environment of the system (e.g., availability of low power, inter-device networking); the shared data storage of a group of devices; establishment of a geofence by a group of devices; service as blockchain nodes; the performance of asset, collateral, or entity monitoring; the relay of data between devices; ability to aggregate data from a plurality of sensors or monitoring devices, and the like. While specific examples of IoT systems and considerations are described herein for purposes of illustration, any system benefitting from the disclosures herein, and any considerations understood to one of skill in the art having the benefit of the disclosures herein, are specifically contemplated within the scope of the present disclosure.

The term data collection services (and similar terms) as utilized herein should be understood broadly. Without limitation to any other aspect or description of the present disclosure, a data collection service includes any service that collects data or information, including any circuit, controller, device, or application that may store, transmit, transfer, share, process, organize, compare, report on and/or aggregate data. The data collection service may include data collection devices (e.g., sensors) and/or may be in communication with data collection devices. The data collection service may monitor entities, such as to identify data or information for collection. The data collection service may be event-driven, run on a periodic basis, or retrieve data from an application at particular points in the application's execution. Certain processes may not be considered to be a data collection service individually, but may be considered a data collection service in an aggregated system—for example, a networked storage device may be a component of a data collection service in one instance, but in another instance, may have stand-alone functionality. Accordingly, the benefits of the present disclosure may be applied in a wide variety of processes systems, and any such processes or systems may be considered a data collection service herein, while in certain embodiments a given service may not be considered a data collection service herein. One of skill in the art, having the benefit of the disclosure herein and knowledge about a contemplated system ordinarily available to that person, can readily determine which aspects of the present disclosure will benefit a particular system and how to combine processes and systems from the present disclosure implement a data collection service and/or to enhance operations of the contemplated system. Certain considerations for the person of skill in the art, in determining whether a contemplated system is a data collection service and/or whether aspects of the present disclosure can benefit or enhance the contemplated system include, without limitation: ability to modify a business rule on the fly and alter a data collection protocol; perform real-time monitoring of events; connection of a device for data collection to a monitoring infrastructure, execution of computer readable instructions that cause a processor to log or track events; use of an automated inspection system; occurrence of sales at a networked point-of-sale; need for data from one or more distributed sensors or cameras; and the like. While specific examples of data collection services and considerations are described herein for purposes of illustration, any system benefitting from the disclosures herein, and any considerations understood to one of skill in the art having the benefit of the disclosures herein, are specifically contemplated within the scope of the present disclosure.

The term data integration services (and similar terms) as utilized herein should be understood broadly. Without limitation to any other aspect or description of the present disclosure, a data integration service includes any service that integrates data or information, including any device or application that may extract, transform, load, normalize, compress, decompress, encode, decode, and otherwise process data packets, signals, and other information. The data integration service may monitor entities, such as to identify data or information for integration. The data integration service may integrate data regardless of required frequency, communication protocol, or business rules needed for intricate integration patterns. Accordingly, the benefits of the present disclosure may be applied in a wide variety of processes systems, and any such processes or systems may be considered a data integration service herein, while in certain embodiments a given service may not be considered a data integration service herein. One of skill in the art, having the benefit of the disclosure herein and knowledge about a contemplated system ordinarily available to that person, can readily determine which aspects of the present disclosure will benefit a particular system and how to combine processes and systems from the present disclosure to implement a data integration service and/or enhance operations of the contemplated system. Certain considerations for the person of skill in the art, in determining whether a contemplated system is a data integration service and/or whether aspects of the present disclosure can benefit or enhance the contemplated system include, without limitation: ability to modify a business rule on the fly and alter a data integration protocol; communication with third party databases to pull in data to integrate with; synchronization of data across disparate platforms; connection to a central data warehouse; data storage capacity, processing capacity, and/or communication capacity distributed throughout the system; the connection of separate, automated workflows; and the like. While specific examples of data integration services and considerations are described herein for purposes of illustration, any system benefitting from the disclosures herein, and any considerations understood to one of skill in the art having the benefit of the disclosures herein, are specifically contemplated within the scope of the present disclosure.

The term computational services (and similar terms) as utilized herein should be understood broadly. Without limitation to any other aspect or description of the present disclosure, computational services may be included as a part of one or more services, platforms, or microservices, such as blockchain services, data collection services, data integration services, valuation services, smart contract services, data monitoring services, data mining, and/or any service that facilitates collection, access, processing, transformation, analysis, storage, visualization, or sharing of data. Certain processes may not be considered to be a computational service. For example, a process may not be considered a computational service depending on the sorts of rules governing the service, an end product of the service, or the intent of the service. Accordingly, the benefits of the present disclosure may be applied in a wide variety of processes systems, and any such processes or systems may be considered a computational service herein, while in certain embodiments a given service may not be considered a computational service herein. One of skill in the art, having the benefit of the disclosure herein and knowledge about a contemplated system ordinarily available to that person, can readily determine which aspects of the present disclosure will benefit a particular system and how to combine processes and systems from the present disclosure to implement one or more computational service, and/or to enhance operations of the contemplated system. Certain considerations for the person of skill in the art, in determining whether a contemplated system is a computational service and/or whether aspects of the present disclosure can benefit or enhance the contemplated system include, without limitation: agreement-based access to the service; mediate an exchange between different services; provides on demand computational power to a web service; accomplishes one or more of monitoring, collection, access, processing, transformation, analysis, storage, integration, visualization, mining, or sharing of data. While specific examples of computational services and considerations are described herein for purposes of illustration, any system benefitting from the disclosures herein, and any considerations understood to one of skill in the art having the benefit of the disclosures herein, are specifically contemplated within the scope of the present disclosure.

The term sensor as utilized herein should be understood broadly. Without limitation to any other aspect or description of the present disclosure, a sensor may be a device, module, machine, or subsystem that detects or measures a physical quality, event, or change. In embodiments, may record, indicate, transmit, or otherwise respond to the detection or measurement. Examples of sensors may be sensors for sensing movement of entities, for sensing temperatures, pressures or other attributes about entities or their environments, cameras that capture still or video images of entities, sensors that collect data about collateral or assets, such as, for example, regarding the location, condition (health, physical, or otherwise), quality, security, possession, or the like. In embodiments, sensors may be sensitive to, but not influential on, the property to be measured but insensitive to other properties. Sensors may be analog or digital. Sensors may include processors, transmitters, transceivers, memory, power, sensing circuit, electrochemical fluid reservoirs, light sources, and the like. Further examples of sensors contemplated for use in the system include biosensors, chemical sensors, black silicon sensor, IR sensor, acoustic sensor, induction sensor, motion sensor, optical sensor, opacity sensor, proximity sensor, inductive sensor, Eddy-current sensor, passive infrared proximity sensor, radar, capacitance sensor, capacitive displacement sensor, hall-effect sensor, magnetic sensor, GPS sensor, thermal imaging sensor, thermocouple, thermistor, photoelectric sensor, ultrasonic sensor, infrared laser sensor, inertial motion sensor, MEMS internal motion sensor, ultrasonic 3D motion sensor, accelerometer, inclinometer, force sensor, piezoelectric sensor, rotary encoders, linear encoders, ozone sensor, smoke sensor, heat sensor, magnetometer, carbon dioxide detector, carbon monoxide detector, oxygen sensor, glucose sensor, smoke detector, metal detector, rain sensor, altimeter, GPS, detection of being outside, detection of context, detection of activity, object detector (e.g. collateral), marker detector (e.g. geo-location marker), laser rangefinder, sonar, capacitance, optical response, heart rate sensor, or an RF/micro-power impulse radio (MIR) sensor. In certain embodiments, a sensor may be a virtual sensor—for example determining a parameter of interest as a calculation based on other sensed parameters in the system. In certain embodiments, a sensor may be a smart sensor—for example reporting a sensed value as an abstracted communication (e.g., as a network communication) of the sensed value. In certain embodiments, a sensor may provide a sensed value directly (e.g., as a voltage level, frequency parameter, etc.) to a circuit, controller, or other device in the system. One of skill in the art, having the benefit of the disclosure herein and knowledge about a contemplated system ordinarily available to that person, can readily determine which aspects of the present disclosure will benefit from a sensor. Certain considerations for the person of skill in the art, in determining whether a contemplated device is a sensor and/or whether aspects of the present disclosure can benefit from or be enhanced by the contemplated sensor include, without limitation: the conditioning of an activation/deactivation of a system to an environmental quality; the conversion of electrical output into measured quantities; the ability to enforce a geofence; the automatic modification of a loan in response to change in collateral; and the like. While specific examples of sensors and considerations are described herein for purposes of illustration, any system benefitting from the disclosures herein, and any considerations understood to one of skill in the art having the benefit of the disclosures herein, are specifically contemplated within the scope of the present disclosure.

The term storage condition and similar terms, as utilized herein should be understood broadly. Without limitation to any other aspect or description of the present disclosure, storage condition includes an environment, physical location, environmental quality, level of exposure, security measures, maintenance description, accessibility description, and the like related to the storage of an asset, collateral, or an entity specified and monitored in a contract, loan, or agreement or backing the contract, loan or other agreement, and the like. Based on a storage condition of a collateral, an asset, or entity, actions may be taken to, maintain, improve, and/or confirm a condition of the asset or the use of that asset as collateral. Based on a storage condition, actions may be taken to alter the terms or conditions of a loan or bond. Storage condition may be classified in accordance with various rules, thresholds, conditional procedures, workflows, model parameters, and the like and may be based on self-reporting or on data from Internet of Things devices (IoT data), data from a set of environmental condition sensors, data from a set of social network analytic services and a set of algorithms for querying network domains, social media data, crowdsourced data, and the like. The storage condition may be tied to a geographic location relating to the collateral, the issuer, the borrower, the distribution of the funds or other geographic locations. Examples of IoT data may include images, sensor data, location data, and the like. Examples of social media data or crowdsourced data may include behavior of parties to the loan, financial condition of parties, adherence to a parties to a term or condition of the loan, or bond, or the like. Parties to the loan may include issuers of a bond, related entities, lender, borrower, 3rd parties with an interest in the debt. Storage condition may relate to an asset or type of collateral such as a municipal asset, a vehicle, a ship, a plane, a building, a home, real estate property, undeveloped land, a farm, a crop, a municipal facility, a warehouse, a set of inventory, a commodity, a security, a currency, a token of value, a ticket, a cryptocurrency, a consumable item, an edible item, a beverage, a precious metal, an item of jewelry, a gemstone, an item of intellectual property, an intellectual property right, a contractual right, an antique, a fixture, an item of furniture, an item of equipment, a tool, an item of machinery, and an item of personal property. The storage condition may include an environment where environment may include an environment selected from among a municipal environment, a corporate environment, a securities trading environment, a real property environment, a commercial facility, a warehousing facility, a transportation environment, a manufacturing environment, a storage environment, a home, and a vehicle. Actions based on the storage condition of a collateral, an asset or an entity may include managing, reporting on, altering, syndicating, consolidating, terminating, maintaining, modifying terms and/or conditions, foreclosing an asset, or otherwise handling a loan, contract, or agreement. One of skill in the art, having the benefit of the disclosure herein and knowledge about a contemplated storage condition, can readily determine which aspects of the present disclosure will benefit a particular application for a storage condition. Certain considerations for the person of skill in the art, or embodiments of the present disclosure in choosing an appropriate storage condition to manage and/or monitor, include, without limitation: the legality of the condition given the jurisdiction of the transaction, the data available for a given collateral, the anticipated transaction type (loan, bond or debt), the specific type of collateral, the ratio of the loan to value, the ratio of the collateral to the loan, the gross transaction/loan amount, the credit scores of the borrower and the lender, ordinary practices in the industry, and other considerations. While specific examples of storage conditions are described herein for purposes of illustration, any embodiment benefitting from the disclosures herein, and any considerations understood to one of skill in the art having the benefit of the disclosures herein are specifically contemplated within the scope of the present disclosure.

The term geolocation and similar terms, as utilized herein should be understood broadly. Without limitation to any other aspect or description of the present disclosure, geolocation includes the identification or estimation of the real-world geographic location of an object, including the generation of a set of geographic coordinates (e.g. latitude and longitude) and/or street address. Based on a geolocation of a collateral, an asset, or entity, actions may be taken to maintain or improve a condition of the asset or the use of that asset as collateral. Based on a geolocation, actions may be taken to alter the terms or conditions of a loan or bond. Based on a geolocation, determinations or predictions related to a transaction may be performed—for example based upon the weather, civil unrest in a particular area, and/or local disasters (e.g., an earthquake, flood, tornado, hurricane, industrial accident, etc.). Geolocations may be determined in accordance with various rules, thresholds, conditional procedures, workflows, model parameters, and the like and may be based on self-reporting or on data from Internet of Things devices, data from a set of environmental condition sensors, data from a set of social network analytic services and a set of algorithms for querying network domains, social media data, crowdsourced data, and the like. Examples of geolocation data may include GPS coordinates, images, sensor data, street address, and the like. Geolocation data may be quantitative (e.g., longitude/latitude, relative to a plat map, etc.) and/or qualitative (e.g., categorical such as "coastal", "rural", etc.; "within New York City", etc.). Geolocation data may be absolute (e.g., GPS location) or relative (e.g., within 100 yards of an expected location). Examples of social media data or crowdsourced data may include behavior of parties to the loan as inferred by their geolocation, financial condition of parties inferred by geolocation, adherence of parties to a term or condition of the loan, or bond, or the like. Geolocation may be determined for an asset or type of collateral such as a municipal asset, a vehicle, a ship, a plane, a building, a home, real estate property, undeveloped land, a farm, a crop, a municipal facility, a warehouse, a set of inventory, a commodity, a security, a currency, a token of value, a ticket, a consumable item, an edible item, a beverage, a precious metal, an item of jewelry, a gemstone, an antique, a fixture, an item of furniture, an item of equipment, a tool, an item of machinery, and an item of personal property. Geolocation may be determined for an entity such as one of the parties, a third-party (e.g., an inspection service, maintenance service, cleaning service, etc. relevant to a transaction), or any other entity related to a transaction. The geolocation may include an environment selected from among a municipal environment, a corporate environment, a securities trading environment, a real property environment, a commercial facility, a warehousing facility, a transportation environment, a manufacturing environment, a storage environment, a home, and a vehicle. Actions based on the geolocation of a collateral, an asset or an entity may include managing, reporting on, altering, syndicating, consolidating, terminating, maintaining, modifying terms and/or conditions, foreclosing an asset, or otherwise handling a loan, contract, or agreement. One of skill in the art, having the benefit of the disclosure herein and knowledge about a contemplated system, can readily determine which aspects of the present disclosure will benefit a particular application for a geolocation, and which location aspect of an item is a geolocation for the contemplated system. Certain considerations for the person of skill in the art, or embodiments of the present disclosure in choosing an appropriate geolocation to manage, include, without limitation: the legality of the geolocation given the jurisdiction of the transaction, the data available for a given collateral, the anticipated transaction type (loan, bond or debt), the specific type of collateral, the ratio of the loan to value, the ratio of the collateral to the loan, the gross transaction/loan amount, the frequency of travel of the borrower to certain jurisdictions and other considerations, the mobility of the collateral, and/or a likelihood of location-specific event occurrence relevant to the transaction (e.g., weather, location of a relevant industrial facility, availability of relevant services, etc.). While specific examples of geolocation are described herein for purposes of illustration, any embodiment benefitting from the disclosures herein, and any considerations understood to one of skill in the art having the benefit of the disclosures herein are specifically contemplated within the scope of the present disclosure.

The term jurisdictional location and similar terms, as utilized herein should be understood broadly. Without limitation to any other aspect or description of the present disclosure, jurisdictional location refers to the laws and legal authority governing a loan entity. The jurisdictional location may be based on a geolocation of an entity, a registration location of an entity (e.g. a ship's flag state, a state of incorporation for a business, and the like), a granting state for certain rights such as intellectual priority, and the like. In certain embodiments, a jurisdictional location may be one or more of the geolocations for an entity in the system. In certain embodiments, a jurisdictional location may not be the same as the geolocation of any entity in the system (e.g., where an agreement specifies some other jurisdiction). In certain embodiments, a jurisdictional location may vary for entities in the system (e.g., borrower at A, lender at B, collateral positioned at C, agreement enforced at D, etc.). In certain embodiments, a jurisdictional location for a given entity may vary during the operations of the system (e.g., due to movement of collateral, related data, changes in terms and conditions, etc.). In certain embodiments, a given entity of the system may have more than one jurisdictional location (e.g., due to operations of the relevant law, and/or options available to one or more parties), and/or may have distinct jurisdictional locations for different purposes. A jurisdictional location of an item of collateral, an asset, or entity, actions may dictate certain terms or conditions of a loan or bond, and/or may indicate different obligations for notices to parties, foreclosure and/or default execution, treatment of collateral and/or debt security, and/or treatment of various data within the system. While specific examples of jurisdictional location are described herein for purposes of illustration, any embodiment benefitting from the disclosures herein, and any considerations understood to one of skill in the art having the benefit of the disclosures herein are specifically contemplated within the scope of the present disclosure.

The terms token of value, token, and variations such as cryptocurrency token, and the like, as utilized herein, in the context of increments of value, may be understood broadly to describe either: (a) a unit of currency or cryptocurrency (e.g. a cryptocurrency token), and (b) may also be used to represent a credential that can be exchanged for a good, service, data or other valuable consideration (e.g. a token of value). Without limitation to any other aspect or description of the present disclosure, in the former case, a token may also be used in conjunction with investment applications, token-trading applications, and token-based marketplaces. In the latter case, a token can also be associated with rendering consideration, such as providing goods, services, fees, access to a restricted area or event, data, or other valuable benefit. Tokens can be contingent (e.g. contingent access token) or not contingent. For example, a token of value may be exchanged for accommodations, (e.g. hotel rooms), dining/food goods and services, space (e.g. shared space, workspace, convention space, etc.), fitness/wellness goods or services, event tickets or event admissions, travel, flights or other transportation, digital content, virtual goods, license keys, or other valuable goods, services, data, or consideration. Tokens in various forms may be included where discussing a unit of consideration, collateral, or value, whether currency, cryptocurrency, or any other form of value such as goods, services, data or other benefits. One of skill in the art, having the benefit of the disclosure herein and knowledge about a token, can readily determine the value symbolized or represented by a token, whether currency, cryptocurrency, good, service, data, or other value. While specific examples of tokens are described herein for purposes of illustration, any embodiment benefitting from the disclosures herein, and any considerations understood to one of skill in the art having the benefit of the disclosures herein, are specifically contemplated within the scope of the present disclosure.

The term pricing data as utilized herein may be understood broadly to describe a quantity of information such as a price or cost, of one or more items in a marketplace. Without limitation to any other aspect or description of the present disclosure, pricing data may also be used in conjunction with spot market pricing, forward market pricing, pricing discount information, promotional pricing, and other information relating to the cost or price of items. Pricing data may satisfy one or more conditions, or may trigger application of one or more rules of a smart contract. Pricing data may be used in conjunction with other forms of data such as market value data, accounting data, access data, asset and facility data, worker data, event data, underwriting data, claims data or other forms of data. Pricing data may be adjusted for the context of the valued item (e.g., condition, liquidity, location, etc.) and/or for the context of a particular party. One of skill in the art, having the benefit of the disclosure herein and knowledge about pricing data, can readily determine the purposes and use of pricing data in various embodiments and contexts disclosed herein.

Without limitation to any other aspect or description of the present disclosure, a token includes any token including, without limitation, a token of value, such as collateral, an asset, a reward, such as in a token serving as representation of value, such as a value holding voucher that can be exchanged for goods or services. Certain components may not be considered tokens individually, but may be considered tokens in an aggregated system—for example, a value placed on an asset may not be in itself be a token, but the value of an asset may be placed in a token of value, such as to be stored, exchanged, traded, and the like. For instance, in a non-limiting example, a blockchain circuit may be structured to provide lenders a mechanism to store the value of assets, where the value attributed to the token is stored in a distributed ledger of the blockchain circuit, but the token itself, assigned the value, may be exchanged or traded such as through a token marketplace. In certain embodiments, a toke may be considered a token for some purposes but not for other purposes—for example, a token may be used to as an indication of ownership of an asset, but this use of a token would not be traded as a value where a token including the value of the asset might. Accordingly, the benefits of the present disclosure may be applied in a wide variety of systems, and any such systems may be considered a token herein, while in certain embodiments a given system may not be considered a token herein. One of skill in the art, having the benefit of the disclosure herein and knowledge about a contemplated system ordinarily available to that person, can readily determine which aspects of the present disclosure will benefit a particular system, and/or how to combine processes and systems from the present disclosure to enhance operations of the contemplated system. Certain considerations for the person of skill in the art, in determining whether a contemplated system is a token and/or whether aspects of the present disclosure can benefit or enhance the contemplated system include, without limitation, access data such as relating to rights of access, tickets, and tokens; use in an investment application such as for investment in shares, interests, and tokens; a token-trading application; a token-based marketplace; forms of consideration such as monetary rewards and tokens; translating the value of a resources in tokens; a cryptocurrency token; indications of ownership such as identity information, event information, and token information; a blockchain-based access token traded in a marketplace application; pricing application such as for setting and monitoring pricing for contingent access rights, underlying access rights, tokens, and fees; trading applications such as for trading or exchanging contingent access rights or underlying access rights or tokens; tokens created and stored on a blockchain for contingent access rights resulting in an ownership (e.g., a ticket); and the like.

The term financial data as utilized herein may be understood broadly to describe a collection of financial information about an asset, collateral or other item or items. Financial data may include revenues, expenses, assets, liabilities, equity, bond ratings, default, return on assets (ROA), return on investment (ROI), past performance, expected future performance, earnings per share (EPS), internal rate of return (IRR), earnings announcements, ratios, statistical analysis of any of the foregoing (e.g. moving averages), and the like. Without limitation to any other aspect or description of the present disclosure, financial data may also be used in conjunction with pricing data and market value data. Financial data may satisfy one or more conditions, or may trigger application of one or more rules of a smart contract. Financial data may be used in conjunction with other forms of data such as market value data, pricing data, accounting data, access data, asset and facility data, worker data, event data, underwriting data, claims data or other forms of data. One of skill in the art, having the benefit of the disclosure herein and knowledge about financial data, can readily determine the purposes and use of pricing data in various embodiments and contexts disclosed herein.

The term covenant as utilized herein may be understood broadly to describe a term, agreement or promise, such as performance of some action or inaction. For example, a covenant may relate to behavior of a party or legal status of a party. Without limitation to any other aspect or description of the present disclosure, a covenant may also be used in conjunction with other related terms to an agreement or loan, such as a representation, a warranty, an indemnity, a balance of debt, a fixed interest rate, a variable interest rate, a payment amount, a payment schedule, a balloon payment schedule, a specification of collateral, a specification of substitutability of collateral, a party, a guarantee, a guarantor, a security, a personal guarantee, a lien, a duration, a foreclose condition, a default condition, and a consequence of default. A covenant or lack of performance of a covenant may satisfy one or more conditions, or may trigger collection, breach or other terms and conditions. In certain embodiments, a smart contract may calculate whether a covenant is satisfied and in cases where the covenant is not satisfied, may enable automated action or trigger other conditions or terms. One of skill in the art, having the benefit of the disclosure herein and knowledge about covenants, can readily determine the purposes and use of covenants in various embodiments and contexts disclosed herein.

The term entity as utilized herein may be understood broadly to describe a party, a third-party (e.g., an auditor, regulator, service provider, etc.), and/or an identifiable related object such as an item of collateral related to a transaction. Example entities include an individual, partnership, corporation, limited liability company or other legal organization. Other example entities include an identifiable item of collateral, offset collateral, potential collateral, or the like. For example, an entity may be a given party, such as an individual, to an agreement or loan. Data or other terms herein may be characterized as having a context relating to an entity, such as entity-oriented data. An entity may be characterized with a specific context or application, such as a human entity, physical entity, transactional entity or a financial entity, without limitation. An entity may have representatives that represent or act on its behalf. Without limitation to any other aspect or description of the present disclosure, an entity may also be used in conjunction with other related entities or terms to an agreement or loan, such as a representation, a warranty, an indemnity, a covenant, a balance of debt, a fixed interest rate, a variable interest rate, a payment amount, a payment schedule, a balloon payment schedule, a specification of collateral, a specification of substitutability of collateral, a party, a guarantee, a guarantor, a security, a personal guarantee, a lien, a duration, a foreclose condition, a default condition, and a consequence of default. An entity may have a set of attributes such as: a publicly stated valuation, a set of property owned by the entity as indicated by public records, a valuation of a set of property owned by the entity, a bankruptcy condition, a foreclosure status, a contractual default status, a regulatory violation status, a criminal status, an export controls status, an embargo status, a tariff status, a tax status, a credit report, a credit rating, a web site rating, a set of customer reviews for a product of an entity, a social network rating, a set of credentials, a set of referrals, a set of testimonials, a set of behavior, a location, and a geolocation, without limitation. In certain embodiments, a smart contract may calculate whether an entity has satisfied conditions or covenants and in cases where the entity has not satisfied such conditions or covenants, may enable automated action or trigger other conditions or terms. One of skill in the art, having the benefit of the disclosure herein and knowledge about entities, can readily determine the purposes and use of entities in various embodiments and contexts disclosed herein.

The term party as utilized herein may be understood broadly to describe a member of an agreement, such as an individual, partnership, corporation, limited liability company or other legal organization. For example, a party may be a primary lender, a secondary lender, a lending syndicate, a corporate lender, a government lender, a bank lender, a secured lender, a bond issuer, a bond purchaser, an unsecured lender, a guarantor, a provider of security, a borrower, a debtor, an underwriter, an inspector, an assessor, an auditor, a valuation professional, a government official, an accountant or other entities having rights or obligations to an agreement, transaction or loan. A party may characterize a different term, such as transaction as in the term multi-party transaction, where multiple parties are involved in a transaction, or the like, without limitation. A party may have representatives that represent or act on its behalf. In certain embodiments, the term party may reference a potential party or a prospective party—for example, an intended lender or borrower interacting with a system, that may not yet be committed to an actual agreement during the interactions with the system. Without limitation to any other aspect or description of the present disclosure, an party may also be used in conjunction with other related parties or terms to an agreement or loan, such as a representation, a warranty, an indemnity, a covenant, a balance of debt, a fixed interest rate, a variable interest rate, a payment amount, a payment schedule, a balloon payment schedule, a specification of collateral, a specification of substitutability of collateral, an entity, a guarantee, a guarantor, a security, a personal guarantee, a lien, a duration, a foreclose condition, a default condition, and a consequence of default. A party may have a set of attributes such as: an identity, a creditworthiness, an activity, a behavior, a business practice, a status of performance of a contract, information about accounts receivable, information about accounts payable, information about the value of collateral, and other types of information, without limitation. In certain embodiments, a smart contract may calculate whether a party has satisfied conditions or covenants and in cases where the party has not satisfied such conditions or covenants, may enable automated action or trigger other conditions or terms. One of skill in the art, having the benefit of the disclosure herein and knowledge about parties, can readily determine the purposes and use of parties in various embodiments and contexts disclosed herein.

The term party attribute, entity attribute, or party/entity attribute as utilized herein may be understood broadly to describe a value, characteristic, or status of a party or entity. For example, attributes of a party or entity may be, without limitation: value, quality, location, net worth, price, physical condition, health condition, security, safety, ownership, identity, creditworthiness, activity, behavior, business practice, status of performance of a contract, information about accounts receivable, information about accounts payable, information about the value of collateral, and other types of information, and the like. In certain embodiments, a smart contract may calculate values, status or conditions associated with attributes of a party or entity, and in cases where the party or entity has not satisfied such conditions or covenants, may enable automated action or trigger other conditions or terms. One of skill in the art, having the benefit of the disclosure herein and knowledge about attributes of a party or entity, can readily determine the purposes and use of these attributes in various embodiments and contexts disclosed herein.

The term lender as utilized herein may be understood broadly to describe a party to an agreement offering an asset for lending, proceeds of a loan, and may include an individual, partnership, corporation, limited liability company, or other legal organization. For example, a lender may be a primary lender, a secondary lender, a lending syndicate, a corporate lender, a government lender, a bank lender, a secured lender, an unsecured lender, or other party having rights or obligations to an agreement, transaction or loan offering a loan to a borrower, without limitation. A lender may have representatives that represent or act on its behalf. Without limitation to any other aspect or description of the present disclosure, a party may also be used in conjunction with other related parties or terms to an agreement or loan, such as a borrower, a guarantor, a representation, a warranty, an indemnity, a covenant, a balance of debt, a fixed interest rate, a variable interest rate, a payment amount, a payment schedule, a balloon payment schedule, a specification of collateral, a specification of substitutability of collateral, a security, a personal guarantee, a lien, a duration, a foreclose condition, a default condition, and a consequence of default. In certain embodiments, a smart contract may calculate whether a lender has satisfied conditions or covenants and in cases where the lender has not satisfied such conditions or covenants, may enable automated action, a notification or alert, or trigger other conditions or terms. One of skill in the art, having the benefit of the disclosure herein and knowledge about a lender, can readily determine the purposes and use of a lender in various embodiments and contexts disclosed herein.

The term crowdsourcing services as utilized herein may be understood broadly to describe services offered or rendered in conjunction with a crowdsourcing model or transaction, wherein a large group of people or entities supply contributions to fulfill a need, such as a loan, for the transaction. Crowdsourcing services may be provided by a platform or system, without limitation. A crowdsourcing request may be communicated to a group of information suppliers and by which responses to the request may be collected and processed to provide a reward to at least one successful information supplier. The request and parameters may be configured to obtain information related to the condition of a set of collateral for a loan. The crowdsourcing request may be published. In certain embodiments, without limitation, crowdsourcing services may be performed by a smart contract, wherein the reward is managed by a smart contract that processes responses to the crowdsourcing request and automatically allocates a reward to information that satisfies a set of parameter configured for the crowdsourcing request. One of skill in the art, having the benefit of the disclosure herein and knowledge about crowdsourcing services, can readily determine the purposes and use of crowdsourcing services in various embodiments and contexts disclosed herein.

The term publishing services as utilized herein may be understood to describe a set of services to publish a crowdsourcing request. Publishing services may be provided by a platform or system, without limitation. In certain embodiments, without limitation, publishing services may be performed by a smart contract, wherein the crowdsourcing request is published or publication is initiated by the smart contract. One of skill in the art, having the benefit of the disclosure herein and knowledge about publishing services, can readily determine the purposes and use of publishing services in various embodiments and contexts disclosed herein.

The term interface as utilized herein may be understood broadly to describe a component by which interaction or communication is achieved, such as a component of a computer, which may be embodied in software, hardware or a combination thereof. For example, an interface may serve a number of different purposes or be configured for different applications or contexts, such as, without limitation: an application programming interface, a graphic user interface, user interface, software interface, marketplace interface, demand aggregation interface, crowdsourcing interface, secure access control interface, network interface, data integration interface or a cloud computing interface, or combinations thereof. An interface may serve to act as a way to enter, receive or display data, within the scope of lending, refinancing, collection, consolidation, factoring, brokering or foreclosure, without limitation. An interface may serve as an interface for another interface. Without limitation to any other aspect or description of the present disclosure, an interface may be used in conjunction with applications, processes, modules, services, layers, devices, components, machines, products, sub-systems, interfaces, connections, or as part of a system. In certain embodiments, an interface may be embodied in software, hardware or a combination thereof, as well as stored on a medium or in memory. One of skill in the art, having the benefit of the disclosure herein and knowledge about an interface, can readily determine the purposes and use of an interface in various embodiments and contexts disclosed herein.

The term graphical user interface as utilized herein may be understood as a type of interface to allow a user to interact with a system, computer or other interface, in which interaction or communication is achieved through graphical devices or representations. A graphical user interface may be a component of a computer, which may be embodied in computer readable instructions, hardware, or a combination thereof. A graphical user interface may serve a number of different purposes or be configured for different applications or contexts. Such an interface may serve to act as a way to receive or display data using visual representation, stimulus or interactive data, without limitation. A graphical user interface may serve as an interface for another graphical user interface or other interface. Without limitation to any other aspect or description of the present disclosure, a graphical user interface may be used in conjunction with applications, processes, modules, services, layers, devices, components, machines, products, sub-systems, interfaces, connections, or as part of a system. In certain embodiments, a graphical user interface may be embodied in computer readable instructions, hardware or a combination thereof, as well as stored on a medium or in memory. Graphical user interfaces may be configured for any input types, including keyboards, a mouse, a touch screen, and the like. Graphical user interfaces may be configured for any desired user interaction environments, including for example a dedicated application, a web page interface, or combinations of these. One of skill in the art, having the benefit of the disclosure herein and knowledge about a graphical user interface, can readily determine the purposes and use of a graphical user interface in various embodiments and contexts disclosed herein.

The term user interface as utilized herein may be understood as a type of interface to allow a user to interact with a system, computer, or other apparatus, in which interaction or communication is achieved through graphical devices or representations. A user interface may be a component of a computer, which may be embodied in software, hardware, or a combination thereof. The user interface may be stored on a medium or in memory. User interfaces may include drop-down menus, tables, forms, or the like with default, templated, recommended, or pre-configured conditions. In certain embodiments, a user interface may include voice interaction. Without limitation to any other aspect or description of the present disclosure, a user interface may be used in conjunction with applications, circuits, controllers, processes, modules, services, layers, devices, components, machines, products, sub-systems, interfaces, connections, or as part of a system. User interfaces may serve a number of different purposes or be configured for different applications or contexts. For example, a lender-side user interface may include features to view a plurality of customer profiles, but may be restricted from making certain changes. A debtor-side user interface may include features to view details and make changes to a user account. A 3rd party neutral-side interface (e.g. a $3^{rd}$ party not having an interest in an underlying transaction, such as a regulator, auditor, etc.) may have features that enable a view of company oversight and anonymized user data without the ability to manipulate any data, and may have scheduled access depending upon the 3rd party and the purpose for the access. A 3rd party interested-side interface (e.g. a $3^{rd}$ party that may have an interest in an underlying transaction, such as a collector, debtor advocate, investigator, partial owner, etc.) may include features enabling a view of particular user data with restrictions on making changes. Many more features of these user interfaces may be available to implement embodiments of the systems and/or procedures described throughout the present disclosure. Accordingly, the benefits of the present disclosure may be applied in a wide variety of processes and systems, and any such processes or systems may be considered a service herein. One of skill in the art, having the benefit of the disclosure herein and knowledge about a user interface, can readily determine the purposes and use of a user interface in various embodiments and contexts disclosed herein. Certain considerations for the person of skill in the art, in determining whether a contemplated interface is a user interface and/or whether aspects of the present disclosure can benefit or enhance the contemplated system include, without limitation: configurable views, ability to restrict manipulation or views, report functions, ability to manipulate user profile and data, implement regulatory requirements, provide the desired user features for borrowers, lenders, and $3^{rd}$ parties, and the like.

Interfaces and dashboards as utilized herein may further be understood broadly to describe a component by which interaction or communication is achieved, such as a component of a computer, which may be embodied in software, hardware, or a combination thereof. Interfaces and dashboards may acquire, receive, present, or otherwise administrate an item, service, offering or other aspect of a transaction or loan. For example, interfaces and dashboards may serve a number of different purposes or be configured for different applications or contexts, such as, without limitation: an application programming interface, a graphic user interface, user interface, software interface, marketplace interface, demand aggregation interface, crowdsourcing interface, secure access control interface, network interface, data integration interface or a cloud computing interface, or combinations thereof. An interface or dashboard may serve to act as a way to receive or display data, within the context of lending, refinancing, collection, consolidation, factoring, brokering or foreclosure, without limitation. An interface or dashboard may serve as an interface or dashboard for another interface or dashboard. Without limitation to any other aspect or description of the present disclosure, an interface may be used in conjunction with applications, circuits, controllers, processes, modules, services, layers, devices, components, machines, products, sub-systems, interfaces, connections, or as part of a system. In certain embodiments, an interface or dashboard may be embodied in computer readable instructions, hardware, or a combination thereof, as well as stored on a medium or in memory. One of skill in the art, having the benefit of the disclosure herein and knowledge ordinarily available about a contemplated system, can readily determine the purposes and use of interfaces and/or dashboards in various embodiments and contexts disclosed herein.

The term domain as utilized herein may be understood broadly to describe a scope or context of a transaction and/or communications related to a transaction. For example, a domain may serve a number of different purposes or be configured for different applications or contexts, such as, without limitation: a domain for execution, a domain for a digital asset, domains to which a request will be published, domains to which social network data collection and monitoring services will be applied, domains to which Internet of Things data collection and monitoring services will be applied, network domains, geolocation domains, jurisdictional location domains, and time domains. Without limitation to any other aspect or description of the present disclosure, one or more domains may be utilized relative to any applications, circuits, controllers, processes, modules, services, layers, devices, components, machines, products, sub-systems, interfaces, connections, or as part of a system. In certain embodiments, a domain may be embodied in computer readable instructions, hardware, or a combination thereof, as well as stored on a medium or in memory. One of skill in the art, having the benefit of the disclosure herein and knowledge about a domain, can readily determine the purposes and use of a domain in various embodiments and contexts disclosed herein.

The term request (and variations) as utilized herein may be understood broadly to describe the action or instance of initiating or asking for a thing (e.g. information, a response, an object, and the like) to be provided. A specific type of request may also serve a number of different purposes or be configured for different applications or contexts, such as, without limitation: a formal legal request (e.g. a subpoena), a request to refinance (e.g. a loan), or a crowdsourcing request. Systems may be utilized to perform requests as well as fulfill requests. Requests in various forms may be included where discussing a legal action, a refinancing of a loan, or a crowdsourcing service, without limitation. One of skill in the art, having the benefit of the disclosure herein and knowledge about a contemplated system, can readily determine the value of a request implemented in an embodiment. While specific examples of requests are described herein for purposes of illustration, any embodiment benefitting from the disclosures herein, and any considerations understood to one of skill in the art having the benefit of the disclosures herein, are specifically contemplated within the scope of the present disclosure.

The term reward (and variations) as utilized herein may be understood broadly to describe a thing or consideration received or provided in response to an action or stimulus. Rewards can be of a financial type, or non-financial type, without limitation. A specific type of reward may also serve a number of different purposes or be configured for different applications or contexts, such as, without limitation: a reward event, claims for rewards, monetary rewards, rewards captured as a data set, rewards points, and other forms of rewards. Rewards may be triggered, allocated, generated for innovation, provided for the submission of evidence, requested, offered, selected, administrated, managed, configured, allocated, conveyed, identified, without limitation, as well as other actions. Systems may be utilized to perform the aforementioned actions. Rewards in various forms may be included where discussing a particular behavior, or encouragement of a particular behavior, without limitation. In certain embodiments herein, a reward may be utilized as a specific incentive (e.g., rewarding a particular person that responds to a crowdsourcing request) or as a general incentive (e.g., providing a reward responsive to a successful crowdsourcing request, in addition to or alternatively to a reward to the particular person that responded). One of skill in the art, having the benefit of the disclosure herein and knowledge about a reward, can readily determine the value of a reward implemented in an embodiment. While specific examples of rewards are described herein for purposes of illustration, any embodiment benefitting from the disclosures herein, and any considerations understood to one of skill in the art having the benefit of the disclosures herein, are specifically contemplated within the scope of the present disclosure.

The term robotic process automation system as utilized herein may be understood broadly to describe a system capable of performing tasks or providing needs for a system of the present disclosure. For example, a robotic process automation system, without limitation, can be configured for: negotiation of a set of terms and conditions for a loan, negotiation of refinancing of a loan, loan collection, consolidating a set of loans, managing a factoring loan, brokering a mortgage loan, training for foreclosure negotiations, configuring a crowdsourcing request based on a set of attributes for a loan, setting a reward, determining a set of domains to which a request will be published, configuring the content of a request, configuring a data collection and monitoring action based on a set of attributes of a loan, determining a set of domains to which the Internet of Things data collection and monitoring services will be applied, and iteratively training and improving based on a set of outcomes. A robotic process automation system may include: a set of data collection and monitoring services, an artificial intelligence system, and another robotic process automation system which is a component of the higher level robotic process automation system. The robotic process automation system may include: at least one of the set of mortgage loan activities and the set of mortgage loan interactions includes activities among marketing activity, identification of a set of prospective borrowers, identification of property, identification of collateral, qualification of borrower, title search, title verification, property assessment, property inspection, property valuation, income verification, borrower demographic analysis, identification of capital providers, determination of available interest rates, determination of available payment terms and conditions, analysis of existing mortgage, comparative analysis of existing and new mortgage terms, completion of application workflow, population of fields of application, preparation of mortgage agreement, completion of schedule to mortgage agreement, negotiation of mortgage terms and conditions with capital provider, negotiation of mortgage terms and conditions with borrower, transfer of title, placement of lien and closing of mortgage agreement. Example and non-limiting robotic process automation systems may include one or more user interfaces, interfaces with circuits and/or controllers throughout the system to provide, request, and/or share data, and/or one or more artificial intelligence circuits configured to iteratively improve one or more operations of the robotic process automation system. One of skill in the art, having the benefit of the disclosure herein and knowledge ordinarily available about a contemplated robotic process automation system, can readily determine the circuits, controllers, and/or devices to include to implement a robotic process automation system performing the selected functions for the contemplated system. While specific examples of robotic process automation systems are described herein for purposes of illustration, any embodiment benefitting from the disclosures herein, and any considerations understood.

The term loan-related action (and other related terms such as loan-related event and loan-related activity) are utilized herein and may be understood broadly to describe one or multiple actions, events or activities relating to a transaction that includes a loan within the transaction. The action, event or activity may occur in many different contexts of loans, such as lending, refinancing, consolidation, factoring, brokering, foreclosure, administration, negotiating, collecting, procuring, enforcing, and data processing (e.g. data collection), or combinations thereof, without limitation. A loan-related action may be used in the form of a noun (e.g. a notice of default has been communicated to the borrower with formal notice, which could be considered a loan-related action). A loan-related action, event, or activity may refer to a single instance, or may characterize a group of actions, events, or activities. For example, a single action such as providing a specific notice to a borrower of an overdue payment may be considered a loan-related action. Similarly, a group of actions from start to finish relating to a default may also be considered a single loan-related action. Appraisal, inspection, funding and recording, without limitation, may all also be considered loan-related actions that have occurred, as well as events relating to the loan, and may also be loan-related events. Similarly, these activities of completing these actions may also be considered loan-related activities (e.g. appraising, inspecting, funding, recording, etc.), without limitation. In certain embodiments, a smart contract or robotic process automation system may perform loan-related actions, loan-related events, or loan-related activities for one or more of the parties, and process appropriate tasks for completion of the same. In some cases the smart contract or robotic process automation system may not complete a loan-related action, and depending upon such outcome this may enable an automated action or may trigger other conditions or terms. One of skill in the art, having the benefit of the disclosure herein and knowledge about loan-related actions, events, and activities can readily determine the purposes and use of this term in various forms and embodiments as described throughout the present disclosure.

The term loan-related action, events, and activities, as noted herein, may also more specifically be utilized to describe a context for calling of a loan. A calling of a loan is an action wherein the lender can demand the loan be repaid, usually triggered by some other condition or term, such as delinquent payment(s). For example, a loan-related action for calling of the loan may occur when a borrower misses three payments in a row, such that there is a severe delinquency in the loan payment schedule, and the loan goes into default. In such a scenario, a lender may be initiating loan-related actions for calling of the loan to protect its rights. In such a scenario, perhaps the borrower pays a sum to cure the delinquency and penalties, which may also be considered as a loan-related action for calling of the loan. In some circumstances a smart contract or robotic process automation system may initiate, administrate, or process loan-related actions for calling of the loan, which without limitation, may including providing notice, researching, and collecting payment history, or other tasks performed as a part of the calling of the loan. One of skill in the art, having the benefit of the disclosure herein and knowledge about loan-related actions for calling of the loan, or other forms of the term and its various forms, can readily determine the purposes and use of this term in the context of an event or other various embodiments and contexts disclosed herein.

The term loan-related action, events, and activities, as noted herein, may also more specifically be utilized to describe a context for payment of a loan. Typically in transactions involving loans, without limitation, a loan is repaid on a payment schedule. Various actions may be taken to provide a borrower with information to pay back the loan, as well as actions for a lender to receive payment for the loan. For example, if a borrower makes a payment on the loan, a loan-related action for payment of the loan may occur. Without limitation, such a payment may comprise several actions that may occur with respect to the payment on the loan, such as: the payment being tendered to the lender, the loan ledger or accounting reflecting that a payment has been made, a receipt provided to the borrower of the payment made, and the next payment being requested of the borrower. In some circumstances a smart contract or robotic process automation system may initiate, administrate, or process such loan-related actions for payment of the loan, which without limitation, may including providing notice to the lender, researching, and collecting payment history, providing a receipt to the borrower, providing notice of the next payment due to the borrower, or other actions associated with payment of the loan. One of skill in the art, having the benefit of the disclosure herein and knowledge about loan-related actions for payment of a loan, or other forms of the term and its various forms, can readily determine the purposes and use of this term in the context of an event or other various embodiments and contexts disclosed herein.

The term loan-related action, events, and activities, as noted herein, may also more specifically be utilized to describe a context for a payment schedule or alternative payment schedule. Typically in transactions involving loans, without limitation, a loan is repaid on a payment schedule, which may be modified over time. Or, such a payment schedule may be developed and agreed in the alternative, with an alternative payment schedule. Various actions may be taken in the context of a payment schedule or alternate payment schedule for the lender or the borrower, such as: the amount of such payments, when such payments are due, what penalties or fees may attach to late payments, or other terms. For example, if a borrower makes an early payment on the loan, a loan-related action for payment schedule and alternative payment schedule of the loan may occur; in such case, perhaps the payment is applied as principal, with the regular payment still being due. Without limitation, loan-related actions for a payment schedule and alternative payment schedule may comprise several actions that may occur with respect to the payment on the loan, such as: the payment being tendered to the lender, the loan ledger or accounting reflecting that a payment has been made, a receipt provided to the borrower of the payment made, a calculation if any fees are attached or due, and the next payment being requested of the borrower. In certain embodiments, an activity to determine a payment schedule or alternative payment schedule may be a loan-related action, event, or activity. In certain embodiments, an activity to communicate the payment schedule or alternative payment schedule (e.g., to the borrower, the lender, or a $3^{rd}$ party) may be a loan-related action, event, or activity. In some circumstances a smart contract circuit or robotic process automation system may initiate, administrate, or process such loan-related actions for payment schedule and alternative payment schedule, which without limitation, may include providing notice to the lender, researching and collecting payment history, providing a receipt to the borrower, calculating the next due date, calculating the final payment amount and date, providing notice of the next payment due to the borrower, determining the payment schedule or an alternate payment schedule, communicating the payment scheduler or an alternate payment schedule, or other actions associated with payment of the loan. One of skill in the art, having the benefit of the disclosure herein and knowledge about loan-related actions for payment schedule and alternative payment schedule, or other forms of the term and its various forms, can readily determine the purposes and use of this term in the context of an event or other various embodiments and contexts disclosed herein.

The term regulatory notice requirement (and any derivatives) as utilized herein may be understood broadly to describe an obligation or condition to communicate a notification or message to another party or entity. The regulatory notice requirement may be required under one or more conditions that are triggered, or generally required. For example, a lender may have a regulatory notice requirement to provide notice to a borrower of a default of a loan, or change of an interest rate of a loan, or other notifications relating to a transaction or loan. The regulatory aspect of the term may be attributed to jurisdiction-specific laws, rules, or codes that require certain obligations of communication. In certain embodiments, a policy directive may be treated as a regulatory notice requirement—for example where a lender has an internal notice policy that may exceed the regulatory requirements of one or more of the jurisdictional locations related to a transaction. The notice aspect generally relates to formal communications, which may take many different forms, but may specifically be specified as a particular form of notice, such as a certified mail, facsimile, email transmission, or other physical or electronic form, a content for the notice, and/or a timing requirement related to the notice. The requirement aspect relates to the necessity of a party to complete its obligation to be in compliance with laws, rules, codes, policies, standard practices, or terms of an agreement or loan. In certain embodiments, a smart contract may process or trigger regulatory notice requirements and provide appropriate notice to a borrower. This may be based on location of at least one of: the lender, the borrower, the funds provided via the loan, the repayment of the loan, and the collateral of the loan, or other locations as designated by the terms of the loan, transaction, or agreement. In cases where a party or entity has not satisfied such regulatory notice requirements, certain changes in the rights or obligations between the parties may be triggered—for example where a lender provides a non-compliant notice to the borrower, an automated action or trigger based on the terms and conditions of the loan, and/or based on external information (e.g., a regulatory prescription, internal policy of the lender, etc.) may be effected by a smart contract circuit and/or robotic process automation system may be implemented. One of skill in the art, having the benefit of the disclosure herein and knowledge ordinarily available about a contemplated system, can readily determine the purposes and use of regulatory notice requirements in various embodiments and contexts disclosed herein.

The term regulatory notice requirement may also be utilized herein to describe an obligation or condition to communicate a notification or message to another party or entity based upon a general or specific policy, rather than based on a particular jurisdiction, or laws, rules, or codes of a particular location (as in regulatory notice requirement that may be jurisdiction-specific). The regulatory notice requirement may be prudent or suggested, rather than obligatory or required, under one or more conditions that are triggered, or generally required. For example, a lender may have a regulatory notice requirement that is policy based to provide notice to a borrower of a new informational website, or will experience a change of an interest rate of a loan in the future, or other notifications relating to a transaction or loan that are advisory or helpful, rather than mandatory (although mandatory notices may also fall under a policy basis). Thus, in policy based uses of the regulatory notice requirement term, a smart contract circuit may process or trigger regulatory notice requirements and provide appropriate notice to a borrower which may or may not necessarily be required by a law, rule, or code. The basis of the notice or communication may be out of prudence, courtesy, custom, or obligation.

The term regulatory notice may also be utilized herein to describe an obligation or condition to communicate a notification or message to another party or entity specifically, such as a lender or borrower. The regulatory notice may be specifically directed toward any party or entity, or a group of parties or entities. For example, a particular notice or communication may be advisable or required to be provided to a borrower, such as on circumstances of a borrower's failure to provide scheduled payments on a loan resulting in a default. As such, such a regulatory notice directed to a particular user, such as a lender or borrower, may be as a result of a regulatory notice requirement that is jurisdiction-specific or policy-based, or otherwise. Thus, in some circumstances a smart contract may process or trigger a regulatory notice and provide appropriate notice to a specific party such as a borrower, which may or may not necessarily be required by a law, rule, or code, but may otherwise be provided out of prudence, courtesy or custom. In cases where a party or entity has not satisfied such regulatory notice requirements to a specific party or parties, it may create circumstances where certain rights may be forgiven by one or more parties or entities, or may enable automated action or trigger other conditions or terms. One of skill in the art, having the benefit of the disclosure herein and knowledge ordinarily available about a contemplated system, can readily determine the purposes and use of regulatory notice requirements based in various embodiments and contexts disclosed herein.

The term regulatory foreclosure requirement (and any derivatives) as utilized herein may be understood broadly to describe an obligation or condition in order to trigger, process or complete default of a loan, foreclosure or recapture of collateral, or other related foreclosure actions. The regulatory foreclosure requirement may be required under one or more conditions that are triggered, or generally required. For example, a lender may have a regulatory foreclosure requirement to provide notice to a borrower of a default of a loan, or other notifications relating to the default of a loan prior to foreclosure. The regulatory aspect of the term may be attributed to jurisdiction-specific laws, rules, or codes, that require certain obligations of communication. The foreclosure aspect generally relates to the specific remedy of foreclosure, or a recapture of collateral property and default of a loan, which may take many different forms, but may be specified in the terms of the loan. The requirement aspect relates to the necessity of a party to complete its obligation in order to be in compliance or performance of laws, rules, codes, or terms of an agreement or loan. In certain embodiments, a smart contract circuit may process or trigger regulatory foreclosure requirements and process appropriate tasks relating to such a foreclosure action. Foreclosure action(s) may be based on a jurisdictional location of at least one of the lender, the borrower, the fund provided via the loan, the repayment of the loan, and the collateral of the loan, or other locations as designated by the terms of the loan, transaction, or agreement. In cases where a party or entity has not satisfied such regulatory foreclosure requirements, certain rights may be forgiven by the party or entity (e.g. a lender), or such a failure to comply with the regulatory notice requirement may enable automated action or trigger other conditions or terms. One of skill in the art, having the benefit of the disclosure herein and knowledge ordinarily available about a contemplated system, can readily determine the purposes and use of regulatory foreclosure requirements in various embodiments and contexts disclosed herein.

The term regulatory foreclosure requirement may also be utilized herein to describe an obligation or to trigger, process, or complete default of a loan, foreclosure or recapture of collateral, or other related foreclosure actions, based upon a general or specific policy rather than based on a particular jurisdiction, or laws, rules, or codes of a particular location (as in regulatory foreclosure requirement that may be jurisdiction-specific). The regulatory foreclosure requirement may be prudent or suggested, rather than obligatory or required, under one or more conditions that are triggered, or generally required. For example, a lender may have a regulatory foreclosure requirement that is policy based to provide notice to a borrower of a default of a loan, or other notifications relating to a transaction or loan that are advisory or helpful, rather than mandatory (although mandatory notices may also fall under a policy basis). Thus, in policy based uses of the regulatory foreclosure requirement term, a smart contract may process or trigger regulatory foreclosure requirements and provide appropriate notice to a borrower which may or may not necessarily be required by a law, rule, or code. The basis of the notice or communication may be out of prudence, courtesy, custom, industry practice, or obligation.

The term regulatory foreclosure requirements may also be utilized herein to describe an obligation or condition that is to be performed with regard to a specific user, such as a lender or a borrower. The regulatory notice may be specifically directed toward any party or entity, or a group of parties or entities. For example, a particular notice or communication may be advisable or required to be provided to a borrower, such as on circumstances of a borrower's failure to provide scheduled payments on a loan resulting in a default. As such, such a regulatory foreclosure requirement is directed to a particular user, such as a lender or borrower, and may be a result of a regulatory foreclosure requirement that is jurisdiction-specific or policy-based, or otherwise. For example, the foreclosure requirement may be related to a specific entity involved with a transaction (e.g., the current borrower has been a customer for 30 years, so s/he receives unique treatment), or to a class of entities (e.g., "preferred" borrowers, or "first time default" borrowers). Thus, in some circumstances a smart contract circuit may process or trigger an obligation or action that must be taken pursuant to a foreclosure, where the action is directed or from a specific party such as a lender or a borrower, which may or may not necessarily be required by a law, rule, or code, but may otherwise be provided out of prudence, courtesy, or custom. In certain embodiments, the obligation or condition that is to be performed with regard to the specific user may form a part of the terms and conditions or otherwise be known to the specific user to which it applies (e.g., an insurance company or bank that advertises a specific practice with regard to a specific class of customers, such as first-time default customers, first-time accident customers, etc.), and in certain embodiments the obligation or condition that is to be performed with regard to the specific user may be unknown to the specific user to which it applies (e.g., a bank has a policy relating to a class of users to which the specific user belongs, but the specific user is not aware of the classification).

The terms value, valuation, and valuation model (and similar terms) as utilized herein should be understood broadly to describe an approach to evaluate and determine the estimated value for collateral. Without limitation to any other aspect or description of the present disclosure, a valuation model may be used in conjunction with: collateral (e.g. a secured property), artificial intelligence services (e.g. to improve a valuation model), data collection and monitoring services (e.g. to set a valuation amount), valuation services (e.g. the process of informing, using, and/or improving a valuation model), and/or outcomes relating to transactions in collateral (e.g. as a basis of improving the valuation model). "Jurisdiction-specific valuation model" is also used as a valuation model used in a specific geographic/ jurisdictional area or region; wherein, the jurisdiction can be specific to jurisdiction of the lender, the borrower, the delivery of funds, the payment of the loan or the collateral of the loan, or combinations thereof. In certain embodiments, a jurisdiction-specific valuation model considers jurisdictional effects on a valuation of collateral, including at least: rights and obligations for borrowers and lenders in the relevant jurisdiction(s); jurisdictional effects on the ability to move, import, export, substitute, and/or liquidate the collateral; jurisdictional effects on the timing between default and foreclosure or collection of collateral; and/or jurisdictional effects on the volatility and/or sensitivity of collateral value determinations. In certain embodiments, a geolocation-specific valuation model considers geolocation effects on a valuation of the collateral, which may include a similar list of considerations of relative jurisdictional effects (although the jurisdictional location(s) may be distinct from the geolocation(s)), but may also include additional effects, such as: weather-related effects; distance of the collateral from monitoring, maintenance, or seizure services; and/or proximity of risk phenomenon (e.g., fault lines, industrial locations, a nuclear plant, etc.). A valuation model may utilize a valuation of offset collateral (e.g., a similar item of collateral, a generic value such as a market value of similar or fungible collateral, and/or a value of an item that correlates with a value of the collateral) as a part of the valuation of the collateral. In certain embodiments, an artificial intelligence circuit includes one or more machine learning and/or artificial intelligence algorithms, to improve a valuation model, including, for example, utilizing information over time between multiple transactions involving similar or offset collateral, and/or utilizing outcome information (e.g., where loan transactions are completed successfully or unsuccessfully, and/or in response to collateral seizure or liquidation events that demonstrate real-world collateral valuation determinations) from the same or other transactions to iteratively improve the valuation model. In certain embodiments, an artificial intelligence circuit is trained on a collateral valuation data set, for example previously determined valuations and/or through interactions with a trainer (e.g., a human, accounting valuations, and/or other valuation data). In certain embodiments, the valuation model and/or parameters of the valuation model (e.g., assumptions, calibration values, etc.) may be determined and/or negotiated as a part of the terms and conditions of the transaction (e.g., a loan, a set of loans, and/or a subset of the set of loans). One of skill in the art, having the benefit of the disclosure herein and knowledge ordinarily available about a contemplated system, can readily determine which aspects of the present disclosure will benefit a particular application for a valuation model, and how to choose or combine valuation models to implement an embodiment of a valuation model. Certain considerations for the person of skill in the art, or embodiments of the present disclosure in choosing an appropriate valuation model, include, without limitation: the legal considerations of a valuation model given the jurisdiction of the collateral; the data available for a given collateral; the anticipated transaction/loan type(s); the specific type of collateral; the ratio of the loan to value; the ratio of the collateral to the loan; the gross transaction/loan amount; the credit scores of the borrower; accounting practices for the loan type and/or related industry; uncertainties related to any of the foregoing; and/or sensitivities related to any of the foregoing. While specific examples of valuation models and considerations are described herein for purposes of illustration, any embodiment benefitting from the disclosures herein, and any considerations understood to one of skill in the art having the benefit of the disclosures herein, are specifically contemplated within the scope of the present disclosure.

The term market value data, or marketplace information, (and other forms or variations) as utilized herein may be understood broadly to describe data or information relating to the valuation of a property, asset, collateral or other valuable item which may be used as the subject of a loan, or transaction. Market value data or marketplace information may change from time to time, and may be estimated, calculated, or objectively or subjectively determined from various sources of information. Market value data or marketplace information may be related directly to an item of collateral or to an offset item of collateral. Market value data or marketplace information may include financial data, market ratings, product ratings, customer data, market research to understand customer needs or preferences, competitive intelligence regarding competitors, suppliers, and the like, entities sales, transactions, customer acquisition cost, customer lifetime value, brand awareness, churn rate, and the like. The term may occur in many different contexts of contracts or loans, such as lending, refinancing, consolidation, factoring, brokering, foreclosure, and data processing (e.g. data collection), or combinations thereof, without limitation. Market value data or marketplace information may be used as a noun to identify a single figure or a plurality of figures or data. For example, market value data or marketplace information may be utilized by a lender to determine if a property or asset will serve as collateral for a secured loan, or may alternatively be utilized in the determination of foreclosure if a loan is in default, without limitation to these circumstances in use of the term. Marketplace value data or marketplace information may also be used to determine loan-to-value figures or calculations. In certain embodiments, a collection service, smart contract circuit, and/or robotic process automation system may estimate or calculate market value data or marketplace information from one or more sources of data or information. In some cases market data value or marketplace information, depending upon the data/information contained therein, may enable automated action or trigger other conditions or terms. One of skill in the art, having the benefit of the disclosure herein and knowledge ordinarily available about a contemplated system and available relevant marketplace information, can readily determine the purposes and use of this term in various forms, embodiments and contexts disclosed herein.

The terms similar collateral, similar to collateral, offset collateral, and other forms or variations as utilized herein may be understood broadly to describe a property, asset, or valuable item that may be like in nature to a collateral (e.g. an article of value held in security) regarding a loan or other transaction. Similar collateral may refer to a property, asset, collateral, or other valuable item which may be aggregated, substituted, or otherwise referred to in conjunction with other collateral, whether the similarity comes in the form of a common attribute such as type of item of collateral, category of the item of collateral, an age of the item of collateral, a condition of the item of collateral, a history of the item of collateral, an ownership of the item of collateral, a caretaker of the item of collateral, a security of the item of collateral, a condition of an owner of the item of collateral, a lien on the item of collateral, a storage condition of the item of collateral, a geolocation of the item of collateral, and a jurisdictional location of the item of collateral, and the like. In certain embodiments, an offset collateral references an item that has a value correlation with an item of collateral—for example, an offset collateral may exhibit similar price movements, volatility, storage requirements, or the like for an item of collateral. In certain embodiments, similar collateral may be aggregated to form a larger security interest or collateral for an additional loan or distribution, or transaction. In certain embodiments, offset collateral may be utilized to inform a valuation of the collateral. In certain embodiments, a smart contract circuit or robotic process automation system may estimate or calculate figures, data or information relating to similar collateral, or may perform a function with respect to aggregating similar collateral. One of skill in the art, having the benefit of the disclosure herein and knowledge ordinarily available about a contemplated system can readily determine the purposes and use of similar collateral, offset collateral, or related terms as they relate to collateral in various forms, embodiments, and contexts disclosed herein.

The term restructure (and other forms such as restructuring) as utilized herein may be understood broadly to describe a modification of terms or conditions, properties, collateral, or other considerations affecting a loan or transaction. Restructuring may result in a successful outcome where amended terms or conditions are adopted between parties, or an unsuccessful outcome where no modification or restructure occurs, without limitation. Restructuring can occur in many contexts of contracts or loans, such as application, lending, refinancing, collection, consolidation, factoring, brokering, foreclosure, and combinations thereof, without limitation. Debt may also be restructured, which may indicate that debts owed to a party are modified as to timing, amounts, collateral, or other terms. For example, a borrower may restructure debt of a loan to accommodate a change of financial conditions, or a lender may offer to a borrower the restructuring of a debt for its own needs or prudence. In certain embodiments, a smart contract circuit or robotic process automation system may automatically or manually restructure debt based on a monitored condition, or create options for restructuring a debt, administrate the process of negotiating or effecting the restructuring of a debt, or other actions in connection with restructuring or modifying terms of a loan or transaction. One of skill in the art, having the benefit of the disclosure herein and knowledge ordinarily available about a contemplated system, can readily determine the purposes and use of this term, whether in the context of debt or otherwise, in various embodiments and contexts disclosed herein.

The term social network data collection, social network monitoring services, and social network data collection and monitoring services (and its various forms or derivatives) as utilized herein may be understood broadly to describe services relating to the acquisition, organizing, observing, or otherwise acting upon data or information derived from one or more social networks. The social network data collection and monitoring services may be a part of a related system of services or a standalone set of services. Social network data collection and monitoring services may be provided by a platform or system, without limitation. Social network data collection and monitoring services may be used in a variety of contexts such as lending, refinancing, negotiation, collection, consolidation, factoring, brokering, foreclosure, and combinations thereof, without limitation. Requests of social network data collection and monitoring, with configuration parameters, may be requested by other services, automatically initiated, or automatically triggered to occur based on conditions or circumstances that occur. An interface may be provided to configure, initiate, display, or otherwise interact with social network data collection and monitoring services. Social networks, as utilized herein, reference any mass platform where data and communications occur between individuals and/or entities, where the data and communications are at least partially accessible to an embodiment system. In certain embodiments, the social network data includes publicly available (e.g., accessible without any authorization) information. In certain embodiments, the social network data includes information that is properly accessible to an embodiment system, but may include subscription access or other access to information that is not freely available to the public, but may be accessible (e.g., consistent with a privacy policy of the social network with its users). A social network may be primarily social in nature, but may additionally or alternatively include professional networks, alumni networks, industry related networks, academically oriented networks, or the like. In certain embodiments, a social network may be a crowdsourcing platform, such as a platform configured to accept queries or requests directed to users (and/or a subset of users, potentially meeting specified criteria), where users may be aware that certain communications will be shared and accessible to requestors, at least a portion of users of the platform, and/or publicly available. In certain embodiments, without limitation, social network data collection and monitoring services may be performed by a smart contract circuit or a robotic process automation system. One of skill in the art, having the benefit of the disclosure herein and knowledge ordinarily available about a contemplated system, can readily determine the purposes and use of social network data collection and monitoring services in various embodiments and contexts disclosed herein.

The term crowdsource and social network information as utilized herein may further be understood broadly to describe information acquired or provided in conjunction with a crowdsourcing model or transaction, or information acquired or provided on or in conjunction with a social network. Crowdsource and social network information may be provided by a platform or system, without limitation. Crowdsource and social network information may be acquired, provided, or communicated to or from a group of information suppliers and by which responses to the request may be collected and processed. Crowdsource and social network information may provide information, conditions, or factors relating to a loan or agreement. Crowdsource and social network information may be private or published, or combinations thereof, without limitation. In certain embodiments, without limitation, crowdsource and social network information may be acquired, provided, organized, or processed, without limitation, by a smart contract circuit, wherein the crowdsource and social network information may be managed by a smart contract circuit that processes the information to satisfy a set of configured parameters. One of skill in the art, having the benefit of the disclosure herein and knowledge ordinarily available about a contemplated system can readily determine the purposes and use of this term in various embodiments and contexts disclosed herein.

The term negotiate (and other forms such as negotiating or negotiation) as utilized herein may be understood broadly to describe discussions or communications to bring about or obtain a compromise, outcome, or agreement between parties or entities. Negotiation may result in a successful outcome where terms are agreed between parties, or an unsuccessful outcome where the parties do not agree to specific terms, or combinations thereof, without limitation. A negotiation may be successful in one aspect or for a particular purpose, and unsuccessful in another aspect or for another purpose. Negotiation can occur in many contexts of contracts or loans, such as lending, refinancing, collection, consolidation, factoring, brokering, foreclosure, and combinations thereof, without limitation. For example, a borrower may negotiate an interest rate or loan terms with a lender. In another example, a borrower in default may negotiate an alternative resolution to avoid foreclosure with a lender. In certain embodiments, a smart contract circuit or robotic process automation system may negotiate for one or more of the parties, and process appropriate tasks for completing or attempting to complete a negotiation of terms. In some cases negotiation by the smart contract or robotic process automation system may not complete or be successful. Successful negotiation may enable automated action or trigger other conditions or terms to be implemented by the smart contract circuit or robotic process automation system. One of skill in the art, having the benefit of the disclosure herein and knowledge ordinarily available about a contemplated system, can readily determine the purposes and use of negotiation in various embodiments and contexts disclosed herein.

The term negotiate in various forms may more specifically be utilized herein in verb form (e.g. to negotiate) or in noun forms (e.g. a negotiation), or other forms to describe a context of mutual discussion leading to an outcome. For example, a robotic process automation system may negotiate terms and conditions on behalf of a party, which would be a use as a verb clause. In another example, a robotic process automation system may be negotiating terms and conditions for modification of a loan, or negotiating a consolidation offer, or other terms. As a noun clause, a negotiation (e.g. an event) may be performed by a robotic process automation system. Thus, in some circumstances a smart contract circuit or robotic process automation system may negotiate (e.g. as a verb clause) terms and conditions, or the description of doing so may be considered a negotiation (e.g. as a noun clause). One of skill in the art, having the benefit of the disclosure herein and knowledge about negotiating and negotiation, or other forms of the word negotiate, can readily determine the purposes and use of this term in various embodiments and contexts disclosed herein.

The term negotiate in various forms may also specifically be utilized to describe an outcome, such as a mutual compromise or completion of negotiation leading to an outcome. For example, a loan may, by robotic process automation system or otherwise, be considered negotiated as a successful outcome that has resulted in an agreement between parties, where the negotiation has reached completion. Thus, in some circumstances a smart contract circuit or robotic process automation system may have negotiated to completion a set of terms and conditions, or a negotiated loan. One of skill in the art, having the benefit of the disclosure herein and knowledge ordinarily available for a contemplated system, can readily determine the purposes and use of this term as it relates to a mutually agreed outcome through completion of negotiation in various embodiments and contexts disclosed herein.

The term negotiate in various forms may also specifically be utilized to characterize an event such as a negotiating event, or an event negotiation, including reaching a set of agreeable terms between parties. An event requiring mutual agreement or compromise between parties may be considered a negotiating event, without limitation. For example, during the procurement of a loan, the process of reaching a mutually acceptable set of terms and conditions between parties could be considered a negotiating event. Thus, in some circumstances a smart contract circuit or robotic process automation system may accommodate the communications, actions, or behaviors of the parties for a negotiated event.

The term collection (and other forms such as collect or collecting) as utilized herein may be understood broadly to describe the acquisition of a tangible (e.g. physical item), intangible (e.g. data, a license, or a right), or monetary (e.g. payment) item, or other obligation or asset from a source. The term generally may relate to the entire prospective acquisition of such an item from related tasks in early stages to related tasks in late stages or full completion of the acquisition of the item. Collection may result in a successful outcome where the item is tendered to a party, or may or an unsuccessful outcome where the item is not tendered or acquired to a party, or combinations thereof (e.g., a late or otherwise deficient tender of the item), without limitation. Collection may occur in many different contexts of contracts or loans, such as lending, refinancing, consolidation, factoring, brokering, foreclosure, and data processing (e.g. data collection), or combinations thereof, without limitation. Collection may be used in the form of a noun (e.g. data collection or the collection of an overdue payment where it refers to an event or characterizes an event), may refer as a noun to an assortment of items (e.g. a collection of collateral for a loan where it refers to a number of items in a transaction), or may be used in the form of a verb (e.g. collecting a payment from the borrower). For example, a lender may collect an overdue payment from a borrower through an online payment, or may have a successful collection of overdue payments acquired through a customer service telephone call. In certain embodiments, a smart contract circuit or robotic process automation system may perform collection for one or more of the parties, and process appropriate tasks for completing or attempting collection for one or more items (e.g. an overdue payment). In some cases negotiation by the smart contract or robotic process automation system may not complete or be successful, and depending upon such outcomes this may enable automated action or trigger other conditions or terms. One of skill in the art, having the benefit of the disclosure herein and knowledge ordinarily available about a contemplated system, can readily determine the purposes and use of collection in various forms, embodiments, and contexts disclosed herein.

The term collection in various forms may also more specifically be utilized herein in noun form to describe a context for an event or thing, such as a collection event, or a collection payment. For example, a collection event may refer to a communication to a party or other activity that relates to acquisition of an item in such an activity, without limitation. A collection payment, for example, may relate to a payment made by a borrower that has been acquired through the process of collection, or through a collection department with a lender. Although not limited to an overdue, delinquent, or defaulted loan, collection may characterize an event, payment or department, or other noun associated with a transaction or loan, as being a remedy for something that has become overdue. Thus, in some circumstances a smart contract circuit or robotic process automation system may collect a payment or installment from a borrower, and the activity of doing so may be considered a collection event, without limitation.

The term collection in various forms may also more specifically be utilized herein as an adjective or other forms to describe a context relating to litigation, such as the outcome of a collection litigation (e.g. litigation regarding overdue or default payments on a loan). For example, the outcome of a collection litigation may be related to delinquent payments which are owed by a borrower or other party, and collection efforts relating to those delinquent payments may be litigated by parties. Thus, in some circumstances a smart contract circuit or robotic process automation system may receive, determine, or otherwise administrate the outcome of collection litigation.

The term collection in various forms may also more specifically be utilized herein as an adjective or other forms to describe a context relating to an action of acquisition, such as a collection action (e.g. actions to induce tendering or acquisition of overdue or default payments on a loan or other obligation). The terms collection yield, financial yield of collection, and/or collection financial yield may be used. The result of such a collection action may or may not have a financial yield. For example, a collection action may result in the payment of one or more outstanding payments on a loan, which may render a financial yield to another party such as the lender. Thus, in some circumstances a smart contract circuit or robotic process automation system may render a financial yield from a collection action, or otherwise administrate or in some manner assist in a financial yield of a collection action. In embodiments, a collection action may include the need for collection litigation.

The term collection in various forms (collection ROI, ROI on collection, ROI on collection activity, collection activity ROI, and the like) may also more specifically be utilized herein to describe a context relating to an action of receiving value, such as a collection action (e.g. actions to induce tendering or acquisition of overdue or default payments on a loan or other obligation), wherein there is a return on investment (ROI). The result of such a collection action may or may not have an ROI, either with respect to the collection action itself (as an ROI on the collection action) or as an ROI on the broader loan or transaction that is the subject of the collection action. For example, an ROI on a collection action may be prudent or not with respect to a default loan, without limitation, depending upon whether the ROI will be provided to a party such as the lender. A projected ROI on collection may be estimated, or may also be calculated given real events that transpire. In some circumstances a smart contract circuit or robotic process automation system may render an estimated ROI for a collection action or collection event, or may calculate an ROI for actual events transpiring in a collection action or collection event, without limitation. In embodiments, such a ROI may be a positive or negative figure, whether estimated or actual.

The term reputation, measure of reputation, lender reputation, borrower reputation, entity reputation, and the like may include general, widely held beliefs, opinions, and/or perceptions that are generally held about an individual, entity, collateral, and the like. A measure for reputation may be determined based on social data including likes/dislikes, review of entity or products and services provided by the entity, rankings of the company or product, current and historic market and financial data include price, forecast, buy/sell recommendations, financial news regarding entity, competitors, and partners. Reputations may be cumulative in that a product reputation and the reputation of a company leader or lead scientist may influence the overall reputation of the entity. Reputation of an institute associated with an entity (e.g. a school being attended by a student) may influence the reputation of the entity. In some circumstances a smart contract circuit or robotic process automation system may collect or initiate collection of data related to the above and determine a measure or ranking of reputation. A measure or ranking of an entity's reputation may be used by a smart contract circuit or robotic process automation system in determining whether to enter into an agreement with the entity, determination of terms and conditions of a loan, interest rates, and the like. In certain embodiments, indicia of a reputation determination may be related to outcomes of one or more transactions (e.g., a comparison of "likes" on a particular social media data set to an outcome index, such as successful payments, successful negotiation outcomes, ability to liquidate a particular type of collateral, etc.) to determine the measure or ranking of an entity's reputation. One of skill in the art, having the benefit of the disclosure herein and knowledge ordinarily available about a contemplated system, can readily determine the purposes and use of the reputation, a measure or ranking of the reputation, and/or utilization of the reputation in negotiations, determination of terms and conditions, determination of whether to proceed with a transaction, and other various embodiments and contexts disclosed herein.

The term collection in various forms (e.g. collector) may also more specifically be utilized herein to describe a party or entity that induces, administrates, or facilitates a collection action, collection event, or other collection related context. The measure of reputation of a party involved, such as a collector, or during the context of a collection, may be estimated or calculated using objective, subjective, or historical metrics or data. For example, a collector may be involved in a collection action, and the reputation of that collector may be used to determine decisions, actions or conditions. Similarly, a collection may be also used to describe objective, subjective, or historical metrics or data to measure the reputation of a party involved, such as a lender, borrower, or debtor. In some circumstances a smart contract circuit or robotic process automation system may render a collection or measures, or implement a collector, within the context of a transaction or loan.

The term collection and data collection in various forms, including data collection systems, may also more specifically be utilized herein to describe a context relating to the acquisition, organization, or processing of data, or combinations thereof, without limitation. The result of such a data collection may be related or wholly unrelated to a collection of items (e.g., grouping of the items, either physically or logically), or actions taken for delinquent payments (e.g., collection of collateral, a debt, or the like), without limitation. For example, a data collection may be performed by a data collection system, wherein data is acquired, organized, or processed for decision-making, monitoring, or other purposes of prospective or actual transaction or loan. In some circumstances a smart contract or robotic process automation system may incorporate data collection or a data collection system, to perform portions or entire tasks of data collection, without limitation. One of skill in the art, having the benefit of the disclosure herein and knowledge ordinarily available for a contemplated system, can readily determine and distinguish the purposes and use of collection in the context of data or information as used herein.

The terms refinance, refinancing activity(ies), refinancing interactions, refinancing outcomes, and similar terms, as utilized herein should be understood broadly. Without limitation to any other aspect or description of the present disclosure refinance and refinancing activities include replacing an existing mortgage, loan, bond, debt transaction, or the like with a new mortgage, loan, bond, or debt transaction that pays off or ends the previous financial arrangement. In certain embodiments, any change to terms and conditions of a loan, and/or any material change to terms and conditions of a loan, may be considered a refinancing activity. In certain embodiments, a refinancing activity is considered only those changes to a loan agreement that result in a different financial outcome for the loan agreement. Typically, the new loan should be advantageous to the borrower or issuer, and/or mutually agreeable (e.g., improving a raw financial outcome of one, and a security or other outcome for the other). Refinancing may be done to reduce interest rates, lower regular payments, change the loan term, change the collateral associated with the loan, consolidate debt into a single loan, restructure debt, change a type of loan (e.g. variable rate to fixed rate), pay off a loan that is due, in response to an improved credit score, to enlarge the loan, and/or in response to a change in market conditions (e.g. interest rates, value of collateral, and the like).

Refinancing activity may include initiating an offer to refinance, initiating a request to refinance, configuring a refinancing interest rate, configuring a refinancing payment schedule, configuring a refinancing balance in a response to the amount or terms of the refinanced loan, configuring collateral for a refinancing including changes in collateral used, changes in terms and conditions for the collateral, a change in the amount of collateral and the like, managing use of proceeds of a refinancing, removing or placing a lien on different items of collateral as appropriate given changes in terms and conditions as part of a refinancing, verifying title for a new or existing item of collateral to be used to secure the refinanced loan, managing an inspection process title for a new or existing item of collateral to be used to secure the refinanced loan, populating an application to refinance a loan, negotiating terms and conditions for a refinanced loan and closing a refinancing. Refinance and refinancing activities may be disclosed in the context of data collection and monitoring services that collect a training set of interactions between entities for a set of loan refinancing activities. Refinance and refinancing activities may be disclosed in the context of an artificial intelligence system that is trained using the collected training set of interactions that includes both refinancing activities and outcomes. The trained artificial intelligence may then be used to recommend a refinance activity, evaluate a refinance activity, make a prediction around an expected outcome of refinancing activity, and the like. Refinance and refinancing activities may be disclosed in the context of smart contract systems which may automate a subset of the interactions and activities of refinancing. In an example, a smart contract system may automatically adjust an interest rate for a loan based on information collected via at least one of an Internet of Things system, a crowdsourcing system 120, a set of social network analytic services and a set of data collection and monitoring services. The interest rate may be adjusted based on rules, thresholds, model parameters that determine, or recommend, an interest rate for refinancing a loan based on interest rates available to the lender from secondary lenders, risk factors of the borrower (including predicted risk based on one or more predictive models using artificial intelligence), marketing factors (such as competing interest rates offered by other lenders), and the like. Outcomes and events of a refinancing activity may be recorded in a distributed ledger. Based on the outcome of a refinance activity, a smart contract for the refinance loan may be automatically reconfigured to define the terms and conditions for the new loan such as a principal amount of debt, a balance of debt, a fixed interest rate, a variable interest rate, a payment amount, a payment schedule, a balloon payment schedule, a specification of collateral, a specification of substitutability of collateral, a party, a guarantee, a guarantor, a security, a personal guarantee, a lien, a duration, a covenant, a foreclose condition, a default condition, and a consequence of default.

One of skill in the art, having the benefit of the disclosure herein and knowledge ordinarily available about a contemplated system can readily determine which aspects of the present disclosure will benefit from a particular application of a refinance activity, how to choose or combine refinance activities, how to implement systems, services, or circuits to automatically perform of one or more (or all) aspects of a refinance activity, and the like. Certain considerations for the person of skill in the art, for embodiments of the present disclosure in choosing an appropriate training sets of interactions with which to train an artificial intelligence to take action, recommend or predict the outcome of certain refinance activities. While specific examples of refinance and refinancing activities are described herein for purposes of illustration, any embodiment benefitting from the disclosures herein, and any considerations understood to one of skill in the art having the benefit of the disclosures herein, are specifically contemplated within the scope of the present disclosure.

The terms consolidate, consolidation activity(ies), loan consolidation, debt consolidation, consolidation plan, and similar terms, as utilized herein should be understood broadly. Without limitation to any other aspect or description of the present disclosure, consolidate, consolidation activity (ies), loan consolidation, debt consolidation, or consolidation plan are related to the use of a single large loan to pay off several smaller loans, and/or the use of one or more of a set of loans to pay off at least a portion of one or more of a second set of loans. In embodiments, loan consolidation may be secured (i.e. backed by collateral) or unsecured. Loans may be consolidated to obtain a lower interest rate than one or more of the current loans, to reduce total monthly loan payments, and/or to bring a debtor into compliance on the consolidated loans or other debt obligations of the debtor. Loans that may be classified as candidates for consolidation may be determined based on a model that processes attributes of entities involved in the set of loans including identity of a party, interest rate, payment balance, payment terms, payment schedule, type of loan, type of collateral, financial condition of party, payment status, condition of collateral, and value of collateral. Consolidation activities may include managing at least one of identification of loans from a set of candidate loans, preparation of a consolidation offer, preparation of a consolidation plan, preparation of content communicating a consolidation offer, scheduling a consolidation offer, communicating a consolidation offer, negotiating a modification of a consolidation offer, preparing a consolidation agreement, executing a consolidation agreement, modifying collateral for a set of loans, handling an application workflow for consolidation, managing an inspection, managing an assessment, setting an interest rate, deferring a payment requirement, setting a payment schedule, and closing a consolidation agreement. In embodiments, there may be systems, circuits, and/or services configured to create, configure (such as using one or more templates or libraries), modify, set, or otherwise handle (such as in a user interface) various rules, thresholds, conditional procedures, workflows, model parameters, and the like to determine, or recommend, a consolidation action or plan for a lending transaction or a set of loans based on one or more events, conditions, states, actions, or the like. In embodiments, a consolidation plan may be based on various factors, such as the status of payments, interest rates of the set of loans, prevailing interest rates in a platform marketplace or external marketplace, the status of the borrowers of a set of loans, the status of collateral or assets, risk factors of the borrower, the lender, one or more guarantors, market risk factors and the like. Consolidation and consolidation activities may be disclosed in the context of data collection and monitoring services that collect a training set of interactions between entities for a set of loan consolidation activities. consolidation and consolidation activities may be disclosed in the context of an artificial intelligence system that is trained using the collected training set of interactions that includes both consolidation activities and outcomes associated with those activities. The trained artificial intelligence may then be used to recommend a consolidation activity, evaluate a consolidation activity, make a prediction around an expected outcome of consolidation activity, and the like based models including status of debt, condition of collateral or assets used to secure or back a set of loans, the state of a business or business operation (e.g., receivables, payables, or the like), conditions of parties (such as net worth, wealth, debt, location, and other conditions), behaviors of parties (such as behaviors indicating preferences, behaviors indicating debt preferences), and others. Debt consolidation, loan consolidation and associated consolidation activities may be disclosed in the context of smart contract systems which may automate a subset of the interactions and activities of consolidation. In embodiments, consolidation may include consolidation with respect to terms and conditions of sets of loans, selection of appropriate loans, configuration of payment terms for consolidated loans, configuration of payoff plans for pre-existing loans, communications to encourage consolidation, and the like. In embodiments the artificial intelligence of a smart contract may automatically recommend or set rules, thresholds, actions, parameters and the like (optionally by learning to do so based on a training set of outcomes over time), resulting in a recommended consolidation plan, which may specify a series of actions required to accomplish a recommended or desired outcome of consolidation (such as within a range of acceptable outcomes), which may be automated and may involve conditional execution of steps based on monitored conditions and/or smart contract terms, which may be created, configured, and/or accounted for by the consolidation plan. Consolidation plans may be determined and executed based at least one part on market factors (such as competing interest rates offered by other lenders, values of collateral, and the like) as well as regulatory and/or compliance factors. Consolidation plans may be generated and/or executed for creation of new consolidated loans, for secondary loans related to consolidated loans, for modifications of existing loans related to consolidation, for refinancing terms of a consolidated loan, for foreclosure situations (e.g., changing from secured loan rates to unsecured loan rates), for bankruptcy or insolvency situations, for situations involving market changes (e.g., changes in prevailing interest rates) and others. consolidation.

Certain of the activities related to loans, collateral, entities, and the like, may apply to a wide variety of loans and may not apply explicitly to consolidation activities. The categorization of the activities as consolidation activities may be based on the context of the loan for which the activities are taking place. However, one of skill in the art, having the benefit of the disclosure herein and knowledge ordinarily available about a contemplated system can readily determine which aspects of the present disclosure will benefit from a particular application of a consolidation activity, how to choose or combine consolidation activities, how to implement selected services, circuits, and/or systems described herein to perform certain loan consolidation operations, and the like. While specific examples of consolidation and consolidation activities are described herein for purposes of illustration, any embodiment benefitting from the disclosures herein, and any considerations understood to one of skill in the art having the benefit of the disclosures herein, are specifically contemplated within the scope of the present disclosure.

The terms factoring a loan, factoring a loan transaction, factors, factoring a loan interaction, factoring assets or sets of assets used for factoring and similar terms, as utilized herein should be understood broadly. Without limitation to any other aspect or description of the present disclosure factoring may be applied to factoring assets such as invoices, inventory, accounts receivable, and the like, where the realized value of the item is in the future. For example, the accounts receivable is worth more when it has been paid and there is less risk of default. Inventory and Work in Progress (WIP) may be worth more as final product rather than components. References to accounts receivable should be understood to encompass these terms and not be limiting. Factoring may include a sale of accounts receivable at a discounted rate for value in the present (often cash). Factoring may also include the use of accounts receivable as collateral for a short term loan. In both cases the value of the accounts receivable or invoices may be discounted for multiple reasons including the future value of money, a term of the accounts receivable (e.g., 30 day net payment vs. 90 day net payment), a degree of default risk on the accounts receivable, a status of receivables, a status of work-in-progress (WIP), a status of inventory, a status of delivery and/or shipment, financial condition(s) of parties owing against the accounts receivable, a status of shipped and/or billed, a status of payments, a status of the borrower, a status of inventory, a risk factor of a borrower, a lender, one or more guarantors, market risk factors, a status of debt (are there other liens present on the accounts receivable or payment owed on the inventory, a condition of collateral assets (e.g. the condition of the inventory—is it current or out of date, are invoices in arrears), a state of a business or business operation, a condition of a party to the transaction (such as net worth, wealth, debt, location, and other conditions), a behavior of a party to the transaction (such as behaviors indicating preferences, behaviors indicating negotiation styles, and the like), current interest rates, any current regulatory and compliance issues associated with the inventory or accounts receivable (e.g. if inventory is being factored, has the intended product received appropriate approvals), and there legal actions against the borrower, and many others, including predicted risk based on one or more predictive models using artificial intelligence). A factor is an individual, business, entity, or groups thereof which agree to provide value inf exchange for either the outright acquisition of the invoices in a sale or the use of the invoices as collateral for a loan for the value. Factoring a loan may include the identification of candidates (both lenders and borrowers) for factoring, a plan for factoring specifying the proposed receivables (e.g. all, some, only those meeting certain criteria), and a proposed discount factor, communication of the plan to potential parties, proffering an offer and receiving an offer, verification of quality of receivables, conditions regarding treatment of the receivables for the term of the loan. While specific examples of factoring and factoring activities are described herein for purposes of illustration, any embodiment benefitting from the disclosures herein, and any considerations understood to one of skill in the art having the benefit of the disclosures herein, are specifically contemplated within the scope of the present disclosure.

The terms mortgage, brokering a mortgage, mortgage collateral, mortgage loan activities, and/or mortgage related activities as utilized herein should be understood broadly. Without limitation to any other aspect or description of the present disclosure, a mortgage is an interaction where a borrower provides the title or a lien on the title of an item of value, typically property, to a lender as security in exchange for money or another item of value, to be repaid, typically with interest, to the lender. The exchange includes the condition that, upon repayment of the loan, the title reverts to the borrower and/or the lien on the property is removed. The brokering of a mortgage may include the identification of potential properties, lenders, and other parties to the loan, and arranging or negotiating the terms of the mortgage. Certain components or activities may not be considered mortgage related individually, but may be considered mortgage related when used in conjunction with a mortgage, act upon a mortgage, are related to an entity or party to a mortgage, and the like. For example, brokering may apply to the offering of a variety of loans including unsecured loans, outright sale of property and the like. Mortgage activities and mortgage interactions may include mortgage marketing activity, identification of a set of prospective borrowers, identification of property to mortgage, identification of collateral property to mortgage, qualification of borrower, title search and/or title verification for prospective mortgage property, property assessment, property inspection, or property valuation for prospective mortgage property, income verification, borrower demographic analysis, identification of capital providers, determination of available interest rates, determination of available payment terms and conditions, analysis of existing mortgage(s), comparative analysis of existing and new mortgage terms, completion of application workflow (e.g. keep the application moving forward by initiating next steps in the process as appropriate), population of fields of application, preparation of mortgage agreement, completion of schedule for mortgage agreement, negotiation of mortgage terms and conditions with capital provider, negotiation of mortgage terms and conditions with borrower, transfer of title, placement of lien on mortgaged property and closing of mortgage agreement, and similar terms, as utilized herein should be understood broadly. While specific examples of mortgages and mortgage brokering are described herein for purposes of illustration, any embodiment benefitting from the disclosures herein, and any considerations understood to one of skill in the art having the benefit of the disclosures herein, are specifically contemplated within the scope of the present disclosure.

The terms debt management, debt transactions, debt actions, debt terms and conditions, syndicating debt, consolidating debt, and/or debt portfolios, as utilized herein should be understood broadly. Without limitation to any other aspect or description of the present disclosure a debt includes something of monetary value that is owed to another. A loan typically results in the borrower holding the debt (e.g. the money that must be paid back according to the terms of the loan, which may include interest). Consolidation of debt includes the use of a new, single loan to pay back multiple loans (or various other configurations of debt structuring as described herein, and as understood to one of skill in the art). Often the new loan may have better terms or lower interest rates. Debt portfolios include a number of pieces or groups of debt, often having different characteristics including term, risk, and the like. Debt portfolio management may involve decisions regarding the quantity and quality of the debt being held and how best to balance the various debts to achieve a desired risk/reward position based on: investment policy, return on risk determinations for individual pieces of debt, or groups of debt. Debt may be syndicated where multiple lenders fund a single loan (or set of loans) to a borrower. Debt portfolios may be sold to a third party (e.g., at a discounted rate). Debt compliance includes the various measures taken to ensure that debt is repaid. Demonstrating compliance may include documentation of the actions taken to repay the debt.

Transactions related to a debt (debt transactions) and actions related to the debt (debt actions) may include offering a debt transaction, underwriting a debt transaction, setting an interest rate, deferring a payment requirement, modifying an interest rate, validating title, managing inspection, recording a change in title, assessing the value of an asset, calling a loan, closing a transaction, setting terms and conditions for a transaction, providing notices required to be provided, foreclosing on a set of assets, modifying terms and conditions, setting a rating for an entity, syndicating debt, and/or consolidating debt. Debt terms and conditions may include a balance of debt, a principal amount of debt, a fixed interest rate, a variable interest rate, a payment amount, a payment schedule, a balloon payment schedule, a specification of assets that back the bond, a specification of substitutability of assets, a party, an issuer, a purchaser, a guarantee, a guarantor, a security, a personal guarantee, a lien, a duration, a covenant, a foreclose condition, a default condition, and a consequence of default. While specific examples of debt management and debt management activities are described herein for purposes of illustration, any embodiment benefitting from the disclosures herein, and any considerations understood to one of skill in the art having the benefit of the disclosures herein, are specifically contemplated within the scope of the present disclosure.

The terms condition, condition classification, classification models, condition management, and similar terms, as utilized herein should be understood broadly. Without limitation to any other aspect or description of the present disclosure condition, condition classification, classification models, condition management, include classifying or determining a condition of an asset, issuer, borrower, loan, debt, bond, regulatory status, term or condition for a bond, loan or debt transaction that is specified and monitored in the contract, and the like. Based on a classified condition of an asset, condition management may include actions to maintain or improve a condition of the asset or the use of that asset as collateral. Based on a classified condition of an issuer, borrower, party regulatory status, and the like, condition management may include actions to alter the terms or conditions of a loan or bond. Condition classification may include various rules, thresholds, conditional procedures, workflows, model parameters, and the like to classify a condition of an asset, issuer, borrower, loan, debt, bond, regulatory status, term or condition for a bond, loan or debt transaction, and the like based on data from Internet of Things devices, data from a set of environmental condition sensors, data from a set of social network analytic services and a set of algorithms for querying network domains, social media data, crowdsourced data, and the like. Condition classification may include grouping or labeling entities, or clustering the entities, as similarly positioned with regard to some aspect of the classified condition (e.g., a risk, quality, ROI, likelihood for recovery, likelihood to default, or some other aspect of the related debt).

Various classification models are disclosed where the classification and classification model may be tied to a geographic location relating to the collateral, the issuer, the borrower, the distribution of the funds or other geographic locations. Classification and classification models are disclosed where artificial intelligence is used to improve a classification model (e.g. refine a model by making refinements using artificial intelligence data). Thus artificial intelligence may be considered, in some instances, as a part of a classification model and vice versa. Classification and classification models are disclosed where social media data, crowdsourced data, or IoT data is used as input for refining a model, or as input to a classification model. Examples of IoT data may include images, sensor data, location data, and the like. Examples of social media data or crowdsourced data may include behavior of parties to the loan, financial condition of parties, adherence to a parties to a term or condition of the loan, or bond, or the like. Parties to the loan may include issuers of a bond, related entities, lender, borrower, 3rd parties with an interest in the debt. Condition management may be discussed in connection with smart contract services which may include condition classification, data collection and monitoring, and bond, loan and debt transaction management. Data collection and monitoring services are also discussed in conjunction with classification and classification models which are related when classifying an issuer of a bond issuer, an asset or collateral asset related to the bond, collateral assets backing the bond, parties to the bond, and sets of the same. In some embodiments a classification model may be included when discussing bond types. Specific steps, factors or refinements may be considered a part of a classification model. In various embodiments, the classification model may change both in an embodiment, or in the same embodiment which is tied to a specific jurisdiction. Different classification models may use different data sets (e.g. based on the issuer, the borrower, the collateral assets, the bond type, the loan type, and the like) and multiple classification models may be used in a single classification. For example, one type of bond, such as a municipal bond, may allow a classification model that is based on bond data from municipalities of similar size and economic prosperity, whereas another classification model may emphasize data from IoT sensors associated with a collateral asset. Accordingly, different classification models will offer benefits or risks over other classification models, depending upon the embodiment and the specifics of the bond, loan or debt transaction. A classification model includes an approach or concept for classification. Conditions classified for a bond, loan, or debt transaction may include a principal amount of debt, a balance of debt, a fixed interest rate, a variable interest rate, a payment amount, a payment schedule, a balloon payment schedule, a specification of assets that back the bond, loan or debt transaction, a specification of substitutability of assets, a party, an issuer, a purchaser, a guarantee, a guarantor, a security, a personal guarantee, a lien, a duration, a covenant, a foreclose condition, a default condition, and/or a consequence of default. Conditions classified may include type of bond issuer such as a municipality, a corporation, a contractor, a government entity, a non-governmental entity, and a non-profit entity. Entities may include a set of issuers, a set of bonds, a set of parties, and/or a set of assets. Conditions classified may include an entity condition such as net worth, wealth, debt, location, and other conditions), behaviors of parties (such as behaviors indicating preferences, behaviors indicating debt preferences), and the like. Conditions classified may include an asset or type of collateral such as a municipal asset, a vehicle, a ship, a plane, a building, a home, real estate property, undeveloped land, a farm, a crop, a municipal facility, a warehouse, a set of inventory, a commodity, a security, a currency, a token of value, a ticket, a cryptocurrency, a consumable item, an edible item, a beverage, a precious metal, an item of jewelry, a gemstone, an item of intellectual property, an intellectual property right, a contractual right, an antique, a fixture, an item of furniture, an item of equipment, a tool, an item of machinery, and an item of personal property. Conditions classified may include a bond type where bond type may include a municipal bond, a government bond, a treasury bond, an asset-backed bond, and a corporate bond. Conditions classified may include a default condition, a foreclosure condition, a condition indicating violation of a covenant, a financial risk condition, a behavioral risk condition, a policy risk condition, a financial health condition, a physical defect condition, a physical health condition, an entity risk condition and an entity health condition. Conditions classified may include an environment where environment may include an environment selected from among a municipal environment, a corporate environment, a securities trading environment, a real property environment, a commercial facility, a warehousing facility, a transportation environment, a manufacturing environment, a storage environment, a home, and a vehicle. Actions based on the condition of an asset, issuer, borrower, loan, debt, bond, regulatory status and the like, may include managing, reporting on, syndicating, consolidating, or otherwise handling a set of bonds (such as municipal bonds, corporate bonds, performance bonds, and others), a set of loans (subsidized and unsubsidized, debt transactions and the like, monitoring, classifying, predicting, or otherwise handling the reliability, quality, status, health condition, financial condition, physical condition or other information about a guarantee, a guarantor, a set of collateral supporting a guarantee, a set of assets backing a guarantee, or the like. Bond transaction activities in response to a condition of the bond may include offering a debt transaction, underwriting a debt transaction, setting an interest rate, deferring a payment requirement, modifying an interest rate, validating title, managing inspection, recording a change in title, assessing the value of an asset, calling a loan, closing a transaction, setting terms and conditions for a transaction, providing notices required to be provided, foreclosing on a set of assets, modifying terms and conditions, setting a rating for an entity, syndicating debt, and/or consolidating debt.

One of skill in the art, having the benefit of the disclosure herein and knowledge ordinarily available about a contemplated system, can readily determine which aspects of the present disclosure will benefit a particular application for a classification model, how to choose or combine classification models to arrive at a condition, and/or calculate a value of collateral given the required data. Certain considerations for the person of skill in the art, or embodiments of the present disclosure in choosing an appropriate condition to manage, include, without limitation: the legality of the condition given the jurisdiction of the transaction, the data available for a given collateral, the anticipated transaction type (loan, bond or debt), the specific type of collateral, the ratio of the loan to value, the ratio of the collateral to the loan, the gross transaction/loan amount, the credit scores of the borrower and the lender, and other considerations. While specific examples of conditions, condition classification, classification models, and condition management are described herein for purposes of illustration, any embodiment benefitting from the disclosures herein, and any considerations understood to one of skill in the art having the benefit of the disclosures herein, are specifically contemplated within the scope of the present disclosure.

The terms classify, classifying, classification, categorization, categorizing, categorize (and similar terms) as utilized herein should be understood broadly. Without limitation to any other aspect or description of the present disclosure, classifying a condition or item may include actions to sort the condition or item into a group or category based on some aspect, attribute, or characteristic of the condition or item where the condition or item is common or similar for all the items placed in that classification, despite divergent classifications or categories based on other aspects or conditions at the time. Classification may include recognition of one or more parameters, features, characteristics, or phenomena associated with a condition or parameter of an item, entity, person, process, item, financial construct, or the like. Conditions classified by a condition classifying system may include a default condition, a foreclosure condition, a condition indicating violation of a covenant, a financial risk condition, a behavioral risk condition, a contractual performance condition, a policy risk condition, a financial health condition, a physical defect condition, a physical health condition, an entity risk condition, and/or an entity health condition. A classification model may automatically classify or categorize items, entities, process, items, financial constructs or the like based on data received from a variety of sources. The classification model may classify items based on a single attribute or a combination of attributes, and/or may utilize data regarding the items to be classified and a model. The classification model may classify individual items, entities, financial constructs or groups of the same. A bond may be classified based on the type of bond ((e.g. municipal bonds, corporate bonds, performance bonds, and the like), rate of return, bond rating ($3^{rd}$ party indicator of bond quality with respect to bond issuer's financial strength, and/or ability to bap bond's principal and interest, and the like. Lenders or bond issuers may be classified based on the type of lender or issuer, permitted attributes (e.g. based on income, wealth, location (domestic or foreign), various risk factors, status of issuers, and the like. Borrowers may be classified based on permitted attributes (e.g. income, wealth, total assets, location, credit history), risk factors, current status (e.g. employed, a student), behaviors of parties (such as behaviors indicating preferences, reliability, and the like), and the like. A condition classifying system may classify a student recipient of a loan based on progress of the student toward a degree, the student's grades or standing in their classes, student's status at the school (matriculated, on probation and the like), the participation of a student in a non-profit activity, a deferment status of the student, and the participation of the student in a public interest activity. Conditions classified by a condition classifying system may include a state of a set of collateral for a loan or a state of an entity relevant to a guarantee for a loan. Conditions classified by a condition classifying system may include a medical condition of a borrower, guarantor, subsidizer or the like. Conditions classified by a condition classifying system may include compliance with at least one of a law, a regulation, or a policy related to a lending transaction or lending institute. Conditions classified by a condition classifying system may include a condition of an issuer for a bond, a condition of a bond, a rating of a loan-related entity, and the like. Conditions classified by a condition classifying system may include an identify of a machine, a component, or an operational mode. Conditions classified by a condition classifying system may include a state or context (such as a state of a machine, a process, a workflow, a marketplace, a storage system, a network, a data collector, or the like). A condition classifying system may classify a process involving a state or context (e.g., a data storage process, a network coding process, a network selection process, a data marketplace process, a power generation process, a manufacturing process, a refining process, a digging process, a boring process, and/or other process described herein. A condition classifying system may classify a set of loan refinancing actions based on a predicted outcome of the set of loan refinancing actions. A condition classifying system may classify a set of loans as candidates for consolidation based on attributes such as identity of a party, an interest rate, a payment balance, payment terms, payment schedule, a type of loan, a type of collateral, a financial condition of party, a payment status, a condition of collateral, a value of collateral, and the like. A condition classifying system may classify the entities involved in a set of factoring loans, bond issuance activities, mortgage loans, and the like. A condition classifying system may classify a set of entities based on projected outcomes from various loan management activities. A condition classifying system may classify a condition of a set of issuers based on information from Internet of Things data collection and monitoring services, a set of parameters associated with an issuer, a set of social network monitoring and analytic services, and the like. A condition classifying system may classify a set of loan collection actions, loan consolidation actions, loan negotiation actions, loan refinancing actions and the like based on a set of projected outcomes for those activities and entities.

The term subsidized loan, subsidizing a loan, (and similar terms) as utilized herein should be understood broadly. Without limitation to any other aspect or description of the present disclosure, a subsidized loan is the loan of money or an item of value wherein payment of interest on the value of the loan may be deferred, postponed or delayed, with or without accrual, such as while the borrower is in school, is unemployed, is ill, and the like. In embodiments, a loan may be subsidized when the payment of interest on a portion or subset of the loan is borne or guaranteed by someone other than the borrower. Examples of subsidized loans may include a municipal subsidized loan, a government subsidized loan, a student loan, an asset-backed subsidized loan, and a corporate subsidized loan. An example of a subsidized student loan may include student loans which may be subsidized by the government and on which interest may be deferred or not accrue based on progress of the student toward a degree, the participation of a student in a non-profit activity, a deferment status of the student, and the participation of the student in a public interest activity. An example of a government subsidized housing loan may include governmental subsidies which may exempt the borrower from paying closing costs, first mortgage payment and the like. Conditions for such subsidized loans may include location of the property (rural or urban), income of the borrower, military status of the borrower, ability of the purchased home to meet health and safety standards, a limit on the profits you can earn on the sale of your home, and the like. Certain usages of the word loan may not apply to a subsidized loan but rather to a regular loan. One of skill in the art, having the benefit of the disclosure herein and knowledge about a contemplated system ordinarily available to that person, can readily determine which aspects of the present disclosure will benefit from consideration of a subsidized loan (e.g., in determining the value of the loan, negotiations related to the loan, terms and conditions related to the loan, etc.) wherein the borrower may be relieved of some of the loan obligations common for non-subsidized loans, where the subsidy may include forgiveness, delay or deferment of interest on a loan, or the payment of the interest by a third party. The subsidy may include the payment of closing costs including points, first payment and the like by a person or entity other than the borrower, and/or how to combine processes and systems from the present disclosure to enhance or benefit from title validation.

The term subsidized loan management (and similar terms) as utilized herein should be understood broadly. Without limitation to any other aspect or description of the present disclosure, subsidized loan management may include a plurality of activities and solutions for managing or responding to one or more events related to a subsidized loan wherein such events may include requests for a subsidized loan, offering a subsidized loan, accepting a subsidized loan, providing underwriting information for a subsidized loan, providing a credit report on a borrower seeking a subsidized loan, deferring a required payment as part of the loan subsidy, setting an interest rate for a subsidized loan where a lower interest rate may be part of the subsidy, deferring a payment requirement as part of the loan subsidy, identifying collateral for a loan, validating title for collateral or security for a loan, recording a change in title of property, assessing the value of collateral or security for a loan, inspecting property that is involved in a loan, identifying a change in condition of an entity relevant to a loan, a change in value of an entity that is relevant to a loan, a change in job status of a borrower, a change in financial rating of a lender, a change in financial value of an item offered as a security, providing insurance for a loan, providing evidence of insurance for property related to a loan, providing evidence of eligibility for a loan, identifying security for a loan, underwriting a loan, making a payment on a loan, defaulting on a loan, calling a loan, closing a loan, setting terms and conditions for a loan, foreclosing on property subject to a loan, modifying terms and conditions for a loan, for setting terms and conditions for a loan (such as a principal amount of debt, a balance of debt, a fixed interest rate, a variable interest rate, a payment amount, a payment schedule, a balloon payment schedule, a specification of collateral, a specification of substitutability of collateral, a party, a guarantee, a guarantor, a security, a personal guarantee, a lien, a duration, a covenant, a foreclose condition, a default condition, and a consequence of default), or managing loan-related activities (such as, without limitation, finding parties interested in participating in a loan transaction, handling an application for a loan, underwriting a loan, forming a legal contract for a loan, monitoring performance of a loan, making payments on a loan, restructuring or amending a loan, settling a loan, monitoring collateral for a loan, forming a syndicate for a loan, foreclosing on a loan, collecting on a loan, consolidating a set of loans, analyzing performance of a loan, handling a default of a loan, transferring title of assets or collateral, and closing a loan transaction), and the like. In embodiments, a system for handling a subsidized loan may include classifying a set of parameters of a set of subsidized loans on the basis of data relating to those parameters obtained from an Internet of Things data collection and monitoring service. Classifying the set of parameters of the set of subsidized loans may also be on the bases of data obtained from one or more configurable data collection and monitoring services that leverage social network analytic services, crowd sourcing services, and the like for obtaining parameter data (e.g., determination that a person or entity is qualified for the subsidized loan, determining a social value of providing the subsidized loan or removing a subsidization from a loan, determining that a subsidizing entity is legitimate, determining appropriate subsidization terms based on characteristics of the buyer and/or subsidizer, etc.).

The term foreclose, foreclosure, foreclose or foreclosure condition, default foreclosure collateral, default collateral, (and similar terms) as utilized herein should be understood broadly. Without limitation to any other aspect or description of the present disclosure, foreclose condition, default and the like describe the failure of a borrower to meet the terms of a loan. Without limitation to any other aspect or description of the present disclosure foreclose and foreclosure include processes by which a lender attempts to recover, from a borrower in a foreclose or default condition, the balance of a loan or take away in lieu, the right of a borrower to redeem a mortgage held in security for the loan. Failure to meet the terms of the loan may include failure to make specified payments, failure to adhere to a payment schedule, failure to make a balloon payment, failure to appropriately secure the collateral, failure to sustain collateral in a specified condition (e.g. in good repair), acquisition of a second loan, and the like. Foreclosure may include a notification to the borrower, the public, jurisdictional authorities of the forced sale of an item collateral such as through a foreclosure auction. Upon foreclosure, an item of collateral may be placed on a public auction site (such as eBay™ or an auction site appropriate for a particular type of property. The minimum opening bid for the item of collateral may be set by the lender and may cover the balance of the loan, interest on the loan, fees associated with the foreclosure and the like.

Attempts to recover the balance of the loan may include the transfer of the deed for an item of collateral in lieu of foreclosure (e.g. a real-estate mortgage where the borrower holds the deed for a property which acts as collateral for the mortgage loan). Foreclosure may include taking possession of or repossessing the collateral (e.g. a car, a sports vehicle such as a boat, ATV, ski-mobile, jewelry). Foreclosure may include securing an item of collateral associated with the loan (such as by locking a connected device, such as a smart lock, smart container, or the like that contains or secures collateral). Foreclosure may include arranging for the shipping of an item of collateral by a carrier, freight forwarder of the like. Foreclosure may include arranging for the transport of an item of collateral by a drone, a robot, or the like for transporting collateral. In embodiments, a loan may allow for the substitution of collateral or the shifting of the lien from an item of collateral initially used to secure the loan to a substitute collateral where the substitute collateral is of higher value (to the lender) than the initial collateral or is an item in which the borrower has a greater equity. The result of the substitution of collateral is that when the loan goes into foreclosure, it is the substitute collateral that may be the subject of a forced sale or seizure. Certain usages of the word default may not apply to such as to foreclose but rather to a regular or default condition of an item. One of skill in the art, having the benefit of the disclosure herein and knowledge about a contemplated system ordinarily available to that person, can readily determine which aspects of the present disclosure will benefit from foreclosure, and/or how to combine processes and systems from the present disclosure to enhance or benefit from foreclosure. Certain considerations for the person of skill in the art, in determining whether the term foreclosure, foreclose condition, default and the like is referring to failure of a borrower to meet the terms of a loan and the related attempts by the lender to recover the balance of the loan or obtain ownership of the collateral.

The terms validation of title, title validation, validating title, and similar terms, as utilized herein should be understood broadly. Without limitation to any other aspect or description of the present disclosure validation of title and title validation include any efforts to verify or confirm the ownership or interest by an individual or entity in an item of property such as a vehicle, a ship, a plane, a building, a home, real estate property, undeveloped land, a farm, a crop, a municipal facility, a warehouse, a set of inventory, a commodity, a security, a currency, a token of value, a ticket, a cryptocurrency, a consumable item, an edible item, a beverage, a precious metal, an item of jewelry, a gemstone, an item of intellectual property, an intellectual property right, a contractual right, an antique, a fixture, an item of furniture, an item of equipment, a tool, an item of machinery, and an item of personal property. Efforts to verify ownership may include reference to bills of sale, government documentation of transfer of ownership, a legal will transferring ownership, documentation of retirement of liens on the item of property, verification of assignment of Intellectual Property to the proposed borrower in the appropriate jurisdiction, and the like. For real-estate property validation may include a review of deeds and records at a courthouse of a country, a state, a county or a district in which a building, a home, real estate property, undeveloped land, a farm, a crop, a municipal facility, a vehicle, a ship, a plane, or a warehouse is located or registered. Certain usages of the word validation may not apply to validation of a title or title validation but rather to confirmation that a process is operating correctly, that an individual has been correctly identified using biometric data, that intellectual property rights are in effect, that data is correct and meaningful, and the like. One of skill in the art, having the benefit of the disclosure herein and knowledge about a contemplated system ordinarily available to that person, can readily determine which aspects of the present disclosure will benefit from title validation, and/or how to combine processes and systems from the present disclosure to enhance or benefit from title validation. Certain considerations for the person of skill in the art, in determining whether the term validation is referring to title validation, are specifically contemplated within the scope of the present disclosure.

Without limitation to any other aspect or description of the present disclosure, validation includes any validating system including, without limitation, validating title for collateral or security for a loan, validating conditions of collateral for security or a loan, validating conditions of a guarantee for a loan, and the like. For instance, a validation service may provide lenders a mechanism to deliver loans with more certainty, such as through validating loan or security information components (e.g., income, employment, title, conditions for a loan, conditions of collateral, and conditions of an asset). In a non-limiting example, a validation service circuit may be structured to validate a plurality of loan information components with respect to a financial entity configured to determine a loan condition for an asset. Certain components may not be considered a validating system individually, but may be considered validating in an aggregated system—for example, an Internet of Things component may not be considered a validating component on its own, however an Internet of Things component utilized for asset data collection and monitoring may be considered a validating component when applied to validating a reliability parameter of a personal guarantee for a load when the Internet of Things component is associated with a collateralized asset. In certain embodiments, otherwise similar looking systems may be differentiated in determining whether such systems are for validation. For example, a blockchain-based ledger may be used to validate identities in one instance and to maintain confidential information in another instance. Accordingly, the benefits of the present disclosure may be applied in a wide variety of systems, and any such systems may be considered a system for validation herein, while in certain embodiments a given system may not be considered a validating system herein. One of skill in the art, having the benefit of the disclosure herein and knowledge about a contemplated system ordinarily available to that person, can readily determine which aspects of the present disclosure will benefit a particular system, and/or how to combine processes and systems from the present disclosure to enhance operations of the contemplated system. Certain considerations for the person of skill in the art, in determining whether a contemplated system is a validating system and/or whether aspects of the present disclosure can benefit or enhance the contemplated system include, without limitation: a lending platform having a social network monitoring system for validating the reliability of a guarantee for a loan; a lending platform having an Internet of Things data collection and monitoring system for validating reliability of a guarantee for a loan; a lending platform having a crowdsourcing and automated classification system for validating conditions of an issuer for a bond; a crowdsourcing system for validating quality, title, or other conditions of collateral for a loan; a biometric identify validation application such as utilizing DNA or fingerprints; IoT devices utilized to collectively validate location and identity of a fixed asset that is tagged by a virtual asset tag;

validation systems utilizing voting or consensus protocols; artificial intelligence systems trained to recognize and validate events; validating information such as title records, video footage, photographs, or witnessed statements; validation representations related to behavior, such as to validate occurrence of conditions of compliance, to validate occurrence of conditions of default, to deter improper behavior or misrepresentations, to reduce uncertainty, or to reduce asymmetries of information; and the like.

The term underwriting (and similar terms) as utilized herein should be understood broadly. Without limitation to any other aspect or description of the present disclosure, underwriting includes any underwriting, including, without limitation, relating to underwriters, providing underwriting information for a loan, underwriting a debt transaction, underwriting a bond transaction, underwriting a subsidized loan transaction, underwriting a securities transaction, and the like. Underwriting services may be provided by financial entities, such as banks, insurance or investment houses, and the like, whereby the financial entity guarantees payment in case of a determination of a loss condition (e.g., damage or financial loss) and accept the financial risk for liability arising from the guarantee. For instance, a bank may underwrite a loan through a mechanism to perform a credit analysis that may lead to a determination of a loan to be granted, such as through analysis of personal information components related to an individual borrower requesting a consumer loan (e.g., employment history, salary and financial statements publicly available information such as the borrower's credit history), analysis of business financial information components from a company requesting a commercial load (e.g., tangible net worth, ratio of debt to worth (leverage), and available liquidity (current ratio)), and the like. In a non-limiting example, an underwriting services circuit may be structured to underwrite a financial transaction including a plurality of financial information components with respect to a financial entity configured to determine a financial condition for an asset. In certain embodiments, underwriting components may be considered underwriting for some purposes but not for other purposes— for example, an artificial intelligence system to collect and analyze transaction data may be utilized in conjunction with a smart contract platform to monitor loan transactions, but alternately used to collect and analyze underwriting data, such as utilizing a model trained by human expert underwriters. Accordingly, the benefits of the present disclosure may be applied in a wide variety of systems, and any such systems may be considered underwriting herein, while in certain embodiments a given system may not be considered underwriting herein. One of skill in the art, having the benefit of the disclosure herein and knowledge about a contemplated system ordinarily available to that person, can readily determine which aspects of the present disclosure will benefit a particular system, and/or how to combine processes and systems from the present disclosure to enhance operations of the contemplated system. Certain considerations for the person of skill in the art, in determining whether a contemplated system is underwriting and/or whether aspects of the present disclosure can benefit or enhance the contemplated system include, without limitation: a lending platform having an underwriting system for a loan with a set of data-integrated microservices such as including data collection and monitoring services, blockchain services, artificial intelligence services, and smart contract services for underwriting lending entities and transactions; underwriting processes, operations, and services; underwriting data, such as data relating to identities of prospective and actual parties involved insurance and other transactions, actuarial data, data relating to probability of occurrence and/or extent of risk associated with activities, data relating to observed activities and other data used to underwrite or estimate risk; an underwriting application, such as, without limitation, for underwriting any insurance offering, any loan, or any other transaction, including any application for detecting, characterizing or predicting the likelihood and/or scope of a risk, an underwriting or inspection flow about an entity serving a lending solution, an analytics solution, or an asset management solution; underwriting of insurance policies, loans, warranties, or guarantees; a blockchain and smart contract platform for aggregating identity and behavior information for insurance underwriting, such as with an optional distributed ledger to record a set of events, transactions, activities, identities, facts, and other information associated with an underwriting process; a crowdsourcing platform such as for underwriting of various types of loans, and guarantees; an underwriting system for a loan with a set of data-integrated microservices including data collection and monitoring services, blockchain services, artificial intelligence services, and smart contract services for underwriting lending entities and transactions; an underwriting solution to create, configure, modify, set or otherwise handle various rules, thresholds, conditional procedures, workflows, or model parameters; an underwriting action or plan for management a set of loans of a given type or types based on one or more events, conditions, states, actions, secondary loans or transactions to back loans, for collection, consolidation, foreclosure, situations of bankruptcy of insolvency, modifications of existing loans, situations involving market changes, foreclosure activities; adaptive intelligent systems including artificial intelligent models trained on a training set of underwriting activities by experts and/or on outcomes of underwriting actions to generate a set of predictions, classifications, control instructions, plans, models; underwriting system for a loan with a set of data-integrated microservices including data collection and monitoring services, blockchain services, artificial intelligence services, and smart contract services for underwriting lending entities and transactions; and the like.

The term insuring (and similar terms) as utilized herein should be understood broadly. Without limitation to any other aspect or description of the present disclosure, insuring includes any insuring, including, without limitation, providing insurance for a loan, providing evidence of insurance for an asset related to a loan, a first entity accepting a risk or liability for another entity, and the like. Insuring, or insurance, may be a mechanism through which a holder of the insurance is provided protection from a financial loss, such as in a form of risk management against the risk of a contingent or uncertain loss. The insuring mechanism may provide for an insurance, determine the need for an insurance, determine evidence of insurance, and the like, such as related to an asset, transaction for an asset, loan for an asset, security, and the like. An entity which provides insurance may be known as an insurer, insurance company, insurance carrier, underwriter, and the like. For instance, a mechanism for insuring may provide a financial entity with a mechanism to determine evidence of insurance for an asset related to a loan. In a non-limiting example, an insurance service circuit may be structured to determine an evidence condition of insurance for an asset based on a plurality of insurance information components with respect to a financial entity configured to determine a loan condition for an asset. In certain embodiments, components may be considered insuring for some purposes but not for other purposes—for example, a blockchain and smart contract platform may be utilized to manage aspects of a loan transaction such as for identity and confidentiality, but may alternately be utilized to aggregate identity and behavior information for insurance underwriting. Accordingly, the benefits of the present disclosure may be applied in a wide variety of systems, and any such systems may be considered insuring herein, while in certain embodiments a given system may not be considered insuring herein. One of skill in the art, having the benefit of the disclosure herein and knowledge about a contemplated system ordinarily available to that person, can readily determine which aspects of the present disclosure will benefit a particular system, and/or how to combine processes and systems from the present disclosure to enhance operations of the contemplated system. Certain considerations for the person of skill in the art, in determining whether a contemplated system is insuring and/or whether aspects of the present disclosure can benefit or enhance the contemplated system include, without limitation: insurance facilities such as branches, offices, storage facilities, data centers, underwriting operations and others; insurance claims, such as for business interruption insurance, product liability insurance, insurance on goods, facilities, or equipment, flood insurance, insurance for contract-related risks, and many others, as well as claims data relating to product liability, general liability, workers compensation, injury and other liability claims and claims data relating to contracts, such as supply contract performance claims, product delivery requirements, contract claims, claims for damages, claims to redeem points or rewards, claims of access rights, warranty claims, indemnification claims, energy production requirements, delivery requirements, timing requirements, milestones, key performance indicators and others; insurance-related lending; an insurance service, an insurance brokerage service, a life insurance service, a health insurance service, a retirement insurance service, a property insurance service, a casualty insurance service, a finance and insurance service, a reinsurance service; a blockchain and smart contract platform for aggregating identity and behavior information for insurance underwriting; identities of applicants for insurance, identities of parties that may be willing to offer insurance, information regarding risks that may be insured (of any type, without limitation, such as property, life, travel, infringement, health, home, commercial liability, product liability, auto, fire, flood, casualty, retirement, unemployment; distributed ledger may be utilized to facilitate offering and underwriting of microinsurance, such as for defined risks related to defined activities for defined time periods that are narrower than for typical insurance policies; providing insurance for a loan, providing evidence of insurance for property related to a loan; and the like.

The term aggregation (and similar terms) as utilized herein should be understood broadly. Without limitation to any other aspect or description of the present disclosure, an aggregation or to aggregate includes any aggregation including, without limitation, aggregating items together, such as aggregating or linking similar items together (e.g., collateral to provide collateral for a set of loans, collateral items for a set of loans is aggregated in real time based on a similarity in status of the set of items, and the like), collecting data together (e.g., for storage, for communication, for analysis, as training data for a model, and the like), summarizing aggregated items or data into a simpler description, or any other method for creating a whole formed by combining several (e.g., disparate) elements. Further, an aggregator may be any system or platform for aggregating, such as described. Certain components may not be considered aggregation individually but may be considered aggregation in an aggregated system—for example, a collection of loans may not be considered an aggregation of loans of itself but may be an aggregation if collected as such. In a non-limiting example, an aggregation circuit may be structured to provide lenders a mechanism to aggregate loans together from a plurality of loans, such as based on a loan attribute, parameter, term or condition, financial entity, and the like, to become an aggregation of loans. In certain embodiments, an aggregation may be considered an aggregation for some purposes but not for other purposes—for example for example, an aggregation of asset collateral conditions may be collected for the purpose of aggregating loans together in one instance and for the purpose of determining a default action in another instance. Additionally, in certain embodiments, otherwise similar looking systems may be differentiated in determining whether such systems are aggregators, and/or which type of aggregating systems. For example, a first and second aggregator may both aggregate financial entity data, where the first aggregator aggregates for the sake of building a training set for an analysis model circuit and where the second aggregator aggregates financial entity data for storage in a blockchain-based distributed ledger. Accordingly, the benefits of the present disclosure may be applied in a wide variety of systems, and any such systems may be considered as aggregation herein, while in certain embodiments a given system may not be considered aggregation herein. One of skill in the art, having the benefit of the disclosure herein and knowledge about a contemplated system ordinarily available to that person, can readily determine which aspects of the present disclosure will benefit a particular system, and/or how to combine processes and systems from the present disclosure to enhance operations of the contemplated system. Certain considerations for the person of skill in the art, in determining whether a contemplated system is aggregation and/or whether aspects of the present disclosure can benefit or enhance the contemplated system include, without limitation forward market demand aggregation (e.g., blockchain and smart contract platform for forward market demand aggregation, interest expressed or committed in a demand aggregation interface, blockchain used to aggregate future demand in a forward market with respect to a variety of products and services, process a set of potential configurations having different parameters for a subset of configurations that are consistent with each other and the subset of configurations used to aggregate committed future demand for the offering that satisfies a sufficiently large subset at a profitable price, and the like); correlated aggregated data (including trend information) on worker ages, credentials, experience (including by process type) with data on the processes in which those workers are involved; demand for accommodations aggregated in advance and conveniently fulfilled by automatic recognition of conditions that satisfy pre-configured commitments represented on a blockchain (e.g., distributed ledger); transportation offerings aggregated and fulfilled (e.g., with a wide range of pre-defined contingencies); aggregation of goods and services on the blockchain (e.g., a distributed ledger used for demand planning); with respect to a demand aggregation interface (e.g., presented to one or more consumers); aggregation of multiple submissions; aggregating identity and behavior information (e.g., insurance underwriting); accumulation and aggregation of multiple parties; aggregation of data for a set of collateral; aggregated value of collateral or assets (e.g., based on real time condition monitoring, real-time market data collection and integration, and the like); aggregated tranches of loans; collateral for smart contract aggregated with other similar collateral; and the like.

The term linking (and similar terms) as utilized herein should be understood broadly. Without limitation to any other aspect or description of the present disclosure, linking includes any linking, including, without limitation, linking as a relationship between two things or situations (e.g., where one thing affects the other). For instance, linking a subset of similar items such as collateral to provide collateral for a set of loans. Certain components may not be considered linked individually, but may be considered in a process of linking in an aggregated system—for example, a smart contracts circuit may be structured to operate in conjunction with a blockchain circuit as part of a loan processing platform but where the smart contracts circuit processes contracts without storing information through the blockchain circuit, however the two circuits could be linked through the smart contracts circuit linking financial entity information through a distributed ledger on the blockchain circuit. In certain embodiments, linking may be considered linking for some purposes but not for other purposes—for example, linking goods and services for users and radio frequency linking between access points are different forms of linking, where the linking of goods and services for users links things together while an RF link is a communications link between transceivers. Additionally, in certain embodiments, otherwise similar looking systems may be differentiated in determining whether such system are linking, and/or which type of linking. For example, linking similar data together for analysis is different from linking similar data together for graphing. Accordingly, the benefits of the present disclosure may be applied in a wide variety of systems, and any such systems may be considered linking herein, while in certain embodiments a given system may not be considered a linking herein. One of skill in the art, having the benefit of the disclosure herein and knowledge about a contemplated system ordinarily available to that person, can readily determine which aspects of the present disclosure will benefit a particular system, and/or how to combine processes and systems from the present disclosure to enhance operations of the contemplated system. Certain considerations for the person of skill in the art, in determining whether a contemplated system is linking and/or whether aspects of the present disclosure can benefit or enhance the contemplated system include, without limitation linking marketplaces or external marketplaces with a system or platform; linking data (e.g., data cluster including links and nodes); storage and retrieval of data linked to local processes; links (e.g. with respect to nodes) in a common knowledge graph; data linked to proximity or location (e.g., of the asset); linking to an environment (e.g., goods, services, assets, and the like); linking events (e.g., for storage such as in a blockchain, for communication or analysis); linking ownership or access rights; linking to access tokens (e.g., travel offerings linked to access tokens); links to one or more resources (e.g., secured by cryptographic or other techniques); linking a message to a smart contract; and the like.

The term indicator of interest (and similar terms) as utilized herein should be understood broadly. Without limitation to any other aspect or description of the present disclosure, an indicator of interest includes any indicator of interest including, without limitation, an indicator of interest from a user or plurality of users or parties related to a transaction and the like (e.g., parties interested in participating in a loan transaction), the recording or storing of such an interest (e.g., a circuit for recording an interest input from a user, entity, circuit, system, and the like), a circuit analyzing interest related data and setting an indicator of interest (e.g., a circuit setting or communicating an indicator based on inputs to the circuit, such as from users, parties, entities, systems, circuits, and the like), a model trained to determine an indicator of interest from input data related to an interest by one of a plurality of inputs from users, parties, or financial entities, and the like. Certain components may not be considered indicators of interest individually, but may be considered an indicator of interest in an aggregated system—for example, a party may seek information relating to a transaction such as though a translation marketplace where the party is interested in seeking information, but that may not be considered an indicator of interest in a transaction. However, when the party asserts a specific interest (e.g., through a user interface with control inputs for indicating interest) the party's interest may be recorded (e.g., in a storage circuit, in a blockchain circuit), analyzed (e.g., through an analysis circuit, a data collection circuit), monitored (e.g., through a monitoring circuit), and the like. In a non-limiting example, indicators of interest may be recorded (e.g., in a blockchain through a distributed ledger) from a set of parties with respect to the product, service, or the like, such as ones that define parameters under which a party is willing to commit to purchase a product or service. In certain embodiments, an indicator of interest may be considered an indicator of interest for some purposes but not for other purposes—for example, a user may indicate an interest for a loan transaction but that does not necessarily mean the user is indicating an interest in providing a type of collateral related to the loan transaction. For instance, a data collection circuit may record an indicator of interest for the transaction but may have a separate circuit structure for determining an indication of interest for collateral. Additionally, in certain embodiments, otherwise similar looking systems may be differentiated in determining whether such system are determining an indication of interest, and/or which type of indicator of interest exists. For example, one circuit or system may collect data from a plurality of parties to determine an indicator of interest in securing a loan and a second circuit or system may collect data from a plurality of parties to determine an indicator of interest in a determining ownership rights related to a loan. Accordingly, the benefits of the present disclosure may be applied in a wide variety of systems, and any such systems may be considered an indicator of interest herein, while in certain embodiments a given system may not be considered an indicator of interest herein. One of skill in the art, having the benefit of the disclosure herein and knowledge about a contemplated system ordinarily available to that person, can readily determine which aspects of the present disclosure will benefit a particular system, and/or how to combine processes and systems from the present disclosure to enhance operations of the contemplated system. Certain considerations for the person of skill in the art, in determining whether a contemplated system is an indicator of interest and/or whether aspects of the present disclosure can benefit or enhance the contemplated system include, without limitation parties indicating an interest in participating in a transaction (e.g., a loan transaction), parties indicating an interest in securing in a product or service, recording or storing an indication of interest (e.g., through a storage circuit or blockchain circuit), analyzing an indication of interest (e.g., through a data collection and/or monitoring circuit), and the like.

The term accommodations (and similar terms) as utilized herein should be understood broadly. Without limitation to any other aspect or description of the present disclosure, an accommodation includes any service, activity, event, and the like such as including, without limitation, a room, group of rooms, table, seating, building, event, shared spaces offered by individuals (e.g., Airbnb™ spaces), bed-and-breakfasts, workspaces, conference rooms, convention spaces, fitness accommodations, health and wellness accommodations, dining accommodations, and the like, in which someone may live, stay, sit, reside, participate, and the like. As such, an accommodation may be purchased (e.g., a ticket through a sports ticketing application), reserved or booked (e.g., a reservation through a hotel reservation application), provided as a reward or gift, traded or exchanged (e.g., through a marketplace), provided as an access right (e.g., offering by way of an aggregation demand), provided based on a contingency (e.g., a reservation for a room being contingent on the availability of a nearby event), and the like. Certain components may not be considered an accommodation individually but may be considered an accommodation in an aggregated system—for example, a resource such as a room in a hotel may not in itself be considered an accommodation but a reservation for the room may be. For instance, a blockchain and smart contract platform for forward market rights for accommodations may provide a mechanism to provide access rights with respect to accommodations. In a non-limiting example, a blockchain circuit may be structured to store access rights in a forward demand market, where the access rights may be stored in a distributed ledger with related shared access to a plurality of actionable entities. In certain embodiments, an accommodation may be considered an accommodation for some purposes but not for other purposes—for example, a reservation for a room may be an accommodation on its own, but may not be accommodation that is satisfied if a related contingency is not met as agreed upon at the time of the e.g. reservation. Additionally, in certain embodiments, otherwise similar looking systems may be differentiated in determining whether such systems are related to an accommodation, and/or which type of accommodation. For example, an accommodation offering may be made based on different systems, such as one where the accommodation offering is determined by a system collecting data related to forward demand and a second one where the accommodation offering is provided as a reward based on a system processing a performance parameter. Accordingly, the benefits of the present disclosure may be applied in a wide variety of systems, and any such systems may be considered as related to an accommodation herein, while in certain embodiments a given system may not be considered related to an accommodation herein. One of skill in the art, having the benefit of the disclosure herein and knowledge about a contemplated system ordinarily available to that person, can readily determine which aspects of the present disclosure will benefit a particular system, and/or how to combine processes and systems from the present disclosure to enhance operations of the contemplated system. Certain considerations for the person of skill in the art, in determining whether a contemplated system is related to accommodation and/or whether aspects of the present disclosure can benefit or enhance the contemplated system include, without limitation an accommodations provided as determined through a service circuit, trading or exchanging services (e.g., through an application and/or user interface), as an accommodation offering such as with respect to a combination of products, services, and access rights, processed (e.g., aggregation demand for the offering in a forward market), accommodation through booking in advance, accommodation through booking in advance upon meeting a certain condition (e.g., relating to a price within a given time window), and the like.

The term contingencies (and similar terms) as utilized herein should be understood broadly. Without limitation to any other aspect or description of the present disclosure, a contingency includes any contingency including, without limitation, any action that is dependent upon a second action. For instance, a service may be provided as contingent on a certain parameter value, such as collecting data as condition upon an asset tag indication from an Internet of Things circuit. In another instance, an accommodation such as a hotel reservation may be contingent upon a concert (local to the hotel and at the same time as the reservation) proceeding as scheduled. Certain components may not be considered as relating to a contingency individually, but may be considered related to a contingency in an aggregated system—for example, a data input collected from a data collection service circuit may be stored, analyzed, processed, and the like, and not be considered with respect to a contingency, however a smart contracts service circuit may apply a contract term as being contingent upon the collected data. For instance, the data may indicate a collateral status with respect to a loan transaction, and the smart contracts service circuit may apply that data to a term of contract that depends upon the collateral. In certain embodiments, a contingency may be considered contingency for some purposes but not for other purposes—for example, a delivery of contingent access rights for a future event may be contingent upon a loan condition being satisfied, but the loan condition on its own may not be considered a contingency in the absence of the contingency linkage between the condition and the access rights. Additionally, in certain embodiments, otherwise similar looking systems may be differentiated in determining whether such systems are related to a contingency, and/or which type of contingency. For example, two algorithms may both create a forward market event access right token, but where the first algorithm creates the token free of contingencies and the second algorithm creates a token with a contingency for delivery of the token. Accordingly, the benefits of the present disclosure may be applied in a wide variety of systems, and any such systems may be considered a contingency herein, while in certain embodiments a given system may not be considered a contingency herein. One of skill in the art, having the benefit of the disclosure herein and knowledge about a contemplated system ordinarily available to that person, can readily determine which aspects of the present disclosure will benefit a particular system, and/or how to combine processes and systems from the present disclosure to enhance operations of the contemplated system. Certain considerations for the person of skill in the art, in determining whether a contemplated system is a contingency and/or whether aspects of the present disclosure can benefit or enhance the contemplated system include, without limitation a forward market operated within or by the platform may be a contingent forward market, such as one where a future right is vested, is triggered, or emerges based on the occurrence of an event, satisfaction of a condition, or the like; a blockchain used to make a contingent market in any form of event or access token by securely storing access rights on a distributed ledger; setting and monitoring pricing for contingent access rights, underlying access rights, tokens, fees and the like; optimizing offerings, timing, pricing, or the like, to recognize and predict patterns, to establish rules and contingencies; exchanging contingent access rights or underlying access rights or tokens access tokens and/or contingent access tokens; creating a contingent forward market event access right token where a token may be created and stored on a blockchain for contingent access right that could result in the ownership of a ticket; discovery and delivery of contingent access rights to future events; contingencies that influence or represent future demand for an offering, such as including a set of products, services, or the like; pre-defined contingencies; optimized offerings, timing, pricing, or the like, to recognize and predict patterns, to establish rules and contingencies; creation of a contingent future offering within the dashboard; contingent access rights that may result in the ownership of the virtual good or each smart contract to purchase the virtual good if and when it becomes available under defined conditions; and the like.

The term level of service (and similar terms) as utilized herein should be understood broadly. Without limitation to any other aspect or description of the present disclosure, a level of service includes any level of service including, without limitation, any qualitative or quantitative measure of the extent to which a service is provided, such as, and without limitation, a first class vs. business class service (e.g., travel reservation or postal delivery), the degree to which a resource is available (e.g., service level A indicating that the resource is highly available vs. service level C indicating that the resource is constrained, such as in terms of traffic flow restrictions on a roadway), the degree to which an operational parameter is performing (e.g., a system is operating at a high state of service vs a low state of service, and the like. In embodiments, level of service may be multi-modal such that the level of service is variable where a system or circuit provides a service rating (e.g., where the service rating is used as an input to an analytical circuit for determining an outcome based on the service rating). Certain components may not be considered relative to a level of service individually, but may be considered relative to a level of service in an aggregated system—for example a system for monitoring a traffic flow rate may provide data on a current rate but not indicate a level of service, but when the determined traffic flow rate is provided to a monitoring circuit the monitoring circuit may compare the determined traffic flow rate to past traffic flow rates and determine a level of service based on the comparison. In certain embodiments, a level of service may be considered a level of service for some purposes but not for other purposes—for example, the availability of first class travel accommodation may be considered a level of service for determining whether a ticket will be purchased but not to project a future demand for the flight. Additionally, in certain embodiments, otherwise similar looking systems may be differentiated in determining whether such system utilizes a level of service, and/or which type of level of service. For example, an artificial intelligence circuit may be trained on past level of service with respect to traffic flow patterns on a certain freeway and used to predict future traffic flow patterns based on current flow rates, but a similar artificial intelligence circuit may predict future traffic flow patterns based on the time of day. Accordingly, the benefits of the present disclosure may be applied in a wide variety of systems, and any such systems may be considered with respect to levels of service herein, while in certain embodiments a given system may not be considered with respect to levels of service herein. One of skill in the art, having the benefit of the disclosure herein and knowledge about a contemplated system ordinarily available to that person, can readily determine which aspects of the present disclosure will benefit a particular system, and/or how to combine processes and systems from the present disclosure to enhance operations of the contemplated system. Certain considerations for the person of skill in the art, in determining whether a contemplated system is a level of service and/or whether aspects of the present disclosure can benefit or enhance the contemplated system include, without limitation transportation or accommodation offerings with predefined contingencies and parameters such as with respect to price, mode of service, and level of service; warranty or guarantee application, transportation marketplace, and the like.

The term payment (and similar terms) as utilized herein should be understood broadly. Without limitation to any other aspect or description of the present disclosure, a payment includes any payment including, without limitation, an action or process of paying (e.g., a payment to a loan) or of being paid (e.g., a payment from insurance), an amount paid or payable (e.g., a payment of $1000 being made), a repayment (e.g., to pay back a loan), a mode of payment (e.g., use of loyalty programs, rewards points, or particular currencies, including cryptocurrencies) and the like. Certain components may not be considered payments individually, but may be considered payments in an aggregated system—for example, submitting an amount of money may not be considered a payment as such, but when applied to a payment to satisfy the requirement of a loan may be considered a payment (or repayment). For instance, a data collection circuit may provide lenders a mechanism to monitor repayments of a loan. In a non-limiting example, the data collection circuit may be structured to monitor the payments of a plurality of loan components with respect to a financial loan contract configured to determine a loan condition for an asset. In certain embodiments, a payment may be considered a payment for some purposes but not for other purposes—for example, a payment to a financial entity may be for a repayment amount to pay back the loan, or it may be to satisfy a collateral obligation in a loan default condition. Additionally, in certain embodiments, otherwise similar looking systems may be differentiated in determining whether such system are related to a payment, and/or which type of payment. For example, funds may be applied to reserve an accommodation or to satisfy the delivery of services after the accommodation has been satisfied. Accordingly, the benefits of the present disclosure may be applied in a wide variety of systems, and any such systems may be considered a payment herein, while in certain embodiments a given system may not be considered a payment herein. One of skill in the art, having the benefit of the disclosure herein and knowledge about a contemplated system ordinarily available to that person, can readily determine which aspects of the present disclosure will benefit a particular system, and/or how to combine processes and systems from the present disclosure to enhance operations of the contemplated system. Certain considerations for the person of skill in the art, in determining whether a contemplated system is a payment and/or whether aspects of the present disclosure can benefit or enhance the contemplated system include, without limitation, deferring a required payment; deferring a payment requirement; payment of a loan; a payment amount; a payment schedule; a balloon payment schedule; payment performance and satisfaction; modes of payment; and the like.

The term location (and similar terms) as utilized herein should be understood broadly. Without limitation to any other aspect or description of the present disclosure, a location includes any location including, without limitation, a particular place or position of a person, place, or item, or location information regarding the position of a person, place, or item, such as a geolocation (e.g., geolocation of a collateral), a storage location (e.g., the storage location of an asset), a location of a person (e.g., lender, borrower, worker), location information with respect to the same, and the like. Certain components may not be considered with respect to location individually, but may be considered with respect to location in an aggregated system—for example, a smart contract circuit may be structured to specify a requirement for a collateral to be stored at a fixed location but not specify the specific location for a specific collateral. In certain embodiments, a location may be considered a location for some purposes but not for other purposes—for example, the address location of a borrower may be required for processing a loan in one instance, and a specific location for processing a default condition in another instance. Additionally, in certain embodiments, otherwise similar looking systems may be differentiated in determining whether such system are a location, and/or which type of location. For example, the location of a music concert may be required to be in a concert hall seating 10,000 people in one instance but specify the location of an actual concert hall in another. Accordingly, the benefits of the present disclosure may be applied in a wide variety of systems, and any such systems may be considered with respect to a location herein, while in certain embodiments a given system may not be considered with respect to a location herein. One of skill in the art, having the benefit of the disclosure herein and knowledge about a contemplated system ordinarily available to that person, can readily determine which aspects of the present disclosure will benefit a particular system, and/or how to combine processes and systems from the present disclosure to enhance operations of the contemplated system. Certain considerations for the person of skill in the art, in determining whether a contemplated system is considered with respect to a location and/or whether aspects of the present disclosure can benefit or enhance the contemplated system include, without limitation a geolocation of an item or collateral; a storage location of item or asset; location information; location of a lender or a borrower; location-based product or service targeting application; a location-based fraud detection application; indoor location monitoring systems (e.g., cameras, IR systems, motion-detection systems); locations of workers (including routes taken through a location); location parameters; event location; specific location of an event; and the like.

The term route (and similar terms) as utilized herein should be understood broadly. Without limitation to any other aspect or description of the present disclosure, a route includes any route including, without limitation, a way or course taken in getting from a starting point to a destination, to send or direct along a specified course, and the like. Certain components may not be considered with respect to a route individually, but may be considered a route in an aggregated system—for example, a mobile data collector may specify a requirement for a route for collecting data based on an input from a monitoring circuit, but only in receiving that input does the mobile data collector determine what route to take and begin traveling along the route. In certain embodiments, a route may be considered a route for some purposes but not for other purposes—for example possible routes through a road system may be considered differently than specific routes taken through from one location to another location. Additionally, in certain embodiments, otherwise similar looking systems may be differentiated in determining whether such system are specified with respect to a location, and/or which types of locations. For example, routes depicted on a map may indicate possible routes or actual routes taken by individuals. Accordingly, the benefits of the present disclosure may be applied in a wide variety of systems, and any such systems may be considered with respect to a route herein, while in certain embodiments a given system may not be considered with respect to a route herein. One of skill in the art, having the benefit of the disclosure herein and knowledge about a contemplated system ordinarily available to that person, can readily determine which aspects of the present disclosure will benefit a particular system, and/or how to combine processes and systems from the present disclosure to enhance operations of the contemplated system. Certain considerations for the person of skill in the art, in determining whether a contemplated system is utilizing a route and/or whether aspects of the present disclosure can benefit or enhance the contemplated system include, without limitation delivery routes; routes taken through a location; heat map showing routes traveled by customers or workers within an environment; determining what resources are deployed to what routes or types of travel; direct route or multi-stop route, such as from the destination of the consumer to a specific location or to wherever an event takes place; a route for a mobile data collector; and the like.

The term future offering (and similar terms) as utilized herein should be understood broadly. Without limitation to any other aspect or description of the present disclosure, a future offing includes any offer of an item or service in the future including, without limitation, a future offer to provide an item or service, a future offer with respect to a proposed purchase, a future offering made through a forward market platform, a future offering determined by a smart contract circuit, and the like. Further, a future offering may be a contingent future offer or an offer based on conditions resulting on the offer being a future offering, such as where the future offer is contingent upon or with the conditions imposed by a predetermined condition (e.g., a security may be purchased for $1000 at a set future date contingent upon a predetermine state of a market indicator). Certain components may not be considered a future offering individually, but may be considered a future offering in an aggregated system—for example, an offer for a loan may not be considered a future offering if the offer is not authorized through a collective agreement amongst a plurality of parties related to the offer, but may be considered a future offer once a vote has been collected and stored through a distributed ledger, such as through a blockchain circuit. In certain embodiments, a future offering may be considered a future offering for some purposes but not for other purposes—for example, a future offering may be contingent upon a condition being meet in the future, and so the future offering may not be considered a future offer until the condition is met. Additionally, in certain embodiments, otherwise similar looking systems may be differentiated in determining whether such system are future offerings, and/or which type of future offerings. For example, two security offerings may be determined to be offerings to be made at a future time, however, one may have immediate contingencies to be met and thus may not be considered to be a future offering but rather an immediate offering with future declarations. Accordingly, the benefits of the present disclosure may be applied in a wide variety of systems, and any such systems may be considered in association with a future offering herein, while in certain embodiments a given system may not be considered in association with a future offering herein. One of skill in the art, having the benefit of the disclosure herein and knowledge about a contemplated system ordinarily available to that person, can readily determine which aspects of the present disclosure will benefit a particular system, and/or how to combine processes and systems from the present disclosure to enhance operations of the contemplated system. Certain considerations for the person of skill in the art, in determining whether a contemplated system is in association with a future offering and/or whether aspects of the present disclosure can benefit or enhance the contemplated system include, without limitation a forward offering, a contingent forward offering, a forward offing in a forward market platform (e.g., for creating a future offering or contingent future offering associated with identifying offering data from a platform-operated marketplace or external marketplace); a future offering with respect to entering into a smart contract (e.g., by executing an indication of a commitment to purchase, attend, or otherwise consume a future offering), and the like.

The term access right (and derivatives or variations) as utilized herein may be understood broadly to describe an entitlement to acquire or possess a property, article, or other thing of value. A contingent access right may be conditioned upon a trigger or condition being met before such an access right becomes entitled, vested or otherwise defensible. An access right or contingent access right may also serve specific purposes or be configured for different applications or contexts, such as, without limitation, loan-related actions or any service or offering. Without limitation, notices may be required to be provided to the owner of a property, article or item of value before such access rights or contingent access rights are exercised. Access rights and contingent access rights in various forms may be included where discussing a legal action, a delinquent or defaulted loan or agreement, or other circumstances where a lender may be seeking remedy, without limitation. One of skill in the art, having the benefit of the disclosure herein and knowledge ordinarily available about a contemplated system, can readily determine the value of such rights implemented in an embodiment. While specific examples of access rights and contingent access rights are described herein for purposes of illustration, any embodiment benefitting from the disclosures herein, and any considerations understood to one of skill in the art having the benefit of the disclosures herein, are specifically contemplated within the scope of the present disclosure.

The term smart contract (and other forms or variations) as utilized herein may be understood broadly to describe a method, system, connected resource or wide area network offering one or more resources useful to assist or perform actions, tasks or things by embodiments disclosed herein. A smart contract may be a set of steps or a process to negotiate, administrate, restructure or implement an agreement or loan between parties. A smart contract may also be implemented as an application, website, FTP site, server, appliance or other connected component or Internet related system that renders resources to negotiate, administrate, restructure or implement an agreement or loan between parties. A smart contract may be a self-contained system, or may be part of a larger system or component that may also be a smart contract. For example, a smart contract may refer to a loan or an agreement itself, conditions or terms, or may refer to a system to implement such a loan or agreement. In certain embodiments, a smart contract circuit or robotic process automation system may incorporate or be incorporated into automatic robotic process automation system to perform one or more purposes or tasks, whether part of a loan or transaction process, or otherwise. One of skill in the art, having the benefit of the disclosure herein and knowledge ordinarily available about a contemplated system can readily determine the purposes and use of this term as it relates to a smart contract in various forms, embodiments and contexts disclosed herein.

The term allocation of reward (and variations) as utilized herein may be understood broadly to describe a thing or consideration allocated or provided as consideration, or provided for a purpose. The allocation of rewards can be of a financial type, or non-financial type, without limitation. A specific type of allocation of reward may also serve a number of different purposes or be configured for different applications or contexts, such as, without limitation: a reward event, claims for rewards, monetary rewards, rewards captured as a data set, rewards points, and other forms of rewards. Thus an allocation of rewards may be provided as a consideration within the context of a loan or agreement. Systems may be utilized to allocate rewards. The allocation of rewards in various forms may be included where discussing a particular behavior, or encouragement of a particular behavior, without limitation. An allocation of a reward may include an actual dispensation of the award, and/or a recordation of the reward. The allocation of rewards may be performed by a smart contract circuit or a robotic processing automation system. One of skill in the art, having the benefit of the disclosure herein and knowledge ordinarily available about a contemplated system, can readily determine the value of the allocation of rewards in an embodiment. While specific examples of the allocation of rewards are described herein for purposes of illustration, any embodiment benefitting from the disclosures herein, and any considerations understood to one of skill in the art having the benefit of the disclosures herein, are specifically contemplated within the scope of the present disclosure.

The term satisfaction of parameters or conditions (and other derivatives, forms, or variations) as utilized herein may be understood broadly to describe completion, presence or proof of parameters or conditions that have been met. The term generally may relate to a process of determining such satisfaction of parameters or conditions, or may relate to the completion of such a process with a result, without limitation. Satisfaction may result in a successful outcome of other triggers or conditions or terms that may come into execution, without limitation. Satisfaction of parameters or conditions may occur in many different contexts of contracts or loans, such as lending, refinancing, consolidation, factoring, brokering, foreclosure, and data processing (e.g. data collection), or combinations thereof, without limitation. Satisfaction of parameters or conditions may be used in the form of a noun (e.g. the satisfaction of the debt repayment), or may be used in a verb form to describe the process of determining a result to parameters or conditions. For example, a borrower may have satisfaction of parameters by making a certain number of payments on time, or may cause satisfaction of a condition allowing access rights to an owner if a loan defaults, without limitation. In certain embodiments, a smart contract or robotic process automation system may perform or determine satisfaction of parameters or conditions for one or more of the parties and process appropriate tasks for satisfaction of parameters or conditions. In some cases satisfaction of parameters or conditions by the smart contract or robotic process automation system may not complete or be successful, and depending upon such outcomes, this may enable automated action or trigger other conditions or terms. One of skill in the art, having the benefit of the disclosure herein and knowledge ordinarily available about a contemplated system can readily determine the purposes and use of this term in various forms, embodiments and contexts disclosed herein.

The term information (and other forms such as info or informational, without limitation) as utilized herein may be understood broadly in a variety of contexts with respect to an agreement or a loan. The term generally may relate to a larger context, such as information regarding an agreement or loan, or may specifically relate to a finite piece of information (e.g. a specific detail of an event that happened on a specific date). Thus, information may occur in many different contexts of contracts or loans, and may be used in the contexts, without limitation of evidence, transactions, access, and the like. Or, without limitation, information may be used in conjunction with stages of an agreement or transaction, such as lending, refinancing, consolidation, factoring, brokering, foreclosure, and information processing (e.g. data or information collection), or combinations thereof. For example, information as evidence, transaction, access, etc. may be used in the form of a noun (e.g. the information was acquired from the borrower), or may refer as a noun to an assortment of informational items (e.g. the information about the loan may be found in the smart contract), or may be used in the form of characterizing as an adjective (e.g. the borrower was providing an information submission). For example, a lender may collect an overdue payment from a borrower through an online payment, or may have a successful collection of overdue payments acquired through a customer service telephone call. In certain embodiments, a smart contract circuit or robotic process automation system may perform collection, administration, calculating, providing, or other tasks for one or more of the parties and process appropriate tasks relating to information (e.g. providing notice of an overdue payment). In some cases information by the smart contract circuit or robotic process automation system may be incomplete, and depending upon such outcomes this may enable automated action or trigger other conditions or terms. One of skill in the art, having the benefit of the disclosure herein and knowledge ordinarily available about a contemplated system can readily determine the purposes and use of information as evidence, transaction, access, etc. in various forms, embodiments and contexts disclosed herein.

Information may be linked to external information (e.g. external sources). The term more specifically may relate to the acquisition, parsing, receiving, or other relation to an external origin or source, without limitation. Thus, information linked to external information or sources may be used in conjunction with stages of an agreement or transaction, such as lending, refinancing, consolidation, factoring, brokering, foreclosure, and information processing (e.g. data or information collection), or combinations thereof. For example, information linked to external information may change as the external information changes, such as a borrower's credit score, which is based on an external source. In certain embodiments, a smart contract circuit or robotic process automation system may perform acquisition, administration, calculating, receiving, updating, providing or other tasks for one or more of the parties and process appropriate tasks relating to information that is linked to external information. In some cases information that is linked to external information by the smart contract or robotic process automation system may be incomplete, and depending upon such outcomes this may enable automated action or trigger other conditions or terms. One of skill in the art, having the benefit of the disclosure herein and knowledge ordinarily available about a contemplated system can readily determine the purposes and use of this term in various forms, embodiments and contexts disclosed herein.

Information that is a part of a loan or agreement may be separated from information presented in an access location. The term more specifically may relate to the characterization that information can be apportioned, split, restricted, or otherwise separated from other information within the context of a loan or agreement. Thus, information presented or received on an access location may not necessarily be the whole information available for a given context. For example, information provided to a borrower may be different information received by a lender from an external source, and may be different than information received or presented from an access location. In certain embodiments, a smart contract circuit or robotic process automation system may perform separation of information or other tasks for one or more of the parties and process appropriate tasks. One of skill in the art, having the benefit of the disclosure herein and knowledge ordinarily available about a contemplated system, can readily determine the purposes and use of this term in various forms, embodiments and contexts disclosed herein.

The term encryption of information and control of access (and other related terms) as utilized herein may be understood broadly to describe generally whether a party or parties may observe or possess certain information, actions, events or activities relating to a transaction or loan. Encryption of information may be utilized to prevent a party from accessing, observing or receiving information, or may alternatively be used to prevent parties outside the transaction or loan from being able to access, observe or receive confidential (or other) information. Control of access to information relates to the determination of whether a party is entitled to such access of information. Encryption of information or control of access may occur in many different contexts of loans, such as lending, refinancing, consolidation, factoring, brokering, foreclosure, administration, negotiating, collecting, procuring, enforcing, and data processing (e.g. data collection), or combinations thereof, without limitation. An encryption of information or control of access to information may refer to a single instance, or may characterize a larger amount of information, actions, events or activities, without limitation. For example, a borrower or lender may have access to information about a loan, but other parties outside the loan or agreement may not be able to access the loan information due to encryption of the information, or a control of access to the loan details. In certain embodiments, a smart contract circuit or robotic process automation system may perform encryption of information or control of access to information for one or more of the parties and process appropriate tasks for encryption or control of access of information. One of skill in the art, having the benefit of the disclosure herein and knowledge ordinarily available about a contemplated system can readily determine the purposes and use of this term in various forms, embodiments and contexts disclosed herein.

The term potential access party list (and other related terms) as utilized herein may be understood broadly to describe generally whether a party or parties may observe or possess certain information, actions, events, or activities relating to a transaction or loan. A potential access party list may be utilized to authorize one or more parties to access, observe or receive information, or may alternatively be used to prevent parties from being able to do so. A potential access party list information relates to the determination of whether a party (either on the potential access party list or not on the list) is entitled to such access of information. A potential access party list may occur in many different contexts of loans, such as lending, refinancing, consolidation, factoring, brokering, foreclosure, administration, negotiating, collecting, procuring, enforcing and data processing (e.g. data collection), or combinations thereof, without limitation. A potential access party list may refer to a single instance, or may characterize a larger amount of parties or information, actions, events or activities, without limitation. For example, a potential access party list may grant (or deny) access to information about a loan, but other parties outside potential access party list may not be able to (or may be granted) access the loan information. In certain embodiments, a smart contract circuit or robotic process automation system may perform administration or enforcement of a potential access party list for one or more of the parties and process appropriate tasks for encryption or control of access of information. One of skill in the art, having the benefit of the disclosure herein and knowledge ordinarily available about a contemplated system can readily determine the purposes and use of this term in various forms, embodiments and contexts disclosed herein.

The term offering, making an offer, and similar terms as utilized herein should be understood broadly. Without limitation to any other aspect or description of the present disclosure, an offering includes any offer of an item or service including, without limitation, an insurance offering, a security offering, an offer to provide an item or service, an offer with respect to a proposed purchase, an offering made through a forward market platform, a future offering, a contingent offering, offers related to lending (e.g. lending, refinancing, collection, consolidation, factoring, brokering, foreclosure), an offering determined by a smart contract circuit, an offer directed to a customer/debtor, an offering directed to a provider/lender, a 3rd party offer (e.g. regulator, auditor, partial owner, tiered provider) and the like. Offerings may include physical goods, virtual goods, software, physical services, access rights, entertainment content, accommodations, or many other items, services, solutions, or considerations. In an example, a third party offer may be to schedule a band instead of just an offer of tickets for sale. Further, an offer may be based on pre-determined conditions or contingencies. Certain components may not be considered an offering individually, but may be considered an offering in an aggregated system—for example, an offer for insurance may not be considered an offering if the offer is not approved by one or more parties related to the offer, however once approval has been granted, it may be considered an offer. Accordingly, the benefits of the present disclosure may be applied in a wide variety of systems, and any such systems may be considered in association with an offering herein, while in certain embodiments a given system may not be considered in association with an offering herein. One of skill in the art, having the benefit of the disclosure herein and knowledge about a contemplated system ordinarily available to that person, can readily determine which aspects of the present disclosure will benefit a particular system, and/or how to combine processes and systems from the present disclosure to enhance operations of the contemplated system. Certain considerations for the person of skill in the art, in determining whether a contemplated system is in association with an offering and/or whether aspects of the present disclosure can benefit or enhance the contemplated system include, without limitation the item or service being offered, a contingency related to the offer, a way of tracking if a contingency or condition has been met, an approval of the offering, an execution of an exchange of consideration for the offering, and the like.

The term artificial intelligence (AI) solution should be understood broadly. Without limitation to any other aspect of the present disclosure, an AI solution includes a coordinated group of AI related aspects to perform one or more tasks or operations as set forth throughout the present disclosure. An example AI solution includes one or more AI components, including any AI components set forth herein, including at least a neural network, an expert system, and/or a machine learning component. The example AI solution may include as an aspect the types of components of the solution, such as a heuristic AI component, a model based AI component, a neural network of a selected type (e.g., recursive, convolutional, perceptron, etc.), and/or an AI component of any type having a selected processing capability (e.g., signal processing, frequency component analysis, auditory processing, visual processing, speech processing, text recognition, etc.). Without limitation to any other aspect of the present disclosure, a given AI solution may be formed from the number and type of AI components of the AI solution, the connectivity of the AI components (e.g., to each other, to inputs from a system including or interacting with the AI solution, and/or to outputs to the system including or interacting with the AI solution). The given AI solution may additionally be formed from the connection of the AI components to each other within the AI solution, and to boundary elements (e.g., inputs, outputs, stored intermediary data, etc.) in communication with the AI solution. The given AI solution may additionally be formed from a configuration of each of the AI components of the AI solution, where the configuration may include aspects such as: model calibrations for an AI component; connectivity and/or flow between AI components (e.g., serial and/or parallel coupling, feedback loops, logic junctions, etc.); the number, selected input data, and/or input data processing of inputs to an AI component; a depth and/or complexity of a neural network or other component; a training data description of an AI component (e.g., training data parameters such as content, amount of training data, statistical description of valid training data, etc.); and/or a selection and/or hybrid description of a type for an AI component. An AI solution includes a selection of AI elements, flow connectivity of those AI elements, and/or configuration of those AI elements.

One of skill in the art, having the benefit of the present disclosure, can readily determine an AI solution for a given system, and/or configure operations to perform a selection and/or configuration operation for an AI solution for a given system. Certain considerations to determining an AI solution, and/or configuring operations to perform a selection and/or configuration operation for an AI solution include, without limitation: an availability of AI components and/or component types for a given implementation; an availability of supporting infrastructure to implement given AI components (e.g., data input values available, including data quality, level of service, resolution, sampling rate, etc.; availability of suitable training data for a given AI solution; availability of expert inputs, such as for an expert system and/or to develop a model training data set; regulatory and/or policy based considerations including permitted action by the AI solution, requirements for acquisition and/or retention of sensitive data, difficult to obtain data, and/or expensive data); operational considerations for a system including or interacting with the AI solution, including response time specifications, safety considerations, liability considerations, etc.; available computing resources such as processing capability, network communication capability, and/or memory storage capability (e.g., to support initial data, training data, input data such as cached, buffered, or stored input data, iterative improvement state data, output data such as cached, buffered, or stored output data, and/or intermediate data storage, such as data to support ongoing calculations, historical data, and/or accumulation data); the types of tasks to be performed by the AI solution, and the suitability of AI components for those tasks, sensitivity of AI components performing the tasks (e.g., variability of the output space relative to a disturbance size of the input space); the interactions of AI components within the entire AI solution (e.g., a low capability rationality AI component may be coupled with a higher capability AI component that may provide high sensitivity and/or unbounded response to inputs); and/or model implementation considerations (e.g., requirements to re-calibrate, aging constraints of a model, etc.).

A selected and/or configured AI solution may be utilized with any of the systems, procedures, and/or aspects of embodiments as set forth throughout the present disclosure. For example, a system utilizing an expert system may include the expert system as all or a part of a selected, configured AI solution. In another example, a system utilizing a neural network, and/or a combination of neural networks, may include the neural network(s) as all or a part of a selected, configured AI solution. The described aspects of an AI solution, including the selection and configuration of the AI solution, are non-limiting illustrations.

Referring to FIG. 1, an embodiment 100 of a financial, transactional and marketplace enablement system is illustrated wherein a lending enablement platform 100 is enabled and wherein a platform-oriented marketplace 132 may comprise a lending application 144. The lending enablement platform 100 may include a set of systems, applications, processes, modules, services, layers, devices, components, machines, products, sub-systems, interfaces, connections, and other elements (collectively referred in the alternative, except where context indicates otherwise, as the "platform," the "lending platform," the "system," and the like) working in coordination (such as by data integration and organization in a services oriented architecture) to enable intelligent management of a set of entities 198 that may occur, operate, transact or the like within, or own, operate, support or enable, one or more applications, services, solutions, programs or the like of the lending application 144 or external marketplaces 188 that involve lending transactions or lending-related entities, or that may otherwise be part of, integrated with, linked to, or operated on by the lending enablement platform 100. References to a set of services herein should be understood, except where context indicates otherwise, these and other various systems, applications, processes, modules, services, layers, devices, components, machines, products, sub-systems, interfaces, connections, and other types of elements. FIG. 1 includes a management application platform 126 comprising a lending application 144, adaptive intelligence systems 158, monitoring systems 164, data collection system 166, data storage systems 186, all interfacing with data handling layers 168. FIG. 1 also depicts the disclosed systems having process and application outputs and outcomes 151 and in communication with entities 198. Components of the lending application 144 may include underwriting 103, risk management 122, analytics 130, pricing 131, tax 124, crowdsourcing system 120, smart contract 134, blockchain 136, lending model 108, trust and custody 150, platform marketplace 132, fraud 138, regulatory 142, payments 146, and security 148. A set may include multiple members or a single member. The adaptive intelligence systems 158 may include opportunity miners 153, robotic process automation (RPA) 154, artificial intelligence 156, artificial intelligence store 157, and clustering 104. The monitoring systems 164 and data collection system 166 may include software interaction observation 160, functional imaging 161, and physical process observation 162. The data storage system 186 may include access data 170, pricing data 178, asset and facility data 172, claims data 180, worker data 174, accounting data 182, event data 176, and underwriting data 184. Entities 198 may include external marketplaces 188, collateral 102, facilities 190, collaborative robotics 193, workers 194, wearable/portable devices 195, processes 196, and machines 197. As with other embodiments, the lending enablement platform 100 may have various data handling layers, with components, modules, systems, services, components, functions and other elements described in connection with other embodiments described throughout this disclosure and the documents incorporated herein by reference. This may include various adaptive intelligent systems 158, monitoring systems 164, data collection systems 166, and data storage systems 186, as well as a set of interfaces 187 of, to, and/or among each of those systems and/or the various other elements of the lending enablement platform 100. In embodiments the interfaces 187 may include application programming interfaces 112; data integration technologies for extracting, transforming, cleansing, normalizing, deduplicating, loading and the like as data is moved among various services using various protocols and formats (collectively referred to as ETL systems 114); and various ports, portals, connectors, gateways, wired connections, sockets, virtual private networks, containers, secure channels and other connections configured among elements on a one-to-one, one-to-many, or many-to-one basis, such as in unicast, broadcast and multicast transmission (collectively referred to as ports 118). Interfaces 187 may include, be enabled by, integrate with, or interface with a real time operating system (RTOS) 110, such as the FreeRTOS™ operating system, that has a deterministic execution pattern in which a user may define an execution pattern, such as based on assignment of a priority to each thread of execution. An instance of the RTOS 110 may be embedded, such as on a microcontroller of an Internet of Things device, such as one used to monitor various entities 198. The RTOS 110 may provide real-time scheduling (such as scheduling of data transmissions to monitoring systems 164 and data collection systems 166, scheduling of inter-task communication among various service elements, and other timing and synchronization elements). In embodiments the interfaces 187 may use or include a set of libraries that enable secure connection between small, low-power edge devices, such as Internet of Things devices used to monitor various entities 198, and various cloud-deployed services of the lending enablement platform 100, as well as a set of edge devices and the systems that enable them, such as ones running local data processing and computing systems such as AWS IoT Greengrass™ and/or AWS Lambda™ functions, such as to allow local calculation, configuration of data communication, execution of machine learning models (such as for prediction or classification), synchronization of devices or device data, and communication among devices and services. This may include use of local device resources such as serial ports, GPUs, sensors and cameras. In embodiments, data may be encrypted for secure end-to-end communication.

In the context of a lending enablement platform 100 and set of lending application 144, various entities 198 may include any of the wide variety of assets, systems, devices, machines, facilities, individuals or other entities mentioned throughout this disclosure or in the documents incorporated herein by reference, such as, without limitation: machines 197 and their components (e.g., machines that are the subject of a loan or collateral for a loan, such as various vehicles and equipment, as well as machines used to conduct lending transactions, such as automated teller machines, point of sale machines, vending machines, kiosks, smart-card-enabled machines, and many others, including ones used to enable microloans, payday loans and others); financial and transactional processes 196 (such as lending processes, inspection processes, collateral tracking processes, valuation processes, credit checking processes, creditworthiness processes, syndication processes, interest rate-setting processes, software processes (including applications, programs, services, and others), production processes, collection processes, banking processes (e.g., lending processes, underwriting processes, investing processes, and many others), financial service processes, diagnostic processes, security processes, safety processes, assessment processes, payment processes, valuation processes, issuance processes, factoring processes, consolidation processes, syndication processes, collection processes, foreclosure processes, title transfer processes, title verification processes, collateral monitoring processes, and many others); wearable and portable devices 195 (such as mobile phones, tablets, dedicated portable devices for financial applications, data collectors (including mobile data collectors), sensor-based devices, watches, glasses, hearables, head-worn devices, clothing-integrated devices, arm bands, bracelets, neck-worn devices, AR/VR devices, headphones, and many others); workers 194 (such as banking workers, loan officers, financial service personnel, managers, inspectors, brokers (e.g., mortgage brokers), attorneys, underwriters, regulators, assessors, appraisers, process supervisors, security personnel, safety personnel and many others); robotic systems 192 (e.g., physical robots, collaborative robots (e.g., "cobots"), software bots and others); and facilities 190 (such as banking facilities, inventory warehousing facilities, factories, homes, buildings, storage facilities (such as for loan-related collateral, property that is the subject of a loan, inventory (such as related to loans on inventory), personal property, components, packaging materials, goods, products, machinery, equipment, and other items), banking facilities (such as for commercial banking, investing, consumer banking, lending and many other banking activities) and others. In embodiments, various entities 198 may include external marketplaces 188, such as financial, commodities, e-commerce, advertising, and other external marketplaces 188 (including current and futures markets), such as ones within which transactions occur in various goods and services, such that monitoring of the external marketplaces 188 and various entities 198 within them may provide lending-relevant information, such as with respect to the price or value of items, the liquidity of items, the characteristics of items, the rate of depreciation of items, or the like. For example, for various entities that may comprise collateral 102 or assets for asset-backed lending, a monitoring system 164 may monitor not only the collateral 102 or assets, such as by cameras, sensors, or other monitoring systems 164, but may also collect data, such as via data collection systems 166 of various types, with respect to the value, price, or other condition of the collateral 102 or assets, such as by determining market conditions for collateral 102 or assets that are in similar condition, of similar age, having similar specifications, having similar location, or the like. In embodiments, an adaptive intelligent system 158 may include a clustering circuit 104, such as one that groups or clusters various entities 198, including collateral 102, parties, assets, or the like by similarity of attributes, such as a k-means clustering system, self-organizing map system, or other system as described herein and in the documents incorporated herein by reference. The clustering system may organize collections of collateral, collections of assets, collections of parties, and collections of loans, for example, such that they may be monitored and analyzed based on common attributes, such as to enable performance of a subset of transactions to be used to predict performance of others, which in turn may be used for underwriting 103, pricing 131, fraud prevention applications 138, or other applications, including any of the services, solutions, or applications described in connection with FIG. 1 and FIG. 2 or elsewhere throughout this disclosure or the documents incorporated herein by reference. In embodiments condition information about collateral 102 or assets is continuously monitored by a monitoring system 164, such as a set of sensors on the collateral 102 or assets, a set of sensors or cameras in the environment of the collateral 102 or assets, or the like, and market information is collected in real time by a data collection system 166, such that the condition and market information may be time-aligned and used as a basis for real time estimation of the value of the collateral or assets and forward prediction of the future value of the collateral or assets. Present and predicted value for the collateral 102 or assets may be based on a model, which may be accessed and used, such as in a smart contract, to enable automated, or machine-assisted lending on the collateral or assets, such as the underwriting or offering of a microloan on the collateral 102 or assets. Aggregation of data for a set of collateral 102 or set of assets, such as a collection or fleet of collateral 102 or fleet of assets owned by an entity 198 may allow real time portfolio valuation and larger scale lending, including via smart contracts that automatically adjust interest rates and other terms and conditions based on the individual or aggregated value of collateral 102 or assets based on real time condition monitoring and real-time market data collection and integration. Transactions, party information, transfers of title, changes in terms and conditions, and other information may be stored in a blockchain 136, including loan transactions and information (such as condition information for collateral 102 or assets and marketplace data) about the collateral 102 or assets. The smart contract may be configured to require a party to confirm condition information and/or market value information, such as by representations and warranties that are supported or verified by the monitoring systems 164 (which may flag fraud in a fraud prevention application 138). A lending model 108 may be used to value collateral 102 or assets, to determine eligibility for lending based on the condition and/or value of collateral 102 or assets, to set pricing (e.g., interest rates), to adjust terms and conditions, and the like. The lending model 108 may be created by a set of experts, such as using calculated analytics 130 on past lending transactions. The lending model 108 may be populated by data from monitoring systems 164 and data collection systems 166, may pull data from data storage systems 186, and the like. The lending model 108 may be used to configure parameters of a smart contract, such that smart contract terms and conditions automatically adjust based on adjustments in the lending model 108. The lending model 108 may be configured to be improved by artificial intelligence 156, such as by training it on a set of outcomes, such as outcomes from lending transactions (e.g., payment outcomes, default outcomes, performance outcomes, and the like), outcomes on collateral 102 or assets (such as prices or value patterns of collateral or assets over time), outcomes on entities (such as defaults, foreclosures, performance results, on time payments, late payments, bankruptcies, and the like), and others. Training may be used to adjust and improve model parameters and performance, including for classification of collateral or assets (such as automatic classification of type and/or condition, such as using vision-based classification from camera-based monitoring systems 164), prediction of value of collateral 102 or assets, prediction of defaults, prediction of performance, and the like. In embodiments, configuration or handling of smart contracts for lending on collateral 102 or assets may be learned and automated in a robotic process automation (RPA) system 154, such as by training the RPA system 154 to create smart contracts, configure parameters of smart contracts, confirm title to collateral 102 or assets, set terms and conditions of smart contracts, initiate security interests on collateral 102 for smart contracts, monitor status or performance of smart contracts, terminate or initiate termination for default of smart contracts, close smart contracts, foreclose on collateral 102 or assets, transfer title, or the like, such as by using monitoring systems 164 to monitor expert entities 198, such as human managers, as they undertake a training set of similar tasks and actions in the creation, configuration, title confirmation, initiation of security interests, monitoring, termination, closing, foreclosing, and the like for a training set of smart contracts. Once an RPA system 154 is trained, it may efficiently create the ability to provide lending at scale across a wide range of entities and assets that may serve as collateral 102, that may provide guarantees or security, or the like, thereby making loans more readily available for a wider range of situations, entities 198, and collateral 102. The RPA system 154 may itself be improved by artificial intelligence 156, such as by continuously adjusting model parameters, weights, configurations, or the like based on outcomes, such as loan performance outcomes, collateral valuation outcomes, default outcomes, closing rate outcomes, interest rate outcomes, yield outcomes, return-on-investment outcomes, or others. Smart contracts may include or be used for direct lending, syndicated lending, and secondary lending contracts, individual loans or aggregated tranches of loans, and the like.

In embodiments, the lending application 144 of the management application platform 126 may, in various optional embodiments, include, integrate with, or interact with (such as within other embodiments of the lending enablement platform) a set of applications, such as ones by which a lender, a borrower, a guarantor, an operator or owner of a transactional or financial entity, or other user, may manage, monitor, control, analyze, or otherwise interact with one or more elements related to a loan, such as an entity 198 that is a party to a loan, the subject of a loan, the collateral for a loan, or otherwise relevant to the loan. This may include any of the elements noted above in connection with FIG. 1. The set of applications may include a lending application 144 (such as, without limitation, for personal lending, commercial lending, collateralized lending, microlending, peer-to-peer lending, insurance-related lending, asset-backed lending, secured debt lending, corporate debt lending, student loans, subsidized loans, mortgage lending, municipal lending, sovereign debt, automotive lending, pay day loans, loans against receivables, factoring transactions, loans against guaranteed or assured payments (such as tax refunds, annuities, and the like), and many others). The lending application 144 may include, integrate with, or link with one or more of any of a wide range of other types of applications that may be relevant to lending, such as an investment application (such as, without limitation, for investment in tranches of loans, corporate debt, bonds, syndicated loans, municipal debt, sovereign debt, or other types of debt-related securities); an asset management application (such as, without limitation, for managing assets that may be the subject of a loan, the collateral for a loan, assets that back a loan, the collateral for a loan guarantee, or evidence of creditworthiness, assets related to a bond, investment assets, real property, fixtures, personal property, real estate, equipment, intellectual property, vehicles, and other assets); a risk management solution 122 (such as, without limitation, for managing risk or liability with respect to subject of a loan, a party to a loan, or an activity relevant to the performance of a loan, such as a product, an asset, a person, a home, a vehicle, an item of equipment, a component, an information technology system, a security system, a security event, a cybersecurity system, an item of property, a health condition, mortality, fire, flood, weather, disability, business interruption, injury, damage to property, damage to a business, breach of a contract, and others); a marketing application 202 (such as, without limitation, an application for marketing a loan or a tranche of loans, a customer relationship management application for lending, a search engine optimization application for attracting relevant parties, a sales management application, an advertising network application, a behavioral tracking application, a marketing analytics application, a location-based product or service targeting application, a collaborative filtering application, a recommendation engine for loan-related product or service, and others); a trading application (such as, without limitation, an application for trading a loan, a tranche of loans, a portion of a loan, a loan-related interest, or the like, such as a buying application, a selling application, a bidding application, an auction application, a reverse auction application, a bid/ask matching application, or others); a tax application 262 (such as, without limitation, for managing, calculating, reporting, optimizing, or otherwise handling data, events, workflows, or other factors relating to a tax-related impact of a loan); a fraud prevention application 138 (such as, without limitation, one or more of an identity verification application, a biometric identity validation application, a transactional pattern-based fraud detection application, a location-based fraud detection application, a user behavior-based fraud detection application, a network address-based fraud detection application, a black list application, a white list application, a content inspection-based fraud detection application, or other fraud detection application; a security application, solution or service (referred to herein as a security application 148, such as, without limitation, any of the fraud prevention applications 138 noted above, as well as a physical security system (such as for an access control system (such as using biometric access controls, fingerprinting, retinal scanning, passwords, and other access controls), a safe, a vault, a cage, a safe room, or the like), a monitoring system (such as using cameras, motion sensors, infrared sensors and other sensors), a cyber security system (such as for virus detection and remediation, intrusion detection and remediation, spam detection and remediation, phishing detection and remediation, social engineering detection and remediation, cyberattack detection and remediation, packet inspection, traffic inspection, DNS attack remediation and detection, and others) or other security application); an underwriting application 103 (such as, without limitation, for underwriting any loan, guarantee, or other loan-related transaction or obligation, including any application for detecting, characterizing or predicting the likelihood and/or scope of a risk, including underwriting based on any of the data sources, events or entities noted throughout this disclosure or the documents incorporated herein by reference); a blockchain application for storing information as a blockchain 136 (such as, without limitation, a distributed ledger capturing a series of transactions, such as debits or credits, purchases or sales, exchanges of in kind consideration, smart contract events, or the like, a cryptocurrency application, or other blockchain-based application); a real estate application (such as, without limitation, a real estate brokerage application, a real estate valuation application, a real estate mortgage or lending application, a real estate assessment application, or other); a regulatory and/or compliance solution 142 (such as, without limitation, an application for regulating the terms and conditions of a loan, such as the permitted parties, the permitted collateral, the permitted terms for repayment, the permitted interest rates, the required disclosures, the required underwriting process, conditions for syndication, and many others); a platform-oriented marketplace 500 such as marketplace application, solution or service (referred to as a marketplace application, such as, without limitation, a loan syndication marketplace, a blockchain-based marketplace, a cryptocurrency marketplace, a token-based marketplace, a marketplace for items used as collateral, or other marketplace); a warranty or guarantee application (such as, without limitation, an application for a warranty or guarantee with respect to an item that is the subject of a loan, collateral for a loan, or the like, such as a product, a service, an offering, a solution, a physical product, software, a level of service, quality of service, a financial instrument, a debt, an item of collateral, performance of a service, or other item); an analyst application 130 (such as, without limitation, an analytic application with respect to any of the data types, applications, events, workflows, or entities mentioned throughout this disclosure or the documents incorporated by reference herein, such as a big data application, a user behavior application, a prediction application, a classification application, a dashboard, a pattern recognition application, an econometric application, a financial yield application, a return on investment application, a scenario planning application, a decision support application, and many others); a pricing application 131 (such as, without limitation, for pricing of interest rates and other terms and conditions for a loan). Thus, the management application platform 126 may host and enable interaction among a wide range of disparate applications (such term including the above-referenced and other financial or transactional applications, services, solutions, and the like), such that by virtue of shared microservices, shared data infrastructure, and shared intelligence, any pair or larger combination or permutation of such services may be improved relative to an isolated application of the same type.

In embodiments the data collection systems 166 and the monitoring systems 164 may monitor one or more events related to a loan, debt, bond, factoring agreement, or other lending transaction, such as events related to requesting a loan, offering a loan, accepting a loan, providing underwriting information for a loan, providing a credit report, deferring a required payment, setting an interest rate for a loan, deferring a payment requirement, identifying collateral or assets for a loan, validating title for collateral or security for a loan, recording a change in title of property, assessing the value of collateral or security for a loan, inspecting property that is involved in a loan, a change in condition of an entity relevant to a loan, a change in value of an entity that is relevant to a loan, a change in job status of a borrower, a change in financial rating of a lender, a change in financial value of an item offered as a security, providing insurance for a loan, providing evidence of insurance for property related to a loan, providing evidence of eligibility for a loan, identifying security for a loan, underwriting a loan, making a payment on a loan, defaulting on a loan, calling a loan, closing a loan, setting terms and conditions for a loan, foreclosing on property subject to a loan, and modifying terms and conditions for a loan.

Microservices Lending Platform with Data Collection Services, Blockchain and Smart Contracts In embodiments, provided herein is a platform, consisting of various services, components, modules, programs, systems, devices, algorithms, and other elements, for lending. In embodiments, the platform or system includes a set of microservices having a set of application programming interfaces that facilitate connection among the microservices and to the microservices by programs that are external to the platform, wherein the microservices include (a) a multi-modal set of data collection services that collect information about and monitor entities related to a lending transaction; (b) a set of blockchain services for maintaining a secure historical ledger of events related to a loan, the blockchain services having access control features that govern access by a set of parties involved in a loan; (c) a set of application programming interfaces, data integration services, data processing workflows and user interfaces for handling loan-related events and loan-related activities; and (d) a set of smart contract services for specifying terms and conditions of smart contracts that govern at least one of loan terms and conditions, loan-related events and loan-related activities.

In embodiments the entities relevant to lending include a set of entities among lenders, borrowers, guarantors, equipment, goods, systems, fixtures, buildings, storage facilities, and items of collateral.

In embodiments collateral items are monitored and the collateral items are selected from among a vehicle, a ship, a plane, a building, a home, real estate property, undeveloped land, a farm, a crop, a municipal facility, a warehouse, a set of inventory, a commodity, a security, a currency, a token of value, a ticket, a cryptocurrency, a consumable item, an edible item, a beverage, a precious metal, an item of jewelry, a gemstone, an item of intellectual property, an intellectual property right, a contractual right, an antique, a fixture, an item of furniture, an item of equipment, a tool, an item of machinery, and an item of personal property.

In embodiments the multi-modal set of data collection services include services selected from among a set of Internet of Things systems that monitor the entities, a set of cameras that monitor the entities, a set of software services that pull information related to the entities from publicly available information sites, a set of mobile devices that report on information related to the entities, a set of wearable devices worn by human entities, a set of user interfaces by which entities provide information about the entities and a set of crowdsourcing services configured to solicit and report information related to the entities.

In embodiments the events related to a loan are selected from requesting a loan, offering a loan, accepting a loan, providing underwriting information for a loan, providing a credit report, deferring a required payment, setting an interest rate for a loan, deferring a payment requirement, identifying collateral for a loan, validating title for collateral or security for a loan, recording a change in title of property, assessing the value of collateral or security for a loan, inspecting property that is involved in a loan, a change in condition of an entity relevant to a loan, a change in value of an entity that is relevant to a loan, a change in job status of a borrower, a change in financial rating of a lender, a change in financial value of an item offered as a security, providing insurance for a loan, providing evidence of insurance for property related to a loan, providing evidence of eligibility for a loan, identifying security for a loan, underwriting a loan, making a payment on a loan, defaulting on a loan, calling a loan, closing a loan, setting terms and conditions for a loan, foreclosing on property subject to a loan, and modifying terms and conditions for a loan.

In embodiments the set of terms and conditions for the loan that are specified and managed by the set of smart contract services is selected from among a principal amount of debt, a balance of debt, a fixed interest rate, a variable interest rate, a payment amount, a payment schedule, a balloon payment schedule, a specification of collateral, a specification of substitutability of collateral, a party, a guarantee, a guarantor, a security, a personal guarantee, a lien, a duration, a covenant, a foreclose condition, a default condition, and a consequence of default.

In embodiments a set of parties to the loan is selected from among a primary lender, a secondary lender, a lending syndicate, a corporate lender, a government lender, a bank lender, a secured lender, bond issuer, a bond purchaser, an unsecured lender, a guarantor, a provider of security, a borrower, a debtor, an underwriter, an inspector, an assessor, an auditor, a valuation professional, a government official, and an accountant.

In embodiments loan-related activities include activities selected from the set of finding parties interested in participating in a loan transaction, an application for a loan, underwriting a loan, forming a legal contract for a loan, monitoring performance of a loan, making payments on a loan, restructuring or amending a loan, settling a loan, monitoring collateral for a loan, forming a syndicate for a loan, foreclosing on a loan, and closing a loan transaction.

In embodiments the loan is of at least one type selected from among an auto loan, an inventory loan, a capital equipment loan, a bond for performance, a capital improvement loan, a building loan, a loan backed by an account receivable, an invoice finance arrangement, a factoring arrangement, a pay day loan, a refund anticipation loan, a student loan, a syndicated loan, a title loan, a home loan, a venture debt loan, a loan of intellectual property, a loan of a contractual claim, a working capital loan, a small business loan, a farm loan, a municipal bond, and a subsidized loan.

In embodiments smart contract services configure at least one smart contract to automatically undertake a loan-related action based on based on information collected by the multi-modal set of data collection services.

In embodiments the loan-related action is selected from among offering a loan, accepting a loan, underwriting a loan, setting an interest rate for a loan, deferring a payment requirement, modifying an interest rate for a loan, validating title for collateral, recording a change in title, assessing the value of collateral, initiating inspection of collateral, calling a loan, closing a loan, setting terms and conditions for a loan, providing notices required to be provided to a borrower, foreclosing on property subject to a loan, and modifying terms and conditions for a loan.

In embodiments the platform or system may further include an automated agent that processes events relevant to at least one of the value, the condition and the ownership of items of collateral and undertakes an action related to a loan to which the collateral is subject.

In embodiments the loan-related action is selected from among offering a loan, accepting a loan, underwriting a loan, setting an interest rate for a loan, deferring a payment requirement, modifying an interest rate for a loan, validating title for collateral, recording a change in title, assessing the value of collateral, initiating inspection of collateral, calling a loan, closing a loan, setting terms and conditions for a loan, providing notices required to be provided to a borrower, foreclosing on property subject to a loan, and modifying terms and conditions for a loan.

Figure 2:
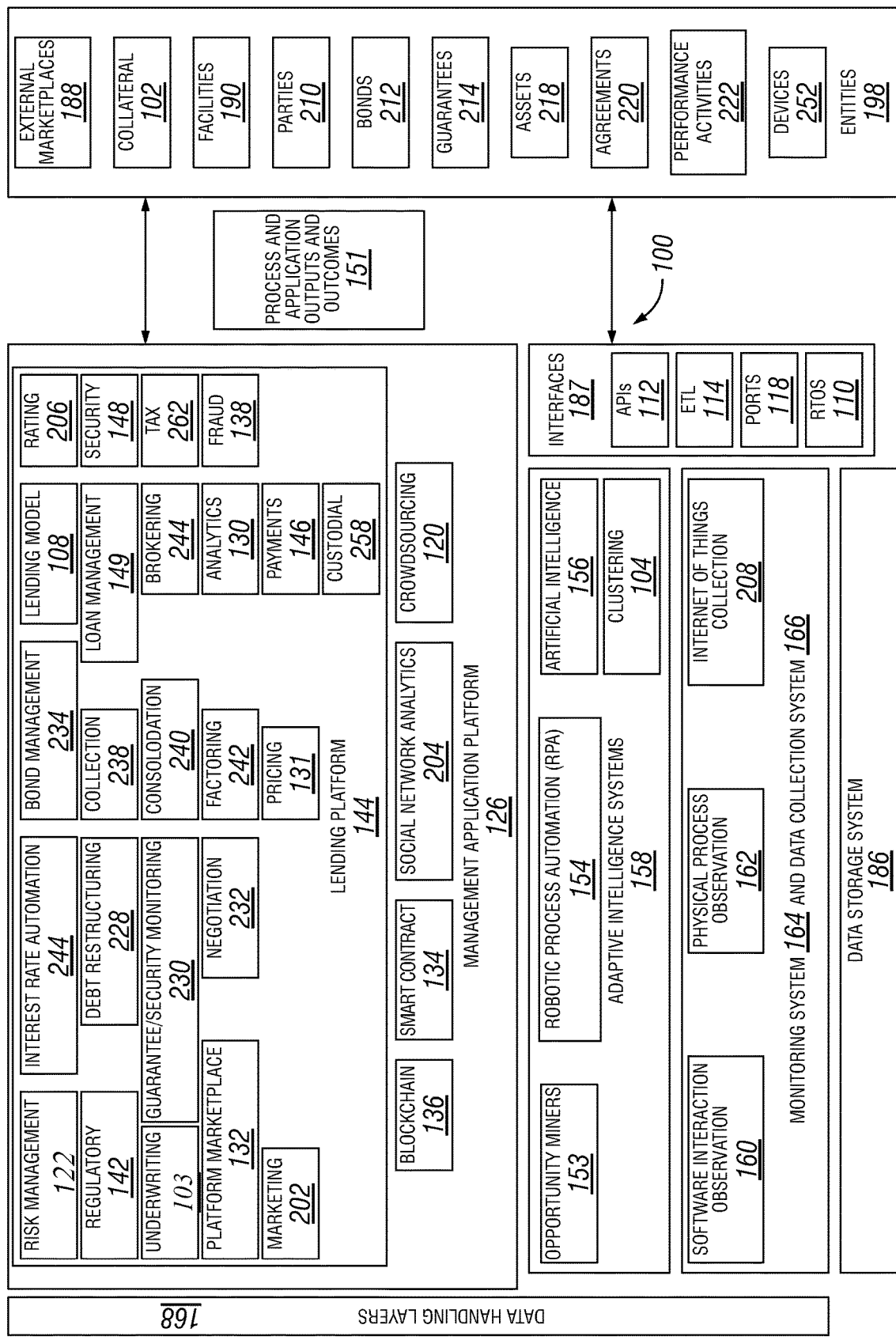
FIG. 2 depicts components and interactions of an embodiment of a lending platform in which a set of lending solutions are supported by a data-integrated set of data collection and monitoring services, adaptive intelligent systems, and data storage systems.

Referring to FIG. 2, additional applications, solutions, programs, systems, services and the like that may be present in a lending application 144 are depicted, which may be interchangeably included in the management application platform 126 with other elements noted in connection with FIG. 1 and elsewhere throughout this disclosure and the documents incorporated herein by reference. Also depicted are additional entities 198, which should be understood to be interchangeable with the other entities 198 described in connection with various embodiments described herein. In addition to elements already noted above, the lending application 144 may include a set of applications, solutions, programs, systems, services and the like that include one or more of a social network analytics application 204 that may find and analyze information about various entities 198 as depicted in one or more social networks (such as, without limitation, information about parties, behavior of parties, conditions of assets, events relating to parties or assets, conditions of facilities, location of collateral 102 or assets, and the like), such as by allowing a user to configure queries that may be initiated and managed across a set of social network sites using data collection systems 166 and monitoring systems 164; a crowdsourcing solution 250; a loan management solution 149 (such as for managing or responding to one or more events related to a loan (such events including, among others, requests for a loan, offering a loan, accepting a loan, providing underwriting information for a loan, providing a credit report, deferring a required payment, setting an interest rate for a loan, deferring a payment requirement, identifying collateral for a loan, validating title for collateral or security for a loan, recording a change in title of property, assessing the value of collateral or security for a loan, inspecting property that is involved in a loan, a change in condition of an entity relevant to a loan, a change in value of an entity that is relevant to a loan, a change in job status of a borrower, a change in financial rating of a lender, a change in financial value of an item offered as a security, providing insurance for a loan, providing evidence of insurance for property related to a loan, providing evidence of eligibility for a loan, identifying security for a loan, underwriting a loan, making a payment on a loan, defaulting on a loan, calling a loan, closing a loan, setting terms and conditions for a loan, foreclosing on property subject to a loan, and modifying terms and conditions for a loan) for setting terms and conditions for a loan (such as a principal amount of debt, a balance of debt, a fixed interest rate, a variable interest rate, a payment amount, a payment schedule, a balloon payment schedule, a specification of collateral, a specification of substitutability of collateral, a party, a guarantee, a guarantor, a security, a personal guarantee, a lien, a duration, a covenant, a foreclose condition, a default condition, and a consequence of default), or managing loan-related activities (such as, without limitation, finding parties interested in participating in a loan transaction, handling an application for a loan, underwriting a loan, forming a legal contract for a loan, monitoring performance of a loan, making payments on a loan, restructuring or amending a loan, settling a loan, monitoring collateral for a loan, forming a syndicate for a loan, foreclosing on a loan, collecting on a loan, consolidating a set of loans, analyzing performance of a loan, handling a default of a loan, transferring title of assets or collateral, and closing a loan transaction)); a rating solution 2102 (such as for rating an entity 198 (such as a party 210, collateral 102, asset 218 or the like), such as involving rating of creditworthiness, financial health, physical condition, status, value, presence or absence of defects, quality, or other attribute); regulatory and/or compliance solution 142 (such as for enabling specification, application and/or monitoring of one or more policies, rules, regulations, procedures, protocols, processes, or the like, such as ones that relate to terms and conditions of loan transactions, steps required in forming lending transactions, steps required in performing lending transactions, steps required with respect to security or collateral, steps required for underwriting, steps required for setting prices, interest rates, or the like, steps required to provide required legal disclosures and notices (e.g., presenting annualized percentage rates) and others); a custodial solution or set of custodial solution 1802 (such as for taking custody of a set of assets 218, collateral 102, or the like (including cryptocurrencies, currency, securities, stocks, bonds, agreements evidencing ownership interests, and many other items), such as on behalf of a party 210, client, or other entity 198 that needs assistance in maintaining security of the items, or in order to provide security, backing, or a guarantee for an obligation, such as one involved in a lending transaction); a loan marketing solution 2002 (such as for enabling a lender to market availability of a loan to a set of prospective borrowers, to target a set of borrowers who are appropriate for a type of transaction, to configure marketing or promotional messages (including placement and timing of the message), to configure advertisement and promotional channels for lending transactions, to configure promotional or loyalty program parameters, and many others); a brokering solution 244 (such as for brokering a set of loan transactions among a set of parties, such as a mortgage loan), which may allow a user to configure a set of preferences, profiles, parameters, or the like to find a set of prospective counterparties to a lending transaction; a bond management solution 234 such as for managing, reporting on, syndicating, consolidating, or otherwise handling a set of bonds (such as municipal bonds, corporate bonds, performance bonds, and others); a guarantee and/or security monitoring solution 230, such as for monitoring, classifying, predicting, or otherwise handling the reliability, quality, status, health condition, financial condition, physical condition or other information about a guarantee, a guarantor, a set of collateral supporting a guarantee, a set of assets backing a guarantee, or the like; a negotiation solution 232, such as for assisting, monitoring, reporting on, facilitating and/or automating negotiation of a set of terms and conditions for a lending transaction (such as, without limitation, a principal amount of debt, a balance of debt, a fixed interest rate, a variable interest rate, a payment amount, a payment schedule, a balloon payment schedule, a specification of collateral, a specification of substitutability of collateral, a party, a guarantee, a guarantor, a security, a personal guarantee, a lien, a duration, a covenant, a foreclosure condition, a default condition, and a consequence of default), which may include a set of user interfaces for configuration of parameters, profiles, preferences, or the like for negotiation, such as ones that use or are informed by the lending model 108 and ones that use, are informed by, or that are automated by or with the assistance of a set of artificial intelligence 156 services and systems, by robotic process automation (RPA) 154, or other adaptive intelligent systems 158; a collection solution 238 for collecting on a loan, which may optionally use, be informed by, or be automated by or with the assistance of a set of artificial intelligence 156 services and systems, by robotic process automation 154, or other adaptive intelligent systems 158, such as based on monitoring the status or condition of various entities 198 with the monitoring systems 164 and data collection systems 166 in order to trigger collection, such as when one or more covenants has not been met, when collateral is in poor condition, when financial health of party is below a threshold, or the like; a consolidation solution 240 for consolidating a set of loans, such as using a lending model 108 that is configured for modeling a consolidated set of loans and such as using or being automated by one or more adaptive intelligent systems 158; a custodial solution 258; a factoring solution 242, such as for monitoring, managing, automating or otherwise handling a set of factoring transactions, such as using a lending model 108 that is configured for modeling factoring transactions and such as using or being automated by one or more adaptive intelligent systems 158; a debt restructuring solution 228, such as for restructuring a set of loans or debt, such as using a lending model 108 that is configured for modeling alternative scenarios for restructuring a set of loans or debt and such as using or being automated by one or more adaptive intelligent systems 158; and/or an interest rate automation solution 224, such as for setting or configuring a set of rules or a model for a set of interest rates for a set of lending transactions or for automating interest rate setting based on information collected by data collection systems 166 or monitoring systems 164 (such as information about conditions, status, health, location, geolocation, storage condition, or other relevant information about any of the entities 198), which may set interest rates or facilitate setting of interest rates for a set of loans, such as using a lending model 108 that is configured for modeling interest rate scenarios for a set of loans and such as using or being automated by one or more of the adaptive intelligent systems 158. As with the solutions referenced in connection with FIG. 1, the various solutions may share the adaptive intelligent systems 158, the monitoring systems 164, the data collection systems 166 and the data storage systems 186, such as by being integrated into the lending enablement platform 100 in a microservices architecture having various appropriate data integration services, APIs 112, and interfaces.

As with the entities 198 described in connection with FIG. 2, entities 198 may further include a range of entities that are involved with loans, debt transactions, bonds, factoring agreements, and other lending transactions, such as: collateral 102 and assets 218 that are used to secure, guarantee, or back a payment obligation (such as vehicles, ships, planes, buildings, homes, real estate, undeveloped land, farms, crops, facilities 190 (such as municipal facilities, factories, warehouses, storage facilities, treatment facilities, plants, and others), systems, a set of inventory, commodities, securities, currencies, tokens of value, tickets, cryptocurrencies, consumables, edibles, beverages, precious metals, jewelry, gemstones, intellectual property, intellectual property rights, contractual rights, legal rights, antiques, fixtures, equipment, furniture, tools, machinery and personal property); a set of parties 210 (such as one or more of a primary lender, a secondary lender, a lending syndicate, a corporate lender, a government lender, a bank lender, a secured lender, a bond issuer, a bond purchaser, an unsecured lender, a guarantor, a provider of security, a borrower, a debtor, an underwriter, an inspector, an assessor, an auditor, an agent, an attorney, a valuation professional, a government official, and/or an accountant); a set of lending agreements 220 (such as loans, bonds 212, lending agreements, corporate debt agreements, subsidized loan agreements, factoring agreements, consolidation agreements, syndication agreements, guarantee agreements, underwriting agreements, and others), which may include a set of terms and conditions that may be searched, collected, monitored, modified or otherwise handled by the lending enablement platform 100, such as interest rates, payment schedules, payment amounts, principal amounts, representations and warranties, indemnities, covenants, and other terms and conditions); a set of guarantees 214 (such as provided by personal guarantors, corporate guarantors, government guarantors, municipal guarantors and others to secure or back a payment obligation or other obligation of a lending agreement 220); a set of performance activities 222 (such as making payments of principal and/or interest, maintaining required insurance, maintaining title, satisfying covenants, maintaining condition of collateral 102 or assets 218, conducting business as required by an agreement; and many others); and devices 252 (such as Internet of Things devices that may be disposed on or in goods, equipment or other items, such as ones that are collateral 102 or assets 218 used to back a payment obligation or to satisfy a covenant or other requirement, or that may be disposed on or in packaging for goods, as well as ones disposed in facilities 190 or other environments where entities 198 may be located). In embodiments a lending agreement 220 may be for a bond, a factoring agreement, a syndication agreement, a consolidation agreement, a settlement agreement, or a loan, such as one or more of an auto loan, an inventory loan, a capital equipment loan, a bond for performance, a capital improvement loan, a building loan, a loan backed by an account receivable, an invoice finance arrangement, a factoring arrangement, a pay day loan, a refund anticipation loan, a student loan, a syndicated loan, a title loan, a home loan, a venture debt loan, a loan of intellectual property, a loan of a contractual claim, a working capital loan, a small business loan, a farm loan, a municipal bond, and a subsidized loan.

As noted elsewhere herein and in documents incorporated by reference, artificial intelligence (such as any of the techniques or systems described throughout this disclosure) in connection with various transactional and marketplace entities 198 and related processes and applications may be used to facilitate, among other things: (a) the optimization, automation and/or control of various functions, workflows, applications, features, resource utilization and other factors, (b) recognition or diagnosis of various states, entities, patterns, events, contexts, behaviors, or other elements; and/or (c) the forecasting of various states, events, contexts or other factors. As artificial intelligence improves, a large array of domain-specific and/or general artificial intelligence systems have become available and are likely to continue to proliferate. As developers seek solutions to domain-specific problems, such as ones relevant to entities 198 and applications of the platform 126 described throughout this disclosure they face challenges in selecting artificial intelligence models (such as what set of neural networks, machine learning systems, expert systems, or the like to select) and in discovering and selecting what inputs may enable effective and efficient use of artificial intelligence for a given problem. As noted above, opportunity miners 153 may assist with the discovery of opportunities for increased automation and intelligence; however, once opportunities are discovered, selection and configuration of an artificial intelligence solution still presents a significant challenge, one that is likely to continue to grow as artificial intelligence solutions proliferate.

One set of solutions to these challenges is an artificial intelligence store 157 that is configured to enable collection, organization, recommendation and presentation of relevant sets of artificial intelligence systems based on one or more attributes of a domain and/or a domain-related problem. In embodiments, an artificial intelligence store 157 may include a set of interfaces to artificial intelligence systems, such as enabling the download of relevant artificial intelligence applications, establishment of links or other connections to artificial intelligence systems (such as links to cloud-deployed artificial intelligence systems via APIs, ports, connectors, or other interfaces) and the like. The artificial intelligence store 157 may include descriptive content with respect to each of a variety of artificial intelligence systems, such as metadata or other descriptive material indicating suitability of a system for solving particular types of problems (e.g., forecasting, NLP, image recognition, pattern recognition, motion detection, route optimization, or many others) and/or for operating on domain-specific inputs, data or other entities. In embodiments, the artificial intelligence store 157 may be organized by category, such as domain, input types, processing types, output types, computational requirements and capabilities, cost, energy usage, and other factors. In embodiments, an interface to the application store 157 may take input from a developer and/or from the platform (such as from an opportunity miner 153) that indicates one or more attributes of a problem that may be addressed through artificial intelligence and may provide a set of recommendations, such as via an artificial intelligence attribute search engine, for a subset of artificial intelligence solutions that may represent favorable candidates based on the developer's domain-specific problem.

In embodiments, a criteria for determining the recommendation may include level of anticipated human oversight. This may include, among others, understanding the level and types of decisions delegated to human workers (such as a decision to purchase a security, taking a market decision, taking a license on Intellectual property, financial limits on actions and ordering (e.g. is the RPA able to order or commit to transactions below a certain amount, above which a human is involved), the level and type of anticipated human supervision of robotic process automation operations, anticipated extent of human supervision and/or governance of model training and training data set selection. A further consideration may be the level and type of anticipated human involvement in the curation of model versions (such as identifying historical break points where input data should be discarded); and others.

In embodiments, criteria for determining the recommendation may include security considerations such as adversarial training and complex environments such as network attacks, viruses, and the like. Additional security considerations may include the security and management of historic training datasets, including audit trails. Security considerations may include the model traceability and accuracy—how will the model or controlling parameters be updated, who will have authority to update the model, how will the updates be documented, how will results be correlated with model updates, and the like. How will version control be implemented and documented. Another security consideration will be documentation of the results of the AI for audit trails including financial results and performance results.

In embodiments, criteria for determining the recommendation may include the availability of different AI types, models, algorithms, or systems (including heuristic/model-based AI, neural networks, and others). Availability may be limited by the computational environment that the user intends to use such as a given cloud platform, an on-premises IT system, or in a network (edge or other network), and the like and whether a given type, model, or algorithm will run in the client's environment. In embodiments, computational factors and configurations may be criteria. For example, the available processor types for running the AI solution in the client's environment may be a factor including: chipsets, modules, device, cloud components, number, and architecture of processor types (e.g. multi-core processor availability, GPU availability, CPU availability, FPGA availability, custom ASIC availability, and the like), and the like. Additionally, computational factors, which may be expressed as minimum capability criteria, may include available processing capacity, both for solution training (for example utilizing a cloud computing resource) and solution operation deployment environment/capacity (e.g. IoT, in-vehicle, edge, mesh network, on-premises IT solution, stand along, or other deployment environments). Additional criteria may include software and interface criteria such as software environment such as operating systems (Linux, Mac, PC, and the like), languages and protocols used for APIs for access to input data sources for solution training as well as access to runtime data and data integration and output.

In embodiments, criteria may include various network factors such as available network type, available network bandwidth (input and output) for both AI solution and AI operation, network uptime, network redundance, variability of delivery times (sequencing of data may vary), as well as any of the other networks and network criteria described herein.

In embodiments, criteria may include performance or quality of service factors, either in absolute terms or relative to other AI and/or non-AI solutions (e.g. conventional models or rule-based solutions. Criteria may include speed/latency, time to train/configure and an AI solution, time for the AI solution to provide result in an operations situation, accuracy, reliability (e.g. ability to resolve to a result), consistency, absence of bias, outcome-based measures of quality such as return on investment (ROI), yield (e.g. output from an AI-governed operation), profitability, revenue and other economic measures, performance on safety measures, performance on security measures, energy consumption (e.g. overall consumption, timing-based consumption (e.g. ability to shift processing from peak to off-peak hours), ability to access renewable or low-carbon energy for model training and/or operation, management of cost of new model training initiatives (power costs, latency and validation of new models), and the like.

In embodiments, criteria may include the ability of the client to access a given type or model due to license requirements and limitations, client policies (described elsewhere herein), regulations (including in the client's jurisdiction, the jurisdiction of the data source (e.g. European data privacy laws and Safe Harbor), a jurisdiction governing a particular model, algorithm, or the like (e.g. export controls on technology), permissions (e.g. training data or operational data), and the like. Additionally, the recommendation may be influenced by the type of problem to be solved and whether there are specialized algorithms or methods that are optimized for the type of problem (e.g. quantum annealing based traveling salesperson solver or even classic heuristic methods that provide for reasonable baseline results).

In embodiments, criteria may include conformance or adherence to governance principles and policies. There may be policies regarding what input data sources may be used to train the AI solution. There may be policies regarding what input sources may be used during operation. For example, input data sources may be reviewed for potential bias, appropriate representation (either demographically or of the problem space), scope, and the like. There may be criteria regarding accreditation or approval of the solution by a regulatory body, certification organization, internal IT review, and the like. There may be policies and procedures that must be in place or implemented with respect to security (e.g. physical security of the system, cybersecurity, and the like), safety requirements (e.g. the safety of the user, the safety of output product, and the like), and the like.

In embodiments, the criteria for recommending an AI solution may include criteria regarding data availability such as the availability of data sources of adequate size, granularity, quality, reliability, location, time zones, accuracy, or the like for effective model training. Additional criteria regarding data availability may include the cost of data for: inputs for the model training, input for model operation. Additional criteria may include the availability of data for operation of the AI solution, and the like. Criteria for AI selection may further include upstream data processing requirements, master data management considerations such as dimensional cleanup and data validation, and the like.

In embodiments, criteria for solution selection may include applicability of the model or solution to the given task or workflow of the "problem" Criteria may include benchmark performance of a given model relative to other models performing a known task type (e.g. a convolutional neural network for 2D object classification, a gated recurrent neural network for tasks that tend to produce exploding errors, or the like). In embodiments, selection of a solution may be based on the solution having a configuration that is similar or analogous to how a biological brain solves a similar task (e.g. where a sequence of neural network models are arranged to mimic a sequence or flow which may include serial elements, parallel elements, feedback loops, conditional logic junctions, graph-driven elements and other flow characteristics), such as a flow of modular or quasi-modular processes, such as ones involved in the brain of a human or other species, such as for in visual or auditory processing, language recognition, speech, motion tracking, image recognition, facial recognition, motion coordination, tactile recognition, spatial orientation, and the like. Criteria may include application of class AI heuristic methods to function as guard rails or operations in less impactful areas.

In embodiments, criteria may include model deployment considerations such as requirements for model updates (e.g. frequency and requirement for retirement of models), management of historic models and maintaining historical decision engine, potential for distributed decision making capabilities, model curation rules (e.g. how long a model or input data are considered valid for training), and the like.

Search results or recommendations may, in embodiments, be based at least in part on collaborative filtering, such as by asking developers to indicate or select elements of favorable models, as well as by clustering, such as by using similarity matrices, k-means clustering, or other clustering techniques that associate similar developers, similar domain-specific problems, and/or similar artificial intelligence solutions. The artificial intelligence store 157 may include e-commerce features, such as ratings, reviews, links to relevant content, and mechanisms for provisioning, licensing, delivery and payment (including allocation of payments to affiliates and or contributors), including ones that operate using smart contract and/or blockchain features to automate purchasing, licensing, payment tracking, settlement of transactions, or other features.

In embodiments, once a solution has been selected or recommended, the solution must be configured for the specific client and problem to be solved. Without limitation, configuration may include any of the factors mentioned in connection with the selection of a solution model above.

Configuration of a set of neural network types (e.g., modules) in a flow (with options for serial elements, parallel elements, feedback loops, conditional logic junctions, graph-driven flows and the like) that recognizes the relative strengths and weaknesses of each type of AI solution (based on any or the selection factors noted above) for the specific task involved in the flow is critical. In an illustrative and non-limiting example of a flow, a) identify something by visual classification (such as with a CNN), b) predict its future state (such as with a gated RNN), c) optimize the future state (using a feed forward neural network). Configuration options include selection of neural network type(s) (including hybrids of different neural networks and/or other model types in various flows as noted above); selection of input model type; setting of initial model weights; setting model size (e.g., number of layers in a deep neural network); selection of computational deployment environment; selection of input data sources for training; selection of input data sources for operation; selection of feedback function/outcome measures; selection of data integration language(s) for inputs and outputs; configuration of APIs for model training; configuration of APIs for model inputs; configuration of APIs for outputs; configuration of access controls (role-based, user-based, policy-based and others); configuration of security parameters; configuration of network protocols; configuration of storage parameters (type, location, duration); configuration of economic factors (e.g., pricing for access; cost-allocation; and others); and others. Additional configuration options may include configuration of data flows (e.g. flows from multiple security exchanges into centralized decision engines), configuration of high availability, fault tolerance environments (e.g. trading systems are required to fail down to operation state that meets services levels requirements), price based data acquisition strategies (e.g. detailed financial data may require additional spending), combination with heuristic methods, coordination of massively parallel decision making environments (e.g. distributed vision systems), and the like. Additional configurations may include making decision models if there is an area that requires further consideration (e.g. pushing a decision to the edge to monitor for a specific event).

In embodiments, another set of solutions, which may be deployed alone or in connection with other elements of the platform, including the artificial intelligence store 157, may include a set of functional imaging capabilities 161, which may comprise monitoring systems 164 and data collection systems 166 and, in some cases, physical process observation systems 162 and/or software interaction observation systems 160, such as for monitoring various transactional and marketplace entities 198. Functional imaging systems 161 may, in embodiments, provide considerable insight into the types of artificial intelligence that are likely to be most effective in solving particular types of problems most effectively. As noted elsewhere in this disclosure and in the documents incorporated by reference herein, computational and networking systems, as they grow in scale, complexity and interconnections, manifest problems of information overload, noise, network congestion, energy waste, and many others. As the Internet of Things grows to hundreds of billions of devices, and virtually countless potential interconnections, optimization becomes exceedingly difficult. One source for insight is the human brain, which faces similar challenges and has evolved, over millennia, reasonable solutions to a wide range of very difficult optimization problems. The human brain operates with a massive neural network organized into interconnected modular systems, each of which has a degree of adaptation to solve particular problems, from regulation of biological systems and maintenance of homeostasis to detection of a wide range of static and dynamic patterns, to recognition of threats and opportunities, among many others.

Setting up a robotic process automation (RPA) system includes selection of the best AI solution and configuration. There may be goals to train the RPA system, typically on human interactions with software and or hardware (e.g., tools) and to use the system in operation, both of which be enhanced by understanding what is going on in the human brain as it solves a problem. In a single neural network solution (using one network to solve a problem in a single step, like single-step translation), the process would likely involve setting initial weights for inputs, selection of input data sources, selection of the type of network (e.g., convolutional or not, gated or not, deep or not, among others), the number of layers, and what inputs are provided to it (and outputs if there are complex outputs). The idea would be to pick inputs and weights that are the ones the human brain tends to use to solve the same problem. For hybrids of multiple AI modules/systems and/or AI combined with more conventional software systems (like control systems, analytic models, rule-based systems, conditional logic systems, and others), the value would likely be the above, plus configuring with awareness of time sequences of processing, such as reflecting patterns of brain activity as visual, auditory, tactile and other sensory information is processed to recognize situation, context, motion, objects, etc. and then other regions (that behave differently) to do things like solve a logic puzzle, calculate, follow an algorithm, proliferate possibilities, and many others. For these, a series of "lego blocks", each consisting of a different neural network or other AI type, can be sequenced, set in parallel, linked by conditional logic, etc. to achieve a solution that automate the process.

In embodiments, identification of a type of reasoning and/or a type of processing may be informed by undertaking brain imaging, such as functional MRI or other magnetic imaging, electroencephalogram (EEG), or other imaging, such as by identifying broad brain activity (e.g., wave bands of activity, such as delta, theta, alpha and gamma waves), by identifying a set of brain regions that are activated and/or inactive during the set interactions of the user that are being used for training of the intelligent agent (such as neocortex regions, such as Fp1 (involved in judgment and decision making), F7 (involved in imagination and mimicry), F3 (involved in analytic deduction), T3 (involved in speech), C3 (involved in storage of facts), T5 (involved in mediation and empathy), P3 (involved in tactical navigation), O1 (involved in visual engineering), Fp2 (involved in process management), F8 (involved in belief systems), F4 (involved in expert classification), T4 (involved in listening and intuition), C4 (involved in artistic creativity), T6 (involved in prediction), P4 (involved in strategic gaming), O2 (involved in abstraction), and/or combinations of the foregoing) or by other neuroscientific, psychological, or similar techniques that provide insight into how humans upon which the intelligent agent is trained are solving particular types of problems that are involved in workflows for which intelligent agents are deployed. In embodiments, an intelligent agent may be configured with a neural network type, or combination of types, that is selected to replicate or simulate a processing activity that is similar to the activity of the brain regions of a human expert that is performing a set of activities for which the intelligent agent is to be trained. As one example among many possible, a trader may be shown to use visual processing region O1 and strategic gaming region P4 of the neocortex when making successful trades, and a neural network may be configured with a convolutional neural network to provide effective replication of visual pattern recognition and a gated recurrent neural network to replicate strategic gaming. In embodiments, a library of neural network resources representing combinations of neural network types that mimic or simulate neocortex activities may be configured to allow selection and implementation of modules that replicate the combinations used by human experts to undertake various activities that are subjects of development of intelligent agents, such as involving robotic process automation. In embodiments, various neural network types from the library may be configured in series and/or in parallel configurations to represent processing flows, which may be arranged to mimic or replicate flows of processing in the brain, such as based on spatiotemporal imaging of the brain when involved in the activity that is the subject of automation. In embodiments, an intelligent software agent for agent development may be trained, such as using any of the training techniques described herein, to select a set of neural network resource types, to arrange the neural network resource types according to a processing flow, to configure input data sources for the set of neural network resources, and/or to automatically deploy the set of neural network types on available computational resources to initiate training of the configured set of neural network resources to perform a desired intelligent agent/automation workflows. In embodiments, the intelligent software agent used for agent development operates on an input data set of spatiotemporal imaging data of a human brain, such as an expert who is performing the workflows that is the subject of development of a further, and uses the spatiotemporal imaging data to automatically select and configure the selection and arrangement of the set of neural network types to initiate learning. Thus, a system for developing an intelligent agent may be configured for (optionally automatic) selection of neural network types and/or arrangements based on spatiotemporal neocortical activity patterns of human users involved in workflows for which the agent is trained. Once developed, the resulting intelligent agent/process automation system may be trained as described throughout this disclosure.

In embodiments, a system for developing an intelligent agent (including the aforementioned agent for development of intelligent agents) may use information from brain imaging of human users to infer (optionally automatically) what data sources should be selected as inputs for an intelligent agent. For example, for processes where neocortex region O1 is highly active (involving visual processing), visual inputs (such as available information from cameras, or visual representations of information like price patterns, among many others) may be selected as favorable data sources. Similarly, for processes involving region C3 (involving storage and retrieval of facts), data sources providing reliable factual information (such as blockchain-based distributed ledgers) may be selected. Thus, a system for developing an intelligent agent may be configured for (optionally automatic) selection of input data types and sources based on spatiotemporal neocortical activity patterns of human users involved in workflows for which the agent is trained.

Functional imaging 161, such as functional magnetic resonance imaging (fMRI), electroencephalogram (EEG), computed tomography (CT) and other brain imaging systems have improved to the point that patterns of brain activity can be recognized in real time and temporally associated with other information, such behaviors, stimulus information, environmental condition data, gestures, eye movements, and other information, such that via functional imaging 161, either alone or in combination with other information collected by monitoring systems 164, the platform may determine and classify what brain modules, operations, systems, and/or functions are employed during the undertaking of a set of tasks or activities, such as ones involving software interaction observation systems 160, physical process observations 162, or a combination thereof. This classification may assist in selection and/or configuration of a set of artificial intelligence solutions, such as from an artificial intelligence store 157, that includes a similar set of capabilities and/or functions to the set of modules and functions of the human brain when undertaking an activity, such as for the initial configuration of a robotic process automation (RPA) system 154 that automates a task performed by an expert human.

In embodiments, a system may receive and/or monitor a set of inputs relating to a user, including image/video feeds, audio feeds, motion sensors, heartbeat monitor, other relevant biosensors, and the like. In embodiments, the system may also receive input relating to actions taken by the monitored user, such as input to a computing device or actions taken with respect to a physical environment in which the user is working. In embodiments, all the collected data is time stamped, so that, for example, a video feed may capture a series of images of a user while the user is performing a task and may concurrently capture the eye movements of the user (e.g. eye gaze tracking) to determine what the user is focusing on (e.g., what is the user looking at on a screen). During this time, the system may also track the user's heart rate or other biological sensor measurements to determine whether the user is engaged in a task that requires intense concentration or less focused concentration. The system may also track the actions taken and may further determine the amount of time taken between actions. An RPA solution can then distribute processing, such as to a heavier, more computationally intensive activity to an AI solution on a cloud platform (like a deep neural network with many layers) and placing less computationally intensive tasks, such as ones where a human makes very quick decisions on minimal input data, on an edge or IoT device platform using a much more compact model, such as a TinyML™ model.

In embodiments, the system may determine the relative amount of time taken between actions, such that long periods of inaction may indicate that the user is involved in work that requires lots of thought, while short periods of inaction may indicate that the user is engaged in work that requires less thought and more action. The system may also monitor an audio feed and/or state of the computing device that a user is working on when the period of inaction occurs, which may be indicative of a user being distracted rather than focusing. Assuming that the user is actively working and not exhibiting distraction, then the system can generate a feature vector relating to the work being performed by the user that indicates the time-stamped data entries, which can be then fed into a machine-learned model. In embodiments, the machine-learned model may determine a brain region (or multiple brain regions) from the set of brain regions that were likely engaged during the work period. In embodiments, the machine-learned model may be trained using a training data set that includes labeled training vectors, where the label of each training vector indicates the brain region (or regions) that were being engaged by a subject when the training vector was generated. For example, each training vector may be labeled with one or more of: Fp1 (involved in judgment and decision making), F7 (involved in imagination and mimicry), F3 (involved in analytic deduction), T3 (involved in speech), C3 (involved in storage of facts), T5 (involved in mediation and empathy), P3 (involved in tactical navigation), O1 (involved in visual engineering), Fp2 (involved in process management), F8 (involved in belief systems), F4 (involved in expert classification), T4 (involved in listening and intuition), C4 (involved in artistic creativity), T6 (involved in prediction), P4 (involved in strategic gaming), O2 (involved in abstraction)). In some embodiments, the training vector may indicate additional data, such as the type of task being performed, whether the subject was successful in completing the task, or other suitable information.

In embodiments, these machine-learned models may be trained on different types of work tasks, such as negotiating, drafting, data entry, responding to emails, analyzing data, reviewing documents, or the like. Furthermore, in some embodiments, such machine-learned models may be trained by one party but leveraged by other parties. In these embodiments, the machine-learned models (and/or the training data vectors) may be bought and sold via a marketplace. Such machine-learned models may be used in a broader RPA system, such that the output of the models may be used as a specific signal in an RPA learning process.

In general, using data from organizations for predicting positioning of organization in market and adjusting processes within organization accordingly. In example embodiments, robotic imaging may be used to capture data of users (e.g., employees or workers) within the organization as they complete various tasks and processes while also correlating this information with completion of these tasks/processes. Obtaining various analytics regarding success of completion of tasks (e.g., efficiency). Then, using data obtained from tracking/monitoring users to determine what factors indicate some users as being more successful than other users in completion of tasks (e.g., based on physical movements of users in doing tasks correctly, brain regions activated, physical strength of users, etc.). This may be based on scanning/monitoring of users as they complete tasks. In some example embodiments, using system to segregate data relating to users with successful task completions versus data relating to users with less successful completions. The system may analyze biological data of workers to determine what makes one worker more successful than other workers. In some example embodiments, this analysis may also be combined with data from machines to determine whether workers are using machines accurately/efficiently. This biological data from workers may also be used to determine whether more workers may be needed to improve efficiency. Using historical data and results from process competitions to look at what improvements should be made whether by training, selecting workers who are better are some tasks vs. others, etc. The resulting analytics on outcomes, and contributions to outcomes, may be used, for example, as a feedback function for weighting the value of particular capabilities for design of an AI solution that is intended to perform the same or similar tasks. In some example embodiments, various data and analysis as described above may be used with respect to determining whether improvements made based on the analysis also improves the market positioning of the organization.

An operator skilled in a task may develop strong memory connections to muscle functions—muscle memory—which translates into easily accomplished actions that, without this connection, would be difficult or at least require repeated attempts, slower operation, and the like. A system that can distinguish between actions accomplished using muscle memory and others may better identify which actions are worth following/repeating/learning.

Understanding the mechanisms of muscle memory—e.g., understanding the pathways from cognition (visual, auditory, etc.) inputs to develop muscle memory may be a basis for understanding how to automate human actions. This may involve repetition type actions, association of one type of action with another type of action based on similarities, such as body positioning, expected result (dropping the hammer in the holster, etc.).

Additional value might be in understanding how two individuals can develop a form of muscle memory that allows them to "get into a rhythm", such as when exchanging physical items. What cues are they exchanging, visually recognizable actions (placement of hand/orientation) and how are those interpreted.

In embodiments, an imaging system may analyze brain images of multiple members of a team for a set of tasks or workflows that involve different types of expertise. Team performance can be tracked, and AI solutions may be configured to replicate the types of neural processing that are undertaken by different team members, such as motion tracking and coordination by one team member and executive decision making by another.

In embodiments, an imaging system may analyze brain images of multiple members of a mock trial or negotiation practice sessions for a set of verbal exchanges regarding an argument, point-count-point, and the like for negotiations, and the like. In addition to brain images, audio capture and bio-indicators of response to exchanges could also be harvested to increase the range of multi-dimensional data useful for learning how to automate human actions associated with successful negotiation and the like.

Given the level of abstraction humans use to trigger actions, e.g. recognizing an alarm tone or recognizing an action from a fellow worker, we can get less abstract in machine-machine communication, e.g. the input that triggered the alarm tone can trigger a direct machine-machine communication or, if the fellow worker is now a machine, they can indicate their positioning in their routine indicating they are ready to hand-off their work. This is similar to how less intelligent robots have been automated, even with simple macros where the "intelligence" is wrung out of the process to make it more robust, and there are strategies and methods for this that could be applied to these biologic-type inputs which are a level of abstraction beyond what is needed. This down-shift in complexity can, itself, be trained into the system as they recognize what myriad of "soft" triggers (e.g. image recognition) can be turned into "hard" triggers.)

Using systems like Fp1 (involved in judgment and decision making), P3 (involved in tactical navigation), O1 (involved in visual engineering), Fp2 (involved in process management), F8 (involved in belief systems), and T4 (involved in listening and intuition), the training vectors may indicate, in some embodiments, a system of mixed audio and visual concepts. The system may use an expert system to monitor a set of inputs and reconfigure those inputs to monitor an asset including image feeds at various electromagnetic frequencies (such as visual light, thermal, UV, and the like), and audio feeds from those frequencies to determine use, sounds of use, and possible sounds of concerns. When examples include fixed assets (those that cannot move), ambient measurement of the environment may be measured along with signatures of use or non-use of the product such as lack of motion, thermal imprints, or lack thereof. The changing environment in the room, the contact with asset by user or other fixtures, can cause reconfiguration of the sensors looking to appreciate the space. When fixed in a room, such systems may determine that ambient conditions could be detrimental to the asset such as strong outside lighting (too rich of UV content) relative to more appropriate lighting. Also included is sensing the motion of use. In more moveable assets, detection and parsing of benign motion rather than motion that may have a higher propensity to age or damage an asset can be recorded and characterized as an aggregated feed.

Risk Management—Combination of F3 (analytic deduction) and Fp1 (judgement and decision making)—Analytics and decision making in the human brain are informed by experience and knowledge, which may be partial, limited, negative, positive, factual, emotional, etc. AI can possibly recognize a situation (sensors, image recognition, proximity, text and conversation analysis, etc.), and apply better risk management in decision making using stored fact-based outcomes for similar situations. This could be applied to enable consumers to make better purchasing and financial decisions. In other applications, it could be applied to emergency response, policing actions, etc.

In embodiments, an AI solution may be configured as a companion risk manager for a main operational AI solution, such as sharing common inputs and resources, but focused on identifying risks, externalities, and other factors that are not required for the core process automation, but may improve governance, safety, emergency response, and other aspects.

In embodiments, an AI solution may be configured as a companion risk manager for a main operational AI solution, such as sharing common inputs and resources, but focused on identifying risks, externalities, and other factors that are not required for the core process automation, but may improve governance, safety, emergency response, and other aspects.

Thus, the platform may include a system that takes input from a functional imaging system to configure, optionally automatically based on matching of attributes between one or more biological systems, such as brain systems, and one or more artificial intelligence systems, a set of artificial intelligence capabilities for a robotic process automation system. Selection and configuration may further comprise selection of inputs to robotic process automation and/or artificial intelligence that are configured at least in part based on functional imaging of the brain while workers undertake tasks, such as selection of visual inputs (such as images from cameras) where vision systems of the brain are highly activated, selection of acoustic inputs where auditory systems of the brain are highly activated, selection of chemical inputs (such as chemical sensors) where olfactory systems of the brain are highly activated, or the like. Thus, a biologically aware robotic process automation system may be improved by having initial configuration, or iterative improvement, be guided, either automatically or under developer control, by imaging-derived information collected as workers perform expert tasks that may benefit from automation.

Functional imaging may provide insight into which tasks involve serial processing versus parallel processing, providing insight into the type of AI solution that may be best suited to a similar tasks (e.g. is it best to receive language and visual data/inputs at once (in parallel) or sequentially). Is there an order in which a user takes in data that might suggest an optimal ordering for performance? Analysis of functional images may enable identification of which computations tasks are most quickly processed through visual inputs versus textual (language processing) and may enable improved matching of task to best input/stimulus.

Functional imaging may enable determining efficiencies resulting from the pairing or multiple combinations of stimuli (e.g., is a task/command most efficiently communicated by providing multiple, diverse inputs at once, and/or is it best to omit certain stimuli from inputs/commands.

Functional imaging may enable ranking tasks or events to perform/solve based on the probabilistic improvement in the performance of a subsequent task (where task could be a computation or an actual action performed by a device based on a data/stimulus input).

Functional imaging may enable measuring negative impacts on performance/computation based on "noise," where noise may be unneeded data, irrelevant data, or overwhelming data sizes—similar to determining "negative stimuli" (in the human context this could be ambient noise in distinguishing a human voice within a cascade of auditory inputs, or ambient lighting in image recognition, or movement in counting objects in a region and so forth.

As one example among many possible, a marketplace host may be shown to use prediction region T6 and judgment and decision making region Fp1 when configuring a new marketplace, such as to predict favorable marketplace configuration parameters (such as to optimize marketplace efficiency profitability, and/or fairness) and to generate decisions related to marketplace parameters, and a neural network may be configured with a neural network to provide effective replication of prediction and a neural network to replicate decision making. The marketplace configuration parameters may include, but are not limited to, assets, asset types, description of assets, method for verification of ownership, method for delivery of traded goods, estimated size of marketplace, methods for advertising the marketplace, methods for controlling the marketplace, regulatory constraints, data sources, insider trading detection techniques, liquidity requirements, access requirements (such as whether to implement dealer-to-dealer trading, dealer-to-customer trading, or customer-to-customer trading), anonymity (such as determining whether counterparty identities are disclosed), continuity of order handling (e.g., continuous or periodic order handling), interaction (e.g., bilateral or multilateral), price discovery, pricing drivers (e.g., order-driven pricing or quote-driven pricing), price formation (e.g., centralized price formation or fragmented price formation), custodial requirements, types of orders allowed (such as limit orders, stop orders, market orders, and off-market orders), supported market types (such as dealer markets, auction markets, absolute auction markets, minimum bid auction markets, reverse auction markets, sealed bid auction markets, Dutch auction markets, multi-step auction markets (e.g., two-step, three-step, n-step, etc.), forward markets, futures markets, secondary markets, derivatives markets, contingent markets, markets for aggregates (e.g., mutual funds), and the like), trading rules (e.g., tick size, trading halts, open/close hours, escrow requirements, liquidity requirements, geographic rules, jurisdictional rules, rules on publicity, insider trading prohibitions, conflict of interest rules, timing rules (e.g., involving spot-market trading, futures trading and the like) and many others), asset listing requirements (e.g., financial reporting requirements, auditing requirements, minimum capital requirements), deposit minimums, trading minimums, verification rules, commission rules, fee rules, marketplace lifetime rules (e.g., short-term marketplace with timing constraints vs. long-term marketplace), and transparency (e.g., the amount and extent of information disseminated).

An RPA system may use AI systems related to biological brain functions F3 (involved in analytic deduction) and O1 (involved in visual engineering) in conjunction with one another to perform tasks related to visual calculus. The tasks related to visual calculus may include, for example, processing image sensor data via the O1 visual engineering system to determine what the RPA system "sees," and how to interpret, classify, identify, etc. what is "seen." Then, the F3 analytic deduction system may perform 1) deductions to determine what has led to the current state of what is "seen," and 2) prediction to determine a future state of what is "seen" based on the current state of visual data. The RPA system may use the T6 prediction function to assist in performing such predictions. The deductions may be useful in determining a cause of an issue, inefficiency, or problem in a system being analyzed. The predictions may be useful in determining solutions to problems and/or potential efficiency improvements. The AI system using F3, O1, and/or T6 may then also be used to choose a machine learned model suitable for performing the problem solving and/or efficiency improvement. For example, in a manufacturing environment, the RPA system and AI system may intake data from a plurality of visual IoT sensors, the visual data being from one or more sites on the manufacturing floor. The O1 visual engineering system may determine and/or classify what the visual data is seeing, such as one or more machines, products, assembly lines, etc. The F3 analytic deduction system may determine whether one or more of the machines, products, assembly lines, etc. are indicative of issues or inefficiencies. The T6 system may then make predictions and forward the predictions to a suitable machine learned model for determining solutions to problems and/or improvements to efficiencies.

IoT and Onboard Sensor Platform for Monitoring Collateral for a Loan

In embodiments, provided herein is a platform, consisting of various services, components, modules, programs, systems, devices, algorithms, and other elements, for monitoring collateral for a loan. In embodiments, the platform or system includes (a) a set of Internet of Things services for monitoring an environment for the collateral; a set of sensors positioned on at least one of the collateral, a container for the collateral, and a package for the collateral, the set of sensors configured to associate sensor information sensed by the set of sensors with a unique identifier for the collateral; and a set of blockchain services for taking information from the set of Internet of Things services and the set of sensors and storing the information in a blockchain, wherein access to the blockchain is provided via a secure access control interface for a secured lender for a loan to which the collateral is subject.

In embodiments the loan is of at least one type selected from among an auto loan, an inventory loan, a capital equipment loan, a bond for performance, a capital improvement loan, a building loan, a loan backed by an account receivable, an invoice finance arrangement, a factoring arrangement, a pay day loan, a refund anticipation loan, a student loan, a syndicated loan, a title loan, a home loan, a venture debt loan, a loan of intellectual property, a loan of a contractual claim, a working capital loan, a small business loan, a farm loan, a municipal bond, and a subsidized loan.

In embodiments the collateral items are selected from among a vehicle, a ship, a plane, a building, a home, real estate property, undeveloped land, a farm, a crop, a municipal facility, a warehouse, a set of inventory, a commodity, a security, a currency, a token of value, a ticket, a cryptocurrency, a consumable item, an edible item, a beverage, a precious metal, an item of jewelry, a gemstone, an item of intellectual property, an intellectual property right, a contractual right, an antique, a fixture, an item of furniture, an item of equipment, a tool, an item of machinery, and an item of personal property.

In embodiments the set of Internet of Things services monitors an environment selected from among a real property environment, a commercial facility, a warehousing facility, a transportation environment, a manufacturing environment, a storage environment, a home, and a vehicle.

In embodiments the set of sensors is selected from the group consisting of image, temperature, pressure, humidity, velocity, acceleration, rotational, torque, weight, chemical, magnetic field, electrical field, and position sensors.

In embodiments the platform or system may further include a set of services for reporting on events relevant to at least one of the value, the condition and the ownership of the collateral.

In embodiments the platform or system may further include an automated agent that processes events relevant to at least one of the value, the condition and the ownership of the collateral and undertakes an action related to a loan to which the collateral is subject.

In embodiments the loan-related action is selected from among offering a loan, accepting a loan, underwriting a loan, setting an interest rate for a loan, deferring a payment requirement, modifying an interest rate for a loan, validating title for collateral, recording a change in title, assessing the value of collateral, initiating inspection of collateral, calling a loan, closing a loan, setting terms and conditions for a loan, providing notices required to be provided to a borrower, foreclosing on property subject to a loan, and modifying terms and conditions for a loan.

In embodiments the platform or system may further include a market value data collection service that monitors and reports on marketplace information relevant to the value of the collateral. In embodiments the collateral items are selected from among a vehicle, a ship, a plane, a building, a home, real estate property, undeveloped land, a farm, a crop, a municipal facility, a warehouse, a set of inventory, a commodity, a security, a currency, a token of value, a ticket, a cryptocurrency, a consumable item, an edible item, a beverage, a precious metal, an item of jewelry, a gemstone, an item of intellectual property, an intellectual property right, a contractual right, an antique, a fixture, an item of furniture, an item of equipment, a tool, an item of machinery, and an item of personal property.

In embodiments the market value data collection service monitors pricing or financial data for items that are similar to the collateral in at least one public marketplace.

In embodiments a set of similar items for valuing an item of collateral is constructed using a similarity clustering algorithm based on the attributes of the collateral. In embodiments the attributes are selected from among a category of the collateral, an age of the collateral, a condition of the collateral, a history of the collateral, a storage condition of the collateral and a geolocation of the collateral.

In embodiments the platform or system may further include a set of smart contract services for managing a smart contract for the loan. In embodiments the smart contract services set terms and conditions for the loan. In embodiments the set of terms and conditions for the loan that are specified and managed by the set of smart contract services is selected from among a principal amount of debt, a balance of debt, a fixed interest rate, a variable interest rate, a payment amount, a payment schedule, a balloon payment schedule, a specification of collateral, a specification of substitutability of collateral, a party, a guarantee, a guarantor, a security, a personal guarantee, a lien, a duration, a covenant, a foreclose condition, a default condition, and a consequence of default.

Allocate Collateral for a Loan Using Distributed Ledger and Smart Contract

In embodiments, provided herein is a system for handling a loan having a set of computational services. In embodiments, the platform or system includes (a) a set of blockchain services for supporting a distributed ledger; (b) a set of data collection and monitoring services for monitoring a set of items that provide collateral for a loan; (c) a set of valuation services that use a valuation model to set a value for collateral based on information from the data collection and monitoring services; and (d) a set of smart contract services for establishing a smart lending contract, wherein the smart contract services process output from the set of valuation services and assigns items of collateral sufficient to provide security for the loan to the loan on a distributed ledger that records events relevant to the loan.

In embodiments the set of smart contract services further includes services for specifying terms and conditions of smart contracts that govern at least one of loan terms and conditions, loan-related events and loan-related activities.

In embodiments the loan is of at least one type selected from among an auto loan, an inventory loan, a capital equipment loan, a bond for performance, a capital improvement loan, a building loan, a loan backed by an account receivable, an invoice finance arrangement, a factoring arrangement, a pay day loan, a refund anticipation loan, a student loan, a syndicated loan, a title loan, a home loan, a venture debt loan, a loan of intellectual property, a loan of a contractual claim, a working capital loan, a small business loan, a farm loan, a municipal bond, and a subsidized loan.

In embodiments the set of terms and conditions for the loan that are specified and managed by the set of smart contract services is selected from among a principal amount of debt, a balance of debt, a fixed interest rate, a variable interest rate, a payment amount, a payment schedule, a balloon payment schedule, a specification of collateral, a specification of substitutability of collateral, a party, a guarantee, a guarantor, a security, a personal guarantee, a lien, a duration, a covenant, a foreclose condition, a default condition, and a consequence of default.

In embodiments the collateral items are selected from among a vehicle, a ship, a plane, a building, a home, real estate property, undeveloped land, a farm, a crop, a municipal facility, a warehouse, a set of inventory, a commodity, a security, a currency, a token of value, a ticket, a cryptocurrency, a consumable item, an edible item, a beverage, a precious metal, an item of jewelry, a gemstone, an item of intellectual property, an intellectual property right, a contractual right, an antique, a fixture, an item of furniture, an item of equipment, a tool, an item of machinery, and an item of personal property.

In embodiments the set of data collection and monitoring services includes services selected from among a set of Internet of Things systems that monitor the entities, a set of cameras that monitor the entities, a set of software services that pull information related to the entities from publicly available information sites, a set of mobile devices that report on information related to the entities, a set of wearable devices worn by human entities, a set of user interfaces by which entities provide information about the entities and a set of crowdsourcing services configured to solicit and report information related to the entities.

In embodiments the valuation services include artificial intelligence services that iteratively improve the valuation model based on outcome data relating to transactions in collateral.

In embodiments the valuation services further include a set of market value data collection services that monitor and report on marketplace information relevant to the value of collateral.

In embodiments the set of market value data collection services monitors pricing or financial data for items that are similar to the collateral in at least one public marketplace.

In embodiments a set of similar items for valuing an item of collateral is constructed using a similarity clustering algorithm based on the attributes of the collateral.

In embodiments the attributes are selected from among a category of the collateral, an age of the collateral, a condition of the collateral, a history of the collateral, a storage condition of the collateral and a geolocation of the collateral.

Smart Contract that Sets Primary and Secondary Priority for Lenders on Same Collateral In embodiments, provided herein is a system for handling a loan having a set of computational services. In embodiments, the platform or system includes (a) a set of blockchain services for supporting a distributed ledger; (b) a set of data collection and monitoring services for monitoring a set of items that provide collateral for a loan; and (c) a set of smart contract services for establishing a smart lending contract, wherein the smart contract services assign collateral to a loan on a distributed ledger that records events relevant to the loan and record priority among a set of lending entities with respect to the collateral.

In embodiments the set of smart contract services further includes services for specifying terms and conditions of smart contracts that govern at least one of loan terms and conditions, loan-related events and loan-related activities.

In embodiments the loan is of at least one type selected from among an auto loan, an inventory loan, a capital equipment loan, a bond for performance, a capital improvement loan, a building loan, a loan backed by an account receivable, an invoice finance arrangement, a factoring arrangement, a pay day loan, a refund anticipation loan, a student loan, a syndicated loan, a title loan, a home loan, a venture debt loan, a loan of intellectual property, a loan of a contractual claim, a working capital loan, a small business loan, a farm loan, a municipal bond, and a subsidized loan.

In embodiments the set of terms and conditions for the loan that are specified and managed by the set of smart contract services is selected from among a principal amount of debt, a balance of debt, a fixed interest rate, a variable interest rate, a payment amount, a payment schedule, a balloon payment schedule, a specification of collateral, a specification of substitutability of collateral, a party, a guarantee, a guarantor, a security, a personal guarantee, a lien, a duration, a covenant, a foreclose condition, a default condition, and a consequence of default.

In embodiments the set of the collateral items is selected from among a vehicle, a ship, a plane, a building, a home, real estate property, undeveloped land, a farm, a crop, a municipal facility, a warehouse, a set of inventory, a commodity, a security, a currency, a token of value, a ticket, a cryptocurrency, a consumable item, an edible item, a beverage, a precious metal, an item of jewelry, a gemstone, an item of intellectual property, an intellectual property right, a contractual right, an antique, a fixture, an item of furniture, an item of equipment, a tool, an item of machinery, and an item of personal property.

In embodiments the platform or system may further include a set of valuation services that use a valuation model to set a value for collateral based on information from a set of data collection and monitoring services that monitor items of collateral.

In embodiments the valuation services include artificial intelligence services that iteratively improve the valuation model based on outcome data relating to transactions in collateral.

In embodiments the valuation services further include a set of market value data collection services that monitor and report on marketplace information relevant to the value of collateral.

In embodiments the set of market value data collection services monitors pricing or financial data for items that are similar to the collateral in at least one public marketplace.

In embodiments a set of similar items for valuing an item of collateral is constructed using a similarity clustering algorithm based on the attributes of the collateral.

In embodiments the attributes are selected from among a category of the collateral, an age of the collateral, a condition of the collateral, a history of the collateral, a storage condition of the collateral and a geolocation of the collateral.

In embodiments output from the set of valuation services is used by the smart contract services to apportion value for an item of collateral among a set of lenders.

In embodiments the apportionment of value is based on priority information for the lenders that is recorded in the distributed ledger.

Figure 3:
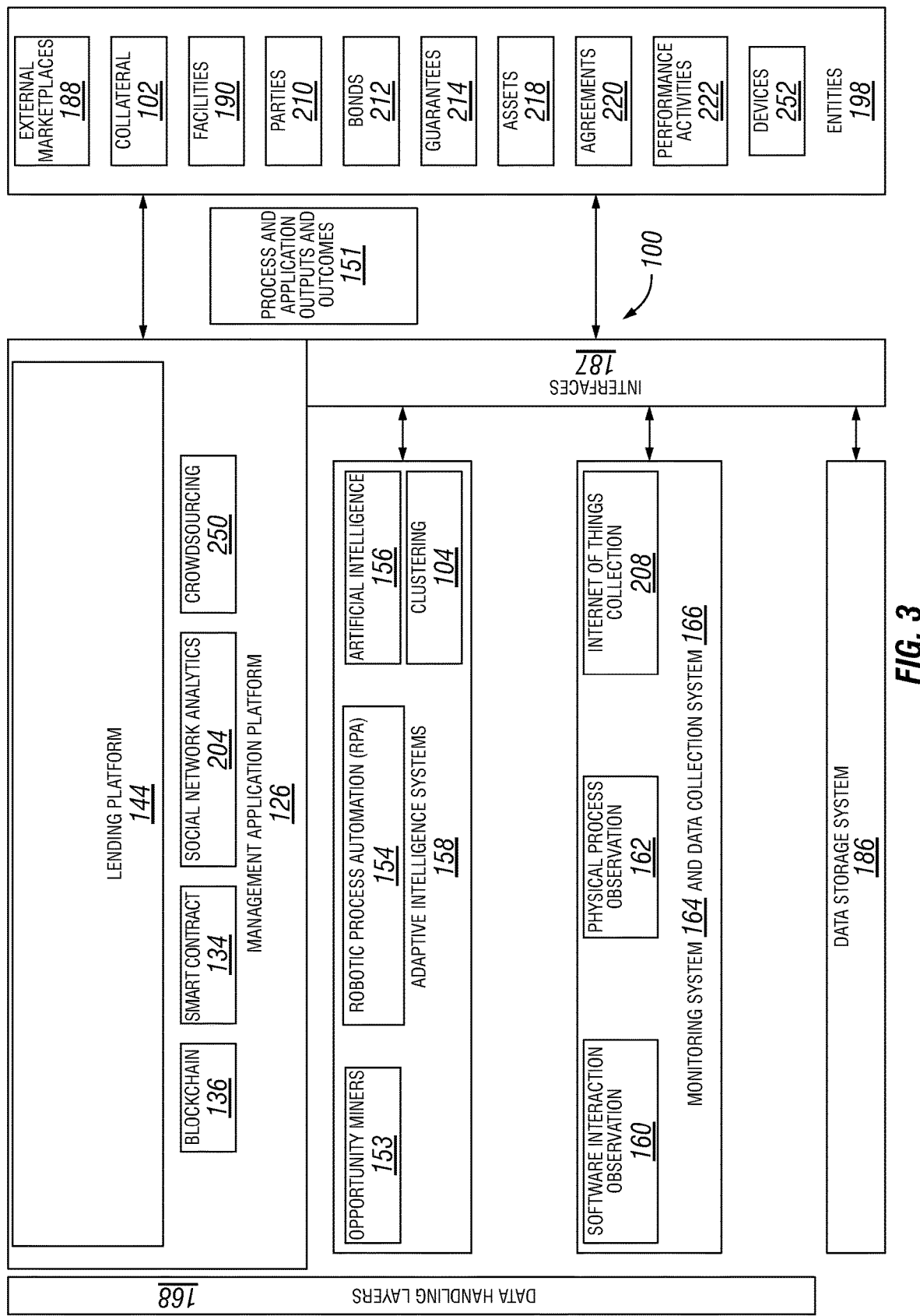
FIG. 3 depicts components and interactions of an embodiment of a lending platform having a set of data integrated blockchain services, smart contract services, social network analytic services, crowdsourcing services and Internet of Things data collection and monitoring services for collecting, monitoring, and processing information about entities involved in or related to a lending transaction.

Referring to FIG. 3, in embodiments, devices 252 may be connected devices that connect (such as through any of the wide range of interfaces 187) to a set of Internet of Things (IoT) data collection services 208, which may be part of or integrated with the data collection systems 166 and monitoring systems 164 of the lending enablement platform 100. The interfaces 187 may include network interfaces, APIs, SDKs, ports, brokers, connectors, gateways, cellular network facilities, data integration interfaces, data migration systems, cloud computing interfaces (including ones that include computational capabilities, such as AWS IoT Greengrass™ Amazon™ Lambda™ and similar systems), and others. For example, the IoT data collection services 208 may be configured to take data from a set of edge data collection devices in the Internet of Things, such as low-power sensor devices (e.g., for sensing movement of entities, for sensing, temperatures, pressures or other attributes about entities 198 or their environments, or the like), cameras that capture still or video images of entities 198, more fully enabled edge devices (such as Raspberry Pi™ or other computing devices, Unix™ devices, and devices running embedded systems, such as including microcontrollers, FPGAs, ASICs and the like), and many others. The IoT data collection services 208 may, in embodiments, collect data about collateral 102 or assets 218, such as, for example, regarding the location, condition (health, physical, or otherwise), quality, security, possession, or the like. For example, an item of personal property, such as a gemstone, vehicle, item of artwork, or the like, may be monitored by a motion sensor and/or a camera having a known location (or having a location confirmed by GPS or other location system), to ensure that it remains in a safe, designated location. The camera can provide evidence that the item remains in undamaged condition and in the possession of a party 210, such as to indicate that it remains appropriate and adequate collateral 102 for a loan. In embodiments this may include items of collateral for microloans, such as clothing, collectibles, and other items.

In embodiments the lending enablement platform 100 has a set of data-integrated microservices including data collection services 166, monitoring services 164, blockchain services for storing data as a blockchain 136, and smart contract services 134 for handling lending entities and transactions. The smart contract services 134 may take data from the data collection systems 166 and monitoring systems 164 (such as from TOT devices) and automatically execute a set of rules or conditions that embody the smart contract based on the collected data. For example, upon recognition that collateral 102 for a loan has been damaged (such as evidenced by a camera or sensor), the smart contract services 134 may automatically initiate a demand for payment of a loan, automatically initiate a foreclosure process, automatically initiate an action to claim substitute or backup collateral, automatically initiate an inspection process, automatically change a payment or interest rate term that is based on the collateral (such as setting an interest rate at a level for an unsecured loan, rather than a secured loan), or the like. Smart contract events may be recorded on a blockchain 136 by the blockchain services, such as in a distributed ledger. Automated monitoring of collateral 102 and assets 218 and handling of loans via smart contract services 134 may facilitate lending to a much wider range of parties 210 and undertaking of loans based on a much wider range of collateral 102 and assets 218 than for conventional loans, as lenders may have greater certainty as to the condition of collateral. Monitoring systems 164 and data collection systems 166 may also monitor and collect data from external marketplaces 188 or for marketplaces operated with the lending enablement platform 100 to maintain awareness of the value of collateral 102 and assets 218, such as to ensure that items remain of adequate value and liquidity to assure repayment of a loan. For example, public e-commerce auction sites like eBay™ can be monitored to confirm that personal property items are of a type and condition likely to be disposed of easily by a lender in a liquid public market, so that the lender is sure to receive payment if the borrower defaults. This may allow loans to be made and administered on a wide range of personal property that is normally difficult to use as collateral. In embodiments an automated foreclosure process may be initiated by a smart contract, which may, upon occurrence of a condition of default that permits foreclosure (such as uncured failure to make payments) include a process for automatically initiating placement of an item of collateral on a public auction site (such as eBay™ or an auction site appropriate for a particular type of property), automatically securing collateral (such as by locking a connected device, such as a smart lock, smart container, or the like that contains or secures collateral), automatically configuring a set of instructions to a carrier, freight forwarder, or the like for shipping collateral, automatically configuring a set of instructions for a drone, a robot, or the like for transporting collateral, or the like.

In embodiments a system is provided for facilitating foreclosure on collateral. The system may include a set of data collection and monitoring services for monitoring at least one condition of a lending agreement; and a set of smart contract services establishing terms and conditions of the lending agreement that include terms and conditions for foreclosure on at least one item that provides collateral securing a repayment obligation of the lending agreement, wherein upon detection of a default based on data collected by the data collection and monitoring services, the set of smart contract services automatically initiates a foreclosure process on the collateral. In embodiments, the set of smart contract services initiates a signal to at least one of a smart lock and a smart container to lock the collateral. In embodiments, the set of smart contract services configures and initiates a listing of the collateral on a public auction site. In embodiments, the set of smart contract services configures and delivers a set of transport instructions for the collateral. In embodiments, the set of smart contract services configures a set of instructions for a drone to transport the collateral. In embodiments, the set of smart contract services configures a set of instructions for a robot to transport the collateral. In embodiments, the set of smart contract services initiates a process for automatically substituting a set of substitute collateral. In embodiments, the set of smart contract services initiates a message to a borrower initiating a negotiation regarding the foreclosure. In embodiments, the negotiation is managed by a robotic process automation system that is trained on a training set of foreclosure negotiations. In embodiments, the negotiation relates to modification of at least one of the interest rate, the payment terms, and the collateral for the lending transaction.

Figure 4:
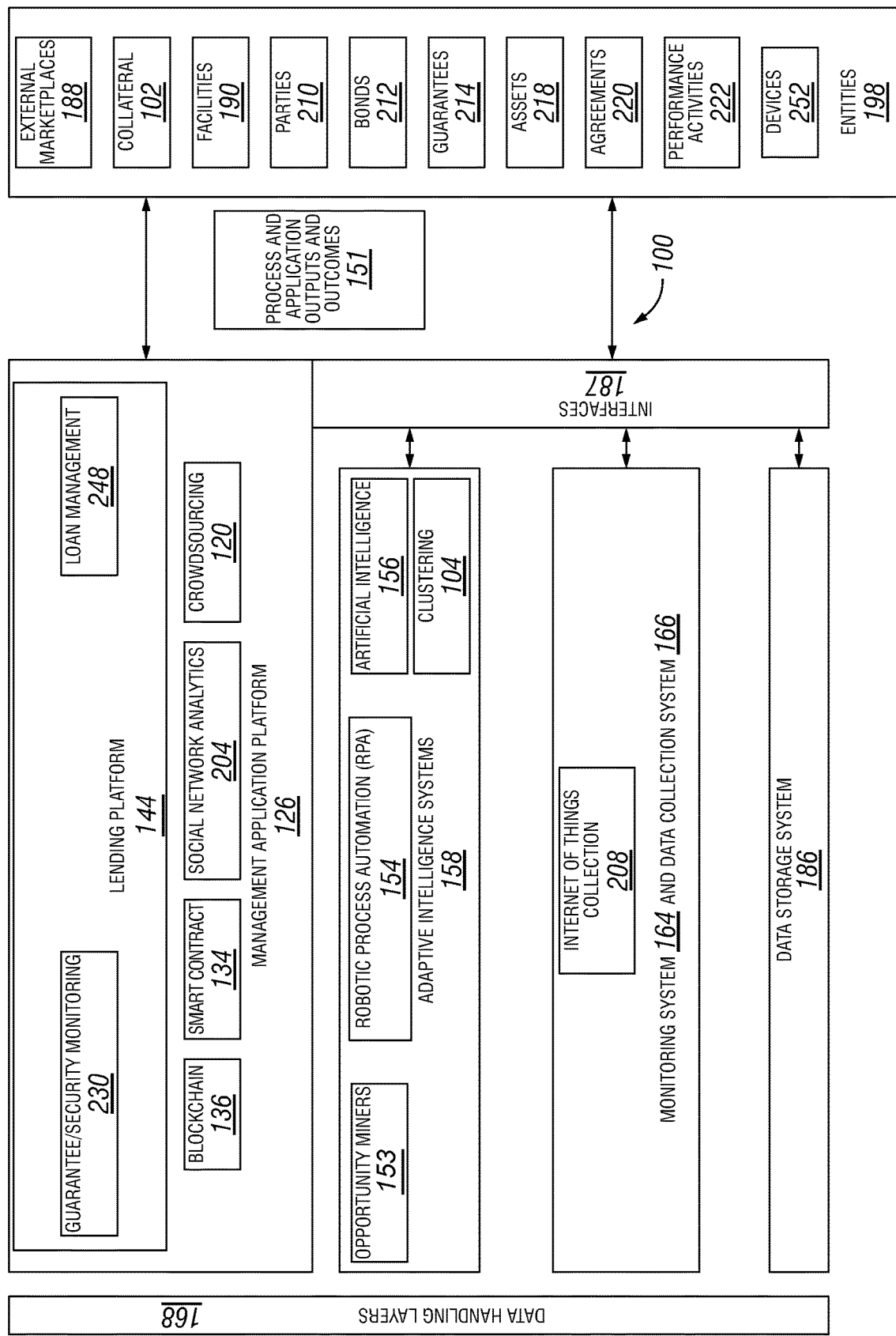
FIG. 4 depicts components and interactions of a lending platform having an Internet of Things and sensor platform for monitoring at least one of a set of assets, a set of collateral, and a guarantee for a loan, a bond, or a debt transaction.

Referring to FIG. 4, in embodiments the lending enablement platform 100 is provided having Internet of Things (IoT) data collection services 208 (with various IoT and edge devices as described throughout this disclosure) for monitoring at least one of a set of assets 218 and a set of collateral 102 for a loan, a bond, or a debt transaction. The lending enablement platform 100 may include a guarantee and/or security monitoring solution 230 for monitoring assets 218 and/or collateral 102 based on the data collected by the IoT data collection services 208, such as where the guarantee and/or security monitoring solution 230 uses various adaptive intelligent systems 158, such as ones that may use model (which may be adjusted, reinforced, trained, or the like, such as using artificial intelligence 156) that determines the condition or value of items based on images, sensor data, location data, or other data of the type collected by the IoT data collection services 208. Monitoring may include monitoring of location of collateral 102 or assets 218, behavior of parties 210, financial condition of parties 210, or the like. The guarantee and/or security monitoring solution 230 may include a set of interfaces by which a user may configure parameters for monitoring, such as rules or thresholds regarding conditions, behaviors, attributes, financial values, locations, or the like, in order to obtain alerts regarding collateral 102 or assets 218. For example, a user may set a rule that collateral must remain in a given jurisdiction, a threshold value of the collateral as a percentage of a loan balance, a minimum status condition (e.g., freedom from damage or defects), or the like. Configured parameters may be used to provide alerts to personnel responsible for monitoring loan compliance and/or used or embodied into one or more smart contract contracts that may take input from the interface of the guarantee and/or security monitoring solution 230 to configure conditions for foreclosure, conditions for changing interest rates, conditions for accelerating payments, or the like. The lending enablement platform 100 may have a loan management solution 248 that allows a loan manager to access information from the IoT data collection services 208 and/or the guarantee and/or security monitoring solution 230, such that a user may manage various actions with respect to a loan (of the many types describe herein, such as setting interest rates, foreclosing, sending notices, and the like) based on the condition of collateral 102 or assets 218, based on events involving entities 198, based on behaviors, based on loan-related actions (such as payments) and other factors. The loan management solution 248 may include a set of interfaces, workflows, models (including adaptive intelligent systems 158) that are configured for a particular type of loan (of the many types described herein) and that allow a user to configure parameters, set rules, set thresholds, design workflows, configure smart contract services, configure blockchain services, and the like in order to facilitate automated or assisted management of a loan, such as enabling automated handing of loan actions by a smart contract in response to collected data from the IoT data collection services 208 or enabling generation of a set of recommended actions for a human user based on that data.

In embodiments a lending platform is provided having a smart contract and distributed ledger platform for managing at least one of ownership of a set of collateral and a set of events related to a set of collateral. A set of smart contract services 134 may, for example, transfer ownership of the collateral 102 or other assets 218 upon recognition of an event of failure to make payment or other default, occurrence of a foreclosure condition (such as failure to satisfy with a covenant or failure to comply with an obligation), or the like, where the ownership transfer and related events are recorded by the set of blockchain services in a distributed ledger, such as one that provides a secure record of title to the assets 218 or collateral 102. As an example, a covenant of a loan embodied in a smart contract may require that collateral 102 have a value that exceeds a minimum fraction (or multiple) of the remaining balance of a loan. Based on data collected about the value of collateral (such as by monitoring one or more external marketplaces 188 or marketplaces of the lending enablement platform 100), a smart contract may calculate whether the covenant is satisfied and record the outcome on a blockchain. If the covenant is not satisfied, such as if market factors indicate that the type of collateral has diminished, while the loan balance remains high, the smart contract may initiate a foreclosure, including recording an ownership transfer on a distributed ledger via the blockchain services. A smart contract may also process events related to an entity 198 such as a party 210. For example, a covenant of a loan may require the party to maintain a level of debt below a threshold or ratio, to maintain a level of income, to maintain a level of profit, or the like. The monitoring systems 164 or data collection systems 166 may provide data used by the smart contract services 134 to determine covenant compliance and to enable automated action, including recording events like foreclosure and ownership transfers on a distributed ledger. In another example, a covenant may relate to a behavior of a party 210 or a legal status of a party 210, such as requiring the party to refrain from taking a particular action with respect to an item of property. For example, a covenant may require a party to comply with zoning regulations that prohibit certain usage of real property. IoT data collection services 208 may be used to monitor the party 210, the property, or other items to confirm compliance with the covenant or to trigger alerts or automated actions in cases of non-compliance.

Smart Contract with Automatic Foreclosure Based on Collateral Value Falling Below Covenant Requirement In embodiments, provided herein is a system for handling a loan having a set of computational services. In embodiments, the platform or system includes (a) a set of data collection and monitoring services for monitoring a set of items that provide collateral for a loan; (b) a set of valuation services that uses a valuation model to set a value for collateral based on information from the data collection and monitoring services; and (c) a set of smart contract services for managing a smart lending contract, wherein the set of smart contract services processes output from the set of valuation services, compares the output to a covenant of the loan that is specified in a smart contract and automatically initiates at least one of a notice of default and a foreclosure action when the value of the collateral is insufficient to satisfy the covenant.

In embodiments the set of smart contract services further includes services for specifying terms and conditions of smart contracts that govern at least one of loan terms and conditions, loan-related events and loan-related activities.

In embodiments the loan is of at least one type selected from among an auto loan, an inventory loan, a capital equipment loan, a bond for performance, a capital improvement loan, a building loan, a loan backed by an account receivable, an invoice finance arrangement, a factoring arrangement, a pay day loan, a refund anticipation loan, a student loan, a syndicated loan, a title loan, a home loan, a venture debt loan, a loan of intellectual property, a loan of a contractual claim, a working capital loan, a small business loan, a farm loan, a municipal bond, and a subsidized loan.

In embodiments the set of terms and conditions for the loan that are specified and managed by the set of smart contract services is selected from among a principal amount of debt, a balance of debt, a fixed interest rate, a variable interest rate, a payment amount, a payment schedule, a balloon payment schedule, a specification of collateral, a specification of substitutability of collateral, a party, a guarantee, a guarantor, a security, a personal guarantee, a lien, a duration, a covenant, a foreclose condition, a default condition, and a consequence of default.

In embodiments the set of collateral items is selected from among a vehicle, a ship, a plane, a building, a home, real estate property, undeveloped land, a farm, a crop, a municipal facility, a warehouse, a set of inventory, a commodity, a security, a currency, a token of value, a ticket, a cryptocurrency, a consumable item, an edible item, a beverage, a precious metal, an item of jewelry, a gemstone, an item of intellectual property, an intellectual property right, a contractual right, an antique, a fixture, an item of furniture, an item of equipment, a tool, an item of machinery, and an item of personal property.

In embodiments the set of data collection and monitoring services includes services selected from among a set of Internet of Things systems that monitor the entities, a set of cameras that monitor the entities, a set of software services that pull information related to the entities from publicly available information sites, a set of mobile devices that report on information related to the entities, a set of wearable devices worn by human entities, a set of user interfaces by which entities provide information about the entities and a set of crowdsourcing services configured to solicit and report information related to the entities.

In embodiments the set of valuation services includes artificial intelligence services that iteratively improve the valuation model based on outcome data relating to transactions in collateral.

In embodiments the set of valuation services further includes a set of market value data collection services that monitor and report on marketplace information relevant to the value of collateral.

In embodiments the set of market value data collection services monitors pricing or financial data for items that are similar to the collateral in at least one public marketplace.

In embodiments a set of similar items for valuing an item of collateral is constructed using a similarity clustering algorithm based on the attributes of the collateral.

In embodiments the attributes are selected from among a category of the collateral, an age of the collateral, a condition of the collateral, a history of the collateral, a storage condition of the collateral and a geolocation of the collateral.

Collateral for Smart Contract Aggregated with Other Similar Collateral

In embodiments, provided herein is a smart contract system for handling a loan having a set of computational services. In embodiments, the platform or system includes (a) a set of data collection and monitoring services for identifying a set of items that provide collateral for a set of loans and collecting information with respect to the collateral items; (b) a set of clustering services for grouping the collateral items based on similarity of attributes of the collateral items; and (c) a set of smart contract services for managing a smart lending contract, wherein the set of smart contract services processes output from the set of clustering services and aggregates and links a subset of similar items of collateral to provide collateral for a set of loans. The clustering circuit 104 may be part of the adaptive intelligent systems 158 and may use any of a wide range of clustering models and techniques, such as ones that are based on attributes of entities 198 that are collected by the monitoring systems 164 or data collection systems 166 and/or stored in the data storage system 186.

In embodiments the loan for which collateral is aggregated may be any of an auto loan, an inventory loan, a capital equipment loan, a bond for performance, a capital improvement loan, a building loan, a loan backed by an account receivable, an invoice finance arrangement, a factoring arrangement, a pay day loan, a refund anticipation loan, a student loan, a syndicated loan, a title loan, a home loan, a venture debt loan, a loan of intellectual property, a loan of a contractual claim, a working capital loan, a small business loan, a farm loan, a municipal bond, and a subsidized loan.

In embodiments the set of collateral items is selected from among a vehicle, a ship, a plane, a building, a home, real estate property, undeveloped land, a farm, a crop, a municipal facility, a warehouse, a set of inventory, a commodity, a security, a currency, a token of value, a ticket, a cryptocurrency, a consumable item, an edible item, a beverage, a precious metal, an item of jewelry, a gemstone, an item of intellectual property, an intellectual property right, a contractual right, an antique, a fixture, an item of furniture, an item of equipment, a tool, an item of machinery, and an item of personal property.

In embodiments clustering the collateral is performed by a clustering algorithm that groups collateral based on attributes collected by the data collection and monitoring services.

In embodiments attributes used for grouping are selected from among a type of item, a category of item, a specification of an item, a product feature set of an item, a model of item, a brand of item, a manufacturer of item, a status of item, a context of item, a state of item, a value of item, a storage location of item, a geolocation of item, an age of item, a maintenance history of item, a usage history of item, an accident history of item, a fault history of item, an ownership of item, an ownership history of item, a price of a type of item, a value of a type of item, an assessment of an item, and a valuation of an item.

In embodiments the set of smart contract services allocates a group of similar items as collateral across a set of loans among different parties, thereby diversifying risk across the loans.

In embodiments the platform or system may further include a set of valuation services that uses a valuation model to set a value for collateral based on information from the data collection and monitoring services, wherein the set of smart contract services automatically rebalances items of collateral for a set of loans based on the value of the collateral.

In embodiments a set of similar collateral items for a set of loans is aggregated in real time based on a similarity in status of the set of items.

In embodiments the similarity in status is based on the items being in transit during a defined time period.

In embodiments a set of collateral items is selected from among a vehicle, a ship, a plane, a building, a home, real estate property, undeveloped land, a farm, a crop, a municipal facility, a warehouse, a set of inventory, a commodity, a security, a currency, a token of value, a ticket, a cryptocurrency, a consumable item, an edible item, a beverage, a precious metal, an item of jewelry, a gemstone, an item of intellectual property, an intellectual property right, a contractual right, an antique, a fixture, an item of furniture, an item of equipment, a tool, an item of machinery, and an item of personal property.

In embodiments the set of smart contract services further includes services for specifying terms and conditions of smart contracts that govern at least one of loan terms and conditions, loan-related events and loan-related activities.

In embodiments the set of terms and conditions for the loan that are specified and managed by the set of smart contract services is selected from among a principal amount of debt, a balance of debt, a fixed interest rate, a variable interest rate, a payment amount, a payment schedule, a balloon payment schedule, a specification of collateral, a specification of substitutability of collateral, a party, a guarantee, a guarantor, a security, a personal guarantee, a lien, a duration, a covenant, a foreclose condition, a default condition, and a consequence of default.

Smart Contract that Manages, in a Blockchain and Distributed Ledger, a Lien on an Asset Based on Status of a Loan for which the Asset is Collateral In embodiments, provided herein is a smart contract system for managing a lien on collateral for a loan having a set of computational services. In embodiments, the platform or system includes (a) a set of data collection and monitoring services for monitoring the status of a loan and an associated set of items of collateral for the loan; (b) a set of blockchain services for maintaining a secure historical ledger of events related to the loan, the blockchain services having access control features that govern access by a set of parties involved in a loan; and (c) a set of smart contract services for managing a smart lending contract, wherein the set of smart contract services processes information from the set of data collection and monitoring services and automatically at least one of initiates and terminates a lien on at least one item in the set of collateral based on the status of the loan, wherein the action on the lien is recorded in the distributed ledger for the loan.

In embodiments the set of data collection and monitoring services includes services selected from among a set of Internet of Things systems that monitor the entities, a set of cameras that monitor the entities, a set of software services that pull information related to the entities from publicly available information sites, a set of mobile devices that report on information related to the entities, a set of wearable devices worn by human entities, a set of user interfaces by which entities provide information about the entities and a set of crowdsourcing services configured to solicit and report information related to the entities.

In embodiments the loan is of at least one type selected from among an auto loan, an inventory loan, a capital equipment loan, a bond for performance, a capital improvement loan, a building loan, a loan backed by an account receivable, an invoice finance arrangement, a factoring arrangement, a pay day loan, a refund anticipation loan, a student loan, a syndicated loan, a title loan, a home loan, a venture debt loan, a loan of intellectual property, a loan of a contractual claim, a working capital loan, a small business loan, a farm loan, a municipal bond, and a subsidized loan.

In embodiments the status of the loan is determined based on the status of at least one of an entity related to the loan and a state of performance of a condition for the loan.

In embodiments the performance of a condition relates to at least one of a payment performance and satisfaction of a covenant.

In embodiments the set of data collection and monitoring services monitors an entity to determine compliance with a covenant.

In embodiments the entity is a party, and the set of data collection and monitoring services monitors the financial condition of an entity that is a party to the loan.

In embodiments the financial condition is determined based on a set of attributes of the entity selected from among a publicly stated valuation of the entity, a set of property owned by the entity as indicated by public records, a valuation of a set of property owned by the entity, a bankruptcy condition of an entity, a foreclosure status of an entity, a contractual default status of an entity, a regulatory violation status of an entity, a criminal status of an entity, an export controls status of an entity, an embargo status of an entity, a tariff status of an entity, a tax status of an entity, a credit report of an entity, a credit rating of an entity, a web site rating of an entity, a set of customer reviews for a product of an entity, a social network rating of an entity, a set of credentials of an entity, a set of referrals of an entity, a set of testimonials for an entity, a set of behavior of an entity, a location of an entity, and a geolocation of an entity.

In embodiments the party is selected from among a primary lender, a secondary lender, a lending syndicate, a corporate lender, a government lender, a bank lender, a secured lender, bond issuer, a bond purchaser, an unsecured lender, a guarantor, a provider of security, a borrower, a debtor, an underwriter, an inspector, an assessor, an auditor, a valuation professional, a government official, and an accountant.

In embodiments the entity is a set of collateral for the loan and the set of data collection and monitoring services monitor the status of the collateral.

In embodiments the set of collateral items is selected from among a vehicle, a ship, a plane, a building, a home, real estate property, undeveloped land, a farm, a crop, a municipal facility, a warehouse, a set of inventory, a commodity, a security, a currency, a token of value, a ticket, a cryptocurrency, a consumable item, an edible item, a beverage, a precious metal, an item of jewelry, a gemstone, an item of intellectual property, an intellectual property right, a contractual right, an antique, a fixture, an item of furniture, an item of equipment, a tool, an item of machinery, and an item of personal property.

In embodiments the platform or system may further include a set of valuation services that uses a valuation model to set a value for a set of collateral based on information from the data collection and monitoring services.

In embodiments the set of collateral items is selected from among a vehicle, a ship, a plane, a building, a home, real estate property, undeveloped land, a farm, a crop, a municipal facility, a warehouse, a set of inventory, a commodity, a security, a currency, a token of value, a ticket, a cryptocurrency, a consumable item, an edible item, a beverage, a precious metal, an item of jewelry, a gemstone, an item of intellectual property, an intellectual property right, a contractual right, an antique, a fixture, an item of furniture, an item of equipment, a tool, an item of machinery, and an item of personal property.

In embodiments the set of valuation services includes artificial intelligence services that iteratively improve the valuation model based on outcome data relating to transactions in collateral.

In embodiments the set of valuation services further includes a set of market value data collection services that monitor and report on marketplace information relevant to the value of collateral.

In embodiments the set of market value data collection services monitors pricing or financial data for items that are similar to the collateral in at least one public marketplace.

In embodiments a set of similar items for valuing an item of collateral is constructed using a similarity clustering algorithm based on the attributes of the collateral.

In embodiments the attributes are selected from among a category of the collateral, an age of the collateral, a condition of the collateral, a history of the collateral, a storage condition of the collateral and a geolocation of the collateral.

In embodiments terms and conditions for the loan that are specified and managed by the set of smart contract services is selected from among a principal amount of debt, a balance of debt, a fixed interest rate, a variable interest rate, a payment amount, a payment schedule, a balloon payment schedule, a specification of collateral, a specification of substitutability of collateral, a party, a guarantee, a guarantor, a security, a personal guarantee, a lien, a duration, a covenant, a foreclose condition, a default condition, and a consequence of default.

In embodiments the set of smart contract services further includes services for specifying terms and conditions of smart contracts that govern at least one of loan terms and conditions, loan-related events and loan-related activities.

In embodiments the loan is of at least one type selected from among an auto loan, an inventory loan, a capital equipment loan, a bond for performance, a capital improvement loan, a building loan, a loan backed by an account receivable, an invoice finance arrangement, a factoring arrangement, a pay day loan, a refund anticipation loan, a student loan, a syndicated loan, a title loan, a home loan, a venture debt loan, a loan of intellectual property, a loan of a contractual claim, a working capital loan, a small business loan, a farm loan, a municipal bond, and a subsidized loan.

In embodiments the set of terms and conditions for the loan that are specified and managed by the set of smart contract services is selected from among a principal amount of debt, a balance of debt, a fixed interest rate, a variable interest rate, a payment amount, a payment schedule, a balloon payment schedule, a specification of collateral, a specification of substitutability of collateral, a party, a guarantee, a guarantor, a security, a personal guarantee, a lien, a duration, a covenant, a foreclose condition, a default condition, and a consequence of default.

Smart Contract/Blockchain that Allows Substitution of Collateral for a Loan Based on Validated Information about the Collateral (Ownership, Condition, Value)

In embodiments, provided herein is a smart contract system for managing collateral for a loan having a set of computational services. In embodiments, the platform or system includes (a) a set of data collection and monitoring services for monitoring the status of a loan and of an associated set of items of collateral for the loan; (b) a set of blockchain services for maintaining a secure historical ledger of events related to the loan, the blockchain services having access control features that govern access by a set of parties involved in a loan; and (c) a set of smart contract services for managing a smart lending contract, wherein the set of smart contract services processes information from the set of data collection and monitoring services and automatically initiates at least one of substitution, removal, or addition of a set of items to the set of collateral for the loan based on an outcome of the processing, wherein the change in the set of collateral is recorded in the distributed ledger for the loan.

In embodiments the set of data collection and monitoring services includes services selected from among a set of Internet of Things systems that monitor the entities, a set of cameras that monitor the entities, a set of software services that pull information related to the entities from publicly available information sites, a set of mobile devices that report on information related to the entities, a set of wearable devices worn by human entities, a set of user interfaces by which entities provide information about the entities and a set of crowdsourcing services configured to solicit and report information related to the entities.

In embodiments the loan is of at least one type selected from among an auto loan, an inventory loan, a capital equipment loan, a bond for performance, a capital improvement loan, a building loan, a loan backed by an account receivable, an invoice finance arrangement, a factoring arrangement, a pay day loan, a refund anticipation loan, a student loan, a syndicated loan, a title loan, a home loan, a venture debt loan, a loan of intellectual property, a loan of a contractual claim, a working capital loan, a small business loan, a farm loan, a municipal bond, and a subsidized loan.

In embodiments the status of the loan is determined based on the status of at least one of an entity related to the loan and a state of performance of a condition for the loan.

In embodiments the performance of a condition relates to at least one of a payment performance and satisfaction of a covenant.

In embodiments the set of data collection and monitoring services monitors an entity to determine compliance with a covenant.

In embodiments the entity is a party, and the set of data collection and monitoring services monitors the financial condition of an entity that is a party to the loan.

In embodiments the financial condition is determined based on a set of attributes of the entity selected from among a publicly stated valuation of the entity, a set of property owned by the entity as indicated by public records, a valuation of a set of property owned by the entity, a bankruptcy condition of an entity, a foreclosure status of an entity, a contractual default status of an entity, a regulatory violation status of an entity, a criminal status of an entity, an export controls status of an entity, an embargo status of an entity, a tariff status of an entity, a tax status of an entity, a credit report of an entity, a credit rating of an entity, a web site rating of an entity, a set of customer reviews for a product of an entity, a social network rating of an entity, a set of credentials of an entity, a set of referrals of an entity, a set of testimonials for an entity, a set of behavior of an entity, a location of an entity, and a geolocation of an entity.

In embodiments the party is selected from among a primary lender, a secondary lender, a lending syndicate, a corporate lender, a government lender, a bank lender, a secured lender, bond issuer, a bond purchaser, an unsecured lender, a guarantor, a provider of security, a borrower, a debtor, an underwriter, an inspector, an assessor, an auditor, a valuation professional, a government official, and an accountant.

In embodiments the entity is a set of collateral for the loan and the set of data collection and monitoring services monitors the status of the collateral.

In embodiments the set of collateral items is selected from among a vehicle, a ship, a plane, a building, a home, real estate property, undeveloped land, a farm, a crop, a municipal facility, a warehouse, a set of inventory, a commodity, a security, a currency, a token of value, a ticket, a cryptocurrency, a consumable item, an edible item, a beverage, a precious metal, an item of jewelry, a gemstone, an item of intellectual property, an intellectual property right, a contractual right, an antique, a fixture, an item of furniture, an item of equipment, a tool, an item of machinery, and an item of personal property.

In embodiments the platform or system may further include a set of valuation services that uses a valuation model to set a value for a set of collateral based on information from the data collection and monitoring services.

In embodiments the smart contract initiates substitution, removal or addition of collateral items to the set of collateral for the loan to maintain a value of collateral within a stated range.

In embodiments the set of collateral items is selected from among a vehicle, a ship, a plane, a building, a home, real estate property, undeveloped land, a farm, a crop, a municipal facility, a warehouse, a set of inventory, a commodity, a security, a currency, a token of value, a ticket, a cryptocurrency, a consumable item, an edible item, a beverage, a precious metal, an item of jewelry, a gemstone, an item of intellectual property, an intellectual property right, a contractual right, an antique, a fixture, an item of furniture, an item of equipment, a tool, an item of machinery, and an item of personal property.

In embodiments the set of valuation services includes artificial intelligence services that iteratively improve the valuation model based on outcome data relating to transactions in collateral.

In embodiments the set of valuation services further includes a set of market value data collection services that monitor and report on marketplace information relevant to the value of collateral.

In embodiments the set of market value data collection services monitors pricing or financial data for items that are similar to the collateral in at least one public marketplace.

In embodiments a set of similar items for valuing an item of collateral is constructed using a similarity clustering algorithm based on the attributes of the collateral.

In embodiments the attributes are selected from among a category of the collateral, an age of the collateral, a condition of the collateral, a history of the collateral, a storage condition of the collateral and a geolocation of the collateral.

In embodiments terms and conditions for the loan that are specified and managed by the set of smart contract services is selected from among a principal amount of debt, a balance of debt, a fixed interest rate, a variable interest rate, a payment amount, a payment schedule, a balloon payment schedule, a specification of collateral, a specification of substitutability of collateral, a party, a guarantee, a guarantor, a security, a personal guarantee, a lien, a duration, a covenant, a foreclose condition, a default condition, and a consequence of default.

In embodiments the set of smart contract services further includes services for specifying terms and conditions of smart contracts that govern at least one of loan terms and conditions, loan-related events and loan-related activities.

In embodiments the set of terms and conditions for the loan that are specified and managed by the set of smart contract services is selected from among a principal amount of debt, a balance of debt, a fixed interest rate, a variable interest rate, a payment amount, a payment schedule, a balloon payment schedule, a specification of collateral, a specification of substitutability of collateral, a party, a guarantee, a guarantor, a security, a personal guarantee, a lien, a duration, a covenant, a foreclose condition, a default condition, and a consequence of default.

In embodiments a lending platform is provided having a smart contract that automatically adjusts an interest rate for a loan based on at least one of a regulatory factor and a market factor for a specific jurisdiction.

Figure 55:
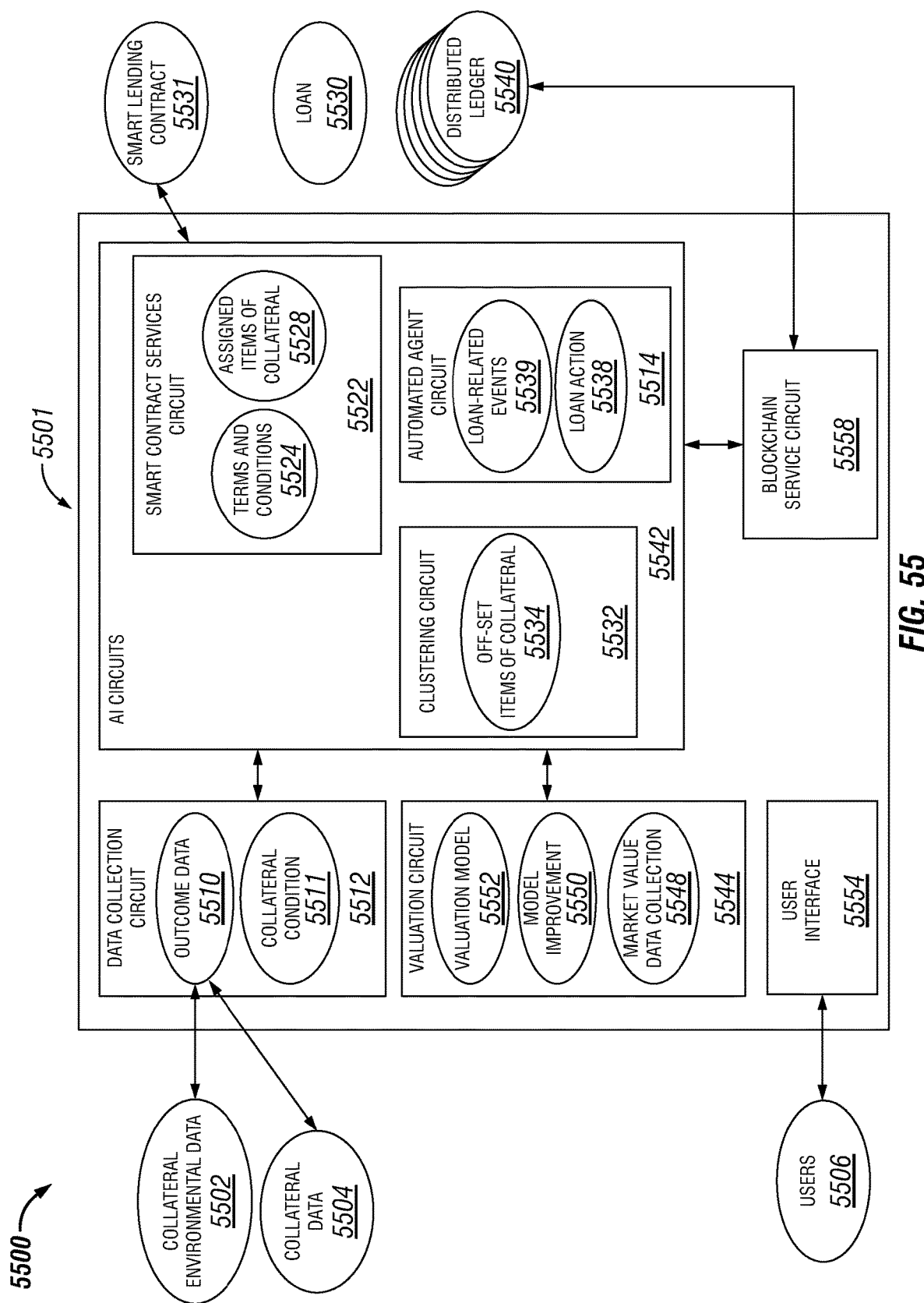
FIG. 55 depicts components and interactions of a lending platform.

Referring to FIG. 55, in embodiments a lending platform is provided having a crowdsourcing system for obtaining information about at least one of a state of a set of collateral for a loan and a state of an entity relevant to a guarantee for a loan. Thus, in embodiments, a platform is provided herein, with systems, methods, processes, services, components and other elements for enabling a blockchain and smart contract platform 5500 for crowdsourcing information relevant to lending. As with other embodiments described above in connection with sourcing innovation, product demand, or the like, a blockchain 136, such as optionally embodying a distributed ledger, may be configured with a set of smart contracts to administer a reward 512 for the submission of loan information 518, such as evidence of ownership of property, evidence of title, information about ownership of collateral, information about condition of collateral, information about the location of collateral, information about a party's identity, information about a party's creditworthiness, information about a party's activities or behavior, information about a party's business practices, information about the status of performance of a contract, information about accounts receivable, information about accounts payable, information about the value of collateral, and many other types of information. In embodiments, a blockchain 136, such as optionally distributed in a distributed ledger, may be used to configure a request for loan information 518 along with terms and conditions 510 related to the information, such as a reward 512 for submission of the loan information 518, a set of terms and conditions 510 related to the use of the loan information 518), and various parameters 508, such as timing parameters, the nature of the information required (such as independently validated information like title records, video footage, photographs, witnessed statements, or the like), and other parameters 508.

The platform 5500 may include a crowdsourcing interface 520, which may be included in or provided in coordination with a website, application, dashboard, communications system (such as for sending emails, texts, voice messages, advertisements, broadcast messages, or other message), by which a message may be presented in the crowdsourcing interface 520 or sent to relevant individuals (whether targeted, such as in the case of a request to a particular individual, or broadcast, such as to individuals in a given location, company, organization, or the like) with an appropriate link to the smart contract and associated blockchain 136, such that a reply message submitting information 518, with relevant attachments, links, or other information, can be automatically associated (such as via an API 112 or data integration system) with the blockchain 136, such that the blockchain 136, and any optionally associated distributed ledger, maintains a secure, definitive record of information 518 submitted in response to the request. Where a reward 512 is offered, the blockchain 136 and/or smart contract may be used to record time of submission, the nature of the submission, and the party submitting, such that at such time as a submission satisfies the conditions for a reward 512 (such as, for example, upon completion of a loan transaction in which the information 518 was useful), the blockchain 136 and any distributed ledger stored thereby can be used to identify the submitter and, by execution of the smart contract, convey the reward 512 (which may take any of the forms of consideration noted throughout this disclosure. In embodiments, the blockchain 136 and any associated ledger may include identifying information for submissions of information 518 without containing actual information 518, such that information may be maintained secret (such as being encrypted or being stored separately with only identifying information), subject to satisfying or verifying conditions for access (such as identification or verification of a person who has legitimate access rights, such as by an identity or security application 148). Rewards 512 may be provided based on outcomes of cases or situations to which information 518 relates, based on a set of rules (which may be automatically applied in some cases, such as using a smart contract in concert with an automation system, a rule processing system, an artificial intelligence system 156 or other expert system, which in embodiments may comprise one that is trained on a training data set created with human experts. For example, a machine vision system may be used to evaluate evidence of the existence and/or condition of collateral based on images of items, and parties submitting information about collateral may be rewarded, such as via tokens or other consideration, via distribution of rewards 512 through the smart contract, blockchain 136 and any distributed ledger. Thus, the platform 500 may be used for a wide variety of fact-gathering and information-gathering purposes, to facilitate validation of collateral, to validate representations about behavior, to validate occurrence of conditions of compliance, to validate occurrence of conditions of default, to deter improper behavior or misrepresentations, to reduce uncertainty, to reduce asymmetries of information, or the like.

In embodiments, information may relate to fact-gathering or data-gathering for a variety of applications and solutions that may be supported by a lending enablement platform 100, including the crowdsourcing system 520, such as for an underwriting solution 103 (e.g., of various types of loans, guarantees, and other items), risk management solutions 122 (such as managing a wide variety of risks noted throughout this disclosure, such as risks associated with individual loans, packages of loans, tranches of loans and the like); lending applications 144 (such as evidence of the ownership and or value of collateral, evidence of the veracity of representations, evidence of performance or compliance with loan covenants, and the like); regulatory and/or compliance solutions 142 (such as with respect to compliance with a wide range of regulations that may govern entities 198 and processes, behaviors or activities of or by entities 198); and fraud prevention applications 138 (such as to detect fraud, misrepresentation, improper behavior, libel, slander, and the like). For example, a capital loan for a building may include a covenant regarding the use of the property, such as permitting certain uses and prohibiting others, permitting a given occupancy, or the like, and the crowdsourcing system 520 may solicit and provide consideration for compliance information about the building (e.g., requesting confirmation from the crowd that a building is in fact being used for its intended use as permitted by zone regulations). Crowdsourced information may be combined with information from monitoring systems 164. In embodiments, an adaptive intelligent system 158 may, for example, continuously monitor a property, an item of collateral 102 or other entity 198 and, upon recognition (such as by an AI system, such as a neural network classifier) of a suspicious event (e.g., one that may indicate violation of a loan covenant), the adaptive intelligent system 158 may provide a signal to the crowdsourcing system 520 indicating that a crowdsourcing process should be initiated to verify the presence or absence of the violation. In embodiments, this may include classifying the covenant-related condition that using a machine classifier, providing the classification along with identifying data about an entity, and automatically configuring, such as based on a model or set of rules, a crowdsource request that identifies what information is requested about what entity 198 and what reward 512 is provided. In embodiment, rewards 512 may be configured by experts, rewards 512 may be based on a set of rules (such as ones that operate on parameters of the loan, the terms and conditions of a covenant in a smart contract (such as loan value, remaining term, and the like), the value of collateral 102, or the like), and/or reward 512 may be set by robotic process automation (RPA) 154, such as where an RPA 154 system is trained on a training set of expert activities in setting rewards in various contexts that collectively show what rewards are appropriate in given situations. Robotic process automation (RPA) 154 of reward configuration may be continuously improved by artificial intelligence 156, such as based on a continuous feedback of outcomes of crowdsourcing, such as outcomes of success (e.g., verification of covenant defaults, yield outcomes, and the like).

Information gathering may include information gathering with respect to entities 198 and their identities, assertions, claims, actions or behaviors, among many other factors and may be accomplished by crowdsourcing in the platform 500 or by data collection systems 166 and monitoring systems 164, optionally with automation via robotic process automation (RPA) 154 and adaptive intelligence, such as using an artificial intelligence system 156.

Figure 5:
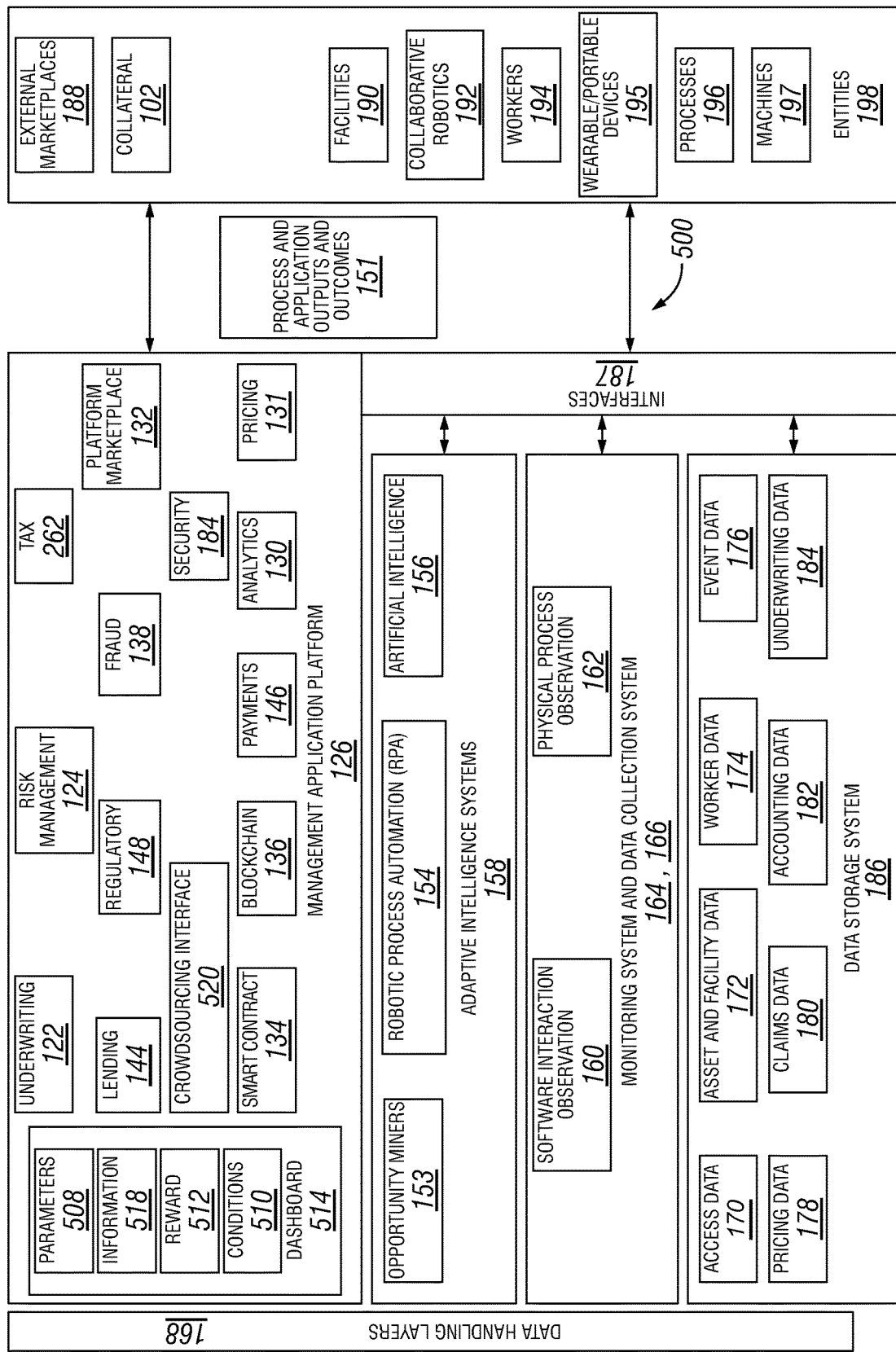
FIG. 5 depicts components and interactions of a lending platform having a crowdsourcing system for collecting information related to entities involved in a lending transaction.

Referring to FIG. 6, a platform-operated marketplace crowdsourcing system 500 may be configured, such as in a crowdsourcing dashboard interface 618 or other user interface for an operator of the platform-operated marketplace crowdsourcing system 120, using the various enabling capabilities of the lending enablement platform 100 described throughout this disclosure. The operator may use the user interface or dashboard 514 to undertake a series of steps to perform or undertake an algorithm to create a crowdsourcing request for information 518 as described in connection with FIG. 5. In embodiments, one or more of the steps of the algorithm to create a reward 512 within the dashboard 514 may include, at a step 602, identifying potential rewards 512, such as what information 518 is likely to be of value in a given situation (such as may be indicated through various communication channels by stakeholders or representatives of an entity, such as an individual or enterprise, such as attorneys, agents, investigators, parties, auditors, detectives, underwriters, inspectors, and many others).

The dashboard 514 may be configured with a crowdsourcing dashboard interface 618, such as with elements (including application programming elements, data integration elements, messaging elements, and the like) that allow a crowdsourcing request to be managed in the platform marketplace 500 and/or in one or more external marketplaces 188. In the dashboard 514, at a step 604 the user may configure one or more parameters 508 or conditions 510, such as comprising or describing the conditions (of the type described herein) for the crowdsourcing request, such as by defining a set of conditions 510 that trigger the reward 512 and determine allocation of the reward 512 to a set of submitters of information 518. The user interface of the dashboard 514, which may include or be associated with the crowdsourcing dashboard interface 620, may include a set of drop down menus, tables, forms, or the like with default, templated, recommended, or pre-configured conditions, parameters 508, conditions 510 and the like, such as ones that are appropriate for various types of crowdsourcing requests. Once the conditions and other parameters of the request are configured, at a step 608 a smart contract and blockchain 136 may be configured to maintain, such as via a ledger, the data required to provision, allocate, and exchange data related to the request and to submissions of information 518. The smart contract and blockchain 136 may be configured to identity information 518, transaction information (such as for exchanges of information), technical information, other evidence data of the type described in connection with FIG. 5, including any data, testimony, photo or video content or other information that may be relevant to a submission of information 518 or the conditions 510 for a reward 512. At a step 610 a smart contract may be configured to embody the conditions 510 that were configured at the step 604 and to operate on the blockchain 136 that was created at the step 608, as well as to operate on other data, such as data indicating facts, conditions, events, or the like in the platform-operated marketplace 500 and/or an external marketplace 188 or other information site or resource, such as ones related to submission information 518, such as sites indicating outcomes of legal cases or portions of cases, sites reporting on investigations, and the like. The smart contract may be configured at the step 610 to apply one or more rules, execute one or more conditional operations, or the like upon data, such as evidence data 518 and data indicating satisfaction of parameters 508 or conditions 510, as well as identity data, transactional data, timing data, and other data. Once configuration of one or more blockchains 136 and one or more smart contracts is complete, at a step 612 the blockchain 136 and smart contract may be deployed in the platform-operated marketplace 500, external marketplace 188 or other site or environment, such as for interaction by one or more submitters or other users, who may, such as in a crowdsourcing dashboard interface 620, such as a website, application, or the like, enter into the smart contract, such as by submitting a submission of information 518 and requesting the reward 512, at which point the platform 500, such as using the adaptive intelligent systems 158 or other capabilities, may store relevant data, such as submission data information 518, identity data for the party or parties entering the smart contract on the blockchain 136 or otherwise on the platform 500. At a step 614, once the smart contract is executed, the platform 500 may monitor, such as by the monitoring systems 164 layer, the platform-operated marketplace 500 and/or one or more external marketplaces 188 or other sites for submission data information 518, event data 176, or other data that may satisfy or indicate satisfaction of one or more conditions 510 or trigger application of one or more rules of the smart contract, such as to trigger a reward 512.

At a step 616, upon satisfaction of conditions 510, smart contracts may be settled, executed, or the like, resulting updates or other operations on the blockchain 136, such as by transferring consideration (such as via a payments system) and transferring access to information 518. Thus, via the above-referenced steps, an operator of the platform-operated marketplace 500 may discover, configure, deploy and have executed a set of smart contracts that crowdsource information relevant to a loan (such as information about value or condition of collateral 102, compliance with covenants, fraud or misrepresentation, and the like) and that are cryptographically secured and transferred on a blockchain 136 from information gatherers to parties seeking information. In embodiments, the adaptive intelligent systems 158 layer may be used to monitor the steps of the algorithm described above, and one or more artificial intelligence systems may be used to automate, such as by robotic process automation (RPA) 154, the entire process or one or more sub-steps or sub-algorithms. This may occur as described above, such as by having an artificial intelligence system 156 learn on a training set of data resulting from observations, such as monitoring software interactions of human users as they undertake the above-referenced steps. Once trained, the adaptive intelligent systems 158 layer may thus enable the lending enablement platform 100 to provide a fully automated platform for crowdsourcing of loan information.

Crowdsourcing System for Validating Quality, Title, or Other Conditions of Collateral for a Loan In embodiments, provided herein is a crowdsourcing system for validating conditions of collateral 102 or assets 218 for a loan. In embodiments, the platform or system includes (a) a set of crowdsourcing services by which a crowdsourcing request is communicated to a group of information suppliers and by which responses to the request are collected and processed to provide a reward to at least one successful information supplier; (b) an interface to the set of crowdsourcing services that enables configuration of parameters of the request, wherein the request and parameters are configured to obtain information related to the condition of a set of collateral for a loan; and (c) a set of publishing services that publish the crowdsourcing request.

In embodiments the reward is managed by a smart contract that processes responses to the crowdsourcing request and automatically allocates a reward to information that satisfies a set of parameters configured for the crowdsourcing request.

In embodiments the loan is of at least one type selected from among an auto loan, an inventory loan, a capital equipment loan, a bond for performance, a capital improvement loan, a building loan, a loan backed by an account receivable, an invoice finance arrangement, a factoring arrangement, a pay day loan, a refund anticipation loan, a student loan, a syndicated loan, a title loan, a home loan, a venture debt loan, a loan of intellectual property, a loan of a contractual claim, a working capital loan, a small business loan, a farm loan, a municipal bond, and a subsidized loan.

In embodiments the set of collateral items is selected from among a vehicle, a ship, a plane, a building, a home, real estate property, undeveloped land, a farm, a crop, a municipal facility, a warehouse, a set of inventory, a commodity, a security, a currency, a token of value, a ticket, a cryptocurrency, a consumable item, an edible item, a beverage, a precious metal, an item of jewelry, a gemstone, an item of intellectual property, an intellectual property right, a contractual right, an antique, a fixture, an item of furniture, an item of equipment, a tool, an item of machinery, and an item of personal property.

In embodiments condition of collateral 102 or assets 218 includes condition attributes selected from the group consisting of the quality of the collateral, the condition of the collateral, the status of title to the collateral, the status of possession of the collateral, the status of a lien on the collateral, a new or used status of item, a type of item, a category of item, a specification of an item, a product feature set of an item, a model of item, a brand of item, a manufacturer of item, a status of item, a context of item, a state of item, a value of item, a storage location of item, a geolocation of item, an age of item, a maintenance history of item, a usage history of item, an accident history of an item, a fault history of an item, an ownership of an item, an ownership history of an item, a price of a type of item, a value of a type of item, an assessment of an item, and a valuation of an item.

In embodiments the platform or system may further include a set of blockchain services that record identifying information and parameters of the request, responses to the crowdsourcing request, and rewards in a distributed ledger for the crowdsourcing request.

In embodiments the interface is a graphical user interface configured to enable a workflow by which a human user enters parameters to establish the crowdsourcing request.

In embodiments the parameters include a type of requested information, a reward, and a condition for receiving the reward.

In embodiments the parameter is a reward, and the reward is selected from among a financial reward, a token, a ticket, a contractual right, a cryptocurrency, a set of reward points, a currency, a discount on a product or service, and an access right.

In embodiments the platform or system may further include a set of smart contract services 134 that administer a smart lending contract, wherein the smart contract services 134 process information from the set of crowdsourcing services and automatically undertake an action related to the loan.

In embodiments the action is at least one of a foreclosure action, a lien administration action, an interest-rate setting action, a default initiation action, a substitution of collateral, and a calling of the loan.

In embodiments the platform or system may further include a robotic process automation system (RPA) 154 that is trained, based on a training set of interactions of human users with the interface to the set of crowdsourcing services, to configure a crowdsourcing request based on a set of attributes of a loan. In embodiments the attributes of the loan are obtained from a set of smart contract services that manage the loan. In embodiments the robotic process automation system is configured to be iteratively trained and improved based on a set of outcomes from a set of crowdsourcing requests. In embodiments training includes training the robotic process automation system to set a reward. In embodiments training includes training the robotic process automation system to determine a set of domains to which the request will be published. In embodiments training includes training the robotic process automation system to configure the content of a request.

Crowdsourcing System for Validating the Quality of a Personal Guarantee for a Loan In embodiments, provided herein is a crowdsourcing system 520 for validating conditions of collateral 102 or assets 218 for a loan. In embodiments, the platform or system includes (a) a set of crowdsourcing services by which a crowdsourcing request is communicated to a group of information suppliers and by which responses to the request are collected and processed to provide a reward to at least one successful information supplier; (b) an interface to the set of crowdsourcing services that enables configuration of parameters of the request, wherein the request and parameters are configured to obtain information related to the condition of guarantor for a loan; and (c) a set of publishing services that publish the crowdsourcing request.

In embodiments the set of crowdsourcing systems 520 obtains information about the financial condition of an entity that is the guarantor for the loan.

In embodiments the financial condition is determined at least in part based on information about the entity selected from among a publicly stated valuation of the entity, a set of property owned by the entity as indicated by public records, a valuation of a set of property owned by the entity, a bankruptcy condition of an entity, a foreclosure status of an entity, a contractual default status of an entity, a regulatory violation status of an entity, a criminal status of an entity, an export controls status of an entity, an embargo status of an entity, a tariff status of an entity, a tax status of an entity, a credit report of an entity, a credit rating of an entity, a web site rating of an entity, a set of customer reviews for a product of an entity, a social network rating of an entity, a set of credentials of an entity, a set of referrals of an entity, a set of testimonials for an entity, a set of behavior of an entity, a location of an entity, and a geolocation of an entity.

In embodiments the reward is managed by a smart contract that processes responses to the crowdsourcing request and automatically allocates a reward to information that satisfies a set of parameters configured for the crowdsourcing request.

In embodiments the loan is of at least one type selected from among an auto loan, an inventory loan, a capital equipment loan, a bond for performance, a capital improvement loan, a building loan, a loan backed by an account receivable, an invoice finance arrangement, a factoring arrangement, a pay day loan, a refund anticipation loan, a student loan, a syndicated loan, a title loan, a home loan, a venture debt loan, a loan of intellectual property, a loan of a contractual claim, a working capital loan, a small business loan, a farm loan, a municipal bond, and a subsidized loan.

In embodiments the platform or system may further include an interface of the crowdsourcing services In embodiments a request is configured to obtain information about condition of a set of collateral for the loan, wherein the set of collateral items is selected from among a vehicle, a ship, a plane, a building, a home, real estate property, undeveloped land, a farm, a crop, a municipal facility, a warehouse, a set of inventory, a commodity, a security, a currency, a token of value, a ticket, a cryptocurrency, a consumable item, an edible item, a beverage, a precious metal, an item of jewelry, a gemstone, an item of intellectual property, an intellectual property right, a contractual right, an antique, a fixture, an item of furniture, an item of equipment, a tool, an item of machinery, and an item of personal property.

In embodiments condition of collateral includes condition attributes selected from the group consisting of the quality of the collateral, the condition of the collateral, the status of title to the collateral, the status of possession of the collateral, the status of a lien on the collateral, a new or used status of item, a type of item, a category of item, a specification of an item, a product feature set of an item, a model of item, a brand of item, a manufacturer of item, a status of item, a context of item, a state of item, a value of item, a storage location of item, a geolocation of item, an age of item, a maintenance history of item, a usage history of item, an accident history of an item, a fault history of an item, an ownership of an item, an ownership history of an item, a price of a type of item, a value of a type of item, an assessment of an item, and a valuation of an item.

In embodiments the platform or system may further include a set of blockchain services that record identifying information and parameters of the request, responses to the crowdsourcing request, and rewards in a distributed ledger for the crowdsourcing request.

In embodiments the interface is a graphical user interface configured to enable a workflow by which a human user enters parameters to establish the crowdsourcing request.

In embodiments the parameters include a type of requested information, a reward, and a condition for receiving the reward.

In embodiments the parameter is a reward, and the reward is selected from among a financial reward, a token, a ticket, a contractual right, a cryptocurrency, a set of reward points, a currency, a discount on a product or service, and an access right.

In embodiments the platform or system may further include a set of smart contract services that administer a smart lending contract, wherein the smart contract services process information from the set of crowdsourcing services and automatically undertake an action related to the loan.

In embodiments the action is at least one of a foreclosure action, a lien administration action, an interest-rate setting action, a default initiation action, a substitution of collateral, and a calling of the loan.

In embodiments the platform or system may further include a robotic process automation system that is trained, based on a training set of interactions of human users with the interface to the set of crowdsourcing services, to configure a crowdsourcing request based on a set of attributes of a loan.

In embodiments the attributes of the loan are obtained from a set of smart contract services that manage the loan.

In embodiments the robotic process automation system is configured to be iteratively trained and improved based on a set of outcomes from a set of crowdsourcing requests.

In embodiments training includes training the robotic process automation system to set a reward, to determine a set of domains to which the request will be published or to configure the content of a request.

Figure 7:
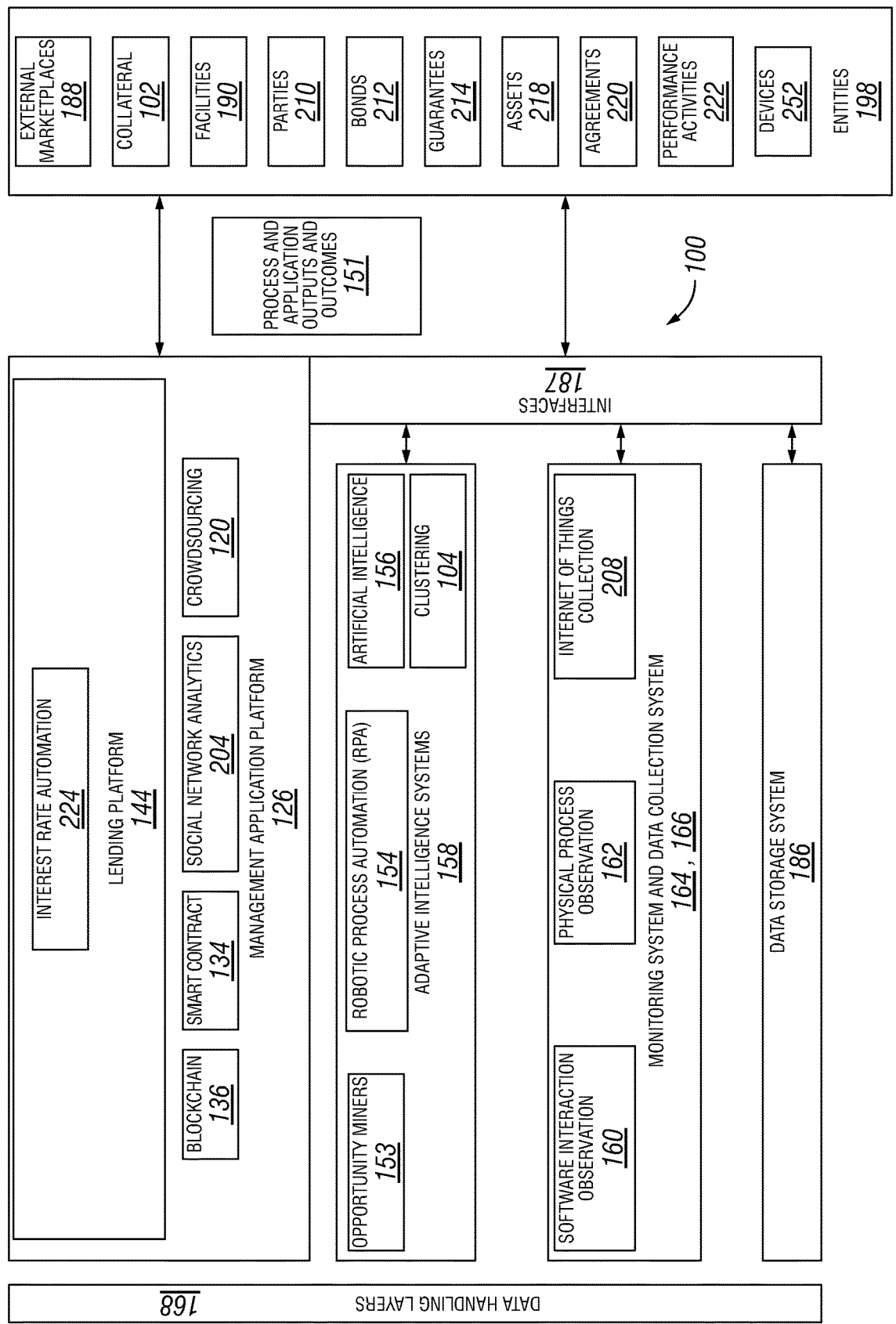
FIG. 7 depicts components and interactions of an embodiment of a lending platform having a smart contract system that automatically adjusts an interest rate for a loan based on information collected via at least one of an Internet of Things system, a crowdsourcing system, a set of social network analytic services and a set of data collection and monitoring services.

Referring to FIG. 7, in embodiments a lending platform is provided having smart contract services 134 that automatically adjusts an interest rate for a loan based on information collected via at least one of an Internet of Things system, a crowdsourcing system, a set of social network analytic services and a set of data collection and monitoring services. The lending enablement platform 100 may include an interest rate automation solution 224 that may include a set of interfaces, workflows, and models (which may include, use or be enabled by various adaptive intelligent systems 158) and other components that are configured to enable automation of the setting of interest rates based on a set of conditions, which may include smart contract terms and conditions, marketplace conditions (of platform marketplaces and/or external marketplaces 188, conditions monitored by monitoring systems 164 and data collection systems 166, and the like (such as of entities 198, including without limitation parties 210, collateral 102 and assets 218, among others). For example, a user of the interest rate automation solution 224 may set (such as in a user interface) rules, thresholds, model parameters, and the like that determine, or recommend, an interest rate for a loan based on the above, such as based on interest rates available to the lender from secondary lenders, risk factors of the borrower (including predicted risk based on one or more predictive models using artificial intelligence 156), or the system may automatically recommend or set such rules, thresholds, parameters and the like (optionally by learning to do so based on a training set of outcomes over time). Interest rates may be determined based on marketing factors (such as competing interest rates offered by other lenders). Interest rates may be calculated for new loans, for modifications of existing loans, for refinancing, for foreclosure situations (e.g., changing from secured loan rates to unsecured loan rates), and the like.

In embodiments, provided herein is a smart contract system for modifying a loan having a set of computational services. In embodiments, the platform or system includes (a) a set of data collection and monitoring services for monitoring a set of entities involved in a loan; and (b) a set of smart contract services for managing a smart lending contract, wherein the set of smart contract services processes information from the set of data collection and monitoring services and automatically initiates a change in an interest rate for the loan based on the information.

In embodiments the change in interest rate is based on the condition of a set of collateral for the loan that is monitored by the set of data collection and monitoring services.

In embodiments the change in interest rate is based on an attribute of a party that is monitored by the set of data collection and monitoring services.

In embodiments the set of smart contract services further includes services for specifying terms and conditions of smart contracts that govern at least one of loan terms and conditions, loan-related events and loan-related activities.

In embodiments the loan is of at least one type selected from among an auto loan, an inventory loan, a capital equipment loan, a bond for performance, a capital improvement loan, a building loan, a loan backed by an account receivable, an invoice finance arrangement, a factoring arrangement, a pay day loan, a refund anticipation loan, a student loan, a syndicated loan, a title loan, a home loan, a venture debt loan, a loan of intellectual property, a loan of a contractual claim, a working capital loan, a small business loan, a farm loan, a municipal bond, and a subsidized loan.

In embodiments the set of terms and conditions for the loan that are specified and managed by the set of smart contract services is selected from among a principal amount of debt, a balance of debt, a fixed interest rate, a variable interest rate, a payment amount, a payment schedule, a balloon payment schedule, a specification of collateral, a specification of substitutability of collateral, a party, a guarantee, a guarantor, a security, a personal guarantee, a lien, a duration, a covenant, a foreclose condition, a default condition, and a consequence of default.

In embodiments the set of data collection and monitoring services includes services selected from among a set of Internet of Things systems that monitor the entities, a set of cameras that monitor the entities, a set of software services that pull information related to the entities from publicly available information sites, a set of mobile devices that report on information related to the entities, a set of wearable devices worn by human entities, a set of user interfaces by which entities provide information about the entities and a set of crowdsourcing services configured to solicit and report information related to the entities.

In embodiments the platform or system may further include a set of valuation services that uses a valuation model to set a value for a set of collateral based on information from the data collection and monitoring services.

In embodiments the change in interest rate is based on the valuation of a set of collateral for the loan that is monitored by the set of data collection and monitoring services.

In embodiments a set of collateral items is selected from among a vehicle, a ship, a plane, a building, a home, real estate property, undeveloped land, a farm, a crop, a municipal facility, a warehouse, a set of inventory, a commodity, a security, a currency, a token of value, a ticket, a cryptocurrency, a consumable item, an edible item, a beverage, a precious metal, an item of jewelry, a gemstone, an item of intellectual property, an intellectual property right, a contractual right, an antique, a fixture, an item of furniture, an item of equipment, a tool, an item of machinery, and an item of personal property.

In embodiments the set of valuation services includes artificial intelligence services that iteratively improve the valuation model based on outcome data relating to transactions in collateral.

In embodiments the set of valuation services further includes a set of market value data collection services that monitor and report on marketplace information relevant to the value of collateral.

In embodiments the set of market value data collection services monitors pricing or financial data for items that are similar to the collateral in at least one public marketplace.

In embodiments a set of similar items for valuing an item of collateral is constructed using a similarity clustering algorithm based on the attributes of the collateral.

In embodiments the attributes are selected from among a category of the collateral, an age of the collateral, a condition of the collateral, a history of the collateral, a storage condition of the collateral and a geolocation of the collateral.

In embodiments, provided herein is a smart contract system for modifying a loan having a set of computational services. In embodiments, the platform or system includes (a) a set of data collection and monitoring services for monitoring public sources of information about a set of entities involved in a loan, wherein the public sources of information are selected from among website information, news article information, social network information and crowdsourced information; and (b) a set of smart contract services for managing a smart lending contract, wherein the set of smart contract services processes information from the set of data collection and monitoring services and automatically initiates a change in an interest rate for the loan based on the information.

In embodiments the set of data collection and monitoring services monitor the financial condition of an entity that is a party to the loan.

In embodiments the loan is of at least one type selected from among an auto loan, an inventory loan, a capital equipment loan, a bond for performance, a capital improvement loan, a building loan, a loan backed by an account receivable, an invoice finance arrangement, a factoring arrangement, a pay day loan, a refund anticipation loan, a student loan, a syndicated loan, a title loan, a home loan, a venture debt loan, a loan of intellectual property, a loan of a contractual claim, a working capital loan, a small business loan, a farm loan, a municipal bond, and a subsidized loan.

In embodiments the financial condition is determined based on a set of attributes of the entity selected from among a publicly stated valuation of the entity, a set of property owned by the entity as indicated by public records, a valuation of a set of property owned by the entity, a bankruptcy condition of an entity, a foreclosure status of an entity, a contractual default status of an entity, a regulatory violation status of an entity, a criminal status of an entity, an export controls status of an entity, an embargo status of an entity, a tariff status of an entity, a tax status of an entity, a credit report of an entity, a credit rating of an entity, a web site rating of an entity, a set of customer reviews for a product of an entity, a social network rating of an entity, a set of credentials of an entity, a set of referrals of an entity, a set of testimonials for an entity, a set of behavior of an entity, a location of an entity, and a geolocation of an entity.

In embodiments the party is selected from among a primary lender, a secondary lender, a lending syndicate, a corporate lender, a government lender, a bank lender, a secured lender, bond issuer, a bond purchaser, an unsecured lender, a guarantor, a provider of security, a borrower, a debtor, an underwriter, an inspector, an assessor, an auditor, a valuation professional, a government official, and an accountant.

In embodiments the platform or system may further include an automated agent that processes events relevant to at least one of the value, the condition and the ownership of items of collateral and undertakes an action related to a loan to which the collateral is subject.

In embodiments the loan-related action is selected from among offering a loan, accepting a loan, underwriting a loan, setting an interest rate for a loan, deferring a payment requirement, modifying an interest rate for a loan, validating title for collateral, recording a change in title, assessing the value of collateral, initiating inspection of collateral, calling a loan, closing a loan, setting terms and conditions for a loan, providing notices required to be provided to a borrower, foreclosing on property subject to a loan, and modifying terms and conditions for a loan.

In embodiments the set of smart contract services further includes services for specifying terms and conditions of smart contracts that govern at least one of loan terms and conditions, loan-related events and loan-related activities.

In embodiments the set of terms and conditions for the loan that are specified and managed by the set of smart contract services is selected from among a principal amount of debt, a balance of debt, a fixed interest rate, a variable interest rate, a payment amount, a payment schedule, a balloon payment schedule, a specification of collateral, a specification of substitutability of collateral, a party, a guarantee, a guarantor, a security, a personal guarantee, a lien, a duration, a covenant, a foreclose condition, a default condition, and a consequence of default.

In embodiments the monitored entity is a set of collateral items that is selected from among a vehicle, a ship, a plane, a building, a home, real estate property, undeveloped land, a farm, a crop, a municipal facility, a warehouse, a set of inventory, a commodity, a security, a currency, a token of value, a ticket, a cryptocurrency, a consumable item, an edible item, a beverage, a precious metal, an item of jewelry, a gemstone, an item of intellectual property, an intellectual property right, a contractual right, an antique, a fixture, an item of furniture, an item of equipment, a tool, an item of machinery, and an item of personal property.

In embodiments, provided herein is a smart contract system for modifying a loan, the system having a set of computational services. In embodiments, the platform or system includes (a) a set of data collection and monitoring services for monitoring a set of entities involved in a loan In embodiments the entities are located in a plurality of different jurisdictions; and (b) a set of smart contract services for managing a smart lending contract, wherein the set of smart contract services processes location information about the entities from the set of data collection and monitoring services and automatically undertakes a loan-related action for the loan based at least in part on the location information.

In embodiments the loan-related action is selected from among offering a loan, accepting a loan, underwriting a loan, setting an interest rate for a loan, deferring a payment requirement, modifying an interest rate for a loan, validating title for collateral, recording a change in title, assessing the value of collateral, initiating inspection of collateral, calling a loan, closing a loan, setting terms and conditions for a loan, providing notices required to be provided to a borrower, foreclosing on property subject to a loan, and modifying terms and conditions for a loan.

In embodiments the smart contract is configured to process a set of jurisdiction-specific regulatory notice requirements and to provide an appropriate notice to a borrower based on location of at least one of the lender, the borrower, the funds provided via the loan, the repayment of the loan, and the collateral for the loan.

In embodiments the smart contract is configured to process a set of jurisdiction-specific regulatory foreclosure requirements and to provide an appropriate foreclosure notice to a borrower based on jurisdiction of at least one of the lender, the borrower, the funds provided via the loan, the repayment of the loan, and the collateral for the loan.

In embodiments the smart contract is configured to process a set of jurisdiction-specific rules for setting terms and conditions of the loan and to configure the smart contract based on the location of at least one of the borrower, the funds provided via the loan, the repayment of the loan, and the collateral for the loan.

In embodiments the smart contract is configured to set the interest rate for the loan to cause the loan to comply with maximum interest rate limitations applicable in a jurisdiction.

In embodiments the change in interest rate is based on the condition of a set of collateral for the loan that is monitored by the set of data collection and monitoring services.

In embodiments the change in interest rate is based on an attribute of a party that is monitored by the set of data collection and monitoring services.

In embodiments the set of smart contract services further includes services for specifying terms and conditions of smart contracts that govern at least one of loan terms and conditions, loan-related events and loan-related activities.

In embodiments the loan is of at least one type selected from among an auto loan, an inventory loan, a capital equipment loan, a bond for performance, a capital improvement loan, a building loan, a loan backed by an account receivable, an invoice finance arrangement, a factoring arrangement, a pay day loan, a refund anticipation loan, a student loan, a syndicated loan, a title loan, a home loan, a venture debt loan, a loan of intellectual property, a loan of a contractual claim, a working capital loan, a small business loan, a farm loan, a municipal bond, and a subsidized loan.

In embodiments the set of terms and conditions for the loan that are specified and managed by the set of smart contract services is selected from among a principal amount of debt, a balance of debt, a fixed interest rate, a variable interest rate, a payment amount, a payment schedule, a balloon payment schedule, a specification of collateral, a specification of substitutability of collateral, a party, a guarantee, a guarantor, a security, a personal guarantee, a lien, a duration, a covenant, a foreclose condition, a default condition, and a consequence of default.

In embodiments the set of data collection and monitoring services includes services selected from among a set of Internet of Things systems that monitor the entities, a set of cameras that monitor the entities, a set of software services that pull information related to the entities from publicly available information sites, a set of mobile devices that report on information related to the entities, a set of wearable devices worn by human entities, a set of user interfaces by which entities provide information about the entities and a set of crowdsourcing services configured to solicit and report information related to the entities.

In embodiments the platform or system may further include a set of valuation services that uses a valuation model to set a value for a set of collateral based on information from the data collection and monitoring services.

In embodiments the valuation model is a jurisdiction-specific valuation model that is based on the jurisdiction of at least one of the lender, the borrower, the delivery of funds provided via loan, the payment of the loan and collateral for the loan.

In embodiments at least one of the terms and conditions for the loan is based on the valuation of a set of collateral for the loan that is monitored by the set of data collection and monitoring services.

In embodiments a set of collateral items is selected from among a vehicle, a ship, a plane, a building, a home, real estate property, undeveloped land, a farm, a crop, a municipal facility, a warehouse, a set of inventory, a commodity, a security, a currency, a token of value, a ticket, a cryptocurrency, a consumable item, an edible item, a beverage, a precious metal, an item of jewelry, a gemstone, an item of intellectual property, an intellectual property right, a contractual right, an antique, a fixture, an item of furniture, an item of equipment, a tool, an item of machinery, and an item of personal property.

In embodiments the set of valuation services includes artificial intelligence services that iteratively improve the valuation model based on outcome data relating to transactions in collateral.

In embodiments the set of valuation services further includes a set of market value data collection services that monitor and report on marketplace information relevant to the value of collateral.

In embodiments the set of market value data collection services monitors pricing or financial data for items that are similar to the collateral in at least one public marketplace.

In embodiments a set of similar items for valuing an item of collateral is constructed using a similarity clustering algorithm based on the attributes of the collateral.

In embodiments the attributes are selected from among a category of the collateral, an age of the collateral, a condition of the collateral, a history of the collateral, a storage condition of the collateral and a geolocation of the collateral.

Figure 8:
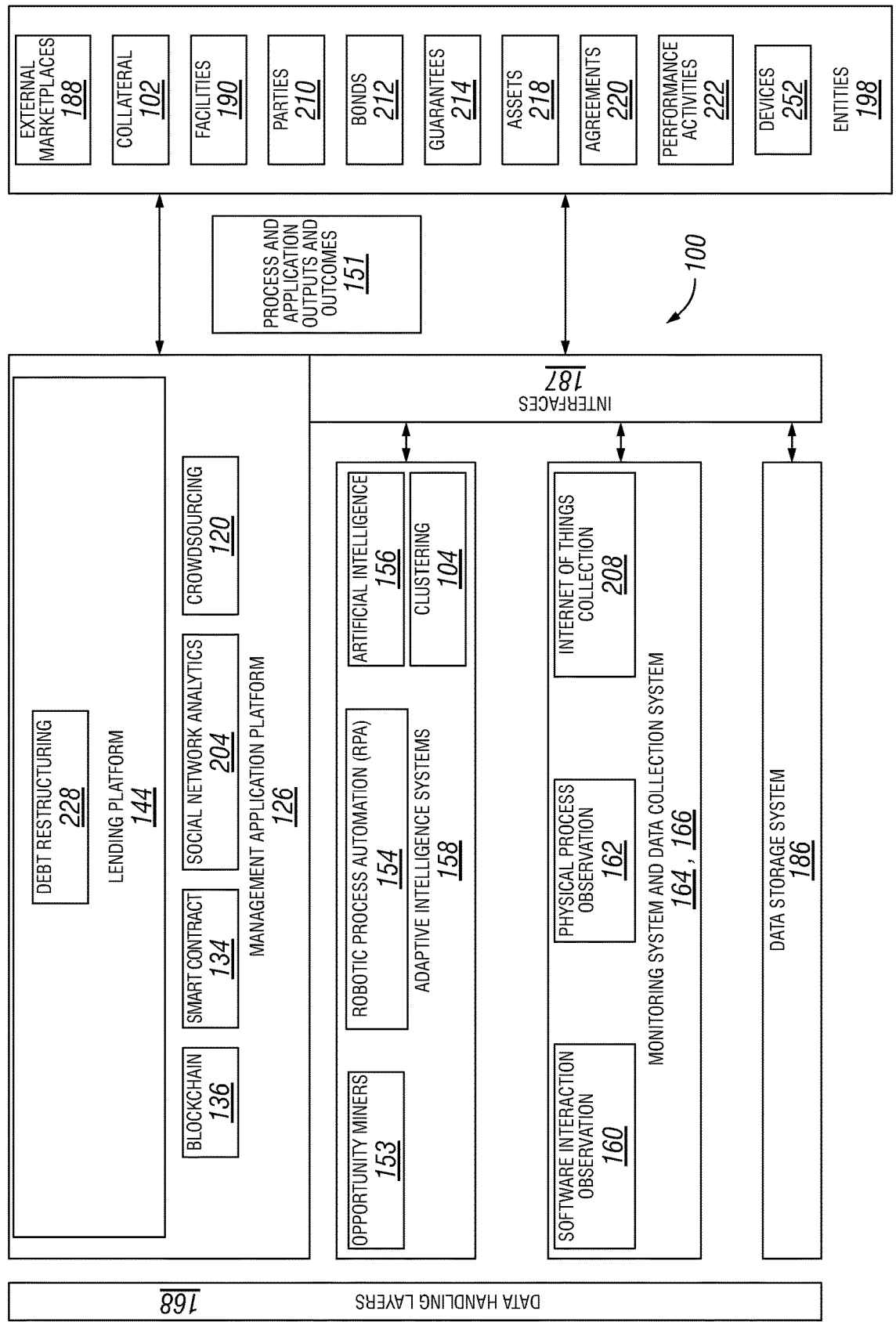
FIG. 8 depicts components and interactions of an embodiment of a lending platform having a having a smart contract that automatically restructures debt based on a monitored condition.

Referring to FIG. 8, in embodiments a lending platform is provided having a smart contract that automatically restructures debt based on a monitored condition. The lending enablement platform 100 may include a debt restructuring solution 228 that may include a set of interfaces, workflows, and models (which may include, use or be enabled by various adaptive intelligent systems 158) and other components that are configured to enable automation of the restructuring of debt based on a set of conditions, which may include smart contract terms and conditions, marketplace conditions (of platform marketplaces and/or external marketplaces 188, conditions monitored by monitoring systems 164 and data collection systems 166, and the like (such as of entities 198, including without limitation parties 210, collateral 102 and assets 218, among others). For example, a user of the debt restructuring solution 228 may create, configure (such as using one or more templates or libraries), modify, set or otherwise handle (such as in a user interface of the debt restructuring solution 228) various rules, thresholds, procedures, workflows, model parameters, and the like that determine, or recommend, a debt restructuring action for a loan based on one or more events, conditions, states, actions, or the like, where restructuring may be based on various factors, such as prevailing market interest rates, interest rates available to the lender from secondary lenders, risk factors of the borrower (including predicted risk based on one or more predictive models using artificial intelligence 156), status of other debt (such as new debt of a borrower, elimination of debt of a borrower, or the like), condition of collateral 102 or assets 218 used to secure or back a loan, state of a business or business operation (e.g., receivables, payables, or the like), and many others. Restructuring may include changes in interest rate, changes in priority of secured parties, changes in collateral 102 or assets 218 used to back or secure debt, changes in parties, changes in guarantors, changes in payment schedule, changes in principal balance (e.g., including forgiveness or acceleration of payments), and others. In embodiments the debt restructuring solution 228 may automatically recommend or set such rules, thresholds, actions, parameters and the like (optionally by learning to do so based on a training set of outcomes over time), resulting in a recommended restructuring plan, which may specify a series of actions required to accomplish a recommended restructuring, which may be automated and may be involved conditional execution of steps based on monitored conditions and/or smart contract terms, which may be created, configured, and/or accounted for by the debt restructuring plan. Restructuring plans may be determined and executed based at least one part on market factors (such as competing interest rates offered by other lenders, values of collateral, and the like) as well as regulatory and/or compliance factors. Restructuring plans may be generated and/or executed for modifications of existing loans, for refinancing, for foreclosure situations (e.g., changing from secured loan rates to unsecured loan rates), for bankruptcy or insolvency situations, for situations involving market changes (e.g., changes in prevailing interest rates) and others. In embodiments, adaptive intelligent systems 158, including artificial intelligence 156 may be trained on a training set of restructuring activities by experts and/or on outcomes of restructuring actions to generate a set of predictions, classifications, control instructions, plans, models, or the like for automated creation, management and/or execution of one or more aspects of a restructuring plan.

In embodiments, provided herein is a smart contract system for modifying a loan, the system having a set of computational services. In embodiments, the platform or system includes (a) a set of data collection and monitoring services for monitoring a set of entities involved in a loan; and (b) a set of smart contract services for managing a smart lending contract, wherein the set of smart contract services processes information from the set of data collection and monitoring services and automatically restructures debt based on a monitored condition.

In embodiments the restructuring is based on the condition of a set of collateral for the loan that is monitored by the set of data collection and monitoring services.

In embodiments the restructuring is according to a set of rules that are based on a covenant of the loan, wherein the restructuring occurs upon an event that is determined with respect to at least one of the monitored entities that relates to the covenant.

In embodiments the event is the failure of collateral for a loan to exceed a required fractional value of the remaining balance of the loan.

In embodiments the event is a default of the buyer with respect to a loan covenant.

In embodiments the restructuring is based on an attribute of a party that is monitored by the set of data collection and monitoring services.

In embodiments the set of smart contract services further includes services for specifying terms and conditions of smart contracts that govern at least one of loan terms and conditions, loan-related events and loan-related activities.

In embodiments the loan is of at least one type selected from among an auto loan, an inventory loan, a capital equipment loan, a bond for performance, a capital improvement loan, a building loan, a loan backed by an account receivable, an invoice finance arrangement, a factoring arrangement, a pay day loan, a refund anticipation loan, a student loan, a syndicated loan, a title loan, a home loan, a venture debt loan, a loan of intellectual property, a loan of a contractual claim, a working capital loan, a small business loan, a farm loan, a municipal bond, and a subsidized loan.

In embodiments the set of terms and conditions for the loan that are specified and managed by the set of smart contract services is selected from among a principal amount of debt, a balance of debt, a fixed interest rate, a variable interest rate, a payment amount, a payment schedule, a balloon payment schedule, a specification of collateral, a specification of substitutability of collateral, a party, a guarantee, a guarantor, a security, a personal guarantee, a lien, a duration, a covenant, a foreclose condition, a default condition, and a consequence of default.

In embodiments the set of data collection and monitoring services includes services selected from among a set of Internet of Things systems that monitor the entities, a set of cameras that monitor the entities, a set of software services that pull information related to the entities from publicly available information sites, a set of mobile devices that report on information related to the entities, a set of wearable devices worn by human entities, a set of user interfaces by which entities provide information about the entities and a set of crowdsourcing services configured to solicit and report information related to the entities.

In embodiments the platform or system may further include a set of valuation services that uses a valuation model to set a value for a set of collateral based on information from the data collection and monitoring services.

In embodiments the restructuring of the debt is based on the valuation of a set of collateral for the loan that is monitored by the set of data collection and monitoring services.

In embodiments a set of collateral items is selected from among a vehicle, a ship, a plane, a building, a home, real estate property, undeveloped land, a farm, a crop, a municipal facility, a warehouse, a set of inventory, a commodity, a security, a currency, a token of value, a ticket, a cryptocurrency, a consumable item, an edible item, a beverage, a precious metal, an item of jewelry, a gemstone, an item of intellectual property, an intellectual property right, a contractual right, an antique, a fixture, an item of furniture, an item of equipment, a tool, an item of machinery, and an item of personal property.

In embodiments the set of valuation services includes artificial intelligence services that iteratively improve the valuation model based on outcome data relating to transactions in collateral.

In embodiments the set of valuation services further includes a set of market value data collection services that monitor and report on marketplace information relevant to the value of collateral.

In embodiments the set of market value data collection services monitors pricing or financial data for items that are similar to the collateral in at least one public marketplace.

In embodiments a set of similar items for valuing an item of collateral is constructed using a similarity clustering algorithm based on the attributes of the collateral.

In embodiments the attributes are selected from among a category of the collateral, an age of the collateral, a condition of the collateral, a history of the collateral, a storage condition of the collateral and a geolocation of the collateral.

Figure 9:
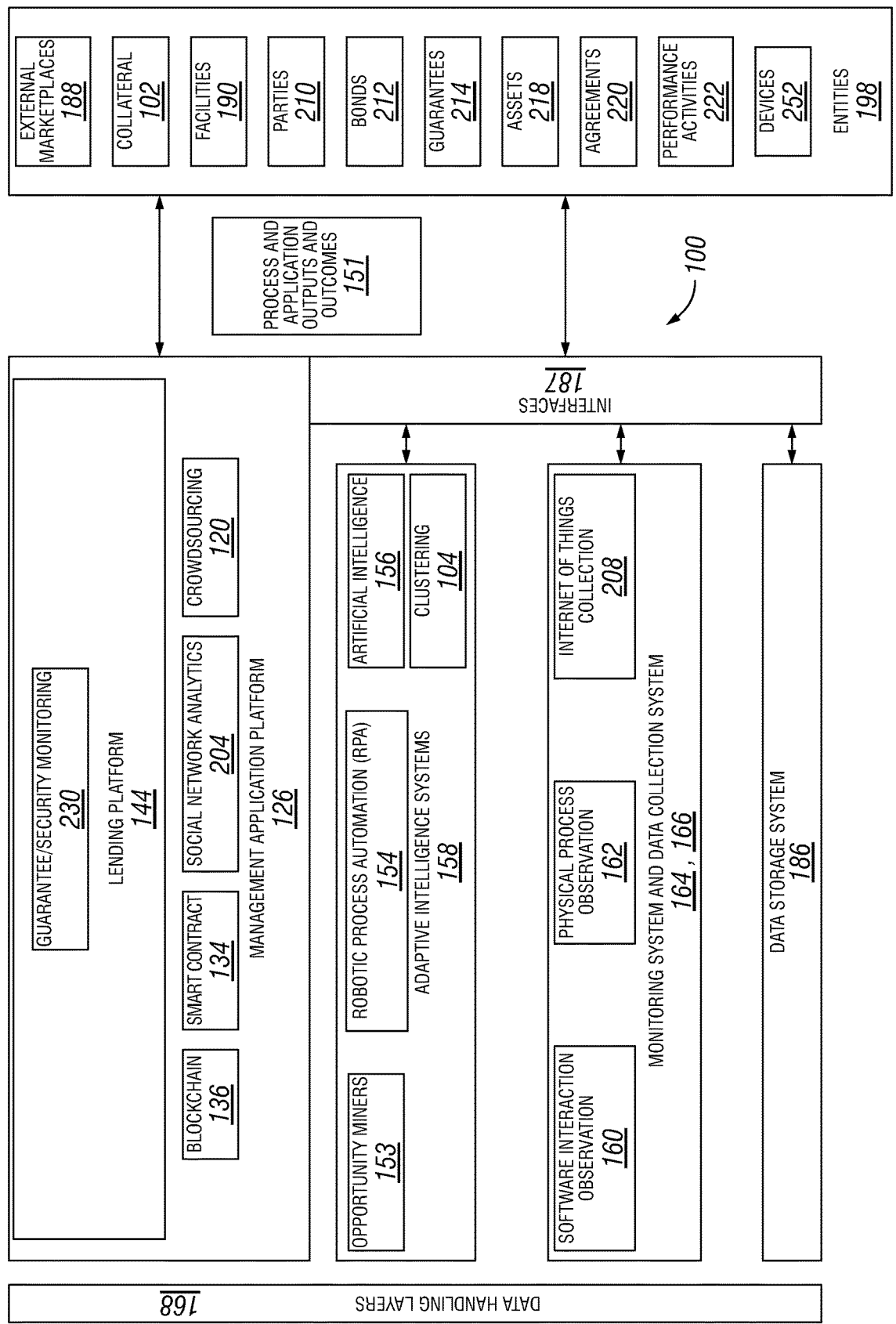
FIG. 9 depicts components and interactions of a lending platform having a set of data collection and monitoring systems for validating the reliability of a guarantee for a loan, including an Internet of Things system and a social network analytics system.

Referring to FIG. 9, in embodiments a lending enablement platform 100 is provided having a social network analytics application 204 for monitoring social media, collecting data and determining analytics for validating the reliability of a guarantee for a loan. The lending enablement platform 100 may include a guarantee and/or security monitoring solution 230 that may include a set of interfaces, workflows, and models (which may include, use or be enabled by various adaptive intelligent systems 158) and other components that are configured to enable monitoring of a guarantee and/or security for a lending transaction based on a set of conditions, which may include smart contract terms and conditions, marketplace conditions (of platform marketplaces and/or external marketplaces 188, conditions monitored by monitoring systems 164 and data collection systems 166, and the like (such as of entities 198, including without limitation parties 210, collateral 102 and assets 218, among others). For example, a user of the guarantee and/or security monitoring solution 230 may set (such as in a user interface) rules, thresholds, model parameters, and the like that determine, or recommend, a monitoring plan for lending transaction such as based on risk factors of the borrower, risk factors of the lender, market risk factors, and/or risk factors of collateral 102 or assets 218 (including predicted risk based on one or more predictive models using artificial intelligence 156), or the lending enablement platform 100 may automatically recommend or set such rules, thresholds, parameters and the like (optionally by learning to do so based on a training set of outcomes over time). The guarantee and/or security monitoring solution 230 may configure a set of social network analytics services 204 and/or other monitoring systems 164 and/or data collection systems 166 to search, parse, extract, and process data from one or more social networks, website, or the like, such as ones that may contain information about collateral 102 or assets 218 (e.g., photos that show a vehicle, boat, or other personal property of a party 210, photos of a home or other real property, photos or text that describes activities of a party 210 (including ones that indicate financial risk, physical risk, health risk, or other risk that may be relevant to the quality of the guarantor and/or the guarantee for a payment obligation and/or the ability of the borrower to repay a loan when due). For example, a photo showing a borrower driving a regular passenger vehicle in off-road conditions may be flagged as indicating that the vehicle cannot be fully relied upon as collateral for an automobile loan that has a high remaining balance.

Thus, in embodiments, provided herein is a social network monitoring system for validating conditions of a guarantee for a loan. In embodiments, the platform or system includes (a) a set of social network data collection and monitoring services by which data is collected by a set of algorithms that are configured to monitor social network information about entities involved in a loan; and (b) an interface to the set of social networking services that enables configuration of parameters of the social network data collection and monitoring services to obtain information related to the condition of guarantee.

In embodiments the set of social network data collection and monitoring services obtains information about the financial condition of an entity that is the guarantor for the loan.

In embodiments the financial condition is determined at least in part based on information contained in a social network about the entity selected from among a publicly stated valuation of the entity, a set of property owned by the entity as indicated by public records, a valuation of a set of property owned by the entity, a bankruptcy condition of an entity, a foreclosure status of an entity, a contractual default status of an entity, a regulatory violation status of an entity, a criminal status of an entity, an export controls status of an entity, an embargo status of an entity, a tariff status of an entity, a tax status of an entity, a credit report of an entity, a credit rating of an entity, a web site rating of an entity, a set of customer reviews for a product of an entity, a social network rating of an entity, a set of credentials of an entity, a set of referrals of an entity, a set of testimonials for an entity, a set of behavior of an entity, a location of an entity, and a geolocation of an entity.

In embodiments the loan is of at least one type selected from among an auto loan, an inventory loan, a capital equipment loan, a bond for performance, a capital improvement loan, a building loan, a loan backed by an account receivable, an invoice finance arrangement, a factoring arrangement, a pay day loan, a refund anticipation loan, a student loan, a syndicated loan, a title loan, a home loan, a venture debt loan, a loan of intellectual property, a loan of a contractual claim, a working capital loan, a small business loan, a farm loan, a municipal bond, and a subsidized loan.

In embodiments the platform or system may further include an interface of the social network data collection and monitoring services In embodiments the data collection and monitoring service is configured to obtain information about condition of a set of collateral for the loan, wherein the set of collateral items is selected from among a vehicle, a ship, a plane, a building, a home, real estate property, undeveloped land, a farm, a crop, a municipal facility, a warehouse, a set of inventory, a commodity, a security, a currency, a token of value, a ticket, a cryptocurrency, a consumable item, an edible item, a beverage, a precious metal, an item of jewelry, a gemstone, an item of intellectual property, an intellectual property right, a contractual right, an antique, a fixture, an item of furniture, an item of equipment, a tool, an item of machinery, and an item of personal property.

In embodiments condition of collateral includes condition attributes selected from the group consisting of the quality of the collateral, the condition of the collateral, the status of title to the collateral, the status of possession of the collateral, the status of a lien on the collateral, a new or used status of item, a type of item, a category of item, a specification of an item, a product feature set of an item, a model of item, a brand of item, a manufacturer of item, a status of item, a context of item, a state of item, a value of item, a storage location of item, a geolocation of item, an age of item, a maintenance history of item, a usage history of item, an accident history of an item, a fault history of an item, an ownership of an item, an ownership history of an item, a price of a type of item, a value of a type of item, an assessment of an item, and a valuation of an item.

In embodiments the interface is a graphical user interface configured to enable a workflow by which a human user enters parameters to establish the social network data collection and monitoring request.

In embodiments the platform or system may further include a set of smart contract services that administer a smart lending contract, wherein the smart contract services process information from the set of social network data collection and monitoring services and automatically undertake an action related to the loan.

In embodiments the action is at least one of a foreclosure action, a lien administration action, an interest-rate setting action, a default initiation action, a substitution of collateral, and a calling of the loan.

In embodiments the platform or system may further include a robotic process automation system that is trained, based on a training set of interactions of human users with the interface to the set of social network data collection and monitoring services, to configure a data collection and monitoring action based on a set of attributes of a loan.

In embodiments the attributes of the loan are obtained from a set of smart contract services that manage the loan.

In embodiments the robotic process automation system is configured to be iteratively trained and improved based on a set of outcomes from a set of social network data collection and monitoring requests.

In embodiments training includes training the robotic process automation system to determine a set of domains to which the social network data collection and monitoring services will applied.

In embodiments training includes training the robotic process automation system to configure the content of a social network data collection and monitoring search.

Referring still to FIG. 9, in embodiments a lending platform is provided having an Internet of Things data collection and monitoring system for validating reliability of a guarantee for a loan. The guarantee and/or security monitoring solution 230 may include the capability to use data from, and configure collection activities by, a set of Internet of Things services 208 (which may include various IoT devices, edge devices, edge computation and processing capabilities, and the like as described in connection with various embodiments), such as ones that monitor various entities 198 and their environments involved in lending transactions.

In embodiments, provided herein is a monitoring system for validating conditions of a guarantee for a loan. For example, a set of algorithms may be configured to initiate data collection by IoT devices, to manage data collection, and the like such as based on the conditions referenced above, including conditions that relate to risk factors of the borrower or lender, market risk factors, physical risk factors, or the like. For example, an IoT system may be configured to capture video or images of a home during periods of bad weather, such as to determine whether the home is at risk of a flood, wind damage, or the like, in order to confirm whether the home can be predicted to serve as adequate collateral for a home loan, a line of credit, or other lending transaction.

In embodiments, the platform or system includes (a) a set of Internet of Things data collection and monitoring services by which data is collected by a set of algorithms that are configured to monitor Internet of Things information collected from and about entities involved in a loan; and (b) an interface to the set of Internet of Things data collection and monitoring services that enables configuration of parameters of the social network data collection and monitoring services to obtain information related to the condition of guarantee.

In embodiments the set of Internet of Things data collection and monitoring services obtains information about the financial condition of an entity that is the guarantor for the loan.

In embodiments the financial condition is determined at least in part based on information collected by an Internet of Things device about the entity selected from among a publicly stated valuation of the entity, a set of property owned by the entity as indicated by public records, a valuation of a set of property owned by the entity, a bankruptcy condition of an entity, a foreclosure status of an entity, a contractual default status of an entity, a regulatory violation status of an entity, a criminal status of an entity, an export controls status of an entity, an embargo status of an entity, a tariff status of an entity, a tax status of an entity, a credit report of an entity, a credit rating of an entity, a website rating of an entity, a set of customer reviews for a product of an entity, a social network rating of an entity, a set of credentials of an entity, a set of referrals of an entity, a set of testimonials for an entity, a set of behavior of an entity, a location of an entity, and a geolocation of an entity.

In embodiments the loan is of at least one type selected from among an auto loan, an inventory loan, a capital equipment loan, a bond for performance, a capital improvement loan, a building loan, a loan backed by an account receivable, an invoice finance arrangement, a factoring arrangement, a pay day loan, a refund anticipation loan, a student loan, a syndicated loan, a title loan, a home loan, a venture debt loan, a loan of intellectual property, a loan of a contractual claim, a working capital loan, a small business loan, a farm loan, a municipal bond, and a subsidized loan.

In embodiments the platform or system may further include an interface of the set of Internet of Things data collection and monitoring services In embodiments the set of data collection and monitoring services is configured to obtain information about condition of a set of collateral for the loan, wherein the set of collateral items is selected from among a vehicle, a ship, a plane, a building, a home, real estate property, undeveloped land, a farm, a crop, a municipal facility, a warehouse, a set of inventory, a commodity, a security, a currency, a token of value, a ticket, a cryptocurrency, a consumable item, an edible item, a beverage, a precious metal, an item of jewelry, a gemstone, an item of intellectual property, an intellectual property right, a contractual right, an antique, a fixture, an item of furniture, an item of equipment, a tool, an item of machinery, and an item of personal property.

In embodiments condition of collateral includes condition attributes selected from the group consisting of the quality of the collateral, the condition of the collateral, the status of title to the collateral, the status of possession of the collateral, the status of a lien on the collateral, a new or used status of item, a type of item, a category of item, a specification of an item, a product feature set of an item, a model of item, a brand of item, a manufacturer of item, a status of item, a context of item, a state of item, a value of item, a storage location of item, a geolocation of item, an age of item, a maintenance history of item, a usage history of item, an accident history of an item, a fault history of an item, an ownership of an item, an ownership history of an item, a price of a type of item, a value of a type of item, an assessment of an item, and a valuation of an item.

In embodiments the interface is a graphical user interface configured to enable a workflow by which a human user enters parameters to establish an Internet of Things data collection and monitoring services monitoring action.

In embodiments the platform or system may further include a set of smart contract services that administer a smart lending contract, wherein the set of smart contract services process information from the set of Internet of Things data collection and monitoring services and automatically undertakes an action related to the loan.

In embodiments the action is at least one of a foreclosure action, a lien administration action, an interest-rate setting action, a default initiation action, a substitution of collateral, and a calling of the loan.

In embodiments the platform or system may further include a robotic process automation system that is trained, based on a training set of interactions of human users with the interface to the set of Internet of Things data collection and monitoring services, to configure a data collection and monitoring action based on a set of attributes of a loan.

In embodiments the attributes of the loan are obtained from a set of smart contract services that manage the loan.

In embodiments the robotic process automation system is configured to be iteratively trained and improved based on a set of outcomes from a set of Internet of Things data collection and monitoring services activities.

In embodiments training includes training the robotic process automation system to determine a set of domains to which the Internet of Things data collection and monitoring services will applied.

In embodiments training includes training the robotic process automation system to configure the content of Internet of Things data collection and monitoring services activities.

Figure 10:
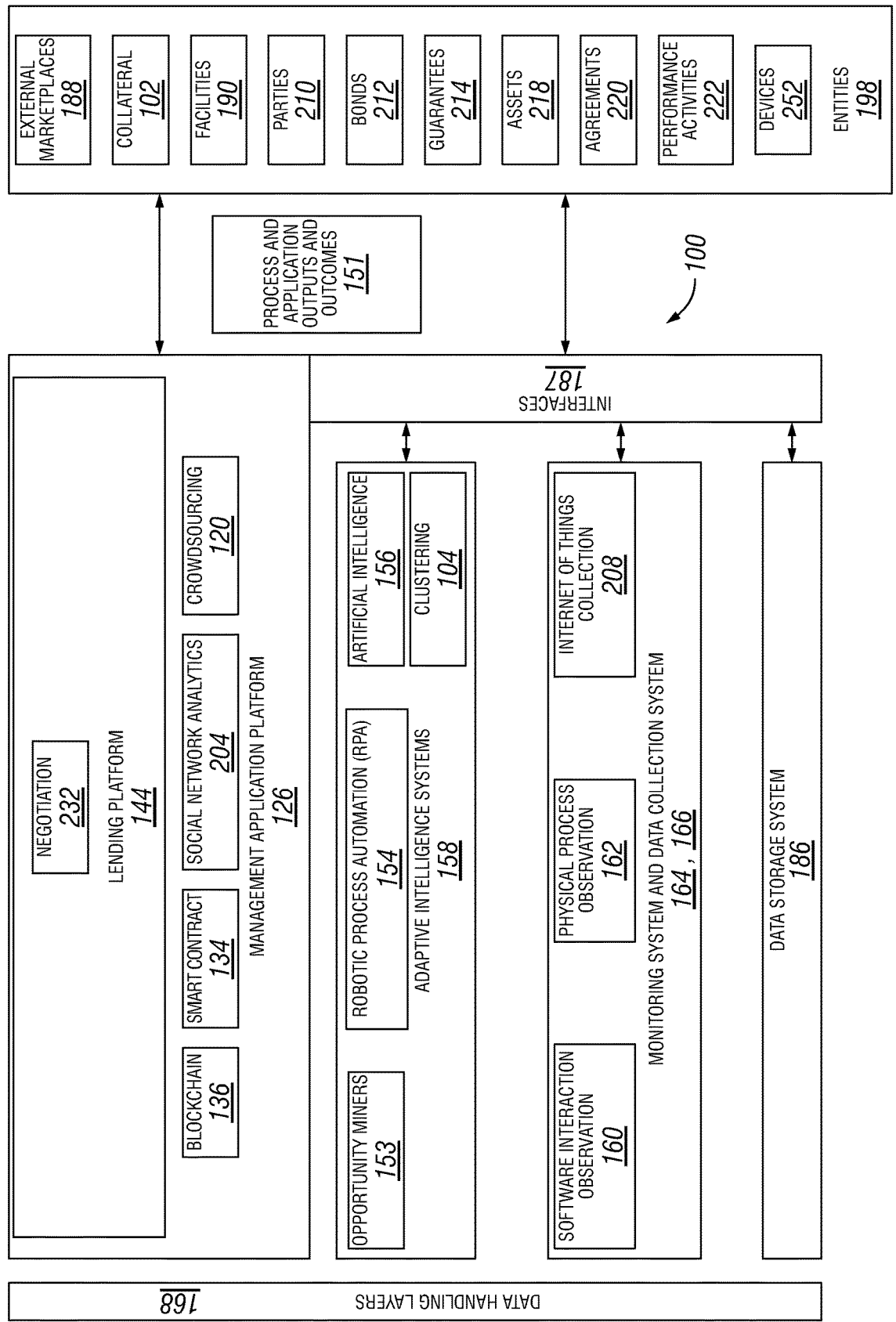
FIG. 10 depicts components and interactions of a lending platform having a robotic process automation system for negotiation of a set of terms and conditions for a loan.

Referring to FIG. 10, in embodiments a lending platform is provided having a robotic process automation system (RPA) 154 for negotiation of a set of terms and conditions for a loan. The RPA system 154 may provide automation for one or more aspects of a negotiation solution 232 that enables automated negotiation and/or provides a recommendation or plan for a negotiation relevant to a lending transaction. The negotiation solution 232 and/or RPA system 154 for negotiation may include a set of interfaces, workflows, and models (which may include, use or be enabled by various adaptive intelligent systems 158) and other components that are configured to enable automation of one or more aspects of a negotiation of one or more terms and conditions of a lending transaction, such as based on a set of conditions, which may include smart contract terms and conditions, marketplace conditions (of platform marketplaces and/or external marketplaces 188, conditions monitored by monitoring systems 164 and data collection systems 166, and the like (such as of entities 198, including without limitation parties 210, collateral 102 and assets 218, among others). For example, a user of the negotiation solution 232 may create, configure (such as using one or more templates or libraries), modify, set or otherwise handle (such as in a user interface of the negotiation solution 232 and/or RPA system 154) various rules, thresholds, conditional procedures, workflows, model parameters, and the like that determine, or recommend, a negotiation action or plan for a lending transaction negotiation based on one or more events, conditions, states, actions, or the like, where the negotiation plan may be based on various factors, such as prevailing market interest rates, interest rates available to the lender from secondary lenders, risk factors of the borrower, the lender, one or more guarantors, market risk factors and the like (including predicted risk based on one or more predictive models using artificial intelligence 156), status of debt, condition of collateral 102 or assets 218 used to secure or back a loan, state of a business or business operation (e.g., receivables, payables, or the like), conditions of parties 210 (such as net worth, wealth, debt, location, and other conditions), behaviors of parties (such as behaviors indicating preferences, behaviors indicating negotiation styles), and many others. Negotiation may include negotiation of lending transaction terms and conditions, debt restructuring, foreclosure activities, setting interest rates, changes in interest rate, changes in priority of secured parties, changes in collateral 102 or assets 218 used to back or secure debt, changes in parties, changes in guarantors, changes in payment schedule, changes in principal balance (e.g., including forgiveness or acceleration of payments), and many other transactions or terms and conditions. In embodiments the negotiation solution 232 may automatically recommend or set rules, thresholds, actions, parameters and the like (optionally by learning to do so based on a training set of outcomes over time), resulting in a recommended negotiation plan, which may specify a series of actions required to accomplish a recommended or desired outcome of negotiation (such as within a range of acceptable outcomes), which may be automated and may involve conditional execution of steps based on monitored conditions and/or smart contract terms, which may be created, configured, and/or accounted for by the negotiation plan. Negotiation plans may be determined and executed based at least one part on market factors (such as competing interest rates offered by other lenders, values of collateral, and the like) as well as regulatory and/or compliance factors. Negotiation plans may be generated and/or executed for creation of new loans, for creation of guarantees and security, for secondary loans, for modifications of existing loans, for refinancing, for foreclosure situations (e.g., changing from secured loan rates to unsecured loan rates), for bankruptcy or insolvency situations, for situations involving market changes (e.g., changes in prevailing interest rates) and others. In embodiments, adaptive intelligent systems 158, including artificial intelligence 156 may be trained on a training set of negotiation activities by experts and/or on outcomes of negotiation actions to generate a set of predictions, classifications, control instructions, plans, models, or the like for automated creation, management and/or execution of one or more aspects of a negotiation plan.

In embodiments, provided herein is a robotic process automation system for negotiating a loan. In embodiments, the platform or system includes (a) a set of data collection and monitoring services for collecting a training set of interactions among entities for a set of loan transactions; (b) an artificial intelligence system that is trained on the training set of interactions to classify a set of loan negotiation actions; and (c) a robotic process automation system that is trained on a set of loan transaction interactions and a set of loan transaction outcomes to negotiate the terms and conditions of a loan on behalf of a party to a loan.

In embodiments the set of data collection and monitoring services includes services selected from among a set of Internet of Things systems that monitor the entities, a set of cameras that monitor the entities, a set of software services that pull information related to the entities from publicly available information sites, a set of mobile devices that report on information related to the entities, a set of wearable devices worn by human entities, a set of user interfaces by which entities provide information about the entities and a set of crowdsourcing services configured to solicit and report information related to the entities.

In embodiments the entities are a set of parties to a loan transaction.

In embodiments the set of parties is selected from among a primary lender, a secondary lender, a lending syndicate, a corporate lender, a government lender, a bank lender, a secured lender, bond issuer, a bond purchaser, an unsecured lender, a guarantor, a provider of security, a borrower, a debtor, an underwriter, an inspector, an assessor, an auditor, a valuation professional, a government official, and an accountant.

In embodiments the artificial intelligence system includes at least one of a machine learning system, a model-based system, a rule-based system, a deep learning system, a hybrid system, a neural network, a convolutional neural network, a feed forward neural network, a feedback neural network, a self-organizing map, a fuzzy logic system, a random walk system, a random forest system, a probabilistic system, a Bayesian system, and a simulation system.

In embodiments the robotic process automation is trained on a set of interactions of parties with a set of user interfaces involved in a set of lending processes.

In embodiments upon completion of negotiation a smart contract for a loan is automatically configured by a set of smart contract services based on the outcome of the negotiation.

In embodiments at least one of an outcome and a negotiating event of the negotiation is recorded in a distributed ledger associated with the loan.

In embodiments the loan is of a type selected from among an auto loan, an inventory loan, a capital equipment loan, a bond for performance, a capital improvement loan, a building loan, a loan backed by an account receivable, an invoice finance arrangement, a factoring arrangement, a pay day loan, a refund anticipation loan, a student loan, a syndicated loan, a title loan, a home loan, a venture debt loan, a loan of intellectual property, a loan of a contractual claim, a working capital loan, a small business loan, a farm loan, a municipal bond, and a subsidized loan.

In embodiments the artificial intelligence system includes at least one of a machine learning system, a model-based system, a rule-based system, a deep learning system, a hybrid system, a neural network, a convolutional neural network, a feed forward neural network, a feedback neural network, a self-organizing map, a fuzzy logic system, a random walk system, a random forest system, a probabilistic system, a Bayesian system, and a simulation system.

In embodiments, provided herein is a robotic process automation system for negotiating refinancing of a loan. In embodiments, the platform or system includes (a) a set of data collection and monitoring services for collecting a training set of interactions between entities for a set of loan refinancing activities; an artificial intelligence system that is trained on the training set of interactions to classify a set of loan refinancing actions; and (c) a robotic process automation system that is trained on a set of loan refinancing interactions and a set of loan refinancing outcomes to undertake a loan refinancing activity on behalf of a party to a loan.

In embodiments the loan refinancing activity includes initiating an offer to refinance, initiating a request to refinance, configuring a refinancing interest rate, configuring a refinancing payment schedule, configuring a refinancing balance, configuring collateral for a refinancing, managing use of proceeds of a refinancing, removing or placing a lien associated with a refinancing, verifying title for a refinancing, managing an inspection process, populating an application, negotiating terms and conditions for a refinancing and closing a refinancing.

In embodiments the set of data collection and monitoring services includes services selected from among a set of Internet of Things systems that monitor the entities, a set of cameras that monitor the entities, a set of software services that pull information related to the entities from publicly available information sites, a set of mobile devices that report on information related to the entities, a set of wearable devices worn by human entities, a set of user interfaces by which entities provide information about the entities and a set of crowdsourcing services configured to solicit and report information related to the entities.

In embodiments the entities are a set of parties to a loan transaction.

In embodiments the set of parties is selected from among a primary lender, a secondary lender, a lending syndicate, a corporate lender, a government lender, a bank lender, a secured lender, bond issuer, a bond purchaser, an unsecured lender, a guarantor, a provider of security, a borrower, a debtor, an underwriter, an inspector, an assessor, an auditor, a valuation professional, a government official, and an accountant.

In embodiments the artificial intelligence system includes at least one of a machine learning system, a model-based system, a rule-based system, a deep learning system, a hybrid system, a neural network, a convolutional neural network, a feed forward neural network, a feedback neural network, a self-organizing map, a fuzzy logic system, a random walk system, a random forest system, a probabilistic system, a Bayesian system, and a simulation system.

In embodiments the robotic process automation is trained on a set of interactions of parties with a set of user interfaces involved in a set of lending processes.

In embodiments upon completion of a refinancing process a smart contract for a refinance loan is automatically configured by a set of smart contract services based on the outcome of the refinancing activity.

In embodiments at least one of an outcome and an event of the refinancing is recorded in a distributed ledger associated with the refinancing loan.

In embodiments the loan is of a type selected from among an auto loan, an inventory loan, a capital equipment loan, a bond for performance, a capital improvement loan, a building loan, a loan backed by an account receivable, an invoice finance arrangement, a factoring arrangement, a pay day loan, a refund anticipation loan, a student loan, a syndicated loan, a title loan, a home loan, a venture debt loan, a loan of intellectual property, a loan of a contractual claim, a working capital loan, a small business loan, a farm loan, a municipal bond, and a subsidized loan.

In embodiments the artificial intelligence system includes at least one of a machine learning system, a model-based system, a rule-based system, a deep learning system, a hybrid system, a neural network, a convolutional neural network, a feed forward neural network, a feedback neural network, a self-organizing map, a fuzzy logic system, a random walk system, a random forest system, a probabilistic system, a Bayesian system, and a simulation system.

Figure 11:
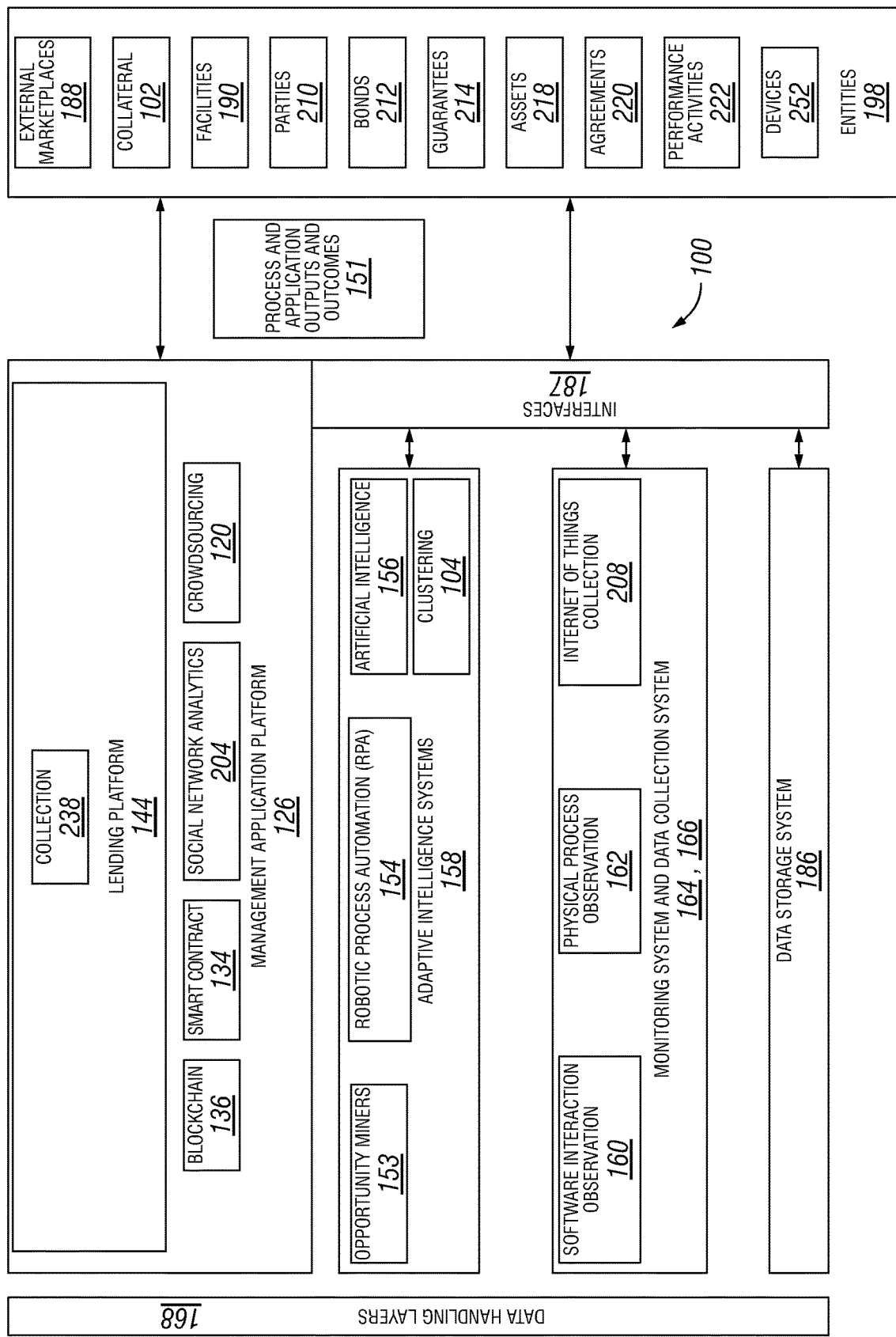
FIG. 11 depicts components and interactions of a lending platform having a robotic process automation system for loan collection.

Referring to FIG. 11, in embodiments a lending platform is provided having a robotic process automation system for loan collection. The RPA system 154 may provide automation for one or more aspects of a collection solution 238 that enables automated collection and/or provides a recommendation or plan for a collection activity relevant to a lending transaction. The collection solution 238 and/or RPA system 154 for collection may include a set of interfaces, workflows, and models (which may include, use or be enabled by various adaptive intelligent systems 158) and other components that are configured to enable automation of one or more aspects of a collection action of one or more terms and conditions of a collection process for a lending transaction, such as based on a set of conditions, which may include smart contract terms and conditions, marketplace conditions (of platform marketplaces and/or external marketplaces 188, conditions monitored by monitoring systems 164 and data collection systems 166, and the like (such as of entities 198, including without limitation parties 210, collateral 102 and assets 218, among others). For example, a user of the collection solution 238 may create, configure (such as using one or more templates or libraries), modify, set or otherwise handle (such as in a user interface of the collection solution 238 and/or RPA system 154) various rules, thresholds, conditional procedures, workflows, model parameters, and the like that determine, or recommend, a collection action or plan for a lending transaction or loan monitoring solution based on one or more events, conditions, states, actions, or the like, where the collection plan may be based on various factors, such as the status of payments, the status of the borrower, the status of collateral 102 or assets 218, risk factors of the borrower, the lender, one or more guarantors, market risk factors and the like (including predicted risk based on one or more predictive models using artificial intelligence 156), status of debt, condition of collateral 102 or assets 218 used to secure or back a loan, state of a business or business operation (e.g., receivables, payables, or the like), conditions of parties 210 (such as net worth, wealth, debt, location, and other conditions), behaviors of parties (such as behaviors indicating preferences, behaviors indicating how borrowers respond to communication styles, communication cadence, and the like), and many others. Collection may include collection with respect to loans, communications to encourage payments, and the like. In embodiments the collection solution 238 may automatically recommend or set rules, thresholds, actions, parameters and the like (optionally by learning to do so based on a training set of outcomes over time), resulting in a recommended collection plan, which may specify a series of actions required to accomplish a recommended or desired outcome of collection (such as within a range of acceptable outcomes), which may be automated and may involve conditional execution of steps based on monitored conditions and/or smart contract terms, which may be created, configured, and/or accounted for by the collection plan. Collection plans may be determined and executed based at least one part on market factors (such as competing interest rates offered by other lenders, values of collateral, and the like) as well as regulatory and/or compliance factors. Collection plans may be generated and/or executed for creation of new loans, for secondary loans, for modifications of existing loans, for refinancing, for foreclosure situations (e.g., changing from secured loan rates to unsecured loan rates), for bankruptcy or insolvency situations, for situations involving market changes (e.g., changes in prevailing interest rates) and others. In embodiments, adaptive intelligent systems 158, including artificial intelligence 156 may be trained on a training set of collection activities by experts and/or on outcomes of collection actions to generate a set of predictions, classifications, control instructions, plans, models, or the like for automated creation, management and/or execution of one or more aspects of a collection plan.

In embodiments, provided herein is a robotic process automation system for handling collection of a loan. In embodiments, the platform or system includes (a) a set of data collection and monitoring services for collecting a training set of interactions among entities for a set of loan transactions that involve collection of a set of payments for a set of loans; (b) an artificial intelligence system that is trained on the training set of interactions to classify a set of loan collection actions; and (c) a robotic process automation system that is trained on a set of loan transaction interactions and a set of loan collection outcomes to undertake a loan collection action on behalf of a party to a loan.

In embodiments the loan collection action undertaken by the robotic process automation system is selected from among initiation of a collection process, referral of a loan to an agent for collection, configuration of a collection communication, scheduling of a collection communication, configuration of content for a collection communication, configuration of an offer to settle a loan, termination of a collection action, deferral of a collection action, configuration of an offer for an alternative payment schedule, initiation of a litigation, initiation of a foreclosure, initiation of a bankruptcy process, a repossession process, and placement of a lien on collateral.

In embodiments the set of loan collection outcomes is selected from among a response to a collection contact event, a payment of a loan, a default of the borrower on a loan, a bankruptcy of a borrower of a loan, an outcome of a collection litigation, a financial yield of a set of collection actions, a return on investment on collection and a measure of reputation of a party involved in collection.

In embodiments the set of data collection and monitoring services includes services selected from among a set of Internet of Things systems that monitor the entities, a set of cameras that monitor the entities, a set of software services that pull information related to the entities from publicly available information sites, a set of mobile devices that report on information related to the entities, a set of wearable devices worn by human entities, a set of user interfaces by which entities provide information about the entities and a set of crowdsourcing services configured to solicit and report information related to the entities. In embodiments the entities are set of parties to a loan transaction. In embodiments the set of parties is selected from among a primary lender, a secondary lender, a lending syndicate, a corporate lender, a government lender, a bank lender, a secured lender, bond issuer, a bond purchaser, an unsecured lender, a guarantor, a provider of security, a borrower, a debtor, an underwriter, an inspector, an assessor, an auditor, a valuation professional, a government official, and an accountant.

In embodiments the artificial intelligence system includes at least one of a machine learning system, a model-based system, a rule-based system, a deep learning system, a hybrid system, a neural network, a convolutional neural network, a feed forward neural network, a feedback neural network, a self-organizing map, a fuzzy logic system, a random walk system, a random forest system, a probabilistic system, a Bayesian system, and a simulation system.

In embodiments the robotic process automation is trained on a set of interactions of parties with a set of user interfaces involved in a set of lending processes.

In embodiments upon completion of negotiation of a collection process a smart contract for a loan is automatically configured by a set of smart contract services based on the outcome of the negotiation.

In embodiments at least one of a collection outcome and a collection event is recorded in a distributed ledger associated with the loan.

In embodiments the loan is of a type selected from among an auto loan, an inventory loan, a capital equipment loan, a bond for performance, a capital improvement loan, a building loan, a loan backed by an account receivable, an invoice finance arrangement, a factoring arrangement, a pay day loan, a refund anticipation loan, a student loan, a syndicated loan, a title loan, a home loan, a venture debt loan, a loan of intellectual property, a loan of a contractual claim, a working capital loan, a small business loan, a farm loan, a municipal bond, and a subsidized loan.

In embodiments the artificial intelligence system includes at least one of a machine learning system, a model-based system, a rule-based system, a deep learning system, a hybrid system, a neural network, a convolutional neural network, a feed forward neural network, a feedback neural network, a self-organizing map, a fuzzy logic system, a random walk system, a random forest system, a probabilistic system, a Bayesian system, and a simulation system.

Figure 12:
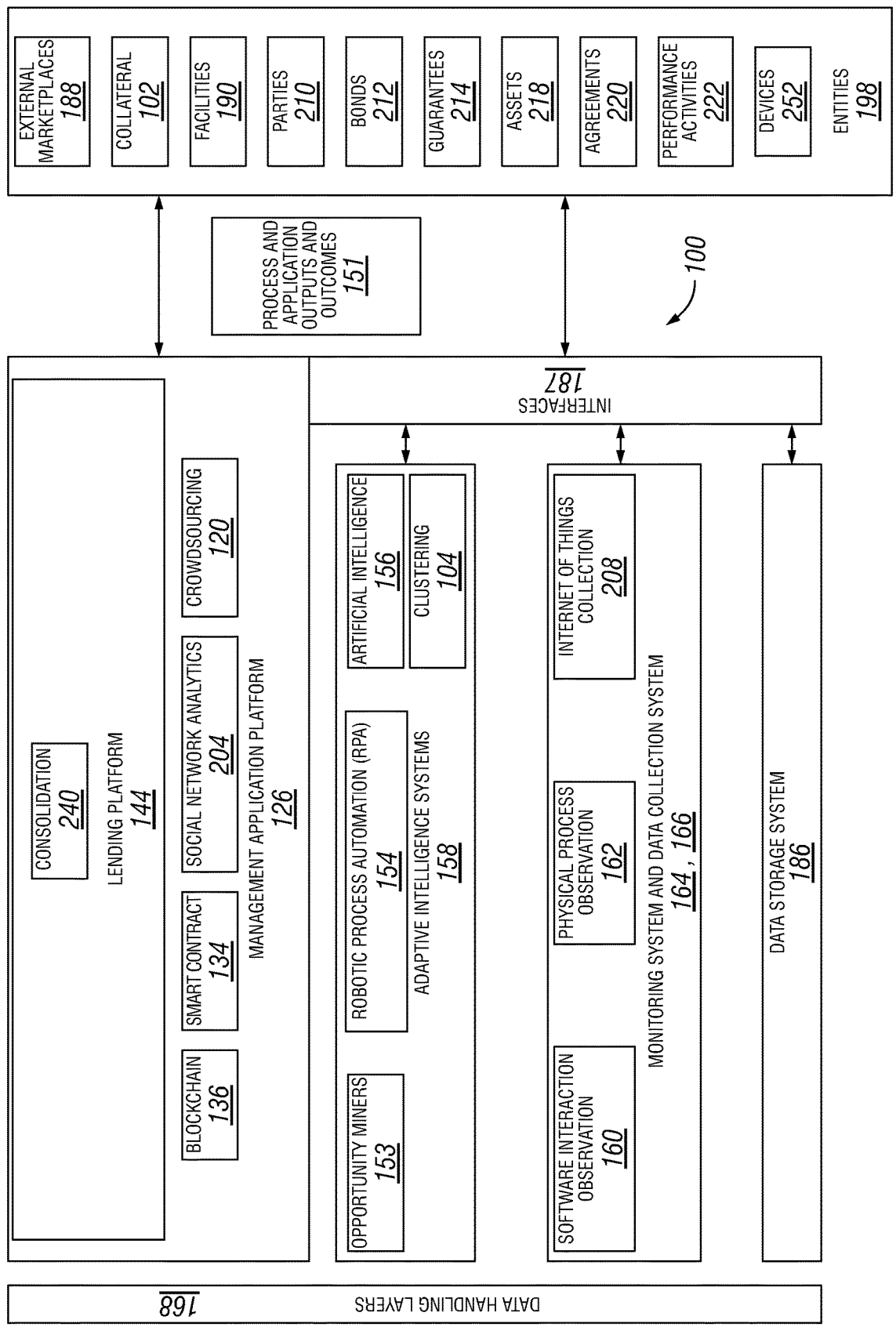
FIG. 12 depicts components and interactions of a lending platform having a robotic process automation system for consolidating a set of loans.

Referring to FIG. 12, in embodiments a lending platform is provided having a robotic process automation system for consolidating a set of loans. The RPA system 154 may provide automation for one or more aspects of a consolidation solution 240 that enables automated consolidation and/or provides a recommendation or plan for a consolidation activity relevant to a lending transaction. The consolidation solution 240 and/or RPA system 154 for consolidation may include a set of interfaces, workflows, and models (which may include, use or be enabled by various adaptive intelligent systems 158) and other components that are configured to enable automation of one or more aspects of a consolidation action or a consolidation process for a lending transaction, such as based on a set of conditions, which may include smart contract terms and conditions, marketplace conditions (of platform marketplaces and/or external marketplaces 188, conditions monitored by monitoring systems 164 and data collection systems 166, and the like (such as of entities 198, including without limitation parties 210, collateral 102 and assets 218, among others). For example, a user of the consolidation solution 240 may create, configure (such as using one or more templates or libraries), modify, set or otherwise handle (such as in a user interface of the consolidation solution 240 and/or RPA system 154) various rules, thresholds, conditional procedures, workflows, model parameters, and the like that determine, or recommend, a consolidation action or plan for a lending transaction or a set of loans based on one or more events, conditions, states, actions, or the like, where the consolidation plan may be based on various factors, such as the status of payments, interest rates of the set of loans, prevailing interest rates in a platform marketplace or external marketplace, the status of the borrowers of a set of loans, the status of collateral 102 or assets 218, risk factors of the borrower, the lender, one or more guarantors, market risk factors and the like (including predicted risk based on one or more predictive models using artificial intelligence 156), status of debt, condition of collateral 102 or assets 218 used to secure or back a set of loans, the state of a business or business operation (e.g., receivables, payables, or the like), conditions of parties 210 (such as net worth, wealth, debt, location, and other conditions), behaviors of parties (such as behaviors indicating preferences, behaviors indicating debt preferences), and many others. Consolidation may include consolidation with respect to terms and conditions of sets of loans, selection of appropriate loans, configuration of payment terms for consolidated loans, configuration of payoff plans for pre-existing loans, communications to encourage consolidation, and the like. In embodiments the consolidation solution 240 may automatically recommend or set rules, thresholds, actions, parameters and the like (optionally by learning to do so based on a training set of outcomes over time), resulting in a recommended consolidation plan, which may specify a series of actions required to accomplish a recommended or desired outcome of consolidation (such as within a range of acceptable outcomes), which may be automated and may involve conditional execution of steps based on monitored conditions and/or smart contract terms, which may be created, configured, and/or accounted for by the consolidation plan. Consolidation plans may be determined and executed based at least one part on market factors (such as competing interest rates offered by other lenders, values of collateral, and the like) as well as regulatory and/or compliance factors. Consolidation plans may be generated and/or executed for creation of new consolidated loans, for secondary loans related to consolidated loans, for modifications of existing loans related to consolidation, for refinancing terms of a consolidated loan, for foreclosure situations (e.g., changing from secured loan rates to unsecured loan rates), for bankruptcy or insolvency situations, for situations involving market changes (e.g., changes in prevailing interest rates) and others. In embodiments, adaptive intelligent systems 158, including artificial intelligence 156 may be trained on a training set of consolidation activities by experts and/or on outcomes of consolidation actions to generate a set of predictions, classifications, control instructions, plans, models, or the like for automated creation, management and/or execution of one or more aspects of a consolidation plan.

In embodiments, provided herein is a robotic process automation system for consolidating a set of loans. In embodiments, the platform or system includes (a) a set of data collection and monitoring services for collecting information about a set of loans and for collecting a training set of interactions between entities for a set of loan consolidation transactions; (b) an artificial intelligence system that is trained on the training set of interactions to classify a set of loans as candidates for consolidation; and (c) a robotic process automation system that is trained on a set of loan consolidation interactions to manage consolidation of at least a subset of the set of loans on behalf of a party to the consolidation.

In embodiments the set of data collection and monitoring services includes services selected from among a set of Internet of Things systems that monitor the entities, a set of cameras that monitor the entities, a set of software services that pull information related to the entities from publicly available information sites, a set of mobile devices that report on information related to the entities, a set of wearable devices worn by human entities, a set of user interfaces by which entities provide information about the entities and a set of crowdsourcing services configured to solicit and report information related to the entities.

In embodiments the set of loans that are classified as candidates for consolidation are determined based on a model that processes attributes of entities involved in the set of loans, wherein the attributes selected from among identity of a party, interest rate, payment balance, payment terms, payment schedule, type of loan, type of collateral, financial condition of party, payment status, condition of collateral, and value of collateral.

In embodiments managing consolidation includes managing at least one of identification of loans from a set of candidate loans, preparation of a consolidation offer, preparation of a consolidation plan, preparation of content communicating a consolidation offer, scheduling a consolidation offer, communicating a consolidation offer, negotiating a modification of a consolidation offer, preparing a consolidation agreement, executing a consolidation agreement, modifying collateral for a set of loans, handling an application workflow for consolidation, managing an inspection, managing an assessment, setting an interest rate, deferring a payment requirement, setting a payment schedule, and closing a consolidation agreement. In embodiments the entities are a set of parties to a loan transaction. In embodiments the set of parties is selected from among a primary lender, a secondary lender, a lending syndicate, a corporate lender, a government lender, a bank lender, a secured lender, bond issuer, a bond purchaser, an unsecured lender, a guarantor, a provider of security, a borrower, a debtor, an underwriter, an inspector, an assessor, an auditor, a valuation professional, a government official, and an accountant.

In embodiments the artificial intelligence system includes at least one of a machine learning system, a model-based system, a rule-based system, a deep learning system, a hybrid system, a neural network, a convolutional neural network, a feed forward neural network, a feedback neural network, a self-organizing map, a fuzzy logic system, a random walk system, a random forest system, a probabilistic system, a Bayesian system, and a simulation system.

In embodiments the robotic process automation is trained on a set of interactions of parties with a set of user interfaces involved in a set of consolidation processes. In embodiments upon completion of negotiation a smart contract for a consolidated loan is automatically configured by a set of smart contract services based on the outcome of the negotiation. In embodiments at least one of an outcome and a negotiating event of the negotiation is recorded in a distributed ledger associated with the loan.

In embodiments the loan is of a type selected from among an auto loan, an inventory loan, a capital equipment loan, a bond for performance, a capital improvement loan, a building loan, a loan backed by an account receivable, an invoice finance arrangement, a factoring arrangement, a pay day loan, a refund anticipation loan, a student loan, a syndicated loan, a title loan, a home loan, a venture debt loan, a loan of intellectual property, a loan of a contractual claim, a working capital loan, a small business loan, a farm loan, a municipal bond, and a subsidized loan.

In embodiments the artificial intelligence system includes at least one of a machine learning system, a model-based system, a rule-based system, a deep learning system, a hybrid system, a neural network, a convolutional neural network, a feed forward neural network, a feedback neural network, a self-organizing map, a fuzzy logic system, a random walk system, a random forest system, a probabilistic system, a Bayesian system, and a simulation system.

Figure 13:
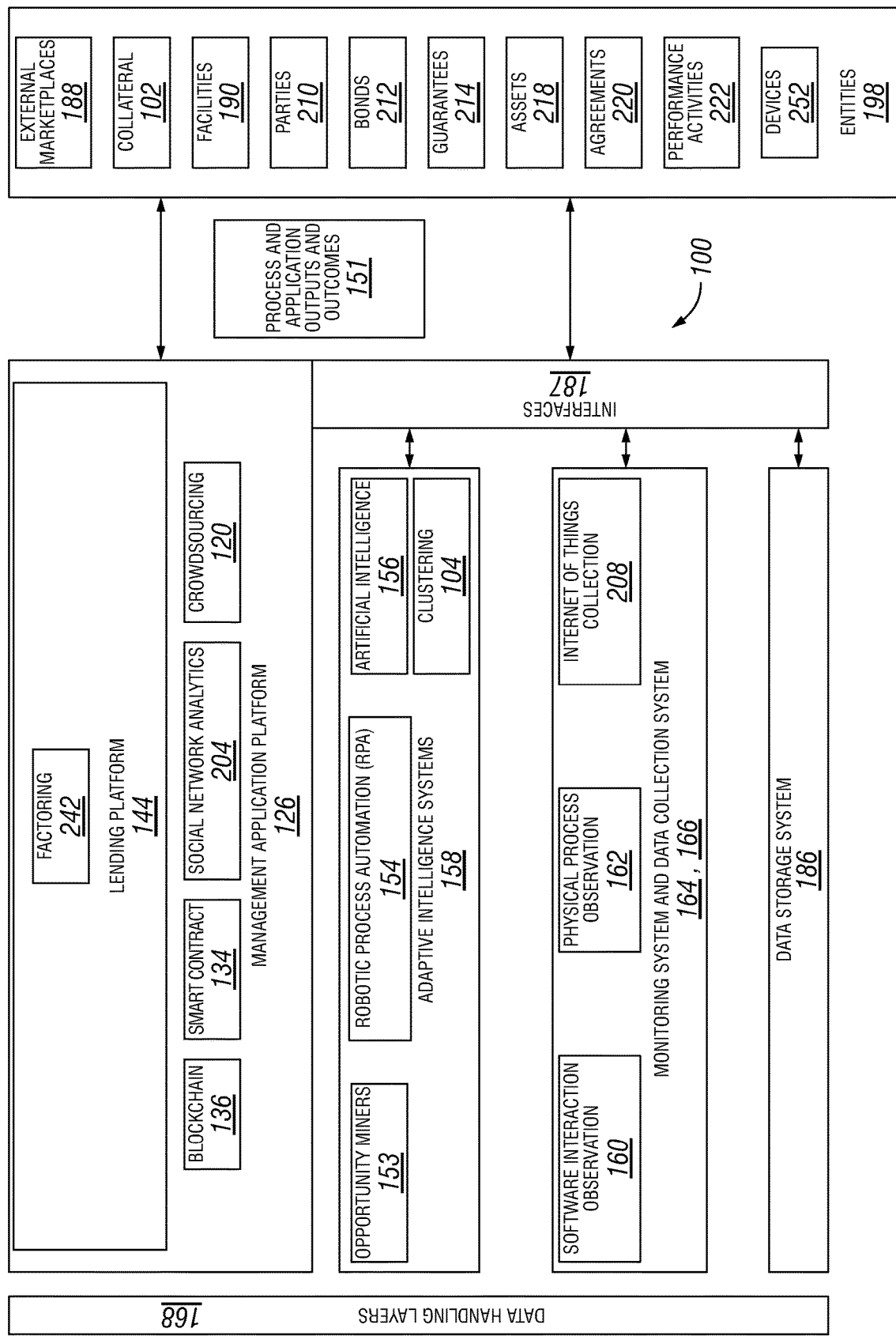
FIG. 13 depicts components and interactions of a lending platform having a robotic process automation system for managing a factoring loan.

Referring to FIG. 13, in embodiments a lending platform is provided having a robotic process automation system for managing a factoring transaction. The RPA system 154 may provide automation for one or more aspects of a factoring solution 242 that enables automated factoring and/or provides a recommendation or plan for a factoring activity relevant to a lending transaction, such as one involving factoring of receivables. The factoring solution 242 and/or RPA system 154 for factoring may include a set of interfaces, workflows, and models (which may include, use or be enabled by various adaptive intelligent systems 158) and other components that are configured to enable automation of one or more aspects of a factoring action of one or more terms and conditions of a factoring transaction, such as based on a set of conditions, which may include smart contract terms and conditions, marketplace conditions (of platform marketplaces and/or external marketplaces 188, conditions monitored by monitoring systems 164 and data collection systems 166, and the like (such as of entities 198, including without limitation parties 210, collateral 102 and assets 218, accounts receivable, and inventory, among others). For example, a user of the factoring solution 242 may create, configure (such as using one or more templates or libraries), modify, set or otherwise handle (such as in a user interface of the factoring solution 242 and/or RPA system 154) various rules, thresholds, conditional procedures, workflows, model parameters, and the like that determine, or recommend, a factoring action or plan for a factoring transaction or monitoring solution based on one or more events, conditions, states, actions, or the like, where the factoring plan may be based on various factors, such as the status of receivables, the status of work-in-progress, the status of inventory, the status of delivery and/or shipment, the status of payments, the status of the borrower, the status of collateral 102 or assets 218, risk factors of the borrower, the lender, one or more guarantors, market risk factors and the like (including predicted risk based on one or more predictive models using artificial intelligence 156), status of debt, condition of collateral 102 or assets 218 used to secure or back a loan, state of a business or business operation (e.g., receivables, payables, or the like), conditions of parties 210 (such as net worth, wealth, debt, location, and other conditions), behaviors of parties (such as behaviors indicating preferences, behaviors indicating negotiation styles, and the like), and many others. Factoring may include factoring with respect to loans, communications to encourage payments, and the like. In embodiments the factoring solution 242 may automatically recommend or set rules, thresholds, actions, parameters and the like (optionally by learning to do so based on a training set of outcomes over time), resulting in a recommended factoring plan, which may specify a series of actions required to accomplish a recommended or desired outcome of factoring (such as within a range of acceptable outcomes), which may be automated and may involve conditional execution of steps based on monitored conditions and/or smart contract terms, which may be created, configured, and/or accounted for by the factoring plan. Factoring plans may be determined and executed based at least one part on market factors (such as competing interest rates or other terms and conditions offered by other lenders, values of collateral, values of accounts receivable, interest rates, and the like) as well as regulatory and/or compliance factors. Factoring plans may be generated and/or executed for creation of new factoring arrangements, for modifications of existing factoring arrangements, and others. In embodiments, adaptive intelligent systems 158, including artificial intelligence 156 may be trained on a training set of factoring activities by experts and/or on outcomes of factoring actions to generate a set of predictions, classifications, control instructions, plans, models, or the like for automated creation, management and/or execution of one or more aspects of a factoring plan.

In embodiments, provided herein is a robotic process automation system for consolidating a set of loans. In embodiments, the platform or system includes (a) a set of data collection and monitoring services for collecting information about entities involved in a set of factoring loans and for collecting a training set of interactions between entities for a set of factoring loan transactions; (b) an artificial intelligence system that is trained on the training set of interactions to classify the entities involved in the set of factoring loans; and (c) a robotic process automation system that is trained on the set of factoring loan interactions to manage a factoring loan.

In embodiments the set of data collection and monitoring services includes services selected from among a set of Internet of Things systems that monitor the entities, a set of cameras that monitor the entities, a set of software services that pull information related to the entities from publicly available information sites, a set of mobile devices that report on information related to the entities, a set of wearable devices worn by human entities, a set of user interfaces by which entities provide information about the entities and a set of crowdsourcing services configured to solicit and report information related to the entities.

In embodiments the artificial intelligence system uses a model that processes attributes of entities involved in the set of factoring loans, wherein the attributes selected from assets used for factoring, identity of a party, interest rate, payment balance, payment terms, payment schedule, type of loan, type of collateral, financial condition of party, payment status, condition of collateral, and value of collateral.

In embodiments the assets used for factoring include a set of accounts receivable.

In embodiments managing a factoring loan includes managing at least one of a set of assets for factoring, identification of loans for factoring from a set of candidate loans, preparation of a factoring offer, preparation of a factoring plan, preparation of content communicating a factoring offer, scheduling a factoring offer, communicating a factoring offer, negotiating a modification of a factoring offer, preparing a factoring agreement, executing a factoring agreement, modifying collateral for a set of factoring loans, handing transfer of a set of accounts receivable, handling an application workflow for factoring, managing an inspection, managing an assessment of a set of assets to be factored, setting an interest rate, deferring a payment requirement, setting a payment schedule, and closing a factoring agreement.

In embodiments the entities are a set of parties to a loan transaction.

In embodiments the set of parties is selected from among a primary lender, a secondary lender, a lending syndicate, a corporate lender, a government lender, a bank lender, a secured lender, bond issuer, a bond purchaser, an unsecured lender, a guarantor, a provider of security, a borrower, a debtor, an underwriter, an inspector, an assessor, an auditor, a valuation professional, a government official, and an accountant.

In embodiments the artificial intelligence system includes at least one of a machine learning system, a model-based system, a rule-based system, a deep learning system, a hybrid system, a neural network, a convolutional neural network, a feed forward neural network, a feedback neural network, a self-organizing map, a fuzzy logic system, a random walk system, a random forest system, a probabilistic system, a Bayesian system, and a simulation system.

In embodiments the robotic process automation is trained on a set of interactions of parties with a set of user interfaces involved in a set of factoring processes.

In embodiments upon completion of negotiation a smart contract for a factoring loan is automatically configured by a set of smart contract services based on the outcome of the negotiation.

In embodiments at least one of an outcome and a negotiating event of the negotiation is recorded in a distributed ledger associated with the loan.

In embodiments the artificial intelligence system includes at least one of a machine learning system, a model-based system, a rule-based system, a deep learning system, a hybrid system, a neural network, a convolutional neural network, a feed forward neural network, a feedback neural network, a self-organizing map, a fuzzy logic system, a random walk system, a random forest system, a probabilistic system, a Bayesian system, and a simulation system.

Figure 14:
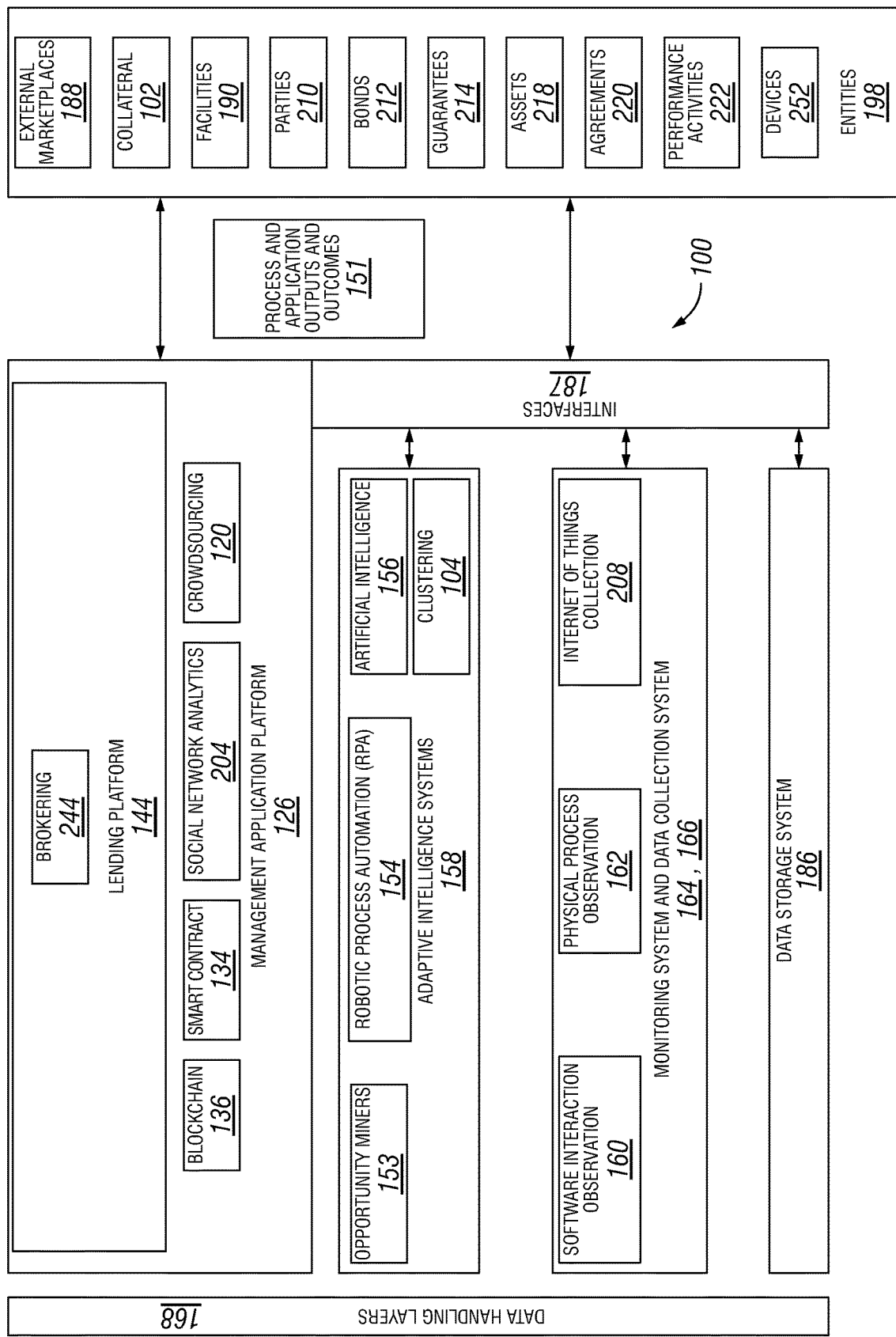
FIG. 14 depicts components and interactions of a lending platform having a robotic process automation system for brokering a mortgage loan.

Referring to FIG. 14, in embodiments a lending platform is provided having a robotic process automation system for brokering a loan. The loan may be, for example, a mortgage loan.

The RPA system 154 may provide automation for one or more aspects of a brokering solution 244 that enables automated brokering and/or provides a recommendation or plan for a brokering activity relevant to a lending transaction, such as for brokering a set of mortgage loans, home loans, lines of credit, automobile loans, construction loans, or other loans of any of the types described herein. The brokering solution 244 and/or RPA system 154 for brokering may include a set of interfaces, workflows, and models (which may include, use or be enabled by various adaptive intelligent systems 158) and other components that are configured to enable automation of one or more aspects of a brokering action or a brokering process for a lending transaction, such as based on a set of conditions, which may include smart contract terms and conditions, marketplace conditions (of platform marketplaces and/or external marketplaces 188, conditions monitored by monitoring systems 164 and data collection systems 166, and the like (such as of entities 198, including without limitation parties 210, collateral 102 and assets 218, among others, as well as of interest rates, available lenders, available terms and the like). For example, a user of the brokering solution 244 may create, configure (such as using one or more templates or libraries), modify, set or otherwise handle (such as in a user interface of the brokering solution 244 and/or RPA system 154) various rules, thresholds, conditional procedures, workflows, model parameters, and the like that determine, or recommend, a brokering action or plan for brokering a set of loans of a given type or types based on one or more events, conditions, states, actions, or the like, where the brokering plan may be based on various factors, such as the interest rates of the set of loans available from various primary and secondary lenders, permitted attributes of borrowers (e.g., based on income, wealth, location, or the like) prevailing interest rates in a platform marketplace or external marketplace, the status of the borrowers of a set of loans, the status or other attributes of collateral 102 or assets 218, risk factors of the borrower, the lender, one or more guarantors, market risk factors and the like (including predicted risk based on one or more predictive models using artificial intelligence 156), status of debt, condition of collateral 102 or assets 218 available to secure or back a set of loans, the state of a business or business operation (e.g., receivables, payables, or the like), conditions of parties 210 (such as net worth, wealth, debt, location, and other conditions), behaviors of parties (such as behaviors indicating preferences, behaviors indicating debt preferences), and many others. Brokering may include brokering with respect to terms and conditions of sets of loans, selection of appropriate loans, configuration of payment terms for consolidated loans, configuration of payoff plans for pre-existing loans, communications to encourage borrowing, and the like. In embodiments the brokering solution 244 may automatically recommend or set rules, thresholds, actions, parameters and the like (optionally by learning to do so based on a training set of outcomes over time), resulting in a recommended brokering plan, which may specify a series of actions required to accomplish a recommended or desired outcome of brokering (such as within a range of acceptable outcomes), which may be automated and may involve conditional execution of steps based on monitored conditions and/or smart contract terms, which may be created, configured, and/or accounted for by the brokering plan. Brokering plans may be determined and executed based at least one part on market factors (such as competing interest rates offered by other lenders, property values, attributes of borrowers, values of collateral, and the like) as well as regulatory and/or compliance factors. Brokering plans may be generated and/or executed for creation of new loans, for secondary loans, for modifications of existing loans, for refinancing terms, for situations involving market changes (e.g., changes in prevailing interest rates or property values) and others. In embodiments, adaptive intelligent systems 158, including artificial intelligence 156 may be trained on a training set of brokering activities by experts and/or on outcomes of brokering actions to generate a set of predictions, classifications, control instructions, plans, models, or the like for automated creation, management and/or execution of one or more aspects of a brokering plan.

In embodiments, provided herein is a robotic process automation system for automating brokering of a mortgage. In embodiments, the platform or system includes (a) a set of data collection and monitoring services for collecting information about entities involved in a set of mortgage loan activities and for collecting a training set of interactions between entities for a set of mortgage loan transactions; (b) an artificial intelligence system that is trained on the training set of interactions to classify the entities involved in the set of mortgage loans; and (c) a robotic process automation system that is trained on at least one of the set of mortgage loan activities and the set of mortgage loan interactions to broker a mortgage loan.

In embodiments at least one of the set of mortgage loan activities and the set of mortgage loan interactions includes activities among marketing activity, identification of a set of prospective borrowers, identification of property, identification of collateral, qualification of borrower, title search, title verification, property assessment, property inspection, property valuation, income verification, borrower demographic analysis, identification of capital providers, determination of available interest rates, determination of available payment terms and conditions, analysis of existing mortgage, comparative analysis of existing and new mortgage terms, completion of application workflow, population of fields of application, preparation of mortgage agreement, completion of schedule to mortgage agreement, negotiation of mortgage terms and conditions with capital provider, negotiation of mortgage terms and conditions with borrower, transfer of title, placement of lien and closing of mortgage agreement.

In embodiments the set of data collection and monitoring services includes services selected from among a set of Internet of Things systems that monitor the entities, a set of cameras that monitor the entities, a set of software services that pull information related to the entities from publicly available information sites, a set of mobile devices that report on information related to the entities, a set of wearable devices worn by human entities, a set of user interfaces by which entities provide information about the entities and a set of crowdsourcing services configured to solicit and report information related to the entities.

In embodiments the artificial intelligence system uses a model that processes attributes of entities involved in the set of mortgage loans, wherein the attributes are selected from properties that are subject to mortgages, assets used for collateral, identity of a party, interest rate, payment balance, payment terms, payment schedule, type of mortgage, type of property, financial condition of party, payment status, condition of property, and value of property.

In embodiments managing a mortgage loan includes managing at least one of a property that is subject to a mortgage, identification of candidate mortgages from a set of borrower situations, preparation of a mortgage offer, preparation of content communicating a mortgage offer, scheduling a mortgage offer, communicating a mortgage offer, negotiating a modification of a mortgage offer, preparing a mortgage agreement, executing a mortgage agreement, modifying collateral for a set of mortgage loans, handing transfer of a lien, handling an application workflow, managing an inspection, managing an assessment of a set of assets to be subject to a mortgage, setting an interest rate, deferring a payment requirement, setting a payment schedule, and closing a mortgage agreement. In embodiments the entities are a set of parties to a loan transaction. In embodiments the set of parties is selected from among a primary lender, a secondary lender, a lending syndicate, a corporate lender, a government lender, a bank lender, a secured lender, bond issuer, a bond purchaser, an unsecured lender, a guarantor, a provider of security, a borrower, a debtor, an underwriter, an inspector, an assessor, an auditor, a valuation professional, a government official, and an accountant.

In embodiments the artificial intelligence system includes at least one of a machine learning system, a model-based system, a rule-based system, a deep learning system, a hybrid system, a neural network, a convolutional neural network, a feed forward neural network, a feedback neural network, a self-organizing map, a fuzzy logic system, a random walk system, a random forest system, a probabilistic system, a Bayesian system, and a simulation system.

In embodiments the robotic process automation is trained on a set of interactions of parties with a set of user interfaces involved in a set of mortgage-related activities. In embodiments upon completion of negotiation a smart contract for a mortgage loan is automatically configured by a set of smart contract services based on the outcome of the negotiation. In embodiments at least one of an outcome and a negotiating event of the negotiation is recorded in a distributed ledger associated with the loan. In embodiments the artificial intelligence system includes at least one of a machine learning system, a model-based system, a rule-based system, a deep learning system, a hybrid system, a neural network, a convolutional neural network, a feed forward neural network, a feedback neural network, a self-organizing map, a fuzzy logic system, a random walk system, a random forest system, a probabilistic system, a Bayesian system, and a simulation system.

Figure 15:
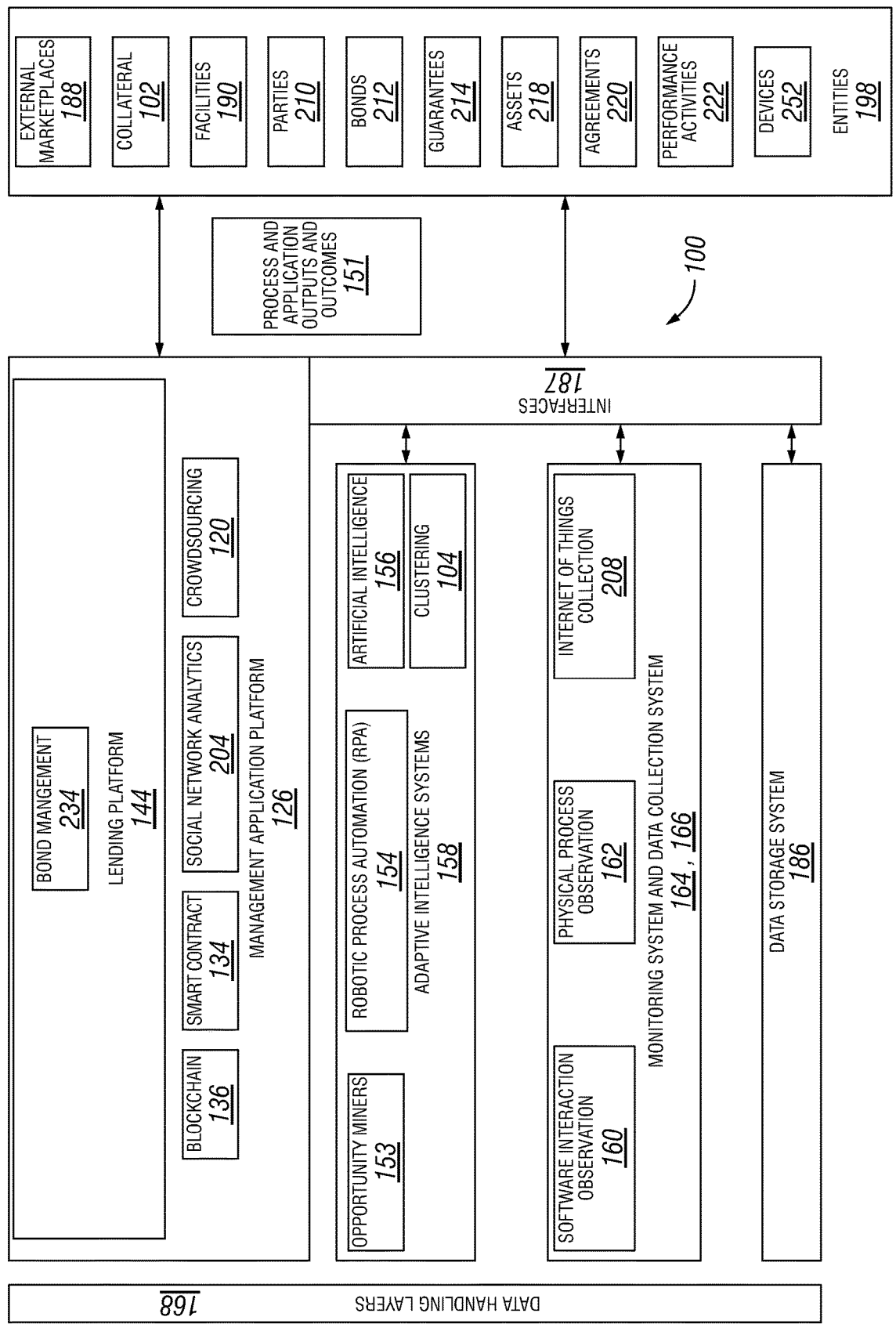
FIG. 15 depicts components and interactions of a lending platform having a crowdsourcing and automated classification system for validating condition of an issuer for a bond, a social network monitoring system with artificial intelligence for classifying a condition about a bond, and an Internet of Things data collection and monitoring system with artificial intelligence for classifying a condition about a bond.

Referring to FIG. 15, in embodiments a lending platform is provided having a crowdsourcing and automated classification system for validating condition of an issuer for a bond. The RPA system 154 may provide automation for one or more aspects of a bond management solution 234 that enables automated bond management and/or provides a recommendation or plan for a bond management activity relevant to a bond transaction, such as for municipal bonds, corporate bonds, government bonds, or other bonds that may be backed by assets, collateral, or commitments of a bond issuer. The bond management solution 234 and/or RPA system 154 for bond management may include a set of interfaces, workflows, and models (which may include, use or be enabled by various adaptive intelligent systems 158) and other components that are configured to enable automation of one or more aspects of a bond management action or a management process for a bond transaction, such as based on a set of conditions, which may include smart contract terms and conditions, marketplace conditions (of platform marketplaces and/or external marketplaces 188, conditions monitored by monitoring systems 164 and data collection systems 166, and the like (such as of entities 198, including without limitation parties 210, collateral 102 and assets 218, among others, as well as of interest rates, available lenders, available terms and the like). For example, a user of the bond management solution 234 may create, configure (such as using one or more templates or libraries), modify, set or otherwise handle (such as in a user interface of the bond management solution 234 and/or RPA system 154) various rules, thresholds, conditional procedures, workflows, model parameters, and the like that determine, or recommend, a bond management action or plan for management a set of bonds of a given type or types based on one or more events, conditions, states, actions, or the like, where the bond management plan may be based on various factors, such as the interest rates available from various primary and secondary lenders or issuers, permitted attributes of issuers and buyers (e.g., based on income, wealth, location, or the like) prevailing interest rates in a platform marketplace or external marketplace, the status of the issuers of a set of bonds, the status or other attributes of collateral 102 or assets 218, risk factors of the issuer, one or more guarantors, market risk factors and the like (including predicted risk based on one or more predictive models using artificial intelligence 156), status of debt, condition of collateral 102 or assets 218 available to secure or back a set of bonds, the state of a business or business operation (e.g., receivables, payables, or the like), conditions of parties 210 (such as net worth, wealth, debt, location, and other conditions), behaviors of parties (such as behaviors indicating preferences, behaviors indicating debt preferences), and many others. Bond management may include management with respect to terms and conditions of sets of bonds, selection of appropriate bonds, communications to encourage transactions, and the like. In embodiments the bond management solution 234 may automatically recommend or set rules, thresholds, actions, parameters and the like (optionally by learning to do so based on a training set of outcomes over time), resulting in a recommended bond management plan, which may specify a series of actions required to accomplish a recommended or desired outcome of bond management (such as within a range of acceptable outcomes), which may be automated and may involve conditional execution of steps based on monitored conditions and/or smart contract terms, which may be created, configured, and/or accounted for by the bond management plan. Bond management plans may be determined and executed based at least one part on market factors (such as competing interest rates offered by other issuers, property values, attributes of issuers, values of collateral or assets, and the like) as well as regulatory and/or compliance factors. Bond management plans may be generated and/or executed for creation of new bonds, for secondary loans or transactions to back bonds, for modifications of existing bonds, for situations involving market changes (e.g., changes in prevailing interest rates or property values) and others. In embodiments, adaptive intelligent systems 158, including artificial intelligence 156 may be trained on a training set of bond management activities by experts and/or on outcomes of bond management actions to generate a set of predictions, classifications, control instructions, plans, models, or the like for automated creation, management and/or execution of one or more aspects of a bond management plan.

In embodiments, provided herein is a platform, consisting of various services, components, modules, programs, systems, devices, algorithms, and other elements, for monitoring condition of an issuer for a bond. In embodiments, the platform or system includes (a) a set of crowdsourcing systems 520 for collecting information about a set of entities involved in a set of bond transactions; and (b) a condition classifying system having a model and a set of artificial intelligence services for classifying the condition of the set of issuers using information from the set of crowdsourcing services, wherein the model is trained using a training data set of outcomes related to the issuers.

In embodiments the set of entities includes entities among a set of issuers, a set of bonds, a set of parties, and a set of assets.

In embodiments a set of issuers includes at least one of a municipality, a corporation, a contractor, a government entity, a non-governmental entity, and a non-profit entity.

In embodiments the set of bonds includes at least one of a municipal bond, a government bond, a treasury bond, an asset-backed bond, and a corporate bond.

In embodiments the condition classified by the condition classifying system is among a default condition, a foreclosure condition, a condition indicating violation of a covenant, a financial risk condition, a behavioral risk condition, a policy risk condition, a financial health condition, a physical defect condition, a physical health condition, an entity risk condition and an entity health condition.

In embodiments the set of crowdsourcing services enables a user interface by which a user may configure a crowdsourcing request for information relevant to the condition about the set of issuers.

In embodiments the platform or system may further include a set of configurable data collection and monitoring services for monitoring the issuers that includes at least one of a set of Internet of Things devices, a set of environmental condition sensors, a set of social network analytic services and a set of algorithms for querying network domains.

In embodiments the set of configurable data collection and monitoring services monitors an environment selected from among a municipal environment, a corporate environment, a securities trading environment, a real property environment, a commercial facility, a warehousing facility, a transportation environment, a manufacturing environment, a storage environment, a home, and a vehicle.

In embodiments the set of bonds is backed by a set of assets.

In embodiments the set of assets includes assets among municipal asset, a vehicle, a ship, a plane, a building, a home, real estate property, undeveloped land, a farm, a crop, a municipal facility, a warehouse, a set of inventory, a commodity, a security, a currency, a token of value, a ticket, a cryptocurrency, a consumable item, an edible item, a beverage, a precious metal, an item of jewelry, a gemstone, intellectual property, an intellectual property right, a contractual right, an antique, a fixture, an item of furniture, an item of equipment, a tool, an item of machinery, and an item of personal property.

In embodiments the platform or system may further include an automated agent that processes events relevant to at least one of the value, the condition and the ownership of the assets and undertakes an action related to a debt transaction to which the asset is related.

In embodiments the action is selected from among offering a debt transaction, underwriting a debt transaction, setting an interest rate, deferring a payment requirement, modifying an interest rate, validating title, managing inspection, recording a change in title, assessing the value of an asset, calling a loan, closing a transaction, setting terms and conditions for a transaction, providing notices required to be provided, foreclosing on a set of assets, modifying terms and conditions, setting a rating for an entity, syndicating debt, and consolidating debt.

In embodiments the artificial intelligence services include at least one of a machine learning system, a model-based system, a rule-based system, a deep learning system, a hybrid system, a neural network, a convolutional neural network, a feed forward neural network, a feedback neural network, a self-organizing map, a fuzzy logic system, a random walk system, a random forest system, a probabilistic system, a Bayesian system, and a simulation system.

In embodiments the platform or system may further include an automated bond management system that manages an action related to the bond, wherein the automated bond management system is trained on a training set of bond management activities.

In embodiments the automated bond management system is trained on a set of interactions of parties with a set of user interfaces involved in a set of bond transaction activities.

In embodiments the set of bond transaction activities includes activities among offering a debt transaction, underwriting a debt transaction, setting an interest rate, deferring a payment requirement, modifying an interest rate, validating title, managing inspection, recording a change in title, assessing the value of an asset, calling a loan, closing a transaction, setting terms and conditions for a transaction, providing notices required to be provided, foreclosing on a set of assets, modifying terms and conditions, setting a rating for an entity, syndicating debt, and consolidating debt.

In embodiments the platform or system may further include a market value data collection service that monitors and reports on marketplace information relevant to the value of at least one of the issuer and a set of assets.

In embodiments reporting is on a set of assets that includes at least one of a municipal asset, a vehicle, a ship, a plane, a building, a home, real estate property, undeveloped land, a farm, a crop, a municipal facility, a warehouse, a set of inventory, a commodity, a security, a currency, a token of value, a ticket, a cryptocurrency, a consumable item, an edible item, a beverage, a precious metal, an item of jewelry, a gemstone, intellectual property, an intellectual property right, a contractual right, an antique, a fixture, an item of furniture, an item of equipment, a tool, an item of machinery, and an item of personal property.

In embodiments the market value data collection service monitors pricing or financial data for items that are similar to the assets in at least one public marketplace.

In embodiments a set of similar items for valuing the assets is constructed using a similarity clustering algorithm based on the attributes of the assets.

In embodiments the attributes are selected from among a category of the assets, asset age, asset condition, asset history, asset storage, and geolocation of assets.

In embodiments the platform or system may further include a set of smart contract services for managing a smart contract for the bond transaction.

In embodiments the smart contract services set terms and conditions for the bond.

In embodiments the set of terms and conditions for the debt transaction that are specified and managed by the set of smart contract services is selected from among a principal amount of debt, a balance of debt, a fixed interest rate, a variable interest rate, a payment amount, a payment schedule, a balloon payment schedule, a specification of assets that back the bond, a specification of substitutability of assets, a party, an issuer, a purchaser, a guarantee, a guarantor, a security, a personal guarantee, a lien, a duration, a covenant, a foreclose condition, a default condition, and a consequence of default.

In embodiments the lending platform is provided having a social network monitoring system with artificial intelligence for classifying a condition about a bond.

In embodiments, provided herein is a platform, consisting of various services, components, modules, programs, systems, devices, algorithms, and other elements, for monitoring condition of an issuer for a bond. In embodiments, the platform or system includes (a) a set of social network analytics applications 204 for collecting information about a set of entities involved in a set of bond transactions; and (b) a condition classifying system having a model and a set of artificial intelligence services for classifying the condition of the set of issuers based on information from the set of social network monitoring and analytic services, wherein the model is trained using a training data set of outcomes related to the issuers.

In embodiments the set of entities includes entities among a set of issuers, a set of bonds, a set of parties, and a set of assets.

In embodiments a set of issuers includes at least one of a municipality, a corporation, a contractor, a government entity, a non-governmental entity, and a non-profit entity.

In embodiments the set of bonds includes at least one of a municipal bond, a government bond, a treasury bond, an asset-backed bond, and a corporate bond.

In embodiments the condition classified by the condition classifying system is among a default condition, a foreclosure condition, a condition indicating violation of a covenant, a financial risk condition, a behavioral risk condition, a policy risk condition, a financial health condition, a physical defect condition, a physical health condition, an entity risk condition and an entity health condition.

In embodiments the set of social network monitoring and analytic services enables a user interface by which a user may configure a query for information about the set of entities.

In embodiments the platform or system may further include a set of data collection and monitoring services for monitoring the entities that includes at least one of a set of Internet of Things devices, a set of environmental condition sensors, a set of crowdsourcing services, and a set of algorithms for querying network domains.

In embodiments the set of data collection and monitoring services monitors an environment selected from among a municipal environment, a corporate environment, a securities trading environment, a real property environment, a commercial facility, a warehousing facility, a transportation environment, a manufacturing environment, a storage environment, a home, and a vehicle.

In embodiments the set of bonds is backed by a set of assets. In embodiments the set of assets includes assets among municipal asset, a vehicle, a ship, a plane, a building, a home, real estate property, undeveloped land, a farm, a crop, a municipal facility, a warehouse, a set of inventory, a commodity, a security, a currency, a token of value, a ticket, a cryptocurrency, a consumable item, an edible item, a beverage, a precious metal, an item of jewelry, a gemstone, intellectual property, an intellectual property right, a contractual right, an antique, a fixture, an item of furniture, an item of equipment, a tool, an item of machinery, and an item of personal property.

In embodiments the platform or system may further include an automated agent that processes events relevant to at least one of the value, the condition and the ownership of the assets and undertakes an action related to a bond transaction to which the asset is related.

In embodiments the action is selected from among offering a bond transaction, underwriting a bond transaction, setting an interest rate, deferring a payment requirement, modifying an interest rate, validating title, managing inspection, recording a change in title, assessing the value of an asset, calling a loan, closing a transaction, setting terms and conditions for a transaction, providing notices required to be provided, foreclosing on a set of assets, modifying terms and conditions, setting a rating for an entity, syndicating bonds, and consolidating bonds.

In embodiments the artificial intelligence services include at least one of a machine learning system, a model-based system, a rule-based system, a deep learning system, a hybrid system, a neural network, a convolutional neural network, a feed forward neural network, a feedback neural network, a self-organizing map, a fuzzy logic system, a random walk system, a random forest system, a probabilistic system, a Bayesian system, and a simulation system.

In embodiments the platform or system may further include an automated bond management system that manages an action related to the bond, wherein the automated bond management system is trained on a training set of bond management activities.

In embodiments the automated bond management system is trained on a set of interactions of parties with a set of user interfaces involved in a set of bond transaction activities.

In embodiments the set of bond transaction activities includes activities among offering a bond transaction, underwriting a bond transaction, setting an interest rate, deferring a payment requirement, modifying an interest rate, validating title, managing inspection, recording a change in title, assessing the value of an asset, calling a loan, closing a transaction, setting terms and conditions for a transaction, providing notices required to be provided, foreclosing on a set of assets, modifying terms and conditions, setting a rating for an entity, syndicating bonds, and consolidating bonds.

In embodiments the platform or system may further include a market value data collection service that monitors and reports on marketplace information relevant to the value of at least one of the issuer, a set of bonds, and a set of assets.

In embodiments reporting is on a set of assets that includes at least one of a municipal asset, a vehicle, a ship, a plane, a building, a home, real estate property, undeveloped land, a farm, a crop, a municipal facility, a warehouse, a set of inventory, a commodity, a security, a currency, a token of value, a ticket, a cryptocurrency, a consumable item, an edible item, a beverage, a precious metal, an item of jewelry, a gemstone, intellectual property, an intellectual property right, a contractual right, an antique, a fixture, an item of furniture, an item of equipment, a tool, an item of machinery, and an item of personal property.

In embodiments the market value data collection service monitors pricing or financial data for items that are similar to the assets in at least one public marketplace.

In embodiments a set of similar items for valuing the assets is constructed using a similarity clustering algorithm based on the attributes of the assets.

In embodiments the attributes are selected from among a category of the assets, asset age, asset condition, asset history, asset storage, and geolocation of assets.

In embodiments the platform or system may further include a set of smart contract services for managing a smart contract for the bond transaction.

In embodiments the smart contract services set terms and conditions for the bond.

In embodiments the set of terms and conditions for the debt transaction that are specified and managed by the set of smart contract services is selected from among a principal amount of debt, a balance of debt, a fixed interest rate, a variable interest rate, a payment amount, a payment schedule, a balloon payment schedule, a specification of assets that back the bond, a specification of substitutability of assets, a party, an issuer, a purchaser, a guarantee, a guarantor, a security, a personal guarantee, a lien, a duration, a covenant, a foreclose condition, a default condition, and a consequence of default.

In embodiments a lending platform is provided having an Internet of Things data collection and monitoring system with artificial intelligence for classifying a condition about a bond.

In embodiments, provided herein is a platform, consisting of various services, components, modules, programs, systems, devices, algorithms, and other elements, for monitoring condition of an issuer for a bond. In embodiments, the platform or system includes (a) a set of Internet of Things data collection and monitoring services for collecting information about a set of entities involved in a set of bond transactions; and (b) a condition classifying system having a model and a set of artificial intelligence services for classifying the condition of the set of issuers based on information from IoT data collection services 208, wherein the model is trained using a training data set of outcomes related to the issuers.

In embodiments the set of entities includes entities among a set of issuers, a set of bonds, a set of parties, and a set of assets.

In embodiments a set of issuers includes at least one of a municipality, a corporation, a contractor, a government entity, a non-governmental entity, and a non-profit entity.

In embodiments the set of bonds includes at least one of a municipal bond, a government bond, a treasury bond, an asset-backed bond, and a corporate bond.

In embodiments the condition classified by the condition classifying system is among a default condition, a foreclosure condition, a condition indicating violation of a covenant, a financial risk condition, a behavioral risk condition, a policy risk condition, a financial health condition, a physical defect condition, a physical health condition, an entity risk condition and an entity health condition.

In embodiments the set of Internet of Things data collection and monitoring services enables a user interface by which a user may configure a query for information about the set of entities.

In embodiments the platform or system may further include a set of configurable data collection and monitoring services for monitoring the entities that includes at least one of a set of social network analytic services, a set of environmental condition sensors, a set of crowdsourcing services, and a set of algorithms for querying network domains.

In embodiments the set of configurable data collection and monitoring services monitors an environment selected from among a municipal environment, a corporate environment, a securities trading environment, a real property environment, a commercial facility, a warehousing facility, a transportation environment, a manufacturing environment, a storage environment, a home, and a vehicle.

In embodiments the set of bonds is backed by a set of assets.

In embodiments the set of assets includes assets among municipal asset, a vehicle, a ship, a plane, a building, a home, real estate property, undeveloped land, a farm, a crop, a municipal facility, a warehouse, a set of inventory, a commodity, a security, a currency, a token of value, a ticket, a cryptocurrency, a consumable item, an edible item, a beverage, a precious metal, an item of jewelry, a gemstone, intellectual property, an intellectual property right, a contractual right, an antique, a fixture, an item of furniture, an item of equipment, a tool, an item of machinery, and an item of personal property.

In embodiments the platform or system may further include an automated agent that processes events relevant to at least one of the value, the condition and the ownership of the assets and undertakes an action related to a bond transaction to which the asset is related.

In embodiments the action is selected from among offering a bond transaction, underwriting a bond transaction, setting an interest rate, deferring a payment requirement, modifying an interest rate, validating title, managing inspection, recording a change in title, assessing the value of an asset, calling a loan, closing a transaction, setting terms and conditions for a transaction, providing notices required to be provided, foreclosing on a set of assets, modifying terms and conditions, setting a rating for an entity, syndicating bonds, and consolidating bonds.

In embodiments the artificial intelligence services include at least one of a machine learning system, a model-based system, a rule-based system, a deep learning system, a hybrid system, a neural network, a convolutional neural network, a feed forward neural network, a feedback neural network, a self-organizing map, a fuzzy logic system, a random walk system, a random forest system, a probabilistic system, a Bayesian system, and a simulation system.

In embodiments the platform or system may further include an automated bond management system that manages an action related to the bond, wherein the automated bond management system is trained on a training set of bond management activities.

In embodiments the automated bond management system is trained on a set of interactions of parties with a set of user interfaces involved in a set of bond transaction activities.

In embodiments the set of bond transaction activities includes activities among offering a bond transaction, underwriting a bond transaction, setting an interest rate, deferring a payment requirement, modifying an interest rate, validating title, managing inspection, recording a change in title, assessing the value of an asset, calling a loan, closing a transaction, setting terms and conditions for a transaction, providing notices required to be provided, foreclosing on a set of assets, modifying terms and conditions, setting a rating for an entity, syndicating bonds, and consolidating bonds.

In embodiments the platform or system may further include a market value data collection service that monitors and reports on marketplace information relevant to the value of at least one of the issuer, a set of bonds, and a set of assets.

In embodiments reporting is on a set of assets that includes at least one of a municipal asset, a vehicle, a ship, a plane, a building, a home, real estate property, undeveloped land, a farm, a crop, a municipal facility, a warehouse, a set of inventory, a commodity, a security, a currency, a token of value, a ticket, a cryptocurrency, a consumable item, an edible item, a beverage, a precious metal, an item of jewelry, a gemstone, intellectual property, an intellectual property right, a contractual right, an antique, a fixture, an item of furniture, an item of equipment, a tool, an item of machinery, and an item of personal property.

In embodiments the market value data collection service monitors pricing or financial data for items that are similar to the assets in at least one public marketplace.

In embodiments a set of similar items for valuing the assets is constructed using a similarity clustering algorithm based on the attributes of the assets.

In embodiments the attributes are selected from among a category of the assets, asset age, asset condition, asset history, asset storage, and geolocation of assets.

In embodiments the platform or system may further include a set of smart contract services for managing a smart contract for the bond transaction.

In embodiments the smart contract services set terms and conditions for the bond.

In embodiments the set of terms and conditions for the debt transaction that are specified and managed by the set of smart contract services is selected from among a principal amount of debt, a balance of debt, a fixed interest rate, a variable interest rate, a payment amount, a payment schedule, a balloon payment schedule, a specification of assets that back the bond, a specification of substitutability of assets, a party, an issuer, a purchaser, a guarantee, a guarantor, a security, a personal guarantee, a lien, a duration, a covenant, a foreclose condition, a default condition, and a consequence of default.

In embodiments, provided herein is a platform, consisting of various services, components, modules, programs, systems, devices, algorithms, and other elements, for monitoring condition of an entity and managing debt related to the entity. In embodiments, the platform or system includes (a) a set of data collection and monitoring services for collecting information about entities involved in a set of debt transactions; (b) a condition classifying system having a model and a set of artificial intelligence services for classifying the condition of the set of entities, wherein the model is trained using a training data set of outcomes related to the entities; and (c) an automated debt management system that manages an action related to the debt, wherein the automated debt management system is trained on a training set of debt management activities.

In embodiments the data collection and monitoring services includes at least one of a set of Internet of Things devices, a set of environmental condition sensors, a set of crowdsourcing services, a set of social network analytic services and a set of algorithms for querying network domains.

In embodiments the set of data collection and monitoring services monitors an environment selected from among a municipal environment, a corporate environment, a securities trading environment, a real property environment, a commercial facility, a warehousing facility, a transportation environment, a manufacturing environment, a storage environment, a home, and a vehicle.

In embodiments the debt transaction is of a type selected from among an auto loan, an inventory loan, a capital equipment loan, a bond for performance, a capital improvement loan, a building loan, a loan backed by an account receivable, an invoice finance arrangement, a factoring arrangement, a pay day loan, a refund anticipation loan, a student loan, a syndicated loan, a title loan, a home loan, a venture debt loan, a loan of intellectual property, a loan of a contractual claim, a working capital loan, a small business loan, a farm loan, a municipal bond, and a subsidized loan.

In embodiments the entities involved in the set of debt transactions include a set of parties and a set of assets.

In embodiments the set of assets includes assets among municipal asset, a vehicle, a ship, a plane, a building, a home, real estate property, undeveloped land, a farm, a crop, a municipal facility, a warehouse, a set of inventory, a commodity, a security, a currency, a token of value, a ticket, a cryptocurrency, a consumable item, an edible item, a beverage, a precious metal, an item of jewelry, a gemstone, intellectual property, an intellectual property right, a contractual right, an antique, a fixture, an item of furniture, an item of equipment, a tool, an item of machinery, and an item of personal property.

In embodiments the platform or system may further include a set of sensors positioned on at least one of the assets, on a container for the asset and on a package for the asset, the set of sensors configured to associate sensor information sensed by the set of sensors with a unique identifier for the asset and a set of blockchain services for taking information from the data collection and monitoring services and the set of sensors and storing the information in a blockchain, wherein access to the blockchain is provided via a secure access control interface for a party for a debt transaction involving the asset.

In embodiments the set of sensors is selected from the group consisting of image, temperature, pressure, humidity, velocity, acceleration, rotational, torque, weight, chemical, magnetic field, electrical field, and position sensors.

In embodiments the platform or system may further include an automated agent that processes events relevant to at least one of the value, the condition and the ownership of the assets and undertakes an action related to a debt transaction to which the asset is related.

In embodiments the action is selected from among offering a debt transaction, underwriting a debt transaction, setting an interest rate, deferring a payment requirement, modifying an interest rate, validating title, managing inspection, recording a change in title, assessing the value of an asset, calling a loan, closing a transaction, setting terms and conditions for a transaction, providing notices required to be provided, foreclosing on a set of assets, modifying terms and conditions, setting a rating for an entity, syndicating debt, and consolidating debt.

In embodiments the artificial intelligence services include at least one of a machine learning system, a model-based system, a rule-based system, a deep learning system, a hybrid system, a neural network, a convolutional neural network, a feed forward neural network, a feedback neural network, a self-organizing map, a fuzzy logic system, a random walk system, a random forest system, a probabilistic system, a Bayesian system, and a simulation system.

In embodiments the automated debt management system is trained on a set of interactions of parties with a set of user interfaces involved in a set of debt transaction activities.

In embodiments the set of debt transaction activities includes activities among offering a debt transaction, underwriting a debt transaction, setting an interest rate, deferring a payment requirement, modifying an interest rate, validating title, managing inspection, recording a change in title, assessing the value of an asset, calling a loan, closing a transaction, setting terms and conditions for a transaction, providing notices required to be provided, foreclosing on a set of assets, modifying terms and conditions, setting a rating for an entity, syndicating debt, and consolidating debt.

In embodiments the platform or system may further include a market value data collection service that monitors and reports on marketplace information relevant to the value of a set of assets.

In embodiments the set of assets includes assets among municipal asset, a vehicle, a ship, a plane, a building, a home, real estate property, undeveloped land, a farm, a crop, a municipal facility, a warehouse, a set of inventory, a commodity, a security, a currency, a token of value, a ticket, a cryptocurrency, a consumable item, an edible item, a beverage, a precious metal, an item of jewelry, a gemstone, intellectual property, an intellectual property right, a contractual right, an antique, a fixture, an item of furniture, an item of equipment, a tool, an item of machinery, and an item of personal property.

In embodiments the market value data collection service monitors pricing or financial data for items that are similar to the assets in at least one public marketplace.

In embodiments a set of similar items for valuing the assets is constructed using a similarity clustering algorithm based on the attributes of the assets.

In embodiments the attributes are selected from among a category of the assets, asset age, asset condition, asset history, asset storage, and geolocation of assets.

In embodiments the platform or system may further include a set of smart contract services for managing a smart contract for the debt transaction.

In embodiments the smart contract services set terms and conditions for the transaction.

In embodiments the set of terms and conditions for the debt transaction that are specified and managed by the set of smart contract services is selected from among a principal amount of debt, a balance of debt, a fixed interest rate, a variable interest rate, a payment amount, a payment schedule, a balloon payment schedule, a specification of collateral, a specification of substitutability of collateral, a party, a guarantee, a guarantor, a security, a personal guarantee, a lien, a duration, a covenant, a foreclose condition, a default condition, and a consequence of default.

Figure 16:
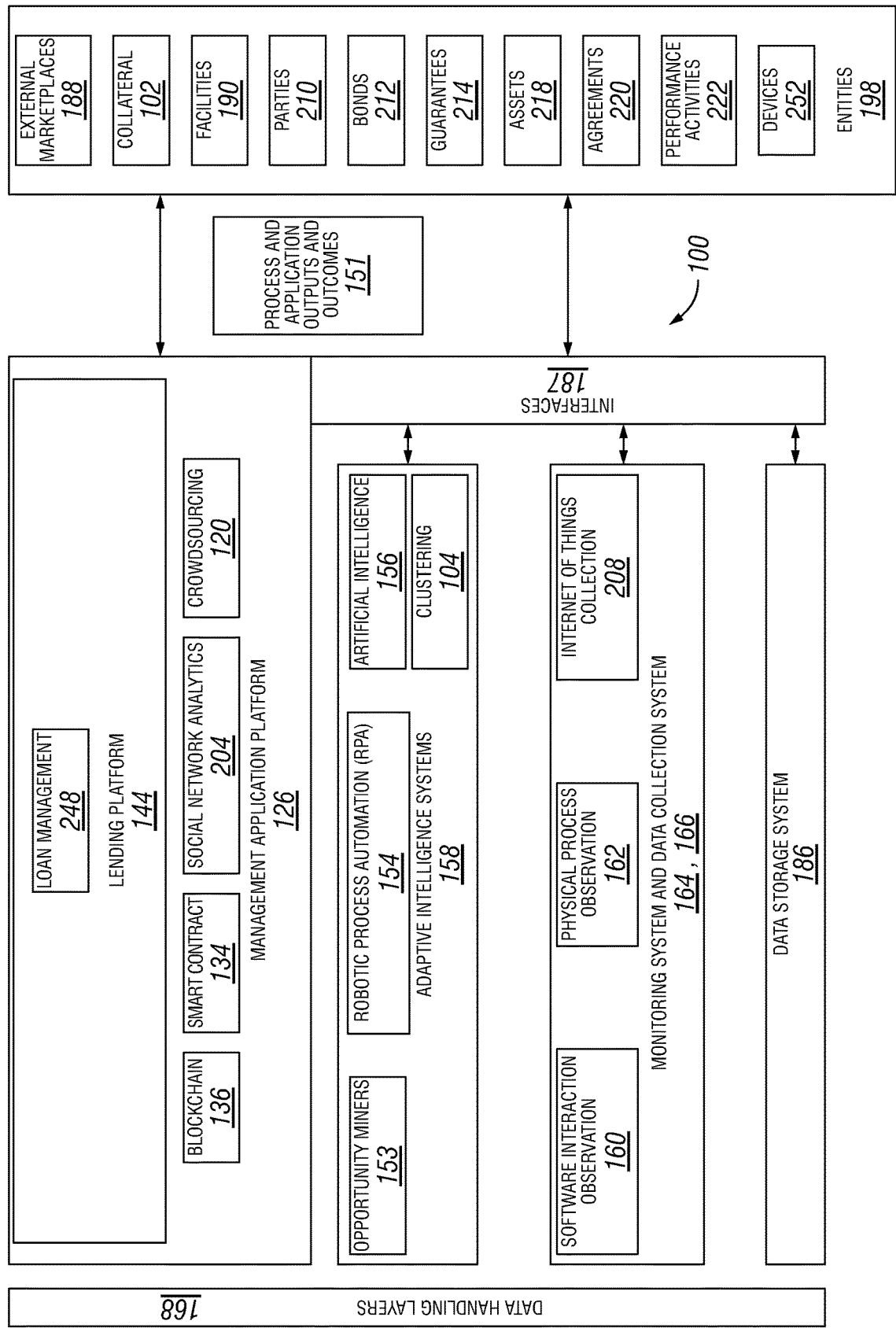
FIG. 16 depicts components and interactions of a lending platform having a system that manages the terms and conditions of a loan based on a parameter monitored by the IoT, by a parameter determined by a social network analytic system, or a parameter determined by a crowdsourcing system.

Referring to FIG. 16, in embodiments a lending platform is provided having a system that varies the terms and conditions of loan based on a parameter monitored by the IoT. The loan may be a subsidized loan. The RPA system 154 may provide automation for one or more aspects of a loan management solution 248 that enables automated loan management and/or provides a recommendation or plan for a loan management activity relevant to a loan transaction, such as for personal loans, corporate loans, subsidized loans, student loans, or other loans, including ones that may be backed by assets, collateral, or commitments of a borrower. The loan management solution 248 and/or RPA system 154 for loan management may include a set of interfaces, workflows, and models (which may include, use or be enabled by various adaptive intelligent systems 158) and other components that are configured to enable automation of one or more aspects of a loan management action or a management process for a loan transaction, such as based on a set of conditions, which may include smart contract terms and conditions, marketplace conditions (of platform marketplaces and/or external marketplaces 188, conditions monitored by monitoring systems 164 and data collection systems 166, and the like (such as of entities 198, including without limitation parties 210, collateral 102 and assets 218, among others, as well as of interest rates, available lenders, available terms and the like). For example, a user of the loan management solution 248 may create, configure (such as using one or more templates or libraries), modify, set or otherwise handle (such as in a user interface of the loan management solution 248 and/or RPA system 154) various rules, thresholds, conditional procedures, workflows, model parameters, and the like that determine, or recommend, a loan management action or plan for management a set of loans of a given type or types based on one or more events, conditions, states, actions, or the like, where the loan management plan may be based on various factors, such as the interest rates available from various primary and secondary lenders or issuers, permitted attributes of borrowers (e.g., based on income, wealth, location, or the like) prevailing interest rates in a platform marketplace or external marketplace, the status of the parties of a set of loans, the status or other attributes of collateral 102 or assets 218, risk factors of the borrower, one or more guarantors, market risk factors and the like (including predicted risk based on one or more predictive models using artificial intelligence 156), status of debt, condition of collateral 102 or assets 218 available to secure or back a set of loans, the state of a business or business operation (e.g., receivables, payables, or the like), conditions of parties 210 (such as net worth, wealth, debt, location, and other conditions), behaviors of parties (such as behaviors indicating preferences, behaviors indicating debt preferences, payment preferences, or communication preferences), and many others. Loan management may include management with respect to terms and conditions of sets of loans, selection of appropriate loans, communications to encourage transactions, and the like. In embodiments the loan management solution 248 may automatically recommend or set rules, thresholds, actions, parameters and the like (optionally by learning to do so based on a training set of outcomes over time), resulting in a recommended loan management plan, which may specify a series of actions required to accomplish a recommended or desired outcome of loan management (such as within a range of acceptable outcomes), which may be automated and may involve conditional execution of steps based on monitored conditions and/or smart contract terms, which may be created, configured, and/or accounted for by the loan management plan. Loan management plans may be determined and executed based at least one part on market factors (such as competing interest rates offered by other issuers, property values, attributes of issuers, values of collateral or assets, and the like) as well as regulatory and/or compliance factors. Loan management plans may be generated and/or executed for creation of new loans, for secondary loans or transactions to back loans, for collection, for consolidation, for foreclosure, for situations of bankruptcy of insolvency, for modifications of existing loans, for situations involving market changes (e.g., changes in prevailing interest rates or property values) and others. In embodiments, adaptive intelligent systems 158, including artificial intelligence 156 may be trained on a training set of loan management activities by experts and/or on outcomes of loan management actions to generate a set of predictions, classifications, control instructions, plans, models, or the like for automated creation, management and/or execution of one or more aspects of a loan management plan.

In embodiments, provided herein is a system for automating handling of a subsidized loan. In embodiments, the platform or system includes (a) a set of Internet of Things data collection and monitoring services for collecting information about a set of entities involved in a set of subsidized loan transactions; (b) a condition classifying system having a model and a set of artificial intelligence services for classifying a set of parameters of the set of subsidized loans involved in the transactions based on information from the set of IoT data collection services 208, wherein the model is trained using a training data set of outcomes related to subsidized loans; and (c) a set of smart contract for automatically modifying the terms and conditions of a subsidized loan based on the classified set of parameters from the condition classifying system.

In embodiments the set of entities includes entities among a set of subsidized loans, a set of parties, a set of subsidies, a set of guarantors, a set of subsidizing parties, and a set of collateral.

In embodiments a set of subsidizing parties includes at least one of a municipality, a corporation, a contractor, a government entity, a non-governmental entity, and a non-profit entity.

In embodiments the set of subsidized loans includes at least one of a municipal subsidized loan, a government subsidized loan, a student loan, an asset-backed subsidized loan, and a corporate subsidized loan.

In embodiments the condition classified by the condition classifying system is among a default condition, a foreclosure condition, a condition indicating violation of a covenant, a financial risk condition, a behavioral risk condition, a contractual performance condition, a policy risk condition, a financial health condition, a physical defect condition, a physical health condition, an entity risk condition and an entity health condition.

In embodiments the loan is a student loan and the condition classifying system classifies at least one of the progress of a student toward a degree, the participation of a student in a non-profit activity, and the participation of the student in a public interest activity.

In embodiments the set of Internet of Things data collection and monitoring services enables a user interface by which a user may configure a query for information about the set of entities.

In embodiments the platform or system may further include a set of configurable data collection and monitoring services for monitoring the entities that includes at least one of a set of social network analytic services, a set of environmental condition sensors, a set of crowdsourcing services, and a set of algorithms for querying network domains.

In embodiments the set of configurable data collection and monitoring services monitors an environment selected from among a municipal environment, an educational environment, a corporate environment, a securities trading environment, a real property environment, a commercial facility, a warehousing facility, a transportation environment, a manufacturing environment, a storage environment, a home, and a vehicle.

In embodiments the set of subsidized loans is backed by a set of assets.

In embodiments the set of assets includes assets among municipal asset, a vehicle, a ship, a plane, a building, a home, real estate property, undeveloped land, a farm, a crop, a municipal facility, a warehouse, a set of inventory, a commodity, a security, a currency, a token of value, a ticket, a cryptocurrency, a consumable item, an edible item, a beverage, a precious metal, an item of jewelry, a gemstone, intellectual property, an intellectual property right, a contractual right, an antique, a fixture, an item of furniture, an item of equipment, a tool, an item of machinery, and an item of personal property.

In embodiments the platform or system may further include an automated agent that processes events relevant to at least one of the value, the condition and the ownership of the assets and undertakes an action related to a subsidized loan transaction to which the asset is related.

In embodiments the action is selected from among offering a subsidized loan transaction, underwriting a subsidized loan transaction, setting an interest rate, deferring a payment requirement, modifying an interest rate, validating title, managing inspection, recording a change in title, assessing the value of an asset, calling a loan, closing a transaction, setting terms and conditions for a transaction, providing notices required to be provided, foreclosing on a set of assets, modifying terms and conditions, setting a rating for an entity, syndicating subsidized loans, and consolidating subsidized loans.

In embodiments the artificial intelligence services include at least one of a machine learning system, a model-based system, a rule-based system, a deep learning system, a hybrid system, a neural network, a convolutional neural network, a feed forward neural network, a feedback neural network, a self-organizing map, a fuzzy logic system, a random walk system, a random forest system, a probabilistic system, a Bayesian system, and a simulation system.

In embodiments the platform or system may further include an automated subsidized loan management system that manages an action related to the subsidized loan, wherein the automated subsidized loan management system is trained on a training set of subsidized loan management activities.

In embodiments the automated subsidized loan management system is trained on a set of interactions of parties with a set of user interfaces involved in a set of subsidized loan transaction activities.

In embodiments the set of subsidized loan transaction activities includes activities among offering a subsidized loan transaction, underwriting a subsidized loan transaction, setting an interest rate, deferring a payment requirement, modifying an interest rate, validating title, managing inspection, recording a change in title, assessing the value of an asset, calling a loan, closing a transaction, setting terms and conditions for a transaction, providing notices required to be provided, foreclosing on a set of assets, modifying terms and conditions, setting a rating for an entity, syndicating subsidized loans, and consolidating subsidized loans.

In embodiments the platform or system may further include a set of blockchain services for recording the modified set of terms and conditions for the set of subsidized loans in a distributed ledger.

In embodiments the platform or system may further include a market value data collection service that monitors and reports on marketplace information relevant to the value of at least one of the issuer, a set of subsidized loans, and a set of assets.

In embodiments reporting is on a set of assets that includes at least one of a municipal asset, a vehicle, a ship, a plane, a building, a home, real estate property, undeveloped land, a farm, a crop, a municipal facility, a warehouse, a set of inventory, a commodity, a security, a currency, a token of value, a ticket, a cryptocurrency, a consumable item, an edible item, a beverage, a precious metal, an item of jewelry, a gemstone, intellectual property, an intellectual property right, a contractual right, an antique, a fixture, an item of furniture, an item of equipment, a tool, an item of machinery, and an item of personal property.

In embodiments the market value data collection service monitors pricing or financial data for items that are similar to the assets in at least one public marketplace.

In embodiments a set of similar items for valuing the assets is constructed using a similarity clustering algorithm based on the attributes of the assets.

In embodiments the attributes are selected from among a category of the assets, asset age, asset condition, asset history, asset storage, and geolocation of assets.

In embodiments the platform or system may further include a set of smart contract services for managing a smart contract for the subsidized loan transaction.

In embodiments the smart contract services set terms and conditions for the subsidized loan.

In embodiments the set of terms and conditions for the debt transaction that are specified and managed by the set of smart contract services is selected from among a principal amount of debt, a balance of debt, a fixed interest rate, a variable interest rate, a payment amount, a payment schedule, a balloon payment schedule, a specification of assets that back the subsidized loan, a specification of substitutability of assets, a party, an issuer, a purchaser, a guarantee, a guarantor, a security, a personal guarantee, a lien, a duration, a covenant, a foreclose condition, a default condition, and a consequence of default.

In embodiments a lending platform is provided having a system that varies the terms and conditions of a subsidized loan based on a parameter monitored in a social network.

In embodiments, provided herein is a system for automating handling of a subsidized loan. In embodiments, the platform or system includes (a) a set of social network analytic data collection and monitoring services for collecting information about a set of entities involved in a set of subsidized loan transactions; (b) a condition classifying system having a model and a set of artificial intelligence services for classifying a set of parameters of the set of subsidized loans involved in the transactions based on information from the set of social network analytics applications 204 which include data collection, monitoring, and analysis, wherein the model is trained using a training data set of outcomes related to subsidized loans; and (c) a set of smart contract for automatically modifying the terms and conditions of a subsidized loan based on the classified set of parameters from the condition classifying system.

In embodiments the set of entities includes entities among a set of subsidized loans, a set of parties, a set of subsidies, a set of guarantors, a set of subsidizing parties, and a set of collateral.

In embodiments a set of subsidizing parties includes at least one of a municipality, a corporation, a contractor, a government entity, a non-governmental entity, and a non-profit entity.

In embodiments the set of subsidized loans includes at least one of a municipal subsidized loan, a government subsidized loan, a student loan, an asset-backed subsidized loan, and a corporate subsidized loan.

In embodiments the condition classified by the condition classifying system is among a default condition, a foreclosure condition, a condition indicating violation of a covenant, a financial risk condition, a behavioral risk condition, a contractual performance condition, a policy risk condition, a financial health condition, a physical defect condition, a physical health condition, an entity risk condition and an entity health condition.

In embodiments the loan is a student loan and the condition classifying system classifies at least one of the progress of a student toward a degree, the participation of a student in a non-profit activity, and the participation of the student in a public interest activity.

In embodiments the set of social network analytic data collection and monitoring services enables a user interface by which a user may configure a query for information about the set of entities and the social network analytic data collection and monitoring services initiates a set of algorithms that search and retrieve data from social networks based on the query.

In embodiments the platform or system may further include a set of configurable data collection and monitoring services for monitoring the entities that includes at least one of a set of Internet of Things services, a set of environmental condition sensors, a set of crowdsourcing services, and a set of algorithms for querying network domains.

In embodiments the set of configurable data collection and monitoring services monitors an environment selected from among a municipal environment, an educational environment, a corporate environment, a securities trading environment, a real property environment, a commercial facility, a warehousing facility, a transportation environment, a manufacturing environment, a storage environment, a home, and a vehicle.

In embodiments the set of subsidized loans is backed by a set of assets.

In embodiments the set of assets includes assets among municipal asset, a vehicle, a ship, a plane, a building, a home, real estate property, undeveloped land, a farm, a crop, a municipal facility, a warehouse, a set of inventory, a commodity, a security, a currency, a token of value, a ticket, a cryptocurrency, a consumable item, an edible item, a beverage, a precious metal, an item of jewelry, a gemstone, intellectual property, an intellectual property right, a contractual right, an antique, a fixture, an item of furniture, an item of equipment, a tool, an item of machinery, and an item of personal property.

In embodiments the platform or system may further include an automated agent that processes events relevant to at least one of the value, the condition and the ownership of the assets and undertakes an action related to a subsidized loan transaction to which the asset is related.

In embodiments the action is selected from among offering a subsidized loan transaction, underwriting a subsidized loan transaction, setting an interest rate, deferring a payment requirement, modifying an interest rate, validating title, managing inspection, recording a change in title, assessing the value of an asset, calling a loan, closing a transaction, setting terms and conditions for a transaction, providing notices required to be provided, foreclosing on a set of assets, modifying terms and conditions, setting a rating for an entity, syndicating subsidized loans, and consolidating subsidized loans.

In embodiments the artificial intelligence services include at least one of a machine learning system, a model-based system, a rule-based system, a deep learning system, a hybrid system, a neural network, a convolutional neural network, a feed forward neural network, a feedback neural network, a self-organizing map, a fuzzy logic system, a random walk system, a random forest system, a probabilistic system, a Bayesian system, and a simulation system.

In embodiments the platform or system may further include an automated subsidized loan management system that manages an action related to the subsidized loan, wherein the automated subsidized loan management system is trained on a training set of subsidized loan management activities.

In embodiments the automated subsidized loan management system is trained on a set of interactions of parties with a set of user interfaces involved in a set of subsidized loan transaction activities.

In embodiments the set of subsidized loan transaction activities includes activities among offering a subsidized loan transaction, underwriting a subsidized loan transaction, setting an interest rate, deferring a payment requirement, modifying an interest rate, validating title, managing inspection, recording a change in title, assessing the value of an asset, calling a loan, closing a transaction, setting terms and conditions for a transaction, providing notices required to be provided, foreclosing on a set of assets, modifying terms and conditions, setting a rating for an entity, syndicating subsidized loans, and consolidating subsidized loans.

In embodiments the platform or system may further include a set of blockchain services for recording the modified set of terms and conditions for the set of subsidized loans in a distributed ledger.

In embodiments the platform or system may further include a market value data collection service that monitors and reports on marketplace information relevant to the value of at least one of a party, a set of subsidized loans, and a set of assets.

In embodiments reporting is on a set of assets that includes at least one of a municipal asset, a vehicle, a ship, a plane, a building, a home, real estate property, undeveloped land, a farm, a crop, a municipal facility, a warehouse, a set of inventory, a commodity, a security, a currency, a token of value, a ticket, a cryptocurrency, a consumable item, an edible item, a beverage, a precious metal, an item of jewelry, a gemstone, intellectual property, an intellectual property right, a contractual right, an antique, a fixture, an item of furniture, an item of equipment, a tool, an item of machinery, and an item of personal property.

In embodiments the market value data collection service monitors pricing or financial data for items that are similar to the assets in at least one public marketplace.

In embodiments a set of similar items for valuing the assets is constructed using a similarity clustering algorithm based on the attributes of the assets.

In embodiments the attributes are selected from among a category of the assets, asset age, asset condition, asset history, asset storage, and geolocation of assets.

In embodiments the platform or system may further include a set of smart contract services for managing a smart contract for the subsidized loan transaction.

In embodiments the smart contract services set terms and conditions for the subsidized loan.

In embodiments the set of terms and conditions for the debt transaction that are specified and managed by the set of smart contract services is selected from among a principal amount of debt, a balance of debt, a fixed interest rate, a variable interest rate, a payment amount, a payment schedule, a balloon payment schedule, a specification of assets that back the subsidized loan, a specification of substitutability of assets, a party, an issuer, a purchaser, a guarantee, a guarantor, a security, a personal guarantee, a lien, a duration, a covenant, a foreclose condition, a default condition, and a consequence of default.

In embodiments a lending platform is provided having a system that varies the terms and conditions of a subsidized loan based on a parameter monitored by crowdsourcing.

In embodiments, provided herein is a system for automating handling of a subsidized loan. In embodiments, the platform or system includes (a) a set of crowdsourcing systems 520 for collecting information about a set of entities involved in a set of subsidized loan transactions; (b) a condition classifying system having a model and a set of artificial intelligence services for classifying a set of parameters of the set of subsidized loans involved in the transactions based on information from the set of crowdsourcing services, wherein the model is trained using a training data set of outcomes related to subsidized loans; and (c) a set of smart contract for automatically modifying the terms and conditions of a subsidized loan based on the classified set of parameters from the condition classifying system.

In embodiments the set of entities includes entities among a set of subsidized loans, a set of parties, a set of subsidies, a set of guarantors, a set of subsidizing parties, and a set of collateral.

In embodiments a set of subsidizing parties includes at least one of a municipality, a corporation, a contractor, a government entity, a non-governmental entity, and a non-profit entity.

In embodiments the set of subsidized loans includes at least one of a municipal subsidized loan, a government subsidized loan, a student loan, an asset-backed subsidized loan, and a corporate subsidized loan.

In embodiments the condition classified by the condition classifying system is among a default condition, a foreclosure condition, a condition indicating violation of a covenant, a financial risk condition, a behavioral risk condition, a contractual performance condition, a policy risk condition, a financial health condition, a physical defect condition, a physical health condition, an entity risk condition and an entity health condition.

In embodiments the loan is a student loan and the condition classifying system classifies at least one of the progress of a student toward a degree, the participation of a student in a non-profit activity, and the participation of the student in a public interest activity.

In embodiments the set of crowdsourcing services enables a user interface by which a user may configure a query for information about the set of entities and the set of crowdsourcing services automatically configures initiates a crowdsourcing request based on the query.

In embodiments the platform or system may further include a set of configurable data collection and monitoring services for monitoring the entities that includes at least one of a set of Internet of Things services, a set of environmental condition sensors, a set of social network analytic services, and a set of algorithms for querying network domains.

In embodiments the set of configurable data collection and monitoring services monitors an environment selected from among a municipal environment, an educational environment, a corporate environment, a securities trading environment, a real property environment, a commercial facility, a warehousing facility, a transportation environment, a manufacturing environment, a storage environment, a home, and a vehicle.

In embodiments the set of subsidized loans is backed by a set of assets.

In embodiments the set of assets includes assets among municipal asset, a vehicle, a ship, a plane, a building, a home, real estate property, undeveloped land, a farm, a crop, a municipal facility, a warehouse, a set of inventory, a commodity, a security, a currency, a token of value, a ticket, a cryptocurrency, a consumable item, an edible item, a beverage, a precious metal, an item of jewelry, a gemstone, intellectual property, an intellectual property right, a contractual right, an antique, a fixture, an item of furniture, an item of equipment, a tool, an item of machinery, and an item of personal property.

In embodiments the platform or system may further include an automated agent that processes events relevant to at least one of the value, the condition and the ownership of the assets and undertakes an action related to a subsidized loan transaction to which the asset is related.

In embodiments the action is selected from among offering a subsidized loan transaction, underwriting a subsidized loan transaction, setting an interest rate, deferring a payment requirement, modifying an interest rate, validating title, managing inspection, recording a change in title, assessing the value of an asset, calling a loan, closing a transaction, setting terms and conditions for a transaction, providing notices required to be provided, foreclosing on a set of assets, modifying terms and conditions, setting a rating for an entity, syndicating subsidized loans, and consolidating subsidized loans.

In embodiments the artificial intelligence services include at least one of a machine learning system, a model-based system, a rule-based system, a deep learning system, a hybrid system, a neural network, a convolutional neural network, a feed forward neural network, a feedback neural network, a self-organizing map, a fuzzy logic system, a random walk system, a random forest system, a probabilistic system, a Bayesian system, and a simulation system.

In embodiments the platform or system may further include an automated subsidized loan management system that manages an action related to the subsidized loan, wherein the automated subsidized loan management system is trained on a training set of subsidized loan management activities.

In embodiments the automated subsidized loan management system is trained on a set of interactions of parties with a set of user interfaces involved in a set of subsidized loan transaction activities.

In embodiments the set of subsidized loan transaction activities includes activities among offering a subsidized loan transaction, underwriting a subsidized loan transaction, setting an interest rate, deferring a payment requirement, modifying an interest rate, validating title, managing inspection, recording a change in title, assessing the value of an asset, calling a loan, closing a transaction, setting terms and conditions for a transaction, providing notices required to be provided, foreclosing on a set of assets, modifying terms and conditions, setting a rating for an entity, syndicating subsidized loans, and consolidating subsidized loans.

In embodiments the platform or system may further include a set of blockchain services for recording the modified set of terms and conditions for the set of subsidized loans in a distributed ledger.

In embodiments the platform or system may further include a market value data collection service that monitors and reports on marketplace information relevant to the value of at least one of a party, a set of subsidized loans, and a set of assets.

In embodiments reporting is on a set of assets that includes at least one of a municipal asset, a vehicle, a ship, a plane, a building, a home, real estate property, undeveloped land, a farm, a crop, a municipal facility, a warehouse, a set of inventory, a commodity, a security, a currency, a token of value, a ticket, a cryptocurrency, a consumable item, an edible item, a beverage, a precious metal, an item of jewelry, a gemstone, intellectual property, an intellectual property right, a contractual right, an antique, a fixture, an item of furniture, an item of equipment, a tool, an item of machinery, and an item of personal property.

In embodiments the market value data collection service monitors pricing or financial data for items that are similar to the assets in at least one public marketplace.

In embodiments a set of similar items for valuing the assets is constructed using a similarity clustering algorithm based on the attributes of the assets.

In embodiments the attributes are selected from among a category of the assets, asset age, asset condition, asset history, asset storage, and geolocation of assets.

In embodiments the platform or system may further include a set of smart contract services for managing a smart contract for the subsidized loan transaction.

In embodiments the smart contract services set terms and conditions for the subsidized loan.

In embodiments the set of terms and conditions for the debt transaction that are specified and managed by the set of smart contract services is selected from among a principal amount of debt, a balance of debt, a fixed interest rate, a variable interest rate, a payment amount, a payment schedule, a balloon payment schedule, a specification of assets that back the subsidized loan, a specification of substitutability of assets, a party, an issuer, a purchaser, a guarantee, a guarantor, a security, a personal guarantee, a lien, a duration, a covenant, a foreclose condition, a default condition, and a consequence of default.

Figure 17:
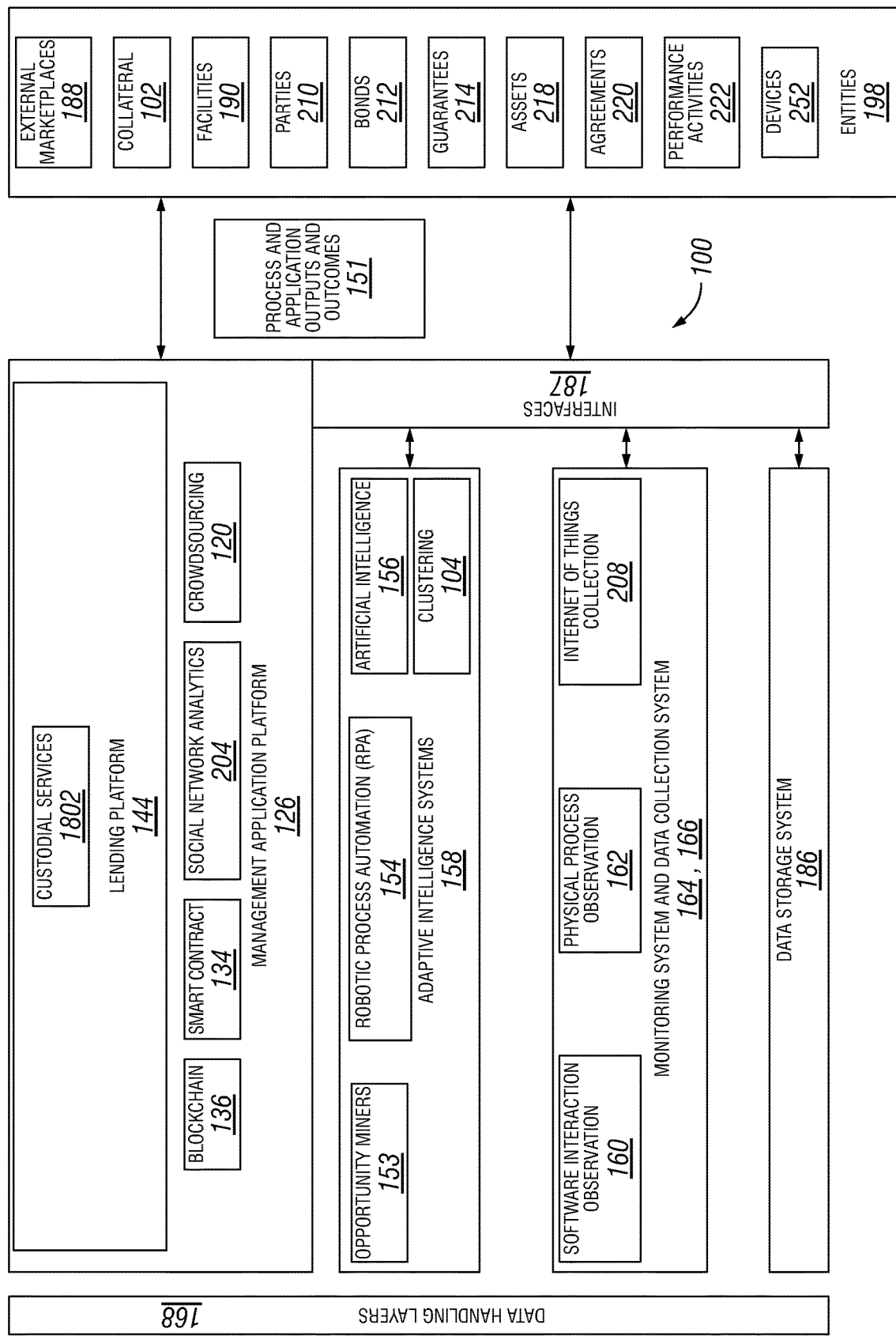
FIG. 17 depicts components and interactions of a lending platform having an automated blockchain custody service for managing a set of custodial assets.

Referring to FIG. 17, in embodiments a lending platform is provided having an automated blockchain custody service and solution for managing a set of custodial assets. The RPA system 154 may provide automation for one or more aspects of a custodial solution 1802 that enables automated custodial management and/or provides a recommendation or plan for a custodial activity relevant to a set of assets, such as ones involved in or backing a lending transaction or ones for which clients seek custodial for security or administrative purposes, such as for assets of any of the types described herein, including cryptocurrencies and other currencies, stock certificates and other evidence of ownership, securities, and many others. The custodial solution 1802 and/or RPA system 154 for handling custodial activity may include a set of interfaces, workflows, and models (which may include, use or be enabled by various adaptive intelligent systems 158) and other components that are configured to enable automation of one or more aspects of a custodial action or a management process for trust or custody of a set of assets 218, such as based on a set of conditions, which may include smart contract terms and conditions, marketplace conditions (of platform marketplaces and/or external marketplaces 188, conditions monitored by monitoring systems 164 and data collection systems 166, and the like (such as of entities 198, including without limitation parties 210, collateral 102 and assets 218, among others, and the like). For example, a user of the custodial solution 1802 may create, configure (such as using one or more templates or libraries), modify, set or otherwise handle (such as in a user interface of the custodial solution 1802 and/or RPA system 154) various rules, thresholds, conditional procedures, workflows, model parameters, and the like that determine, or recommend, a custodial action or plan for management a set of assets of a given type or types based on one or more events, conditions, states, actions, status or the like, where the custodial plan may be based on various factors, such as the storage options available, the basis for retrieval of assets, the basis for transfer of ownership of assets, and the like, condition of assets 218 for which custodial services will be required, behaviors of parties (such as behaviors indicating preferences), and many others. Custodial services may include management with respect to terms and conditions of sets of assets, selection of appropriate terms and conditions for trust and custody 150, selection of parameters for transfer of ownership, selection and provision of storage, selection and provision of secure infrastructure for data storage, and others. In embodiments the custodial solution 1802 may automatically recommend or set rules, thresholds, actions, parameters and the like (optionally by learning to do so based on a training set of outcomes over time), resulting in a recommended custodial plan, which may specify a series of actions required to accomplish a recommended or desired outcome of custodial services (such as within a range of acceptable outcomes), which may be automated and may involve conditional execution of steps based on monitored conditions and/or smart contract terms, which may be created, configured, and/or accounted for by the custodial plan. Custodial plans may be determined and executed based at least one part on market factors (such as competing terms and conditions offered by other custodians, property values, attributes of clients, values of collateral or assets, costs of physical storage, costs of data storage, and the like) as well as regulatory and/or compliance factors. In embodiments, adaptive intelligent systems 158, including artificial intelligence 156 may be trained on a training set of custodial activities by experts and/or on outcomes of custodial actions to generate a set of predictions, classifications, control instructions, plans, models, or the like for automated creation, management and/or execution of one or more aspects of a custodial plan. In embodiments, actions with respect to custody of a set of assets may be stored in a blockchain 136, such as in a distributed ledger.

In embodiments, provided herein is a system for handling trust and custody 150 for a set of assets. The platform or system may include (a) a set of asset identification services for identifying a set of assets for which a financial institution is responsible for taking custody; (b) a set of identity management services by which the financial institution verifies identities and credentials of a set of entities entitled to take action with respect to the assets; and (c) set of blockchain services wherein at least one of the set of assets and identifying information for the set of assets is stored in a blockchain and wherein events related to the set of assets are recorded in a distributed ledger.

In embodiments the credentials include owner credentials, agent credentials, beneficiary credentials, trustee credentials, and custodian credentials.

In embodiments the events related to the set of assets include transfer of title, death of an owner, disability of an owner, bankruptcy of an owner, foreclosure, placement of a lien, use of assets as collateral, designation of a beneficiary, undertaking a loan against assets, providing a notice with respect to assets, inspection of assets, assessment of assets, reporting on assets for taxation purposes, allocation of ownership of assets, disposal of assets, sale of assets, purchase of assets, and designation of an ownership status.

In embodiments the platform or system further includes a set of data collection and monitoring services for monitoring at least one of the set of assets, a set of entities, and a set of events related to the assets.

In embodiments the set of entities includes at least one of an owner, a beneficiary, an agent, a trustee and a custodian.

In embodiments the platform or system further includes a set of smart contract services for managing the custody of the set of assets, wherein at least one event related to the set of assets is managed automatically by the smart contract based on a set of terms and conditions embodied in the smart contract and based on information collected by the set of data collection and monitoring services.

In embodiments the events related to the set of assets include transfer of title, death of an owner, disability of an owner, bankruptcy of an owner, foreclosure, placement of a lien, use of assets as collateral, designation of a beneficiary, undertaking a loan against assets, providing a notice with respect to assets, inspection of assets, assessment of assets, reporting on assets for taxation purposes, allocation of ownership of assets, disposal of assets, sale of assets, purchase of assets, and designation of an ownership status.

Figure 18:
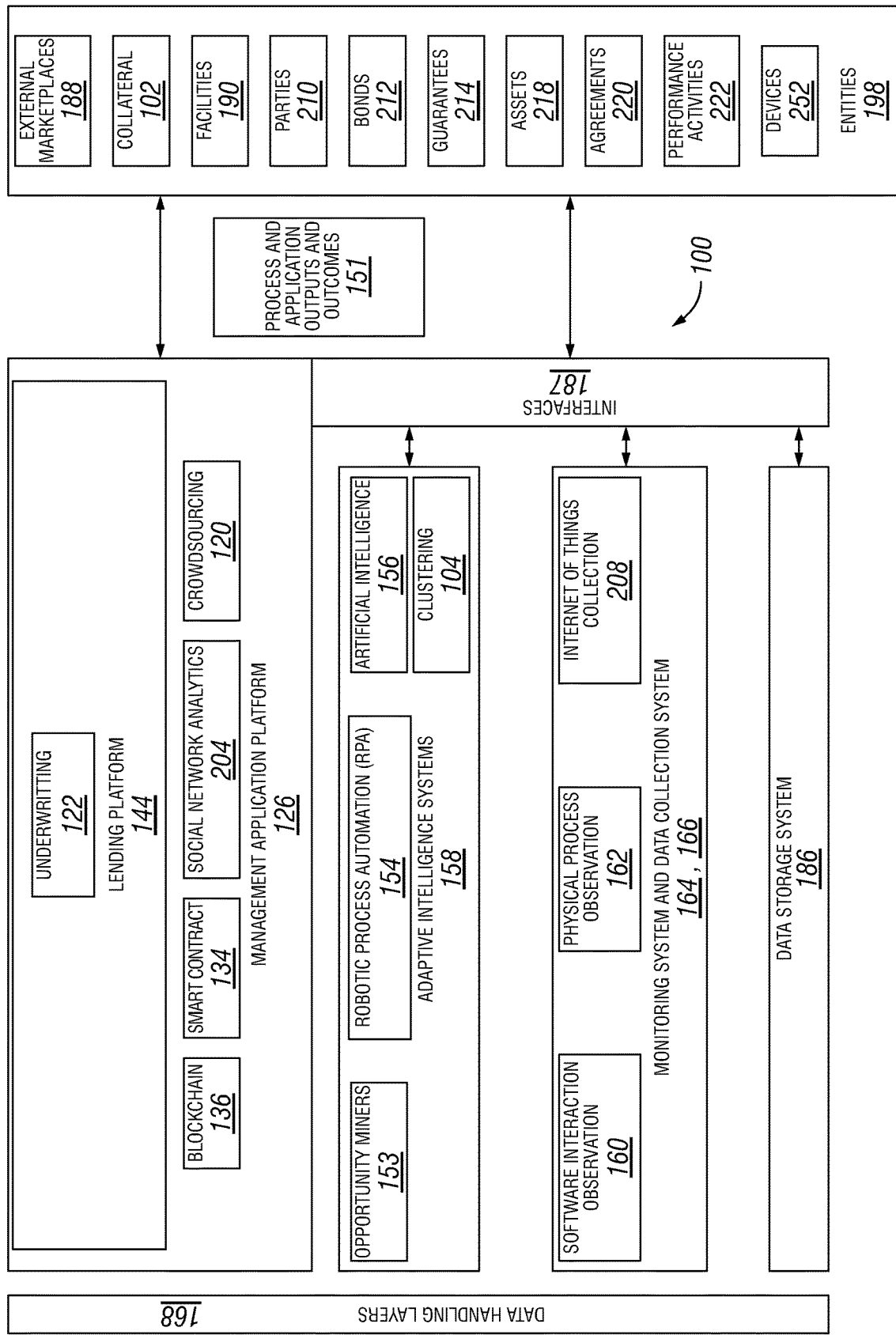
FIG. 18 depicts components and interactions of a lending platform having an underwriting system for a loan with a set of data-integrated microservices including data collection and monitoring services, blockchain services, artificial intelligence services, and smart contract services for underwriting lending entities and transactions.

Referring to FIG. 18, in embodiments a lending platform is provided having an underwriting system for a loan with a set of data-integrated microservices including data collection and monitoring services, blockchain services, artificial intelligence services, and smart contract services for underwriting lending entities and transactions. The RPA system 154 may provide automation for one or more aspects of an underwriting solution 103 that enables automated underwriting and/or provides a recommendation or plan for an underwriting activity relevant to a loan transaction, such as for personal loans, corporate loans, subsidized loans, student loans, or other loans, including ones that may be backed by assets, collateral, or commitments of a borrower. The underwriting solution 103 and/or RPA system 154 for underwriting may include a set of interfaces, workflows, and models (which may include, use or be enabled by various adaptive intelligent systems 158) and other components that are configured to enable automation of one or more aspects of an underwriting action or a management process for a loan transaction, such as based on a set of conditions, which may include smart contract terms and conditions, marketplace conditions (of platform marketplaces and/or external marketplaces 188, conditions monitored by monitoring systems 164 and data collection systems 166, and the like (such as of entities 198, including without limitation parties 210, collateral 102 and assets 218, among others, as well as of interest rates, available lenders, available terms and the like)). For example, a user of the underwriting solution 103 may create, configure (such as using one or more templates or libraries), modify, set or otherwise handle (such as in a user interface of the underwriting solution 103 and/or RPA system 154) various rules, thresholds, conditional procedures, workflows, model parameters, and the like that determine, or recommend, an underwriting action or plan for management a set of loans of a given type or types based on one or more events, conditions, states, actions, or the like, where the underwriting plan may be based on various factors, such as the interest rates available from various primary and secondary lenders or issuers, permitted attributes of borrowers (e.g., based on income, wealth, location, or the like), prevailing interest rates in a platform marketplace or external marketplace, the status of the parties of a set of loans, the status or other attributes of collateral 102 or assets 218, risk factors of the borrower, one or more guarantors, market risk factors and the like (including predicted risk based on one or more predictive models using artificial intelligence 156), status of debt, condition of collateral 102 or assets 218 available to secure or back a set of loans, the state of a business or business operation (e.g., receivables, payables, or the like), conditions of parties 210 (such as net worth, wealth, debt, location, and other conditions), behaviors of parties (such as behaviors indicating preferences, behaviors indicating debt preferences, payment preferences, or communication preferences), and many others. Underwriting may include management with respect to terms and conditions of sets of loans, selection of appropriate loans, communications relevant to underwriting processes, and the like. In embodiments the underwriting solution 103 may automatically recommend or set rules, thresholds, actions, parameters and the like (optionally by learning to do so based on a training set of outcomes over time), resulting in a recommended underwriting plan, which may specify a series of actions required to accomplish a recommended or desired outcome of underwriting (such as within a range of acceptable outcomes), which may be automated and may involve conditional execution of steps based on monitored conditions and/or smart contract terms, which may be created, configured, and/or accounted for by the underwriting plan. Underwriting plans may be determined and executed based at least one part on market factors (such as competing interest rates offered by other issuers, property values, borrower behavior, demographic trends, payment trends, attributes of issuers, values of collateral or assets, and the like) as well as regulatory and/or compliance factors. Underwriting plans may be generated and/or executed for new loans, for secondary loans or transactions to back loans, for collection, for consolidation, for foreclosure, for situations of bankruptcy of insolvency, for modifications of existing loans, for situations involving market changes (e.g., changes in prevailing interest rates or property values), for foreclosure activities, and others. In embodiments, adaptive intelligent systems 158, including artificial intelligence 156 may be trained on a training set of underwriting activities by experts and/or on outcomes of underwriting actions to generate a set of predictions, classifications, control instructions, plans, models, or the like for automated creation, management and/or execution of one or more aspects of an underwriting plan. In embodiments events and outcomes of underwriting may be recorded in a blockchain 136, such as in a distributed ledger, for secure access and retrieval by authorized users. Adaptive intelligent systems 158 may, such as using various artificial intelligence 156 or expert systems disclosed herein and in the documented incorporated by reference herein, may improve or automated one or more aspects of underwriting, such as by training a model, a neural net, a deep learning system, or the like based on a training set of expert interactions and/or a training set of outcomes from underwriting activities.

Figure 19:
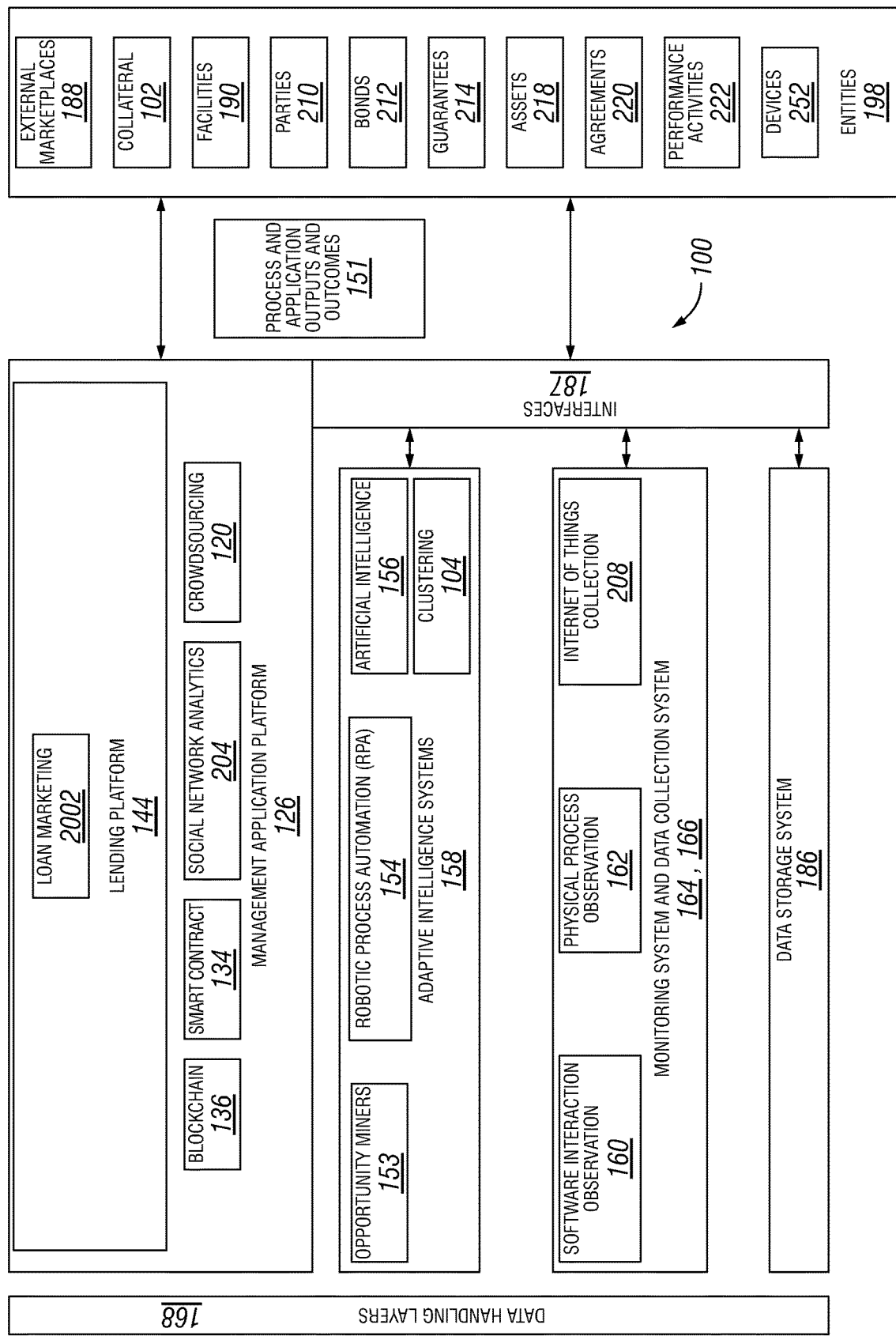
FIG. 19 depicts components and interactions of a lending platform having a loan marketing system with a set of data-integrated microservices including data collection and monitoring services, blockchain services, artificial intelligence services and smart contract services for marketing a loan to a set of prospective parties.

Referring to FIG. 19, in embodiments a lending platform is provided having a loan marketing system with a set of data-integrated microservices including data collection and monitoring services, blockchain services, artificial intelligence services and smart contract services for marketing a loan to a set of prospective parties. The lending enablement platform 100 may enable one or more aspects of a loan marketing solution 2002 that enables automated loan marketing and/or provides a recommendation or plan for a loan marketing activity relevant to a loan transaction, such as for personal loans, corporate loans, subsidized loans, student loans, or other loans, including ones that may be backed by assets, collateral, or commitments of a borrower. The loan marketing solution 2002 (which in embodiments may include or use an RPA system 154 configured for loan marketing) may include a set of interfaces, workflows, and models (which may include, use or be enabled by various adaptive intelligent systems 158) and other components that are configured to enable automation of one or more aspects of a loan marketing action or a management process for a loan transaction, such as based on a set of conditions, which may include smart contract terms and conditions (which may be configured, e.g., for a marketed set of loans), available capital for lending, regulatory factors, marketplace conditions (of platform marketplaces and/or external marketplaces 188, conditions monitored by monitoring systems 164 and data collection systems 166, and the like (such as of entities 198, including without limitation parties 210, collateral 102 and assets 218, among others, as well as of interest rates, available lenders, available terms and the like)), and others. For example, a user of the loan marketing solution 2002 may create, configure (such as using one or more templates or libraries), modify, set or otherwise handle (such as in a user interface of the loan marketing solution 2002 and/or RPA system 154) various rules, thresholds, conditional procedures, workflows, model parameters, and the like that determine, or recommend, a loan marketing action or plan for management a set of loans of a given type or types based on one or more events, conditions, states, actions, or the like, where the loan marketing plan may be based on various factors, such as the interest rates available from various primary and secondary lenders or issuers, returns on the capital that is made available for loans, permitted or desired attributes of borrowers (e.g., based on income, wealth, location, or the like), prevailing interest rates in a platform marketplace or external marketplace, the status of the parties of a set of loans, the status or other attributes of collateral 102 or assets 218, risk factors of the borrower, one or more guarantors, market risk factors and the like (including predicted risk based on one or more predictive models using artificial intelligence 156), status of debt, condition of collateral 102 or assets 218 available to secure or back a set of loans, the state of a business or business operation (e.g., receivables, payables, or the like), conditions of parties 210 (such as net worth, wealth, debt, location, and other conditions), behaviors of parties (such as behaviors indicating preferences, behaviors indicating debt preferences, payment preferences, or communication preferences), and many others. Loan marketing may include management with respect to terms and conditions of sets of loans, selection of appropriate loans, communications relevant to loan marketing processes, and the like. In embodiments the loan marketing solution 2002 may automatically recommend or set rules, thresholds, actions, parameters and the like (optionally by learning to do so based on a training set of outcomes over time), resulting in a recommended loan marketing plan, which may specify a series of actions required to accomplish a recommended or desired outcome of loan marketing (such as within a range of acceptable outcomes), which may be automated and may involve conditional execution of steps based on monitored conditions and/or smart contract terms, which may be created, configured, and/or accounted for by the loan marketing plan. Loan marketing plans may be determined and executed based at least one part on market factors (such as competing interest rates offered by other issuers, property values, borrower behavior, demographic trends, payment trends, attributes of issuers, values of collateral or assets, and the like) as well as regulatory and/or compliance factors. Loan marketing plans may be generated and/or executed for new loans, for secondary loans or transactions to back loans, for collection, for consolidation, for foreclosure situations (e.g., as an alternative to foreclosure), for situations of bankruptcy of insolvency, for modifications of existing loans, for situations involving market changes (e.g., changes in prevailing interest rates, available capital, or property values), and others. In embodiments, adaptive intelligent systems 158, including artificial intelligence 156 may be trained on a training set of loan marketing activities by experts and/or on outcomes of loan marketing actions to generate a set of predictions, classifications, control instructions, plans, models, or the like for automated creation, management and/or execution of one or more aspects of a loan marketing plan. In embodiments events and outcomes of loan marketing may be recorded in a blockchain 136, such as in a distributed ledger, for secure access and retrieval by authorized users. Adaptive intelligent systems 158 may, such as using various artificial intelligence 156 or expert systems disclosed herein and in the documented incorporated by reference herein, may improve or automated one or more aspects of entity rating, such as by training a model, a neural net, a deep learning system, or the like based on a training set of expert interactions and/or a training set of outcomes from loan marketing activities.

Figure 20:
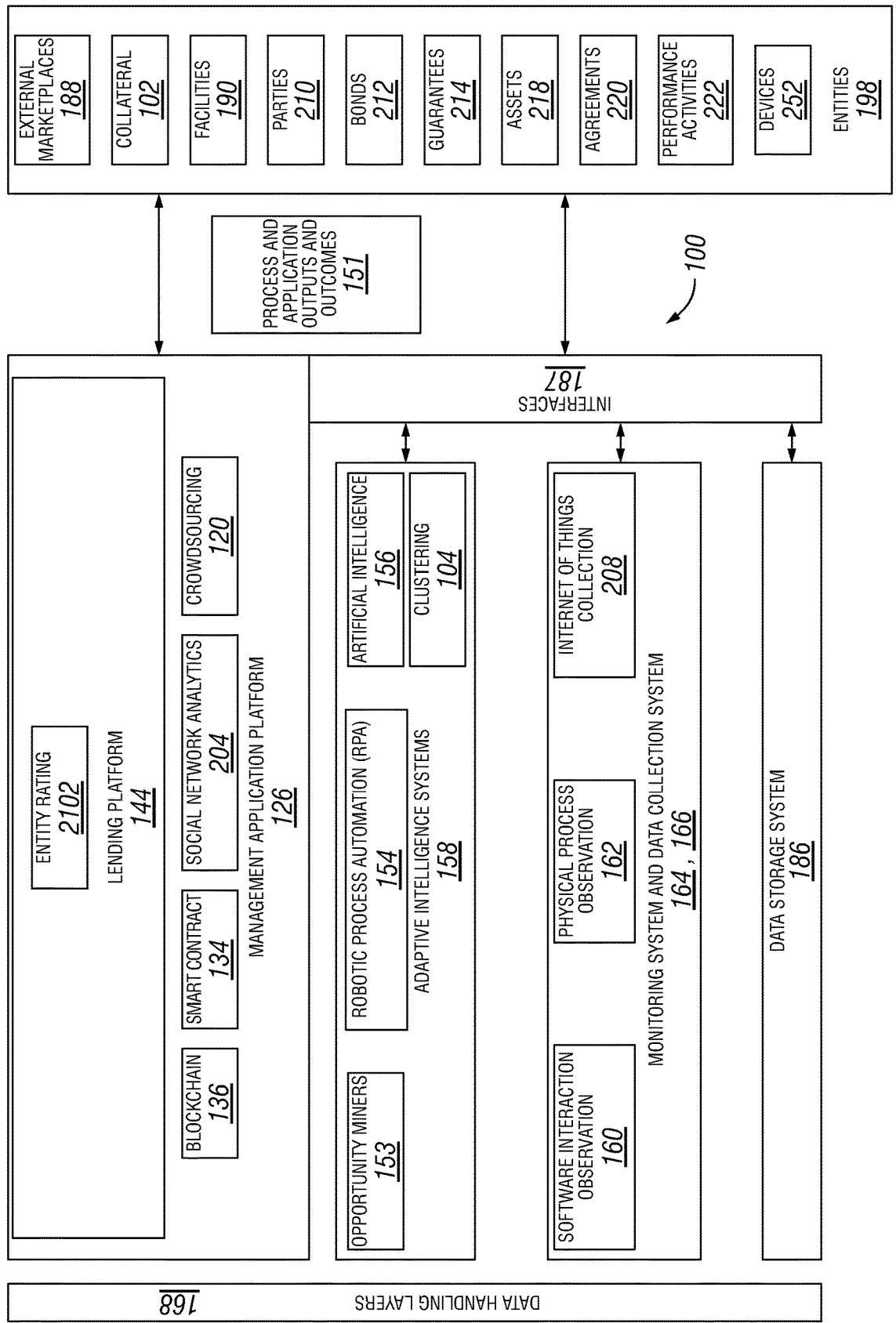
FIG. 20 depicts components and interactions of a lending platform having a rating system with a set of data-integrated microservices including data collection and monitoring services, blockchain services, artificial intelligence services, and smart contract services for rating a set of loan-related entities.

Referring to FIG. 20, in embodiments a lending platform is provided having a rating system with a set of data-integrated microservices including data collection and monitoring services, blockchain services, artificial intelligence services, and smart contract services for rating a set of loan-related entities. The lending enablement platform 100 may enable one or more aspects of an entity rating solution 206 that enables automated entity rating and/or provides a recommendation or plan for an entity rating activity relevant to a loan transaction, such as for personal loans, corporate loans, subsidized loans, student loans, or other loans, including ones that may be backed by assets, collateral, or commitments of a borrower. The entity rating solution 206 (which in embodiments may include or use an RPA system 154 configured for entity rating) may include a set of interfaces, workflows, and models (which may include, use or be enabled by various adaptive intelligent systems 158) and other components that are configured to enable automation of one or more aspects of an entity rating action or a rating process for a loan transaction, such as based on a set of conditions, attributes, events, or the like, which may include attributes of entities 198 (such as value, quality, location, net worth, price, physical condition, health condition, security, safety, ownership and the like), smart contract terms and conditions (which may be configured or populated, e.g., based on ratings for a rated set of loans), regulatory factors, marketplace conditions (of platform marketplaces and/or external marketplaces 188, conditions monitored by monitoring systems 164 and data collection systems 166, and the like (such as of entities 198, including without limitation parties 210, collateral 102 and assets 218, among others, as well as of interest rates, available lenders, available terms and the like)), and others. For example, a user of the entity rating solution 206 may create, configure (such as using one or more templates or libraries), modify, set or otherwise handle (such as in a user interface of the entity rating solution 206 and/or RPA system 154) various rules, thresholds, conditional procedures, workflows, model parameters, and the like that determine, or recommend, an entity rating action or plan for rating a set of loans of a given type or types based on one or more events, attributes, parameters, characteristics, conditions, states, actions, or the like, where the entity rating plan may be based on various factors (e.g., based on income, wealth, location, or the like or parties 210, relative to others, or based on condition of collateral 102 or assets 218, or the like), prevailing conditions of a platform marketplace or external marketplace, the status of the parties of a set of loans, the status or other attributes of collateral 102 or assets 218, risk factors of the borrower, one or more guarantors, market risk factors and the like (including predicted risk based on one or more predictive models using artificial intelligence 156), status of debt, condition of collateral 102 or assets 218 available to secure or back a set of loans, the state of a business or business operation (e.g., receivables, payables, or the like), conditions of parties 210 (such as net worth, wealth, debt, location, and other conditions), behaviors of parties (such as behaviors indicating preferences, behaviors indicating debt preferences, payment preferences, or communication preferences), and many others. Entity rating may include management with respect to terms and conditions of sets of loans, selection of appropriate loans, communications relevant to entity rating processes, and the like. In embodiments the entity rating solution 206 may automatically recommend or set rules, thresholds, actions, parameters and the like (optionally by learning to do so based on a training set of outcomes over time), resulting in a recommended entity rating plan, which may specify a series of actions required to accomplish a recommended or desired outcome of entity rating (such as within a range of acceptable outcomes), which may be automated and may involve conditional execution of steps based on monitored conditions and/or smart contract terms, which may be created, configured, and/or accounted for by the entity rating plan. Entity rating plans may be determined and executed based at least one part on market factors (such as competing interest rates offered by other issuers, property values, borrower behavior, demographic trends, payment trends, attributes of issuers, values of collateral or assets, and the like) as well as regulatory and/or compliance factors. Entity rating plans may be generated and/or executed for new loans, for secondary loans or transactions to back loans, for collection, for consolidation, for foreclosure situations (e.g., as an alternative to foreclosure), for situations of bankruptcy of insolvency, for modifications of existing loans, for situations involving market changes (e.g., changes in prevailing interest rates, available capital, or property values), and others. In embodiments, adaptive intelligent systems 158, including artificial intelligence 156 may be trained on a training set of entity rating activities by experts and/or on outcomes of entity rating actions to generate a set of predictions, classifications, control instructions, plans, models, or the like for automated creation, management and/or execution of one or more aspects of an entity rating plan. In embodiments events and outcomes of entity rating may be recorded in a blockchain 136, such as in a distributed ledger, for secure access and retrieval by authorized users. Adaptive intelligent systems 158 may, such as using various artificial intelligence 156 or expert systems disclosed herein and in the documented incorporated by reference herein, may improve or automated one or more aspects of entity rating, such as by training a model, a neural net, a deep learning system, or the like based on a training set of expert interactions and/or a training set of outcomes from entity rating activities.

Figure 21:
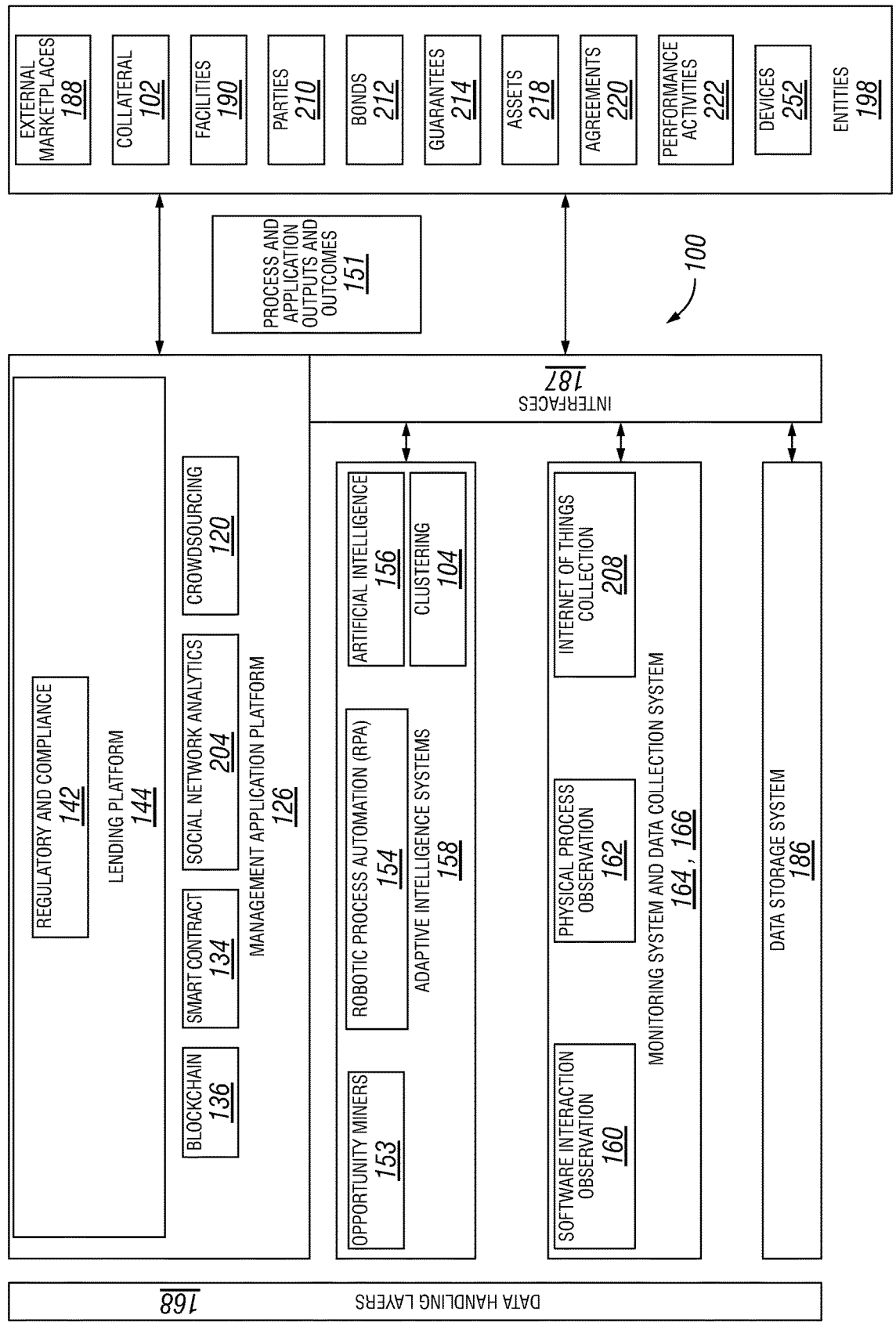
FIG. 21 depicts components and interactions of a lending platform having a regulatory and/or compliance system with a set of data-integrated microservices including data collection and monitoring services, blockchain services, artificial intelligence services, and smart contract services for automatically facilitating compliance with at least one of a law, a regulation and a policy that applies to a lending transaction.
Figure 24:
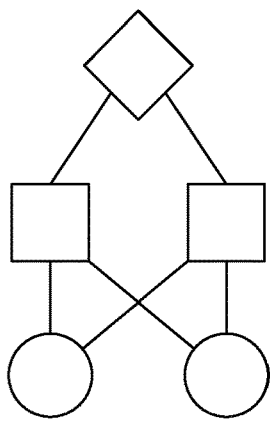
FIG. 22 to FIG. 49 are schematic diagrams of embodiments of neural net systems that may connect to, be integrated in, and be accessible by the platform for enabling intelligent lending and transactions including ones involving expert systems, self-organization, machine learning, artificial intelligence and including neural net systems trained for pattern recognition, for classification of one or more parameters, characteristics, or phenomena, for support of autonomous control, and other purposes in accordance with embodiments of the present disclosure.
Figure 26:
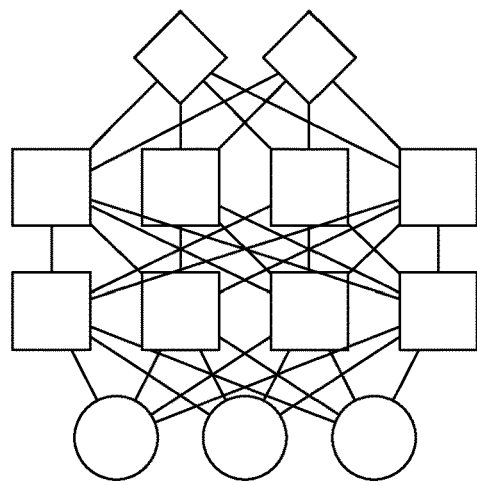

Referring to FIG. 21, in embodiments a lending platform is provided having a regulatory and/or compliance solution 142 with a set of data-integrated microservices including data collection and monitoring services, blockchain services, artificial intelligence services, and smart contract services for automatically facilitating compliance with at least one of a law, a regulation and a policy that applies to a lending transaction. The lending enablement platform 100 may enable one or more aspects of a regulatory and compliance solution 142 that enables automated regulatory and compliance and/or provides a recommendation or plan for a regulatory and compliance activity relevant to a loan transaction, such as for personal loans, corporate loans, subsidized loans, student loans, or other loans, including ones that may be backed by assets, collateral, or commitments of a borrower. The regulatory and compliance solution 142 (which in embodiments may include or use an RPA system 154 configured for automating regulatory and compliance activities based on a training set of interactions by experts in regulatory and/or compliance activities) may include a set of interfaces, workflows, and models (which may include, use or be enabled by various adaptive intelligent systems 158) and other components that are configured to enable automation of one or more aspects of a regulatory and compliance action or a regulatory and/or compliance process for a loan transaction, such as based on a set of policies, regulations, laws, requirements, specifications, conditions, attributes, events, or the like, which may include attributes of or applicable to entities 198 involved in a lending transaction and/or the terms and conditions of loans (including smart contract terms and conditions (which may be configured or populated, e.g., based on terms and conditions that are permitted for a given set of loans)), as well as various marketplace conditions (of platform marketplaces and/or external marketplaces 188, conditions monitored by monitoring systems 164 and data collection systems 166, and the like (such as of entities 198, including without limitation parties 210, collateral 102 and assets LPX218, among others, as well as of interest rates, available lenders, available terms and the like)), and others. For example, a user of the regulatory and compliance solution 142 may create, configure (such as using one or more templates or libraries), modify, set or otherwise handle (such as in a user interface of the regulatory and/or compliance solution 142 and/or RPA system 154) various rules, thresholds, conditional procedures, workflows, model parameters, and the like that determine, or recommend, a regulatory and compliance action or plan for governing a set of loans of a given type or types based on one or more events, attributes, parameters, characteristics, conditions, states, actions, or the like, where the regulatory and compliance plan may be based on various factors (e.g., based on permitted interest rates, required notices (e.g., regarding annualized percentage rate reporting), permitted borrowers (e.g., students for federally subsidized student loans), permitted lenders, permitted issuers, income (e.g., for low-income loans), wealth (e.g., for loans that are permitted by policy to be provided only to adequately capitalized parties), location (e.g., for geographically governed lending programs, such as for municipal development), conditions of a platform marketplace or external marketplace (such as where loans are required to have interest rates that do not exceed a threshold that is calculated based on prevailing interest rates), the status of the parties of a set of loans, the status or other attributes of collateral 102 or assets 218, risk factors of the borrower, one or more guarantors, market risk factors and the like (including predicted risk based on one or more predictive models using artificial intelligence 156), status of debt, condition of collateral 102 or assets 218 available to secure or back a set of loans, the state of a business or business operation (e.g., receivables, payables, or the like), conditions of parties 210 (such as net worth, wealth, debt, location, and other conditions), behaviors of parties (such as behaviors indicating preferences, behaviors indicating debt preferences, payment preferences, or communication preferences), and many others. Regulatory and compliance may include governance with respect to terms and conditions of sets of loans, selection of appropriate loans, notices required to be provided, underwriting policies, communications relevant to regulatory and compliance processes, and the like. In embodiments the regulatory and compliance solution 142 may automatically recommend or set rules, thresholds, actions, parameters and the like (optionally by learning to do so based on a training set of outcomes over time), resulting in a recommended regulatory and compliance plan, which may specify a series of actions required to accomplish a recommended or desired outcome of regulatory and compliance (such as within a range of acceptable outcomes), which may be automated and may involve conditional execution of steps based on monitored conditions and/or smart contract terms, which may be created, configured, and/or accounted for by the regulatory and compliance plan. Regulatory and compliance plans may be determined and executed based at least one part on market factors (such as competing interest rates offered by other issuers, property values, borrower behavior, demographic trends, payment trends, attributes of issuers, values of collateral or assets, and the like) as well as regulatory and/or compliance factors. Regulatory and compliance plans may be generated and/or executed for new loans, for secondary loans or transactions to back loans, for collection, for consolidation, for foreclosure situations (e.g., as an alternative to foreclosure), for situations of bankruptcy of insolvency, for modifications of existing loans, for situations involving market changes (e.g., changes in prevailing interest rates, available capital, or property values), and others. In embodiments, adaptive intelligent systems 158, including artificial intelligence 156 may be trained on a training set of regulatory and compliance activities by experts and/or on outcomes of regulatory and compliance actions to generate a set of predictions, classifications, control instructions, plans, models, or the like for automated creation, management and/or execution of one or more aspects of a regulatory and compliance plan. In embodiments events and outcomes of regulatory and compliance may be recorded in a blockchain 136, such as in a distributed ledger, for secure access and retrieval by authorized users. Adaptive intelligent systems 158 may, such as using various artificial intelligence 156 or expert systems disclosed herein and in the documented incorporated by reference herein, may improve or automate one or more aspects of regulatory and compliance, such as by training a model, a neural net, a deep learning system, or the like based on a training set of expert interactions and/or a training set of outcomes from regulatory and compliance activities.

In embodiments a lending platform is provided herein having a set of data-integrated microservices including data collection and monitoring services, blockchain services, and smart contract services for handling lending entities and transactions and having an Internet of Things and sensor platform for monitoring at least one of a set of assets and a set of collateral for a loan, a bond, or a debt transaction.

In embodiments a lending platform is provided herein having a set of data-integrated microservices including data collection and monitoring services, blockchain services, and smart contract services for handling lending entities and transactions and having a smart contract and distributed ledger platform for managing at least one of ownership of a set of collateral and a set of events related to a set of collateral.

In embodiments a lending platform is provided herein having a set of data-integrated microservices including data collection and monitoring services, blockchain services, and smart contract services for handling lending entities and transactions and having a smart contract system that automatically adjusts an interest rate for a loan based on information collected via at least one of an Internet of Things system, a crowdsourcing system, a set of social network analytic services and a set of data collection and monitoring services.

In embodiments a lending platform is provided herein having a set of data-integrated microservices including data collection and monitoring services, blockchain services, and smart contract services for handling lending entities and transactions and having a crowdsourcing system for obtaining information about at least one of a state of a set of collateral for a loan and a state of an entity relevant to a guarantee for a loan.

In embodiments a lending platform is provided herein having a set of data-integrated microservices including data collection and monitoring services, blockchain services, and smart contract services for handling lending entities and transactions and having a smart contract that automatically adjusts an interest rate for a loan based on at least one of a regulatory factor and a market factor for a specific jurisdiction.

In embodiments a lending platform is provided herein having a set of data-integrated microservices including data collection and monitoring services, blockchain services, and smart contract services for handling lending entities and transactions and having a smart contract that automatically restructures debt based on a monitored condition.

In embodiments a lending platform is provided herein having a set of data-integrated microservices including data collection and monitoring services, blockchain services, and smart contract services for handling lending entities and transactions and having a social network monitoring system for validating the reliability of a guarantee for a loan.

In embodiments a lending platform is provided herein having a set of data-integrated microservices including data collection and monitoring services, blockchain services, and smart contract services for handling lending entities and transactions and having an Internet of Things data collection and monitoring system for validating reliability of a guarantee for a loan.

In embodiments a lending platform is provided herein having a set of data-integrated microservices including data collection and monitoring services, blockchain services, and smart contract services for handling lending entities and transactions and having a robotic process automation system for negotiation of a set of terms and conditions for a loan.

In embodiments a lending platform is provided herein having a set of data-integrated microservices including data collection and monitoring services, blockchain services, and smart contract services for handling lending entities and transactions and having a robotic process automation system for loan collection.

In embodiments a lending platform is provided herein having a set of data-integrated microservices including data collection and monitoring services, blockchain services, and smart contract services for handling lending entities and transactions and having a robotic process automation system for consolidating a set of loans.

In embodiments a lending platform is provided herein having a set of data-integrated microservices including data collection and monitoring services, blockchain services, and smart contract services for handling lending entities and transactions and having a robotic process automation system for managing a factoring loan.

In embodiments a lending platform is provided herein having a set of data-integrated microservices including data collection and monitoring services, blockchain services, and smart contract services for handling lending entities and transactions and having a robotic process automation system for brokering a mortgage loan.

In embodiments a lending platform is provided herein having a set of data-integrated microservices including data collection and monitoring services, blockchain services, and smart contract services for handling lending entities and transactions and having a crowdsourcing and automated classification system for validating condition of an issuer for a bond.

In embodiments a lending platform is provided herein having a set of data-integrated microservices including data collection and monitoring services, blockchain services, and smart contract services for handling lending entities and transactions and having a social network monitoring system with artificial intelligence for classifying a condition about a bond.

In embodiments a lending platform is provided herein having a set of data-integrated microservices including data collection and monitoring services, blockchain services, and smart contract services for handling lending entities and transactions and having an Internet of Things data collection and monitoring system with artificial intelligence for classifying a condition about a bond.

In embodiments a lending platform is provided herein having a set of data-integrated microservices including data collection and monitoring services, blockchain services, and smart contract services for handling lending entities and transactions and having a system that varies the terms and conditions of a subsidized loan based on a parameter monitored by the IoT.

In embodiments a lending platform is provided herein having a set of data-integrated microservices including data collection and monitoring services, blockchain services, and smart contract services for handling lending entities and transactions and having a system that varies the terms and conditions of a subsidized loan based on a parameter monitored in a social network.

In embodiments a lending platform is provided herein having a set of data-integrated microservices including data collection and monitoring services, blockchain services, and smart contract services for handling lending entities and transactions and having a system that varies the terms and conditions of a subsidized loan based on a parameter monitored by crowdsourcing.

In embodiments a lending platform is provided herein having a set of data-integrated microservices including data collection and monitoring services, blockchain services, and smart contract services for handling lending entities and transactions and having an automated blockchain custody service for managing a set of custodial assets.

In embodiments a lending platform is provided herein having a set of data-integrated microservices including data collection and monitoring services, blockchain services, and smart contract services for handling lending entities and transactions and having an underwriting system for a loan with a set of data-integrated microservices including data collection and monitoring services, blockchain services, artificial intelligence services, and smart contract services for underwriting lending entities and transactions.

In embodiments a lending platform is provided herein having a set of data-integrated microservices including data collection and monitoring services, blockchain services, and smart contract services for handling lending entities and transactions and having a loan marketing system with a set of data-integrated microservices including data collection and monitoring services, blockchain services, artificial intelligence services and smart contract services for marketing a loan to a set of prospective parties.

In embodiments a lending platform is provided herein having a set of data-integrated microservices including data collection and monitoring services, blockchain services, and smart contract services for handling lending entities and transactions and having a rating system with a set of data-integrated microservices including data collection and monitoring services, blockchain services, artificial intelligence services, and smart contract services for rating a set of loan-related entities.

In embodiments a lending platform is provided herein having a set of data-integrated microservices including data collection and monitoring services, blockchain services, and smart contract services for handling lending entities and transactions and having a compliance system with a set of data-integrated microservices including data collection and monitoring services, blockchain services, artificial intelligence services, and smart contract services for automatically facilitating compliance with at least one of a law, a regulation and a policy related to a lending transaction.

In embodiments a lending platform is provided herein having an Internet of Things and sensor platform for monitoring at least one of a set of assets and a set of collateral for a loan, a bond, or a debt transaction and having a smart contract and distributed ledger platform for managing at least one of ownership of a set of collateral and a set of events related to a set of collateral.

In embodiments a lending platform is provided herein having an Internet of Things and sensor platform for monitoring at least one of a set of assets and a set of collateral for a loan, a bond, or a debt transaction and having a smart contract system that automatically adjusts an interest rate for a loan based on information collected via at least one of an Internet of Things system, a crowdsourcing system, a set of social network analytic services and a set of data collection and monitoring services.

In embodiments a lending platform is provided herein having an Internet of Things and sensor platform for monitoring at least one of a set of assets and a set of collateral for a loan, a bond, or a debt transaction and having a crowdsourcing system for obtaining information about at least one of a state of a set of collateral for a loan and a state of an entity relevant to a guarantee for a loan.

In embodiments a lending platform is provided herein having an Internet of Things and sensor platform for monitoring at least one of a set of assets and a set of collateral for a loan, a bond, or a debt transaction and having a smart contract that automatically adjusts an interest rate for a loan based on at least one of a regulatory factor and a market factor for a specific jurisdiction.

In embodiments a lending platform is provided herein having an Internet of Things and sensor platform for monitoring at least one of a set of assets and a set of collateral for a loan, a bond, or a debt transaction and having a smart contract that automatically restructures debt based on a monitored condition.

In embodiments a lending platform is provided herein having an Internet of Things and sensor platform for monitoring at least one of a set of assets and a set of collateral for a loan, a bond, or a debt transaction and having a social network monitoring system for validating the reliability of a guarantee for a loan.

In embodiments a lending platform is provided herein having an Internet of Things and sensor platform for monitoring at least one of a set of assets and a set of collateral for a loan, a bond, or a debt transaction and having an Internet of Things data collection and monitoring system for validating reliability of a guarantee for a loan.

In embodiments a lending platform is provided herein having an Internet of Things and sensor platform for monitoring at least one of a set of assets and a set of collateral for a loan, a bond, or a debt transaction and having a robotic process automation system for negotiation of a set of terms and conditions for a loan.

In embodiments a lending platform is provided herein having an Internet of Things and sensor platform for monitoring at least one of a set of assets and a set of collateral for a loan, a bond, or a debt transaction and having a robotic process automation system for loan collection.

In embodiments a lending platform is provided herein having an Internet of Things and sensor platform for monitoring at least one of a set of assets and a set of collateral for a loan, a bond, or a debt transaction and having a robotic process automation system for consolidating a set of loans.

In embodiments a lending platform is provided herein having an Internet of Things and sensor platform for monitoring at least one of a set of assets and a set of collateral for a loan, a bond, or a debt transaction and having a robotic process automation system for managing a factoring loan.

In embodiments a lending platform is provided herein having an Internet of Things and sensor platform for monitoring at least one of a set of assets and a set of collateral for a loan, a bond, or a debt transaction and having a robotic process automation system for brokering a mortgage loan.

In embodiments a lending platform is provided herein having an Internet of Things and sensor platform for monitoring at least one of a set of assets and a set of collateral for a loan, a bond, or a debt transaction and having a crowdsourcing and automated classification system for validating condition of an issuer for a bond.

In embodiments a lending platform is provided herein having an Internet of Things and sensor platform for monitoring at least one of a set of assets and a set of collateral for a loan, a bond, or a debt transaction and having a social network monitoring system with artificial intelligence for classifying a condition about a bond.

In embodiments a lending platform is provided herein having an Internet of Things and sensor platform for monitoring at least one of a set of assets and a set of collateral for a loan, a bond, or a debt transaction and having an Internet of Things data collection and monitoring system with artificial intelligence for classifying a condition about a bond.

In embodiments a lending platform is provided herein having an Internet of Things and sensor platform for monitoring at least one of a set of assets and a set of collateral for a loan, a bond, or a debt transaction and having a system that varies the terms and conditions of a subsidized loan based on a parameter monitored by the IoT.

In embodiments a lending platform is provided herein having an Internet of Things and sensor platform for monitoring at least one of a set of assets and a set of collateral for a loan, a bond, or a debt transaction and having a system that varies the terms and conditions of a subsidized loan based on a parameter monitored in a social network.

In embodiments a lending platform is provided herein having an Internet of Things and sensor platform for monitoring at least one of a set of assets and a set of collateral for a loan, a bond, or a debt transaction and having a system that varies the terms and conditions of a subsidized loan based on a parameter monitored by crowdsourcing.

In embodiments a lending platform is provided herein having an Internet of Things and sensor platform for monitoring at least one of a set of assets and a set of collateral for a loan, a bond, or a debt transaction and having an automated blockchain custody service for managing a set of custodial assets.

In embodiments a lending platform is provided herein having an Internet of Things and sensor platform for monitoring at least one of a set of assets and a set of collateral for a loan, a bond, or a debt transaction and having an underwriting system for a loan with a set of data-integrated microservices including data collection and monitoring services, blockchain services, artificial intelligence services, and smart contract services for underwriting lending entities and transactions.

In embodiments a lending platform is provided herein having an Internet of Things and sensor platform for monitoring at least one of a set of assets and a set of collateral for a loan, a bond, or a debt transaction and having a loan marketing system with a set of data-integrated microservices including data collection and monitoring services, blockchain services, artificial intelligence services and smart contract services for marketing a loan to a set of prospective parties.

In embodiments a lending platform is provided herein having an Internet of Things and sensor platform for monitoring at least one of a set of assets and a set of collateral for a loan, a bond, or a debt transaction and having a rating system with a set of data-integrated microservices including data collection and monitoring services, blockchain services, artificial intelligence services, and smart contract services for rating a set of loan-related entities.

In embodiments a lending platform is provided herein having an Internet of Things and sensor platform for monitoring at least one of a set of assets and a set of collateral for a loan, a bond, or a debt transaction and having a compliance system with a set of data-integrated microservices including data collection and monitoring services, blockchain services, artificial intelligence services, and smart contract services for automatically facilitating compliance with at least one of a law, a regulation and a policy related to a lending transaction.

In embodiments a lending platform is provided herein having a smart contract and distributed ledger platform for managing at least one of ownership of a set of collateral and a set of events related to a set of collateral and having a smart contract system that automatically adjusts an interest rate for a loan based on information collected via at least one of an Internet of Things system, a crowdsourcing system, a set of social network analytic services and a set of data collection and monitoring services.

In embodiments a lending platform is provided herein having a smart contract and distributed ledger platform for managing at least one of ownership of a set of collateral and a set of events related to a set of collateral and having a crowdsourcing system for obtaining information about at least one of a state of a set of collateral for a loan and a state of an entity relevant to a guarantee for a loan.

In embodiments a lending platform is provided herein having a smart contract and distributed ledger platform for managing at least one of ownership of a set of collateral and a set of events related to a set of collateral and having a smart contract that automatically adjusts an interest rate for a loan based on at least one of a regulatory factor and a market factor for a specific jurisdiction.

In embodiments a lending platform is provided herein having a smart contract and distributed ledger platform for managing at least one of ownership of a set of collateral and a set of events related to a set of collateral and having a smart contract that automatically restructures debt based on a monitored condition.

In embodiments a lending platform is provided herein having a smart contract and distributed ledger platform for managing at least one of ownership of a set of collateral and a set of events related to a set of collateral and having a social network monitoring system for validating the reliability of a guarantee for a loan.

In embodiments a lending platform is provided herein having a smart contract and distributed ledger platform for managing at least one of ownership of a set of collateral and a set of events related to a set of collateral and having an Internet of Things data collection and monitoring system for validating reliability of a guarantee for a loan.

In embodiments a lending platform is provided herein having a smart contract and distributed ledger platform for managing at least one of ownership of a set of collateral and a set of events related to a set of collateral and having a robotic process automation system for negotiation of a set of terms and conditions for a loan.

In embodiments a lending platform is provided herein having a smart contract and distributed ledger platform for managing at least one of ownership of a set of collateral and a set of events related to a set of collateral and having a robotic process automation system for loan collection.

In embodiments a lending platform is provided herein having a smart contract and distributed ledger platform for managing at least one of ownership of a set of collateral and a set of events related to a set of collateral and having a robotic process automation system for consolidating a set of loans.

In embodiments a lending platform is provided herein having a smart contract and distributed ledger platform for managing at least one of ownership of a set of collateral and a set of events related to a set of collateral and having a robotic process automation system for managing a factoring loan.

In embodiments a lending platform is provided herein having a smart contract and distributed ledger platform for managing at least one of ownership of a set of collateral and a set of events related to a set of collateral and having a robotic process automation system for brokering a mortgage loan.

In embodiments a lending platform is provided herein having a smart contract and distributed ledger platform for managing at least one of ownership of a set of collateral and a set of events related to a set of collateral and having a crowdsourcing and automated classification system for validating condition of an issuer for a bond.

In embodiments a lending platform is provided herein having a smart contract and distributed ledger platform for managing at least one of ownership of a set of collateral and a set of events related to a set of collateral and having a social network monitoring system with artificial intelligence for classifying a condition about a bond.

In embodiments a lending platform is provided herein having a smart contract and distributed ledger platform for managing at least one of ownership of a set of collateral and a set of events related to a set of collateral and having an Internet of Things data collection and monitoring system with artificial intelligence for classifying a condition about a bond.

In embodiments a lending platform is provided herein having a smart contract and distributed ledger platform for managing at least one of ownership of a set of collateral and a set of events related to a set of collateral and having a system that varies the terms and conditions of a subsidized loan based on a parameter monitored by the IoT.

In embodiments a lending platform is provided herein having a smart contract and distributed ledger platform for managing at least one of ownership of a set of collateral and a set of events related to a set of collateral and having a system that varies the terms and conditions of a subsidized loan based on a parameter monitored in a social network.

In embodiments a lending platform is provided herein having a smart contract and distributed ledger platform for managing at least one of ownership of a set of collateral and a set of events related to a set of collateral and having a system that varies the terms and conditions of a subsidized loan based on a parameter monitored by crowdsourcing.

In embodiments a lending platform is provided herein having a smart contract and distributed ledger platform for managing at least one of ownership of a set of collateral and a set of events related to a set of collateral and having an automated blockchain custody service for managing a set of custodial assets.

In embodiments a lending platform is provided herein having a smart contract and distributed ledger platform for managing at least one of ownership of a set of collateral and a set of events related to a set of collateral and having an underwriting system for a loan with a set of data-integrated microservices including data collection and monitoring services, blockchain services, artificial intelligence services, and smart contract services for underwriting lending entities and transactions.

In embodiments a lending platform is provided herein having a smart contract and distributed ledger platform for managing at least one of ownership of a set of collateral and a set of events related to a set of collateral and having a loan marketing system with a set of data-integrated microservices including data collection and monitoring services, blockchain services, artificial intelligence services and smart contract services for marketing a loan to a set of prospective parties.

In embodiments a lending platform is provided herein having a smart contract and distributed ledger platform for managing at least one of ownership of a set of collateral and a set of events related to a set of collateral and having a rating system with a set of data-integrated microservices including data collection and monitoring services, blockchain services, artificial intelligence services, and smart contract services for rating a set of loan-related entities.

In embodiments a lending platform is provided herein having a smart contract and distributed ledger platform for managing at least one of ownership of a set of collateral and a set of events related to a set of collateral and having a compliance system with a set of data-integrated microservices including data collection and monitoring services, blockchain services, artificial intelligence services, and smart contract services for automatically facilitating compliance with at least one of a law, a regulation and a policy related to a lending transaction.

In embodiments a lending platform is provided herein having a smart contract system that automatically adjusts an interest rate for a loan based on information collected via at least one of an Internet of Things system, a crowdsourcing system, a set of social network analytic services and a set of data collection and monitoring services and having a crowdsourcing system for obtaining information about at least one of a state of a set of collateral for a loan and a state of an entity relevant to a guarantee for a loan.

In embodiments a lending platform is provided herein having a smart contract system that automatically adjusts an interest rate for a loan based on information collected via at least one of an Internet of Things system, a crowdsourcing system, a set of social network analytic services and a set of data collection and monitoring services and having a smart contract that automatically adjusts an interest rate for a loan based on at least one of a regulatory factor and a market factor for a specific jurisdiction.

In embodiments a lending platform is provided herein having a smart contract system that automatically adjusts an interest rate for a loan based on information collected via at least one of an Internet of Things system, a crowdsourcing system, a set of social network analytic services and a set of data collection and monitoring services and having a smart contract that automatically restructures debt based on a monitored condition.

In embodiments a lending platform is provided herein having a smart contract system that automatically adjusts an interest rate for a loan based on information collected via at least one of an Internet of Things system, a crowdsourcing system, a set of social network analytic services and a set of data collection and monitoring services and having a social network monitoring system for validating the reliability of a guarantee for a loan.

In embodiments a lending platform is provided herein having a smart contract system that automatically adjusts an interest rate for a loan based on information collected via at least one of an Internet of Things system, a crowdsourcing system, a set of social network analytic services and a set of data collection and monitoring services and having an Internet of Things data collection and monitoring system for validating reliability of a guarantee for a loan.

In embodiments a lending platform is provided herein having a smart contract system that automatically adjusts an interest rate for a loan based on information collected via at least one of an Internet of Things system, a crowdsourcing system, a set of social network analytic services and a set of data collection and monitoring services and having a robotic process automation system for negotiation of a set of terms and conditions for a loan.

In embodiments a lending platform is provided herein having a smart contract system that automatically adjusts an interest rate for a loan based on information collected via at least one of an Internet of Things system, a crowdsourcing system, a set of social network analytic services and a set of data collection and monitoring services and having a robotic process automation system for loan collection.

In embodiments a lending platform is provided herein having a smart contract system that automatically adjusts an interest rate for a loan based on information collected via at least one of an Internet of Things system, a crowdsourcing system, a set of social network analytic services and a set of data collection and monitoring services and having a robotic process automation system for consolidating a set of loans.

In embodiments a lending platform is provided herein having a smart contract system that automatically adjusts an interest rate for a loan based on information collected via at least one of an Internet of Things system, a crowdsourcing system, a set of social network analytic services and a set of data collection and monitoring services and having a robotic process automation system for managing a factoring loan.

In embodiments a lending platform is provided herein having a smart contract system that automatically adjusts an interest rate for a loan based on information collected via at least one of an Internet of Things system, a crowdsourcing system, a set of social network analytic services and a set of data collection and monitoring services and having a robotic process automation system for brokering a mortgage loan.

In embodiments a lending platform is provided herein having a smart contract system that automatically adjusts an interest rate for a loan based on information collected via at least one of an Internet of Things system, a crowdsourcing system, a set of social network analytic services and a set of data collection and monitoring services and having a crowdsourcing and automated classification system for validating condition of an issuer for a bond.

In embodiments a lending platform is provided herein having a smart contract system that automatically adjusts an interest rate for a loan based on information collected via at least one of an Internet of Things system, a crowdsourcing system, a set of social network analytic services and a set of data collection and monitoring services and having a social network monitoring system with artificial intelligence for classifying a condition about a bond.

In embodiments a lending platform is provided herein having a smart contract system that automatically adjusts an interest rate for a loan based on information collected via at least one of an Internet of Things system, a crowdsourcing system, a set of social network analytic services and a set of data collection and monitoring services and having an Internet of Things data collection and monitoring system with artificial intelligence for classifying a condition about a bond.

In embodiments a lending platform is provided herein having a smart contract system that automatically adjusts an interest rate for a loan based on information collected via at least one of an Internet of Things system, a crowdsourcing system, a set of social network analytic services and a set of data collection and monitoring services and having a system that varies the terms and conditions of a subsidized loan based on a parameter monitored by the IoT.

In embodiments a lending platform is provided herein having a smart contract system that automatically adjusts an interest rate for a loan based on information collected via at least one of an Internet of Things system, a crowdsourcing system, a set of social network analytic services and a set of data collection and monitoring services and having a system that varies the terms and conditions of a subsidized loan based on a parameter monitored in a social network.

In embodiments a lending platform is provided herein having a smart contract system that automatically adjusts an interest rate for a loan based on information collected via at least one of an Internet of Things system, a crowdsourcing system, a set of social network analytic services and a set of data collection and monitoring services and having a system that varies the terms and conditions of a subsidized loan based on a parameter monitored by crowdsourcing.

In embodiments a lending platform is provided herein having a smart contract system that automatically adjusts an interest rate for a loan based on information collected via at least one of an Internet of Things system, a crowdsourcing system, a set of social network analytic services and a set of data collection and monitoring services and having an automated blockchain custody service for managing a set of custodial assets.

In embodiments a lending platform is provided herein having a smart contract system that automatically adjusts an interest rate for a loan based on information collected via at least one of an Internet of Things system, a crowdsourcing system, a set of social network analytic services and a set of data collection and monitoring services and having an underwriting system for a loan with a set of data-integrated microservices including data collection and monitoring services, blockchain services, artificial intelligence services, and smart contract services for underwriting lending entities and transactions.

In embodiments a lending platform is provided herein having a smart contract system that automatically adjusts an interest rate for a loan based on information collected via at least one of an Internet of Things system, a crowdsourcing system, a set of social network analytic services and a set of data collection and monitoring services and having a loan marketing system with a set of data-integrated microservices including data collection and monitoring services, blockchain services, artificial intelligence services and smart contract services for marketing a loan to a set of prospective parties.

In embodiments a lending platform is provided herein having a smart contract system that automatically adjusts an interest rate for a loan based on information collected via at least one of an Internet of Things system, a crowdsourcing system, a set of social network analytic services and a set of data collection and monitoring services and having a rating system with a set of data-integrated microservices including data collection and monitoring services, blockchain services, artificial intelligence services, and smart contract services for rating a set of loan-related entities.

In embodiments a lending platform is provided herein having a smart contract system that automatically adjusts an interest rate for a loan based on information collected via at least one of an Internet of Things system, a crowdsourcing system, a set of social network analytic services and a set of data collection and monitoring services and having a compliance system with a set of data-integrated microservices including data collection and monitoring services, blockchain services, artificial intelligence services, and smart contract services for automatically facilitating compliance with at least one of a law, a regulation and a policy related to a lending transaction.

In embodiments a lending platform is provided herein having a crowdsourcing system for obtaining information about at least one of a state of a set of collateral for a loan and a state of an entity relevant to a guarantee for a loan and having a smart contract that automatically adjusts an interest rate for a loan based on at least one of a regulatory factor and a market factor for a specific jurisdiction.

In embodiments a lending platform is provided herein having a crowdsourcing system for obtaining information about at least one of a state of a set of collateral for a loan and a state of an entity relevant to a guarantee for a loan and having a smart contract that automatically restructures debt based on a monitored condition.

In embodiments a lending platform is provided herein having a crowdsourcing system for obtaining information about at least one of a state of a set of collateral for a loan and a state of an entity relevant to a guarantee for a loan and having a social network monitoring system for validating the reliability of a guarantee for a loan.

In embodiments a lending platform is provided herein having a crowdsourcing system for obtaining information about at least one of a state of a set of collateral for a loan and a state of an entity relevant to a guarantee for a loan and having an Internet of Things data collection and monitoring system for validating reliability of a guarantee for a loan.

In embodiments a lending platform is provided herein having a crowdsourcing system for obtaining information about at least one of a state of a set of collateral for a loan and a state of an entity relevant to a guarantee for a loan and having a robotic process automation system for negotiation of a set of terms and conditions for a loan.

In embodiments a lending platform is provided herein having a crowdsourcing system for obtaining information about at least one of a state of a set of collateral for a loan and a state of an entity relevant to a guarantee for a loan and having a robotic process automation system for loan collection.

In embodiments a lending platform is provided herein having a crowdsourcing system for obtaining information about at least one of a state of a set of collateral for a loan and a state of an entity relevant to a guarantee for a loan and having a robotic process automation system for consolidating a set of loans.

In embodiments a lending platform is provided herein having a crowdsourcing system for obtaining information about at least one of a state of a set of collateral for a loan and a state of an entity relevant to a guarantee for a loan and having a robotic process automation system for managing a factoring loan.

In embodiments a lending platform is provided herein having a crowdsourcing system for obtaining information about at least one of a state of a set of collateral for a loan and a state of an entity relevant to a guarantee for a loan and having a robotic process automation system for brokering a mortgage loan.

In embodiments a lending platform is provided herein having a crowdsourcing system for obtaining information about at least one of a state of a set of collateral for a loan and a state of an entity relevant to a guarantee for a loan and having a crowdsourcing and automated classification system for validating condition of an issuer for a bond.

In embodiments a lending platform is provided herein having a crowdsourcing system for obtaining information about at least one of a state of a set of collateral for a loan and a state of an entity relevant to a guarantee for a loan and having a social network monitoring system with artificial intelligence for classifying a condition about a bond.

In embodiments a lending platform is provided herein having a crowdsourcing system for obtaining information about at least one of a state of a set of collateral for a loan and a state of an entity relevant to a guarantee for a loan and having an Internet of Things data collection and monitoring system with artificial intelligence for classifying a condition about a bond.

In embodiments a lending platform is provided herein having a crowdsourcing system for obtaining information about at least one of a state of a set of collateral for a loan and a state of an entity relevant to a guarantee for a loan and having a system that varies the terms and conditions of a subsidized loan based on a parameter monitored by the IoT.

In embodiments a lending platform is provided herein having a crowdsourcing system for obtaining information about at least one of a state of a set of collateral for a loan and a state of an entity relevant to a guarantee for a loan and having a system that varies the terms and conditions of a subsidized loan based on a parameter monitored in a social network.

In embodiments a lending platform is provided herein having a crowdsourcing system for obtaining information about at least one of a state of a set of collateral for a loan and a state of an entity relevant to a guarantee for a loan and having a system that varies the terms and conditions of a subsidized loan based on a parameter monitored by crowdsourcing.

In embodiments a lending platform is provided herein having a crowdsourcing system for obtaining information about at least one of a state of a set of collateral for a loan and a state of an entity relevant to a guarantee for a loan and having an automated blockchain custody service for managing a set of custodial assets.

In embodiments a lending platform is provided herein having a crowdsourcing system for obtaining information about at least one of a state of a set of collateral for a loan and a state of an entity relevant to a guarantee for a loan and having an underwriting system for a loan with a set of data-integrated microservices including data collection and monitoring services, blockchain services, artificial intelligence services, and smart contract services for underwriting lending entities and transactions.

In embodiments a lending platform is provided herein having a crowdsourcing system for obtaining information about at least one of a state of a set of collateral for a loan and a state of an entity relevant to a guarantee for a loan and having a loan marketing system with a set of data-integrated microservices including data collection and monitoring services, blockchain services, artificial intelligence services and smart contract services for marketing a loan to a set of prospective parties.

In embodiments a lending platform is provided herein having a crowdsourcing system for obtaining information about at least one of a state of a set of collateral for a loan and a state of an entity relevant to a guarantee for a loan and having a rating system with a set of data-integrated microservices including data collection and monitoring services, blockchain services, artificial intelligence services, and smart contract services for rating a set of loan-related entities.

In embodiments a lending platform is provided herein having a crowdsourcing system for obtaining information about at least one of a state of a set of collateral for a loan and a state of an entity relevant to a guarantee for a loan and having a compliance system with a set of data-integrated microservices including data collection and monitoring services, blockchain services, artificial intelligence services, and smart contract services for automatically facilitating compliance with at least one of a law, a regulation and a policy related to a lending transaction.

In embodiments a lending platform is provided herein having a smart contract that automatically adjusts an interest rate for a loan based on at least one of a regulatory factor and a market factor for a specific jurisdiction and having a smart contract that automatically restructures debt based on a monitored condition.

In embodiments a lending platform is provided herein having a smart contract that automatically adjusts an interest rate for a loan based on at least one of a regulatory factor and a market factor for a specific jurisdiction and having a social network monitoring system for validating the reliability of a guarantee for a loan.

In embodiments a lending platform is provided herein having a smart contract that automatically adjusts an interest rate for a loan based on at least one of a regulatory factor and a market factor for a specific jurisdiction and having an Internet of Things data collection and monitoring system for validating reliability of a guarantee for a loan.

In embodiments a lending platform is provided herein having a smart contract that automatically adjusts an interest rate for a loan based on at least one of a regulatory factor and a market factor for a specific jurisdiction and having a robotic process automation system for negotiation of a set of terms and conditions for a loan.

In embodiments a lending platform is provided herein having a smart contract that automatically adjusts an interest rate for a loan based on at least one of a regulatory factor and a market factor for a specific jurisdiction and having a robotic process automation system for loan collection.

In embodiments a lending platform is provided herein having a smart contract that automatically adjusts an interest rate for a loan based on at least one of a regulatory factor and a market factor for a specific jurisdiction and having a robotic process automation system for consolidating a set of loans.

In embodiments a lending platform is provided herein having a smart contract that automatically adjusts an interest rate for a loan based on at least one of a regulatory factor and a market factor for a specific jurisdiction and having a robotic process automation system for managing a factoring loan.

In embodiments a lending platform is provided herein having a smart contract that automatically adjusts an interest rate for a loan based on at least one of a regulatory factor and a market factor for a specific jurisdiction and having a robotic process automation system for brokering a mortgage loan.

In embodiments a lending platform is provided herein having a smart contract that automatically adjusts an interest rate for a loan based on at least one of a regulatory factor and a market factor for a specific jurisdiction and having a crowdsourcing and automated classification system for validating condition of an issuer for a bond.

In embodiments a lending platform is provided herein having a smart contract that automatically adjusts an interest rate for a loan based on at least one of a regulatory factor and a market factor for a specific jurisdiction and having a social network monitoring system with artificial intelligence for classifying a condition about a bond.

In embodiments a lending platform is provided herein having a smart contract that automatically adjusts an interest rate for a loan based on at least one of a regulatory factor and a market factor for a specific jurisdiction and having an Internet of Things data collection and monitoring system with artificial intelligence for classifying a condition about a bond.

In embodiments a lending platform is provided herein having a smart contract that automatically adjusts an interest rate for a loan based on at least one of a regulatory factor and a market factor for a specific jurisdiction and having a system that varies the terms and conditions of a subsidized loan based on a parameter monitored by the IoT.

In embodiments a lending platform is provided herein having a smart contract that automatically adjusts an interest rate for a loan based on at least one of a regulatory factor and a market factor for a specific jurisdiction and having a system that varies the terms and conditions of a subsidized loan based on a parameter monitored in a social network.

In embodiments a lending platform is provided herein having a smart contract that automatically adjusts an interest rate for a loan based on at least one of a regulatory factor and a market factor for a specific jurisdiction and having a system that varies the terms and conditions of a subsidized loan based on a parameter monitored by crowdsourcing.

In embodiments a lending platform is provided herein having a smart contract that automatically adjusts an interest rate for a loan based on at least one of a regulatory factor and a market factor for a specific jurisdiction and having an automated blockchain custody service for managing a set of custodial assets.

In embodiments a lending platform is provided herein having a smart contract that automatically adjusts an interest rate for a loan based on at least one of a regulatory factor and a market factor for a specific jurisdiction and having an underwriting system for a loan with a set of data-integrated microservices including data collection and monitoring services, blockchain services, artificial intelligence services, and smart contract services for underwriting lending entities and transactions.

In embodiments a lending platform is provided herein having a smart contract that automatically adjusts an interest rate for a loan based on at least one of a regulatory factor and a market factor for a specific jurisdiction and having a loan marketing system with a set of data-integrated microservices including data collection and monitoring services, blockchain services, artificial intelligence services and smart contract services for marketing a loan to a set of prospective parties.

In embodiments a lending platform is provided herein having a smart contract that automatically adjusts an interest rate for a loan based on at least one of a regulatory factor and a market factor for a specific jurisdiction and having a rating system with a set of data-integrated microservices including data collection and monitoring services, blockchain services, artificial intelligence services, and smart contract services for rating a set of loan-related entities.

In embodiments a lending platform is provided herein having a smart contract that automatically adjusts an interest rate for a loan based on at least one of a regulatory factor and a market factor for a specific jurisdiction and having a compliance system with a set of data-integrated microservices including data collection and monitoring services, blockchain services, artificial intelligence services, and smart contract services for automatically facilitating compliance with at least one of a law, a regulation and a policy related to a lending transaction.

In embodiments a lending platform is provided herein having a smart contract that automatically restructures debt based on a monitored condition and having a social network monitoring system for validating the reliability of a guarantee for a loan.

In embodiments a lending platform is provided herein having a smart contract that automatically restructures debt based on a monitored condition and having an Internet of Things data collection and monitoring system for validating reliability of a guarantee for a loan.

In embodiments a lending platform is provided herein having a smart contract that automatically restructures debt based on a monitored condition and having a robotic process automation system for negotiation of a set of terms and conditions for a loan.

In embodiments a lending platform is provided herein having a smart contract that automatically restructures debt based on a monitored condition and having a robotic process automation system for loan collection.

In embodiments a lending platform is provided herein having a smart contract that automatically restructures debt based on a monitored condition and having a robotic process automation system for consolidating a set of loans.

In embodiments a lending platform is provided herein having a smart contract that automatically restructures debt based on a monitored condition and having a robotic process automation system for managing a factoring loan.

In embodiments a lending platform is provided herein having a smart contract that automatically restructures debt based on a monitored condition and having a robotic process automation system for brokering a mortgage loan.

In embodiments a lending platform is provided herein having a smart contract that automatically restructures debt based on a monitored condition and having a crowdsourcing and automated classification system for validating condition of an issuer for a bond.

In embodiments a lending platform is provided herein having a smart contract that automatically restructures debt based on a monitored condition and having a social network monitoring system with artificial intelligence for classifying a condition about a bond.

In embodiments a lending platform is provided herein having a smart contract that automatically restructures debt based on a monitored condition and having an Internet of Things data collection and monitoring system with artificial intelligence for classifying a condition about a bond.

In embodiments a lending platform is provided herein having a smart contract that automatically restructures debt based on a monitored condition and having a system that varies the terms and conditions of a subsidized loan based on a parameter monitored by the IoT.

In embodiments a lending platform is provided herein having a smart contract that automatically restructures debt based on a monitored condition and having a system that varies the terms and conditions of a subsidized loan based on a parameter monitored in a social network.

In embodiments a lending platform is provided herein having a smart contract that automatically restructures debt based on a monitored condition and having a system that varies the terms and conditions of a subsidized loan based on a parameter monitored by crowdsourcing.

In embodiments a lending platform is provided herein having a smart contract that automatically restructures debt based on a monitored condition and having an automated blockchain custody service for managing a set of custodial assets.

In embodiments a lending platform is provided herein having a smart contract that automatically restructures debt based on a monitored condition and having an underwriting system for a loan with a set of data-integrated microservices including data collection and monitoring services, blockchain services, artificial intelligence services, and smart contract services for underwriting lending entities and transactions.

In embodiments a lending platform is provided herein having a smart contract that automatically restructures debt based on a monitored condition and having a loan marketing system with a set of data-integrated microservices including data collection and monitoring services, blockchain services, artificial intelligence services and smart contract services for marketing a loan to a set of prospective parties.

In embodiments a lending platform is provided herein having a smart contract that automatically restructures debt based on a monitored condition and having a rating system with a set of data-integrated microservices including data collection and monitoring services, blockchain services, artificial intelligence services, and smart contract services for rating a set of loan-related entities.

In embodiments a lending platform is provided herein having a smart contract that automatically restructures debt based on a monitored condition and having a compliance system with a set of data-integrated microservices including data collection and monitoring services, blockchain services, artificial intelligence services, and smart contract services for automatically facilitating compliance with at least one of a law, a regulation and a policy related to a lending transaction.

In embodiments a lending platform is provided herein having a social network monitoring system for validating the reliability of a guarantee for a loan and having an Internet of Things data collection and monitoring system for validating reliability of a guarantee for a loan.

In embodiments a lending platform is provided herein having a social network monitoring system for validating the reliability of a guarantee for a loan and having a robotic process automation system for negotiation of a set of terms and conditions for a loan.

In embodiments a lending platform is provided herein having a social network monitoring system for validating the reliability of a guarantee for a loan and having a robotic process automation system for loan collection.

In embodiments a lending platform is provided herein having a social network monitoring system for validating the reliability of a guarantee for a loan and having a robotic process automation system for consolidating a set of loans.

In embodiments a lending platform is provided herein having a social network monitoring system for validating the reliability of a guarantee for a loan and having a robotic process automation system for managing a factoring loan.

In embodiments a lending platform is provided herein having a social network monitoring system for validating the reliability of a guarantee for a loan and having a robotic process automation system for brokering a mortgage loan.

In embodiments a lending platform is provided herein having a social network monitoring system for validating the reliability of a guarantee for a loan and having a crowdsourcing and automated classification system for validating condition of an issuer for a bond.

In embodiments a lending platform is provided herein having a social network monitoring system for validating the reliability of a guarantee for a loan and having a social network monitoring system with artificial intelligence for classifying a condition about a bond.

In embodiments a lending platform is provided herein having a social network monitoring system for validating the reliability of a guarantee for a loan and having an Internet of Things data collection and monitoring system with artificial intelligence for classifying a condition about a bond.

In embodiments a lending platform is provided herein having a social network monitoring system for validating the reliability of a guarantee for a loan and having a system that varies the terms and conditions of a subsidized loan based on a parameter monitored by the IoT.

In embodiments a lending platform is provided herein having a social network monitoring system for validating the reliability of a guarantee for a loan and having a system that varies the terms and conditions of a subsidized loan based on a parameter monitored in a social network.

In embodiments a lending platform is provided herein having a social network monitoring system for validating the reliability of a guarantee for a loan and having a system that varies the terms and conditions of a subsidized loan based on a parameter monitored by crowdsourcing.

In embodiments a lending platform is provided herein having a social network monitoring system for validating the reliability of a guarantee for a loan and having an automated blockchain custody service for managing a set of custodial assets.

In embodiments a lending platform is provided herein having a social network monitoring system for validating the reliability of a guarantee for a loan and having an underwriting system for a loan with a set of data-integrated microservices including data collection and monitoring services, blockchain services, artificial intelligence services, and smart contract services for underwriting lending entities and transactions.

In embodiments a lending platform is provided herein having a social network monitoring system for validating the reliability of a guarantee for a loan and having a loan marketing system with a set of data-integrated microservices including data collection and monitoring services, blockchain services, artificial intelligence services and smart contract services for marketing a loan to a set of prospective parties.

In embodiments a lending platform is provided herein having a social network monitoring system for validating the reliability of a guarantee for a loan and having a rating system with a set of data-integrated microservices including data collection and monitoring services, blockchain services, artificial intelligence services, and smart contract services for rating a set of loan-related entities.

In embodiments a lending platform is provided herein having a social network monitoring system for validating the reliability of a guarantee for a loan and having a compliance system with a set of data-integrated microservices including data collection and monitoring services, blockchain services, artificial intelligence services, and smart contract services for automatically facilitating compliance with at least one of a law, a regulation and a policy related to a lending transaction.

In embodiments a lending platform is provided herein having an Internet of Things data collection and monitoring system for validating reliability of a guarantee for a loan and having a robotic process automation system for negotiation of a set of terms and conditions for a loan.

In embodiments a lending platform is provided herein having an Internet of Things data collection and monitoring system for validating reliability of a guarantee for a loan and having a robotic process automation system for loan collection.

In embodiments a lending platform is provided herein having an Internet of Things data collection and monitoring system for validating reliability of a guarantee for a loan and having a robotic process automation system for consolidating a set of loans.

In embodiments a lending platform is provided herein having an Internet of Things data collection and monitoring system for validating reliability of a guarantee for a loan and having a robotic process automation system for managing a factoring loan.

In embodiments a lending platform is provided herein having an Internet of Things data collection and monitoring system for validating reliability of a guarantee for a loan and having a robotic process automation system for brokering a mortgage loan.

In embodiments a lending platform is provided herein having an Internet of Things data collection and monitoring system for validating reliability of a guarantee for a loan and having a crowdsourcing and automated classification system for validating condition of an issuer for a bond.

In embodiments a lending platform is provided herein having an Internet of Things data collection and monitoring system for validating reliability of a guarantee for a loan and having a social network monitoring system with artificial intelligence for classifying a condition about a bond.

In embodiments a lending platform is provided herein having an Internet of Things data collection and monitoring system for validating reliability of a guarantee for a loan and having an Internet of Things data collection and monitoring system with artificial intelligence for classifying a condition about a bond.

In embodiments a lending platform is provided herein having an Internet of Things data collection and monitoring system for validating reliability of a guarantee for a loan and having a system that varies the terms and conditions of a subsidized loan based on a parameter monitored by the IoT.

In embodiments a lending platform is provided herein having an Internet of Things data collection and monitoring system for validating reliability of a guarantee for a loan and having a system that varies the terms and conditions of a subsidized loan based on a parameter monitored in a social network.

In embodiments a lending platform is provided herein having an Internet of Things data collection and monitoring system for validating reliability of a guarantee for a loan and having a system that varies the terms and conditions of a subsidized loan based on a parameter monitored by crowdsourcing.

In embodiments a lending platform is provided herein having an Internet of Things data collection and monitoring system for validating reliability of a guarantee for a loan and having an automated blockchain custody service for managing a set of custodial assets.

In embodiments a lending platform is provided herein having an Internet of Things data collection and monitoring system for validating reliability of a guarantee for a loan and having an underwriting system for a loan with a set of data-integrated microservices including data collection and monitoring services, blockchain services, artificial intelligence services, and smart contract services for underwriting lending entities and transactions.

In embodiments a lending platform is provided herein having an Internet of Things data collection and monitoring system for validating reliability of a guarantee for a loan and having a loan marketing system with a set of data-integrated microservices including data collection and monitoring services, blockchain services, artificial intelligence services and smart contract services for marketing a loan to a set of prospective parties.

In embodiments a lending platform is provided herein having an Internet of Things data collection and monitoring system for validating reliability of a guarantee for a loan and having a rating system with a set of data-integrated microservices including data collection and monitoring services, blockchain services, artificial intelligence services, and smart contract services for rating a set of loan-related entities.

In embodiments a lending platform is provided herein having an Internet of Things data collection and monitoring system for validating reliability of a guarantee for a loan and having a compliance system with a set of data-integrated microservices including data collection and monitoring services, blockchain services, artificial intelligence services, and smart contract services for automatically facilitating compliance with at least one of a law, a regulation and a policy related to a lending transaction.

In embodiments a lending platform is provided herein having a robotic process automation system for negotiation of a set of terms and conditions for a loan and having a robotic process automation system for loan collection.

In embodiments a lending platform is provided herein having a robotic process automation system for negotiation of a set of terms and conditions for a loan and having a robotic process automation system for consolidating a set of loans.

In embodiments a lending platform is provided herein having a robotic process automation system for negotiation of a set of terms and conditions for a loan and having a robotic process automation system for managing a factoring loan.

In embodiments a lending platform is provided herein having a robotic process automation system for negotiation of a set of terms and conditions for a loan and having a robotic process automation system for brokering a mortgage loan.

In embodiments a lending platform is provided herein having a robotic process automation system for negotiation of a set of terms and conditions for a loan and having a crowdsourcing and automated classification system for validating condition of an issuer for a bond.

In embodiments a lending platform is provided herein having a robotic process automation system for negotiation of a set of terms and conditions for a loan and having a social network monitoring system with artificial intelligence for classifying a condition about a bond.

In embodiments a lending platform is provided herein having a robotic process automation system for negotiation of a set of terms and conditions for a loan and having an Internet of Things data collection and monitoring system with artificial intelligence for classifying a condition about a bond.

In embodiments a lending platform is provided herein having a robotic process automation system for negotiation of a set of terms and conditions for a loan and having a system that varies the terms and conditions of a subsidized loan based on a parameter monitored by the IoT.

In embodiments a lending platform is provided herein having a robotic process automation system for negotiation of a set of terms and conditions for a loan and having a system that varies the terms and conditions of a subsidized loan based on a parameter monitored in a social network.

In embodiments a lending platform is provided herein having a robotic process automation system for negotiation of a set of terms and conditions for a loan and having a system that varies the terms and conditions of a subsidized loan based on a parameter monitored by crowdsourcing.

In embodiments a lending platform is provided herein having a robotic process automation system for negotiation of a set of terms and conditions for a loan and having an automated blockchain custody service for managing a set of custodial assets.

In embodiments a lending platform is provided herein having a robotic process automation system for negotiation of a set of terms and conditions for a loan and having an underwriting system for a loan with a set of data-integrated microservices including data collection and monitoring services, blockchain services, artificial intelligence services, and smart contract services for underwriting lending entities and transactions.

In embodiments a lending platform is provided herein having a robotic process automation system for negotiation of a set of terms and conditions for a loan and having a loan marketing system with a set of data-integrated microservices including data collection and monitoring services, blockchain services, artificial intelligence services and smart contract services for marketing a loan to a set of prospective parties.

In embodiments a lending platform is provided herein having a robotic process automation system for negotiation of a set of terms and conditions for a loan and having a rating system with a set of data-integrated microservices including data collection and monitoring services, blockchain services, artificial intelligence services, and smart contract services for rating a set of loan-related entities.

In embodiments a lending platform is provided herein having a robotic process automation system for negotiation of a set of terms and conditions for a loan and having a compliance system with a set of data-integrated microservices including data collection and monitoring services, blockchain services, artificial intelligence services, and smart contract services for automatically facilitating compliance with at least one of a law, a regulation and a policy related to a lending transaction.

In embodiments a lending platform is provided herein having a robotic process automation system for loan collection and having a robotic process automation system for consolidating a set of loans.

In embodiments a lending platform is provided herein having a robotic process automation system for loan collection and having a robotic process automation system for managing a factoring loan.

In embodiments a lending platform is provided herein having a robotic process automation system for loan collection and having a robotic process automation system for brokering a mortgage loan.

In embodiments a lending platform is provided herein having a robotic process automation system for loan collection and having a crowdsourcing and automated classification system for validating condition of an issuer for a bond.

In embodiments a lending platform is provided herein having a robotic process automation system for loan collection and having a social network monitoring system with artificial intelligence for classifying a condition about a bond.

In embodiments a lending platform is provided herein having a robotic process automation system for loan collection and having an Internet of Things data collection and monitoring system with artificial intelligence for classifying a condition about a bond.

In embodiments a lending platform is provided herein having a robotic process automation system for loan collection and having a system that varies the terms and conditions of a subsidized loan based on a parameter monitored by the IoT.

In embodiments a lending platform is provided herein having a robotic process automation system for loan collection and having a system that varies the terms and conditions of a subsidized loan based on a parameter monitored in a social network.

In embodiments a lending platform is provided herein having a robotic process automation system for loan collection and having a system that varies the terms and conditions of a subsidized loan based on a parameter monitored by crowdsourcing.

In embodiments a lending platform is provided herein having a robotic process automation system for loan collection and having an automated blockchain custody service for managing a set of custodial assets.

In embodiments a lending platform is provided herein having a robotic process automation system for loan collection and having an underwriting system for a loan with a set of data-integrated microservices including data collection and monitoring services, blockchain services, artificial intelligence services, and smart contract services for underwriting lending entities and transactions.

In embodiments a lending platform is provided herein having a robotic process automation system for loan collection and having a loan marketing system with a set of data-integrated microservices including data collection and monitoring services, blockchain services, artificial intelligence services and smart contract services for marketing a loan to a set of prospective parties.

In embodiments a lending platform is provided herein having a robotic process automation system for loan collection and having a rating system with a set of data-integrated microservices including data collection and monitoring services, blockchain services, artificial intelligence services, and smart contract services for rating a set of loan-related entities.

In embodiments a lending platform is provided herein having a robotic process automation system for loan collection and having a compliance system with a set of data-integrated microservices including data collection and monitoring services, blockchain services, artificial intelligence services, and smart contract services for automatically facilitating compliance with at least one of a law, a regulation and a policy related to a lending transaction.

In embodiments a lending platform is provided herein having a robotic process automation system for consolidating a set of loans and having a robotic process automation system for managing a factoring loan.

In embodiments a lending platform is provided herein having a robotic process automation system for consolidating a set of loans and having a robotic process automation system for brokering a mortgage loan.

In embodiments a lending platform is provided herein having a robotic process automation system for consolidating a set of loans and having a crowdsourcing and automated classification system for validating condition of an issuer for a bond.

In embodiments a lending platform is provided herein having a robotic process automation system for consolidating a set of loans and having a social network monitoring system with artificial intelligence for classifying a condition about a bond.

In embodiments a lending platform is provided herein having a robotic process automation system for consolidating a set of loans and having an Internet of Things data collection and monitoring system with artificial intelligence for classifying a condition about a bond.

In embodiments a lending platform is provided herein having a robotic process automation system for consolidating a set of loans and having a system that varies the terms and conditions of a subsidized loan based on a parameter monitored by the IoT.

In embodiments a lending platform is provided herein having a robotic process automation system for consolidating a set of loans and having a system that varies the terms and conditions of a subsidized loan based on a parameter monitored in a social network.

In embodiments a lending platform is provided herein having a robotic process automation system for consolidating a set of loans and having a system that varies the terms and conditions of a subsidized loan based on a parameter monitored by crowdsourcing.

In embodiments a lending platform is provided herein having a robotic process automation system for consolidating a set of loans and having an automated blockchain custody service for managing a set of custodial assets.

In embodiments a lending platform is provided herein having a robotic process automation system for consolidating a set of loans and having an underwriting system for a loan with a set of data-integrated microservices including data collection and monitoring services, blockchain services, artificial intelligence services, and smart contract services for underwriting lending entities and transactions.

In embodiments a lending platform is provided herein having a robotic process automation system for consolidating a set of loans and having a loan marketing system with a set of data-integrated microservices including data collection and monitoring services, blockchain services, artificial intelligence services and smart contract services for marketing a loan to a set of prospective parties.

In embodiments a lending platform is provided herein having a robotic process automation system for consolidating a set of loans and having a rating system with a set of data-integrated microservices including data collection and monitoring services, blockchain services, artificial intelligence services, and smart contract services for rating a set of loan-related entities.

In embodiments a lending platform is provided herein having a robotic process automation system for consolidating a set of loans and having a compliance system with a set of data-integrated microservices including data collection and monitoring services, blockchain services, artificial intelligence services, and smart contract services for automatically facilitating compliance with at least one of a law, a regulation and a policy related to a lending transaction.

In embodiments a lending platform is provided herein having a robotic process automation system for managing a factoring loan and having a robotic process automation system for brokering a mortgage loan.

In embodiments a lending platform is provided herein having a robotic process automation system for managing a factoring loan and having a crowdsourcing and automated classification system for validating condition of an issuer for a bond.

In embodiments a lending platform is provided herein having a robotic process automation system for managing a factoring loan and having a social network monitoring system with artificial intelligence for classifying a condition about a bond.

In embodiments a lending platform is provided herein having a robotic process automation system for managing a factoring loan and having an Internet of Things data collection and monitoring system with artificial intelligence for classifying a condition about a bond.

In embodiments a lending platform is provided herein having a robotic process automation system for managing a factoring loan and having a system that varies the terms and conditions of a subsidized loan based on a parameter monitored by the IoT.

In embodiments a lending platform is provided herein having a robotic process automation system for managing a factoring loan and having a system that varies the terms and conditions of a subsidized loan based on a parameter monitored in a social network.

In embodiments a lending platform is provided herein having a robotic process automation system for managing a factoring loan and having a system that varies the terms and conditions of a subsidized loan based on a parameter monitored by crowdsourcing.

In embodiments a lending platform is provided herein having a robotic process automation system for managing a factoring loan and having an automated blockchain custody service for managing a set of custodial assets.

In embodiments a lending platform is provided herein having a robotic process automation system for managing a factoring loan and having an underwriting system for a loan with a set of data-integrated microservices including data collection and monitoring services, blockchain services, artificial intelligence services, and smart contract services for underwriting lending entities and transactions.

In embodiments a lending platform is provided herein having a robotic process automation system for managing a factoring loan and having a loan marketing system with a set of data-integrated microservices including data collection and monitoring services, blockchain services, artificial intelligence services and smart contract services for marketing a loan to a set of prospective parties.

In embodiments a lending platform is provided herein having a robotic process automation system for managing a factoring loan and having a rating system with a set of data-integrated microservices including data collection and monitoring services, blockchain services, artificial intelligence services, and smart contract services for rating a set of loan-related entities.

In embodiments a lending platform is provided herein having a robotic process automation system for managing a factoring loan and having a compliance system with a set of data-integrated microservices including data collection and monitoring services, blockchain services, artificial intelligence services, and smart contract services for automatically facilitating compliance with at least one of a law, a regulation and a policy related to a lending transaction.

In embodiments a lending platform is provided herein having a robotic process automation system for brokering a mortgage loan and having a crowdsourcing and automated classification system for validating condition of an issuer for a bond.

In embodiments a lending platform is provided herein having a robotic process automation system for brokering a mortgage loan and having a social network monitoring system with artificial intelligence for classifying a condition about a bond.

In embodiments a lending platform is provided herein having a robotic process automation system for brokering a mortgage loan and having an Internet of Things data collection and monitoring system with artificial intelligence for classifying a condition about a bond.

In embodiments a lending platform is provided herein having a robotic process automation system for brokering a mortgage loan and having a system that varies the terms and conditions of a subsidized loan based on a parameter monitored by the IoT.

In embodiments a lending platform is provided herein having a robotic process automation system for brokering a mortgage loan and having a system that varies the terms and conditions of a subsidized loan based on a parameter monitored in a social network.

In embodiments a lending platform is provided herein having a robotic process automation system for brokering a mortgage loan and having a system that varies the terms and conditions of a subsidized loan based on a parameter monitored by crowdsourcing.

In embodiments a lending platform is provided herein having a robotic process automation system for brokering a mortgage loan and having an automated blockchain custody service for managing a set of custodial assets.

In embodiments a lending platform is provided herein having a robotic process automation system for brokering a mortgage loan and having an underwriting system for a loan with a set of data-integrated microservices including data collection and monitoring services, blockchain services, artificial intelligence services, and smart contract services for underwriting lending entities and transactions.

In embodiments a lending platform is provided herein having a robotic process automation system for brokering a mortgage loan and having a loan marketing system with a set of data-integrated microservices including data collection and monitoring services, blockchain services, artificial intelligence services and smart contract services for marketing a loan to a set of prospective parties.

In embodiments a lending platform is provided herein having a robotic process automation system for brokering a mortgage loan and having a rating system with a set of data-integrated microservices including data collection and monitoring services, blockchain services, artificial intelligence services, and smart contract services for rating a set of loan-related entities.

In embodiments a lending platform is provided herein having a robotic process automation system for brokering a mortgage loan and having a compliance system with a set of data-integrated microservices including data collection and monitoring services, blockchain services, artificial intelligence services, and smart contract services for automatically facilitating compliance with at least one of a law, a regulation and a policy related to a lending transaction.

In embodiments a lending platform is provided herein having a crowdsourcing and automated classification system for validating condition of an issuer for a bond and having a social network monitoring system with artificial intelligence for classifying a condition about a bond.

In embodiments a lending platform is provided herein having a crowdsourcing and automated classification system for validating condition of an issuer for a bond and having an Internet of Things data collection and monitoring system with artificial intelligence for classifying a condition about a bond.

In embodiments a lending platform is provided herein having a crowdsourcing and automated classification system for validating condition of an issuer for a bond and having a system that varies the terms and conditions of a subsidized loan based on a parameter monitored by the IoT.

In embodiments a lending platform is provided herein having a crowdsourcing and automated classification system for validating condition of an issuer for a bond and having a system that varies the terms and conditions of a subsidized loan based on a parameter monitored in a social network.

In embodiments a lending platform is provided herein having a crowdsourcing and automated classification system for validating condition of an issuer for a bond and having a system that varies the terms and conditions of a subsidized loan based on a parameter monitored by crowdsourcing.

In embodiments a lending platform is provided herein having a crowdsourcing and automated classification system for validating condition of an issuer for a bond and having an automated blockchain custody service for managing a set of custodial assets.

In embodiments a lending platform is provided herein having a crowdsourcing and automated classification system for validating condition of an issuer for a bond and having an underwriting system for a loan with a set of data-integrated microservices including data collection and monitoring services, blockchain services, artificial intelligence services, and smart contract services for underwriting lending entities and transactions.

In embodiments a lending platform is provided herein having a crowdsourcing and automated classification system for validating condition of an issuer for a bond and having a loan marketing system with a set of data-integrated microservices including data collection and monitoring services, blockchain services, artificial intelligence services and smart contract services for marketing a loan to a set of prospective parties.

In embodiments a lending platform is provided herein having a crowdsourcing and automated classification system for validating condition of an issuer for a bond and having a rating system with a set of data-integrated microservices including data collection and monitoring services, blockchain services, artificial intelligence services, and smart contract services for rating a set of loan-related entities.

In embodiments a lending platform is provided herein having a crowdsourcing and automated classification system for validating condition of an issuer for a bond and having a compliance system with a set of data-integrated microservices including data collection and monitoring services, blockchain services, artificial intelligence services, and smart contract services for automatically facilitating compliance with at least one of a law, a regulation and a policy related to a lending transaction.

In embodiments a lending platform is provided herein having a social network monitoring system with artificial intelligence for classifying a condition about a bond and having an Internet of Things data collection and monitoring system with artificial intelligence for classifying a condition about a bond.

In embodiments a lending platform is provided herein having a social network monitoring system with artificial intelligence for classifying a condition about a bond and having a system that varies the terms and conditions of a subsidized loan based on a parameter monitored by the IoT.

In embodiments a lending platform is provided herein having a social network monitoring system with artificial intelligence for classifying a condition about a bond and having a system that varies the terms and conditions of a subsidized loan based on a parameter monitored in a social network.

In embodiments a lending platform is provided herein having a social network monitoring system with artificial intelligence for classifying a condition about a bond and having a system that varies the terms and conditions of a subsidized loan based on a parameter monitored by crowdsourcing.

In embodiments a lending platform is provided herein having a social network monitoring system with artificial intelligence for classifying a condition about a bond and having an automated blockchain custody service for managing a set of custodial assets.

In embodiments a lending platform is provided herein having a social network monitoring system with artificial intelligence for classifying a condition about a bond and having an underwriting system for a loan with a set of data-integrated microservices including data collection and monitoring services, blockchain services, artificial intelligence services, and smart contract services for underwriting lending entities and transactions.

In embodiments a lending platform is provided herein having a social network monitoring system with artificial intelligence for classifying a condition about a bond and having a loan marketing system with a set of data-integrated microservices including data collection and monitoring services, blockchain services, artificial intelligence services and smart contract services for marketing a loan to a set of prospective parties.

In embodiments a lending platform is provided herein having a social network monitoring system with artificial intelligence for classifying a condition about a bond and having a rating system with a set of data-integrated microservices including data collection and monitoring services, blockchain services, artificial intelligence services, and smart contract services for rating a set of loan-related entities.

In embodiments a lending platform is provided herein having a social network monitoring system with artificial intelligence for classifying a condition about a bond and having a compliance system with a set of data-integrated microservices including data collection and monitoring services, blockchain services, artificial intelligence services, and smart contract services for automatically facilitating compliance with at least one of a law, a regulation and a policy related to a lending transaction.

In embodiments a lending platform is provided herein having an Internet of Things data collection and monitoring system with artificial intelligence for classifying a condition about a bond and having a system that varies the terms and conditions of a subsidized loan based on a parameter monitored by the IoT.

In embodiments a lending platform is provided herein having an Internet of Things data collection and monitoring system with artificial intelligence for classifying a condition about a bond and having a system that varies the terms and conditions of a subsidized loan based on a parameter monitored in a social network.

In embodiments a lending platform is provided herein having an Internet of Things data collection and monitoring system with artificial intelligence for classifying a condition about a bond and having a system that varies the terms and conditions of a subsidized loan based on a parameter monitored by crowdsourcing.

In embodiments a lending platform is provided herein having an Internet of Things data collection and monitoring system with artificial intelligence for classifying a condition about a bond and having an automated blockchain custody service for managing a set of custodial assets.

In embodiments a lending platform is provided herein having an Internet of Things data collection and monitoring system with artificial intelligence for classifying a condition about a bond and having an underwriting system for a loan with a set of data-integrated microservices including data collection and monitoring services, blockchain services, artificial intelligence services, and smart contract services for underwriting lending entities and transactions.

In embodiments a lending platform is provided herein having an Internet of Things data collection and monitoring system with artificial intelligence for classifying a condition about a bond and having a loan marketing system with a set of data-integrated microservices including data collection and monitoring services, blockchain services, artificial intelligence services and smart contract services for marketing a loan to a set of prospective parties.

In embodiments a lending platform is provided herein having an Internet of Things data collection and monitoring system with artificial intelligence for classifying a condition about a bond and having a rating system with a set of data-integrated microservices including data collection and monitoring services, blockchain services, artificial intelligence services, and smart contract services for rating a set of loan-related entities.

In embodiments a lending platform is provided herein having an Internet of Things data collection and monitoring system with artificial intelligence for classifying a condition about a bond and having a compliance system with a set of data-integrated microservices including data collection and monitoring services, blockchain services, artificial intelligence services, and smart contract services for automatically facilitating compliance with at least one of a law, a regulation and a policy related to a lending transaction.

In embodiments a lending platform is provided herein having a system that varies the terms and conditions of a subsidized loan based on a parameter monitored by the IoT and having a system that varies the terms and conditions of a subsidized loan based on a parameter monitored in a social network.

In embodiments a lending platform is provided herein having a system that varies the terms and conditions of a subsidized loan based on a parameter monitored by the IoT and having a system that varies the terms and conditions of a subsidized loan based on a parameter monitored by crowdsourcing.

In embodiments a lending platform is provided herein having a system that varies the terms and conditions of a subsidized loan based on a parameter monitored by the IoT and having an automated blockchain custody service for managing a set of custodial assets.

In embodiments a lending platform is provided herein having a system that varies the terms and conditions of a subsidized loan based on a parameter monitored by the IoT and having an underwriting system for a loan with a set of data-integrated microservices including data collection and monitoring services, blockchain services, artificial intelligence services, and smart contract services for underwriting lending entities and transactions.

In embodiments a lending platform is provided herein having a system that varies the terms and conditions of a subsidized loan based on a parameter monitored by the IoT and having a loan marketing system with a set of data-integrated microservices including data collection and monitoring services, blockchain services, artificial intelligence services and smart contract services for marketing a loan to a set of prospective parties.

In embodiments a lending platform is provided herein having a system that varies the terms and conditions of a subsidized loan based on a parameter monitored by the IoT and having a rating system with a set of data-integrated microservices including data collection and monitoring services, blockchain services, artificial intelligence services, and smart contract services for rating a set of loan-related entities.

In embodiments a lending platform is provided herein having a system that varies the terms and conditions of a subsidized loan based on a parameter monitored by the IoT and having a compliance system with a set of data-integrated microservices including data collection and monitoring services, blockchain services, artificial intelligence services, and smart contract services for automatically facilitating compliance with at least one of a law, a regulation and a policy related to a lending transaction.

In embodiments a lending platform is provided herein having a system that varies the terms and conditions of a subsidized loan based on a parameter monitored in a social network and having a system that varies the terms and conditions of a subsidized loan based on a parameter monitored by crowdsourcing.

In embodiments a lending platform is provided herein having a system that varies the terms and conditions of a subsidized loan based on a parameter monitored in a social network and having an automated blockchain custody service for managing a set of custodial assets.

In embodiments a lending platform is provided herein having a system that varies the terms and conditions of a subsidized loan based on a parameter monitored in a social network and having an underwriting system for a loan with a set of data-integrated microservices including data collection and monitoring services, blockchain services, artificial intelligence services, and smart contract services for underwriting lending entities and transactions.

In embodiments a lending platform is provided herein having a system that varies the terms and conditions of a subsidized loan based on a parameter monitored in a social network and having a loan marketing system with a set of data-integrated microservices including data collection and monitoring services, blockchain services, artificial intelligence services and smart contract services for marketing a loan to a set of prospective parties.

In embodiments a lending platform is provided herein having a system that varies the terms and conditions of a subsidized loan based on a parameter monitored in a social network and having a rating system with a set of data-integrated microservices including data collection and monitoring services, blockchain services, artificial intelligence services, and smart contract services for rating a set of loan-related entities.

In embodiments a lending platform is provided herein having a system that varies the terms and conditions of a subsidized loan based on a parameter monitored in a social network and having a compliance system with a set of data-integrated microservices including data collection and monitoring services, blockchain services, artificial intelligence services, and smart contract services for automatically facilitating compliance with at least one of a law, a regulation and a policy related to a lending transaction.

In embodiments a lending platform is provided herein having a system that varies the terms and conditions of a subsidized loan based on a parameter monitored by crowdsourcing and having an automated blockchain custody service for managing a set of custodial assets.

In embodiments a lending platform is provided herein having a system that varies the terms and conditions of a subsidized loan based on a parameter monitored by crowdsourcing and having an underwriting system for a loan with a set of data-integrated microservices including data collection and monitoring services, blockchain services, artificial intelligence services, and smart contract services for underwriting lending entities and transactions.

In embodiments a lending platform is provided herein having a system that varies the terms and conditions of a subsidized loan based on a parameter monitored by crowdsourcing and having a loan marketing system with a set of data-integrated microservices including data collection and monitoring services, blockchain services, artificial intelligence services and smart contract services for marketing a loan to a set of prospective parties.

In embodiments a lending platform is provided herein having a system that varies the terms and conditions of a subsidized loan based on a parameter monitored by crowdsourcing and having a rating system with a set of data-integrated microservices including data collection and monitoring services, blockchain services, artificial intelligence services, and smart contract services for rating a set of loan-related entities.

In embodiments a lending platform is provided herein having a system that varies the terms and conditions of a subsidized loan based on a parameter monitored by crowdsourcing and having a compliance system with a set of data-integrated microservices including data collection and monitoring services, blockchain services, artificial intelligence services, and smart contract services for automatically facilitating compliance with at least one of a law, a regulation and a policy related to a lending transaction.

In embodiments a lending platform is provided herein having an automated blockchain custody service for managing a set of custodial assets and having an underwriting system for a loan with a set of data-integrated microservices including data collection and monitoring services, blockchain services, artificial intelligence services, and smart contract services for underwriting lending entities and transactions.

In embodiments a lending platform is provided herein having an automated blockchain custody service for managing a set of custodial assets and having a loan marketing system with a set of data-integrated microservices including data collection and monitoring services, blockchain services, artificial intelligence services and smart contract services for marketing a loan to a set of prospective parties.

In embodiments a lending platform is provided herein having an automated blockchain custody service for managing a set of custodial assets and having a rating system with a set of data-integrated microservices including data collection and monitoring services, blockchain services, artificial intelligence services, and smart contract services for rating a set of loan-related entities.

In embodiments a lending platform is provided herein having an automated blockchain custody service for managing a set of custodial assets and having a compliance system with a set of data-integrated microservices including data collection and monitoring services, blockchain services, artificial intelligence services, and smart contract services for automatically facilitating compliance with at least one of a law, a regulation and a policy related to a lending transaction.

In embodiments a lending platform is provided herein having an underwriting system for a loan with a set of data-integrated microservices including data collection and monitoring services, blockchain services, artificial intelligence services, and smart contract services for underwriting lending entities and transactions and having a loan marketing system with a set of data-integrated microservices including data collection and monitoring services, blockchain services, artificial intelligence services and smart contract services for marketing a loan to a set of prospective parties.

In embodiments a lending platform is provided herein having an underwriting system for a loan with a set of data-integrated microservices including data collection and monitoring services, blockchain services, artificial intelligence services, and smart contract services for underwriting lending entities and transactions and having a rating system with a set of data-integrated microservices including data collection and monitoring services, blockchain services, artificial intelligence services, and smart contract services for rating a set of loan-related entities.

In embodiments a lending platform is provided herein having an underwriting system for a loan with a set of data-integrated microservices including data collection and monitoring services, blockchain services, artificial intelligence services, and smart contract services for underwriting lending entities and transactions and having a compliance system with a set of data-integrated microservices including data collection and monitoring services, blockchain services, artificial intelligence services, and smart contract services for automatically facilitating compliance with at least one of a law, a regulation and a policy related to a lending transaction.

In embodiments a lending platform is provided herein having a loan marketing system with a set of data-integrated microservices including data collection and monitoring services, blockchain services, artificial intelligence services and smart contract services for marketing a loan to a set of prospective parties and having a rating system with a set of data-integrated microservices including data collection and monitoring services, blockchain services, artificial intelligence services, and smart contract services for rating a set of loan-related entities.

In embodiments a lending platform is provided herein having a loan marketing system with a set of data-integrated microservices including data collection and monitoring services, blockchain services, artificial intelligence services and smart contract services for marketing a loan to a set of prospective parties and having a compliance system with a set of data-integrated microservices including data collection and monitoring services, blockchain services, artificial intelligence services, and smart contract services for automatically facilitating compliance with at least one of a law, a regulation and a policy related to a lending transaction.

In embodiments a lending platform is provided herein having a rating system with a set of data-integrated microservices including data collection and monitoring services, blockchain services, artificial intelligence services, and smart contract services for rating a set of loan-related entities and having a compliance system with a set of data-integrated microservices including data collection and monitoring services, blockchain services, artificial intelligence services, and smart contract services for automatically facilitating compliance with at least one of a law, a regulation and a policy related to a lending transaction.

In embodiments, a database service may be provided herein that embodies, enables, or is associated with a blockchain, ledger, such as a distributed ledger, or the like, such as in connection with any of the embodiments described herein or in the document incorporated by reference that refer to them. In embodiments the database service may comprise a transparent, immutable, and cryptographically verifiable ledger database service, such as the Amazon™ QLDB™ database service. The database service may be included within one or connected with or more of the layers or microservices of a lending enablement platform 100, such as the adaptive intelligent systems 158 layer or the data storage layer 168. The service may be used, for example, in connection with a centralized ledger that records all changes or transactions and maintains an immutable record of these changes, such as by tracing an entity through various environments or processes, tracking the history of debits and credits in a series of transactions, or validating facts relevant to an underwriting process, a claim, or a legal or regulatory proceeding. A ledger may be owned by a single trusted entity or set of trusted entities and may be shared with any other entities, such as ones that working together in a coordinated process, such as a transaction, a production process, a joint service, or many others. As compared to a relational database, the database service may provide immutable, cryptographically verifiable ledger entries, without the need for custom audit tables or trails. As compared to a blockchain framework, such a database service may include capabilities to perform queries, create tables, index data, and the like. The database service may optionally omit requirements for many blockchain frameworks that slow performance, such as requirement of consensus before committing transactions, or the database service may employ optional consensus features. In embodiments, the database service may comprise transparent, immutable, and cryptographically verifiable ledger that users can use to build applications that act as a system of record, where multiple parties are transacting within a centralized, trusted entity or set of entities. The database service may complement or substitute for the building audit functionality into a relational database or for using conventional distributed ledger capabilities in a blockchain framework. The database service may use an immutable transactional log or journal, which may track each application data change and maintain a comprehensive and verifiable history of changes. In embodiments, transactions may be configured to comply with requirements of atomicity, consistency, isolation, and durability (ACID) to be logged in the log or journal, which is configured to prevent deletions or modifications. Changes may be cryptographically chained, such that they are auditable and verifiable, such as in a history that users can query or analyze, such as using conventional query types, such as SQL queries. In embodiments, the database service may be provided in a serverless form, such that there is no need to provision specific server capacity or to configure read/write limits. To initiate the database service, the user can create a ledger, define tables, and the like, and the database service will automatically scale to support application demands. In contrast to blockchain-based ledgers, a database service may omit requirements for a distributed consensus, so it can execute more transactions in the same time.

In embodiments of the present disclosure that refer to a blockchain or distributed ledger, a managed blockchain service may be used, such as the Amazon™ Managed Blockchain™, which may comprise a facility for convenient creation and management of a scaled blockchain network. The managed blockchain service may be provided as part of a layered data services architecture as described in this disclosure. In situations where users want immutable and verifiable capability provided by a blockchain or ledger, they may also seek the ability to allow multiple parties to transact, execute contracts (such as in smart contract embodiments described herein), share data, and the like without a trusted central authority. As setting up conventional blockchain frameworks requires significant time and technical expertise, where each participant in a permissioned network has to provision hardware, install software, create, and manage certificates for access control, and configure network settings. As a given blockchain application grows, there is also activity required to scale the network, monitor resources across blockchain nodes, add or remove hardware and manage network availability. In embodiments, a managed blockchain service may provide for management of each of these requirements and enabling capabilities. This may include supporting open source blockchain frameworks and enabling selection, setup and deployment of a selected framework in a dashboard, console, or other user interface, wherein users may choose their preferred framework, add network members, and configure member nodes that will process transaction requests. The managed blockchain service may then automatically create a blockchain network, such as one that can span multiple accounts with multiple nodes per member, and configure software, security, and network settings. The managed blockchain service may secure and manage network certificates, such as with a key management service, which may allow customer management of the keys. In embodiments, the managed blockchain service may include one or more APIs, such as a voting API, such as one that allows network members to vote, such as to vote to add or remove members. As application usage grows for a given application (such as any of the noted applications described in connection with the lending enablement platform 100), users can add more capacity to the blockchain network, such as with a simple API call. In embodiments, the managed blockchain service may be provided with a range of combinations of compute and memory capacity, such as to give users the ability to choose the right mix of resources for a given blockchain-based application.

Referring to FIGS. 4-31, in embodiments of the present disclosure, including ones involving artificial intelligence 156, adaptive intelligent systems 158, robotic process automation 154, expert systems, self-organization, machine learning, training of models, and the like, may benefit from the use of a neural net, such as a neural net trained for pattern recognition, for prediction, for optimization based on a set of desired outcomes, for classification or recognition of one or more parameters, features characteristics, or phenomena, for support of autonomous control, and other purposes. References to artificial intelligence, expert systems, models, adaptive intelligence, and/or neural networks throughout this disclosure should be understood to optionally encompass use of a wide range of different types of neural networks, machine learning systems, artificial intelligence systems, and the like as particular embodiments permit, such as feed forward neural networks, radial basis function neural networks, self-organizing neural networks (e.g., Kohonen self-organizing neural networks), recurrent neural networks, modular neural networks, artificial neural networks, physical neural networks, multi-layered neural networks, convolutional neural networks, hybrids of neural networks with other expert systems (e.g., hybrid fuzzy logic—neural network systems), Autoencoder neural networks, probabilistic neural networks, time delay neural networks, convolutional neural networks, regulatory feedback neural networks, radial basis function neural networks, recurrent neural networks, Hopfield neural networks, Boltzmann machine neural networks, self-organizing map (SOM) neural networks, learning vector quantization (LVQ) neural networks, fully recurrent neural networks, simple recurrent neural networks, echo state neural networks, long short-term memory neural networks, bi-directional neural networks, hierarchical neural networks, stochastic neural networks, genetic scale RNN neural networks, committee of machines neural networks, associative neural networks, physical neural networks, instantaneously trained neural networks, spiking neural networks, neocognitron neural networks, dynamic neural networks, cascading neural networks, neuro-fuzzy neural networks, compositional pattern-producing neural networks, memory neural networks, hierarchical temporal memory neural networks, deep feed forward neural networks, gated recurrent unit (GCU) neural networks, auto encoder neural networks, variational auto encoder neural networks, de-noising auto encoder neural networks, sparse auto-encoder neural networks, Markov chain neural networks, restricted Boltzmann machine neural networks, deep belief neural networks, deep convolutional neural networks, de-convolutional neural networks, deep convolutional inverse graphics neural networks, generative adversarial neural networks, liquid state machine neural networks, extreme learning machine neural networks, echo state neural networks, deep residual neural networks, support vector machine neural networks, neural Turing machine neural networks, and/or holographic associative memory neural networks, or hybrids or combinations of the foregoing, or combinations with other expert systems, such as rule-based systems, model-based systems (including ones based on physical models, statistical models, flow-based models, biological models, biomimetic models, and the like).

The foregoing neural networks may have a variety of nodes or neurons, which may perform a variety of functions on inputs, such as inputs received from sensors or other data sources, including other nodes. Functions may involve weights, features, feature vectors, and the like. Neurons may include perceptrons, neurons that mimic biological functions (such as of the human senses of touch, vision, taste, hearing, and smell), and the like. Continuous neurons, such as with sigmoidal activation, may be used in the context of various forms of neural net, such as where back propagation is involved.

In many embodiments, an expert system or neural network may be trained, such as by a human operator or supervisor, or based on a data set, model, or the like. Training may include presenting the neural network with one or more training data sets that represent values, such as sensor data, event data, parameter data, and other types of data (including the many types described throughout this disclosure), as well as one or more indicators of an outcome, such as an outcome of a process, an outcome of a calculation, an outcome of an event, an outcome of an activity, or the like. Training may include training in optimization, such as training a neural network to optimize one or more systems based on one or more optimization approaches, such as Bayesian approaches, parametric Bayes classifier approaches, k-nearest-neighbor classifier approaches, iterative approaches, interpolation approaches, Pareto optimization approaches, algorithmic approaches, and the like. Feedback may be provided in a process of variation and selection, such as with a genetic algorithm that evolves one or more solutions based on feedback through a series of rounds.

In embodiments, a plurality of neural networks may be deployed in a cloud platform that receives data streams and other inputs collected (such as by mobile data collectors) in one or more transactional environments and transmitted to the cloud platform over one or more networks, including using network coding to provide efficient transmission. In the cloud platform, optionally using massively parallel computational capability, a plurality of different neural networks of various types (including modular forms, structure-adaptive forms, hybrids, and the like) may be used to undertake prediction, classification, control functions, and provide other outputs as described in connection with expert systems disclosed throughout this disclosure. The different neural networks may be structured to compete with each other (optionally including use evolutionary algorithms, genetic algorithms, or the like), such that an appropriate type of neural network, with appropriate input sets, weights, node types and functions, and the like, may be selected, such as by an expert system, for a specific task involved in a given context, workflow, environment process, system, or the like.

In embodiments, methods and systems described herein that involve an expert system or self-organization capability may use a feed forward neural network, which moves information in one direction, such as from a data input, like a data source related to at least one resource or parameter related to a transactional environment, such as any of the data sources mentioned throughout this disclosure, through a series of neurons or nodes, to an output. Data may move from the input nodes to the output nodes, optionally passing through one or more hidden nodes, without loops. In embodiments, feed forward neural networks may be constructed with various types of units, such as binary McCulloch-Pitts neurons, the simplest of which is a perceptron.

In embodiments, methods and systems described herein that involve an expert system or self-organization capability may use a capsule neural network, such as for prediction, classification, or control functions with respect to a transactional environment, such as relating to one or more of the machines and automated systems described throughout this disclosure.

In embodiments, methods and systems described herein that involve an expert system or self-organization capability may use a radial basis function (RBF) neural network, which may be preferred in some situations involving interpolation in a multi-dimensional space (such as where interpolation is helpful in optimizing a multi-dimensional function, such as for optimizing a data marketplace as described here, optimizing the efficiency or output of a power generation system, a factory system, or the like, or other situation involving multiple dimensions. In embodiments, each neuron in the RBF neural network stores an example from a training set as a "prototype." Linearity involved in the functioning of this neural network offers RBF the advantage of not typically suffering from problems with local minima or maxima.

In embodiments, methods and systems described herein that involve an expert system or self-organization capability may use a radial basis function (RBF) neural network, such as one that employs a distance criterion with respect to a center (e.g., a Gaussian function). A radial basis function may be applied as a replacement for a hidden layer, such as a sigmoidal hidden layer transfer, in a multi-layer perceptron. An RBF network may have two layers, such as where an input is mapped onto each RBF in a hidden layer. In embodiments, an output layer may comprise a linear combination of hidden layer values representing, for example, a mean predicted output. The output layer value may provide an output that is the same as or similar to that of a regression model in statistics. In classification problems, the output layer may be a sigmoid function of a linear combination of hidden layer values, representing a posterior probability. Performance in both cases is often improved by shrinkage techniques, such as ridge regression in classical statistics. This corresponds to a prior belief in small parameter values (and therefore smooth output functions) in a Bayesian framework. RBF networks may avoid local minima, because the only parameters that are adjusted in the learning process are the linear mapping from hidden layer to output layer. Linearity ensures that the error surface is quadratic and therefore has a single minimum. In regression problems, this can be found in one matrix operation. In classification problems, the fixed non-linearity introduced by the sigmoid output function may be handled using an iteratively re-weighted least squares function or the like.

RBF networks may use kernel methods such as support vector machines (SVM) and Gaussian processes (where the RBF is the kernel function). A non-linear kernel function may be used to project the input data into a space where the learning problem can be solved using a linear model.

In embodiments, an RBF neural network may include an input layer, a hidden layer and a summation layer. In the input layer, one neuron appears in the input layer for each predictor variable. In the case of categorical variables, N−1 neurons are used, where N is the number of categories. The input neurons may, in embodiments, standardize the value ranges by subtracting the median and dividing by the interquartile range. The input neurons may then feed the values to each of the neurons in the hidden layer. In the hidden layer, a variable number of neurons may be used (determined by the training process). Each neuron may consist of a radial basis function that is centered on a point with as many dimensions as a number of predictor variables. The spread (e.g., radius) of the RBF function may be different for each dimension. The centers and spreads may be determined by training. When presented with a vector of input values from the input layer, a hidden neuron may compute a Euclidean distance of the test case from the neuron's center point and then apply the RBF kernel function to this distance, such as using the spread values. The resulting value may then be passed to the summation layer. In the summation layer, the value coming out of a neuron in the hidden layer may be multiplied by a weight associated with the neuron and may add to the weighted values of other neurons. This sum becomes the output. For classification problems, one output is produced (with a separate set of weights and summation units) for each target category. The value output for a category is the probability that the case being evaluated has that category. In training of an RBF, various parameters may be determined, such as the number of neurons in a hidden layer, the coordinates of the center of each hidden-layer function, the spread of each function in each dimension, and the weights applied to outputs as they pass to the summation layer. Training may be used by clustering algorithms (such as k-means clustering), by evolutionary approaches, and the like.

In embodiments, a recurrent neural network may have a time-varying, real-valued (more than just zero or one) activation (output). Each connection may have a modifiable real-valued weight. Some of the nodes are called labeled nodes, some output nodes, and others hidden nodes. For supervised learning in discrete time settings, training sequences of real-valued input vectors may become sequences of activations of the input nodes, one input vector at a time. At each time step, each non-input unit may compute its current activation as a nonlinear function of the weighted sum of the activations of all units from which it receives connections. The system can explicitly activate (independent of incoming signals) some output units at certain time steps.

In embodiments, methods and systems described herein that involve an expert system or self-organization capability may use a self-organizing neural network, such as a Kohonen self-organizing neural network, such as for visualization of views of data, such as low-dimensional views of high-dimensional data. The self-organizing neural network may apply competitive learning to a set of input data, such as from one or more sensors or other data inputs from or associated with a transactional environment, including any machine or component that relates to the transactional environment. In embodiments, the self-organizing neural network may be used to identify structures in data, such as unlabeled data, such as in data sensed from a range of data sources about or sensors in or about in a transactional environment, where sources of the data are unknown (such as where events may be coming from any of a range of unknown sources). The self-organizing neural network may organize structures or patterns in the data, such that they can be recognized, analyzed, and labeled, such as identifying market behavior structures as corresponding to other events and signals.

In embodiments, methods and systems described herein that involve an expert system or self-organization capability may use a recurrent neural network, which may allow for a bi-directional flow of data, such as where connected units (e.g., neurons or nodes) form a directed cycle. Such a network may be used to model or exhibit dynamic temporal behavior, such as involved in dynamic systems, such as a wide variety of the automation systems, machines and devices described throughout this disclosure, such as an automated agent interacting with a marketplace for purposes of collecting data, testing spot market transactions, execution transactions, and the like, where dynamic system behavior involves complex interactions that a user may desire to understand, predict, control and/or optimize. For example, the recurrent neural network may be used to anticipate the state of a market, such as one involving a dynamic process or action, such as a change in state of a resource that is traded in or that enables a marketplace of transactional environment. In embodiments, the recurrent neural network may use internal memory to process a sequence of inputs, such as from other nodes and/or from sensors and other data inputs from or about the transactional environment, of the various types described herein. In embodiments, the recurrent neural network may also be used for pattern recognition, such as for recognizing a machine, component, agent, or other item based on a behavioral signature, a profile, a set of feature vectors (such as in an audio file or image), or the like. In a non-limiting example, a recurrent neural network may recognize a shift in an operational mode of a marketplace or machine by learning to classify the shift from a training data set consisting of a stream of data from one or more data sources of sensors applied to or about one or more resources.

In embodiments, methods and systems described herein that involve an expert system or self-organization capability may use a modular neural network, which may comprise a series of independent neural networks (such as ones of various types described herein) that are moderated by an intermediary. Each of the independent neural networks in the modular neural network may work with separate inputs, accomplishing subtasks that make up the task the modular network as whole is intended to perform. For example, a modular neural network may comprise a recurrent neural network for pattern recognition, such as to recognize what type of machine or system is being sensed by one or more sensors that are provided as input channels to the modular network and an RBF neural network for optimizing the behavior of the machine or system once understood. The intermediary may accept inputs of each of the individual neural networks, process them, and create output for the modular neural network, such an appropriate control parameter, a prediction of state, or the like.

Combinations among any of the pairs, triplets, or larger combinations, of the various neural network types described herein, are encompassed by the present disclosure. This may include combinations where an expert system uses one neural network for recognizing a pattern (e.g., a pattern indicating a problem or fault condition) and a different neural network for self-organizing an activity or workflow based on the recognized pattern (such as providing an output governing autonomous control of a system in response to the recognized condition or pattern). This may also include combinations where an expert system uses one neural network for classifying an item (e.g., identifying a machine, a component, or an operational mode) and a different neural network for predicting a state of the item (e.g., a fault state, an operational state, an anticipated state, a maintenance state, or the like). Modular neural networks may also include situations where an expert system uses one neural network for determining a state or context (such as a state of a machine, a process, a work-flow, a marketplace, a storage system, a network, a data collector, or the like) and a different neural network for self-organizing a process involving the state or context (e.g., a data storage process, a network coding process, a network selection process, a data marketplace process, a power generation process, a manufacturing process, a refining process, a digging process, a boring process, or other process described herein).

In embodiments, methods and systems described herein that involve an expert system or self-organization capability may use a physical neural network where one or more hardware elements is used to perform or simulate neural behavior. In embodiments, one or more hardware neurons may be configured to stream voltage values, current values, or the like that represent sensor data, such as to calculate information from analog sensor inputs representing energy consumption, energy production, or the like, such as by one or more machines providing energy or consuming energy for one or more transactions. One or more hardware nodes may be configured to stream output data resulting from the activity of the neural net. Hardware nodes, which may comprise one or more chips, microprocessors, integrated circuits, programmable logic controllers, application-specific integrated circuits, field-programmable gate arrays, or the like, may be provided to optimize the machine that is producing or consuming energy, or to optimize another parameter of some part of a neural net of any of the types described herein. Hardware nodes may include hardware for acceleration of calculations (such as dedicated processors for performing basic or more sophisticated calculations on input data to provide outputs, dedicated processors for filtering or compressing data, dedicated processors for de-compressing data, dedicated processors for compression of specific file or data types (e.g., for handling image data, video streams, acoustic signals, thermal images, heat maps, or the like), and the like. A physical neural network may be embodied in a data collector, including one that may be reconfigured by switching or routing inputs in varying configurations, such as to provide different neural net configurations within the data collector for handling different types of inputs (with the switching and configuration optionally under control of an expert system, which may include a software-based neural net located on the data collector or remotely). A physical, or at least partially physical, neural network may include physical hardware nodes located in a storage system, such as for storing data within a machine, a data storage system, a distributed ledger, a mobile device, a server, a cloud resource, or in a transactional environment, such as for accelerating input/output functions to one or more storage elements that supply data to or take data from the neural net. A physical, or at least partially physical, neural network may include physical hardware nodes located in a network, such as for transmitting data within, to or from an industrial environment, such as for accelerating input/output functions to one or more network nodes in the net, accelerating relay functions, or the like. In embodiments of a physical neural network, an electrically adjustable resistance material may be used for emulating the function of a neural synapse. In embodiments, the physical hardware emulates the neurons, and software emulates the neural network between the neurons. In embodiments, neural networks complement conventional algorithmic computers. They are versatile and can be trained to perform appropriate functions without the need for any instructions, such as classification functions, optimization functions, pattern recognition functions, control functions, selection functions, evolution functions, and others.

In embodiments, methods and systems described herein that involve an expert system or self-organization capability may use a multilayered feed forward neural network, such as for complex pattern classification of one or more items, phenomena, modes, states, or the like. In embodiments, a multilayered feed forward neural network may be trained by an optimization technical, such as a genetic algorithm, such as to explore a large and complex space of options to find an optimum, or near-optimum, global solution. For example, one or more genetic algorithms may be used to train a multilayered feed forward neural network to classify complex phenomena, such as to recognize complex operational modes of machines, such as modes involving complex interactions among machines (including interference effects, resonance effects, and the like), modes involving non-linear phenomena, modes involving critical faults, such as where multiple, simultaneous faults occur, making root cause analysis difficult, and others. In embodiments, a multilayered feed forward neural network may be used to classify results from monitoring of a marketplace, such as monitoring systems, such as automated agents, that operate within the marketplace, as well as monitoring resources that enable the marketplace, such as computing, networking, energy, data storage, energy storage, and other resources.

In embodiments, methods and systems described herein that involve an expert system or self-organization capability may use a feed-forward, back-propagation multi-layer perceptron (MLP) neural network, such as for handling one or more remote sensing applications, such as for taking inputs from sensors distributed throughout various transactional environments. In embodiments, the MLP neural network may be used for classification of transactional environments and resource environments, such as lending markets, spot markets, forward markets, energy markets, renewable energy credit (REC) markets, networking markets, advertising markets, spectrum markets, ticketing markets, rewards markets, compute markets, and others mentioned throughout this disclosure, as well as physical resources and environments that produce them, such as energy resources (including renewable energy environments, mining environments, exploration environments, drilling environments, and the like, including classification of geological structures (including underground features and above ground features), classification of materials (including fluids, minerals, metals, and the like), and other problems. This may include fuzzy classification.

In embodiments, methods and systems described herein that involve an expert system or self-organization capability may use a structure-adaptive neural network, where the structure of a neural network is adapted, such as based on a rule, a sensed condition, a contextual parameter, or the like. For example, if a neural network does not converge on a solution, such as classifying an item or arriving at a prediction, when acting on a set of inputs after some amount of training, the neural network may be modified, such as from a feed forward neural network to a recurrent neural network, such as by switching data paths between some subset of nodes from unidirectional to bi-directional data paths. The structure adaptation may occur under control of an expert system, such as to trigger adaptation upon occurrence of a trigger, rule or event, such as recognizing occurrence of a threshold (such as an absence of a convergence to a solution within a given amount of time) or recognizing a phenomenon as requiring different or additional structure (such as recognizing that a system is varying dynamically or in a non-linear fashion). In one non-limiting example, an expert system may switch from a simple neural network structure like a feed forward neural network to a more complex neural network structure like a recurrent neural network, a convolutional neural network, or the like upon receiving an indication that a continuously variable transmission is being used to drive a generator, turbine, or the like in a system being analyzed.

In embodiments, methods and systems described herein that involve an expert system or self-organization capability may use an autoencoder, autoassociator or Diabolo neural network, which may be similar to a multilayer perceptron (MLP) neural network, such as where there may be an input layer, an output layer and one or more hidden layers connecting them. However, the output layer in the auto-encoder may have the same number of units as the input layer, where the purpose of the MLP neural network is to reconstruct its own inputs (rather than just emitting a target value). Therefore, the auto encoders may operate as an unsupervised learning model. An auto encoder may be used, for example, for unsupervised learning of efficient codings, such as for dimensionality reduction, for learning generative models of data, and the like. In embodiments, an auto-encoding neural network may be used to self-learn an efficient network coding for transmission of analog sensor data from a machine over one or more networks or of digital data from one or more data sources. In embodiments, an auto-encoding neural network may be used to self-learn an efficient storage approach for storage of streams of data.

al environment. In embodiments, methods and systems described herein that involve an expert system or self-organization capability may use a probabilistic neural network (PNN), which in embodiments may comprise a multi-layer (e.g., four-layer) feed forward neural network, where layers may include input layers, hidden layers, pattern/summation layers and an output layer. In an embodiment of a PNN algorithm, a parent probability distribution function (PDF) of each class may be approximated, such as by a Parzen window and/or a non-parametric function. Then, using the PDF of each class, the class probability of a new input is estimated, and Bayes' rule may be employed, such as to allocate it to the class with the highest posterior probability. A PNN may embody a Bayesian network and may use a statistical algorithm or analytic technique, such as Kernel Fisher discriminant analysis technique. The PNN may be used for classification and pattern recognition in any of a wide range of embodiments disclosed herein. In one non-limiting example, a probabilistic neural network may be used to predict a fault condition of an engine based on collection of data inputs from sensors and instruments for the engine.

In embodiments, methods and systems described herein that involve an expert system or self-organization capability may use a time delay neural network (TDNN), which may comprise a feed forward architecture for sequential data that recognizes features independent of sequence position. In embodiments, to account for time shifts in data, delays are added to one or more inputs, or between one or more nodes, so that multiple data points (from distinct points in time) are analyzed together. A time delay neural network may form part of a larger pattern recognition system, such as using a perceptron network. In embodiments, a TDNN may be trained with supervised learning, such as where connection weights are trained with back propagation or under feedback. In embodiments, a TDNN may be used to process sensor data from distinct streams, such as a stream of velocity data, a stream of acceleration data, a stream of temperature data, a stream of pressure data, and the like, where time delays are used to align the data streams in time, such as to help understand patterns that involve understanding of the various streams (e.g., changes in price patterns in spot or forward markets).

In embodiments, methods and systems described herein that involve an expert system or self-organization capability may use a convolutional neural network (referred to in some cases as a CNN, a ConvNet, a shift invariant neural network, or a space invariant neural network), wherein the units are connected in a pattern similar to the visual cortex of the human brain. Neurons may respond to stimuli in a restricted region of space, referred to as a receptive field. Receptive fields may partially overlap, such that they collectively cover the entire (e.g., visual) field. Node responses can be calculated mathematically, such as by a convolution operation, such as using multilayer perceptrons that use minimal preprocessing. A convolutional neural network may be used for recognition within images and video streams, such as for recognizing a type of machine in a large environment using a camera system disposed on a mobile data collector, such as on a drone or mobile robot. In embodiments, a convolutional neural network may be used to provide a recommendation based on data inputs, including sensor inputs and other contextual information, such as recommending a route for a mobile data collector. In embodiments, a convolutional neural network may be used for processing inputs, such as for natural language processing of instructions provided by one or more parties involved in a workflow in an environment. In embodiments, a convolutional neural network may be deployed with a large number of neurons (e.g., 100,000, 500,000 or more), with multiple (e.g., 4, 5, 6 or more) layers, and with many (e.g., millions) of parameters. A convolutional neural net may use one or more convolutional nets.

In embodiments, methods and systems described herein that involve an expert system or self-organization capability may use a regulatory feedback network, such as for recognizing emergent phenomena (such as new types of behavior not previously understood in a transactional environment).

In embodiments, methods and systems described herein that involve an expert system or self-organization capability may use a self-organizing map (SOM), involving unsupervised learning. A set of neurons may learn to map points in an input space to coordinates in an output space. The input space can have different dimensions and topology from the output space, and the SOM may preserve these while mapping phenomena into groups.

In embodiments, methods and systems described herein that involve an expert system or self-organization capability may use a learning vector quantization neural net (LVQ). Prototypical representatives of the classes may parameterize, together with an appropriate distance measure, in a distance-based classification scheme.

In embodiments, methods and systems described herein that involve an expert system or self-organization capability may use an echo state network (ESN), which may comprise a recurrent neural network with a sparsely connected, random hidden layer. The weights of output neurons may be changed (e.g., the weights may be trained based on feedback). In embodiments, an ESN may be used to handle time series patterns, such as, in an example, recognizing a pattern of events associated with a market, such as pattern of price changes in response to stimuli.

In embodiments, methods and systems described herein that involve an expert system or self-organization capability may use a Bi-directional, recurrent neural network (BRNN), such as using a finite sequence of values (e.g., voltage values from a sensor) to predict or label each element of the sequence based on both the past and the future context of the element. This may be done by adding the outputs of two RNNs, such as one processing the sequence from left to right, the other one from right to left. The combined outputs are the predictions of target signals, such as ones provided by a teacher or supervisor. A bi-directional RNN may be combined with a long short-term memory RNN.

In embodiments, methods and systems described herein that involve an expert system or self-organization capability may use a hierarchical RNN that connects elements in various ways to decompose hierarchical behavior, such as into useful subprograms. In embodiments, a hierarchical RNN may be used to manage one or more hierarchical templates for data collection in a transactional environment.

In embodiments, methods and systems described herein that involve an expert system or self-organization capability may use a stochastic neural network, which may introduce random variations into the network. Such random variations can be viewed as a form of statistical sampling, such as Monte Carlo sampling.

In embodiments, methods and systems described herein that involve an expert system or self-organization capability may use a genetic scale recurrent neural network. In such embodiments, a RNN (often a LSTM) is used where a series is decomposed into a number of scales where every scale informs the primary length between two consecutive points. A first order scale consists of a normal RNN, a second order consists of all points separated by two indices and so on. The Nth order RNN connects the first and last node. The outputs from all the various scales may be treated as a committee of members, and the associated scores may be used genetically for the next iteration.

In embodiments, methods and systems described herein that involve an expert system or self-organization capability may use a committee of machines (CoM), comprising a collection of different neural networks that together "vote" on a given example. Because neural networks may suffer from local minima, starting with the same architecture and training, but using randomly different initial weights often gives different results. A CoM tends to stabilize the result.

In embodiments, methods and systems described herein that involve an expert system or self-organization capability may use an associative neural network (ASNN), such as involving an extension of committee of machines that combines multiple feed forward neural networks and a k-nearest neighbor technique. It may use the correlation between ensemble responses as a measure of distance amid the analyzed cases for the kNN. This corrects the bias of the neural network ensemble. An associative neural network may have a memory that can coincide with a training set. If new data become available, the network instantly improves its predictive ability and provides data approximation (self-learns) without retraining. Another important feature of ASNN is the possibility to interpret neural network results by analysis of correlations between data cases in the space of models.

In embodiments, methods and systems described herein that involve an expert system or self-organization capability may use an instantaneously trained neural network (ITNN), where the weights of the hidden and the output layers are mapped directly from training vector data.

In embodiments, methods and systems described herein that involve an expert system or self-organization capability may use a spiking neural network, which may explicitly consider the timing of inputs. The network input and output may be represented as a series of spikes (such as a delta function or more complex shapes). SNNs can process information in the time domain (e.g., signals that vary over time, such as signals involving dynamic behavior of markets or transactional environments). They are often implemented as recurrent networks.

In embodiments, methods and systems described herein that involve an expert system or self-organization capability may use a dynamic neural network that addresses nonlinear multivariate behavior and includes learning of time-dependent behavior, such as transient phenomena and delay effects. Transients may include behavior of shifting market variables, such as prices, available quantities, available counterparties, and the like.

In embodiments, cascade correlation may be used as an architecture and supervised learning algorithm, supplementing adjustment of the weights in a network of fixed topology. Cascade-correlation may begin with a minimal network, then automatically trains and add new hidden units one by one, creating a multi-layer structure. Once a new hidden unit has been added to the network, its input-side weights may be frozen. This unit then becomes a permanent feature-detector in the network, available for producing outputs or for creating other, more complex feature detectors. The cascade-correlation architecture may learn quickly, determine its own size and topology, and retain the structures it has built even if the training set changes and requires no back-propagation.

In embodiments, methods and systems described herein that involve an expert system or self-organization capability may use a neuro-fuzzy network, such as involving a fuzzy inference system in the body of an artificial neural network. Depending on the type, several layers may simulate the processes involved in a fuzzy inference, such as fuzzification, inference, aggregation and defuzzification. Embedding a fuzzy system in a general structure of a neural net as the benefit of using available training methods to find the parameters of a fuzzy system.

In embodiments, methods and systems described herein that involve an expert system or self-organization capability may use a compositional pattern-producing network (CPPN), such as a variation of an associative neural network (ANN) that differs the set of activation functions and how they are applied. While typical ANNs often contain only sigmoid functions (and sometimes Gaussian functions), CPPNs can include both types of functions and many others. Furthermore, CPPNs may be applied across the entire space of possible inputs, so that they can represent a complete image. Since they are compositions of functions, CPPNs in effect encode images at infinite resolution and can be sampled for a particular display at whatever resolution is optimal.

This type of network can add new patterns without re-training. In embodiments, methods and systems described herein that involve an expert system or self-organization capability may use a one-shot associative memory network, such as by creating a specific memory structure, which assigns each new pattern to an orthogonal plane using adjacently connected hierarchical arrays.

In embodiments, methods and systems described herein that involve an expert system or self-organization capability may use a hierarchical temporal memory (HTM) neural network, such as involving the structural and algorithmic properties of the neocortex. HTM may use a biomimetic model based on memory-prediction theory. HTM may be used to discover and infer the high-level causes of observed input patterns and sequences.

In embodiments, methods and systems described herein that involve an expert system or self-organization capability may use a holographic associative memory (HAM) neural network, which may comprise an analog, correlation-based, associative, stimulus-response system. Information may be mapped onto the phase orientation of complex numbers. The memory is effective for associative memory tasks, generalization and pattern recognition with changeable attention.

In embodiments, various embodiments involving network coding may be used to code transmission data among network nodes in neural net, such as where nodes are located in one or more data collectors or machines in a transactional environment.

Referring to FIG. 22 through FIG. 49, embodiments of the present disclosure, including ones involving expert systems, self-organization, machine learning, artificial intelligence, and the like, may benefit from the use of a neural net, such as a neural net trained for pattern recognition, for classification of one or more parameters, characteristics, or phenomena, for support of autonomous control, and other purposes. References to a neural net throughout this disclosure should be understood to encompass a wide range of different types of neural networks, machine learning systems, artificial intelligence systems, and the like, such as feed forward neural networks, radial basis function neural networks, self-organizing neural networks (e.g., Kohonen self-organizing neural networks), recurrent neural networks, modular neural networks, artificial neural networks, physical neural networks, multi-layered neural networks, convolutional neural networks, hybrids of neural networks with other expert systems (e.g., hybrid fuzzy logic—neural network systems), Autoencoder neural networks, probabilistic neural networks, time delay neural networks, convolutional neural networks, regulatory feedback neural networks, radial basis function neural networks, recurrent neural networks, Hopfield neural networks, Boltzmann machine neural networks, self-organizing map (SOM) neural networks, learning vector quantization (LVQ) neural networks, fully recurrent neural networks, simple recurrent neural networks, echo state neural networks, long short-term memory neural networks, bi-directional neural networks, hierarchical neural networks, stochastic neural networks, genetic scale RNN neural networks, committee of machines neural networks, associative neural networks, physical neural networks, instantaneously trained neural networks, spiking neural networks, neocognitron neural networks, dynamic neural networks, cascading neural networks, neuro-fuzzy neural networks, compositional pattern-producing neural networks, memory neural networks, hierarchical temporal memory neural networks, deep feed forward neural networks, gated recurrent unit (GCU) neural networks, auto encoder neural networks, variational auto encoder neural networks, denoising auto encoder neural networks, sparse auto-encoder neural networks, Markov chain neural networks, restricted Boltzmann machine neural networks, deep belief neural networks, deep convolutional neural networks, de-convolutional neural networks, deep convolutional inverse graphics neural networks, generative adversarial neural networks, liquid state machine neural networks, extreme learning machine neural networks, echo state neural networks, deep residual neural networks, support vector machine neural networks, neural Turing machine neural networks, and/or holographic associative memory neural networks, or hybrids or combinations of the foregoing, or combinations with other expert systems, such as rule-based systems, model-based systems (including ones based on physical models, statistical models, flow-based models, biological models, biomimetic models, and the like).

Figure 22:
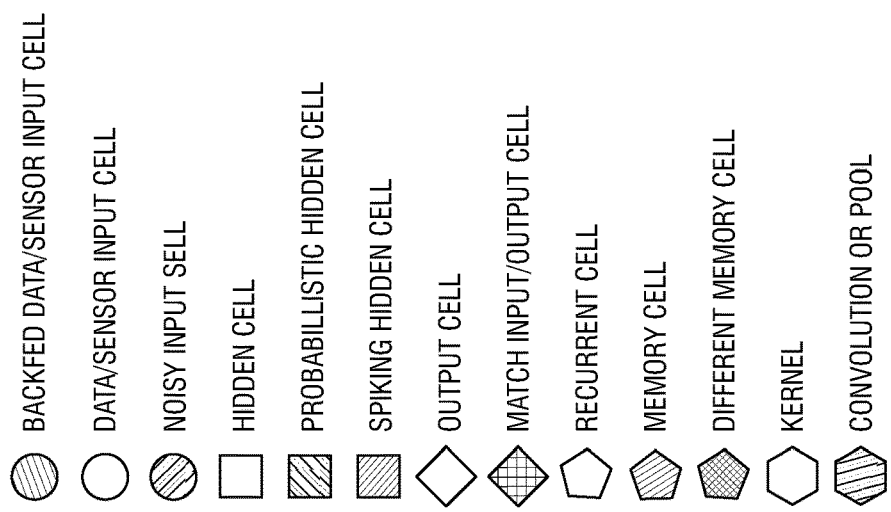
Figure 27:
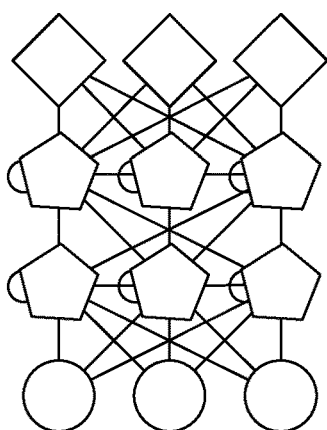
Figure 28:
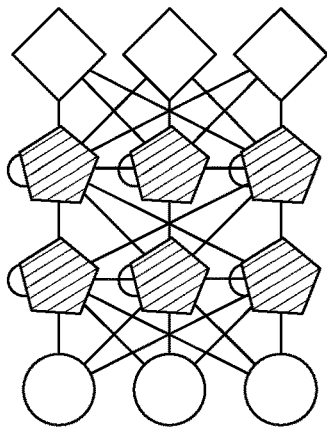

In embodiments, FIGS. 23 through 49 depict exemplary neural networks and FIG. 22 depicts a legend showing the various components of the neural networks depicted throughout FIGS. 23 to 49. FIG. 22 depicts various neural net components depicted in cells that are assigned functions and requirements. In embodiments, the various neural net examples may include (from top to bottom in the example of FIG. 22): back fed data/sensor input cells, data/sensor input cells, noisy input cells, and hidden cells. The neural net components also include probabilistic hidden cells, spiking hidden cells, output cells, match input/output cells, recurrent cells, memory cells, different memory cells, kernels, and convolution or pool cells.

Figure 23:
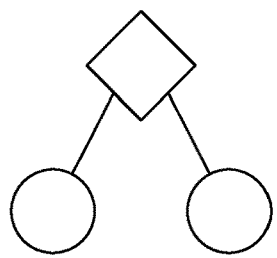
Figure 25:
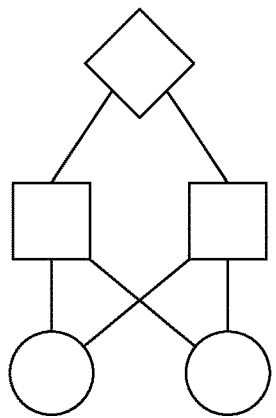
Figure 29:
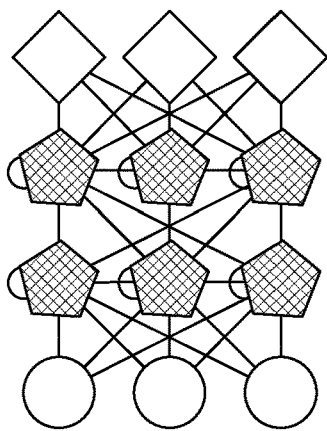
Figure 30:
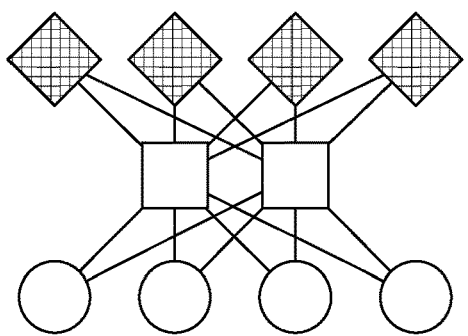
Figure 31:
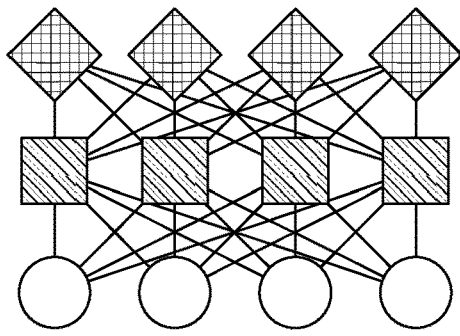
Figure 32:
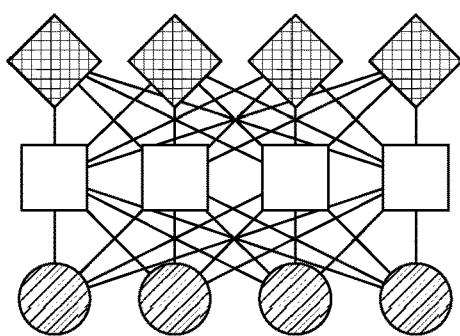
Figure 33:
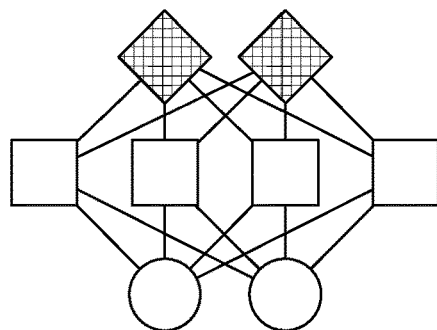
Figure 36:
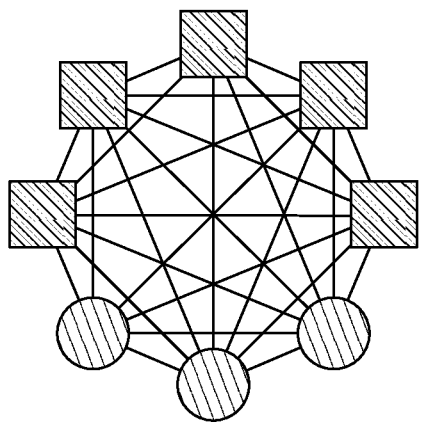
Figure 35:
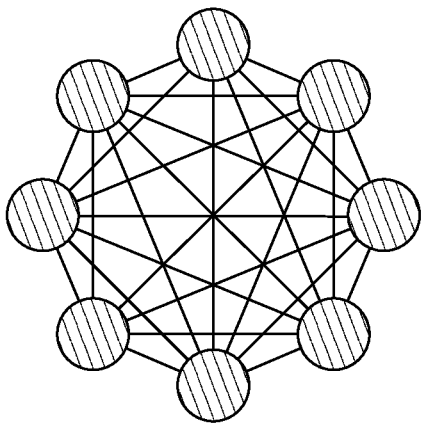
Figure 34:
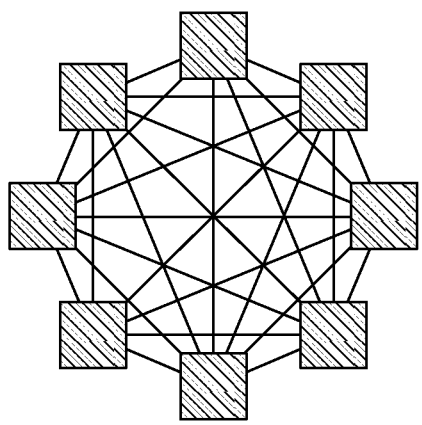
Figure 38:
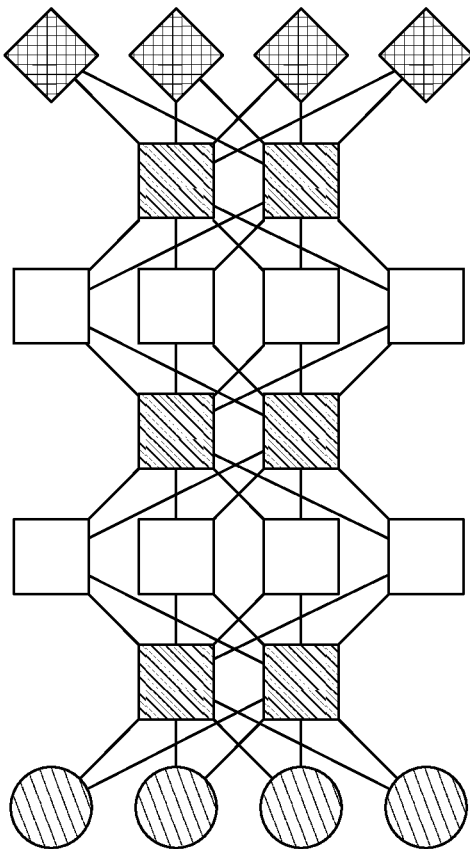
Figure 37:
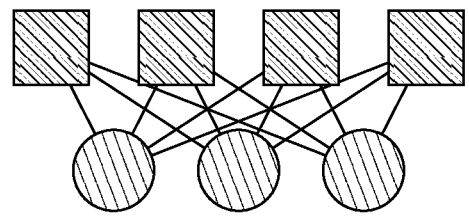
Figure 40:
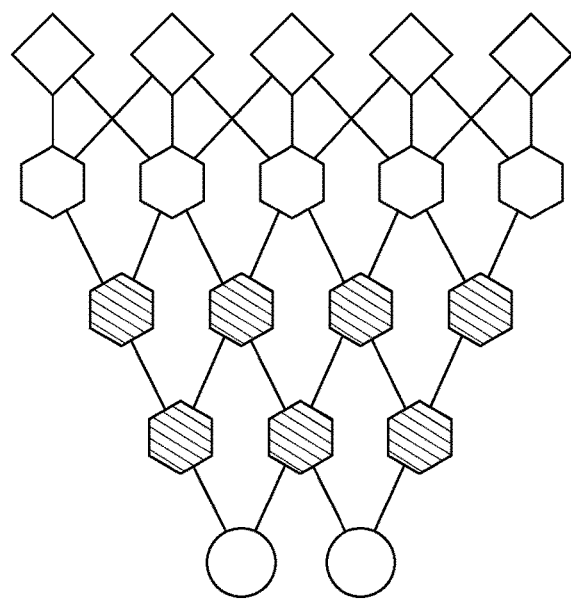
Figure 39:
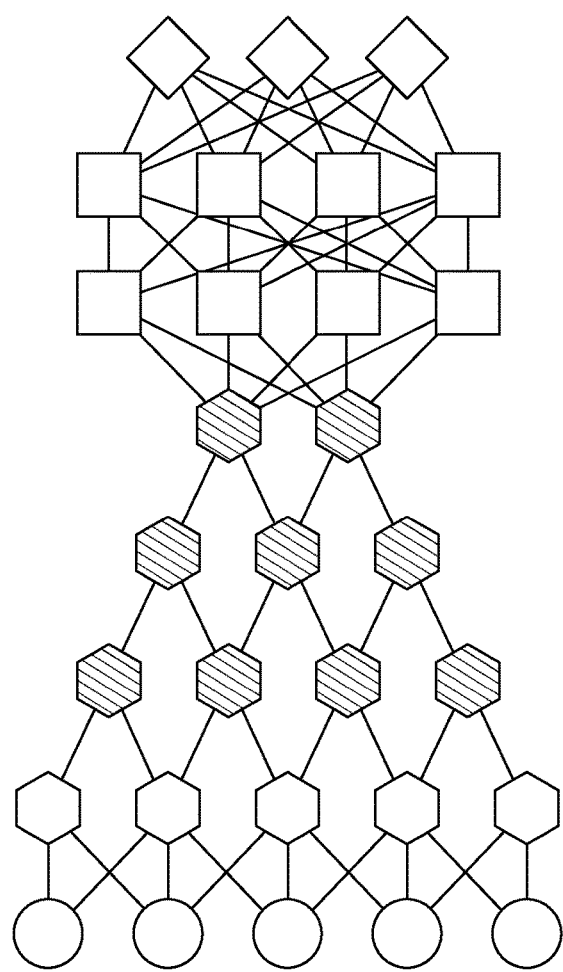
Figure 41:
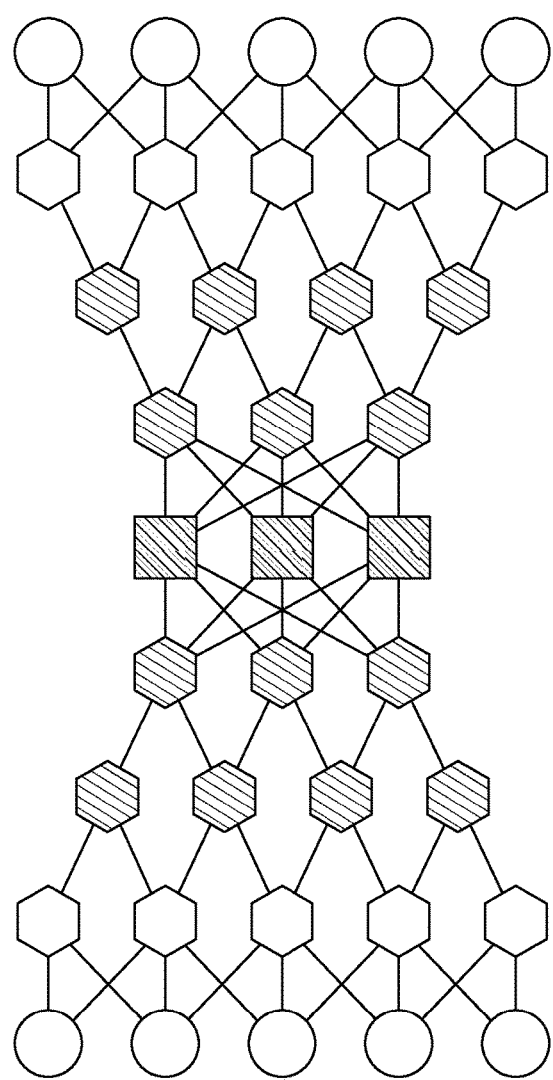
Figure 42:
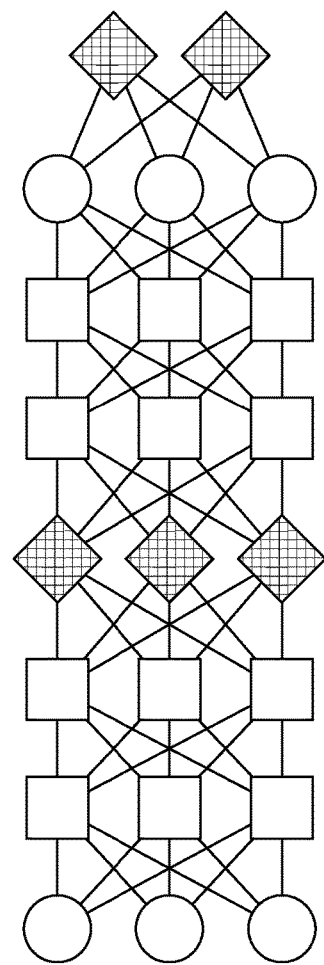
Figure 44:
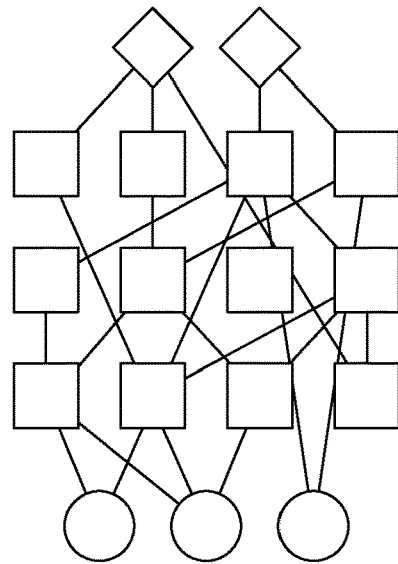
Figure 46:
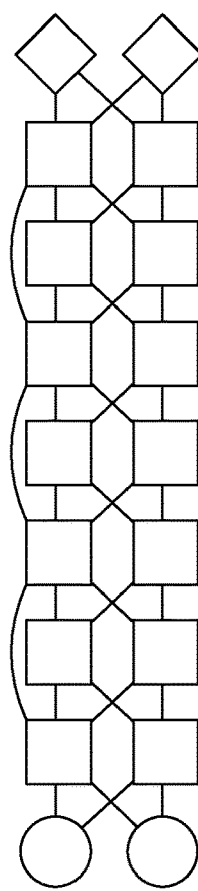
Figure 43:
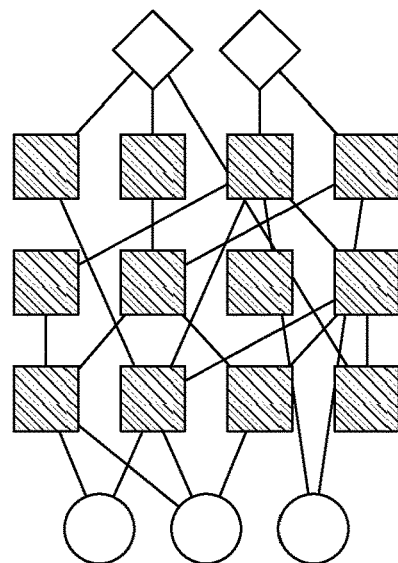
Figure 45:
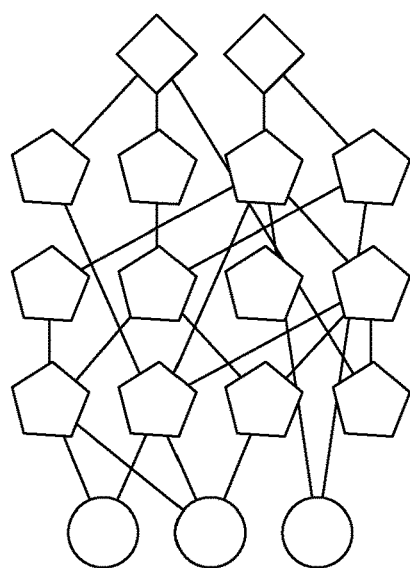
Figure 48:
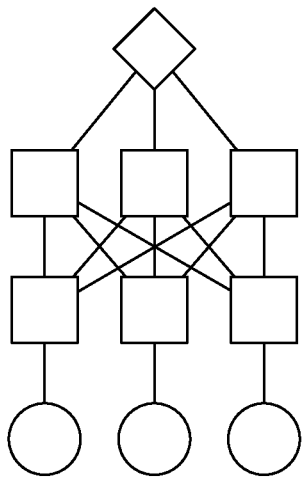
Figure 49:
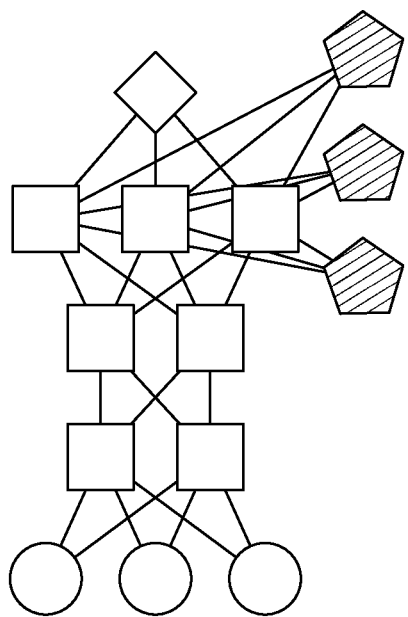
Figure 47:
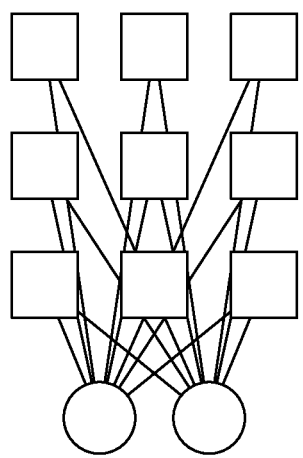

In embodiments, FIG. 23 depicts an exemplary perceptron neural network that may connect to, integrate with, or interface with the platform 100. The platform may also be associated with further neural net systems such as a feed forward neural network (FIG. 24), a radial basis neural network (FIG. 25), a deep feed forward neural network (FIG. 26), a recurrent neural network (FIG. 27), a long/short term neural network (FIG. 28), and a gated recurrent neural network (FIG. 29). The platform may also be associated with further neural net systems such as an auto encoder neural network (FIG. 30), a variational neural network (FIG. 31), a denoising neural network (FIG. 32), a sparse neural network (FIG. 33), a Markov chain neural network (FIG. 34), and a Hopfield network neural network (FIG. 35). The platform may further be associated with additional neural net systems such as a Boltzmann machine neural network (FIG. 36), a restricted BM neural network (FIG. 37), a deep belief neural network (FIG. 38), a deep convolutional neural network (FIG. 39), a deconvolutional neural network (FIG. 40), and a deep convolutional inverse graphics neural network (FIG. 41). The platform may also be associated with further neural net systems such as a generative adversarial neural network (FIG. 42), a liquid state machine neural network (FIG. 43), an extreme learning machine neural network (FIG. 44), an echo state neural network (FIG. 45), a deep residual neural network (FIG. 46), a Kohonen neural network (FIG. 47), a support vector machine neural network (FIG. 48), and a neural Turing machine neural network (FIG. 49).

The foregoing neural networks may have a variety of nodes or neurons, which may perform a variety of functions on inputs, such as inputs received from sensors or other data sources, including other nodes. Functions may involve weights, features, feature vectors, and the like. Neurons may include perceptrons, neurons that mimic biological functions (such as of the human senses of touch, vision, taste, hearing, and smell), and the like. Continuous neurons, such as with sigmoidal activation, may be used in the context of various forms of neural net, such as where back propagation is involved.

In many embodiments, an expert system or neural network may be trained, such as by a human operator or supervisor, or based on a data set, model, or the like. Training may include presenting the neural network with one or more training data sets that represent values, such as sensor data, event data, parameter data, and other types of data (including the many types described throughout this disclosure), as well as one or more indicators of an outcome, such as an outcome of a process, an outcome of a calculation, an outcome of an event, an outcome of an activity, or the like. Training may include training in optimization, such as training a neural network to optimize one or more systems based on one or more optimization approaches, such as Bayesian approaches, parametric Bayes classifier approaches, k-nearest-neighbor classifier approaches, iterative approaches, interpolation approaches, Pareto optimization approaches, algorithmic approaches, and the like. Feedback may be provided in a process of variation and selection, such as with a genetic algorithm that evolves one or more solutions based on feedback through a series of rounds.

In embodiments, a plurality of neural networks may be deployed in a cloud platform that receives data streams and other inputs collected (such as by mobile data collectors) in one or more transactional environments and transmitted to the cloud platform over one or more networks, including using network coding to provide efficient transmission. In the cloud platform, optionally using massively parallel computational capability, a plurality of different neural networks of various types (including modular forms, structure-adaptive forms, hybrids, and the like) may be used to undertake prediction, classification, control functions, and provide other outputs as described in connection with expert systems disclosed throughout this disclosure. The different neural networks may be structured to compete with each other (optionally including use evolutionary algorithms, genetic algorithms, or the like), such that an appropriate type of neural network, with appropriate input sets, weights, node types and functions, and the like, may be selected, such as by an expert system, for a specific task involved in a given context, workflow, environment process, system, or the like.

In embodiments, methods and systems described herein that involve an expert system or self-organization capability may use a feed forward neural network, which moves information in one direction, such as from a data input, like a data source related to at least one resource or parameter related to a transactional environment, such as any of the data sources mentioned throughout this disclosure, through a series of neurons or nodes, to an output. Data may move from the input nodes to the output nodes, optionally passing through one or more hidden nodes, without loops. In embodiments, feed forward neural networks may be constructed with various types of units, such as binary McCulloch-Pitts neurons, the simplest of which is a perceptron.

In embodiments, methods and systems described herein that involve an expert system or self-organization capability may use a capsule neural network, such as for prediction, classification, or control functions with respect to a transactional environment, such as relating to one or more of the machines and automated systems described throughout this disclosure.

In embodiments, methods and systems described herein that involve an expert system or self-organization capability may use a radial basis function (RBF) neural network, which may be preferred in some situations involving interpolation in a multi-dimensional space (such as where interpolation is helpful in optimizing a multi-dimensional function, such as for optimizing a data marketplace as described here, optimizing the efficiency or output of a power generation system, a factory system, or the like, or other situation involving multiple dimensions. In embodiments, each neuron in the RBF neural network stores an example from a training set as a "prototype." Linearity involved in the functioning of this neural network offers RBF the advantage of not typically suffering from problems with local minima or maxima.

In embodiments, methods and systems described herein that involve an expert system or self-organization capability may use a radial basis function (RBF) neural network, such as one that employs a distance criterion with respect to a center (e.g., a Gaussian function). A radial basis function may be applied as a replacement for a hidden layer, such as a sigmoidal hidden layer transfer, in a multi-layer perceptron. An RBF network may have two layers, such as where an input is mapped onto each RBF in a hidden layer. In embodiments, an output layer may comprise a linear combination of hidden layer values representing, for example, a mean predicted output. The output layer value may provide an output that is the same as or similar to that of a regression model in statistics. In classification problems, the output layer may be a sigmoid function of a linear combination of hidden layer values, representing a posterior probability. Performance in both cases is often improved by shrinkage techniques, such as ridge regression in classical statistics. This corresponds to a prior belief in small parameter values (and therefore smooth output functions) in a Bayesian framework. RBF networks may avoid local minima, because the only parameters that are adjusted in the learning process are the linear mapping from hidden layer to output layer. Linearity ensures that the error surface is quadratic and therefore has a single minimum. In regression problems, this may be found in one matrix operation. In classification problems, the fixed non-linearity introduced by the sigmoid output function may be handled using an iteratively re-weighted least squares function or the like. RBF networks may use kernel methods such as support vector machines (SVM) and Gaussian processes (where the RBF is the kernel function). A non-linear kernel function may be used to project the input data into a space where the learning problem may be solved using a linear model.

In embodiments, an RBF neural network may include an input layer, a hidden layer, and a summation layer. In the input layer, one neuron appears in the input layer for each predictor variable. In the case of categorical variables, N−1 neurons are used, where N is the number of categories. The input neurons may, in embodiments, standardize the value ranges by subtracting the median and dividing by the interquartile range. The input neurons may then feed the values to each of the neurons in the hidden layer. In the hidden layer, a variable number of neurons may be used (determined by the training process). Each neuron may consist of a radial basis function that is centered on a point with as many dimensions as a number of predictor variables. The spread (e.g., radius) of the RBF function may be different for each dimension. The centers and spreads may be determined by training. When presented with the vector of input values from the input layer, a hidden neuron may compute a Euclidean distance of the test case from the neuron's center point and then apply the RBF kernel function to this distance, such as using the spread values. The resulting value may then be passed to the summation layer. In the summation layer, the value coming out of a neuron in the hidden layer may be multiplied by a weight associated with the neuron and may add to the weighted values of other neurons. This sum becomes the output. For classification problems, one output is produced (with a separate set of weights and summation units) for each target category. The value output for a category is the probability that the case being evaluated has that category. In training of an RBF, various parameters may be determined, such as the number of neurons in a hidden layer, the coordinates of the center of each hidden-layer function, the spread of each function in each dimension, and the weights applied to outputs as they pass to the summation layer. Training may be used by clustering algorithms (such as k-means clustering), by evolutionary approaches, and the like.

In embodiments, a recurrent neural network may have a time-varying, real-valued (more than just zero or one) activation (output). Each connection may have a modifiable real-valued weight. Some of the nodes are called labeled nodes, some output nodes, and others hidden nodes. For supervised learning in discrete time settings, training sequences of real-valued input vectors may become sequences of activations of the input nodes, one input vector at a time. At each time step, each non-input unit may compute its current activation as a nonlinear function of the weighted sum of the activations of all units from which it receives connections. The system may explicitly activate (independent of incoming signals) some output units at certain time steps.

In embodiments, methods and systems described herein that involve an expert system or self-organization capability may use a self-organizing neural network, such as a Kohonen self-organizing neural network, such as for visualization of views of data, such as low-dimensional views of high-dimensional data. The self-organizing neural network may apply competitive learning to a set of input data, such as from one or more sensors or other data inputs from or associated with a transactional environment, including any machine or component that relates to the transactional environment. In embodiments, the self-organizing neural network may be used to identify structures in data, such as unlabeled data, such as in data sensed from a range of data sources about or sensors in or about in a transactional environment, where sources of the data are unknown (such as where events may be coming from any of a range of unknown sources). The self-organizing neural network may organize structures or patterns in the data, such that they may be recognized, analyzed, and labeled, such as identifying market behavior structures as corresponding to other events and signals.

In embodiments, methods and systems described herein that involve an expert system or self-organization capability may use a recurrent neural network, which may allow for a bi-directional flow of data, such as where connected units (e.g., neurons or nodes) form a directed cycle. Such a network may be used to model or exhibit dynamic temporal behavior, such as involved in dynamic systems, such as a wide variety of the automation systems, machines and devices described throughout this disclosure, such as an automated agent interacting with a marketplace for purposes of collecting data, testing spot market transactions, execution transactions, and the like, where dynamic system behavior involves complex interactions that a user may desire to understand, predict, control and/or optimize. For example, the recurrent neural network may be used to anticipate the state of a market, such as one involving a dynamic process or action, such as a change in state of a resource that is traded in or that enables a marketplace of transactional environment. In embodiments, the recurrent neural network may use internal memory to process a sequence of inputs, such as from other nodes and/or from sensors and other data inputs from or about the transactional environment, of the various types described herein. In embodiments, the recurrent neural network may also be used for pattern recognition, such as for recognizing a machine, component, agent, or other item based on a behavioral signature, a profile, a set of feature vectors (such as in an audio file or image), or the like. In a non-limiting example, a recurrent neural network may recognize a shift in an operational mode of a marketplace or machine by learning to classify the shift from a training data set consisting of a stream of data from one or more data sources of sensors applied to or about one or more resources.

In embodiments, methods and systems described herein that involve an expert system or self-organization capability may use a modular neural network, which may comprise a series of independent neural networks (such as ones of various types described herein) that are moderated by an intermediary. Each of the independent neural networks in the modular neural network may work with separate inputs, accomplishing subtasks that make up the task the modular network as whole is intended to perform. For example, a modular neural network may comprise a recurrent neural network for pattern recognition, such as to recognize what type of machine or system is being sensed by one or more sensors that are provided as input channels to the modular network and an RBF neural network for optimizing the behavior of the machine or system once understood. The intermediary may accept inputs of each of the individual neural networks, process them, and create output for the modular neural network, such an appropriate control parameter, a prediction of state, or the like.

Combinations among any of the pairs, triplets, or larger combinations, of the various neural network types described herein, are encompassed by the present disclosure. This may include combinations where an expert system uses one neural network for recognizing a pattern (e.g., a pattern indicating a problem or fault condition) and a different neural network for self-organizing an activity or workflow based on the recognized pattern (such as providing an output governing autonomous control of a system in response to the recognized condition or pattern). This may also include combinations where an expert system uses one neural network for classifying an item (e.g., identifying a machine, a component, or an operational mode) and a different neural network for predicting a state of the item (e.g., a fault state, an operational state, an anticipated state, a maintenance state, or the like). Modular neural networks may also include situations where an expert system uses one neural network for determining a state or context (such as a state of a machine, a process, a work-flow, a marketplace, a storage system, a network, a data collector, or the like) and a different neural network for self-organizing a process involving the state or context (e.g., a data storage process, a network coding process, a network selection process, a data marketplace process, a power generation process, a manufacturing process, a refining process, a digging process, a boring process, or other process described herein).

In embodiments, methods and systems described herein that involve an expert system or self-organization capability may use a physical neural network where one or more hardware elements is used to perform or simulate neural behavior. In embodiments, one or more hardware neurons may be configured to stream voltage values, current values, or the like that represent sensor data, such as to calculate information from analog sensor inputs representing energy consumption, energy production, or the like, such as by one or more machines providing energy or consuming energy for one or more transactions. One or more hardware nodes may be configured to stream output data resulting from the activity of the neural net. Hardware nodes, which may comprise one or more chips, microprocessors, integrated circuits, programmable logic controllers, application-specific integrated circuits, field-programmable gate arrays, or the like, may be provided to optimize the machine that is producing or consuming energy, or to optimize another parameter of some part of a neural net of any of the types described herein. Hardware nodes may include hardware for acceleration of calculations (such as dedicated processors for performing basic or more sophisticated calculations on input data to provide outputs, dedicated processors for filtering or compressing data, dedicated processors for de-compressing data, dedicated processors for compression of specific file or data types (e.g., for handling image data, video streams, acoustic signals, thermal images, heat maps, or the like), and the like. A physical neural network may be embodied in a data collector, including one that may be reconfigured by switching or routing inputs in varying configurations, such as to provide different neural net configurations within the data collector for handling different types of inputs (with the switching and configuration optionally under control of an expert system, which may include a software-based neural net located on the data collector or remotely). A physical, or at least partially physical, neural network may include physical hardware nodes located in a storage system, such as for storing data within a machine, a data storage system, a distributed ledger, a mobile device, a server, a cloud resource, or in a transactional environment, such as for accelerating input/output functions to one or more storage elements that supply data to or take data from the neural net. A physical, or at least partially physical, neural network may include physical hardware nodes located in a network, such as for transmitting data within, to or from an industrial environment, such as for accelerating input/output functions to one or more network nodes in the net, accelerating relay functions, or the like. In embodiments of a physical neural network, an electrically adjustable resistance material may be used for emulating the function of a neural synapse. In embodiments, the physical hardware emulates the neurons, and software emulates the neural network between the neurons. In embodiments, neural networks complement conventional algorithmic computers. They are versatile and may be trained to perform appropriate functions without the need for any instructions, such as classification functions, optimization functions, pattern recognition functions, control functions, selection functions, evolution functions, and others.

In embodiments, methods and systems described herein that involve an expert system or self-organization capability may use a multilayered feed forward neural network, such as for complex pattern classification of one or more items, phenomena, modes, states, or the like. In embodiments, a multilayered feed forward neural network may be trained by an optimization technique, such as a genetic algorithm, such as to explore a large and complex space of options to find an optimum, or near-optimum, global solution. For example, one or more genetic algorithms may be used to train a multilayered feed forward neural network to classify complex phenomena, such as to recognize complex operational modes of machines, such as modes involving complex interactions among machines (including interference effects, resonance effects, and the like), modes involving non-linear phenomena, modes involving critical faults, such as where multiple, simultaneous faults occur, making root cause analysis difficult, and others. In embodiments, a multilayered feed forward neural network may be used to classify results from monitoring of a marketplace, such as monitoring systems, such as automated agents, that operate within the marketplace, as well as monitoring resources that enable the marketplace, such as computing, networking, energy, data storage, energy storage, and other resources.

In embodiments, methods and systems described herein that involve an expert system or self-organization capability may use a feed-forward, back-propagation multi-layer perceptron (MLP) neural network, such as for handling one or more remote sensing applications, such as for taking inputs from sensors distributed throughout various transactional environments. In embodiments, the MLP neural network may be used for classification of transactional environments and resource environments, such as spot markets, forward markets, energy markets, renewable energy credit (REC) markets, networking markets, advertising markets, spectrum markets, ticketing markets, rewards markets, compute markets, and others mentioned throughout this disclosure, as well as physical resources and environments that produce them, such as energy resources (including renewable energy environments, mining environments, exploration environments, drilling environments, and the like, including classification of geological structures (including underground features and above ground features), classification of materials (including fluids, minerals, metals, and the like), and other problems. This may include fuzzy classification.

In embodiments, methods and systems described herein that involve an expert system or self-organization capability may use a structure-adaptive neural network, where the structure of a neural network is adapted, such as based on a rule, a sensed condition, a contextual parameter, or the like. For example, if a neural network does not converge on a solution, such as classifying an item or arriving at a prediction, when acting on a set of inputs after some amount of training, the neural network may be modified, such as from a feed forward neural network to a recurrent neural network, such as by switching data paths between some subset of nodes from unidirectional to bi-directional data paths. The structure adaptation may occur under control of an expert system, such as to trigger adaptation upon occurrence of a trigger, rule or event, such as recognizing occurrence of a threshold (such as an absence of a convergence to a solution within a given amount of time) or recognizing a phenomenon as requiring different or additional structure (such as recognizing that a system is varying dynamically or in a non-linear fashion). In one non-limiting example, an expert system may switch from a simple neural network structure like a feed forward neural network to a more complex neural network structure like a recurrent neural network, a convolutional neural network, or the like upon receiving an indication that a continuously variable transmission is being used to drive a generator, turbine, or the like in a system being analyzed.

In embodiments, methods and systems described herein that involve an expert system or self-organization capability may use an autoencoder, autoassociator or Diabolo neural network, which may be similar to a multilayer perceptron (MLP) neural network, such as where there may be an input layer, an output layer and one or more hidden layers connecting them. However, the output layer in the auto-encoder may have the same number of units as the input layer, where the purpose of the MLP neural network is to reconstruct its own inputs (rather than just emitting a target value). Therefore, the auto encoders may operate as an unsupervised learning model. An auto encoder may be used, for example, for unsupervised learning of efficient codings, such as for dimensionality reduction, for learning generative models of data, and the like. In embodiments, an auto-encoding neural network may be used to self-learn an efficient network coding for transmission of analog sensor data from a machine over one or more networks or of digital data from one or more data sources. In embodiments, an auto-encoding neural network may be used to self-learn an efficient storage approach for storage of streams of data.

In embodiments, methods and systems described herein that involve an expert system or self-organization capability may use a probabilistic neural network (PNN), which, in embodiments, may comprise a multi-layer (e.g., four-layer) feed forward neural network, where layers may include input layers, hidden layers, pattern/summation layers and an output layer. In an embodiment of a PNN algorithm, a parent probability distribution function (PDF) of each class may be approximated, such as by a Parzen window and/or a non-parametric function. Then, using the PDF of each class, the class probability of a new input is estimated, and Bayes' rule may be employed, such as to allocate it to the class with the highest posterior probability. A PNN may embody a Bayesian network and may use a statistical algorithm or analytic technique, such as Kernel Fisher discriminant analysis technique. The PNN may be used for classification and pattern recognition in any of a wide range of embodiments disclosed herein. In one non-limiting example, a probabilistic neural network may be used to predict a fault condition of an engine based on collection of data inputs from sensors and instruments for the engine.

In embodiments, methods and systems described herein that involve an expert system or self-organization capability may use a time delay neural network (TDNN), which may comprise a feed forward architecture for sequential data that recognizes features independent of sequence position. In embodiments, to account for time shifts in data, delays are added to one or more inputs, or between one or more nodes, so that multiple data points (from distinct points in time) are analyzed together. A time delay neural network may form part of a larger pattern recognition system, such as using a perceptron network. In embodiments, a TDNN may be trained with supervised learning, such as where connection weights are trained with back propagation or under feedback. In embodiments, a TDNN may be used to process sensor data from distinct streams, such as a stream of velocity data, a stream of acceleration data, a stream of temperature data, a stream of pressure data, and the like, where time delays are used to align the data streams in time, such as to help understand patterns that involve understanding of the various streams (e.g., changes in price patterns in spot or forward markets).

In embodiments, methods and systems described herein that involve an expert system or self-organization capability may use a convolutional neural network (referred to in some cases as a CNN, a ConvNet, a shift invariant neural network, or a space invariant neural network), wherein the units are connected in a pattern similar to the visual cortex of the human brain. Neurons may respond to stimuli in a restricted region of space, referred to as a receptive field. Receptive fields may partially overlap, such that they collectively cover the entire (e.g., visual) field. Node responses may be calculated mathematically, such as by a convolution operation, such as using multilayer perceptrons that use minimal preprocessing. A convolutional neural network may be used for recognition within images and video streams, such as for recognizing a type of machine in a large environment using a camera system disposed on a mobile data collector, such as on a drone or mobile robot. In embodiments, a convolutional neural network may be used to provide a recommendation based on data inputs, including sensor inputs and other contextual information, such as recommending a route for a mobile data collector. In embodiments, a convolutional neural network may be used for processing inputs, such as for natural language processing of instructions provided by one or more parties involved in a workflow in an environment. In embodiments, a convolutional neural network may be deployed with a large number of neurons (e.g., 100,000, 500,000 or more), with multiple (e.g., 4, 5, 6 or more) layers, and with many (e.g., millions) of parameters. A convolutional neural net may use one or more convolutional nets.

In embodiments, methods and systems described herein that involve an expert system or self-organization capability may use a regulatory feedback network, such as for recognizing emergent phenomena (such as new types of behavior not previously understood in a transactional environment).

In embodiments, methods and systems described herein that involve an expert system or self-organization capability may use a self-organizing map (SOM), involving unsupervised learning. A set of neurons may learn to map points in an input space to coordinates in an output space. The input space may have different dimensions and topology from the output space, and the SOM may preserve these while mapping phenomena into groups.

In embodiments, methods and systems described herein that involve an expert system or self-organization capability may use a learning vector quantization neural net (LVQ). Prototypical representatives of the classes may parameterize, together with an appropriate distance measure, in a distance-based classification scheme.

In embodiments, methods and systems described herein that involve an expert system or self-organization capability may use an echo state network (ESN), which may comprise a recurrent neural network with a sparsely connected, random hidden layer. The weights of output neurons may be changed (e.g., the weights may be trained based on feedback). In embodiments, an ESN may be used to handle time series patterns, such as, in an example, recognizing a pattern of events associated with a market, such as the pattern of price changes in response to stimuli.

In embodiments, methods and systems described herein that involve an expert system or self-organization capability may use a Bi-directional, recurrent neural network (BRNN), such as using a finite sequence of values (e.g., voltage values from a sensor) to predict or label each element of the sequence based on both the past and the future context of the element. This may be done by adding the outputs of two RNNs, such as one processing the sequence from left to right, the other one from right to left. The combined outputs are the predictions of target signals, such as ones provided by a teacher or supervisor. A bi-directional RNN may be combined with a long short-term memory RNN.

In embodiments, methods and systems described herein that involve an expert system or self-organization capability may use a hierarchical RNN that connects elements in various ways to decompose hierarchical behavior, such as into useful subprograms. In embodiments, a hierarchical RNN may be used to manage one or more hierarchical templates for data collection in a transactional environment.

In embodiments, methods and systems described herein that involve an expert system or self-organization capability may use a stochastic neural network, which may introduce random variations into the network. Such random variations may be viewed as a form of statistical sampling, such as Monte Carlo sampling.

In embodiments, methods and systems described herein that involve an expert system or self-organization capability may use a genetic scale recurrent neural network. In such embodiments, an RNN (often an LSTM) is used where a series is decomposed into a number of scales where every scale informs the primary length between two consecutive points. A first order scale consists of a normal RNN, a second order consists of all points separated by two indices and so on. The Nth order RNN connects the first and last node. The outputs from all the various scales may be treated as a committee of members, and the associated scores may be used genetically for the next iteration.

In embodiments, methods and systems described herein that involve an expert system or self-organization capability may use a committee of machines (CoM), comprising a collection of different neural networks that together "vote" on a given example. Because neural networks may suffer from local minima, starting with the same architecture and training, but using randomly different initial weights often gives different results. A CoM tends to stabilize the result.

In embodiments, methods and systems described herein that involve an expert system or self-organization capability may use an associative neural network (ASNN), such as involving an extension of a committee of machines that combines multiple feed forward neural networks and a k-nearest neighbor technique. It may use the correlation between ensemble responses as a measure of distance amid the analyzed cases for the kNN. This corrects the bias of the neural network ensemble. An associative neural network may have a memory that may coincide with a training set. If new data become available, the network instantly improves its predictive ability and provides data approximation (self-learns) without retraining. Another important feature of ASNN is the possibility to interpret neural network results by analysis of correlations between data cases in the space of models.

In embodiments, methods and systems described herein that involve an expert system or self-organization capability may use an instantaneously trained neural network (ITNN), where the weights of the hidden and the output layers are mapped directly from training vector data.

In embodiments, methods and systems described herein that involve an expert system or self-organization capability may use a spiking neural network, which may explicitly consider the timing of inputs. The network input and output may be represented as a series of spikes (such as a delta function or more complex shapes). SNNs may process information in the time domain (e.g., signals that vary over time, such as signals involving dynamic behavior of markets or transactional environments). They are often implemented as recurrent networks.

In embodiments, methods and systems described herein that involve an expert system or self-organization capability may use a dynamic neural network that addresses nonlinear multivariate behavior and includes learning of time-dependent behavior, such as transient phenomena and delay effects. Transients may include behavior of shifting market variables, such as prices, available quantities, available counterparties, and the like.

In embodiments, cascade correlation may be used as an architecture and supervised learning algorithm, supplementing adjustment of the weights in a network of fixed topology. Cascade-correlation may begin with a minimal network, then automatically trains and add new hidden units one by one, creating a multi-layer structure. Once a new hidden unit has been added to the network, its input-side weights may be frozen. This unit then becomes a permanent feature-detector in the network, available for producing outputs or for creating other, more complex feature detectors. The cascade-correlation architecture may learn quickly, determine its own size and topology, and retain the structures it has built even if the training set changes and requires no back-propagation.

In embodiments, methods and systems described herein that involve an expert system or self-organization capability may use a neuro-fuzzy network, such as involving a fuzzy inference system in the body of an artificial neural network. Depending on the type, several layers may simulate the processes involved in a fuzzy inference, such as fuzzification, inference, aggregation and defuzzification. Embedding a fuzzy system in a general structure of a neural net as the benefit of using available training methods to find the parameters of a fuzzy system.

In embodiments, methods and systems described herein that involve an expert system or self-organization capability may use a compositional pattern-producing network (CPPN), such as a variation of an associative neural network (ANN) that differs the set of activation functions and how they are applied. While typical ANNs often contain only sigmoid functions (and sometimes Gaussian functions), CPPNs may include both types of functions and many others. Furthermore, CPPNs may be applied across the entire space of possible inputs, so that they may represent a complete image. Since they are compositions of functions, CPPNs in effect encode images at infinite resolution and may be sampled for a particular display at whatever resolution is optimal.

This type of network may add new patterns without re-training. In embodiments, methods and systems described herein that involve an expert system or self-organization capability may use a one-shot associative memory network, such as by creating a specific memory structure, which assigns each new pattern to an orthogonal plane using adjacently connected hierarchical arrays.

In embodiments, methods and systems described herein that involve an expert system or self-organization capability may use a hierarchical temporal memory (HTM) neural network, such as involving the structural and algorithmic properties of the neocortex. HTM may use a biomimetic model based on memory-prediction theory. HTM may be used to discover and infer the high-level causes of observed input patterns and sequences.

In embodiments, methods and systems described herein that involve an expert system or self-organization capability may use a holographic associative memory (HAM) neural network, which may comprise an analog, correlation-based, associative, stimulus-response system. Information may be mapped onto the phase orientation of complex numbers. The memory is effective for associative memory tasks, generalization and pattern recognition with changeable attention.

In embodiments, various embodiments involving network coding may be used to code transmission data among network nodes in a neural net, such as where nodes are located in one or more data collectors or machines in a transactional environment.

Figure 50:
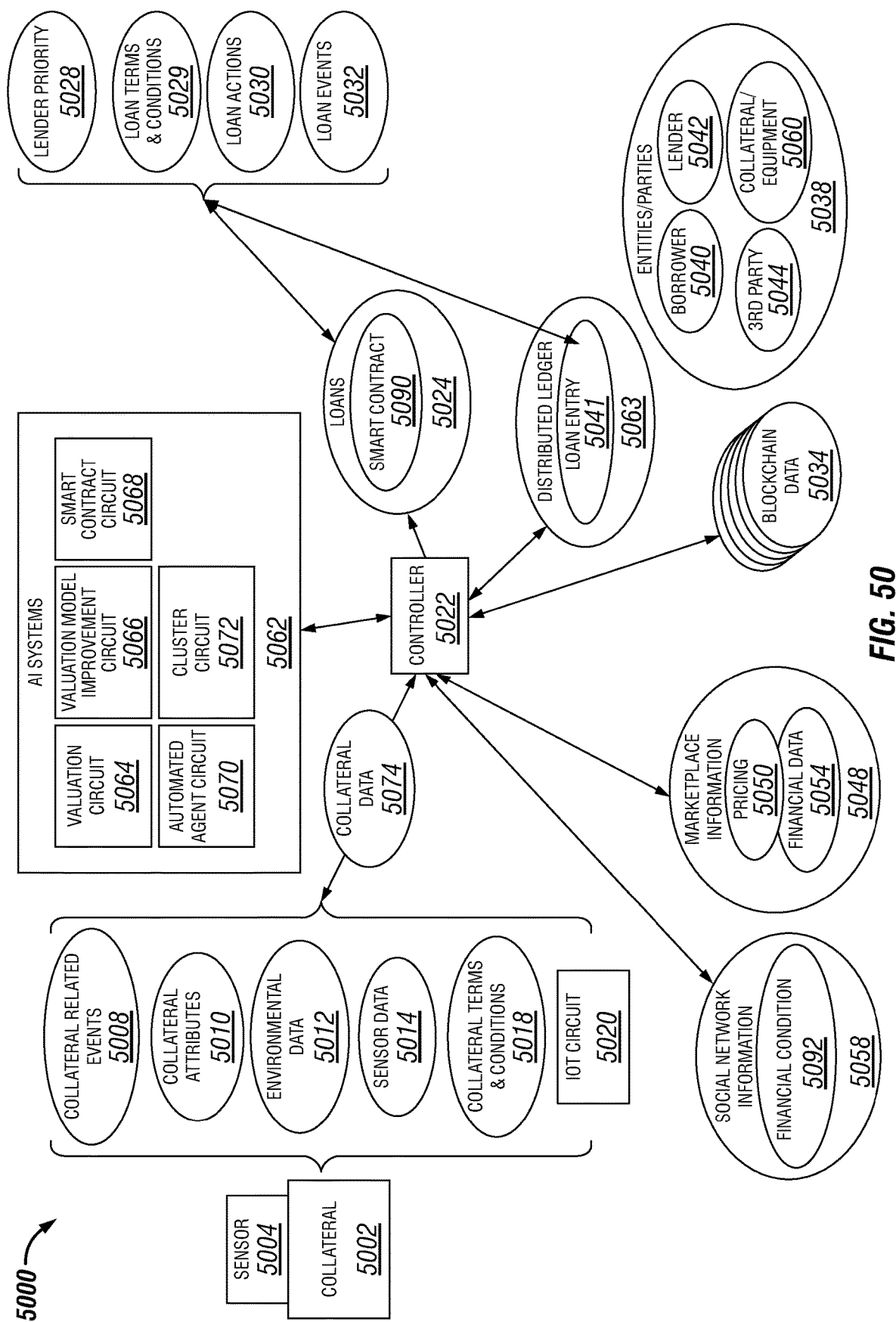
FIG. 50 depicts general components and interactions of a lending platform.

Referring to FIG. 50, a system 5000 for automated loan management is depicted. A variety of entities/parties 5038 may have a connection to a loan 5024 including a borrower 5040, a lender 5042, 3rd parties 5044 such as a neutral 3rd party (e.g. such as an assessor, a collateral/equipment 5060, or an interested 3rd party (e.g. a regulator, company employees, and the like). A loan 5024 may be subject to a smart lending contract 5090 including information such as loan terms and conditions 5029, loan actions 5030, loan events 5032, lender priorities 5028. And the like. The smart lending contract 5090 may be recording in loan entry 5041 in a distributed ledger 5063. The smart lending contract 5090 may be stored as blockchain data 5034.

In an illustrative example, controller 5022 may receive collateral data 5074 such as collateral related events 5008, collateral attributes 5010, environmental data 5012 about an environment in which the collateral 5002 is situated, sensor data 5014 where the senor 5004 may be affixed to an item of collateral, to a case containing an item of collateral or in proximity to an item of collateral. In embodiments, collateral data may be acquired by an Internet of Things Circuit 5020, a camera system, a networked monitoring system, an internet monitoring system, a mobile device system, a wearable device system, a user interface system, and an interactive crowdsourcing system.

The controller 5022 may also monitor and/or receive data from a social network information 5058 from which a financial condition 5092 may be inferred such as a rating of a party, a tax status of a party, a credit report of the party, a credit rating of a party, a website rating of a party, a set of customer reviews for a product of a party, a social network rating of a party, a set of credentials of a party, a set of referrals of a party, a set of testimonials for a party, a set of behavior of a party, and the like. The controller 5022 may also receive marketplace information 5048 such as pricing 5050, financial data 5054 such as a publicly stated valuation of the party, a set of property owned by the party as indicated by public records, a valuation of a set of property owned by the party, a bankruptcy condition of the party, a foreclosure status of the entity, a contractual default status of the entity, a regulatory violation status of the entity, a criminal status of the entity, an export controls status of the entity, an embargo status of the entity, a tariff status of the entity, a tax status of the entity, a credit report of the entity, a credit rating of the entity, and the like.

In embodiments, artificial intelligence systems 5062 may be part of a controller 5022 or on remote systems. The AI systems 5062 may include a valuation circuit 5064 structured to determine a value for an item of collateral based on collateral data 5074 and a valuation model and a value model improvement circuit 5066 to improve the valuation model on the basis of a first set of received collateral data 5074 and the outcome of loans for which collateral associated with that first set of received collateral data acted as security. The AI systems 5062 may include an automated agent circuit 5070 that takes action based on collateral events, loan-events and the like. Actions may include loan-related actions such as offering the loan, accepting the loan, underwriting the loan, setting an interest rate for the loan, deferring a payment requirement, modifying an interest rate for the loan, validating title for collateral, recording a change in title, assessing a value of collateral, initiating inspection of collateral, calling the loan, closing the loan, setting terms and conditions for the loan, providing notices required to be provided to a borrower, foreclosing on property subject to the loan, modifying terms and conditions for the loan, and the like. Actions may include collateral-related actions such as validating title for the one of the assigned set of items of collateral, recording a change in title for the one of the assigned set of items of collateral, assessing the value of the one of the assigned set of items of collateral, initiating inspection of the one of the assigned set of items of collateral, initiating maintenance of the one of the assigned set of items of collateral, initiating security for the one of the assigned set of items of collateral, modifying terms and conditions for the one of the assigned set of items of collateral 5018, and the like. The AI systems 5062 may include a cluster circuit 5072 to create groups of items of collateral based on a common attribute. The cluster circuit 5072 may also determine a group of offset items of collateral where the offset items of collateral share a common attribute with one or more items of collateral. Data may be gathered on the offset items of collateral and use it as representative of the items of collateral. A smart contract circuit 5068 may create a smart lending contract 5090 as described elsewhere herein.

Figure 51:
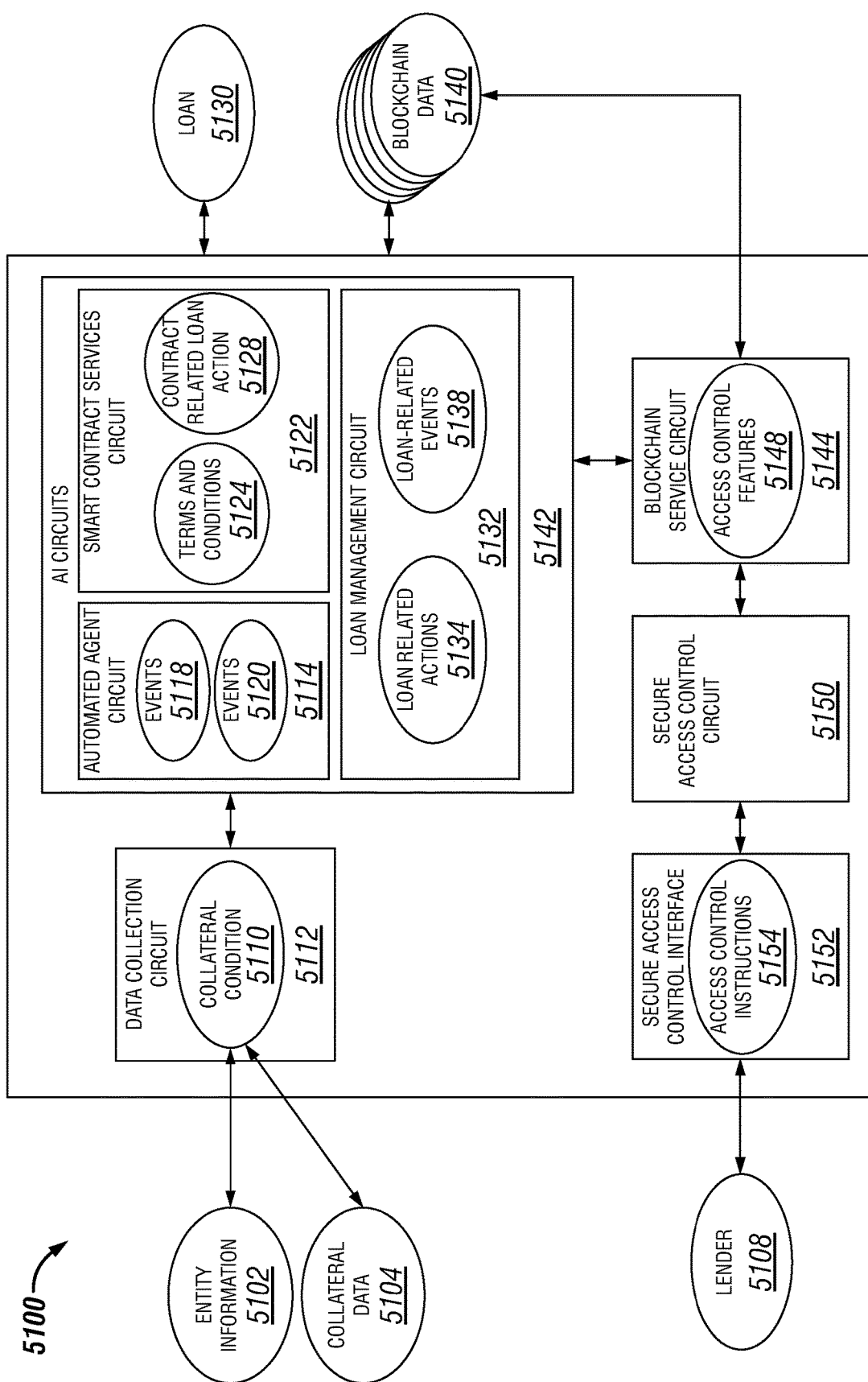
FIG. 51 depicts components and interactions of a lending platform that leverages entity data to identify loan-events and initiate automatic loan-actions.

Referring to FIG. 51, a controller may include a blockchain service circuit 5144 structured to interpret a plurality of access control features 5148 such as corresponding to parties associated with a loan 5130 and associated with blockchain data 5140. The system 5100 may include a data collection circuit 5112 structured to interpret entity information 5102, collateral data 5104, and the like, such as corresponding to entities related to a lending transaction corresponding to the loan, collateral conditions, and the like. The system may include a smart contract circuit 5122 structured to specify loan terms and conditions 5124, contracts 5128, and the like, relating to the loan. The system may include a loan management circuit 5132 structured to interpret loan related actions 5134 and/or events 5138 in response to the entity information, the plurality of access control features, and the loan terms and conditions, where the loan related events are associated with the loan; implement loan related activities in response to the entity information, the plurality of access control features, and the loan terms and conditions, wherein the loan related activities are associated with the loan; and where each of the blockchain service circuit, the data collection circuit, the smart contract circuit, and the loan management circuit further comprise a corresponding application programming interface (API) component structured to facilitate communication among the circuits of the system. For example, a lender 5108 may interface with the controller through secure access control interface 5152 (e.g., through access control instructions 5154) structured to interface to the controller through a secure access control circuit 5150. The data collection circuit 5112 may be structured to receive collateral data 5104 and entity information 5102 such as information about parties to the loan such as a lender, a borrower, or a third party, an item of collateral, a machine or property associated with a party to the loan, a product of a party to the loan, and the like. Collateral data 5104 may include a type of the item of collateral, a category of the item of collateral, a value of the item of collateral, a price of a type of the item of collateral, a value of a type of the item of collateral, a specification of the item of collateral, a product feature set of the item of collateral, a model of the item of collateral, a brand of the item of collateral, a manufacturer of the item of collateral, an age of the item of collateral, a liquidity of the item of collateral, a shelf-life of the item of collateral, a useful life of the item of collateral, a condition of the item of collateral, a valuation of the item of collateral, a status of the item of collateral, a context of the item of collateral, a state of the item of collateral, a storage location of the item of collateral, a history of the item of collateral, an ownership of the item of collateral, a caretaker of the item of collateral, a security of the item of collateral, a condition of an owner of the item of collateral, a lien on the item of collateral, a storage condition of the item of collateral, a maintenance history of the item of collateral, a usage history of the item of collateral, an accident history of the item of collateral, a fault history of the item of collateral, a history of ownership of the item of collateral, an assessment of the item of collateral, a geolocation of the item of collateral, a jurisdictional location of the item of collateral, and the like. The data collection circuit 5112 may determine a collateral condition based on the received data. The received data 5102, 5104 and the collateral condition 5110 may be provided to AI circuits 5142 which may include an automated agent circuit 5114 (e.g., processing events 5118, 5120), a smart contract services circuit 5122 and a loan management circuit 5132.

Figure 52:
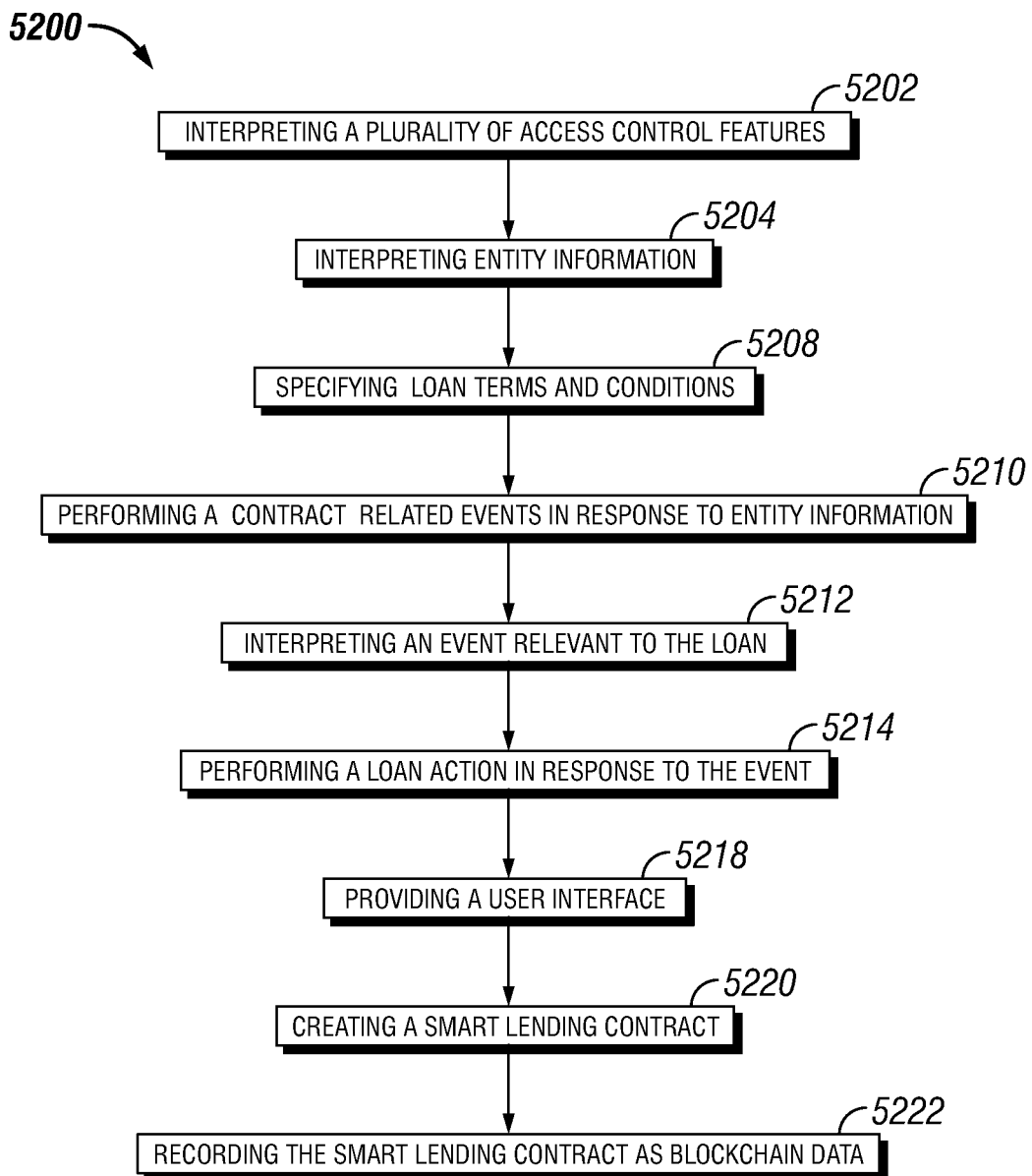
FIG. 52 depicts a method of processing entity data to initiate automatic loan-actions.

Referring to FIG. 52, an illustrative and non-limiting example method for handling a loan 5200 is depicted. The example method may include interpreting a plurality of access control features (step S202); interpreting entity information (step S204); specifying loan terms and conditions (step S208); performing a contract related events in response to entity information (step S210); interpreting an event relevant to the loan (step S212); performing a loan action in response to the event (step S214); providing a user interface (step S218); creating a smart lending contract (step S220); and recording the smart lending contract as blockchain data (step S222).

Figure 53:
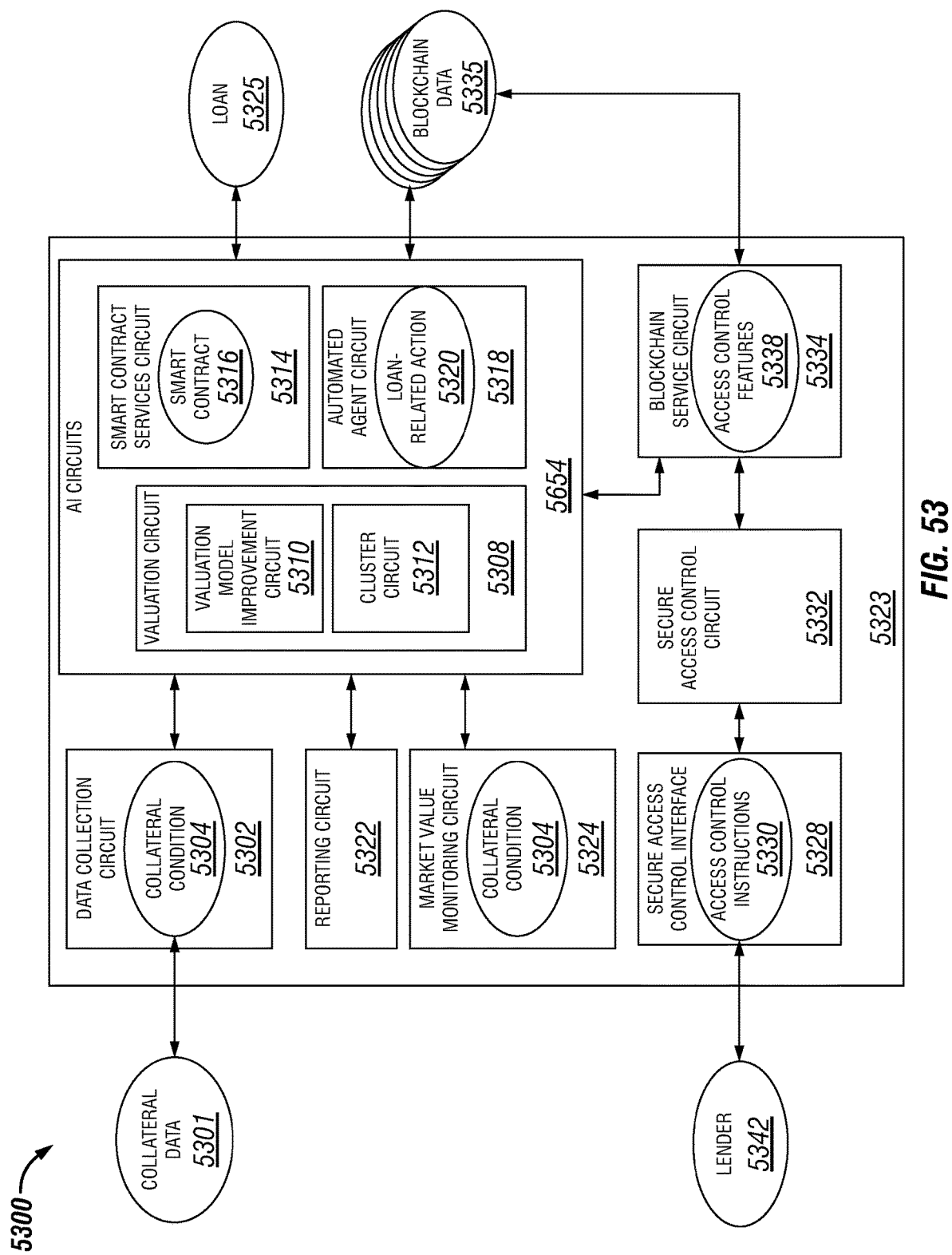
FIG. 53 depicts components and interactions of a lending platform to value collateral and determine collateral condition.

Referring to FIG. 53, depicts a system 5300 for adaptive intelligence and robotic process automation capabilities of a transactional, financial and marketplace enablement. The system 5300 may include a controller 5323 which may include a data collection circuit 5302 which receives collateral data 5301 and determines collateral condition 5304. The controller 5323 may further include a plurality of AI circuits 5654. The plurality of AI circuits 5654 may include a valuation circuit 5308 which may include a valuation model improvement circuit 5310 and a cluster circuit 5312. The plurality of AI circuits 5654 may include a smart contract services circuit 5314 including smart lending contracts 5316 for loans 5325. The plurality of AI circuits 5654 may include an automated agent circuit 5318 which takes loan-related actions 5320. The controller 5323 may further include a reporting circuit 5322 and a market value monitoring circuit 5324 which also determines collateral condition 5304. The controller 5323 may further include a secure access user interface 5328 which receives access control instructions 5330 from lenders 5342. The access control instructions 5330 are provided to a secure access control circuit 5332 which provides instructions to blockchain service circuit 5334 which interprets access control features 5338 and provides access to a lender 5342 or other party. The blockchain service circuit 5334 all stores the collateral data and a unique collateral ID as blockchain data 5335.

Figure 54:
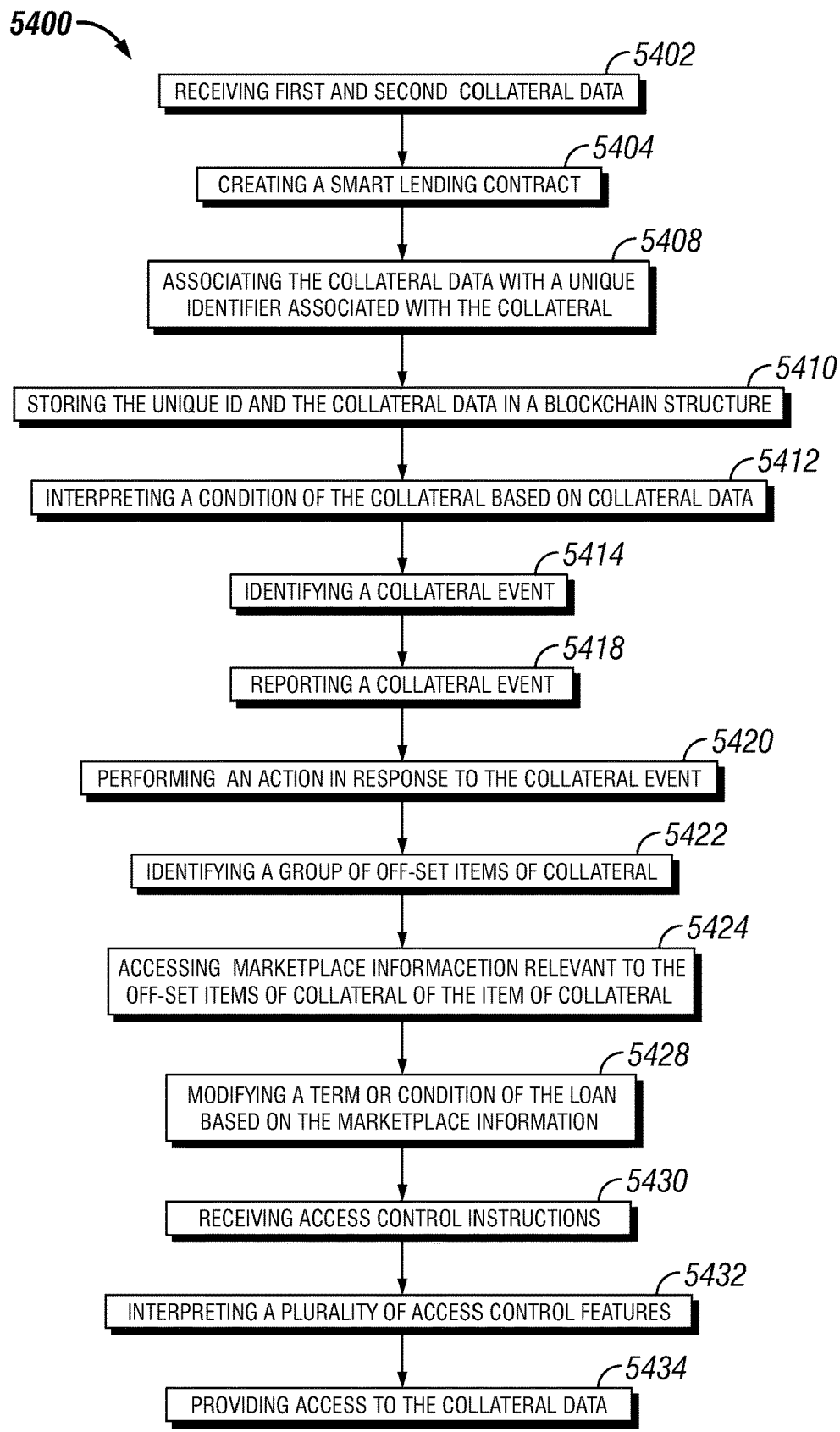
FIG. 54 depicts a method of processing collateral data to determine a collateral condition and initiate loan-actions in response.

Referring to FIG. 54, a method 5400 for automated smart contract creation and collateral assignment is depicted. The method 5400 may include receiving first and second collateral data regarding an item of collateral 5402, creating a smart lending contract 5404, associating the collateral data with a unique identifier for the item of collateral 5408, and storing the unique identifier and the collateral in a blockchain structure 5410. The method may further include interpreting a condition of the collateral based on the collateral data 5412, identifying a collateral event 5414, reporting a collateral event 5418, and performing an action in response to the collateral 5420. The method 5400 may further include identifying a group of offset items of collateral 5422, accessing marketplace information relevant to the offset items of collateral or the item of collateral 5424, and modifying a term or condition of the loan based on the marketplace information 5428. The method 5400 may further include receiving access control instructions 5430, interpreting a plurality of access control features 5432, and providing access to the collateral date 5434.

Referring to FIG. 55, an illustrative and non-limiting example system 5500 for handling a loan 5530 is depicted. The example system may include a controller 5501. The controller 5501 may include a data collection circuit 5512, a valuation circuit 5544, a user interface 5554 (e.g., for interface with a user 5506), a blockchain service circuit 5558, and several artificial intelligence circuits 5542 including a smart contract services circuit 5522, a loan management circuit 5922, a clustering circuit 5532, an automated agent circuit 5514 (e.g., for processing loan related events 5539 and loan actions 5538).

The blockchain service circuit 5558 may be structured to interface with a distributed ledger 5540. The data collection circuit 5512 may be structured to receive data related to a plurality of items of collateral 5504 or data related to environments of the plurality of items of collateral 5502. The valuation circuit 5544 may be structured to determine a value for each of the plurality of items of collateral based on a valuation model 5552 and the received data. The smart contract services circuit 5522 may be structured to interpret a smart lending contract 5531 for a loan, and to modify the smart lending contract 5531 by assigning, based on the determined value for each of the plurality of items of collateral, at least a portion of the plurality of items of collateral 5528 as security for the loan such that the determined value of the of the plurality of items of collateral is sufficient to provide security for the loan. The blockchain service circuit 5558 may be further structured to record the assigned at least a portion of items of collateral 5528 to an entry in the distributed ledger 5540, wherein the entry is used to record events relevant to the loan. Each of the blockchain service circuit, the data collection circuit, the valuation circuit and the smart contract circuit may further include a corresponding application programming interface (API) component structured to facilitate communication among the circuits of the system.

Modifying the smart lending contract 5531 may further include specifying terms and conditions 5524 that govern an item selected from the list consisting of: a loan term, a loan condition, a loan-related event, and a loan-related activity. The terms and conditions 5524 may each include at least one member selected from the group consisting of: a principal amount of the loan, a balance of the loan, a fixed interest rate, a variable interest rate description, a payment amount, a payment schedule, a balloon payment schedule, a collateral specification, a collateral substitution description, a description of at least one of the parties, a guarantee description, a guarantor description, a security description, a personal guarantee, a lien, a foreclosure condition, a default condition, a consequence of default, a covenant related to any one of the foregoing, and a duration of any one of the foregoing.

The loan 5530 may include at least one loan type selected from the loan types consisting of: an auto loan, an inventory loan, a capital equipment loan, a bond for performance, a capital improvement loan, a building loan, a loan backed by an account receivable, an invoice finance arrangement, a factoring arrangement, a pay day loan, a refund anticipation loan, a student loan, a syndicated loan, a title loan, a home loan, a venture debt loan, a loan of intellectual property, a loan of a contractual claim, a working capital loan, a small business loan, a farm loan, a municipal bond, and a subsidized loan.

The item of collateral may include at least one item selected from the items consisting of: a vehicle, a ship, a plane, a building, a home, a real estate property, an undeveloped land property, a farm, a crop, a municipal facility, a warehouse, a set of inventory, a commodity, a security, a currency, a token of value, a ticket, a cryptocurrency, a consumable item, an edible item, a beverage, a precious metal, an item of jewelry, a gemstone, an item of intellectual property, an intellectual property right, a contractual right, an antique, a fixture, an item of furniture, a tool, an item of machinery, and an item of personal property.

The data collection circuit 5512 may be further structured to receive outcome data 5510 related to the loan 5530 and a corresponding item of collateral, and wherein the valuation circuit 5544 comprises an artificial intelligent circuit structured to iteratively improve 5550 the valuation model 5552 based on the outcome data 5510.

The valuation circuit 5544 may further include a market value data collection circuit 5548 structured to monitor and report marketplace information relevant to the value of at least one of the plurality of items of collateral. The market value data collection circuit 5548 may be further structured to monitor pricing or financial data for items that are similar to the item of collateral in at least one public marketplace.

The clustering circuit 5532 may be structured to identify a set of offset items 5534 for use in valuing the item of collateral based on similarity to an attribute of the collateral.

The attribute of the collateral may be selected from among a list of attributes consisting of a category of the collateral, an age of the collateral, a condition of the collateral, a history of the collateral, a storage condition of the collateral, and a geolocation of the collateral.

The data collection circuit 5512 may be further structured to interpret a condition 5511 of the item of collateral.

The data collection circuit may further include at least one system selected from the systems consisting of: an Internet of Things system, a camera system, a networked monitoring system, an internet monitoring system, a mobile device system, a wearable device system, a user interface system, and an interactive crowdsourcing system.

The loan includes at least one loan type selected from the loan types consisting of: an auto loan, an inventory loan, a capital equipment loan, a bond for performance, a capital improvement loan, a building loan, a loan backed by an account receivable, an invoice finance arrangement, a factoring arrangement, a pay day loan, a refund anticipation loan, a student loan, a syndicated loan, a title loan, a home loan, a venture debt loan, a loan of intellectual property, a loan of a contractual claim, a working capital loan, a small business loan, a farm loan, a municipal bond, and a subsidized loan.

A loan management circuit 5922 may be structured to interpret an event relevant to the loan 5539, and to perform an action 5538 related to the loan in response to the event relevant to the loan.

The event relevant to the loan may include an event relevant to at least one of: a value of the loan, a condition of collateral of the loan, or an ownership of collateral of the loan.

The action related to the loan may include at least one of: modifying the terms and conditions for the loan, providing a notice to one of the parties, providing a required notice to a borrower of the loan, and foreclosing on a property subject to the loan.

The corresponding API components of the circuits may further include user interfaces structured to interact with a plurality of users of the system.

The plurality of users may each include: one of the plurality of parties, one of the plurality of entities, or a representative of any one of the foregoing. At least one of the plurality of users may include: a prospective party, a prospective entity, or a representative of any one of the foregoing.

Figure 56:
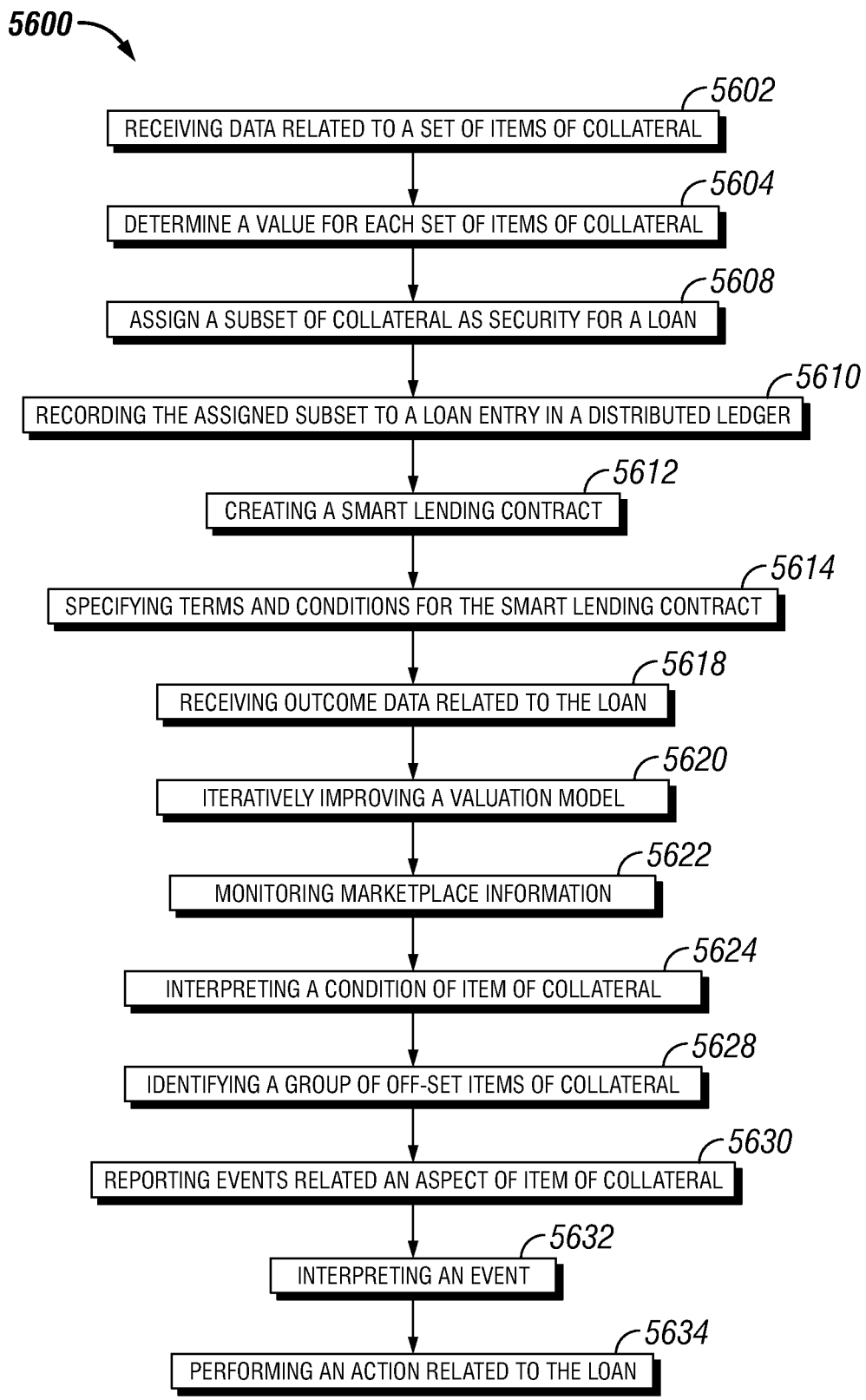
FIG. 56 depicts a method of a lending platform.

Referring to FIG. 56, an illustrative and non-limiting example method for handling a loan 5600 is depicted. The example method may include receiving data related to a plurality of items of collateral (step S602); setting a value for each of the plurality of items of collateral (step S604); assigning at least a portion of the plurality of items of collateral as security for a loan (step S608); and recording the assigned at least a portion of the plurality of items of collateral to an entry in a distributed ledger, wherein the entry is used to record events relevant to the loan (step S610). A smart lending contract may be modified for the loan (step S612).

Terms and conditions may be specified for the loan (step S614). The terms and conditions are each selected from the list consisting of: a principal amount of debt, a balance of debt, a fixed interest rate, a variable interest rate, a payment amount, a payment schedule, a balloon payment schedule, a party, a guarantee, a guarantor, a security, a personal guarantee, a lien, a duration, a covenant, a foreclose condition, a default condition, and a consequence of default.

Outcome data related to the loan may be received (step S618). A valuation model may be iteratively improved based on the outcome data and corresponding collateral (step S620). Marketplace information relevant to the value of at least one of the plurality of items of collateral may be monitored (step S622).

A set of items similar to one of the plurality of items of collateral may be identified based on similarity to an attribute of the one of the plurality of items of collateral (step S624).

A condition of the one of the plurality of items of collateral may be interpreted (step S628).

Events related to a value of the one of the plurality of items of collateral, a condition of the one of the plurality of items of collateral, or an ownership of the one of the items of collateral may be reported (step S630).

An event relevant to: a value of one of the plurality of items of collateral, a condition of one of the plurality of items of collateral, or an ownership of one of the plurality of items of collateral may be interpreted (step S632); and an action related to the secured loan in response to the event relevant to the one of the plurality of items of collateral for said secured loan may be performed (step S634).

The loan-related action may be selected from among the actions consisting of: offering a loan, accepting a loan, underwriting a loan, setting an interest rate for a loan, deferring a payment requirement, modifying an interest rate for a loan, validating title for collateral, recording a change in title, assessing the value of collateral, initiating inspection of collateral, calling a loan, closing a loan, setting terms and conditions for a loan, providing notices required to be provided to a borrower, foreclosing on property subject to a loan, and modifying terms and conditions for a loan.

Figure 57:
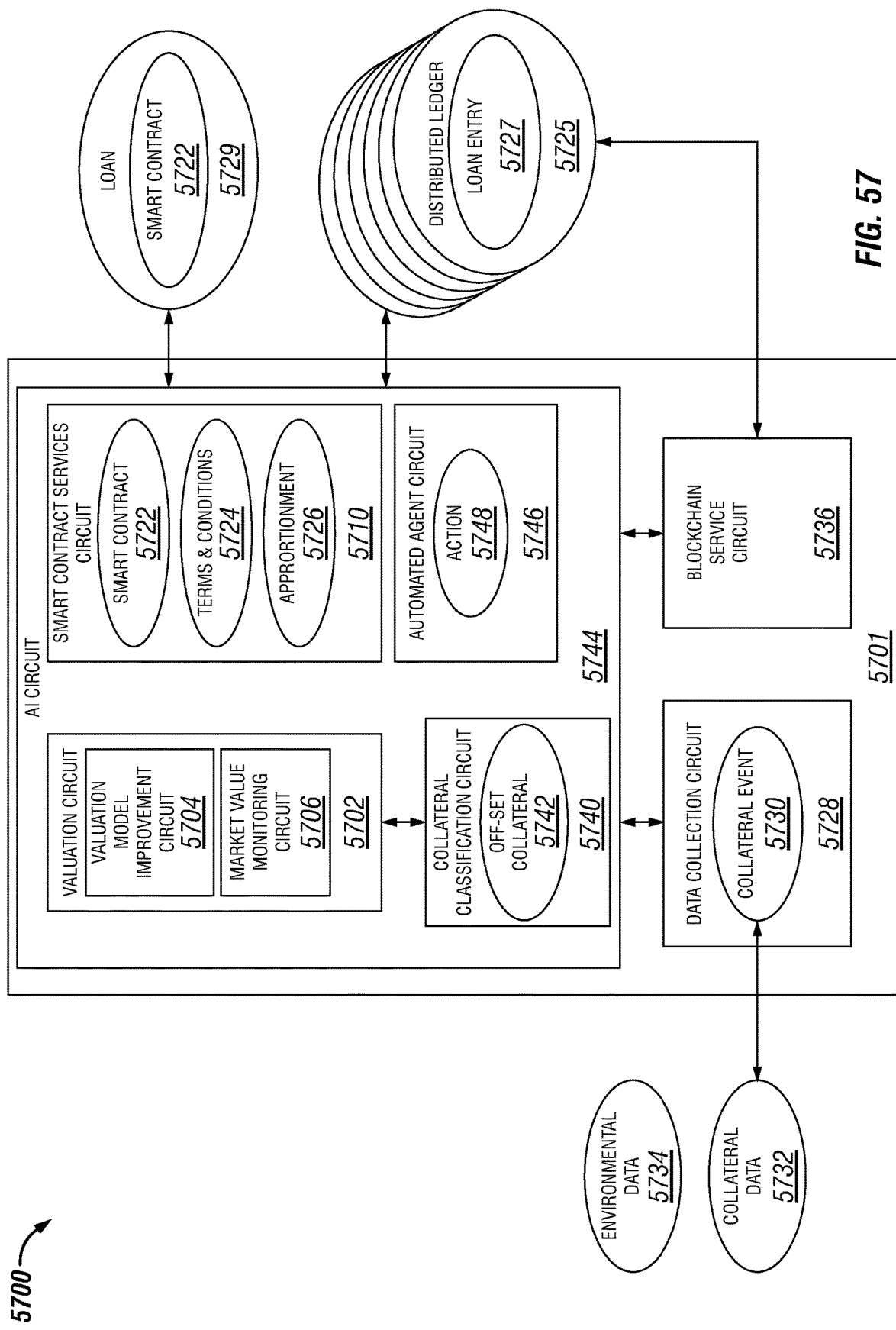
FIG. 57 depicts components and interactions of a lending platform that identifies a collateral event and initiates an automatic action in response.

Referring to FIG. 57, an illustrative and non-limiting example system for system for adaptive intelligence and robotic process automation capabilities 5700 is depicted. The example system may include a controller 5701. The controller may include a data collection circuit 5728 which may collect data such as collateral data 5732, environmental data 5734 related to the collateral, and the like from a variety of sources and systems such as: an Internet of Things system, a camera system, a networked monitoring system, an internet monitoring system, a mobile device system, a wearable device system, a user interface system, and an interactive crowdsourcing system. Based on the received data 5732, 5734 the data collection circuit 5728 may identify a collateral event 5730.

The controller 5701 may also include a variety of AI circuits 5744, including a valuation circuit 5702 which may, based in part on the received data 5732, 5734, determine a value for an item of collateral. The valuation circuit 5702 may include a market value monitoring circuit 5706 structured to determine market data regarding an item of collateral or an offset item of collateral, where the market data may contribute to the valuation for the item of collateral. The AI circuits may also include a smart contract services circuit 5710 to facilitate services related to a loan 5729 such as creating a smart contract 5722, identifying terms and conditions 5724 for the smart contract 5722, identifying lender priorities and tracking apportionment of value 5726 among lenders. The smart contract services circuit 5710 may provide data to a block chain service circuit 5736 which is able to create and modify a loan entry 5727 on a distributed ledger 5725 where the loan entry 5727 may include terms and conditions, data regarding items of collateral used to secure the loan, lender priority and apportionment of value and the like. The AI circuits 5744 may also include a collateral classification circuit 5740 which creates groups of offset items of collateral 5704 which share at least one attribute with one of the items of collateral, where the common attribute may be a category of the items, an age of the items, a condition of the items, a history of the items, an ownership of the items, a caretaker of the items, a security of the items, a condition of an owner of the items, a lien on the items, a storage condition of the items, a geolocation of the items, a jurisdictional location of the items, and the like. The use of offset items of collateral 5742 may facilitate the market value monitoring circuit 5706 in obtaining relevant market data and in the overall determination of value for an item of collateral.

The data collection circuit 5728 may utilize the received data and a determination of value for an item of collateral to identify a collateral event 5730. Based on the collateral event 5730, an automated agent circuit 5746, may take an action 5748. The action 5748 may be a loan-related action such as offering the loan, accepting the loan, underwriting the loan, setting an interest rate for a loan, deferring a payment requirement, modifying the interest rate for the loan, calling the loan, closing the loan, setting terms and conditions for the loan, providing notices required to be provided to a borrower, foreclosing on property subject to the loan, modifying terms and conditions for the loan, and the like. The action 5748 may be a collateral-related action such as validating title for the one of a set of items of collateral, recording a change in title for one of a set of items of collateral, assessing the value of the one of a set of items of collateral, initiating inspection of one of a set of items of collateral, initiating maintenance of one of a set of items of collateral, initiating security for one of a set of items of collateral, modifying terms and conditions for one of a set of items of collateral, and the like.

Figure 58:
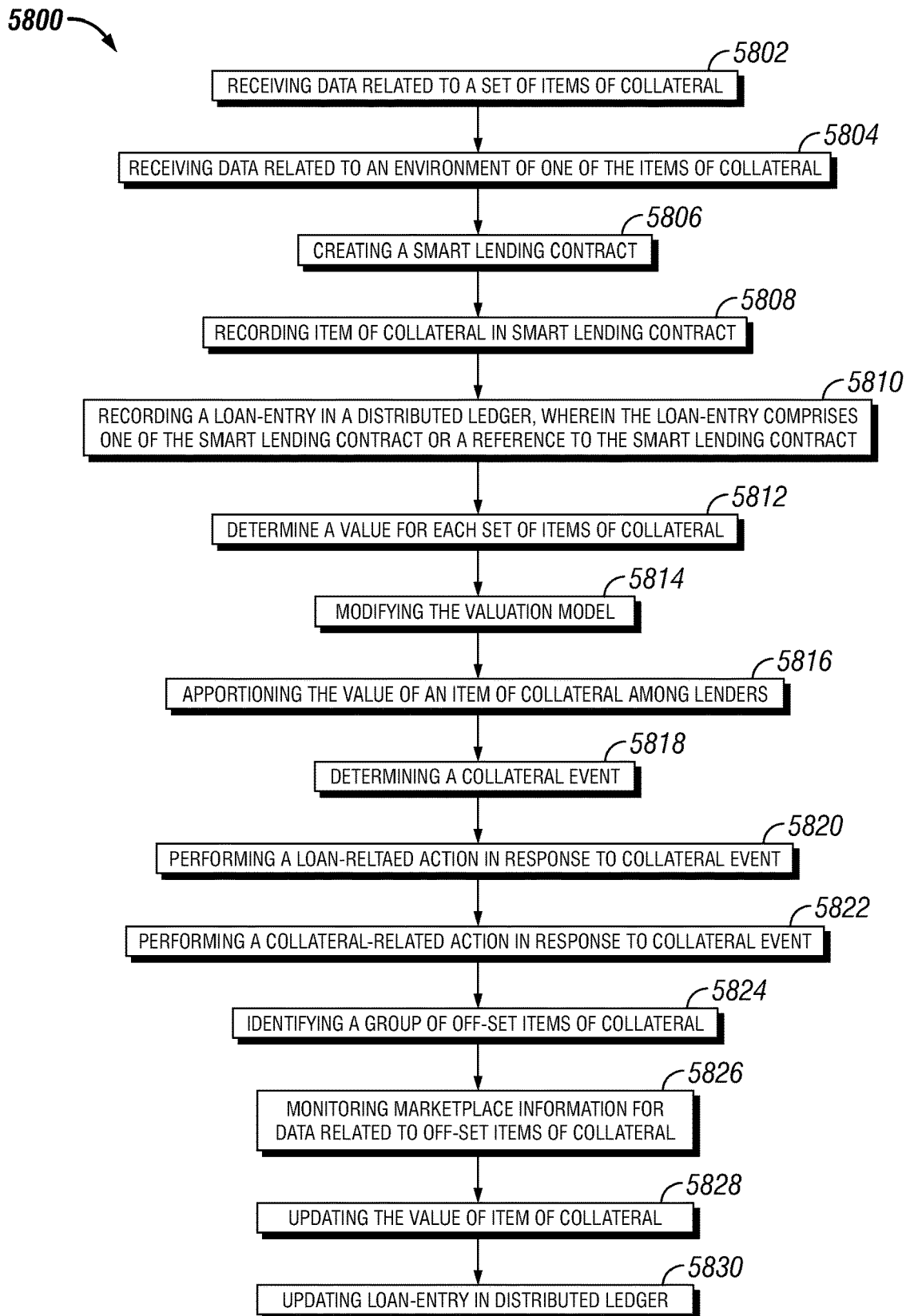
FIG. 58 depicts a method of a lending platform that automatically initiates a loan-action in response to a collateral event.

Referring to FIG. 58, an illustrative and non-limiting example method 5800 for loan creation and management is depicted. The example method 5800 may include receiving data related to a set of items of collateral (step S802) that provide security for a loan and receiving data related to an environment of one of a set of items of collateral (step S804). A smart lending contract for the loan may be created (step S806) and the set of items of collateral may be recorded in the smart lending contract (step S808). A loan-entry may be recoded in a distributed ledger (step S810) where the loan entry includes the smart lending contract or a reference to the smart contract.

The value for each of the set of items of collateral may be determined (5812) and the value of the items of collateral may be apportioned among lenders (step S816) based on the priority of the different lenders. The valuation model may be modified (step S814) based on a learning set including a set of valuation determinations of a set of items of collateral and the outcomes of loans having those items of collateral as security and the valuation of those items of collateral.

A collateral event may be determined (step S818) based on received data or a valuation of one of the items of collateral. A loan-related action may be performed in response to the determined collateral event (step S820) where the loan-related action includes offering the loan, accepting the loan, underwriting the loan, setting an interest rate for a loan, deferring a payment requirement, modifying the interest rate for the loan, calling the loan, closing the loan, setting terms and conditions for the loan, providing notices required to be provided to a borrower, foreclosing on property subject to the loan, modifying terms and conditions for the loan, or the like.

A collateral-related action may be performed in response to the determined collateral event (step S822), where the collateral-related action includes validating title for the one of the set of items of collateral, recording a change in title for the one of the set of items of collateral, assessing the value of the one of the set of items of collateral, initiating inspection of the one of the set of items of collateral, initiating maintenance of the one of the set of items of collateral, initiating security for the one of the set of items of collateral, modifying terms and conditions for the one of the set of items of collateral, or the like.

One or more group of offset items of collateral may be identified (step S824) where each item in a group of offset items of collateral shares a common attribute with at least one of the items of collateral. Marketplace information may then be monitored for data related to offset items of collateral (step S826). The monitored marketplace information regarding one or more offset items of collateral may be used to update a value of an item of collateral (step S828). The loan-entry in the distributed ledger may be updated (5830) with the updated value of the item of collateral.

Figure 59:
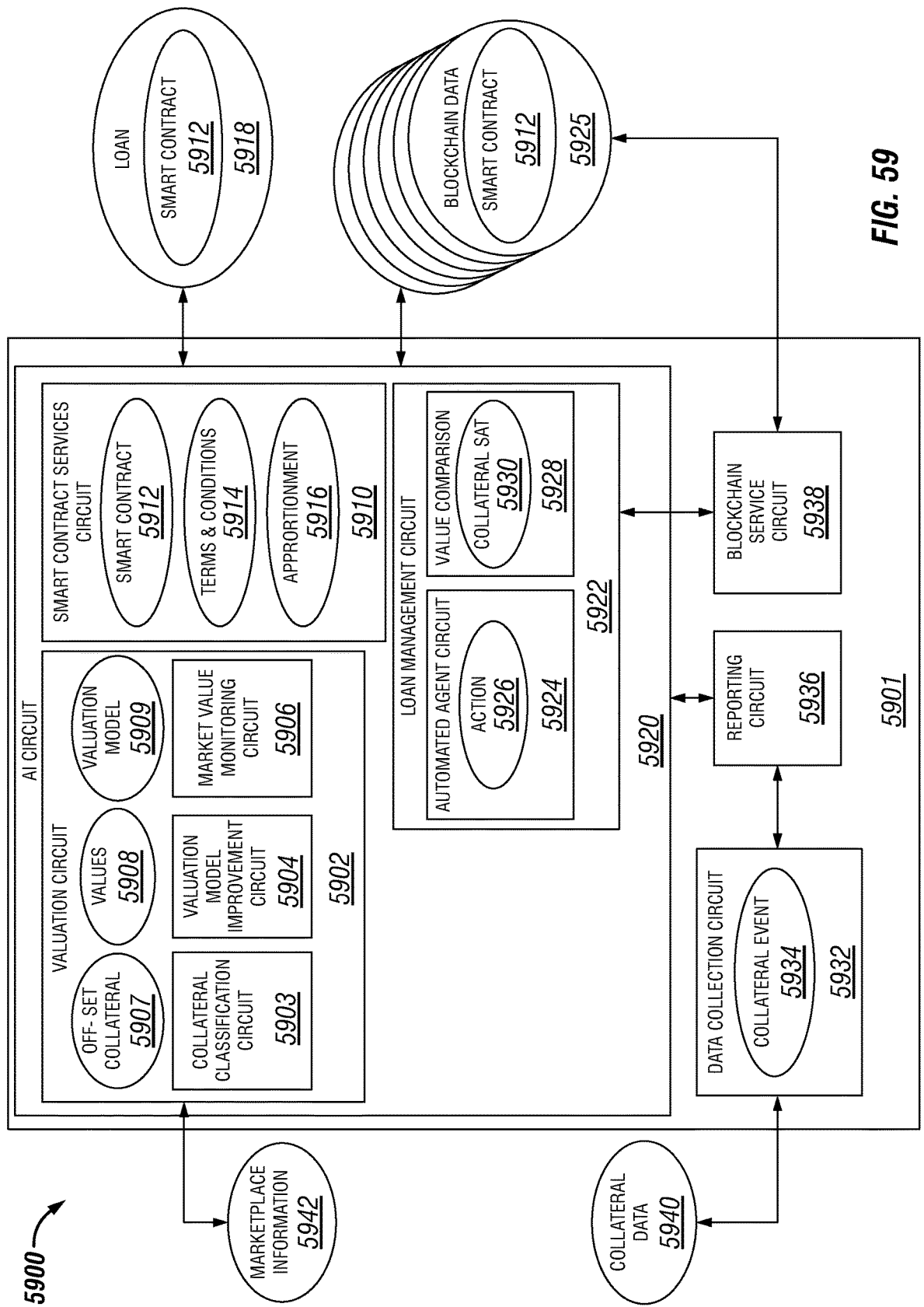
FIG. 59 depicts components and interactions of a lending platform.

Referring to FIG. 59, an example system 5900 for adaptive intelligence and robotic process automation capabilities of a transactional, financial and marketplace enablement is depicted. The system 5900 may include a controller 5901 which may include a plurality of AI circuits 5920. The plurality of AI circuits 5920 may include a smart contract services circuit 5910 to create and modify a smart lending contract 5912 for a loan 5918. Smart lending contracts 5912 may include the terms and conditions 5914 for the loan 5918, a covenant specifying a required value of collateral, information regarding a loan 5918, items of collateral, information on lenders, including lender priorities including apportionment 5916 of the value of items of collateral among the lenders.

The plurality of AI circuits 5920 may include a valuation circuit 5902 structured to determine one or more values 5908 for items of collateral based on a valuation model 5909 and collateral data 5940. The valuation circuit 5902 may include a collateral classification circuit 5903 to identify items of offset collateral 5907 based on common attributes with items of collateral used to secure a loan 5918. A market value monitoring circuit 5906 may receive marketplace information 5942 regarding items of collateral and offset items of collateral 5907. The marketplace information 5942 may be used by the valuation model 5909 in determining values 5908 for items of collateral. The valuation circuit 5902 may further include a valuation model improvement circuit 5904 to improve the valuation model 5909 used to determine values 5908. The valuation model improvement circuit 5904 may utilize a training set including previously determined values 5908 for items of collateral and data regarding the outcome of loans for which those items of collateral acted as security.

The plurality of AI circuits 5920 may include a loan management circuit 5922 which may include a value comparison circuit 5928 to compare a value 5908 of an item of collateral with a required value of the item of collateral as specified in a covenant of the loan, determining a collateral satisfaction value 5930. The smart contract services circuit 5910 may determine, in response to the collateral satisfaction value 5930, a term or a condition 5914 for a loan 5918, where the term of conditions 5914 is related to a loan component such as a loan party, a loan collateral, a loan-related event, and a loan-related activity for the smart lending contract 5912, and the like. The term of condition may be a principal amount of the loan, a balance of the loan, a fixed interest rate, a variable interest rate description, a payment amount, a payment schedule, a balloon payment schedule, a collateral specification, a collateral substitution description, a description of a party, a guarantee description, a guarantor description, a security description, a personal guarantee, a lien, a foreclosure condition, a default condition, a consequence of default, a covenant related to any one of the foregoing, a duration of any one of the foregoing, and the like. The term of condition may be a principal amount of debt, a balance of debt, a fixed interest rate, a variable interest rate, a payment amount, a payment schedule, a balloon payment schedule, a party, a guarantee, a guarantor, a security, a personal guarantee, a lien, a duration, a covenant, a foreclose condition, a default condition, a consequence of default, and the like. The smart contract services circuit 5910 may modify the smart lending contract 5912 to include new terms or conditions 5914, such as those determined in response to the collateral satisfaction value 5930.

The loan management circuit 5922 may also include an automated agent circuit 5924 to take an action 5926 based on the collateral satisfaction value 5930. The action 5926 may be a collateral-related action such as validating title for the item of collateral, recording a change in title for the item of collateral, assessing the value of the item of collateral, initiating inspection of the item of collateral, initiating maintenance of the item of collateral, initiating security for the item of collateral, modifying terms and conditions for the item of collateral, and the like. The action 5926 may be a loan-related action such as offering the loan, accepting the loan, underwriting the loan, setting an interest rate for a loan, deferring a payment requirement, modifying the interest rate for the loan, calling the loan, closing the loan, setting terms and conditions for the loan, providing notices required to be provided to a borrower, foreclosing on property subject to the loan, modifying terms and conditions for the loan, and the like.

The controller 5901 may also include a data collection circuit 5932 to receive collateral data 5940 and determine a collateral event 5934. The collateral event 5934 and collateral data 5940 may then be reported by a reporting circuit 5936. A blockchain service circuit 5938 may create and update blockchain data 5925 where a copy of the smart lending contract 5912 is stored.

Figure 60:
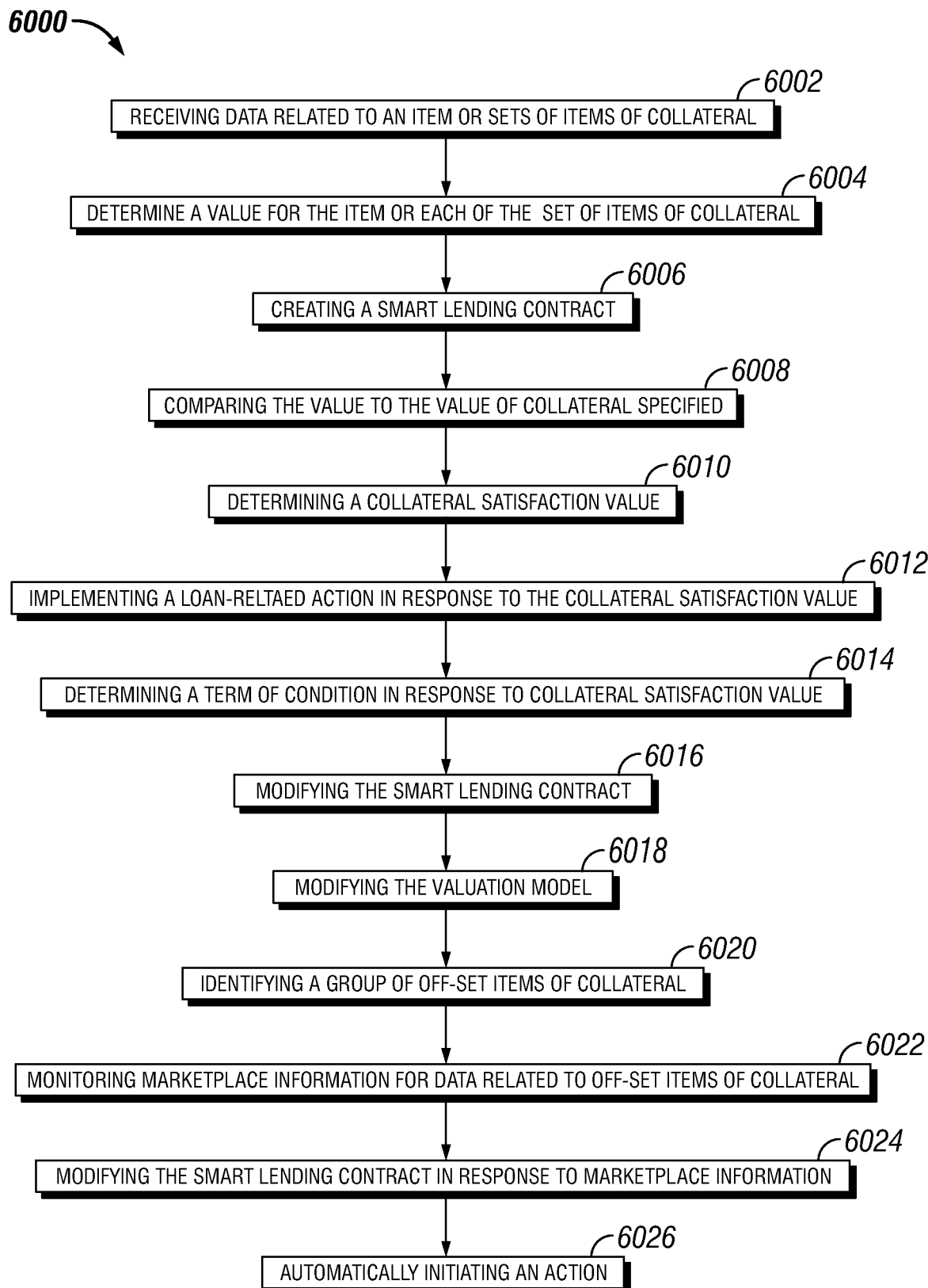
FIG. 60 depicts a method of a lending platform.

Referring to FIG. 60, an illustrative and non-limiting method 6000 for robotic process automation of transactional, financial and marketplace activities is depicted. An example method may include receiving data related to an item or set of items of collateral (step 6002) where the item(s) of collateral are acting as security for a loan. A value for the item of collateral is determined (step 6004) based on received data and a valuation model. A smart lending contract is created (step 6006) which specifies information about the loan including a covenant specifying a required value of collateral needed to secure the loan.

The value of the item(s) of collateral may be compared to the value of collateral specified in the covenant (step 6008) and a collateral satisfaction value determined (step 6010), where the collateral satisfaction value may be positive if the value of the collateral exceeds the required value of collateral or negative if the value of collateral is less than the required value of collateral. A loan-related action may be implemented in response to the collateral satisfaction value (step 6012). A term or condition may be determined in response to the collateral satisfaction value (step 6014) and the smart lending contract modified (step 6016).

The valuation model may be modified (step 6018) based on a first set of valuation determinations for a first set of items of collateral and a corresponding set of loan outcomes having the first set of items of collateral as security, using a machine learning system, a model-based system, a rule-based system, a deep learning system, a neural network, a convolutional neural network, a feed forward neural network, a feedback neural network, a self-organizing map, a fuzzy logic system, a random walk system, a random forest system, a probabilistic system, a Bayesian system, a simulation system, a hybrid system of at least two of any of the foregoing, and the like.

A group of offset items of collateral may be identified (step 6020) based on common attributes with the collateral such as a category of the item of collateral, an age of the item of collateral, a condition of the item of collateral, a history of the item of collateral, an ownership of the item of collateral, a caretaker of the item of collateral, a security of the item of collateral, a condition of an owner of the item of collateral, a lien on the item of collateral, a storage condition of the item of collateral, a geolocation of the item of collateral, and a jurisdictional location of the item of collateral. Marketplace information such as may be monitored for data related to the offset collateral (step 6022) such as pricing or financial data and the smart lending contract modified in response to the marketplace information (step 6024). An action may be automatically initiated (step 6026) based on the marketplace information. The action may include modifying a term of the loan, issuing a notice of default, initiating a foreclosure action modifying a conditions of the loan, providing a notice to a party of the loan, providing a required notice to a borrower of the loan, foreclosing on a property subject to the loan, validating title for the item of collateral, recording a change in title for the item of collateral, assessing the value of the item of collateral, initiating inspection of the item of collateral, initiating maintenance of the item of collateral, initiating security for the item of collateral, and modifying terms and conditions for the item of collateral, and the like.

Figure 61:
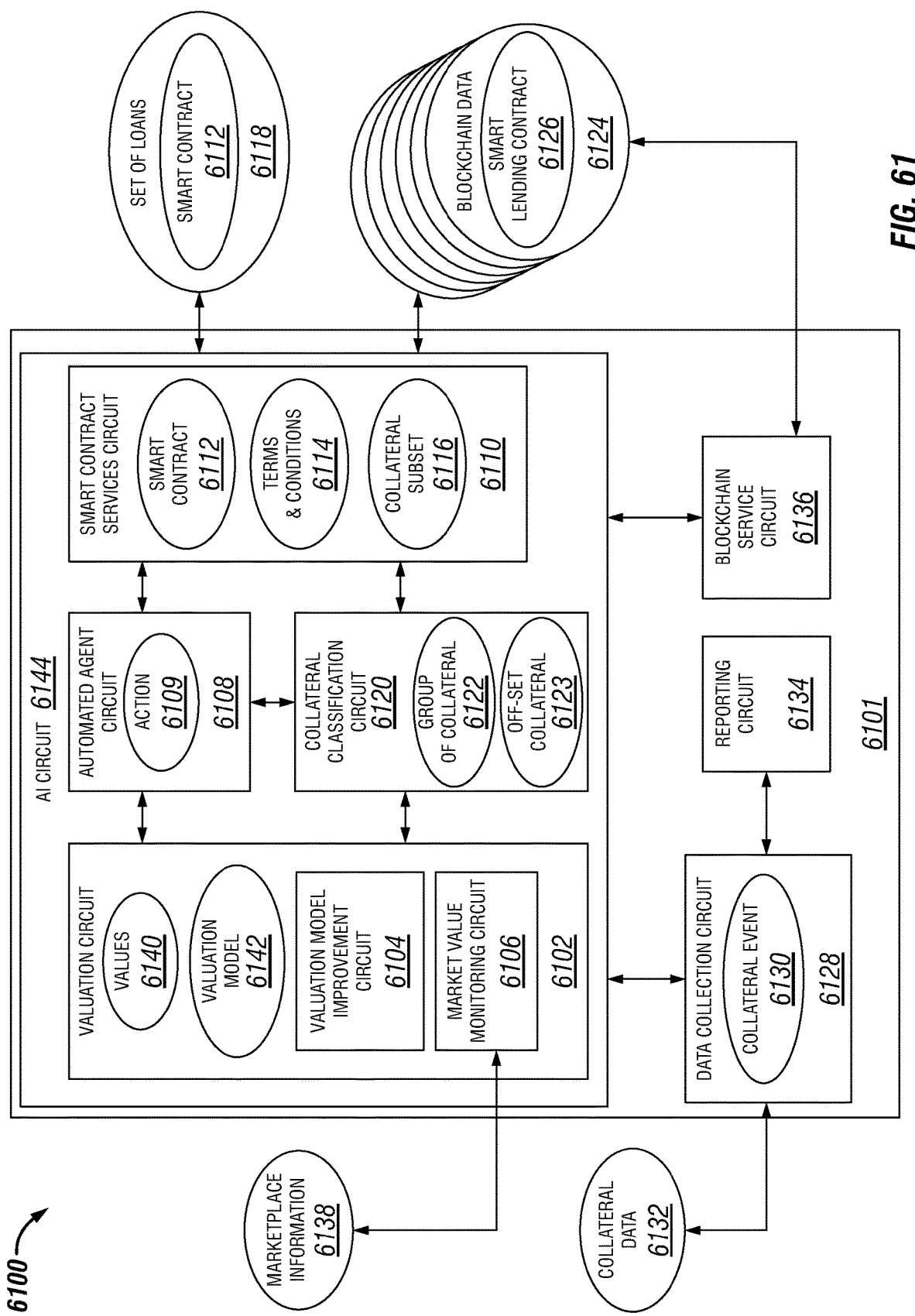
FIG. 61 depicts components and interactions of a lending platform.

Referring to FIG. 61, an illustrative and non-limiting example system for system for adaptive intelligence and robotic process automation capabilities 6100 is depicted. The example system may include a controller 6101 including a data collection circuit 6128 structured to receive collateral data 6132 regarding a plurality of items of collateral used to secure a set of loans 6118. The data collection circuit 6128 may include an Internet of Things system, a camera system, a networked monitoring system, an internet monitoring system, a mobile device system, a wearable device system, a user interface system, an interactive crowdsourcing system, and the like. The items of collateral may include a vehicle, a ship, a plane, a building, a home, a real estate property, an undeveloped land property, a farm, a crop, a municipal facility, a warehouse, a set of inventory, a commodity, a security, a currency, a token of value, a ticket, a cryptocurrency, a consumable item, an edible item, a beverage, a precious metal, an item of jewelry, a gemstone, an item of intellectual property, an intellectual property right, a contractual right, an antique, a fixture, an item of furniture, a tool, an item of machinery, an item of personal property, and the like. The set of loans may include an auto loan, an inventory loan, a capital equipment loan, a bond for performance, a capital improvement loan, a building loan, a loan backed by an account receivable, an invoice finance arrangement, a factoring arrangement, a pay day loan, a refund anticipation loan, a student loan, a syndicated loan, a title loan, a home loan, a venture debt loan, a loan of intellectual property, a loan of a contractual claim, a working capital loan, a small business loan, a farm loan, a municipal bond, a subsidized loan, and the like. The set of loans 6118 may be distributed among a plurality of borrowers as means of diversifying the risk of the loans.

The controller 6101 may also include a plurality of AI circuits 6144, including a collateral classification circuit 6120, to identify, from among the items of collateral, a group of collateral 6122 which related by sharing a common attribute, wherein the common attribute is among the received collateral data 6132, such as a type of the item of collateral, a category of the item of collateral, a value of the item of collateral, a price of a type of the item of collateral, a value of a type of the item of collateral, a specification of the item of collateral, a product feature set of the item of collateral, a model of the item of collateral, a brand of the item of collateral, a manufacturer of the item of collateral, an age of the item of collateral, a liquidity of the item of collateral, a shelf-life of the item of collateral, a useful life of the item of collateral, a condition of the item of collateral, a valuation of the item of collateral, a status of the item of collateral, a context of the item of collateral, a state of the item of collateral, a storage location of the item of collateral, a history of the item of collateral, an ownership of the item of collateral, a caretaker of the item of collateral, a security of the item of collateral, a condition of an owner of the item of collateral, a lien on the item of collateral, a storage condition of the item of collateral, a maintenance history of the item of collateral, a usage history of the item of collateral, an accident history of the item of collateral, a fault history of the item of collateral, a history of ownership of the item of collateral, an assessment of the item of collateral, a geolocation of the item of collateral, a jurisdictional location of the item of collateral, and the like. The collateral classification circuit 6120 may also identify offset collateral 6123 where items of offset collateral 6123 and the items of collateral share a common attribute.

The reporting circuit 6134 may also report a collateral event 6130 based on the collateral data 6132. An automated agent circuit 6108 may automatically perform an action 6109 based on the collateral event 6130. The action 6109 may be a collateral-related action such as validating title for one of the plurality of items of collateral, recording a change in title for one of the plurality of items of collateral, assessing the value of one of the plurality of items of collateral, initiating inspection of one of the plurality of items of collateral, initiating maintenance of the one of the plurality of items of collateral, initiating security for one of the plurality of items of collateral, modifying terms and conditions for one of the plurality of items of collateral, and the like. The action 6109 may be a loan-related action such as offering the loan, accepting the loan, underwriting the loan, setting an interest rate for a loan, deferring a payment requirement, modifying the interest rate for the loan, calling the loan, closing the loan, setting terms and conditions for the loan, providing notices required to be provided to a borrower, foreclosing on property subject to the loan, modifying terms and conditions for the loan, and the like.

The controller 6101 may also include a smart contract services circuit 6110 to create a smart lending contract 6112 for an individual loan or a set of loans 6118 where the smart lending contract 6112 identifies a subset of collateral 6116, selected from the group of related items of collateral 6122 sharing a common attribute, to act as security for the set of loans 6118. The smart contract services circuit 6110 may also redefine the subset of collateral 6116 based on an updated value for an item of collateral, thus rebalancing the items of collateral used for a set of loans based on the values of the collateral items. The identification of the subset of collateral 6116 may be identified in real-time when the common attribute changes in real time (e.g. a status of an item of collateral or whether collateral is in transit during a defined time period). Further, the smart contract services circuit 6110 may determine a term or condition 6114 for the loan based on a value of one of the items of collateral, where the term or the condition 6114 is related to a loan component such as a loan party, a loan collateral, a loan-related event, and a loan-related activity. The term or condition 6114 may be a principal amount of the loan, a balance of the loan, a fixed interest rate, a variable interest rate description, a payment amount, a payment schedule, a balloon payment schedule, a collateral specification, a collateral substitution description, a description of a party, a guarantee description, a guarantor description, a security description, a personal guarantee, a lien, a foreclosure condition, a default condition, a consequence of default, a covenant related to any one of the foregoing, a duration of any one of the foregoing, and the like. The controller 6101 may also include a smart contract services circuit 6110 that uses blockchain data 6124, including a smart lending contract 6126 and a blockchain service circuit 6136, also using blockchain data 6124, in communication with the smart contract services circuit 6110.

The controller may also include a valuation circuit 6102 to determine a value 6140 for each item of collateral in the subset of items collateral based on the received data and a valuation model 6142. A valuation model improvement circuit 6104 may modify the valuation model 6142 based on a first set of valuation determinations for a first set of items of collateral and a corresponding set of loan outcomes having the first set of items of collateral as security. The valuation model improvement circuit 6104 may include a machine learning system, a model-based system, a rule-based system, a deep learning system, a neural network, a convolutional neural network, a feed forward neural network, a feedback neural network, a self-organizing map, a fuzzy logic system, a random walk system, a random forest system, a probabilistic system, a Bayesian system, a simulation system, a hybrid system including at least two of the foregoing, or the like. The valuation circuit 6102 may also include a market value data collection circuit 6106 to monitor and report marketplace information 6138 such as pricing or financial data relevant to offset collateral 6123 or a group of collateral 6122.

Figure 62:
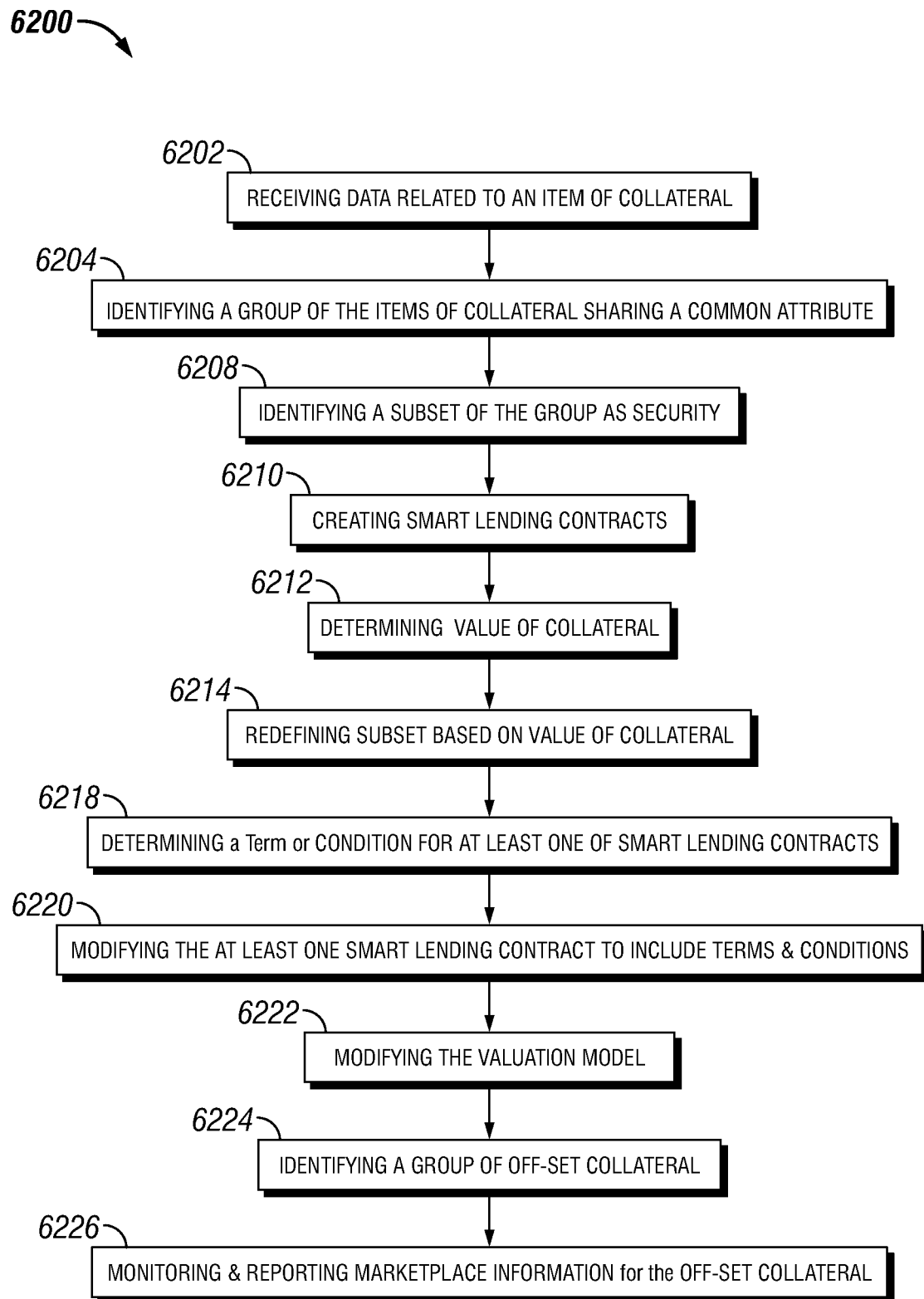
FIG. 62 depicts a method of a lending platform.

Referring to FIG. 62, a method 6200 for automated transactional, financial and marketplace activities. A method may include receiving data related to an item of collateral (6202), identifying a group of items of collateral (6204) where the items in the group share a common attribute or feature, identifying a subset of the group as security for a set of loans (6208) and creating a smart lending contract (6210) for the set of loans where the smart lending contract identifies the subset of group acting as security. The common attribute shared by the group of items of collateral may be in the received data.

The value of each item of collateral may be determined (6212) using the received data and a valuation model. The subset of collateral used as security may then be redefined based on the value of the different items of collateral (6214). A term of condition for at least one of the smart lending contracts may be determined (6218) based on the value for at least one of the items of collateral in the subset of the group and the smart lending contract modified to include the determined term or condition (6220). Further, in some embodiments, the valuation model may be modified (6222) based on a first set of valuation determinations for a first set of items of collateral and a corresponding set of loan outcomes having the first set of items of collateral as security.

A group of offset items of collateral may be identified (step 6224) where each member of the group of offset items of collateral and the group of the plurality of items share a common attribute. An information marketplace may be monitored and marketplace information reported (step 6226) for the group of offset items of collateral.

Figure 63:
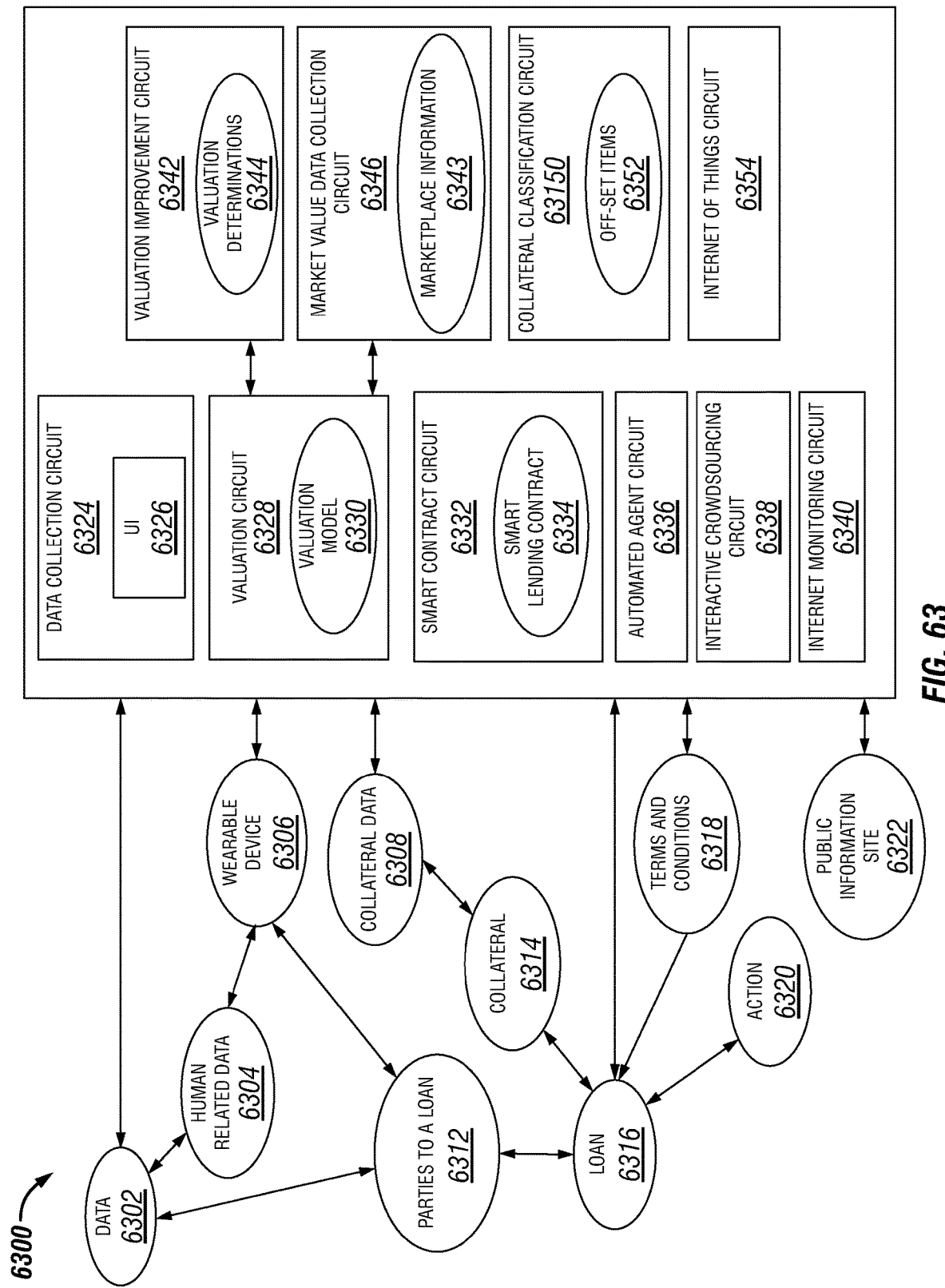
FIG. 63 depicts components and interactions of a lending platform.

FIG. 63 depicts a system 6300 including a data collection circuit 6324 structured to receive data 6302 related to a set of parties to a loan 6312. The data collection circuit may be structured to receive collateral-related data 6308 related to a set of items of collateral 6314 acting as security for the loan and determine a condition of the set of items of collateral, where the change in the interest rate may be based on a condition of the set of items of collateral. The item of collateral may be a vehicle, a ship, a plane, a building, a home, a real estate property, an undeveloped land property, a farm, a crop, a municipal facility, a warehouse, a set of inventory, a commodity, a security, a currency, a token of value, a ticket, a cryptocurrency, a consumable item, an edible item, a beverage, a precious metal, an item of jewelry, a gemstone, an item of intellectual property, an intellectual property right, a contractual right, an antique, a fixture, an item of furniture, a tool, an item of machinery, an item of personal property, and the like. The received data may include an attribute of the set of parties to the loan, where the change in the interest rate may be based in part on the attribute. The data collection circuit may include a system such as an Internet of Things circuit, an image capture device, a networked monitoring circuit, an internet monitoring circuit, a mobile device, a wearable device, a user interface circuit, an interactive crowdsourcing circuit, and the like. For instance, the data collection circuit may include an Internet of Things circuit 6354 structured to monitor attributes of the set of parties to the loan. The data collection circuit may include a wearable device 6306 associated with at least one of the set of parties, where the wearable device is structured to acquire human-related data 6304, and where the received data includes at least a portion of the human-related data. The data collection circuit may include a user interface circuit 6326 structured to receive data from the parties of the loan and provide the data from at least one of the parties of the loan as a portion of the received data. The data collection circuit may include an interactive crowdsourcing circuit 6338 structured to solicit data regarding at least one of the set of parties of the loan, receive solicited data, and provide at least a subset of the solicited data as a portion of the received data. The data collection circuit may include an internet monitoring circuit 6340 structured to retrieve data related to the parties of the loan from at least one publicly available information site 6322. The system may include a smart contract circuit 6332 structured to create a smart lending contract 6334 for the loan 6316. The loan may be a type selected from among loan types such as an inventory loan, a capital equipment loan, a bond for performance, a capital improvement loan, a building loan, a loan backed by an account receivable, an invoice finance arrangement, a factoring arrangement, a pay day loan, a refund anticipation loan, a student loan, a syndicated loan, a title loan, a home loan, a venture debt loan, a loan of intellectual property, a loan of a contractual claim, a working capital loan, a small business loan, a farm loan, a municipal bond, a subsidized loan, and the like. The smart contract circuit may be structured to determine a term or a condition 6318 for the smart lending contract based on the attribute and modify the smart lending contract to include the term or the condition. The term or condition may be related to a loan component, such as a loan party, a loan collateral, a loan-related event, a loan-related activity, and the like. The term or condition may be a principal amount of the loan, a balance of the loan, a fixed interest rate, a variable interest rate description, a payment amount, a payment schedule, a balloon payment schedule, a collateral specification, a collateral substitution description, a description of a party, a guarantee description, a guarantor description, a security description, a personal guarantee, a lien, a foreclosure condition, a default condition, a consequence of default, a covenant related to any one of the foregoing, a duration of any one of the foregoing, and the like. The system may include an automated agent circuit 6336 structured to automatically perform a loan-related action 6320 in response to the received data, where the loan-related action is a change in an interest rate for the loan, and where the smart contract circuit may be further structured to update the smart lending contract with the changed interest rate. The system may include a valuation circuit 6328 structured to determine, such as based on the received data and a valuation model 6330, a value for the at least one of the set of items of collateral. The smart contract circuit may be structured to determine a term or a condition for the smart lending contract based on the value for the at least one of the set of items of collateral and modify the smart lending contract to include the term or the condition. The term or the condition may be related to a loan component, such as a loan party, a loan collateral, a loan-related event, a loan-related activity, and the like. The term or the condition may be a principal amount of the loan, a balance of the loan, a fixed interest rate, a variable interest rate description, a payment amount, a payment schedule, a balloon payment schedule, a collateral specification, a collateral substitution description, a description of a party, a guarantee description, a guarantor description, a security description, a personal guarantee, a lien, a foreclosure condition, a default condition, a consequence of default, a covenant related to any one of the foregoing, a duration of any one of the foregoing, and the like. The valuation circuit may include a valuation model improvement circuit 6342, where the valuation model improvement circuit may modify the valuation model, such as based on a first set of valuation determinations 6344 for a first set of items of collateral and a corresponding set of loan outcomes having the first set of items of collateral as security. The valuation model improvement circuit may include a one system such as a machine learning system, a model-based system, a rule-based system, a deep learning system, a neural network, a convolutional neural network, a feed forward neural network, a feedback neural network, a self-organizing map, a fuzzy logic system, a random walk system, a random forest system, a probabilistic system, a Bayesian system, a simulation system, a hybrid system including at least two of the foregoing, and the like. The change in the interest rate may be further based on the value for the at least one of the set of items of collateral. The valuation circuit may include a market value data collection circuit 6346 structured to monitor and report marketplace information 6343 for offset items of collateral relevant to the value of the item of collateral. The market value data collection circuit may be structured to monitor one of pricing or financial data for the offset items of collateral in at least one public marketplace and report the monitored one of pricing or financial data. The system may include a collateral classification circuit 63150 structured to identify a group of offset items of collateral 6352, where each member of the group of offset items of collateral and at least one of the set of items of collateral share a common attribute. The common attribute may be a category of the item, an age of the item, a condition of the item, a history of the item, an ownership of the item, a caretaker of the item, a security of the item, a condition of an owner of the item, a lien on the item, a storage condition of the item, a geolocation of the item, a jurisdictional location of the item, and the like.

Figure 64:
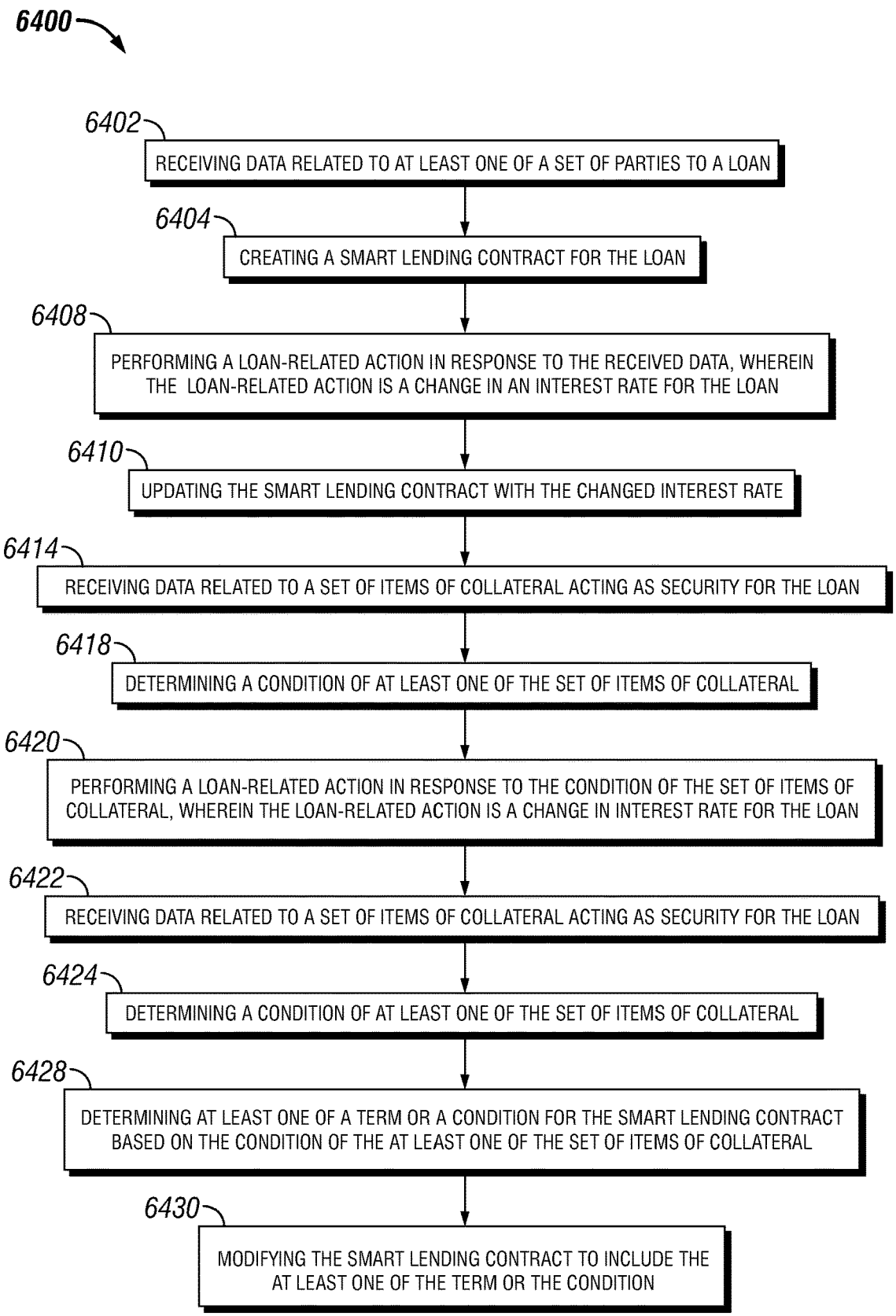
FIG. 64 depicts a method of a lending platform.

FIG. 64 depicts a method 6400 including receiving data related to at least one of a set of parties to a loan 6402, creating a smart lending contract for the loan 6404, performing a loan-related action in response to the received data, wherein the loan-related action is a change in an interest rate for the loan 6408, and updating the smart lending contract with the changed interest rate 6410. The method may further include receiving data related to a set of items of collateral acting as security for the loan 6414, determining a condition the set of items of collateral 6418, and performing a loan-related action in response to the condition of the set of items of collateral, where the loan-related action may be a change in interest rate for the loan 6420. The method may further include receiving data related to a set of items of collateral acting as security for the loan 6422, determining a condition of at least one of the set of items of collateral 6424, determining a term or a condition for the smart lending contract based on the condition of the at least one of the set of items of collateral 6428, and modifying the smart lending contract to include the term or the condition 6430. The method may include identifying a group of offset items of collateral wherein each member of the group of offset items of collateral and at least one of the set of items of collateral share a common attribute, and monitoring the group of offset items of collateral in a public marketplace, and further may report the monitored data. The method may include changing, such as based on the monitored group of offset items of collateral, the interest rate of the loan secured by at least one of the set of items of collateral.

Figure 65:
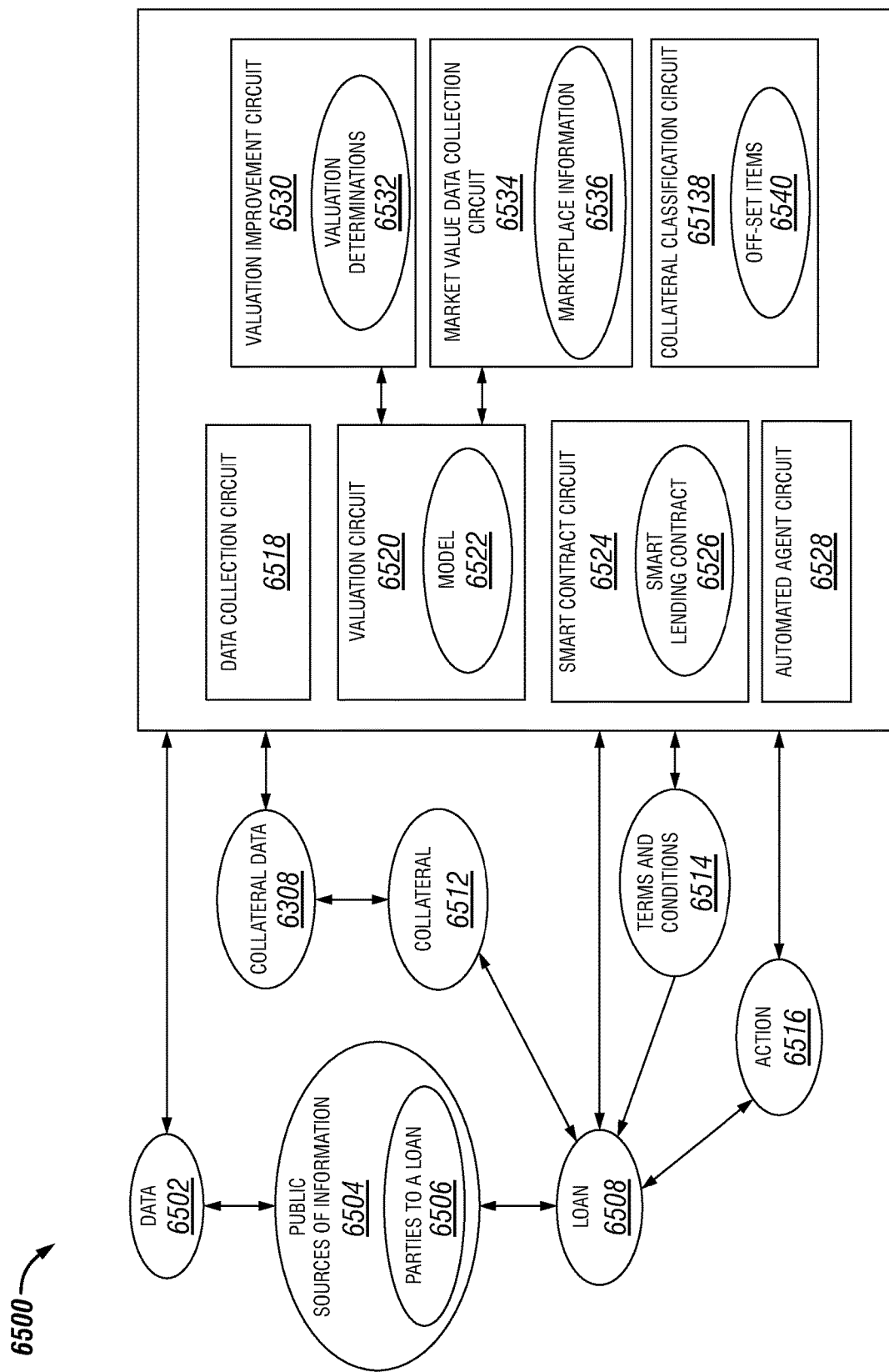
FIG. 65 depicts components and interactions of a lending platform.

FIG. 65 depicts a system 6500 including a data collection circuit 6518 structured to acquire data 6502, from public sources of information 6504 (e.g., a website, a news article, a social network, crowdsourced information, and the like), related to at least one party of a set of parties 6506 to a loan 6508 (e.g., primary lender, a secondary lender, a lending syndicate, a corporate lender, a government lender, a bank lender, a secured lender, bond issuer, a bond purchaser, an unsecured lender, a guarantor, a provider of security, a borrower, a debtor, an underwriter, an inspector, an assessor, an auditor, a valuation professional, a government official, an accountant, and the like). The data collection circuit may be further structured to receive collateral-related data 6308 related to a set of items of collateral 6512 acting as security for the loan and to determine a condition of at least one of the set of items of collateral, wherein the change in the interest rate is further based on the condition of the at least one of the set of items of collateral. The acquired data may include a financial condition of the at least one party of the set of parties to the loan. The financial condition may be determined based on at least one attribute of the at least one party of the set of parties to the loan, the attribute selected from among the list of attributes consisting of: a publicly stated valuation of the party, a set of property owned by the party as indicated by public records, a valuation of a set of property owned by the party, a bankruptcy condition of the party, a foreclosure status of the party, a contractual default status of the party, a regulatory violation status of the party, a criminal status of the party, an export controls status of the party, an embargo status of the party, a tariff status of the party, a tax status of the party, a credit report of the party, a credit rating of the party, a web site rating of the party, a set of customer reviews for a product of the party, a social network rating of the party, a set of credentials of the party, a set of referrals of the party, a set of testimonials for the party, a set of behavior of the party, a location of the party, a geolocation of the party, a judicial location of the party, and the like. The system may include a smart contract circuit 6524 structured to create a smart lending contract 6526 for the loan 6508. The smart contract circuit may be structured to specify terms and conditions in the smart lending contract, wherein one of a term or a condition in the smart lending contract governs one of loan-related events or loan-related activities. The system may include an automated agent circuit 6528 structured to automatically perform a loan-related action 6516 in response to the acquired data, wherein the loan-related action is a change in an interest rate for the loan, and wherein the smart contract circuit is further structured to update the smart lending contract with the changed interest rate. The automated agent circuit may be structured to identify an event relevant to the loan (e.g., a value of the loan, a condition of collateral of the loan, or an ownership of collateral of the loan), based, at least in part, on the received data. The automated agent circuit may be structured to perform, in response to the event relevant to the loan, an action selected from the list of actions, such as offering the loan, accepting the loan, underwriting the loan, setting an interest rate for the loan, deferring a payment requirement, modifying an interest rate for the loan, validating title for at least one of the set of items of collateral, assessing the value of at least one of the set of items of collateral, initiating inspection of at least one of the set of items of collateral, setting or modifying terms and conditions 6514 for the loan (e.g., a principal amount of debt, a balance of debt, a fixed interest rate, a variable interest rate, a payment amount, a payment schedule, a balloon payment schedule, a party, a guarantee, a guarantor, a security, a personal guarantee, a lien, a duration, a covenant, a foreclose condition, a default condition, and a consequence of default), providing a notice to one of the parties, providing a required notice to a borrower of the loan, foreclosing on a property subject to the loan, and the like. The loan may include a loan type, such as an auto loan, an inventory loan, a capital equipment loan, a bond for performance, a capital improvement loan, a building loan, a loan backed by an account receivable, an invoice finance arrangement, a factoring arrangement, a pay day loan, a refund anticipation loan, a student loan, a syndicated loan, a title loan, a home loan, a venture debt loan, a loan of intellectual property, a loan of a contractual claim, a working capital loan, a small business loan, a farm loan, a municipal bond, a subsidized loan, and the like. The acquired data may be related to the set of items of collateral such as a vehicle, a ship, a plane, a building, a home, a real estate property, an undeveloped land property, a farm, a crop, a municipal facility, a warehouse, a set of inventory, a commodity, a security, a currency, a token of value, a ticket, a cryptocurrency, a consumable item, an edible item, a beverage, a precious metal, an item of jewelry, a gemstone, an item of intellectual property, an intellectual property right, a contractual right, an antique, a fixture, an item of furniture, a tool, an item of machinery, an item of personal property, and the like. The system may include a valuation circuit 6520 structured to determine, based on the acquired data and a valuation model 6522, a value for at least one of the set of items of collateral. The valuation circuit may include a valuation model improvement circuit 6530, where the valuation model improvement circuit modifies the valuation model based on a first set of valuation determinations 6532 for a first set of items of collateral and a corresponding set of loan outcomes having the first set of items of collateral as security. The valuation model improvement circuit may include a machine learning system, a model-based system, a rule-based system, a deep learning system, a neural network, a convolutional neural network, a feed forward neural network, a feedback neural network, a self-organizing map, a fuzzy logic system, a random walk system, a random forest system, a probabilistic system, a Bayesian system, a simulation system, a hybrid system including at least two of the foregoing, and the like. The smart contract circuit may be further structured to determine a term or a condition for the smart lending contract based on the value for the at least one of the set of items of collateral and modify the smart lending contract to include the term or the condition, modify a term or condition of the loan based on the marketplace information for offset items of collateral relevant to the value of the item of collateral, and the like. The system may include a collateral classification circuit 65138 structured to identify a group of offset items of collateral, wherein each member of the group of offset items 6540 of collateral and at least one of the set of items of collateral share a common attribute (e.g., a category of the item, an age of the item, a condition of the item, a history of the item, an ownership of the item, a caretaker of the item, a security of the item, a condition of an owner of the item, a lien on the item, a storage condition of the item, a geolocation of the item, a jurisdictional location of the item, and the like). The valuation circuit may further include a market value data collection circuit 6534 structured to monitor and report marketplace information 6536 for offset items of collateral relevant to the value of the item of collateral, monitor pricing or financial data for the offset items of collateral in a public marketplace, and the like, and report the monitored pricing or financial data.

Figure 66:
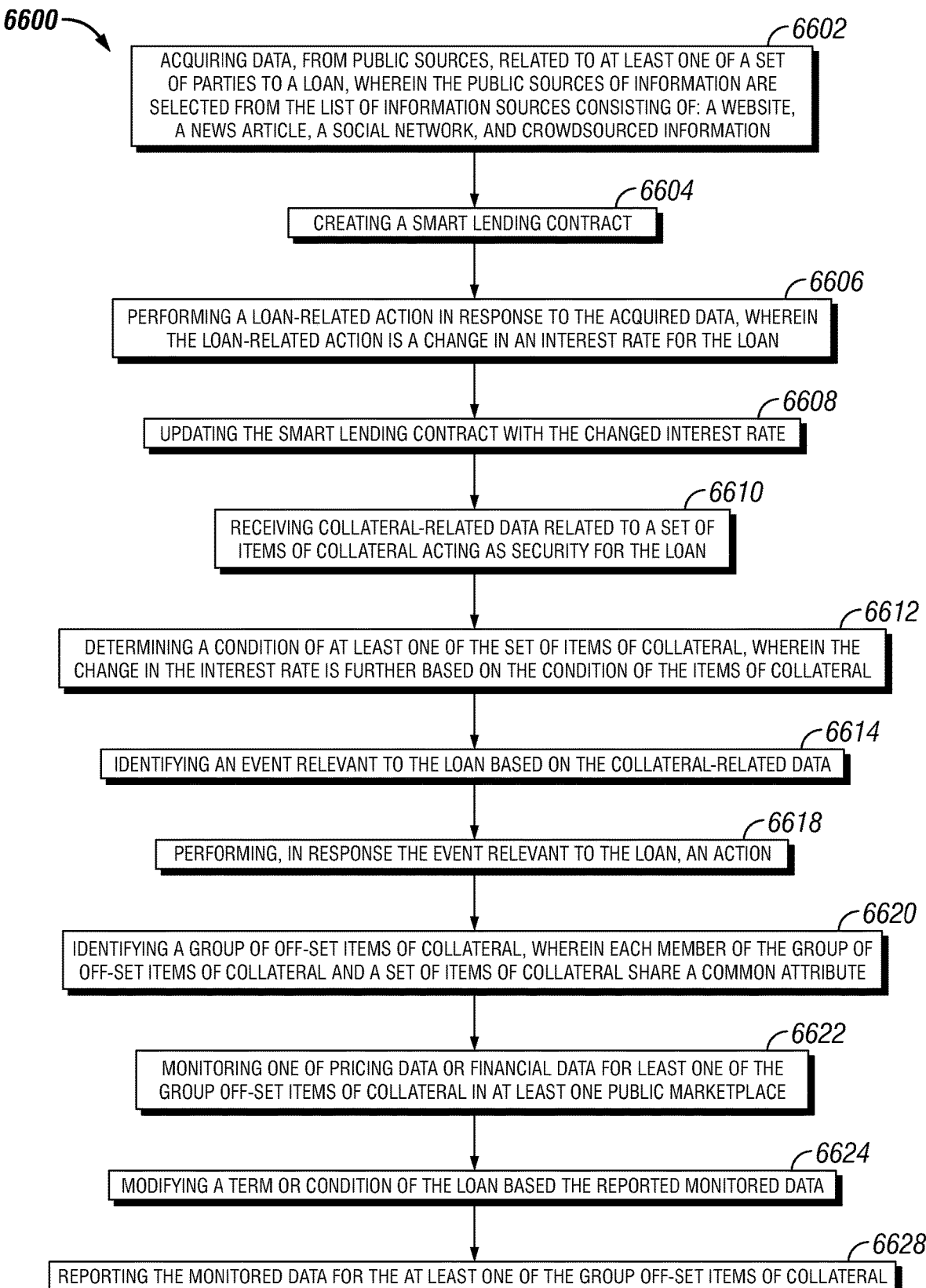
FIG. 66 depicts a method of a lending platform.

FIG. 66 depicts a method 6600 including acquiring data, from public sources, related to at least one of a set of parties to a loan, where the public sources of information may be selected from the list of information sources consisting of a website, a news article, a social network, and crowdsourced information 6602. The method may include creating a smart lending contract 6604. The method may include performing a loan-related action in response to the acquired data, wherein the loan-related action is a change in an interest rate for the loan 6606. The method may include updating the smart lending contract with the changed interest rate 6608. The method may include receiving collateral-related data related to a set of items of collateral acting as security for the loan 6610, and determining a condition of at least one of the set of items of collateral, wherein the change in the interest rate is further based on the condition of the at least one of the set of items of collateral 6612. The method may include identifying an event relevant to the loan based, at least in part, on the collateral-related data 6614, and performing, in response the event relevant to the loan, an action 6618, such as offering the loan, accepting the loan, underwriting the loan, setting an interest rate for the loan, deferring a payment requirement, modifying an interest rate for the loan, validating title for at least one of the set of items of collateral, assessing a value of at least one of the set of items of collateral, initiating inspection of at least one of the set of items of collateral, setting or modifying terms and conditions for the loan, providing a notice to one of the parties, providing a required notice to a borrower of the loan, foreclosing on a property subject to the loan, and the like. The method may include determining, based on at least one of the collateral-related data or the acquired data, and a valuation model, a value for at least one of the set of items of collateral. The method may include determining at least one of a term or a condition for the smart lending contract based on the value for the at least one of the set of items of collateral. The method may include modifying the smart lending contract to include the at least one of the term or the condition. The method may include modifying the valuation model based on a first set of valuation determinations for a first set of items of collateral and a corresponding set of loan outcomes having the first set of items of collateral as security. The method may include identifying a group of offset items of collateral, wherein each member of the group of offset items of collateral and at least one of the set of items of collateral share a common attribute 6620, monitoring one of pricing data or financial data for least one of the group offset items of collateral in at least one public marketplace 6622, reporting the monitored data for the at least one of the group offset items of collateral 6624, and modifying a term or condition of the loan based the reported monitored data 6628.

Figure 67:
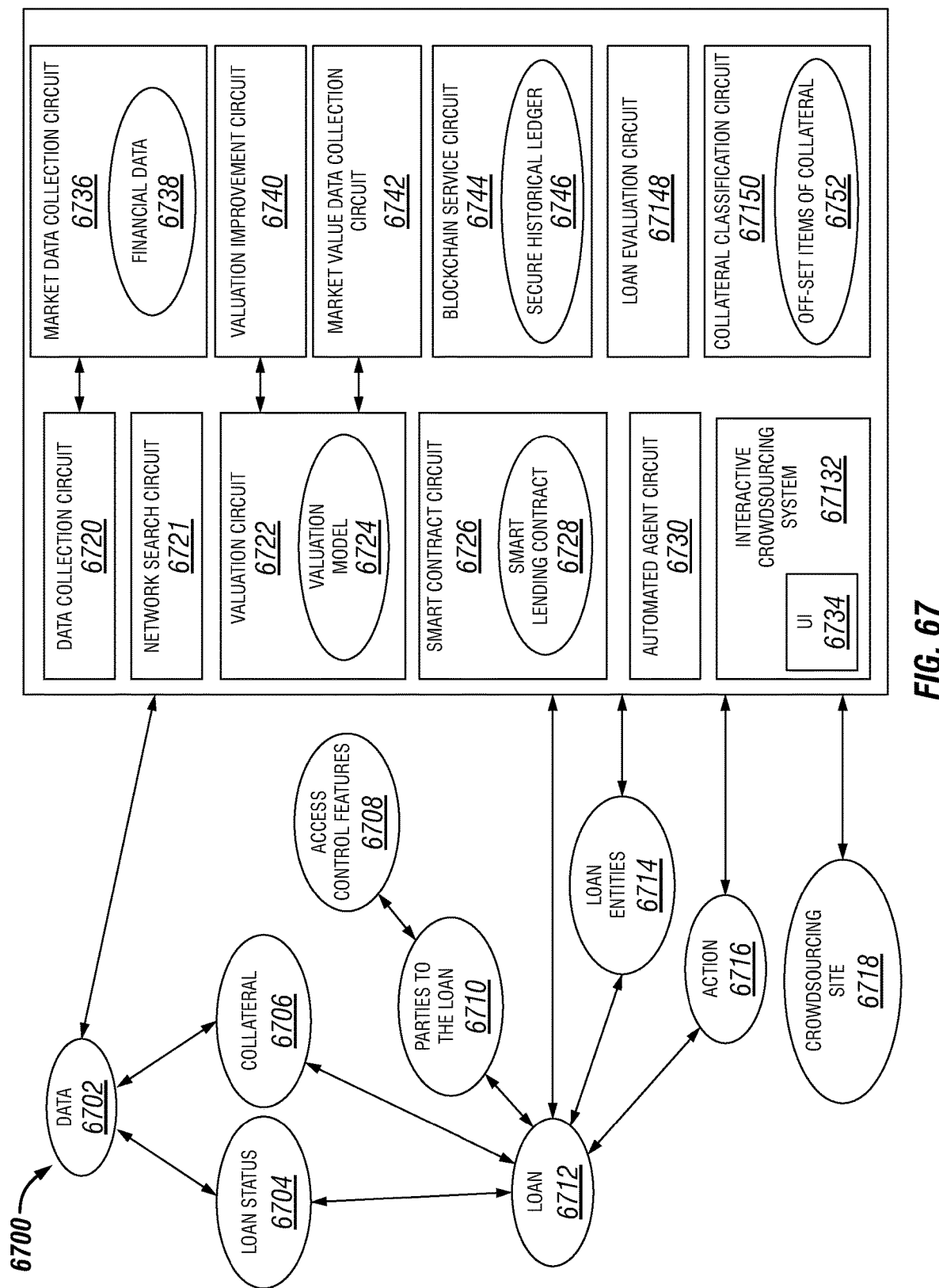
FIG. 67 depicts components and interactions of a lending platform.

FIG. 67 depicts a system 6700 including a data collection circuit 6720 structured to receive data 6702 relating to a status 6704 of a loan 6712 and data relating to a set of items of collateral 6706 acting as security for the loan. The data collection circuit may monitor one or more of the loan entities with a system such as an Internet of Things system, a camera system, a networked monitoring system, an internet monitoring system, a mobile device system, a wearable device system, a user interface system, and an interactive crowdsourcing system 67132. For instance, an interactive crowdsourcing system may include a user interface 6734, the user interface configured to solicit information related to one or more of the loan entities from a crowdsourcing site 6718, and where the user interface is structured to allow one or more of the loan entities to input information one or more of the loan entities. In another instance, a networked monitoring system may include a network search circuit 6721 structured to search publicly available information sites for information related one or more of the loan entities. The system may include a blockchain service circuit 6744 structured to maintain a secure historical ledger 6746 of events related to the loan, such as to interpret a plurality of access control features 6708 corresponding to a plurality of parties 6710 associated with the loan. The system may include a loan evaluation circuit 67148 structured to determine a loan status based on the received data. The data collection circuit may receive data related to one or more loan entities 6714, where the loan evaluation circuit may determine compliance with a covenant based on the data related to the one or more of the loan entities. The loan evaluation circuit may be structured to determine a state of performance for a condition of the loan based on the received data and a status of the one or more of the loan entities, and wherein the determination of the loan status is determined based in part on the status of the at least one or more of the loan entities and the state of performance of the condition for the loan. For instance, the condition of the loan may relate to at least one of a payment performance and a satisfaction on a covenant. The data collection circuit may include a market data collection circuit 6736 structured to receive financial data 6738 regarding at least one of the plurality of parties associated with the loan. The loan evaluation circuit may be structured to determine a financial condition of the least one of the plurality of parties associated with the loan based on the received financial data, where the at least one of the plurality of parties may be a primary lender, a secondary lender, a lending syndicate, a corporate lender, a government lender, a bank lender, a secured lender, bond issuer, a bond purchaser, an unsecured lender, a guarantor, a provider of security, a borrower, a debtor, an underwriter, an inspector, an assessor, an auditor, a valuation professional, a government official, an accountant, and the like. The received financial data may relate to an attribute of the entity for one of the plurality of parties, such as a publicly stated valuation of the party, a set of property owned by the party as indicated by public records, a valuation of a set of property owned by the party, a bankruptcy condition of the party, a foreclosure status of the entity, a contractual default status of the entity, a regulatory violation status of the entity, a criminal status of the entity, an export controls status of the entity, an embargo status of the entity, a tariff status of the entity, a tax status of the entity, a credit report of the entity, a credit rating of the entity, a web site rating of the entity, a set of customer reviews for a product of the entity, a social network rating of the entity, a set of credentials of the entity, a set of referrals of the entity, a set of testimonials for the entity, a set of behavior of the entity, a location of the entity, a geolocation of the entity, and the like. The system may include a smart contract circuit 6726 structured to create a smart lending contract 6728 for the loan. The smart contract circuit may be structured to determine a term or a condition for the smart lending contract based on the value for the at least one of the set of items of collateral and modify the smart lending contract to include the term or the condition, where the terms and conditions may be a principal amount of debt, a balance of debt, a fixed interest rate, a variable interest rate, a payment amount, a payment schedule, a balloon payment schedule, a party, a guarantee, a guarantor, a security, a personal guarantee, a lien, a duration, a covenant, a foreclose condition, a default condition, a consequence of default, and the like. The system may include an automated agent circuit 6730 structured to perform a loan-action 6716 based on the loan status, where the blockchain service circuit may be structured to update the historical ledger of events with the loan action. The system may include a valuation circuit 6722 structured to determine, based on the received data and a valuation model 6724, a value for at least one of the set of items of collateral. The valuation circuit may include a valuation model improvement circuit 6740, where the valuation model improvement circuit modifies the valuation model based on a first set of valuation determinations for a first set of items of collateral and a corresponding set of loan outcomes having the first set of items of collateral as security. The valuation model improvement circuit may include a machine learning system, a model-based system, a rule-based system, a deep learning system, a hybrid system, a neural network, a convolutional neural network, a feed forward neural network, a feedback neural network, a self-organizing map, a fuzzy logic system, a random walk system, a random forest system, a probabilistic system, a Bayesian system, and a simulation system. The valuation circuit may include a market value data collection circuit 6742 structured to monitor and report marketplace information for offset items of collateral relevant to the value of the item of collateral. The market value data collection circuit may be further structured to monitor pricing or financial data for the offset items of collateral in a public marketplace, such as to report the monitored pricing or financial data. The smart contract circuit may be further structured to modify a term or condition of the loan based on the marketplace information for offset items of collateral relevant to the value of the item of collateral. The system may include a collateral classification circuit 67150 structured to identify a group of offset items of collateral 6752, where each member of the group of offset items of collateral and at least one of the set of items of collateral may share a common attribute. The common attribute may be a category of the item of collateral, an age of the item of collateral, a condition of the item of collateral, a history of the item of collateral, an ownership of the item of collateral, a caretaker of the item of collateral, a security of the item of collateral, a condition of an owner of the item of collateral, a lien on the item of collateral, a storage condition of the item of collateral, a geolocation of the item of collateral, a jurisdictional location of the item of collateral, and the like.

Figure 68:
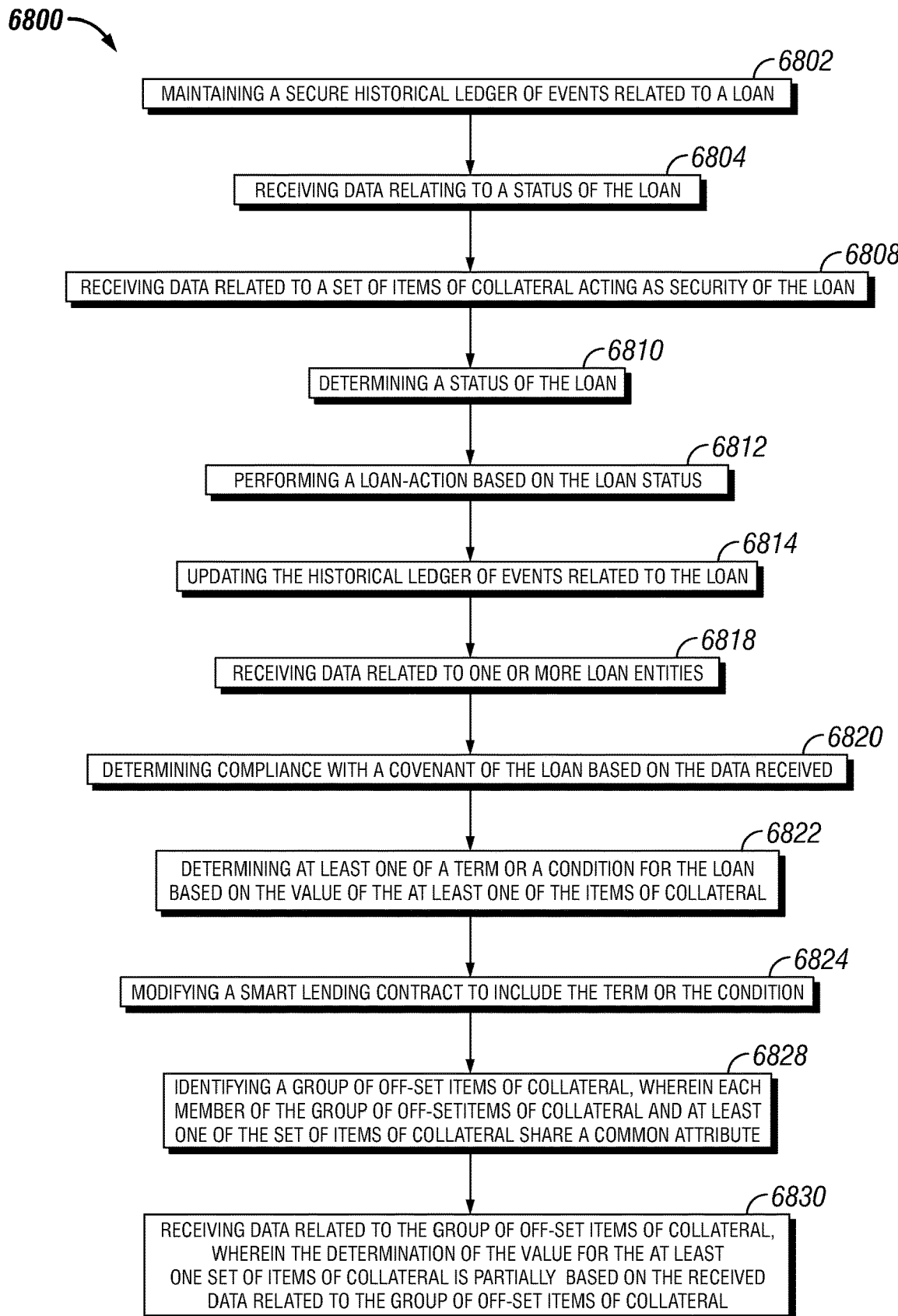
FIG. 68 depicts a method of a lending platform.

FIG. 68 depicts a method 6800 including maintaining a secure historical ledger of events related to a loan 6802, receiving data relating to a status of the loan 6804, receiving data related to a set of items of collateral acting as security of the loan 6808, determining a status of the loan 6810, performing a loan-action based on the loan status 6812 and updating the historical ledger of events related to the loan 6814. The method may further include receiving data related to one or more loan entities 6818 and determining compliance with a covenant of the loan based on the data received 6820. The method may further include determining a state of performance for a condition of the loan, where the determination of the loan status is based on part on the state of performance of the condition of the loan. The method may further include receiving financial data related to at least one party to the loan. The method may further include determining a financial condition of the at least one party to the loan based on the financial data. The method may further include determining a value for at least one set of items of collateral based on the received data and a valuation model. The method may further include determining at least one of a term or a condition for the loan based on the value of the at least one of the items of collateral 6822 and modifying a smart lending contract to include the at least one of the term or the condition 6824. The method may include 270 identifying a group of offset items of collateral, where each member of the group of offset items of collateral and at least one of the set of items of collateral share a common attribute 6828, receiving data related to the group of offset items of collateral, wherein the determination of the value for the at least one set of items of collateral is partially based on the received data related to the group of offset items of collateral 6830.

Figure 69:
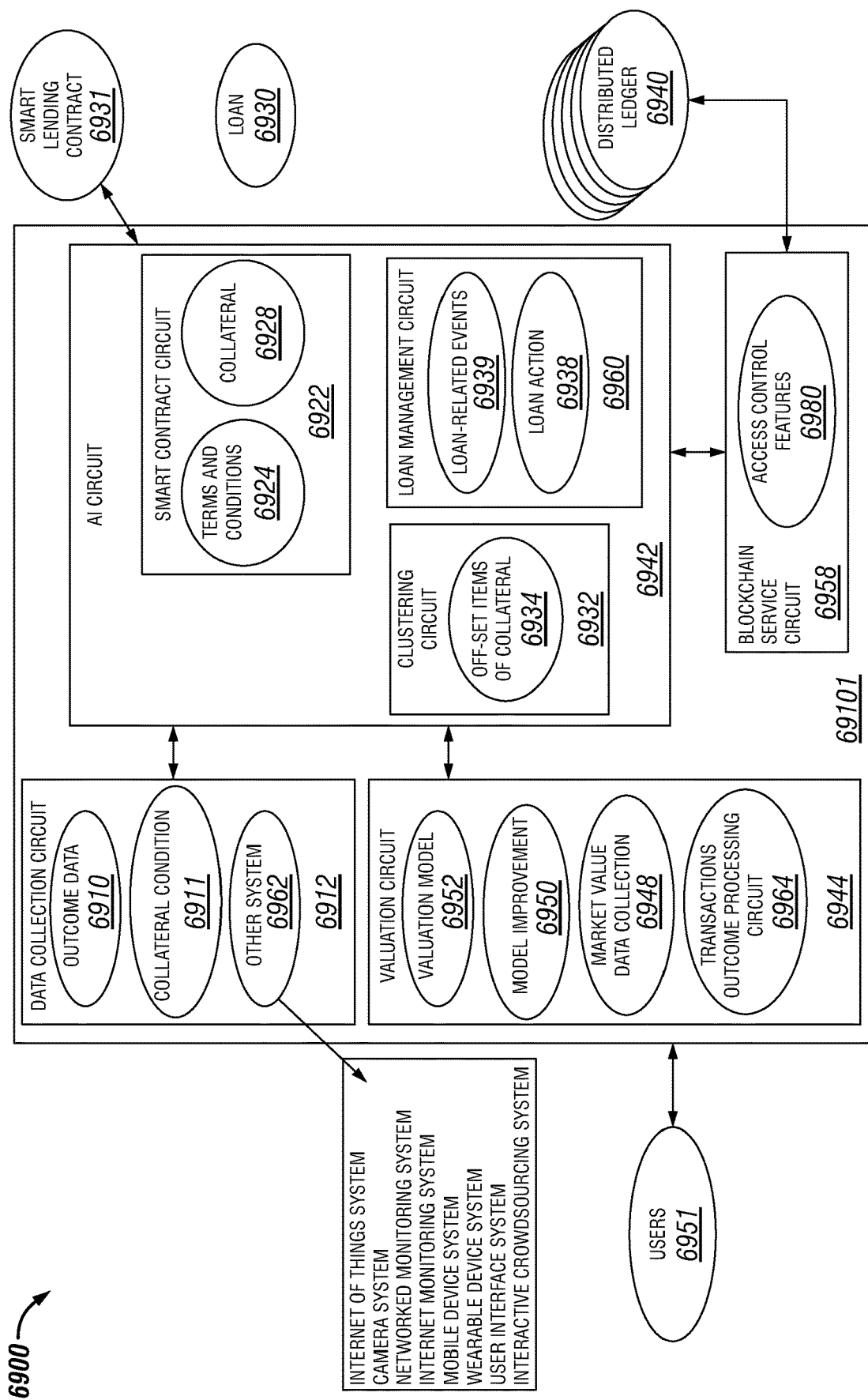
FIG. 69 depicts components and interactions of a lending platform.

Referring to FIG. 69, an illustrative and non-limiting example smart contract system for managing collateral for a loan 6900 is depicted. The example system may include a controller 69101. The controller 69101 may include a data collection circuit 6912 structured to monitor a status of a loan 6930 and of a collateral 6928 for the loan, and several artificial intelligence circuits 6942 including a smart contract circuit 6922 structured to process information from the data collection circuit 6912 and automatically initiate at least one of a substitution, a removal, or an addition of one or items from the collateral for the loan based on the information and a smart lending contract 6931 in response to at least one of the status of the loan or the status of the collateral for the loan; and a blockchain service circuit 6958 structured to interpret a plurality of access control features 6980 corresponding to at least one party associated with the loan and record the at least one substitution, removal, or addition in a distributed ledger 6940 for the loan. The data collection circuit may further include at least one other system 6962 selected from the systems consisting of: an Internet of Things system, a camera system, a networked monitoring system, an internet monitoring system, a mobile device system, a wearable device system, a user interface system, and an interactive crowdsourcing system.

A status of the loan 6930 may be determined based on the status of at least one of an entity (e.g., user 6951) related to the loan and a state of a performance of a condition for the loan. State of the performance of the condition may relate to at least one of a payment performance or a satisfaction of a covenant for the loan. The status of the loan may be determined based on a status of at least one entity related to the loan and a state of performance of a condition for the loan; and the performance of the condition may relate to at least one of a payment performance or a satisfaction of a covenant for the loan. The data collection circuit 6912 may be further structured to determine compliance with the covenant by monitoring the at least one entity. When the at least one entity is a party to the loan, the data collection circuit 6912 may monitor a financial condition of at least one entity that is a party to the loan. The condition for the loan may include a financial condition for the loan, and wherein the state of performance of the financial condition may be determined based on an attribute selected from the attributes consisting of: a publicly stated valuation of the at least one entity, a property owned by the at least one entity as indicated by public records, a valuation of a property owned by the at least one entity, a bankruptcy condition of the at least one entity, a foreclosure status of the at least one entity, a contractual default status of the at least one entity, a regulatory violation status of the at least one entity, a criminal status of the at least one entity, an export controls status of the at least one entity, an embargo status of the at least one entity, a tariff status of the at least one entity, a tax status of the at least one entity, a credit report of the at least one entity, a credit rating of the at least one entity, a website rating of the at least one entity, a plurality of customer reviews for a product of the at least one entity, a social network rating of the at least one entity, a plurality of credentials of the at least one entity, a plurality of referrals of the at least one entity, a plurality of testimonials for the at least one entity, a behavior of the at least one entity, a location of the at least one entity, a geolocation of the at least one entity, and a relevant jurisdiction for the at least one entity.

The party to the loan may be selected from the parties consisting of: a primary lender, a secondary lender, a lending syndicate, a corporate lender, a government lender, a bank lender, a secured lender, bond issuer, a bond purchaser, an unsecured lender, a guarantor, a provider of security, a borrower, a debtor, an underwriter, an inspector, an assessor, an auditor, a valuation professional, a government official, and an accountant.

The data collection circuit 6912 may be further structured to monitor the status of the collateral of the loan based on at least one attribute of the collateral selected from the attributes consisting of: a category of the collateral, an age of the collateral, a condition of the collateral 6911, a history of the collateral, a storage condition of the collateral, and a geolocation of the collateral.

The controller 69101 may include a valuation circuit 6944 which may be structured to use a valuation model 6952 to determine a value for the collateral based on the status of the collateral for the loan. The smart contract circuit 6922 may initiate the at least one substitution, removal or addition of one or more items from the collateral for the loan to maintain a value of collateral within a predetermined range.

The valuation circuit 6944 may further include a transactions outcome processing circuit 6964 structured to interpret outcome data 6910 relating to a transaction in collateral and iteratively improve 6950 the valuation model in response to the outcome data.

The valuation circuit 6944 may further include a market value data collection circuit 6948 structured to monitor and report on marketplace information relevant to a value of collateral. The market value data collection circuit 6948 may monitor pricing data or financial data for an offset collateral item 6934 in at least one public marketplace.

The market value data collection circuit 6948 is further structured to construct a set of offset collateral items 6934 used to value an item of collateral may be constructed using a clustering circuit 6932 of the controller 69101 based on an attribute of the collateral. The attributes may be selected from among a category of the collateral, an age of the collateral, a condition of the collateral, a history of the collateral, a storage condition of the collateral, and a geolocation of the collateral.

Terms and conditions 6924 for the loan may include at least one member selected from the group consisting of: a principal amount of debt, a balance of debt, a fixed interest rate, a variable interest rate, a payment amount, a payment schedule, a balloon payment schedule, a specification of collateral, a specification of substitutability of collateral, a party, a guarantee, a guarantor, a security, a personal guarantee, a lien, a duration, a covenant, a foreclose condition, a default condition, and a consequence of default.

The smart contract circuit may further include or be in communication with a loan management circuit 6960 structured to specify terms and conditions of the smart lending contract 6931 that governs at least one of loan terms and conditions, a loan-related event 6939 or a loan-related activity or action 6938.

Figure 70:
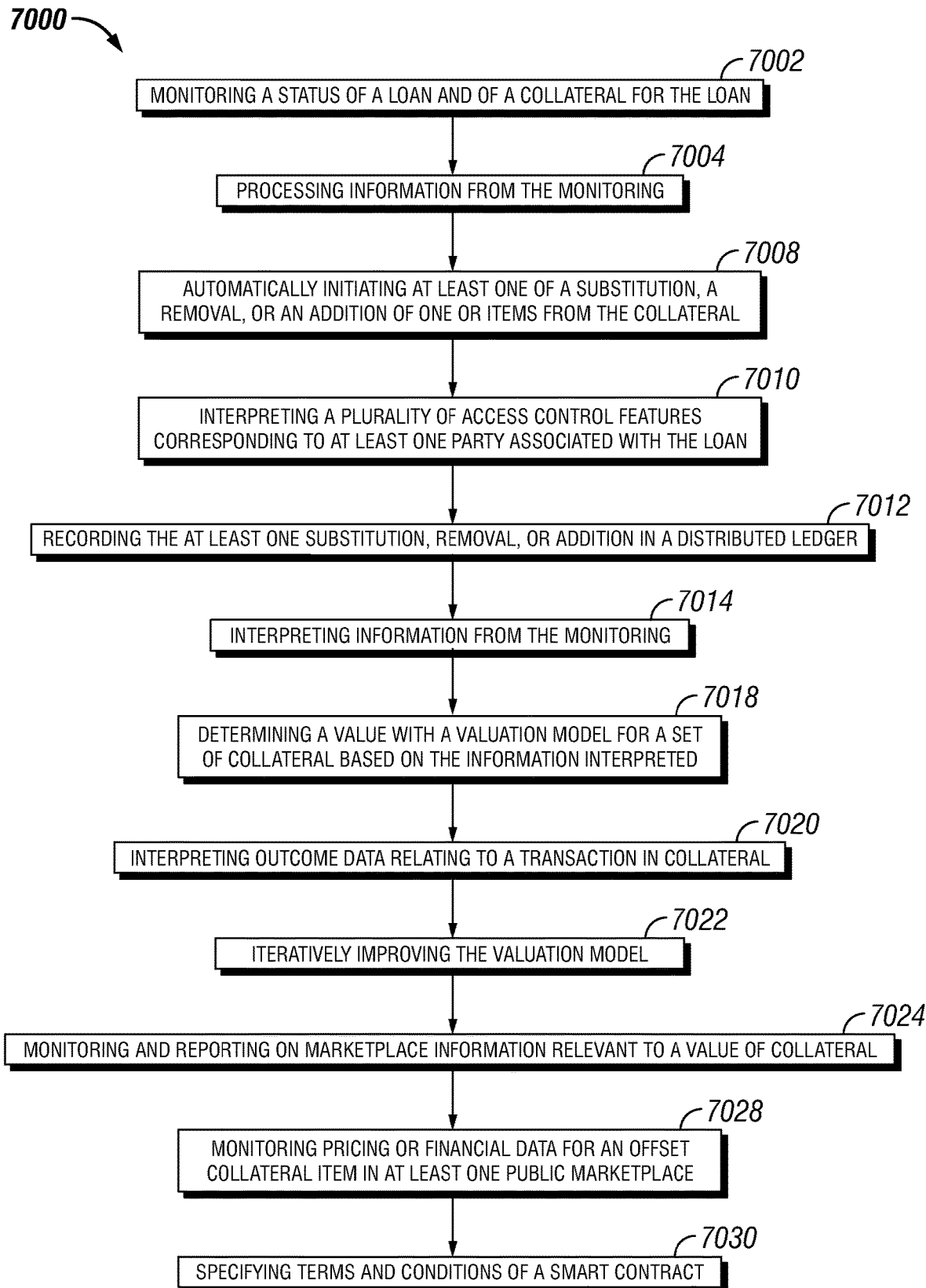
FIG. 70 depicts a method of a lending platform.

Referring to FIG. 70, an example smart contract method 7000 for managing collateral for a loan is depicted. The example method may include monitoring a status of a loan and of a collateral for the loan (step 7002); processing information from the monitoring (step 7004); automatically initiating at least one of a substitution, a removal, or an addition of one or more items from the collateral for the loan based on the information (step 7008); and interpreting a plurality of access control features corresponding to at least one party associated with the loan (step 7010) and recording the at least one substitution, removal, or addition in a distributed ledger for the loan (step 7012). A status of the loan may be determined based on the status of at least one of an entity related to the loan and a state of a performance of a condition for the loan.

The method may further include interpreting information from the monitoring (step 7014) and determining a value with a valuation model for a set of collateral based on at least one of the status of the loan or the collateral for the loan (step 7018). The at least one substitution, removal, or addition may be to maintain a value of collateral within a predetermined range. The method may further include interpreting outcome data relating to a transaction of one of the collateral or an offset collateral (step 7020) and iteratively improving the valuation model in response to the outcome data (step 7022). The method may further include monitoring and reporting on marketplace information relevant to a value of collateral (step 7024).

The method may further include monitoring pricing data or financial data for an offset collateral item in at least one public marketplace (step 7028).

The method may further include specifying terms and conditions of a smart contract that governs at least one of terms and conditions for the loan, a loan-related event or a loan-related activity (step 7030).

Figure 71:
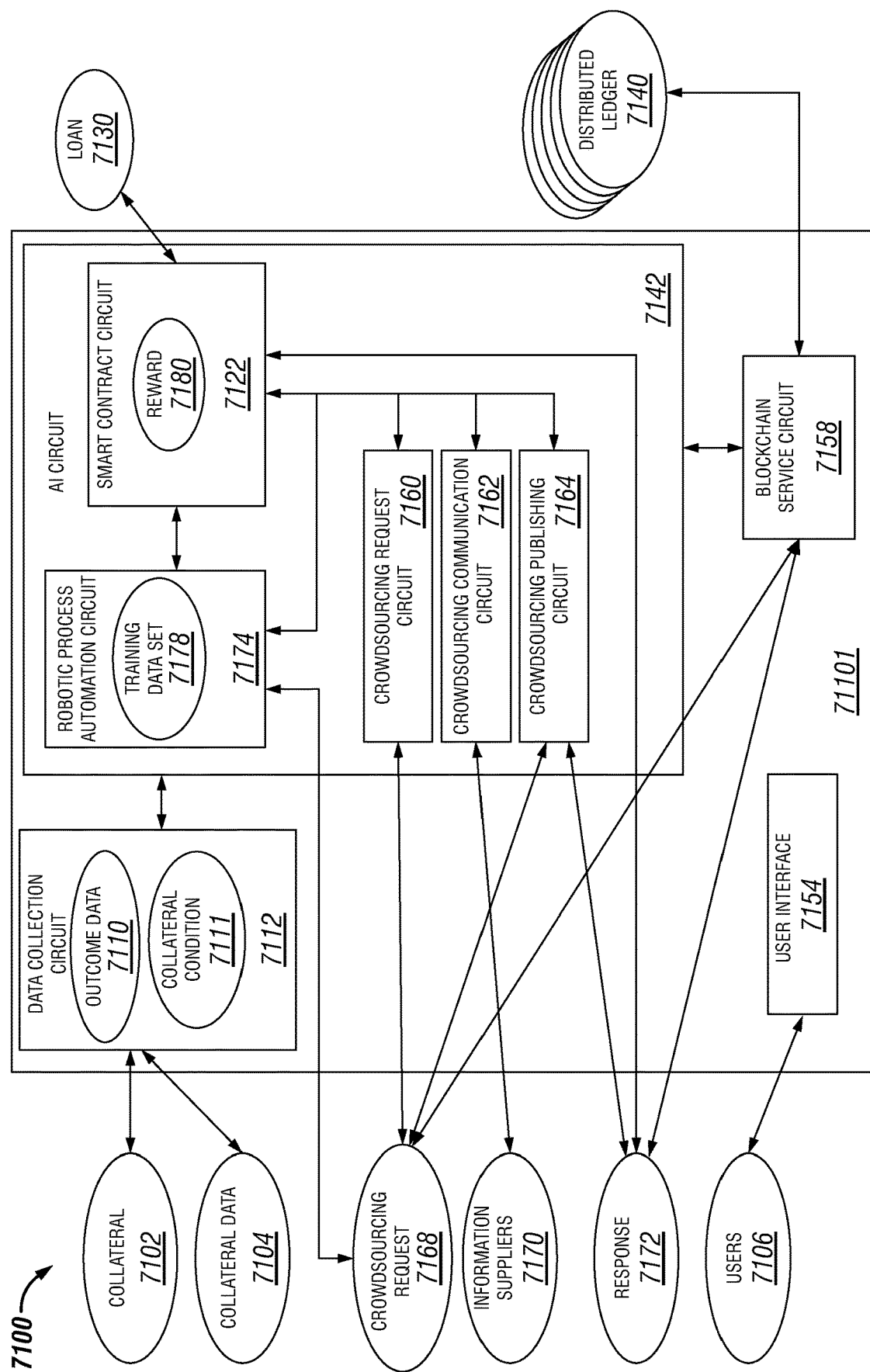
FIG. 71 depicts components and interactions of a lending platform.

Referring to FIG. 71, an illustrative and non-limiting example crowdsourcing system for validating conditions of collateral or a guarantor for a loan 7100 is depicted. The example system may include a controller 71101. The controller 71101 may include a data collection circuit 7112, a user interface 7154, and several artificial intelligence circuits 7142 including a smart contract circuit 7122, robotic process automation circuit 7174, a crowdsourcing request circuit 7160, a crowdsourcing communications circuit 7162, a crowdsourcing publishing circuit 7164, and a blockchain service circuit 7158.

The crowdsourcing request circuit 7160 may be structured to configure at least one parameter of a crowdsourcing request 7168 related to obtaining information 7104 on condition 7111 of a collateral 7102 for a loan 7130 or a condition of a guarantor for the loan 7130. It may also enable a workflow by which a human user 7106 enters the at least one parameter to establish the crowdsourcing request. The at least one parameter may include a type of requested information, the reward, and a condition for receiving the reward. The reward may be selected from selected from the rewards consisting of a financial reward, a token, a ticket, a contractual right, a cryptocurrency, a plurality of reward points, a currency, a discount on a product or service, and an access right.

The crowdsourcing publishing circuit 7164 may be configured to publish the crowdsourcing request 7168 to a group of information suppliers.

The crowdsourcing communications circuit 7162 may be structured to collect and process at least one response 7172 from the group of information suppliers 7170, and to provide a reward 7180 to at least one of the group of information suppliers in response to a successful information supply event.

The crowdsourcing communications circuit 7162 further includes a smart contract circuit 7122 structured to manage the reward 7180 by determining the successful information supply event in response to the at least one parameter configured for the crowdsourcing request 7168, and to automatically allocate the reward 7180 to the at least one of the group of information suppliers 7170 in response to the successful information supply event. It may also be structured to process the at least one response 7172 and, in response, automatically undertake an action related to the loan. The action may be at least one of a foreclosure action, a lien administration action, an interest-rate setting action, a default initiation action, a substitution of collateral, or a calling of the loan.

The loan 7130 may include at least one loan type selected from the loan types consisting of: an auto loan, an inventory loan, a capital equipment loan, a bond for performance, a capital improvement loan, a building loan, a loan backed by an account receivable, an invoice finance arrangement, a factoring arrangement, a pay day loan, a refund anticipation loan, a student loan, a syndicated loan, a title loan, a home loan, a venture debt loan, a loan of intellectual property, a loan of a contractual claim, a working capital loan, a small business loan, a farm loan, a municipal bond, and a subsidized loan.

The crowdsourcing request circuit 7160 may be further structured to configure at least one further parameter of the crowdsourcing request 7168 to obtain information on a condition 7111 of a collateral for the loan.

The collateral 7102 may include at least one item selected from the items consisting of: a vehicle, a ship, a plane, a building, a home, real estate property, undeveloped land, a farm, a crop, a municipal facility, a warehouse, a set of inventory, a commodity, a security, a currency, a token of value, a ticket, a cryptocurrency, a consumable item, an edible item, a beverage, a precious metal, an item of jewelry, a gemstone, an item of intellectual property, an intellectual property right, a contractual right, an antique, a fixture, an item of furniture, an item of equipment, a tool, an item of machinery, and an item of personal property.

The condition 7111 of collateral may be determined based on an attribute selected from the attributes consisting of: a quality of the collateral, a condition of the collateral, a status of a title to the collateral, a status of a possession of the collateral, and a status of a lien on the collateral. When the collateral is an item, the condition may be determined based on an attribute selected from the attributes consisting of: a new or used status of the item, a type of the item, a category of the item, a specification of the item, a product feature set of the item, a model of the item, a brand of the item, a manufacturer of the item, a status of the item, a context of the item, a state of the item, a value of the item, a storage location of the item, a geolocation of the item, an age of the item, a maintenance history of the item, a usage history of the item, an accident history of the item, a fault history of the item, an ownership of the item, an ownership history of the item, a price of a type of the item, a value of a type of the item, an assessment of the item, and a valuation of the item.

The blockchain service circuit 7158 may be structured to record identifying information and the at least one parameter of the crowdsourcing request, the at least one response to the crowdsourcing request, and a reward description in a distributed ledger 7140.

The robotic process automation circuit 7174 may be structured to, based on training on a training data set 7178 comprising human user interactions with at least one of the crowdsourcing request circuit or the crowdsourcing communications circuit, to configure the crowdsourcing request based on at least one attribute of the loan. The at least one attribute of the loan may be obtained from a smart contract circuit 7122 that manages the loan. The training data set 7178 may further include outcomes 7110 from a plurality of crowdsourcing requests.

The robotic process automation circuit 7174 may be further structured to determine a reward 7180.

The robotic process automation circuit 7174 may be further structured to determine at least one domain to which the crowdsourcing publishing circuit 7164 publishes the crowdsourcing request 7168.

Figure 72:
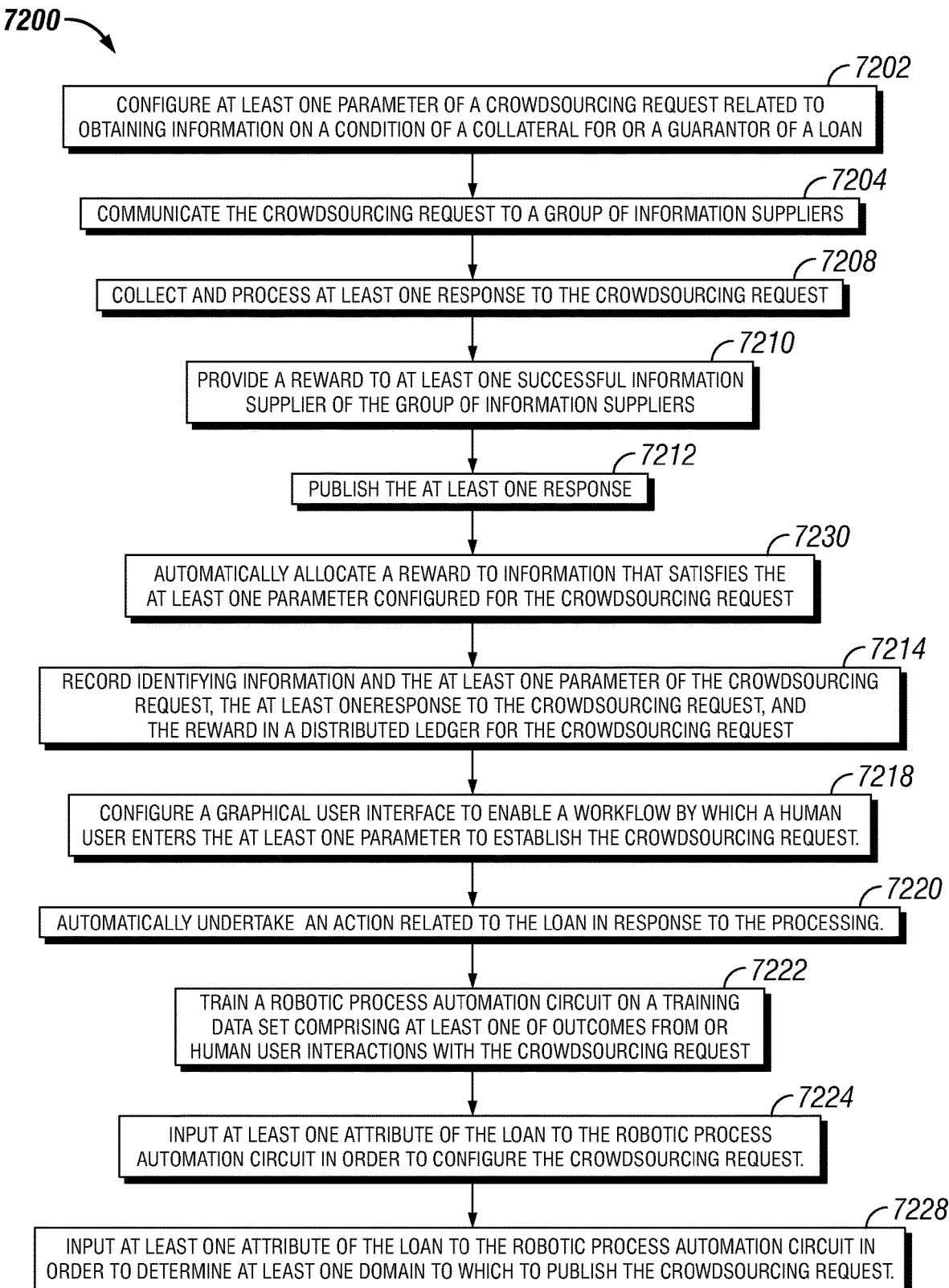
FIG. 72 depicts a method of a lending platform.

Referring to FIG. 72, provided herein is a crowdsourcing method 7200 for validating conditions of collateral or a guarantor for a loan. At least one parameter of a crowdsourcing request may be configured to obtain information on a condition of a collateral for a loan or a condition of a guarantor for the loan (step 7202). The crowdsourcing request may be published to a group of information suppliers (step 7204). At least one response to the crowdsourcing request may be collected and processed (step 7208). A reward may be provided to at least one successful information supplier of the group of information suppliers in response to a successful information supply event (step 7210). A reward description may be published to at least a portion of the group of information suppliers in response to the successful information supply event (step 7212). The reward may be automatically allocated to at least one of the group of information suppliers in response to the successful information supply event (step 7230). The method may further include recording identifying information and the at least one parameter of the crowdsourcing request, the at least one response to the crowdsourcing request, and a reward description in a distributed ledger for the crowdsourcing request (step 7214). A graphical user interface may be configured to enable a workflow by which a human user enters the at least one parameter to establish the crowdsourcing request (step 7218). An action related to the loan may be automatically undertaken in response to the successful information supply event (step 7220). A robotic process automation circuit may be trained on a training data set comprising a plurality of outcomes corresponding to a plurality of the crowdsourcing requests, and operating the robotic process automation circuit to iteratively improve the crowdsourcing request (step 7222). At least one attribute of the loan may be provided to the robotic process automation circuit in order to configure the crowdsourcing request (step 7224). Configuring the crowdsourcing request may include determining a reward. At least one attribute of the loan may be provided to the robotic process automation circuit in order to determine at least one domain to which to publish the crowdsourcing request (step 7228).

Figure 73:
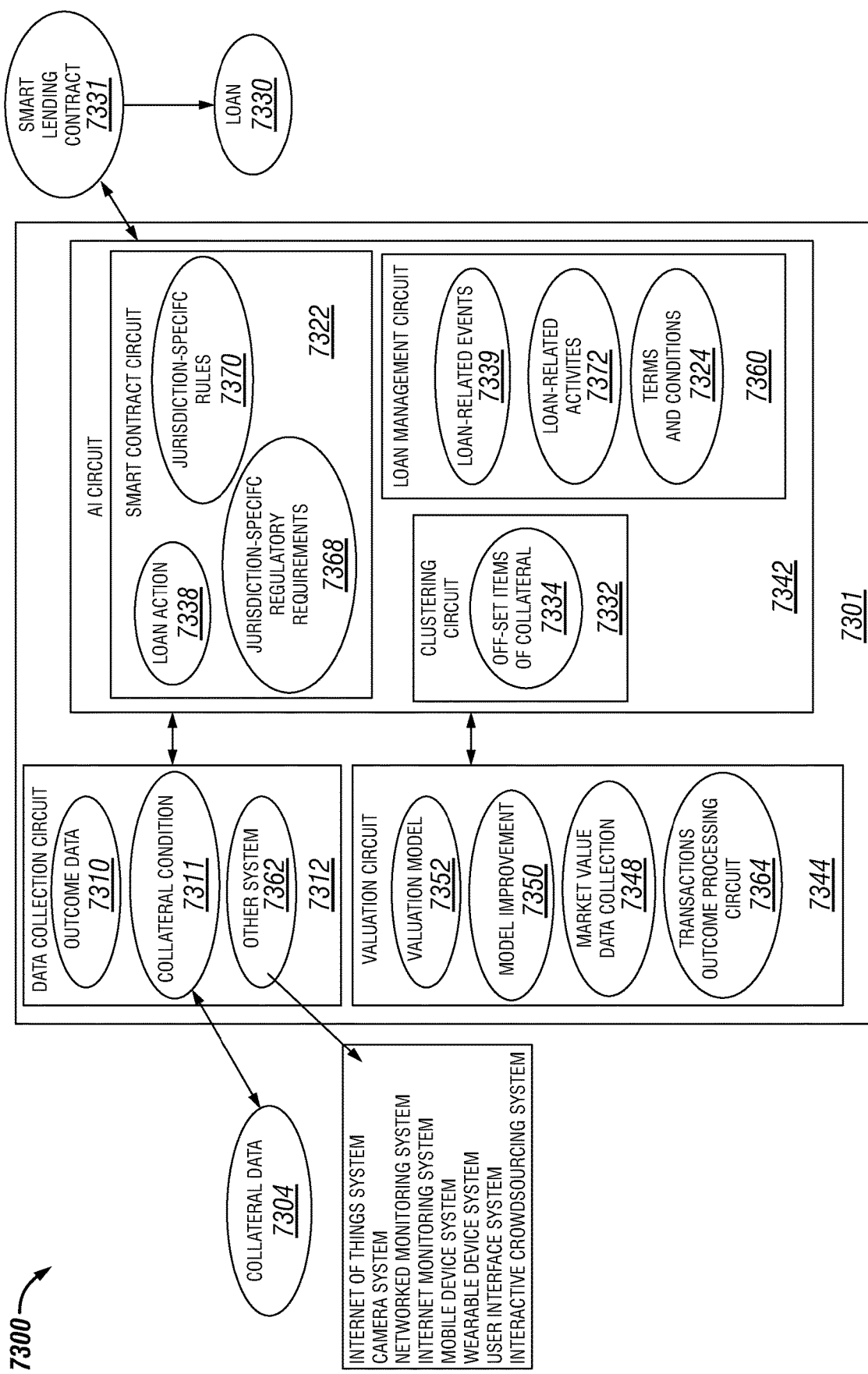
FIG. 73 depicts components and interactions of a lending platform.

Referring to FIG. 73, an illustrative and non-limiting example smart contract system 7300 for modifying a loan 7330 is depicted. The example system may include a controller 7301. The controller 7301 may include a data collection circuit 7312, a valuation circuit 7344, and several artificial intelligence circuits 7342 including a smart contract circuit 7322, a clustering circuit 7332, and a loan management circuit 7360. The data collection circuit 7312 may be structured to determine location information corresponding to each one of a plurality of entities involved in a loan. The smart contract circuit 7322 may be structured to determine a jurisdiction for at least one of the plurality of entities in response to the location information. The smart contract circuit 7322 may be structured to automatically undertake a loan-related action 7338 for the loan based at least in part on the jurisdiction for at least one of the plurality of entities.

The smart contract circuit 7322 may be further structured to automatically undertake the loan-related action in response to a first one of the plurality of entities being in a first jurisdiction, and a second one of the plurality of entities being in a second jurisdiction.

The smart contract circuit 7322 may be further structured to automatically undertake the loan-related action in response to one of the plurality of entities moving from a first jurisdiction to a second jurisdiction.

The loan-related action 7338 may include at least one loan-related action selected from the loan-related actions consisting of: offering the loan, accepting the loan, underwriting the loan, setting an interest rate for the loan, deferring a payment requirement, modifying an interest rate for the loan, validating title for collateral, recording a change in title, assessing a value of collateral, initiating inspection of collateral, calling the loan, closing the loan, setting terms and conditions for the loan, providing notices required to be provided to a borrower, foreclosing on property subject to the loan, and modifying terms and conditions for the loan.

The smart contract circuit 7322 may be further structured to process a plurality of jurisdiction-specific regulatory requirements 7368, such as requirements related to notice, and to provide an appropriate notice to a borrower based on a jurisdiction corresponding to at least one entity selected from the entities consisting of a lender, a borrower, funds provided via the loan, a repayment of the loan, or a collateral for the loan.

The smart contract circuit 7322 may be further structured to process a plurality of jurisdiction-specific regulatory requirements 7368, such as requirement related to foreclosure, and to provide an appropriate foreclosure notice to a borrower based on a jurisdiction of at least one of a lender, a borrower, funds provided via the loan, a repayment of the loan, and a collateral for the loan.

The smart contract circuit 7322 may be further structured to process a plurality of jurisdiction-specific rules 7370 for setting terms and conditions 7324 of the loan and to configure a smart contract 7331 based on a jurisdiction corresponding to at least one entity selected from the entities consisting of: a borrower, funds provided via the loan, a repayment of the loan, and a collateral for the loan.

The smart contract circuit 7322 may be further structured to determine an interest rate for the loan to cause the loan to comply with a maximum interest rate limitation applicable in a jurisdiction corresponding to a selected one of the plurality of entities.

The data collection circuit 7312 may be further structured to monitor outcome data 7310 and a condition 7311 of a collateral for the loan, such as with collateral data 7304, and wherein the smart contract circuit is further structured to determine the interest rate for the loan in response to the condition of the collateral for the loan.

The data collection circuit 7312 may be further structured to monitor an attribute of at least one of the plurality of entities that are party to the loan, and wherein the smart contract circuit is further structured to determine the interest rate for the loan in response to the attribute.

The smart contract circuit 7322 may further include a loan management circuit 7360 for specifying terms and conditions of smart contracts that govern at least one of loan terms and conditions 7324, loan-related events 7339 or loan-related activities 7372.

The loan may include at least one loan type selected from the loan types consisting of: an auto loan, an inventory loan, a capital equipment loan, a bond for performance, a capital improvement loan, a building loan, a loan backed by an account receivable, an invoice finance arrangement, a factoring management, a pay day loan, a refund anticipation loan, a student loan, a syndicated loan, a title loan, a home loan, a venture debt loan, a loan of intellectual property, a loan of a contractual claim, a working capital loan, a small business loan, a farm loan, a municipal bond, and a subsidized loan.

Terms and conditions for the loan may each include at least one member selected from the group consisting of: a principal amount of debt, a balance of debt, a fixed interest rate, a variable interest rate, a payment amount, a payment schedule, a balloon payment schedule, a specification of collateral, a specification of substitutability of collateral, a party, a guarantee, a guarantor, a security, a personal guarantee, a lien, a duration, a covenant, a foreclose condition, a default condition, and a consequence of default.

The data collection circuit 7312 may further include at least one other system 7362 selected from the systems consisting of: an Internet of Things system, a camera system, a networked monitoring system, an internet monitoring system, a mobile device system, a wearable device system, a user interface system, and an interactive crowdsourcing system.

The valuation circuit 7344 may be structured to use a valuation model 7352 to determine a value for a collateral for the loan based on the jurisdiction corresponding to at least one of the plurality of entities. The valuation model 7352 may be a jurisdiction-specific valuation model, and wherein the jurisdiction corresponding to at least one of the plurality of entities comprises a jurisdiction corresponding to at least one entity selected from the entities consisting of: a lender, a borrower, funds provided pursuant to the loan, a delivery location of funds provided pursuant to the loan, a payment of the loan, and a collateral for the loan.

At least one of the terms and conditions for the loan may be based on the value of the collateral for the loan.

The collateral may include at least one item selected from the items consisting of: a vehicle, a ship, a plane, a building, a home, real estate property, undeveloped land, a farm, a crop, a municipal facility, a warehouse, a set of inventory, a commodity, a security, a currency, a token of value, a ticket, a cryptocurrency, a consumable item, an edible item, a beverage, a precious metal, an item of jewelry, a gemstone, an item of intellectual property, an intellectual property right, a contractual right, an antique, a fixture, an item of furniture, an item of equipment, a tool, an item of machinery, and an item of personal property.

The valuation circuit 7344 may further include a transactions outcome processing circuit 7364 structured to interpret outcome data relating to a transaction in collateral and iteratively improve 7350 the valuation model in response to the outcome data.

The valuation circuit 7344 may further include a market value data collection circuit 7348 structured to monitor and report on marketplace information relevant to a value of collateral. The market value data collection circuit may monitor pricing or financial data for an offset collateral item in at least one public marketplace. A set of offset collateral items 7334 for valuing an item of collateral may be constructed using the clustering circuit 7332 based on an attribute of the collateral. The attribute may be selected from among a category of the collateral, an age of the collateral, a condition of the collateral, a history of the collateral, a storage condition of the collateral, and a geolocation of the collateral.

Figure 74:
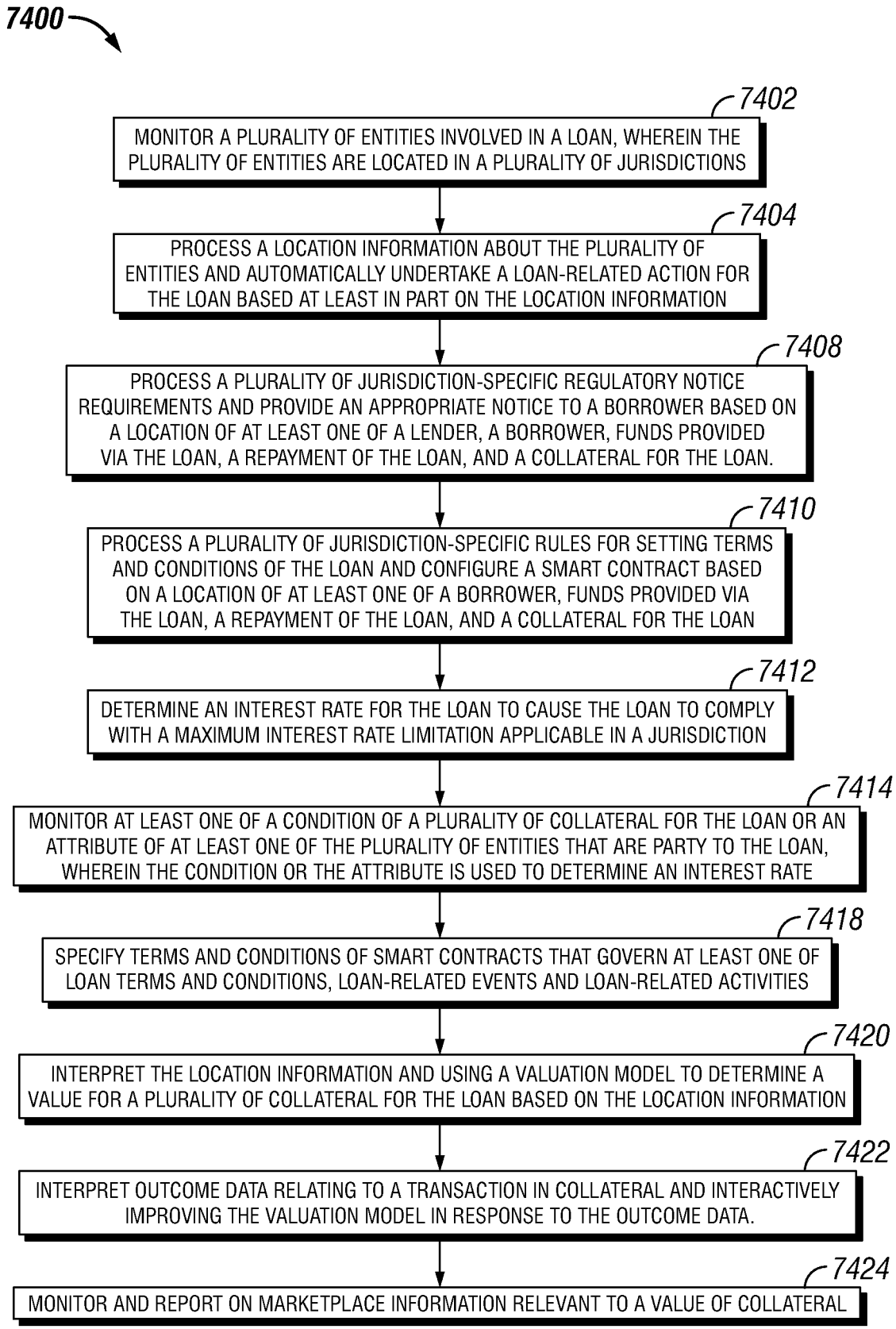
FIG. 74 depicts a method of a lending platform.

Referring to FIG. 74, provided herein is a smart contract method 7400 for modifying a loan. An example method may include monitoring location information corresponding to each one of a plurality of entities involved in a loan (step 7402); processing a location information about the entities and automatically undertaking a loan-related action for the loan based at least in part on the location information (step 7404). The example method includes processing a number of jurisdiction-specific regulatory notice requirements and providing an appropriate notice to a borrower based on a location of the lender, a borrower, funds provided via the loan, a repayment of the loan, and/or a collateral for the loan (step 7408). The example method includes processing a number of jurisdiction-specific rules for setting terms and conditions of the loan, and configuring a smart contract based on a location of the lender, a borrower, funds provided via the loan, a repayment of the loan, and/or a collateral for the loan (step 7410). The example method further includes determining an interest rate of the loan to cause the loan to comply with a maximum interest rate limitation applicable in a jurisdiction (step 7412). The example method includes monitoring at least one of a condition of a number of collateral items for the loan or an attribute of one of the entities that are a party to the loan, where the condition or the attribute is used to determine an interest rate (step 7414). The example method includes specifying terms and conditions of smart contract(s) that govern at least one of the terms and conditions, loan-related events, or loan-related activities (step 7418). The example method includes interpreting the location information and using a valuation model to determine a value for a number of collateral items for the loan based on the location information (step 7420). The example method includes interpreting outcome data relating to a transaction in collateral, and iteratively improving the valuation model in response to the outcome data (step 7422). The example method includes monitoring and reporting on marketplace information relevant to a value of collateral (step 7424).

A plurality of jurisdiction-specific requirements based on a jurisdiction of a relevant one of the plurality of entities may be processed, and performing at least one operation may be selected from the operations consisting of: providing an appropriate notice to a borrower in response to the plurality of jurisdiction-specific requirements comprising regulatory notice requirements; setting specific rules for setting terms and conditions of the loan in response to the plurality of jurisdiction-specific requirements comprising jurisdiction-specific rules for terms and conditions of the loan; determining an interest rate for the loan to cause the loan to comply with a maximum interest rate limitation in response to the plurality of jurisdiction-specific requirements comprising a maximum interest rate limitation; and wherein the relevant one of the plurality of entities comprises at least one entity selected from the entities consisting of: a lender, a borrower, funds provided pursuant to the loan, a repayment of the loan, and a collateral for the loan (step 7408).

At least one of a condition of a plurality of collateral for the loan or an attribute of at least one of the plurality of entities that are party to the loan may be monitored, wherein the condition or the attribute is used to determine an interest rate (step 7414).

A valuation model may be operated to determine a value for a collateral for the loan based on the jurisdiction for at least one of the plurality of entities (step 7420).

Outcome data relating to a transaction in collateral may be interpreted and the valuation model may be iteratively improved in response to the outcome data (step 7422).

Figure 75:
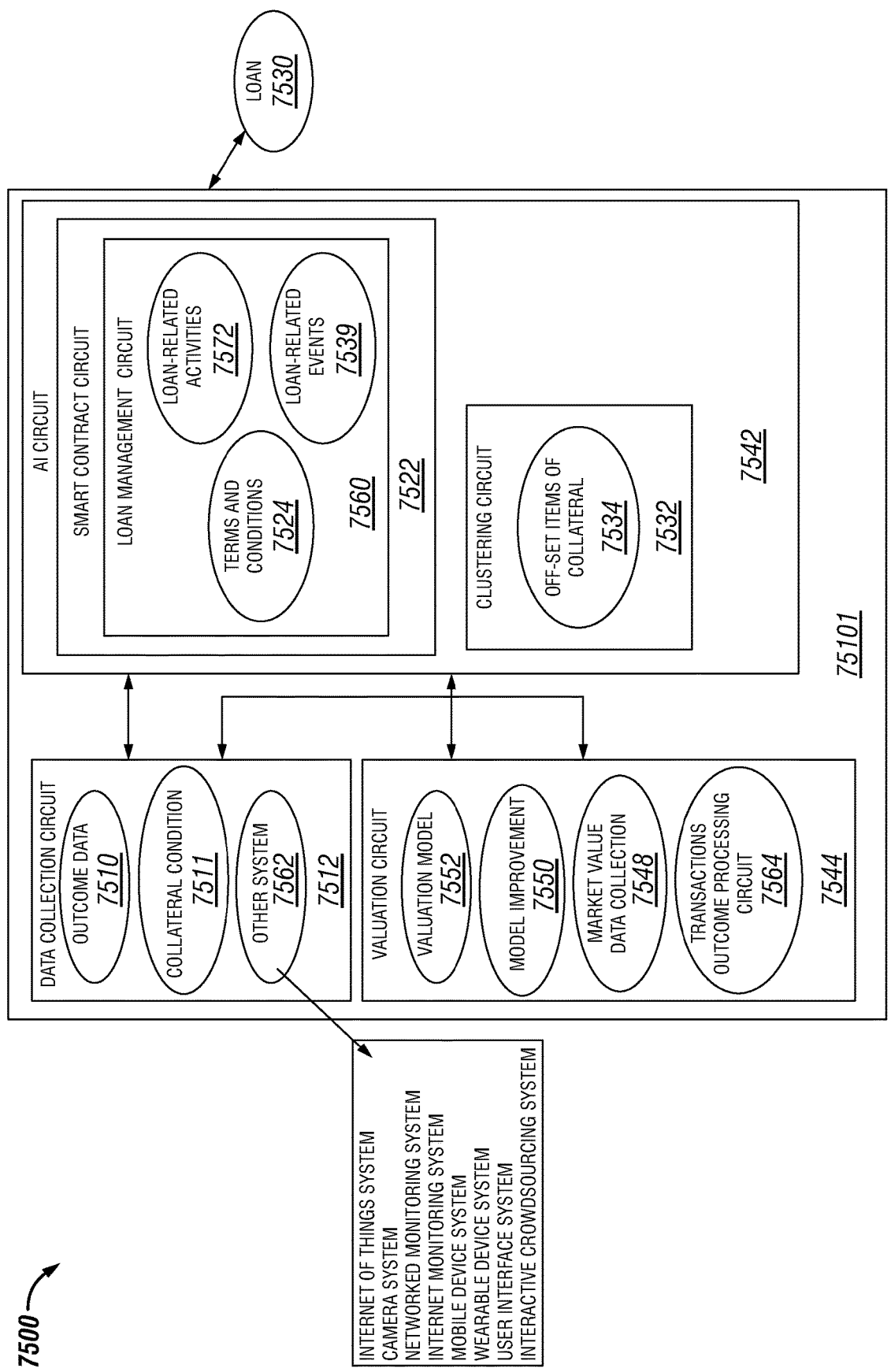
FIG. 75 depicts components and interactions of a lending platform.

Referring now to FIG. 75, an illustrative and non-limiting example smart contract system for modifying a loan 7500 is depicted. The example system may include a controller 75101. The controller 75101 may include a data collection circuit 7512, a valuation circuit 7544, and several artificial intelligence circuits 7542 including a smart contract circuit 7522, a clustering circuit 7532, and a loan management circuit 7560.

The data collection circuit 7512 may be structured to monitor and collect information about at least one entity involved in a loan 7530. The smart contract circuit 7522 may be structured to automatically restructure a debt related to the loan based on the monitored and collected information about the at least one entity involved in the loan. The monitored and collected information may include a condition of a collateral 7511 for the loan, or according to at least one rule that is based on a covenant of the loan and wherein the restructuring occurs upon an event that is determined with respect to the at least one entity that relates to the covenant, or restructuring may be based on an attribute of the at least one entity that is monitored by the data collection circuit. The event may be a failure of collateral for the loan to exceed a required fractional value of a remaining balance of the loan, or a default of a buyer with respect to the covenant.

The smart contract circuit 7522 may be further structured to determine the occurrence of an event based on a covenant of the loan and the monitored and collected information about the at least one entity involved in the loan, and to automatically restructure the debt in response to the occurrence of the event.

The smart contract circuit 7522 may further include a loan management circuit 7560 which may be structured to specify terms and conditions of a smart contract that governs at least one of loan terms and conditions 7524, a loan-related event 7539 or a loan-related activity 7572.

The loan may include at least one loan type selected from the loan types consisting of: an auto loan, an inventory loan, a capital equipment loan, a bond for performance, a capital improvement loan, a building loan, a loan backed by an account receivable, an invoice finance arrangement, a factoring arrangement, a pay day loan, a refund anticipation loan, a student loan, a syndicated loan, a title loan, a home loan, a venture debt loan, a loan of intellectual property, a loan of a contractual claim, a working capital loan, a small business loan, a farm loan, a municipal bond, and a subsidized loan.

Terms and conditions for the loan may include at least one member selected from the group consisting of: a principal amount of debt, a balance of debt, a fixed interest rate, a variable interest rate, a payment amount, a payment schedule, a balloon payment schedule, a specification of collateral, a specification of substitutability of collateral, a party, a guarantee, a guarantor, a security, a personal guarantee, a lien, a duration, a covenant, a foreclose condition, a default condition, and a consequence of default.

The data collection circuit 7512 may further include at least one other system 7562 selected from the systems consisting of: an Internet of Things system, a camera system, a networked monitoring system, an internet monitoring system, a mobile device system, a wearable device system, a user interface system, and an interactive crowdsourcing system.

The valuation circuit 7544 may be structured to use a valuation model 7552 to determine a value for a collateral based on the monitored and collected information about the at least one entity involved in the loan. The smart contract circuit may be further structured to automatically restructure the debt based on the value for the collateral.

The collateral may be at least one item selected from the items consisting of: a vehicle, a ship, a plane, a building, a home, real estate property, undeveloped land, a farm, a crop, a municipal facility, a warehouse, a set of inventory, a commodity, a security, a currency, a token of value, a ticket, a cryptocurrency, a consumable item, an edible item, a beverage, a precious metal, an item of jewelry, a gemstone, an item of intellectual property, an intellectual property right, a contractual right, an antique, a fixture, an item of furniture, an item of equipment, a tool, an item of machinery, and an item of personal property.

The valuation circuit 7544 may further include a transactions outcome processing circuit 7564 structured to interpret outcome data 7510 relating to a transaction in collateral and iteratively improve 7550 the valuation model in response to the outcome data.

The valuation circuit 7544 may further include a market value data collection circuit 7548 structured to monitor and report on marketplace information relevant to a value of collateral. The market value data collection circuit 7548 monitors pricing or financial data for an offset collateral item 7534 in at least one public marketplace. A set of offset collateral items 7534 for valuing an item of collateral may be constructed using a clustering circuit 7532 based on an attribute of the collateral. The attribute may be selected from among a category of the collateral, an age of the collateral, a condition of the collateral, a history of the collateral, a storage condition of the collateral, and a geolocation of the collateral.

Figure 76:
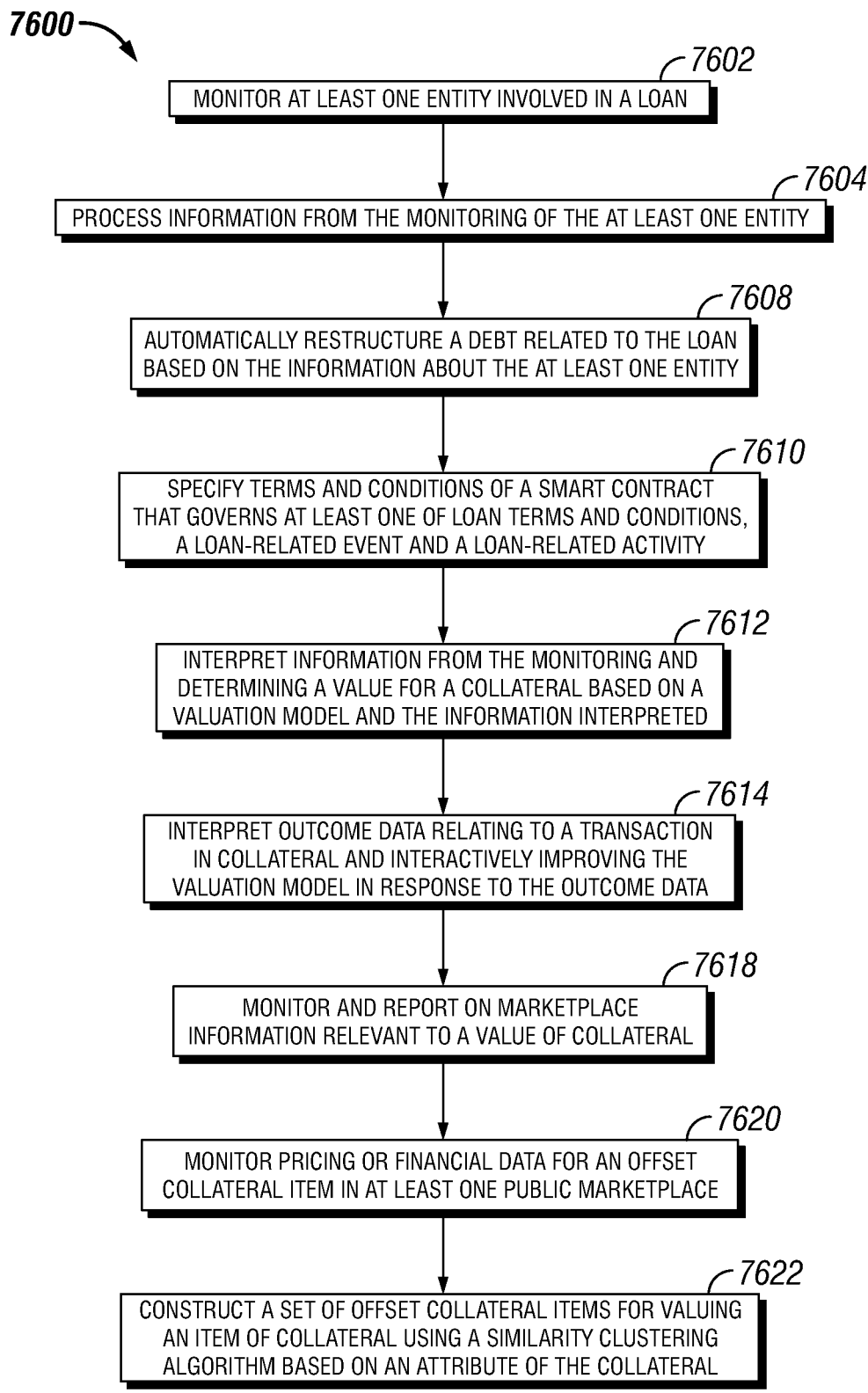
FIG. 76 depicts a method of a lending platform.

Referring now to FIG. 76, an illustrative and non-limiting example smart contract method for modifying a loan 7600 is depicted. The method includes monitoring and collecting information about at least one entity involved in a loan (step 7602); processing information from the monitoring of the at least one entity (step 7604); and automatically restructuring a debt related to the loan based on the monitored and collected information about the at least one entity (step 7608). Determining the occurrence of an event may be based on a covenant of the loan and the monitored and collected information about the at least one entity involved in the loan, and the method may include automatically restructuring the debt in response to the occurrence of the event.

Terms and conditions of a smart contract that governs at least one of loan terms and conditions, a loan-related event and a loan-related activity may be specified (step 7610).

Operating a valuation model to determine a value for a collateral based on the monitored and collected information about the at least one entity involved in the loan (step 7612).

Outcome data relating to a transaction in collateral may be interpreted and the valuation model may be iteratively improved in response to the outcome data (step 7614).

The method may further include monitoring and reporting on marketplace information relevant to a value of collateral (step 7618).

Pricing or financial data for an offset collateral item may be monitored in at least one public marketplace (step 7620).

A set of offset collateral items for valuing an item of collateral may be constructed using a similarity clustering algorithm based on an attribute of the collateral (step 7622).

Figure 77:
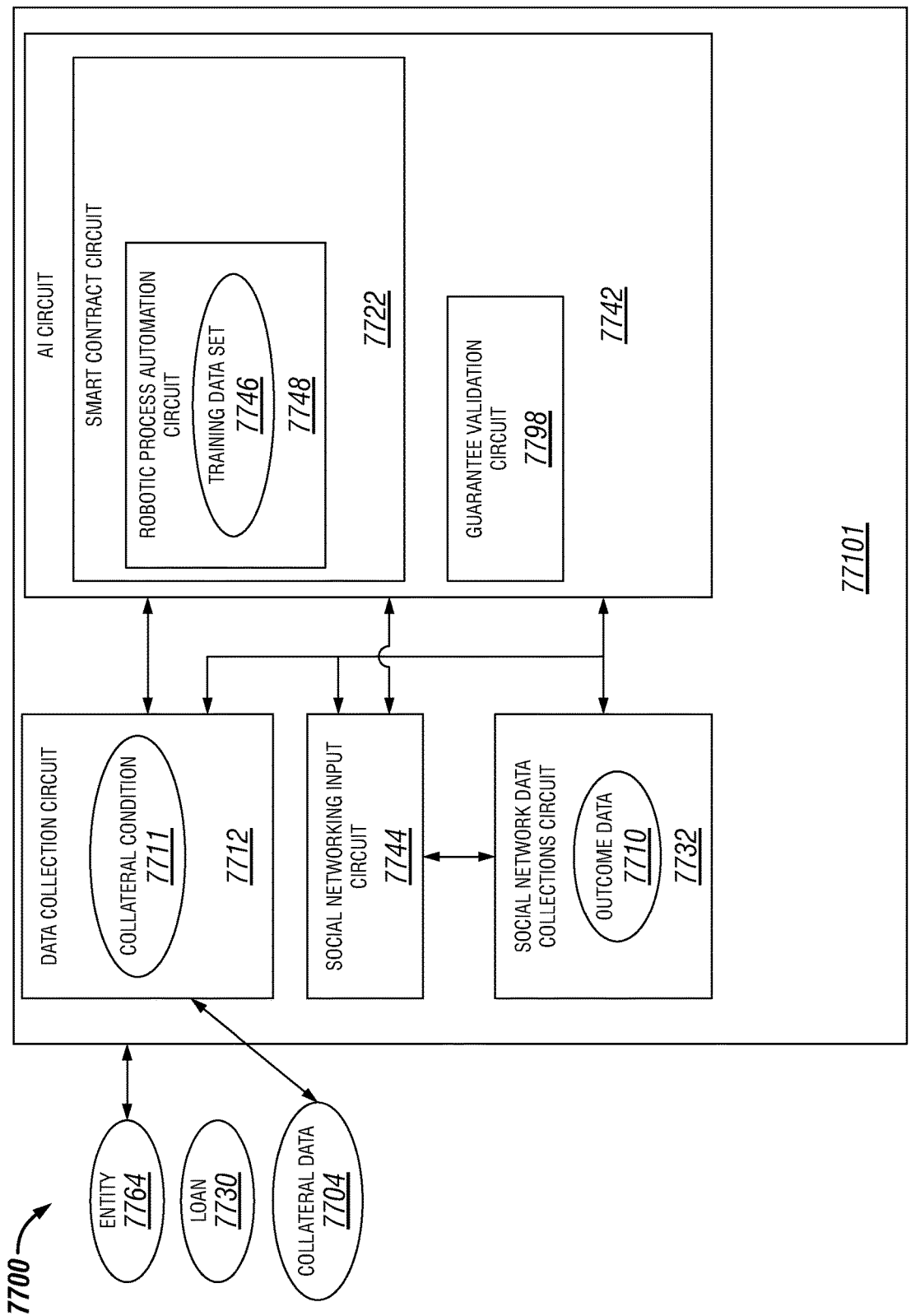
FIG. 77 depicts components and interactions of a lending platform.

Referring now to FIG. 77, an illustrative and non-limiting example smart contract system for modifying a loan 7700 is depicted. The example system may include a controller 77101. The controller 77101 may include a data collection circuit 7712, a social networking input circuit 7744, a social network data collection circuit 7732, and several artificial intelligence circuits 7742 including a smart contract circuit 7722, a guarantee validation circuit 7798, and a robotic process automation circuit 7748.

The social network data collection circuit 7732 may be structured to collect data, such as outcome data 7710, using a plurality of algorithms that are configured to monitor social network information about an entity 7764 involved in a loan 7730 in response to the loan guarantee parameter and to identify data collection outcomes. The social networking input circuit 7744 may be structured to interpret a loan guarantee parameter. The guarantee validation circuit 7798 may be structured to validate a guarantee for the loan in response to the monitored social network information.

The loan guarantee parameter may include a financial condition of the entity, wherein the entity is a guarantor for the loan.

The guarantee validation circuit 7798 may be further structured to determine the financial condition may be determined based on at least one attribute selected from the attributes consisting of: a publicly stated valuation of the entity, a property owned by the entity as indicated by public records, a valuation of a property owned by the entity, a bankruptcy condition of the entity, a foreclosure status of the entity, a contractual default status of the entity, a regulatory violation status of the entity, a criminal status of the entity, an export controls status of the entity, an embargo status of the entity, a tariff status of the entity, a tax status of the entity, a credit report of the entity, a credit rating of the entity, a website rating of the entity, a plurality of customer reviews for a product of the entity, a social network rating of the entity, a plurality of credentials of the entity, a plurality of referrals of the entity, a plurality of testimonials for the entity, a plurality of behaviors of the entity, a location of the entity, a jurisdiction of the entity, and a geolocation of the entity.

The loan may include at least one loan type selected from the loan types consisting of: an auto loan, an inventory loan, a capital equipment loan, a bond for performance, a capital improvement loan, a building loan, a loan backed by an account receivable, an invoice finance arrangement, a factoring arrangement, a pay day loan, a refund anticipation loan, a student loan, a syndicated loan, a title loan, a home loan, a venture debt loan, a loan of intellectual property, a loan of a contractual claim, a working capital loan, a small business loan, a farm loan, a municipal bond, and a subsidized loan.

The data collection circuit 7712 may be structured to obtain information about a condition 7711 of a collateral for the loan, wherein the collateral comprises at least one item selected from the items consisting of: a vehicle, a ship, a plane, a building, a home, real estate property, undeveloped land, a farm, a crop, a municipal facility, a warehouse, a set of inventory, a commodity, a security, a currency, a token of value, a ticket, a cryptocurrency, a consumable item, an edible item, a beverage, a precious metal, an item of jewelry, a gemstone, an item of intellectual property, an intellectual property right, a contractual right, an antique, a fixture, an item of furniture, an item of equipment, a tool, an item of machinery, and an item of personal property and wherein the guarantee validation circuit is further structured to validate the guarantee of the loan in response to the condition of the collateral for the loan.

The condition 7711 of collateral may include a condition attribute selected from the group consisting of a quality of the collateral, a status of title to the collateral, a status of possession of the collateral, a status of a lien on the collateral, a new or used status, a type, a category, a specification, a product feature set, a model, a brand, a manufacturer, a status, a context, a state, a value, a storage location, a geolocation, an age, a maintenance history, a usage history, an accident history, a fault history, an ownership, an ownership history, a price, an assessment, and a valuation. Conditions may be stored as collateral data 7704.

The social networking input circuit 7744 may be further structured to enable a workflow by which a human user enters the loan guarantee parameter to establish a social network data collection and monitoring request.

The smart contract circuit 7722 may be structured to automatically undertake an action related to the loan in response to the validation of the loan. The action may be related to the loan is in response to the loan guarantee not being validated, and wherein the action comprises at least one action selected from the actions consisting of: a foreclosure action, a lien administration action, an interest-rate adjustment action, a default initiation action, a substitution of collateral, a calling of the loan, and providing an alert to a second entity involved in the loan.

The robotic process automation circuit 7748 may be structured to, based on iteratively training on a training data set 7746 comprising human user interactions with the social network data collection circuit, configure the loan guarantee parameter based on at least one attribute of the loan. The at least one attribute of the loan 7730 may be obtained from a smart contract circuit that manages the loan.

The training data set 7746 may further include outcomes from a plurality of social network data collection and monitoring requests performed by the social network data collection circuit.

The robotic process automation circuit 7748 may be further structured to determine at least one domain to which the social network data collection circuit will apply.

Training may include training the robotic process automation circuit 7748 to configure the plurality of algorithms.

Figure 78:
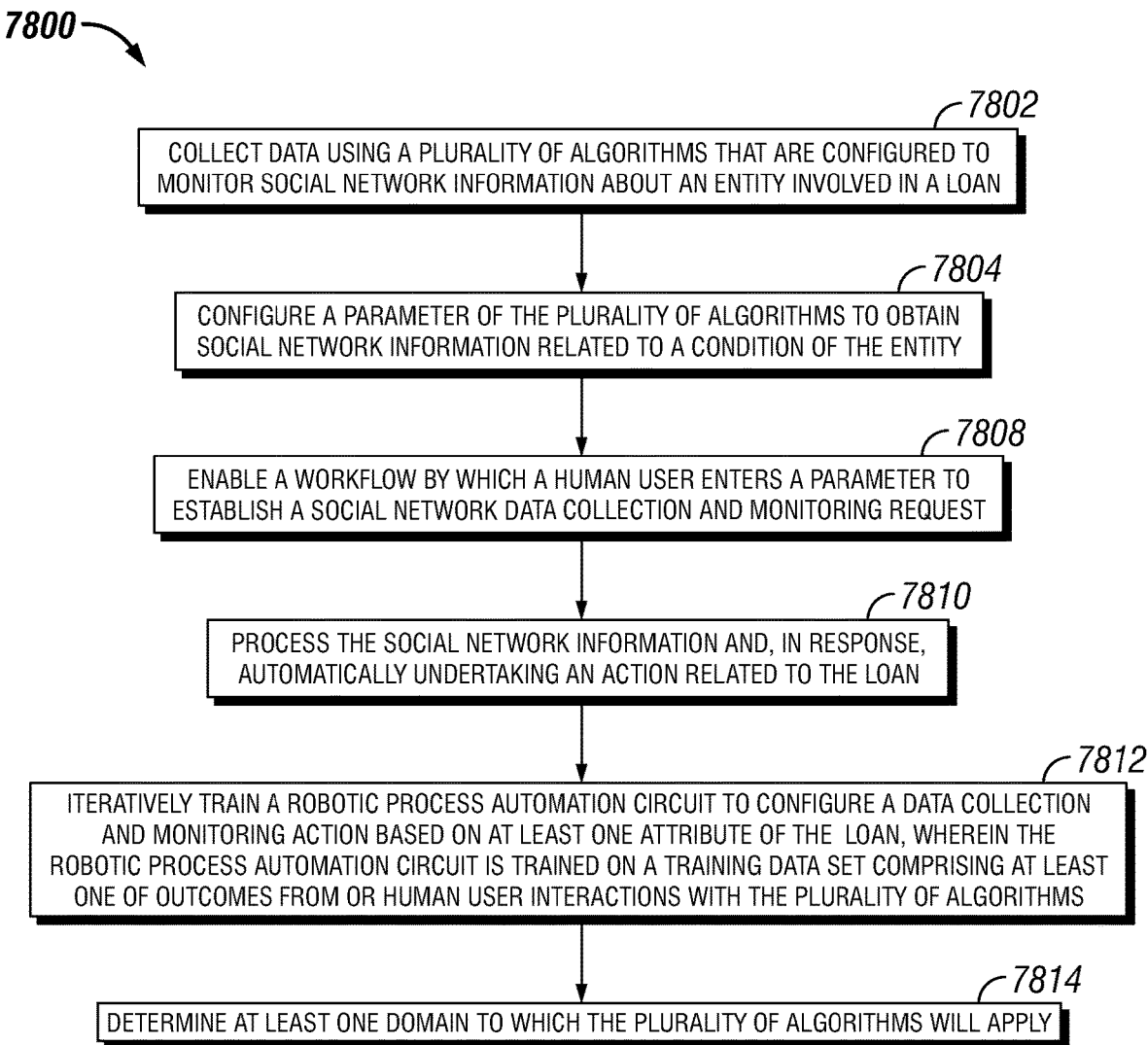
FIG. 78 depicts a method of a lending platform.

Referring now to FIG. 78, an illustrative and non-limiting example smart contract method for modifying a loan 7800 is depicted. A loan guarantee parameter may be interpreted (step 7801). Data may be collected using a plurality of algorithms that are configured to monitor social network information about an entity involved in a loan in response to the loan guarantee parameter (step 7802). A guarantee for the loan may be validated in response to the monitored social network information (step 7804). A workflow may be enabled by which a human user enters the loan guarantee parameter to establish a social network data collection and monitoring request (step 7808). In response to the validation of the loan, an action related to the loan may be undertaken automatically (step 7810). A robotic process automation circuit may be iteratively trained to configure a data collection and monitoring action based on at least one attribute of the loan, wherein the robotic process automation circuit is trained on a training data set comprising at least one of outcomes from or human user interactions with the plurality of algorithms (step 7812). At least one domain to which the plurality of algorithms will apply may be determined (step 7814).

Figure 79:
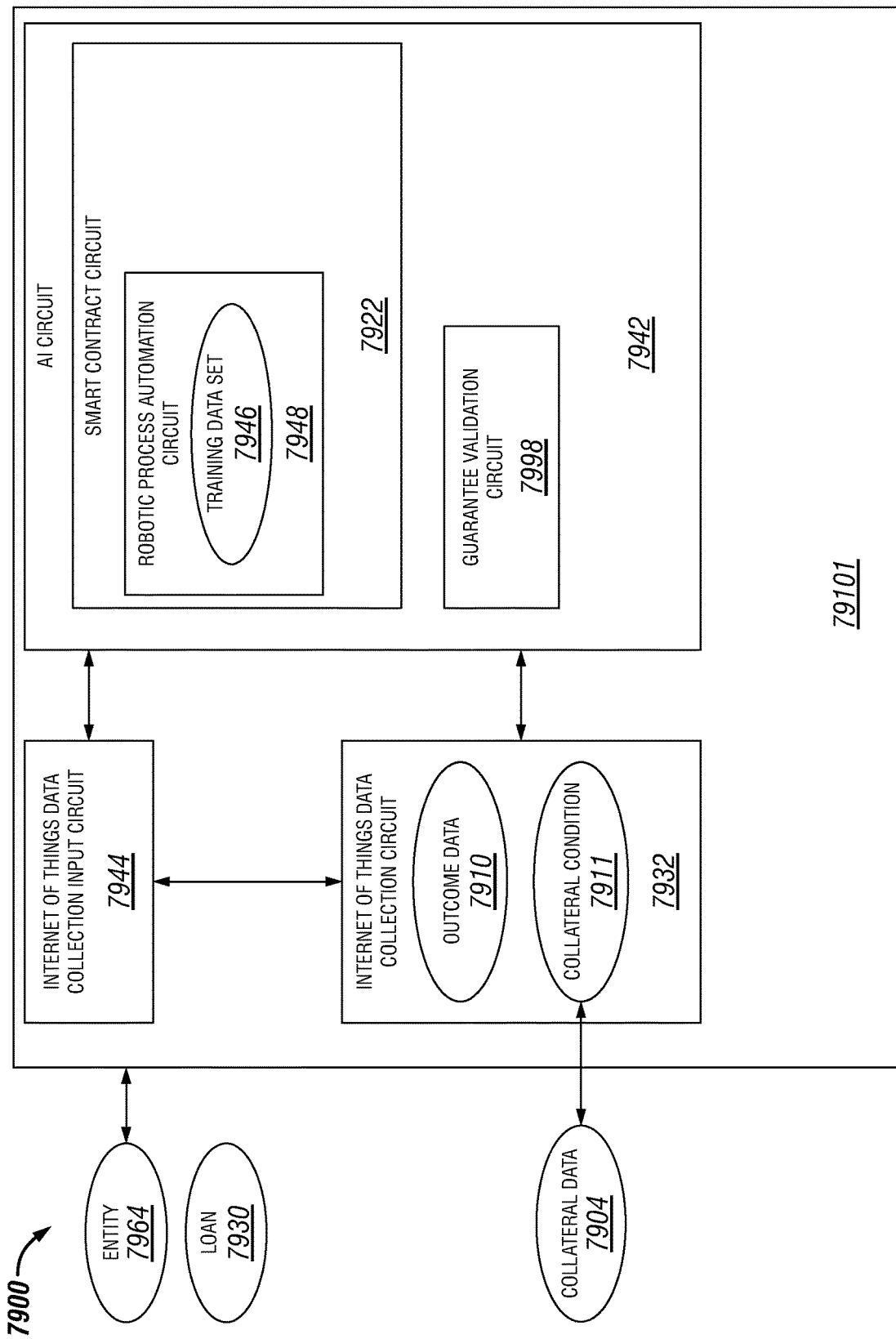
FIG. 79 depicts components and interactions of a lending platform.

Referring to FIG. 79, an illustrative and non-limiting example monitoring system for validating conditions of a guarantee for a loan 7900 is depicted. The example system may include a controller 79101. The controller 79101 may include an Internet of Things data collection input circuit 7944, Internet of Things data collection circuit 7932, and several artificial intelligence circuits 7942 including a smart contract circuit 7922, a guarantee validation circuit 7998, and a robotic process automation circuit 7948.

The Internet of Things data collection input circuit 7944 may be structured to interpret a loan guarantee parameter 7992. The Internet of Things data collection circuit 7932 may be structured to collect data using at least one algorithm that is configured to monitor Internet of Things information collected from and about an entity 7964 involved in a loan 7930 in response to the loan guarantee parameter. The guarantee validation circuit 7998 structured to validate a guarantee for the loan in response to the monitored IoT information The loan guarantee parameter 7992 may include a financial condition of the entity, wherein the entity is a guarantor for the loan. Monitored IoT information includes at least one of a publicly stated valuation of the entity, a property owned by the entity as indicated by public records, a valuation of a property owned by the entity, a bankruptcy condition of the entity, a foreclosure status of the entity, a contractual default status of the entity, a regulatory violation status of the entity, a criminal status of an entity, an export controls status of the entity, an embargo status of the entity, a tariff status of the entity, a tax status of the entity, a credit report of the entity, a credit rating of the entity, a web site rating of the entity, a plurality of customer reviews for a product of the entity, a social network rating of the entity, a plurality of credentials of the entity, a plurality of referrals of the entity, a plurality of testimonials for the entity, a plurality of behaviors of the entity, a location of the entity, a jurisdiction of the entity, and a geolocation of the entity.

The loan may include at least one loan type selected from the loan types consisting of: an auto loan, an inventory loan, a capital equipment loan, a bond for performance, a capital improvement loan, a building loan, a loan backed by an account receivable, an invoice finance arrangement, a factoring arrangement, a pay day loan, a refund anticipation loan, a student loan, a syndicated loan, a title loan, a home loan, a venture debt loan, a loan of intellectual property, a loan of a contractual claim, a working capital loan, a small business loan, a farm loan, a municipal bond, and a subsidized loan.

The Internet of Things data collection circuit 7932 may be further structured to obtain outcome data 7910, collateral data 7904 to determine information about collateral condition 7911 for the loan, wherein the collateral comprises at least one item selected from the items consisting of a vehicle, a ship, a plane, a building, a home, a real estate property, an undeveloped land, a farm, a crop, a municipal facility, a warehouse, a set of inventory, a commodity, a security, a currency, a token of value, a ticket, a cryptocurrency, a consumable item, an edible item, a beverage, a precious metal, an item of jewelry, a gemstone, an item of intellectual property, an intellectual property right, a contractual right, an antique, a fixture, an item of furniture, an item of equipment, a tool, an item of machinery, and an item of personal property, and wherein the guarantee validation circuit 7998 is further structured to validate the guarantee of the loan in response to the condition of the collateral for the loan.

Collateral condition 7911 may include a condition attribute selected from the group consisting of a quality of the collateral, a status of title to the collateral, a status of possession of the collateral, a status of a lien on the collateral, a new or used status, a type, a category, a specification, a product feature set, a model, a brand, a manufacturer, a status, a context, a state, a value, a storage location, a geolocation, an age, a maintenance history, a usage history, an accident history, a fault history, an ownership, an ownership history, a price, an assessment, and a valuation.

The Internet of Things data collection input circuit 7944 may be further structured to enable a workflow by which a human user enters the loan guarantee parameter 7992 to establish an Internet of Things data collection request.

The smart contract circuit 7922 may be structured to automatically undertake an action related to the loan in response to the validation of the loan. The action related to the loan may be in response to the loan guarantee not being validated, and wherein the action comprises at least one action selected from the actions consisting of: a foreclosure action, a lien administration action, an interest-rate adjustment action, a default initiation action, a substitution of collateral, a calling of the loan, and providing an alert to second entity involved in the loan.

The robotic process automation circuit 7948 may be structured to, based on iteratively training on a training data set comprising human user interactions with the Internet of Things data collection circuit, configure the loan guarantee parameter based on at least one attribute of the loan. The at least one attribute of the loan is obtained from a smart contract circuit that manage the loan. The training data set 7946 may further include outcomes from a plurality of Internet of Things data collection and monitoring requests performed by the Internet of Things data collection circuit.

The robotic process automation circuit 7948 may be further structured to determine at least one domain to which the Internet of Things data collection circuit will apply.

Training may include training the robotic process automation circuit 7948 to configure the at least one algorithm.

Figure 80:
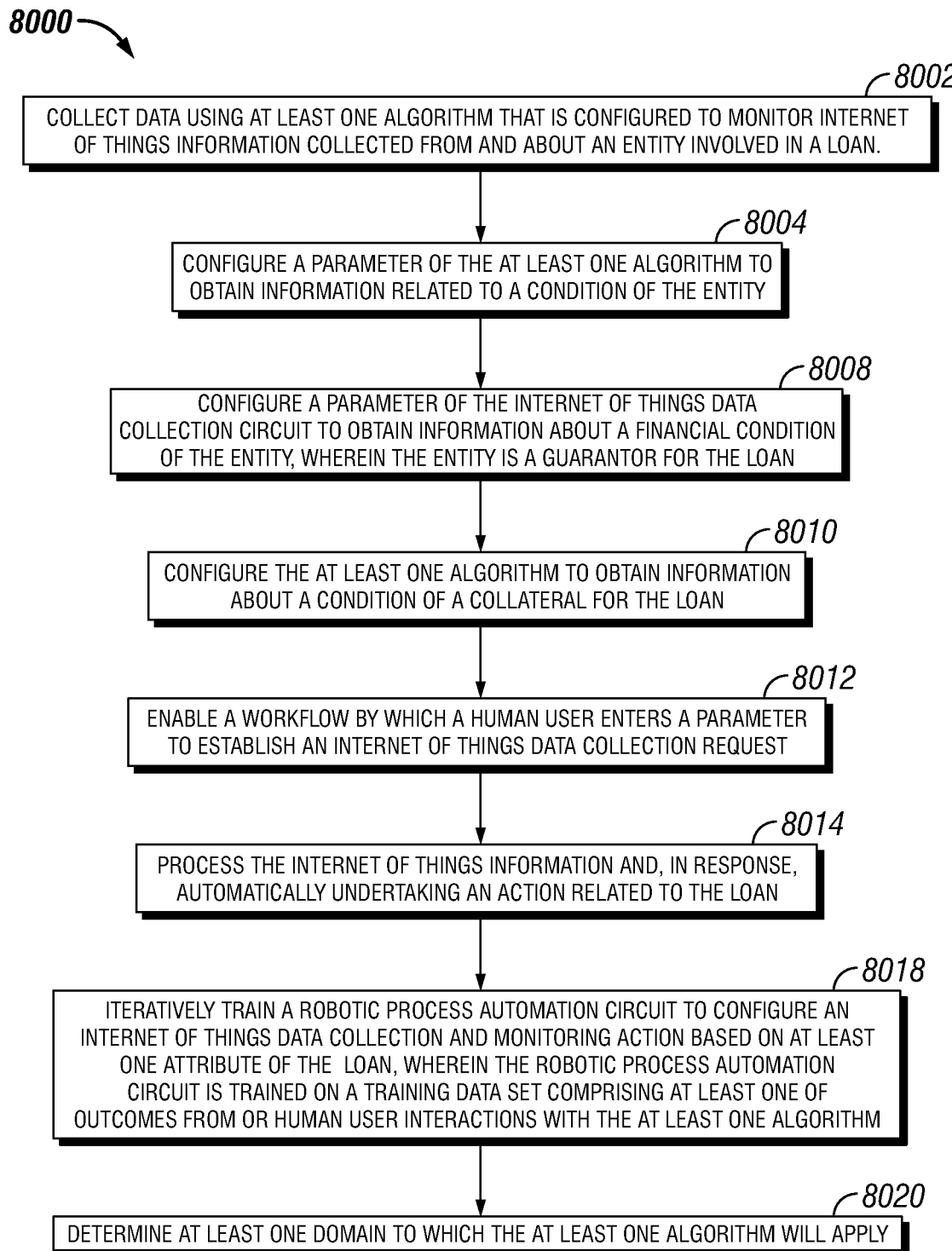
FIG. 80 depicts a method of a lending platform.

Referring to FIG. 80, an illustrative and non-limiting example monitoring method for validating conditions of a guarantee for a loan 8000 is depicted. The example method may include interpreting a loan guarantee parameter (step 8002); collecting data using a plurality of algorithms that are configured to monitor Internet of Things (IoT) information collected from and about an entity involved in a loan in response to the loan guarantee parameter (step 8004); and validating a guarantee for the loan in response to the monitored IoT information (step 8005).

The loan guarantee parameter may be configured to obtain information about a financial condition of the entity, wherein the entity is a guarantor for the loan (step 8008). The at least one algorithm may be configured to obtain information about a condition of a collateral for the loan (step 8010), wherein the collateral comprises at least one item selected from the items consisting of a vehicle, a ship, a plane, a building, a home, a real estate property, an undeveloped land, a farm, a crop, a municipal facility, a warehouse, a set of inventory, a commodity, a security, a currency, a token of value, a ticket, a cryptocurrency, a consumable item, an edible item, a beverage, a precious metal, an item of jewelry, a gemstone, an item of intellectual property, an intellectual property right, a contractual right, an antique, a fixture, an item of furniture, an item of equipment, a tool, an item of machinery, and an item of personal property; and validating the guarantee for the loan further in response to the condition of the collateral for the loan.

A workflow by which a human user enters the loan guarantee parameter to establish an Internet of Things data collection request may be enabled (step 8012).

An action related to the loan may be undertaken automatically in response to the validation (step 8014).

The action related to the loan may be in response to the loan guarantee not being validated, and wherein the action comprises a foreclosure action.

The action related to the loan may be in response to the loan guarantee not being validated, and wherein the action comprises a lien administration action.

The action related to the loan may be in response to the loan guarantee not being validated, and wherein the action comprises an interest-rate adjustment action.

The action related to the loan may be in response to the loan guarantee not being validated, and wherein the action comprises a default initiation action.

The action related to the loan may be in response to the loan guarantee not being validated, and wherein the action comprises a substitution of collateral.

The action related to the loan may be in response to the loan guarantee not being validated, and wherein the action comprises a calling of the loan.

The action related to the loan may be in response to the loan guarantee not being validated, and wherein the action comprises providing an alert to a second entity involved in the loan.

A robotic process automation circuit may be iteratively trained to configure an Internet of Things data collection and monitoring action based on at least one attribute of the loan, wherein the robotic process automation circuit is trained on a training data set comprising at least one of outcomes from or human user interactions with the plurality of algorithms (step 8018).

At least one domain to which the at least one algorithm will apply may be determined (step 8020). Training may include training the robotic process automation circuit to configure the plurality of algorithms.

The training data set may further include outcomes from a set of IoT data collection and monitoring requests.

Figure 81:
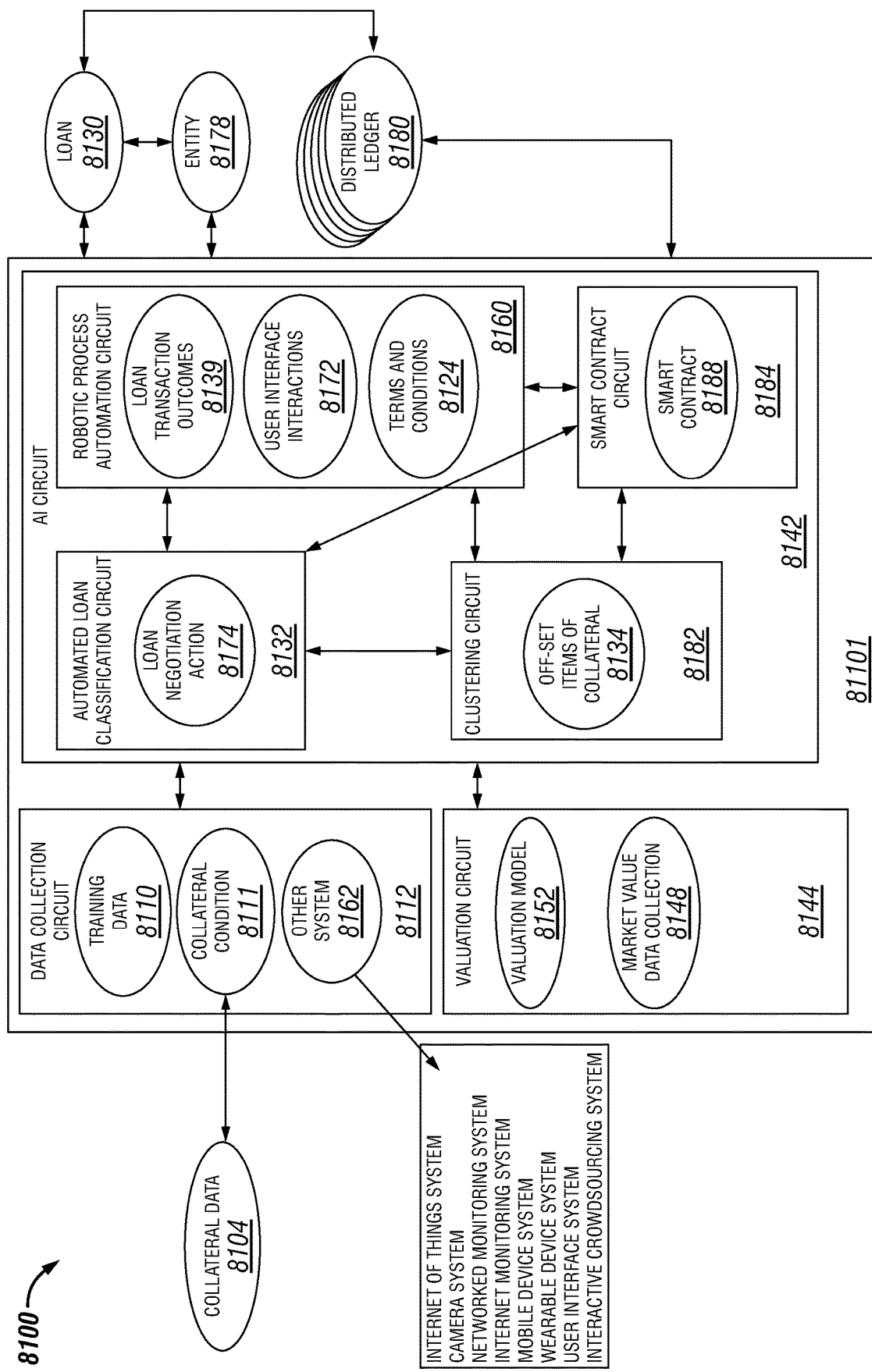
FIG. 81 depicts components and interactions of a lending platform.

Referring now to FIG. 81, an illustrative and non-limiting example robotic process automation system for negotiating a loan 8100 is depicted. The example system may include a controller 81101. The controller 81101 may include a data collection circuit 8112, a valuation circuit 8144, and several artificial intelligence circuits 8142 including an automated loan classification circuit 8132, a robotic process automation circuit 8160, a smart contract circuit 8184, and a clustering circuit 8182.

The data collection circuit 8112 may be structured to collect collateral data 8104 and create a training set of interactions 8110 from at least one entity 8178 related to at least one loan transaction. An automated loan classification circuit 8132 may be trained on the training set of interactions 1SCQ10 to classify a at least one loan negotiation action. The robotic process automation circuit 8160 may be trained on a training set of a plurality of loan negotiation actions 8174 classified by the automated loan classification circuit 8132 and a plurality of loan transaction outcomes 8139 to negotiate a terms and conditions 8124 of a new loan 8130 on behalf of a party to the new loan.

The data collection circuit may further include at least one other system 8162 selected from the systems consisting of: an Internet of Things system, a camera system, a networked monitoring system, an internet monitoring system, a mobile device system, a wearable device system, a user interface system, and an interactive crowdsourcing system. The at least one entity may be a party to the at least one loan transaction and may be selected from the entities consisting of: a primary lender, a secondary lender, a lending syndicate, a corporate lender, a government lender, a bank lender, a secured lender, bond issuer, a bond purchaser, an unsecured lender, a guarantor, a provider of security, a borrower, a debtor, an underwriter, an inspector, an assessor, an auditor, a valuation professional, a government official, and an accountant.

The automated loan classification circuit 8132 may include a system selected from the systems consisting of: a machine learning system, a model-based system, a rule-based system, a deep learning system, a hybrid system, a neural network, a convolutional neural network, a feed forward neural network, a feedback neural network, a self-organizing map, a fuzzy logic system, a random walk system, a random forest system, a probabilistic system, a Bayesian system, and a simulation system.

The robotic process automation circuit 8160 may be further trained on a plurality of interactions of parties with a plurality of user interfaces 8172 involved in a plurality of lending processes.

The smart contract circuit 8184 may be structured to automatically configure a smart contract 8188 for the new loan 8130 based on an outcome of the negotiation.

A distributed ledger 8180 may be associated with the new loan 8130, wherein the distributed ledger 8180 is structured to record at least one of an outcome and a negotiating event of the negotiation.

The new loan may include at least one loan type selected from the loan types consisting of: an auto loan, an inventory loan, a capital equipment loan, a bond for performance, a capital improvement loan, a building loan, a loan backed by an account receivable, an invoice finance arrangement, a factoring arrangement, a pay day loan, a refund anticipation loan, a student loan, a syndicated loan, a title loan, a home loan, a venture debt loan, a loan of intellectual property, a loan of a contractual claim, a working capital loan, a small business loan, a farm loan, a municipal bond, and a subsidized loan.

The valuation circuit 8144 may be structured to use a valuation model 8152 to determine a value for a collateral for the new loan. The collateral may include at least one item selected from the items consisting of: a vehicle, a ship, a plane, a building, a home, real estate property, undeveloped land, a farm, a crop, a municipal facility, a warehouse, a set of inventory, a commodity, a security, a currency, a token of value, a ticket, a cryptocurrency, a consumable item, an edible item, a beverage, a precious metal, an item of jewelry, a gemstone, an item of intellectual property, an intellectual property right, a contractual right, an antique, a fixture, an item of furniture, an item of equipment, a tool, an item of machinery, and an item of personal property.

The valuation circuit may further include a market value data collection circuit 8148 structured to monitor and report on marketplace information relevant to a value of the collateral. The market value data collection circuit 8148 may monitor pricing or financial data for an offset collateral item 8134 in at least one public marketplace. A set of offset collateral items 8134 for valuing the collateral may be constructed using a clustering circuit 8182 based on an attribute of the collateral. The attribute may be selected from among a category of the collateral, an age of the collateral, a condition of the collateral 8111, a history of the collateral, a storage condition of the collateral, and a geolocation of the collateral. The terms and conditions 8124 for the new loan may include at least one member selected from the group consisting of: a principal amount of debt, a balance of debt, a fixed interest rate, a variable interest rate, a payment amount, a payment schedule, a balloon payment schedule, a specification of collateral, a specification of substitutability of collateral, a party, a guarantee, a guarantor, a security, a personal guarantee, a lien, a duration, a covenant, a foreclose condition, a default condition, and a consequence of default.

Figure 82:
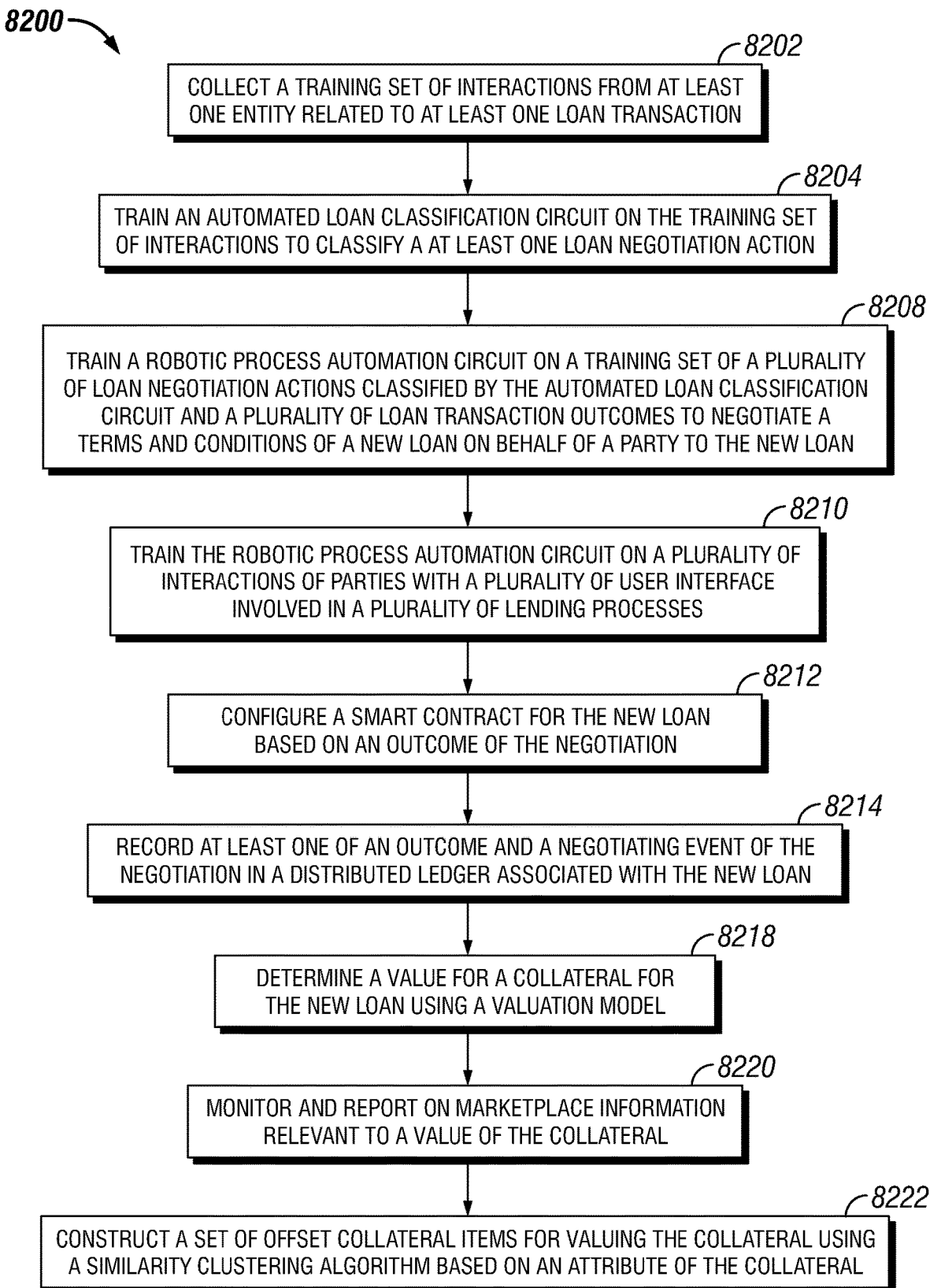
FIG. 82 depicts a method of a lending platform.

Referring now to FIG. 82, an illustrative and non-limiting example robotic process automation method 8200 for negotiating a loan 8100 is depicted. The example method may include collecting a training set of interactions from at least one entity related to at least one loan transaction (step 8202); training an automated loan classification circuit on the training set of interactions to classify a at least one loan negotiation action (step 8204); and training a robotic process automation circuit on a training set of a plurality of loan negotiation actions classified by the automated loan classification circuit and a plurality of loan transaction outcomes to negotiate a terms and conditions of a new loan on behalf of a party to the new loan (step 8208).

The robotic process automation circuit may be trained on a plurality of interactions of parties with a plurality of user interfaces involved in a plurality of lending processes (step 8210).

A smart contract for the new loan may be configured based on an outcome of the negotiation (step 8212).

At least one of an outcome and a negotiating event of the negotiation may be recorded in a distributed ledger associated with the new loan (step 8214).

A value for a collateral for the new loan may be determined using a valuation model (step 8218).

An example method may further include monitoring and reporting on marketplace information relevant to a value of the collateral (step 8220).

A set of offset collateral items for valuing the collateral may be constructed using a similarity clustering algorithm based on an attribute of the collateral (step 8222).

Figure 83:
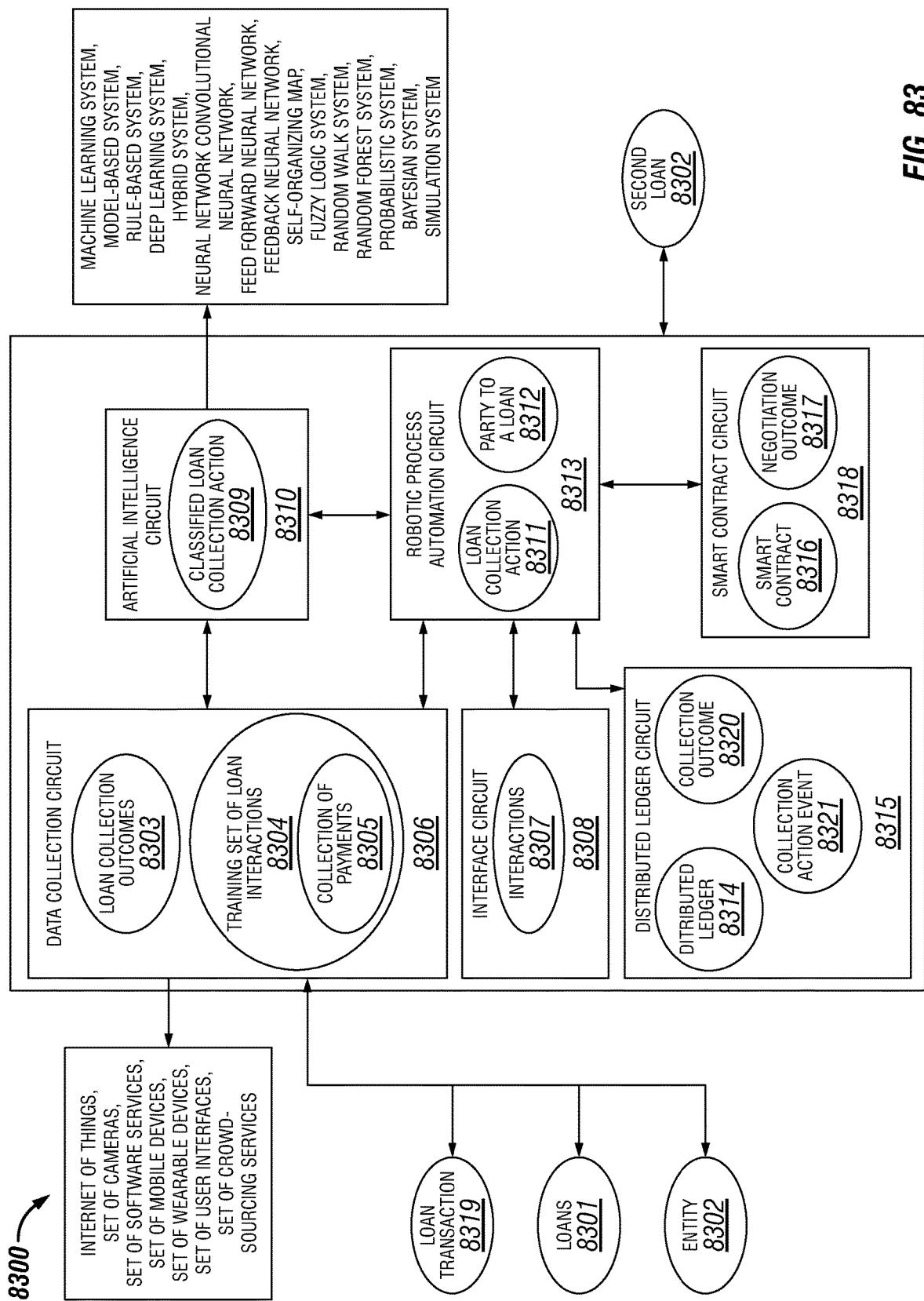
FIG. 83 depicts components and interactions of a lending platform.

Referring to FIG. 83, an illustrative and non-limiting example system for system for adaptive intelligence and robotic process automation capabilities 8300 is depicted. The example system may include a data collection circuit 8306 which may collect data such loan collection outcomes 8303, training set of loan interactions 8304 which may include collection of payments 8305 and the like. The data may be collected from loan transactions 8319, loan data 8301, and data regarding entities 8302 associated with the loan, and the like. The data may be collected from a variety of sources and systems such as: an Internet of Things system, a camera system, a networked monitoring system, an internet monitoring system, a mobile device system, a wearable device system, a user interface system, and an interactive crowdsourcing system. The loan collection outcomes 8303 may include at least outcome such a response to a collection contact event, a payment of a loan, a default of a borrower on a loan, a bankruptcy of a borrower of a loan, an outcome of a collection litigation, a financial yield of a set of collection actions, a return on investment on collection, a measure of reputation of a party involved in collection, and the like.

The system may also include an artificial intelligence circuit 8310 that may be structured to classify a set of loan collection actions 8309 based at least in part on the training set of loan interactions 8304. The artificial intelligence circuit 8310 may include at least one system such as a machine learning system, a model-based system, a rule-based system, a deep learning system, a hybrid system, a neural network, a convolutional neural network, a feed forward neural network, a feedback neural network a self-organizing map, a fuzzy logic system, a random walk system, a random forest system, a probabilistic system, a Bayesian system, a simulation system, and the like.

The system may also include a robotic process automation circuit 8313 structured to perform at least one loan collection action 8311 on behalf of a party to a loan 8312 based at least in part on the training set of loan interactions 8304 and the set of loan collection outcomes 8303. The loan collection action 8311 undertaken by the robotic process automation circuit 8313 may be at least one of a referral of a loan to an agent for collection, configuration of a collection communication, scheduling of a collection communication, configuration of content for a collection communication, configuration of an offer to settle a loan, termination of a collection action, deferral of a collection action, configuration of an offer for an alternative payment schedule, initiation of a litigation, initiation of a foreclosure, initiation of a bankruptcy process, a repossession process, placement of a lien on collateral, and the like. The party to a loan 8312 may include least one such as a primary lender, a secondary lender, a lending syndicate, a corporate lender, a government lender, a bank lender, a secured lender, bond issuer, a bond purchaser, an unsecured lender, a guarantor, a provider of security, a borrower, a debtor, an underwriter, an inspector, an assessor, an auditor, a valuation professional, a government official, an accountant, and the like. Loans may include at least one auto loan, an inventory loan, a capital equipment loan, a bond for performance, a capital improvement loan, a building loan, a loan backed by an account receivable, an invoice finance arrangement, a factoring arrangement, a pay day loan, a refund anticipation loan, a student loan, a syndicated loan, a title loan, a home loan, a venture debt loan, a loan of intellectual property, a loan of a contractual claim, a working capital loan, a small business loan, a farm loan, a municipal bond, a subsidized loan and the like.

The system may further include an interface circuit 8308 structured to receive interactions 8307 from one or more of the loan entities 8302. In some embodiments the robotic process automation circuit 8313 may be trained on the interactions 8307. The system may further include a smart contract circuit 8318 structured to determine completion of a negotiation of the loan collection action 8311 and modify a contract 8316 based on an outcome of the negation 8317.

The system may further include a distributed ledger circuit 8315 structured to determine at least one of a collection outcome 8320 or an event 8321 associated with the loan collection action 8311. The distributed ledger circuit 8315 may be structured to record, in a distributed ledger 8314 associated with the loan, the event 8321 and/or the collection outcome 8320.

Figure 84:
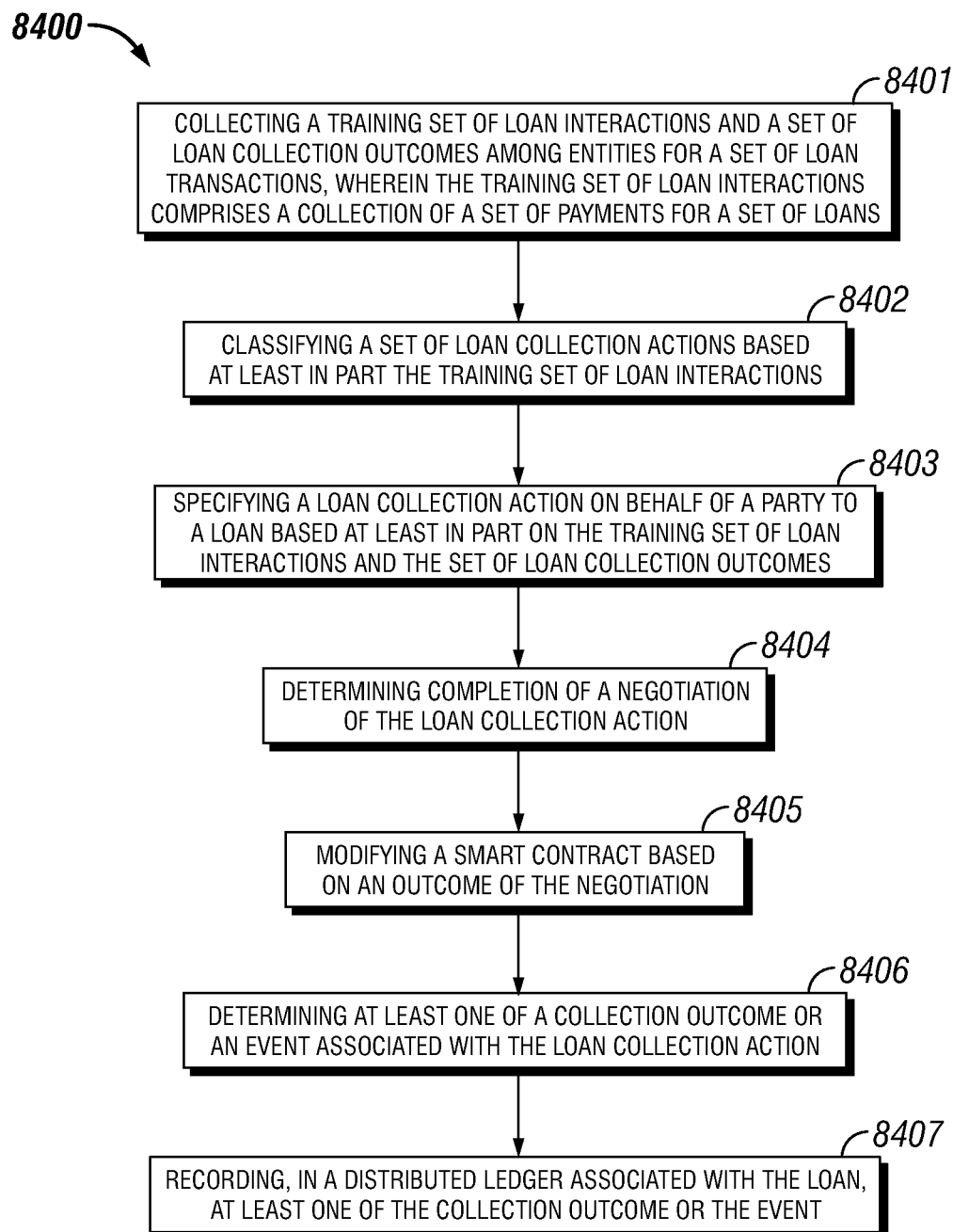
FIG. 84 depicts a method of a lending platform.

Referring to FIG. 84, an illustrative and non-limiting example method 8400 is depicted. The example method 8400 may include step 8401 for collecting a training set of loan interactions and a set of loan collection outcomes among entities for a set of loan transactions, wherein the training set of loan interactions comprises a collection of a set of payments for a set of loans. A set of loan collection actions based at least in part the training set of loan interactions may be classified (step 8402). The method may further include the step 8403 of specifying a loan collection action on behalf of a party to a loan based at least in part on the training set of loan interactions and the set of loan collection outcomes.

The method 8400 may further include the step 8404 of determining completion of a negotiation of the loan collection action. Based on the outcome of the negotiations a smart contract may be modified in step 8405. The method may also include the step 8406 of determining at least one of a collection outcome or an event associated with the loan collection action. The at least one of the collection outcome or the event may be recorded in a distributed ledger associate with the loan in step 8407.

Figure 85:
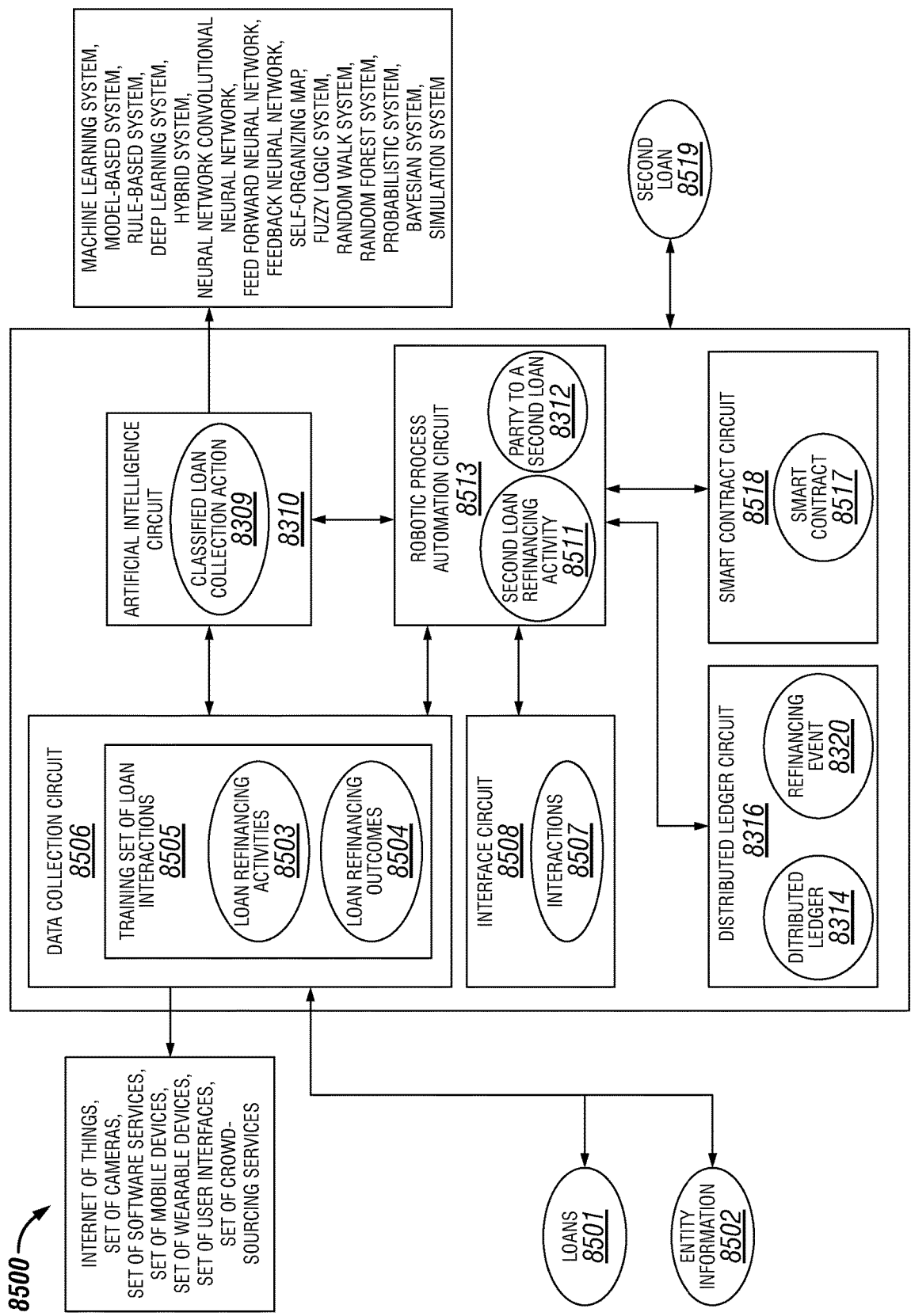
FIG. 85 depicts components and interactions of a lending platform.

Referring to FIG. 85, an illustrative and non-limiting example system for system for adaptive intelligence and robotic process automation capabilities 8500 is depicted. The example system may include a data collection circuit 8506 structured to collect a training set of loan interactions between entities 8502, wherein the training set of loan interactions may include a set of loan refinancing activities 8503 and a set of loan refinancing outcomes 8504. The system may include an artificial intelligence circuit 8310 structured to classify the set of loan refinancing activities, wherein the artificial intelligence circuit is trained on the training set of loan interactions. The system may include a robotic process automation circuit 8513 structured to perform a second loan refinancing activity 8511 on behalf of a party to a second loan 8312, wherein the robotic process automation circuit is trained on the set of loan refinancing activities and the set of loan refinancing outcomes. The example system may include a data collection circuit 8506 which may collect data such as a training set of loan interactions between entities 8502. Data related to the set of loan interactions between entities 8502 may include data related to loan refinancing activities 8503 and loan refinancing outcomes 8504. The data may be collected from loan data 8501, information about entities 8502, and the like. The data may be collected from a variety of sources and systems such as: an Internet of Things system, a camera system, a networked monitoring system, an internet monitoring system, a mobile device system, a wearable device system, a user interface system, and an interactive crowdsourcing system. The loan refinancing activity 8503 may include at least one activity such as initiating an offer to refinance, initiating a request to refinance, configuring a refinancing interest rate, configuring a refinancing payment schedule, configuring a refinancing balance, configuring collateral for a refinancing, managing use of proceeds of a refinancing, removing or placing a lien associated with a refinancing, verifying title for a refinancing, managing an inspection process, populating an application, negotiating terms and conditions for a refinancing, closing a refinancing, and the like.

The system may also include an artificial intelligence circuit 8310 that may be structured to classify the set of loan refinancing activities 8503 based at least in part on the training set of loan interactions 8505. The artificial intelligence circuit 8310 may include at least one system such as a machine learning system, a model-based system, a rule-based system, a deep learning system, a hybrid system, a neural network, a convolutional neural network, a feed forward neural network, a feedback neural network a self-organizing map, a fuzzy logic system, a random walk system, a random forest system, a probabilistic system, a Bayesian system, a simulation system, and the like.

The system may also include a robotic process automation circuit 8513 structured to perform a second loan refinancing activity 8511 on behalf of a party to a second loan 8312 based at least in part on the set of loan refinancing activities 8503 and the set of loan refinancing outcomes 8504. The party to a second loan 8312 may include least one such as a primary lender, a secondary lender, a lending syndicate, a corporate lender, a government lender, a bank lender, a secured lender, bond issuer, a bond purchaser, an unsecured lender, a guarantor, a provider of security, a borrower, a debtor, an underwriter, an inspector, an assessor, an auditor, a valuation professional, a government official, an accountant, and the like.

The second loan 8519 may include at least one auto loan, an inventory loan, a capital equipment loan, a bond for performance, a capital improvement loan, a building loan, a loan backed by an account receivable, an invoice finance arrangement, a factoring arrangement, a pay day loan, a refund anticipation loan, a student loan, a syndicated loan, a title loan, a home loan, a venture debt loan, a loan of intellectual property, a loan of a contractual claim, a working capital loan, a small business loan, a farm loan, a municipal bond, a subsidized loan and the like.

The system may further include an interface circuit 8508 structured to receive interactions 8507 from one or more of the entities 8502. In some embodiments the robotic process automation circuit 8513 may be trained on the interactions 8507. The system may further include a smart contract circuit 8518 structured to determine completion of the second loan refinancing activity 8511 and modify a smart refinance contract 8517 based on an outcome of the second loan refinancing activity 8511.

The system may further include a distributed ledger circuit 8315 structured to determine an event 8321 associated with the second loan refinancing activity 8511. The distributed ledger circuit 8315 may be structured to record, in a distributed ledger 8314 associated with the second loan 8519, the event 8321 associated with the second loan refinancing activity 8511.

Figure 86:
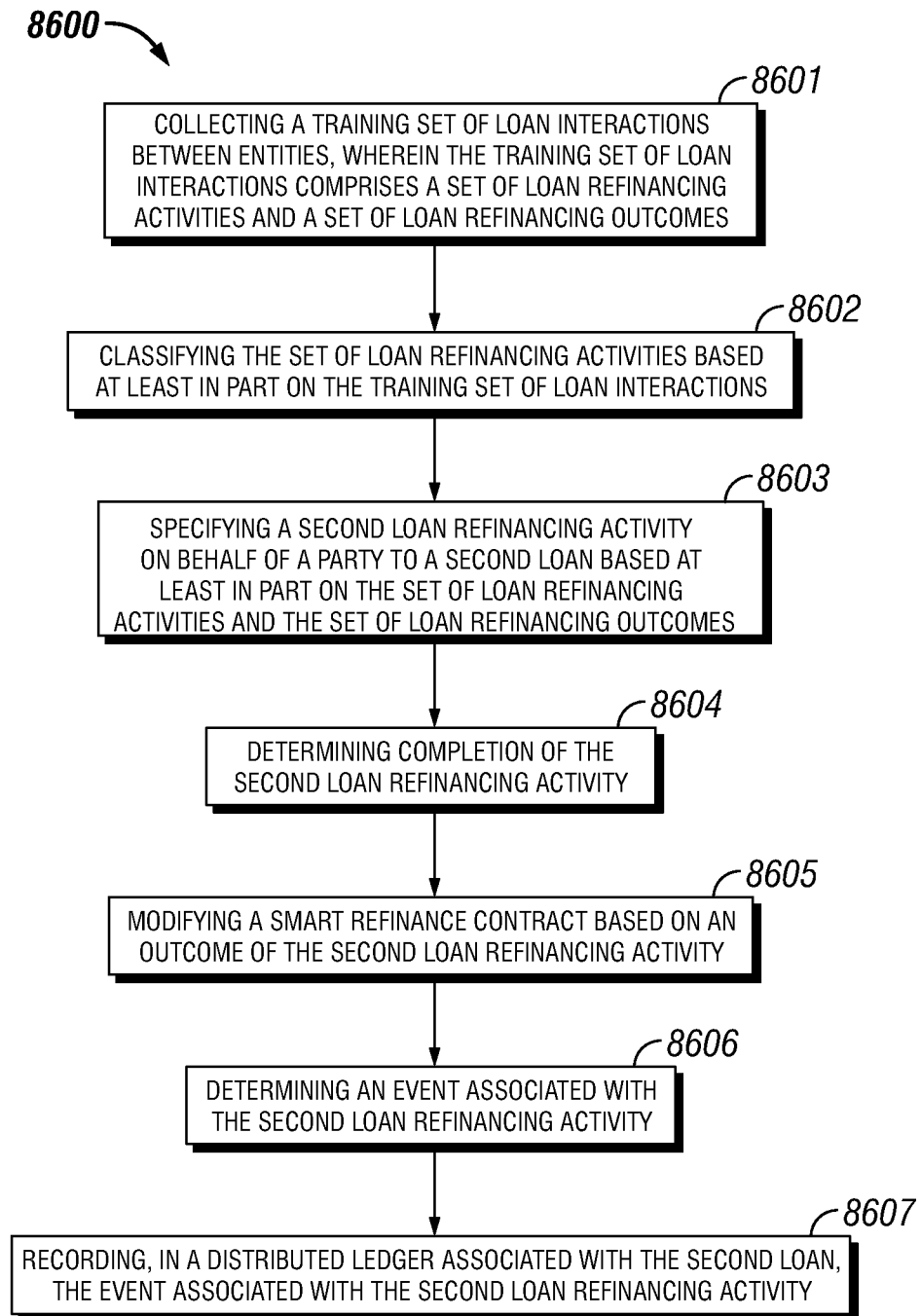
FIG. 86 depicts a method of a lending platform.

Referring to FIG. 86, an illustrative and non-limiting example method 8600 is depicted. The example method 8600 may include step 8601 for collecting a training set of loan interactions between entities, wherein the training set of loan interactions comprises a set of loan refinancing activities and a set of loan refinancing outcomes. A set of loan refinancing activities based at least in part the training set of loan interactions may be classified (step 8602). The method may further include the step 8603 of specifying a second loan refinancing activity on behalf of a party to a second loan based at least in part on the set of loan refinancing activities and the set of loan refinancing outcomes.

The method 8600 may further include the step 8604 of determining completion of the second loan refinancing activity. Based on the outcome of the second loan refinancing activity a smart refinance contract may be modified in step 8605. The method may also include the step 8606 of determining an event associated with the second loan refinancing activity. The event associated with the second loan refinancing activity may be recorded in a distributed ledger associate with the second loan in step 8607.

Figure 87:
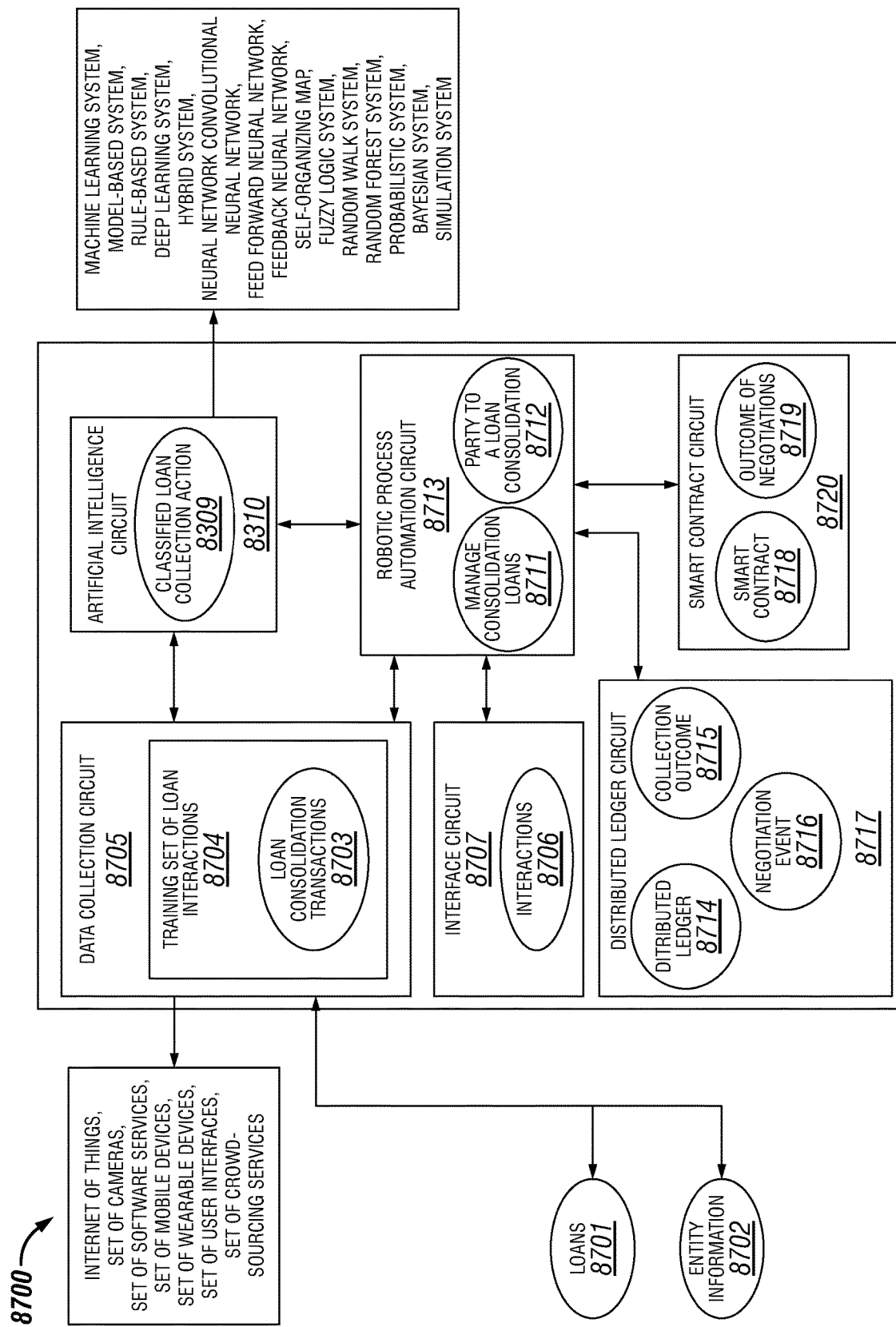
FIG. 87 depicts components and interactions of a lending platform.

Referring to FIG. 87, an illustrative and non-limiting example system for system for adaptive intelligence and robotic process automation capabilities 8700 is depicted. The example system may include a data collection circuit 8705 which may collect data such as a training set of loan interactions 8704 between entities which may include a set of loan consolidation transactions 8703 and the like. The data may be collected from loans 8701, information re. entities 8702, and the like. The data may be collected from a variety of sources and systems such as: an Internet of Things system, a camera system, a networked monitoring system, an internet monitoring system, a mobile device system, a wearable device system, a user interface system, and a crowdsourcing system.

The system may also include an artificial intelligence circuit 8310 that may be structured to classify a set of loans as candidates for consolidation based at least in part on the training set of loan interactions 8704. The artificial intelligence circuit 8310 may include at least one system such as a machine learning system, a model-based system, a rule-based system, a deep learning system, a hybrid system, a neural network, a convolutional neural network, a feed forward neural network, a feedback neural network a self-organizing map, a fuzzy logic system, a random walk system, a random forest system, a probabilistic system, a Bayesian system, a simulation system, and the like.

The system may also include a robotic process automation circuit 8713 structured to manage a consolidation of at least a subset of the set of loans 8711 on behalf of a party to the loan consolidation 8712 based at least in part on the training set of loan consolidation transactions 8703. Managing the consolidation may include identification of loans from a set of candidate loans, preparation of a consolidation offer, preparation of a consolidation plan, preparation of content communicating a consolidation offer, scheduling a consolidation offer, communicating a consolidation offer, negotiating a modification of a consolidation offer, preparing a consolidation agreement, executing a consolidation agreement, modifying collateral for a set of loans, handling an application workflow for consolidation, managing an inspection, managing an assessment, setting an interest rate, deferring a payment requirement, setting a payment schedule, or closing a consolidation agreement.

The artificial intelligence circuit may further include a model that may be used to classify loans are candidates for consolidation. The model may process attributes of entities, the attributes may include identity of a party, interest rate, payment balance, payment terms, payment schedule, type of loan, type of collateral, financial condition of party, payment status, condition of collateral, value of collateral, and the like.

The party to a loan consolidation 8712 may include least one such as a primary lender, a secondary lender, a lending syndicate, a corporate lender, a government lender, a bank lender, a secured lender, bond issuer, a bond purchaser, an unsecured lender, a guarantor, a provider of security, a borrower, a debtor, an underwriter, an inspector, an assessor, an auditor, a valuation professional, a government official, an accountant, and the like.

Loans 8701 may include at least one auto loan, an inventory loan, a capital equipment loan, a bond for performance, a capital improvement loan, a building loan, a loan backed by an account receivable, an invoice finance arrangement, a factoring arrangement, a pay day loan, a refund anticipation loan, a student loan, a syndicated loan, a title loan, a home loan, a venture debt loan, a loan of intellectual property, a loan of a contractual claim, a working capital loan, a small business loan, a farm loan, a municipal bond, a subsidized loan and the like.

The system may further include an interface circuit 8707 structured to receive interactions 8706 from one or more of the entities 8702. In some embodiments the robotic process automation circuit 8713 may be trained on the interactions 8706. The system may further include a smart contract circuit 8720 structured to determine a completion of a negotiations of the consolidation and modify a contract 8718 based on an outcome of the negotiation 8719.

The system may further include a distributed ledger circuit 8717 structured to determine at least one of a collection outcome 8715 or a negotiation event 8716 associated with the consolidation. The distributed ledger circuit 8717 may be structured to record, in a distributed ledger 8714 associated with the loan, the negotiation event 8716 and/or the collection outcome 8715.

Figure 88:
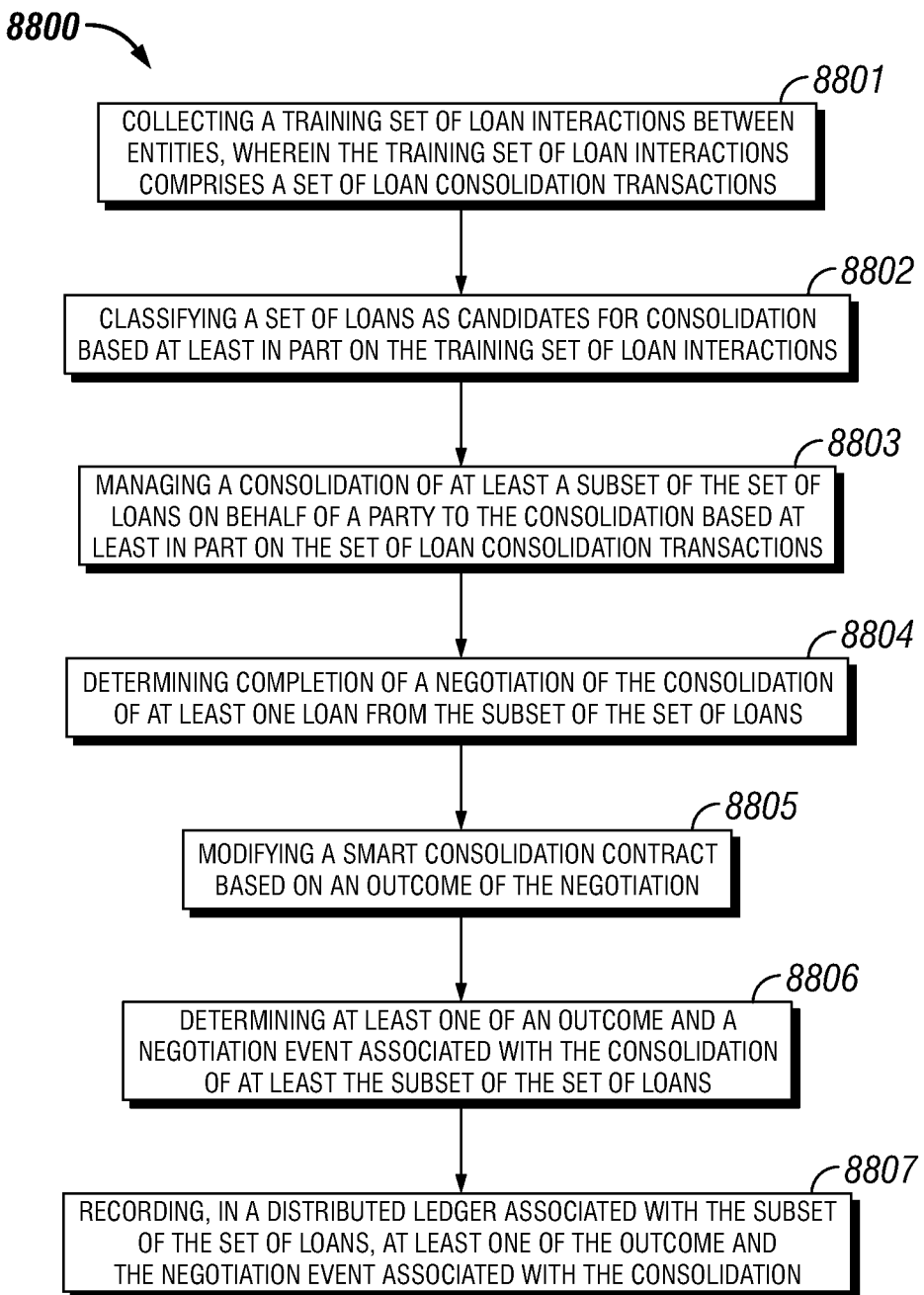
FIG. 88 depicts a method of a lending platform.

Referring to FIG. 88, an illustrative and non-limiting example method 8800 is depicted. The example method 8800 may include step 8801 collecting a training set of loan interactions between entities, wherein the training set of loan interactions comprises a set of loan consolidation transactions. A set of loans as candidates for consolidation based at least in part on the training set of loan interactions may be classified (step 8802). The method may further include the step 8803 of managing a consolidation of at least a subset of the set of loans on behalf of a party to the consolidation based at least in part on the set of loan consolidation transactions.

The method 8800 may further include the step 8804 of determining completion of a negotiation of the consolidation of at least one loan from the subset of the set of loans. Based on the outcome of the negotiations a smart contract may be modified in step 8805. The method may also include the step 8806 of determining at least one of an outcome and a negotiation event associated with the consolidation of at least the subset of the set of loans. The at least one of the outcome and the negotiation event may be recorded in a distributed ledger associate with the consolidation in step 8807.

Figure 89:
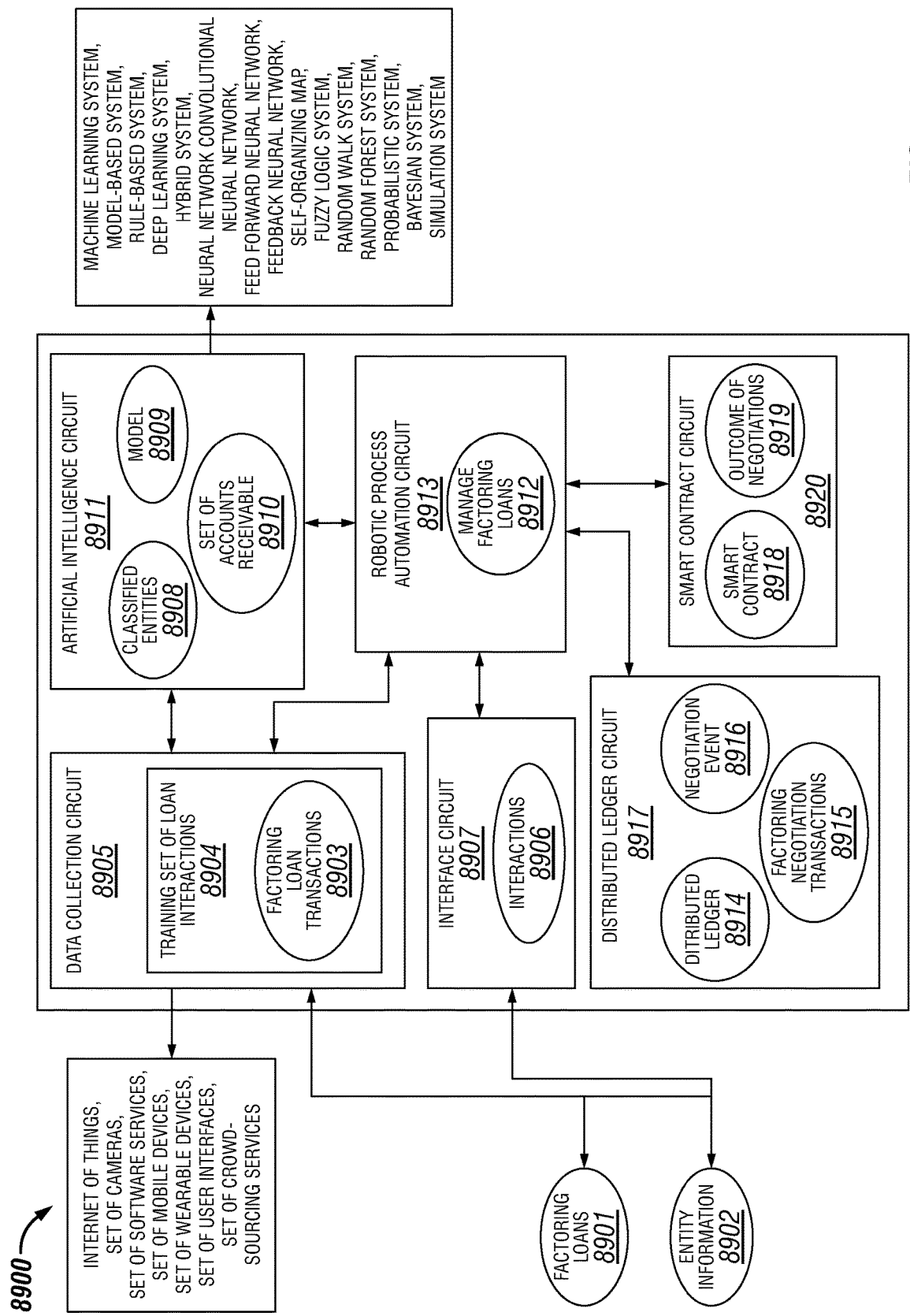
FIG. 89 depicts components and interactions of a lending platform.

Referring to FIG. 89, an illustrative and non-limiting example system for system for adaptive intelligence and robotic process automation capabilities 8900 is depicted. The example system may include a data collection circuit 8905 which may collect data information about entities 8902 involved in a set of factoring loans 8901 and a training set of interactions 8904 between entities for a set of factoring loan transactions 8903. The data may be collected from a variety of sources and systems such as: an Internet of Things system, a camera system, a networked monitoring system, an internet monitoring system, a mobile device system, a wearable device system, a user interface system, and a crowdsourcing system.

The system may also include an artificial intelligence circuit 8911 that may be structured to classify entities 8908 involved in the set of factoring loans based at least in part on the training set of interactions 8904. The artificial intelligence circuit 8911 may include at least one system such as a machine learning system, a model-based system, a rule-based system, a deep learning system, a hybrid system, a neural network, a convolutional neural network, a feed forward neural network, a feedback neural network a self-organizing map, a fuzzy logic system, a random walk system, a random forest system, a probabilistic system, a Bayesian system, a simulation system, and the like.

The system may also include a robotic process automation circuit 8913 structured to manage a factoring loan 8912 based at least in part on the factoring loan transactions 8903. Managing the factoring loan may include managing at least one of a set of assets for factoring, identification of loans for factoring from a set of candidate loans, preparation of a factoring offer, preparation of a factoring plan, preparation of content communicating a factoring offer, scheduling a factoring offer, communicating a factoring offer, negotiating a modification of a factoring offer, preparing a factoring agreement, executing a factoring agreement, modifying collateral for a set of factoring loans, handing transfer of a set of accounts receivable, handling an application workflow for factoring, managing an inspection, managing an assessment of a set of assets to be factored, setting an interest rate, deferring a payment requirement, setting a payment schedule, or dosing a factoring agreement.

The artificial intelligence circuit 8911 may further include a model 8909 that may be used to process attributes of entities involved in the set of factoring loans, the attributes may include assets used for factoring, identity of a party, interest rate, payment balance, payment terms, payment schedule, type of loan, type of collateral, financial condition of party, payment status, condition of collateral, or value of collateral. The assets used for factoring may include a set of accounts receivable 8910. At least one entity of the entities 8902 may be a party to at least one factoring loan transactions 8903. The party may include least one such as a primary lender, a secondary lender, a lending syndicate, a corporate lender, a government lender, a bank lender, a secured lender, bond issuer, a bond purchaser, an unsecured lender, a guarantor, a provider of security, a borrower, a debtor, an underwriter, an inspector, an assessor, an auditor, a valuation professional, a government official, an accountant, and the like.

The system may further include an interface circuit 8907 structured to receive interactions 8906 from one or more of the entities 8902. In some embodiments the robotic process automation circuit 8913 may be trained on the interactions 8906.

The system may further include a smart contract circuit 8920 structured to determine a completion of a negotiations of the factoring loan and modify a contract 8918 based on an outcome of the negotiation 8919.

The system may further include a distributed ledger circuit 8917 structured to determine at least one of an outcome 8915 or a negotiation event 8916 associated with the negotiation of the factoring loan. The distributed ledger circuit 8917 may be structured to record, in a distributed ledger 8914 associated with the factoring loan, the negotiation event 8916 and/or the outcome 8915.

Figure 90:
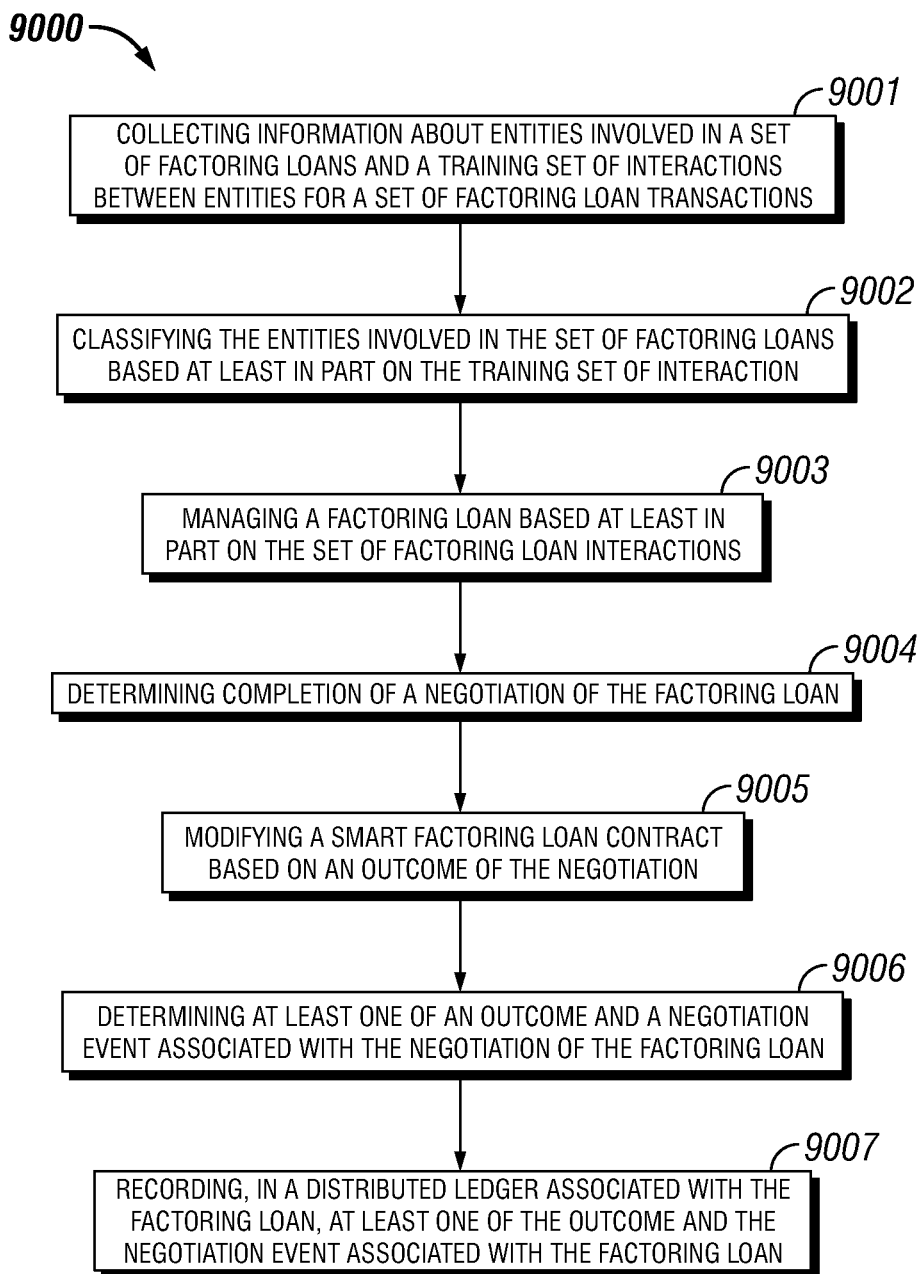
FIG. 90 depicts a method of a lending platform.

Referring to FIG. 90, an illustrative and non-limiting example method 9000 is depicted. The example method 9000 may include step 9001 collecting information about entities involved in a set of factoring loans and a training set of interactions between entities for a set of factoring loan transactions. Entities involved in the set of factoring loans may be classified based at least in part on the training set of loan interactions step 9002. The method may further include the step 9003 of managing a factoring loan based at least in part on the set of factoring loan interactions.

The method 9000 may further include the step 9004 of determining completion of a negotiation of the factoring loan. Based on the outcome of the negotiations a smart contract may be modified in step 9005. The method may also include the step 9006 of determining at least one of an outcome and a negotiation event associated with the negotiation of the factoring loan. The at least one of the outcome and the negotiation event may be recorded in a distributed ledger associate with the factoring loan in step 9007.

Figure 91:
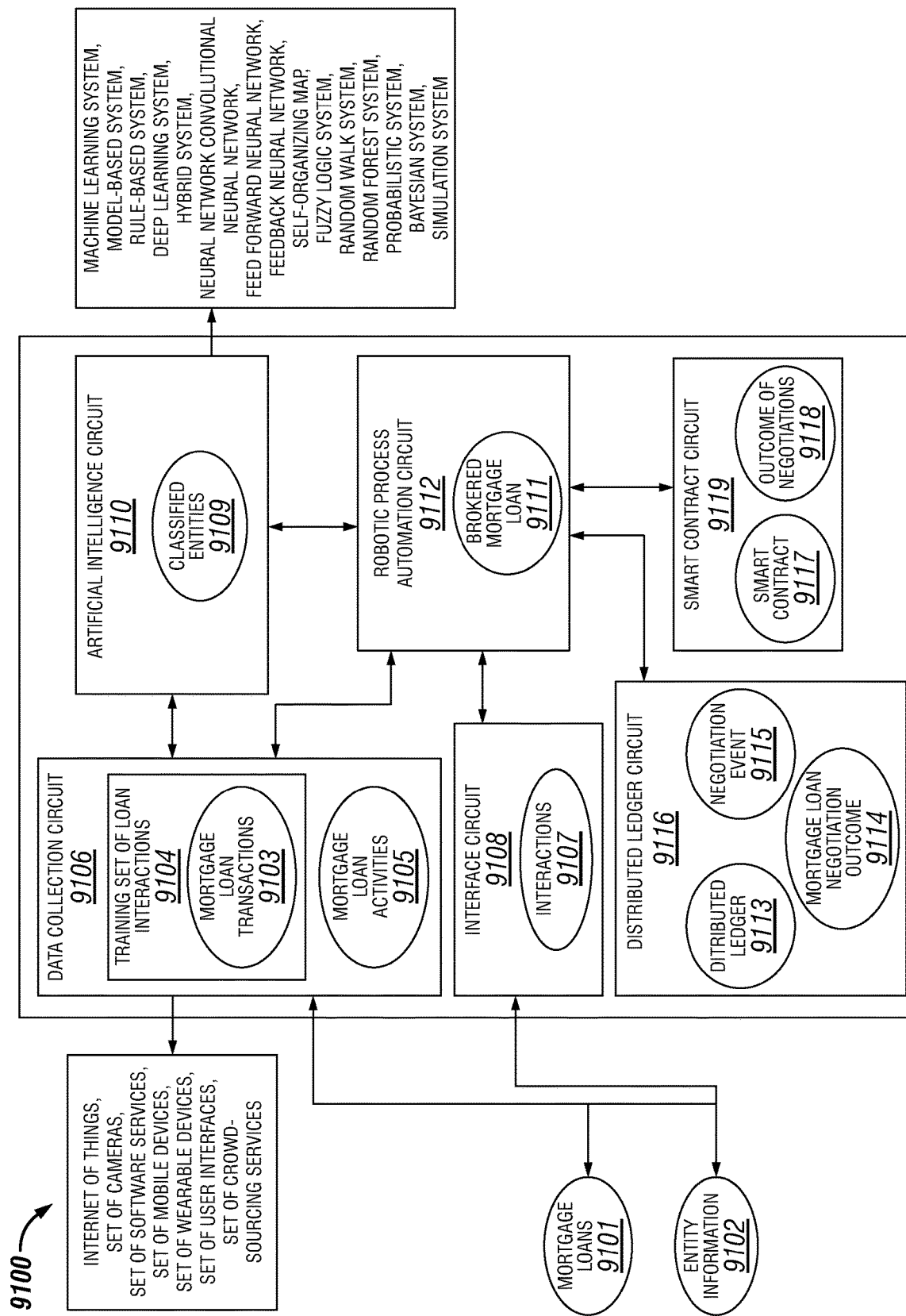
FIG. 91 depicts components and interactions of a lending platform.

Referring to FIG. 91, an illustrative and non-limiting example system for system for adaptive intelligence and robotic process automation capabilities 9100 is depicted. The example system may include a data collection circuit 9106 which may collect data information about mortgage loans 9101 and entities 9102 involved in the set of mortgage loans and mortgage loan activities 9105 and a training set of interactions 9104 between entities for a set of mortgage loan transactions 9103. The data may be collected from a variety of sources and systems such as: an Internet of Things system, a camera system, a networked monitoring system, an internet monitoring system, a mobile device system, a wearable device system, a user interface system, and a crowdsourcing system.

The system may also include an artificial intelligence circuit 9110 that may be structured to classify entities 9109 involved in the set of mortgage loan activities based at least in part on the training set of interactions 9104. The artificial intelligence circuit 9110 may include at least one system such as a machine learning system, a model-based system, a rule-based system, a deep learning system, a hybrid system, a neural network, a convolutional neural network, a feed forward neural network, a feedback neural network a self-organizing map, a fuzzy logic system, a random walk system, a random forest system, a probabilistic system, a Bayesian system, a simulation system, and the like.

The system may also include a robotic process automation circuit 9112 structured to broker a mortgage loan 9111 based at least in part on at least one of the set of mortgage loan activities 9105 and the training set of interactions 9104. The set of mortgage loan activities 9105 and/or the set of mortgage loan transactions 9103 may include activities selected from a group consisting of: among marketing activity, identification of a set of prospective borrowers, identification of property, identification of collateral, qualification of borrower, title search, title verification, property assessment, property inspection, property valuation, income verification, borrower demographic analysis, identification of capital providers, determination of available interest rates, determination of available payment terms and conditions, analysis of existing mortgage, comparative analysis of existing and new mortgage terms, completion of application workflow, population of fields of application, preparation of mortgage agreement, completion of schedule to mortgage agreement, negotiation of mortgage terms and conditions with capital provider, negotiation of mortgage terms and conditions with borrower, transfer of title, placement of lien, or closing of mortgage agreement.

The artificial intelligence circuit 9110 may further include a model that may be used to process attributes of entities involved in the set of mortgage loan activities, the attributes may properties that are subject to mortgages, assets used for collateral, identity of a party, interest rate, payment balance, payment terms, payment schedule, type of mortgage, type of property, financial condition of party, payment status, condition of property, or value of property. In embodiments, brokering the mortgage loan comprises at least one activity such as managing at least one of a property that is subject to a mortgage, identification of candidate mortgages from a set of borrower situations, preparation of a mortgage offer, preparation of content communicating a mortgage offer, scheduling a mortgage offer, communicating a mortgage offer, negotiating a modification of a mortgage offer, preparing a mortgage agreement, executing a mortgage agreement, modifying collateral for a set of mortgage loans, handing transfer of a lien, handling an application workflow, managing an inspection, managing an assessment of a set of assets to be subject to a mortgage, setting an interest rate, deferring a payment requirement, setting a payment schedule, closing a mortgage agreement, and the like In embodiments at least one entity of the entities 9102 may be a party to at least one mortgage loan transactions of the set of mortgage loan transactions 9103. The party may include least one such as a primary lender, a secondary lender, a lending syndicate, a corporate lender, a government lender, a bank lender, a secured lender, bond issuer, a bond purchaser, an unsecured lender, a guarantor, a provider of security, a borrower, a debtor, an underwriter, an inspector, an assessor, an auditor, a valuation professional, a government official, an accountant, and the like.

The system may further include an interface circuit 9108 structured to receive interactions 9107 from one or more of the entities 9102. In some embodiments the robotic process automation circuit 9112 may be trained on the interactions 9107.

The system may further include a smart contract circuit 9119 structured to determine a completion of a negotiations of the mortgage loan and modify a smart contract 9117 based on an outcome of the negotiation 9118.

The system may further include a distributed ledger circuit 9116 structured to determine at least one of an outcome 9114 or a negotiation event 9115 associated with the negotiation of the mortgage loan. The distributed ledger circuit 9116 may be structured to record, in a distributed ledger 9113 associated with the mortgage loan, the negotiation event 9115 and/or the outcome 9114.

Figure 92:
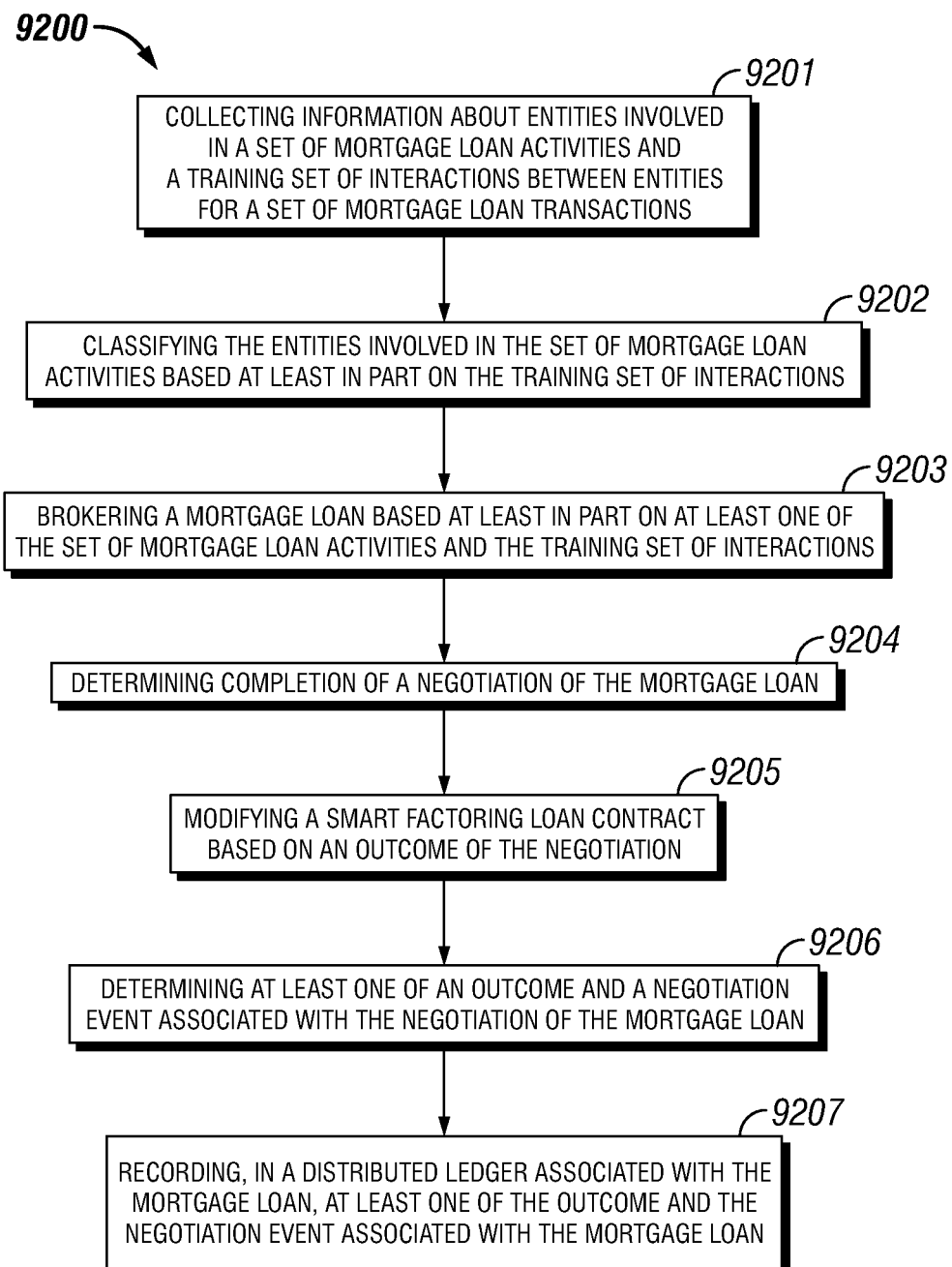
FIG. 92 depicts a method of a lending platform.

Referring to FIG. 92, an illustrative and non-limiting example method 9200 is depicted. The example method 9200 may include step 9201 collecting information about entities involved in a set of mortgage loan activities and a training set of interactions between entities for a set of mortgage loan transactions. Entities involved in the set of factoring loans may be classified based at least in part on the training set of loan interactions step 9202. The method may further include the step 9203 of brokering a mortgage loan based at least in part on at least one of the set of mortgage loan activities and the training set of interactions.

The method 9200 may further include the step 9204 of determining completion of a negotiation of the mortgage loan. Based on the outcome of the negotiations a smart contract may be modified in step 9205. The method may also include the step 9206 of determining at least one of an outcome and a negotiation event associated with the negotiation of the mortgage loan. The at least one of the outcome and the negotiation event may be recorded in a distributed ledger associate with the mortgage loan in step 9207.

Figure 93:
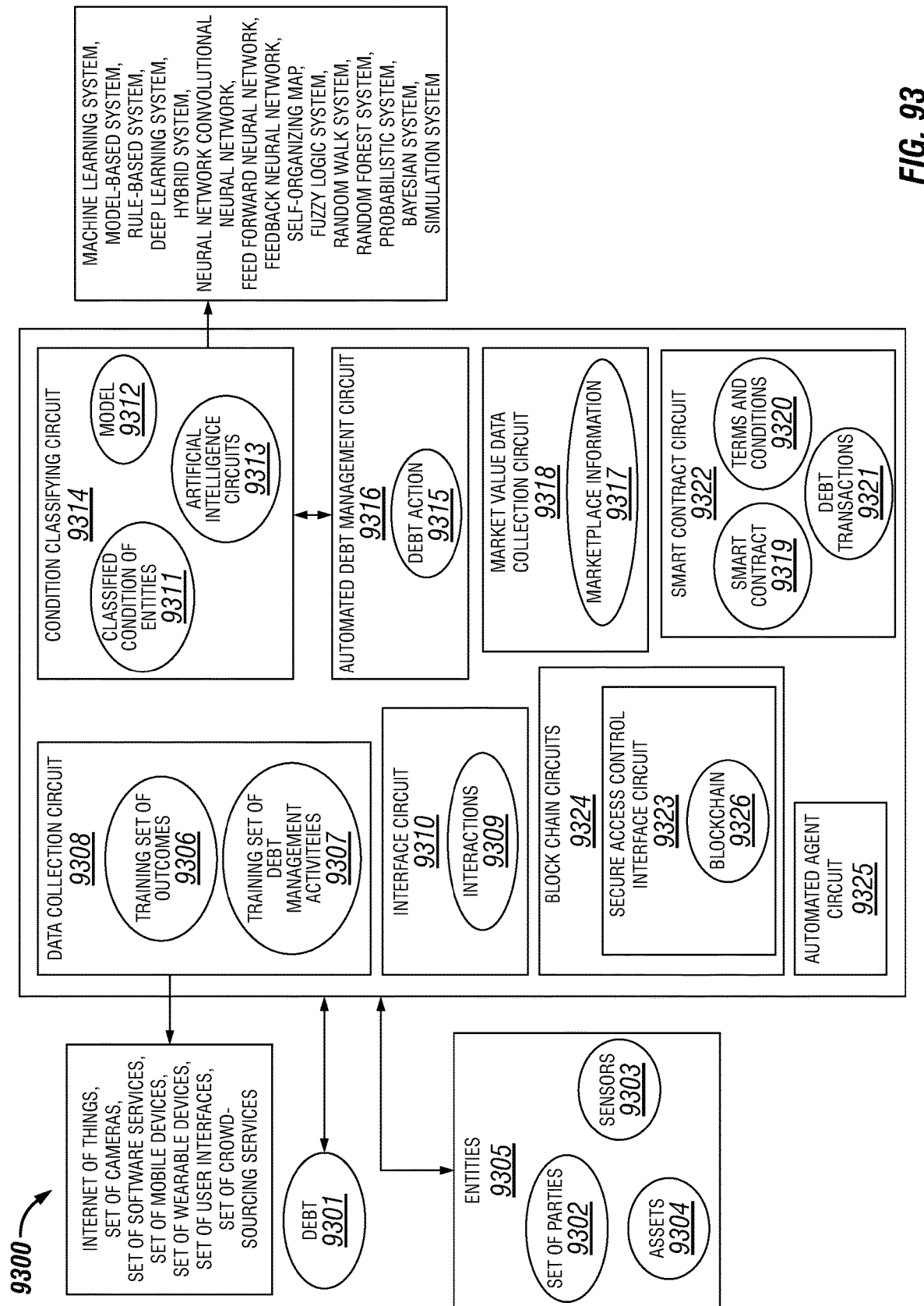
FIG. 93 depicts components and interactions of a lending platform.

Referring to FIG. 93, an illustrative and non-limiting example system for system for adaptive intelligence and robotic process automation capabilities 9300 is depicted. The example system may include a data collection circuit 9308 which may collect data about entities 9305 involved in a set of debt transactions 9301, training data set of outcomes 9306 related to the entities, and a training set of debt management activities 9307. The data may be collected from a variety of sources and systems such as: Internet of Things devices, a set of environmental condition sensors, a set of crowdsourcing services, a set of social network analytic services, or a set of algorithms for querying network domains, and the like.

The system may also include a condition classifying circuit 9314 that may be structured to classify a condition 9311 of at least one entity of the entities 9305. The condition classifying circuit 9314 may include a model 9312 and a set of artificial intelligence circuits 9313. The model 9312 may be trained using the training data set of outcomes 9306 related to the entities. The artificial intelligence circuits 9313 may include at least one system such as machine learning system, a model-based system, a rule-based system, a deep learning system, a hybrid system, a neural network, a convolutional neural network, a feed forward neural network, a feedback neural network, a self-organizing map, a fuzzy logic system, a random walk system, a random forest system, a probabilistic system, a Bayesian system, or a simulation system.

The system may also include an automated debt management circuit 9316 structured to manage an action related to a debt 9315. The automated debt management circuit 9316 may be trained on the training set of debt management activities 9307.

In embodiments, at least one debt transaction of the set of debt transactions 9301 may be include an auto loan, an inventory loan, a capital equipment loan, a bond for performance, a capital improvement loan, a building loan, a loan backed by an account receivable, an invoice finance arrangement, a factoring arrangement, a pay day loan, a refund anticipation loan, a student loan, a syndicated loan, a title loan, a home loan, a venture debt loan, a loan of intellectual property, a loan of a contractual claim, a working capital loan, a small business loan, a farm loan, a municipal bond, a subsidized loan, and the like.

In embodiments, the entities 9305 involved in the set of debt transactions may include at least one of set of parties 9302 and a set of assets 9304. The assets 9304 may include a municipal asset, a vehicle, a ship, a plane, a building, a home, real estate property, undeveloped land, a farm, a crop, a municipal facility, a warehouse, a set of inventory, a commodity, a security, a currency, a token of value, a ticket, a cryptocurrency, a consumable item, an edible item, a beverage, a precious metal, an item of jewelry, a gemstone, intellectual property, an intellectual property right, a contractual right, an antique, a fixture, an item of furniture, an item of equipment, a tool, an item of machinery, or an item of personal property. The system may further include a set of sensors 9303 positioned on at least one asset 9304 from the set of assets, on a container for least one asset from the set of assets, and on a package for at least one asset from the set of assets, wherein the set of sensors configured to associate sensor information sensed by the set of sensors with a unique identifier for the at least one asset from the set of assets. The sensors 9303 may include image, temperature, pressure, humidity, velocity, acceleration, rotational, torque, weight, chemical, magnetic field, electrical field, or position sensors.

In embodiments, the system may further include a set of block chain circuits 9324 structured to receive information from the data collection circuit 9308 and the set of sensors 9303 and storing the information in a blockchain 9326. The access to the blockchain 9326 may be provided via a secure access control interface circuit 9323.

An automated agent circuit 9325 may be structured to process events relevant to at least one of a value, a condition, and an ownership of at least one asset of the set of assets and further structured to undertake a set of actions related to a debt transaction to which the asset is related.

The system may further include an interface circuit 9310 structured to receive interactions 9309 from at least one of the entities 9305. In embodiments the automated debt management circuit 9316 may be trained on the interactions 9309. In some embodiments the system may further include a market value data collection circuit 9318 structured to monitor and report marketplace information 9317 relevant to a value of a of at least one asset of a set of assets 9304. The market value data collection circuit 9318 may be further structured to monitor at least one pricing and financial data for items that are similar to at least one asset in the set of assets in at least one public marketplace. A set of similar items for valuing at least one asset from the set of assets may be constructed using a similarity clustering algorithm based on attributes of the assets. In embodiments, at least one attribute of the attributes of the assets may include a category of assets, asset age, asset condition, asset history, asset storage, geolocation of assets, and the like.

In embodiments, the system may further include a smart contract circuit 9322 structured to manage a smart contract 9319 for a debt transaction 9321. The smart contract circuit 9322 may be further structured to establish a set of terms and conditions 9320 for the debt transaction 9321. At least one of the terms and conditions may include a principal amount of debt, a balance of debt, a fixed interest rate, a variable interest rate, a payment amount, a payment schedule, a balloon payment schedule, a specification of collateral, a specification of substitutability of collateral, a party, a guarantee, a guarantor, a security, a personal guarantee, a lien, a duration, a covenant, a foreclose condition, a default condition, a consequence of default, and the like.

In embodiments at least one action related to a debt 9315 may include offering a debt transaction, underwriting a debt transaction, setting an interest rate, deferring a payment requirement, modifying an interest rate, validating title, managing inspection, recording a change in title, assessing the value of an asset, calling a loan, closing a transaction, setting terms and conditions for a transaction, providing notices required to be provided, foreclosing on a set of assets, modifying terms and conditions, setting a rating for an entity, syndicating debt, or consolidating debt. At least one debt management activity from the training set of debt management activities 9307 may include offering a debt transaction, underwriting a debt transaction, setting an interest rate, deferring a payment requirement, modifying an interest rate, validating title, managing inspection, recording a change in title, assessing a value of an asset, calling a loan, closing a transaction, setting terms and conditions for a transaction, providing notices required to be provided, foreclosing on a set of assets, modifying terms and conditions, setting a rating for an entity, syndicating debt, or consolidating debt.

Figure 94:
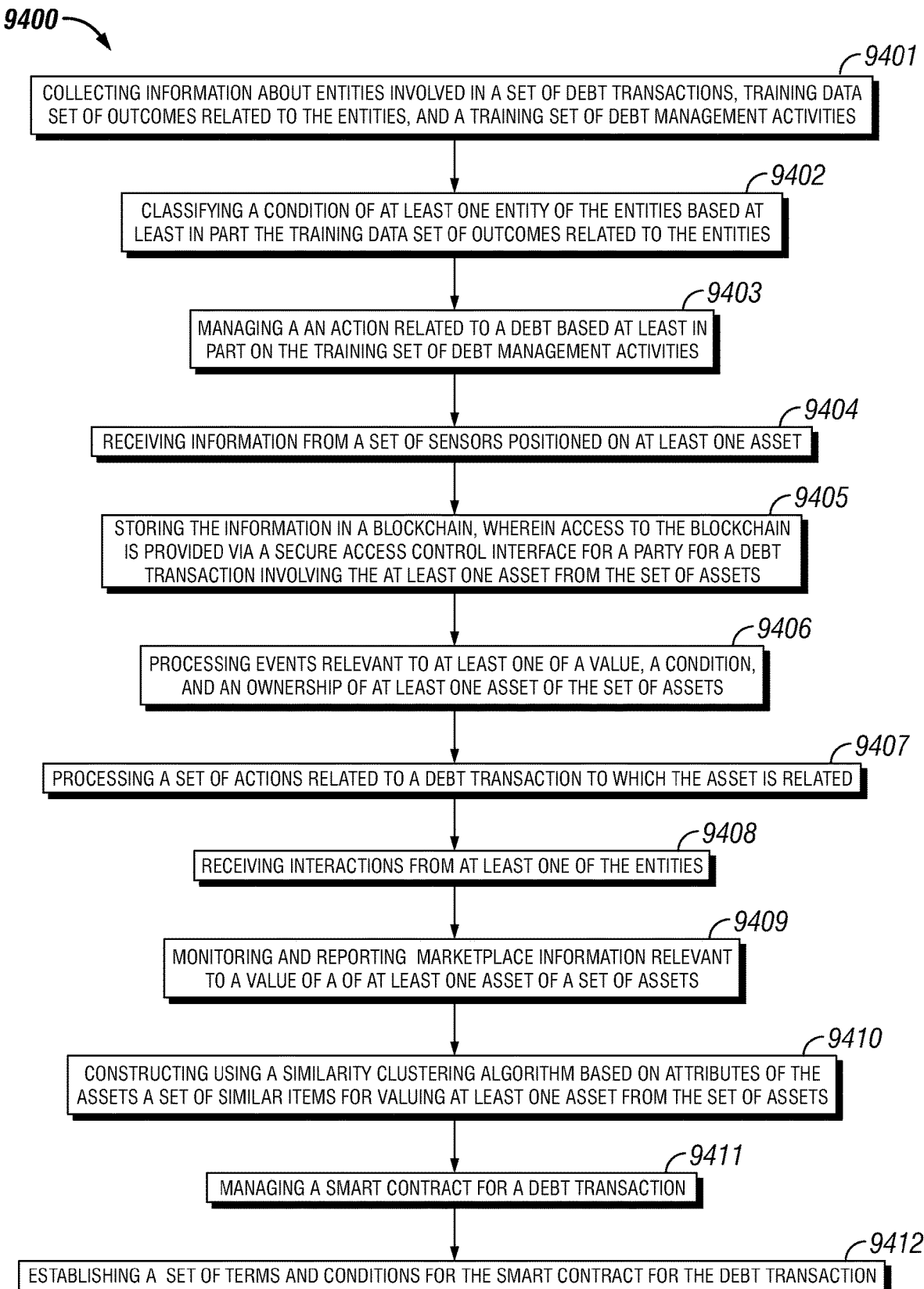
FIG. 94 depicts a method of a lending platform.

Referring to FIG. 94, an illustrative and non-limiting example method 9400 is depicted. The example method 9400 may include step 9401 collecting information about entities involved in a set of debt transactions, training data set of outcomes related to the entities, and a training set of debt management activities. The example method may further include classifying a condition of at least one entity of the entities based at least in part the training data set of outcomes related to the entities (step 9402). The example method may further include managing an action related to a debt based at least in part on the training set of debt management activities (step 9403). The example method may further include receiving information from a set of sensors positioned on at least one asset (step 9404). The example method may further include storing the information in a blockchain, wherein access to the blockchain is provided via a secure access control interface for a party for a debt transaction involving the at least one asset from the set of assets (step 9405). In step 9406 the method may include processing events relevant to at least one of a value, a condition, or an ownership of at least one asset of the set of assets. In step 9407 the method may include processing a set of actions related to a debt transaction to which the asset is related. In embodiments the method may further include receiving interactions from at least one of the entities (step 9408), monitoring and reporting marketplace information relevant to a value of a of at least one asset of a set of assets (step 9409), constructing using a similarity clustering algorithm based on attributes of the assets a set of similar items for valuing at least one asset from the set of assets (step 9410), managing a smart contract for a debt transaction (step 9411) and establishing a set of terms and conditions for the smart contract for the debt transaction (step 9412).

Figure 95:
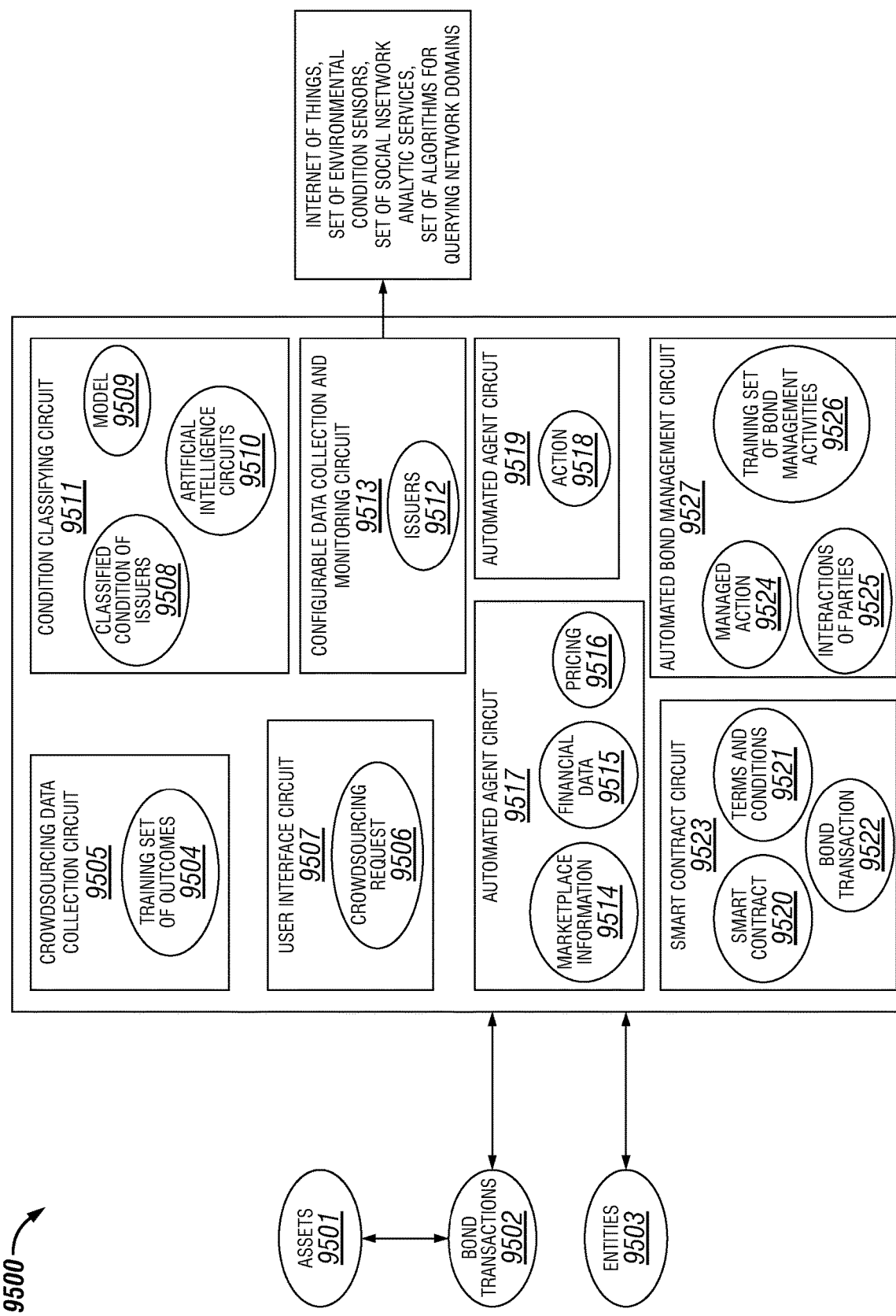
FIG. 95 depicts components and interactions of a lending platform.

Referring to FIG. 95, an illustrative and non-limiting example system for system for adaptive intelligence and robotic process automation capabilities 9500 is depicted.

The example system may include a crowdsourcing data collection circuit 9505 structured to collect information about entities 9503 involved in a set of bond transactions 9502 and a training data set of outcomes related to the entities 9503. The system may further include a condition classifying circuit 9511 structured to classify a condition of a set of issuers 9508 using the information from the crowdsourcing data collection circuit 9505 and a model 9509. The condition classifying circuit 9511 may include artificial intelligence circuits 9510. The model 9509 may be trained using the training data set of outcomes 9504 related to the set of issuers. The example system may further include an automated agent circuit 9519 structured to perform an action related to a debt transaction in response to the classified condition of at least one issuer of the set of issuers. In embodiments at least one entity 9503 may include a set of issuers, a set of bonds, a set of parties, or a set of assets. At least one issuer may include a municipality, a corporation, a contractor, a government entity, a non-governmental entity, or a non-profit entity. At least one bond may include a municipal bond, a government bond, a treasury bond, an asset-backed bond, or a corporate bond.

In embodiments, the condition classified 9508 by the condition classifying circuit 9511 may include a default condition, a foreclosure condition, a condition indicating violation of a covenant, a financial risk condition, a behavioral risk condition, a policy risk condition, a financial health condition, a physical defect condition, a physical health condition, an entity risk condition, an entity health condition, or the like. The crowdsourcing data collection circuit 9505 may be structured to enable a user interface 9507 by which a user may configure a crowdsourcing request 9506 for information relevant to the condition about the set of issuers.

The system may further include a configurable data collection and monitoring circuit 9513 structured to monitor at least one issuer from the set of issuers 9512. The configurable data collection and monitoring circuit 9513 may include a system such as: Internet of Things devices, a set of environmental condition sensors, a set of social network analytic services, or a set of algorithms for querying network domains. The configurable data collection and monitoring circuit 9513 mat be structured to monitor an at least one environment such as: a municipal environment, a corporate environment, a securities trading environment, a real property environment, a commercial facility, a warehousing facility, a transportation environment, a manufacturing environment, a storage environment, a home, or a vehicle.

In embodiments a set of bonds associated with the set of bond transactions 9502 may be backed by a set of assets 9501. At least one asset 9501 may include a municipal asset, a vehicle, a ship, a plane, a building, a home, real estate property, undeveloped land, a farm, a crop, a municipal facility, a warehouse, a set of inventory, a commodity, a security, a currency, a token of value, a ticket, a cryptocurrency, a consumable item, an edible item, a beverage, a precious metal, an item of jewelry, a gemstone, intellectual property, an intellectual property right, a contractual right, an antique, a fixture, an item of furniture, an item of equipment, a tool, an item of machinery, an item of personal property, or the like.

In embodiments, the system may further include an automated agent circuit 9519 structured to processes events relevant to at least one of a value, a condition, or an ownership of at least one asset of the at least one issuer of the set of issuers, and to perform the action related to the debt transaction in response to at least one of the processed events.

The action 9518 may include offering a debt transaction, underwriting a debt transaction, setting an interest rate, deferring a payment requirement, modifying an interest rate, validating title, managing inspection, recording a change in title, assessing the value of an asset, calling a loan, closing a transaction, setting terms and conditions for a transaction, providing notices required to be provided, foreclosing on a set of assets, modifying terms and conditions, setting a rating for an entity, syndicating debt, consolidating debt, and the like. The condition classifying circuit 9511 may include a system such as: a machine learning system, a model-based system, a rule-based system, a deep learning system, a hybrid system, a neural network, a convolutional neural network, a feed forward neural network, a feedback neural network, a self-organizing map, a fuzzy logic system, a random walk system, a random forest system, a probabilistic system, a Bayesian system, or a simulation system.

In embodiments the system may further include an automated bond management circuit 9527 configured to manage an action related to the bond 9524 related to the at least one issuer of the set of issuers. The automated bond management circuit 9527 may be trained on a training set of bond management activities 9526. The automated bond management circuit 9527 may be further trained on a set of interactions of parties 9525 with a set of user interfaces involved in a set of bond transaction activities. At least one bond transaction may include a debt transaction, underwriting a debt transaction, setting an interest rate, deferring a payment requirement, modifying an interest rate, validating title, managing inspection, recording a change in title, assessing the value of an asset, calling a loan, closing a transaction, setting terms and conditions for a transaction, providing notices required to be provided, foreclosing on a set of assets, modifying terms and conditions, setting a rating for an entity, syndicating debt, consolidating debt, or the like.

In embodiments the system may further include a market value data collection circuit 9517 structured to monitor and reports on marketplace information 9514 relevant to a value of at least one of the issuer or a set of assets. Reporting may include reporting on: a municipal asset, a vehicle, a ship, a plane, a building, a home, real estate property, undeveloped land, a farm, a crop, a municipal facility, a warehouse, a set of inventory, a commodity, a security, a currency, a token of value, a ticket, a cryptocurrency, a consumable item, an edible item, a beverage, a precious metal, an item of jewelry, a gemstone, intellectual property, an intellectual property right, a contractual right, an antique, a fixture, an item of furniture, an item of equipment, a tool, an item of machinery, or an item of personal property. The market value data collection circuit 9517 may be structured to monitor pricing 9516 or financial data 9515 for items that are similar to the assets in at least one public marketplace. The market value data collection circuit 9517 may be further structured to construct a set of similar items for valuing the assets using a similarity clustering algorithm based on attributes of the assets. At least one attribute from the attributes may be selected from: a category of the assets, asset age, asset condition, asset history, asset storage, or geolocation of assets.

In embodiments, the system may further include a smart contract circuit 9523 structured for managing a smart contract 9520 for a bond transaction 9522 in response to the classified condition of the at least one issuer of the set of issuers. The smart contract circuit 9523 may be structured to determine terms and conditions 9521 for the bond. At least one term and condition 9521 may include a principal amount of debt, a balance of debt, a fixed interest rate, a variable interest rate, a payment amount, a payment schedule, a balloon payment schedule, a specification of assets that back the bond, a specification of substitutability of assets, a party, an issuer, a purchaser, a guarantee, a guarantor, a security, a personal guarantee, a lien, a duration, a covenant, a foreclose condition, a default condition, a consequence of default, and the like.

Figure 96:
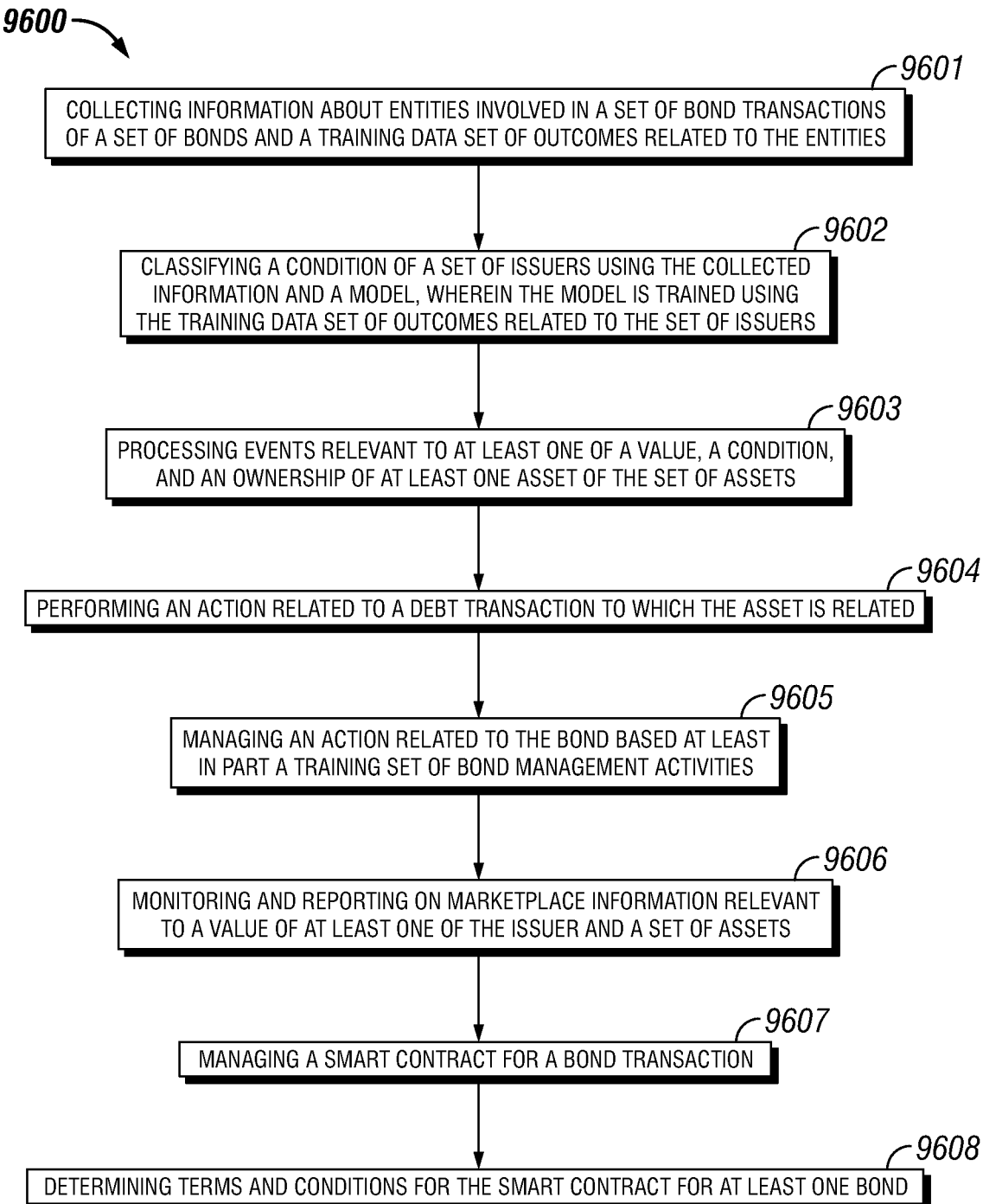
FIG. 96 depicts a method of a lending platform.

Referring to FIG. 96, an illustrative and non-limiting example method 9600 is depicted. The example method 9600 may include step 9601 of collecting information about entities involved in a set of bond transactions of a set of bonds and a training data set of outcomes related to the entities. The method may further include the step 9602 of classifying a condition of a set of issuers using the collected information and a model, wherein the model is trained using the training data set of outcomes related to the set of issuers. The method may further include processing events relevant to at least one of a value, a condition, or an ownership of at least one asset of the set of assets (step 9603). The method may further include the steps of: performing an action 9604 related to a debt transaction to which the asset is related, managing an action 9605 related to the bond based at least in part a training set of bond management activities, monitoring and reporting on marketplace information 9606 relevant to a value of at least one of the issuer and a set of assets, managing a smart contract 9607 for a bond transaction, and determining terms and conditions 9608 for the smart contract for at least one bond.

Figure 97:
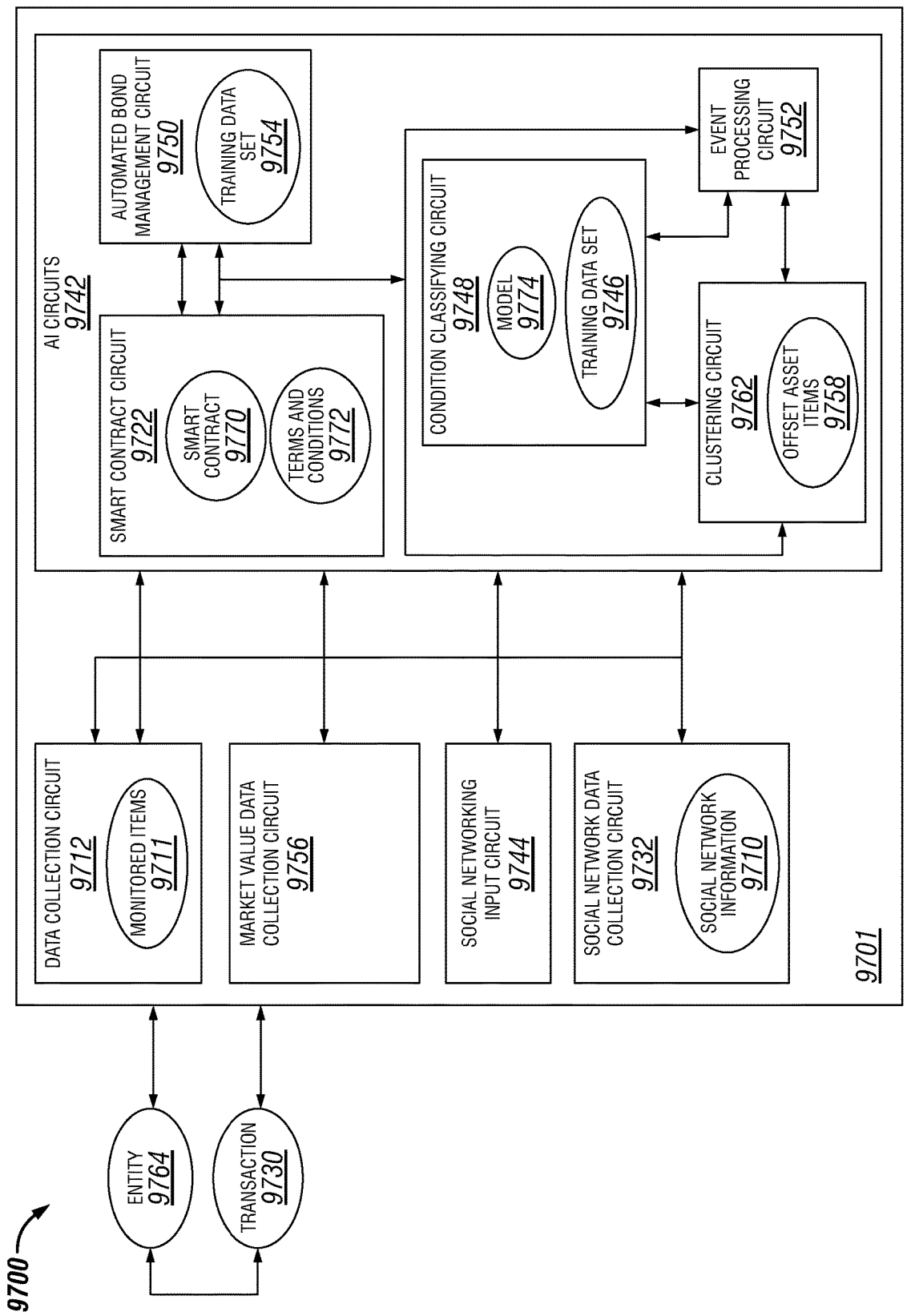
FIG. 97 depicts components and interactions of a lending platform.

Referring now to FIG. 97, an illustrative and non-limiting example system for monitoring a condition of an issuer for a bond 9700 is depicted The example system may include a controller 9701 The controller 9701 may include a data collection circuit 9712, a market value data collection circuit 9756, a social networking input circuit 9744, a social network data collection circuit 9732, and several artificial intelligence circuits 9742 including a smart contract circuit 9722, an automated bond management circuit 9750, a condition classifying circuit 9748, a clustering circuit 9762, and an event processing circuit 9752.

The social network data collection circuit 9732 may be structured to collect social network information 9710 about at least one entity 9764 involved in at least one transaction 9730 comprising at least one bond; and a condition classifying circuit 9748 may be structured to classify a condition of the at least one entity in accordance with a model 9774 and based on information from the social network data collection circuit, wherein the model is trained using a training data set 9754 9746 of a plurality of outcomes related to the at least one entity. The at least one entity may be selected from the entities consisting of: a bond issuer, a bond, a party, and an asset. The bond issuer may be selected from the bond issuers consisting of a municipality, a corporation, a contractor, a government entity, a non-governmental entity, and a non-profit entity. The bond may be selected from the entities consisting of a municipal bond, a government bond, a treasury bond, an asset-backed bond, and a corporate bond.

The condition classified by the condition classifying circuit 9748 may be at least one of a default condition, a foreclosure condition, a condition indicating violation of a covenant, a financial risk condition, a behavioral risk condition, a policy risk condition, a financial health condition, a physical defect condition, a physical health condition, an entity risk condition or an entity health condition.

The social network data collection circuit 9732 may further include a social networking input circuit 9744 which may be structured to receive input from a user used to configure a query for information about the at least one entity.

The data collection circuit 9712 may be structured to monitor at least one of an Internet of Things device, an environmental condition sensor, a crowdsourcing request circuit, a crowdsourcing communication circuit, a crowdsourcing publishing circuit, and an algorithm for querying network domains associated with the monitored items 9711.

The data collection circuit 9712 may be further structured to monitor an environment selected from the group consisting of: a municipal environment, a corporate environment, a securities trading environment, a real property environment, a commercial facility, a warehousing facility, a transportation environment, a manufacturing environment, a storage environment, a home, and a vehicle associated with the monitored items 9711.

The at least one bond is backed by at least one asset. The at least one asset may be selected from the assets consisting of: a municipal asset, a vehicle, a ship, a plane, a building, a home, real estate property, undeveloped land, a farm, a crop, a municipal facility, a warehouse, a set of inventory, a commodity, a security, a currency, a token of value, a ticket, a cryptocurrency, a consumable item, an edible item, a beverage, a precious metal, an item of jewelry, a gemstone, intellectual property, an intellectual property right, a contractual right, an antique, a fixture, an item of furniture, an item of equipment, a tool, an item of machinery, and an item of personal property.

The event processing circuit 9752 may be structured to process an event relevant to at least one of a value, a condition, and an ownership of the at least one asset and undertake an action related to the at least one transaction. The action may be selected from the actions consisting of: a bond transaction, underwriting a bond transaction, setting an interest rate, deferring a payment requirement, modifying an interest rate, validating title, managing inspection, recording a change in title, assessing the value of an asset, calling a loan, closing a transaction, setting terms and conditions for a transaction, providing notices required to be provided, foreclosing on a set of assets, modifying terms and conditions, setting a rating for an entity, syndicating bonds, and consolidating bonds.

The condition classifying circuit 9748 may further include a system selected from the systems consisting of: a machine learning system, a model-based system, a rule-based system, a deep learning system, a hybrid system, a neural network, a convolutional neural network, a feed forward neural network, a feedback neural network, a self-organizing map, a fuzzy logic system, a random walk system, a random forest system, a probabilistic system, a Bayesian system, and a simulation system.

The automated bond management circuit 9750 may be structured to manage an action related to the at least one bond, wherein the automated bond management circuit is trained on a training data set of a plurality of bond management activities.

The automated bond management circuit 9750 may be trained on a training set 9754 comprising a plurality of interactions of parties with a plurality of user interfaces involved in a plurality of bond transaction activities. The plurality of bond transaction activities may be selected from the bond transaction activities consisting of: offering a bond transaction, underwriting a bond transaction, setting an interest rate, deferring a payment requirement, modifying an interest rate, validating title, managing inspection, recording a change in title, assessing a value of an asset, calling a loan, closing a transaction, setting terms and conditions for a transaction, providing notices required to be provided, foreclosing on a set of assets, modifying terms and conditions, setting a rating for an entity, syndicating bonds, and consolidating bonds.

The market value data collection circuit 9756 may be structured to monitor and report on marketplace information relevant to a value of at least one of a bond issuer, the at least one bond, and an asset. The asset may be selected from the assets consisting of: a municipal asset, a vehicle, a ship, a plane, a building, a home, real estate property, undeveloped land, a farm, a crop, a municipal facility, a warehouse, a set of inventory, a commodity, a security, a currency, a token of value, a ticket, a cryptocurrency, a consumable item, an edible item, a beverage, a precious metal, an item of jewelry, a gemstone, intellectual property, an intellectual property right, a contractual right, an antique, a fixture, an item of furniture, an item of equipment, a tool, an item of machinery, and an item of personal property.

The market value data collection circuit 9756 may be further structured to monitor pricing or financial data for an offset asset item in at least one public marketplace.

A set of offset asset items 9758 for valuing the asset may be constructed using a clustering circuit 9762 based on an attribute of the asset. The attribute may be selected from the attributes consisting of a category, an asset age, an asset condition, an asset history, an asset storage, and a geolocation.

The smart contract circuit 9722 may be structured to manage a smart contract 9770 for the at least one transaction. The smart contract circuit may be further structured to determine a terms and conditions 9772 for the at least one bond.

The terms and conditions 9772 may be selected from the group consisting of: a principal amount of debt, a balance of debt, a fixed interest rate, a variable interest rate, a payment amount, a payment schedule, a balloon payment schedule, a specification of assets that back the at least one bond, a specification of substitutability of assets, a party, an issuer, a purchaser, a guarantee, a guarantor, a security, a personal guarantee, a lien, a duration, a covenant, a foreclose condition, a default condition, and a consequence of default.

Figure 98:
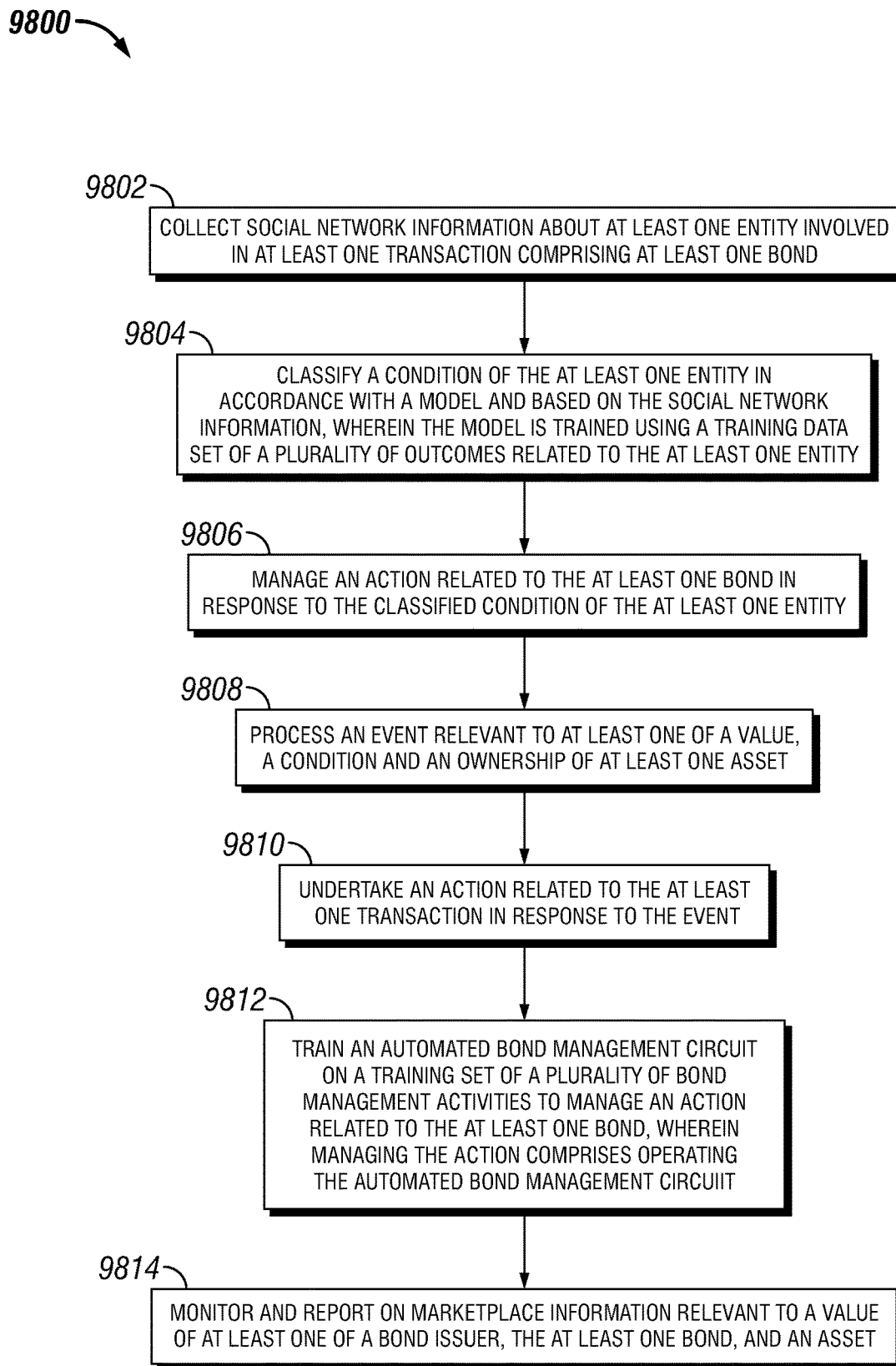
FIG. 98 depicts a method of a lending platform.

Referring now to FIG. 98, an illustrative and non-limiting example method for monitoring a condition of an issuer for a bond 9800 is depicted. An example method may include collecting social network information about at least one entity involved in at least one transaction comprising at least one bond 9802; and classifying a condition of the at least one entity in accordance with a model and based on the social network information, wherein the model is trained using a training data set of a plurality of outcomes related to the at least one entity 9804; and managing an action related to the at least one bond in response to the classified condition of the at least one entity 9806.

An event relevant to at least one of a value, a condition and an ownership of at least one asset may be processed 9808. An action related to the at least one transaction may be undertaken in response to the event, wherein managing the action comprises operating the automated bond management circuit 9810. An automated bond management circuit may be trained on a training set of a plurality of bond management activities to manage an action related to the at least one bond 9812. An example method may further include monitoring and reporting on marketplace information relevant to a value of at least one of a bond issuer, the at least one bond, and an asset 9814.

Figure 99:
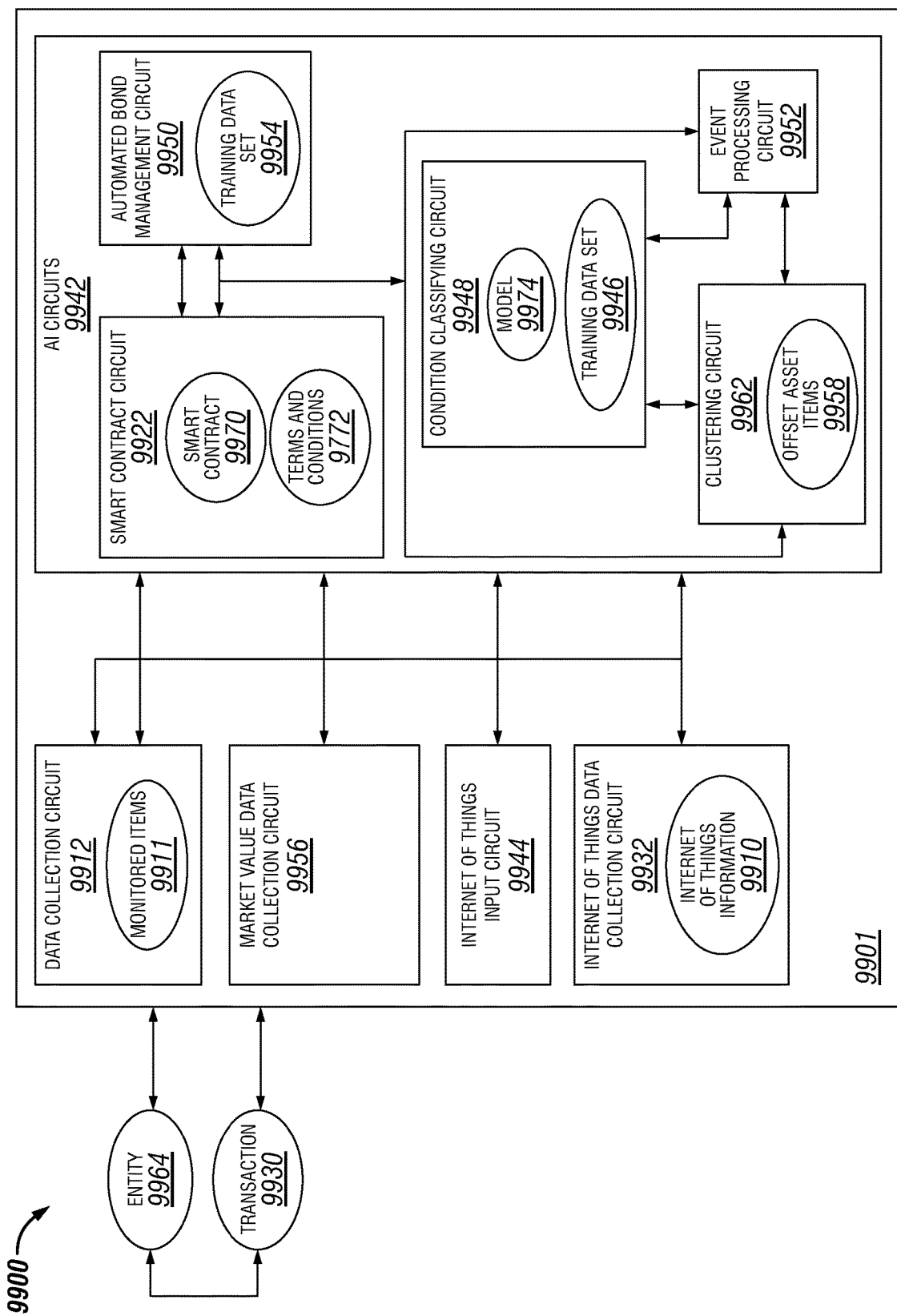
FIG. 99 depicts components and interactions of a lending platform.

Referring now to FIG. 99, an illustrative and non-limiting example system for monitoring a condition of an issuer for a bond 9900 is depicted. The example system may include a controller 9901. The controller 9901 may include a data collection circuit 9912, a market value data collection circuit 9956, an Internet of Things input circuit 9944, an Internet of Things data collection circuit 9932, and several artificial intelligence circuits 9942 including a smart contract circuit 9922, an automated bond management circuit 9950, a condition classifying circuit 9948, a clustering circuit 9962, and an event processing circuit 9952. The condition classifying circuit 9948 may comprise a model 9974 trained with a training data set 9946.

The Internet of Things data collection circuit 9932 may be structured to collect information about at least one entity 9964 involved in at least one transaction 9930 comprising at least one bond; and a condition classifying circuit 9948 may be structured to classify a condition of the at least one entity in accordance with a model 9974 and based on information from the Internet of Things data collection circuit, wherein the model is trained using a training data set 9954 of a plurality of outcomes related to the at least one entity. The at least one entity may be selected from the entities consisting of: a bond issuer, a bond, a party, and an asset. The bond issuer may be selected from the bond issuers consisting of a municipality, a corporation, a contractor, a government entity, a non-governmental entity, and a non-profit entity. The bond may be selected from the entities consisting of a municipal bond, a government bond, a treasury bond, an asset-backed bond, and a corporate bond.

The condition classified by the condition classifying circuit 9948 may be at least one of a default condition, a foreclosure condition, a condition indicating violation of a covenant, a financial risk condition, a behavioral risk condition, a policy risk condition, a financial health condition, a physical defect condition, a physical health condition, an entity risk condition or an entity health condition.

The Internet of Things data collection circuit 9932 may further include an Internet of Things input circuit 9944 which may be structured to receive input from a user used to configure a query for information 9910 about the at least one entity.

The data collection circuit 9912 may be structured to monitor at least one of an Internet of Things device, an environmental condition sensor, a crowdsourcing request circuit, a crowdsourcing communication circuit, a crowdsourcing publishing circuit, and an algorithm for querying network domains for information related to monitored items 9911. The condition classifying circuit 9948 may be further structured to classify the condition in response to the information from the data collection circuit 9912.

The data collection circuit 9912 may be further structured to monitor an environment selected from the group consisting of: a municipal environment, a corporate environment, a securities trading environment, a real property environment, a commercial facility, a warehousing facility, a transportation environment, a manufacturing environment, a storage environment, a home, and a vehicle. The condition classifying circuit 9948 may be further structured to classify the condition in response to the monitored environment.

The at least one bond is backed by at least one asset. The at least one asset may be selected from the assets consisting of: a municipal asset, a vehicle, a ship, a plane, a building, a home, real estate property, undeveloped land, a farm, a crop, a municipal facility, a warehouse, a set of inventory, a commodity, a security, a currency, a token of value, a ticket, a cryptocurrency, a consumable item, an edible item, a beverage, a precious metal, an item of jewelry, a gemstone, intellectual property, an intellectual property right, a contractual right, an antique, a fixture, an item of furniture, an item of equipment, a tool, an item of machinery, and an item of personal property.

The event processing circuit 9952 may be structured to process an event relevant to at least one of a value, a condition and an ownership of the at least one asset and undertake an action related to the at least one transaction. The action may be selected from the actions consisting of: a bond transaction, underwriting a bond transaction, setting an interest rate, deferring a payment requirement, modifying an interest rate, validating title, managing inspection, recording a change in title, assessing the value of an asset, calling a loan, closing a transaction, setting terms and conditions for a transaction, providing notices required to be provided, foreclosing on a set of assets, modifying terms and conditions, setting a rating for an entity, syndicating bonds, and consolidating bonds.

The condition classifying circuit 9948 may further include a system selected from the systems consisting of: a machine learning system, a model-based system, a rule-based system, a deep learning system, a hybrid system, a neural network, a convolutional neural network, a feed forward neural network, a feedback neural network, a self-organizing map, a fuzzy logic system, a random walk system, a random forest system, a probabilistic system, a Bayesian system, and a simulation system.

The automated bond management circuit 9950 may be structured to manage an action related to the at least one bond, wherein the automated bond management circuit is trained on a training data set 9954 of a plurality of bond management activities.

The automated bond management circuit 9950 may be trained on a plurality of interactions of parties with a plurality of user interfaces involved in a plurality of bond transaction activities. The plurality of bond transaction activities may be selected from the bond transaction activities consisting of: offering a bond transaction, underwriting a bond transaction, setting an interest rate, deferring a payment requirement, modifying an interest rate, validating title, managing inspection, recording a change in title, assessing a value of an asset, calling a loan, closing a transaction, setting terms and conditions for a transaction, providing notices required to be provided, foreclosing on a set of assets, modifying terms and conditions, setting a rating for an entity, syndicating bonds, and consolidating bonds.

The market value data collection circuit 9956 may be structured to monitor and report on marketplace information relevant to a value of at least one of a bond issuer, the at least one bond, and an asset. The asset may be selected from the assets consisting of: a municipal asset, a vehicle, a ship, a plane, a building, a home, real estate property, undeveloped land, a farm, a crop, a municipal facility, a warehouse, a set of inventory, a commodity, a security, a currency, a token of value, a ticket, a cryptocurrency, a consumable item, an edible item, a beverage, a precious metal, an item of jewelry, a gemstone, intellectual property, an intellectual property right, a contractual right, an antique, a fixture, an item of furniture, an item of equipment, a tool, an item of machinery, and an item of personal property.

The market value data collection circuit 9956 may be further structured to monitor pricing or financial data for an offset asset item in at least one public marketplace.

A set of offset asset items 9958 for valuing the asset may be constructed using a clustering circuit 9962 based on an attribute of the asset. The attribute may be selected from the attributes consisting of a category, an asset age, an asset condition, an asset history, an asset storage, and a geolocation.

The smart contract circuit 9922 may be structured to manage a smart contract 9970 for the at least one transaction. The smart contract circuit may be further structured to determine a terms and conditions 9772 for the at least one bond.

The terms and conditions may be selected from the group consisting of: a principal amount of debt, a balance of debt, a fixed interest rate, a variable interest rate, a payment amount, a payment schedule, a balloon payment schedule, a specification of assets that back the at least one bond, a specification of substitutability of assets, a party, an issuer, a purchaser, a guarantee, a guarantor, a security, a personal guarantee, a lien, a duration, a covenant, a foreclose condition, a default condition, and a consequence of default.

Figure 100:
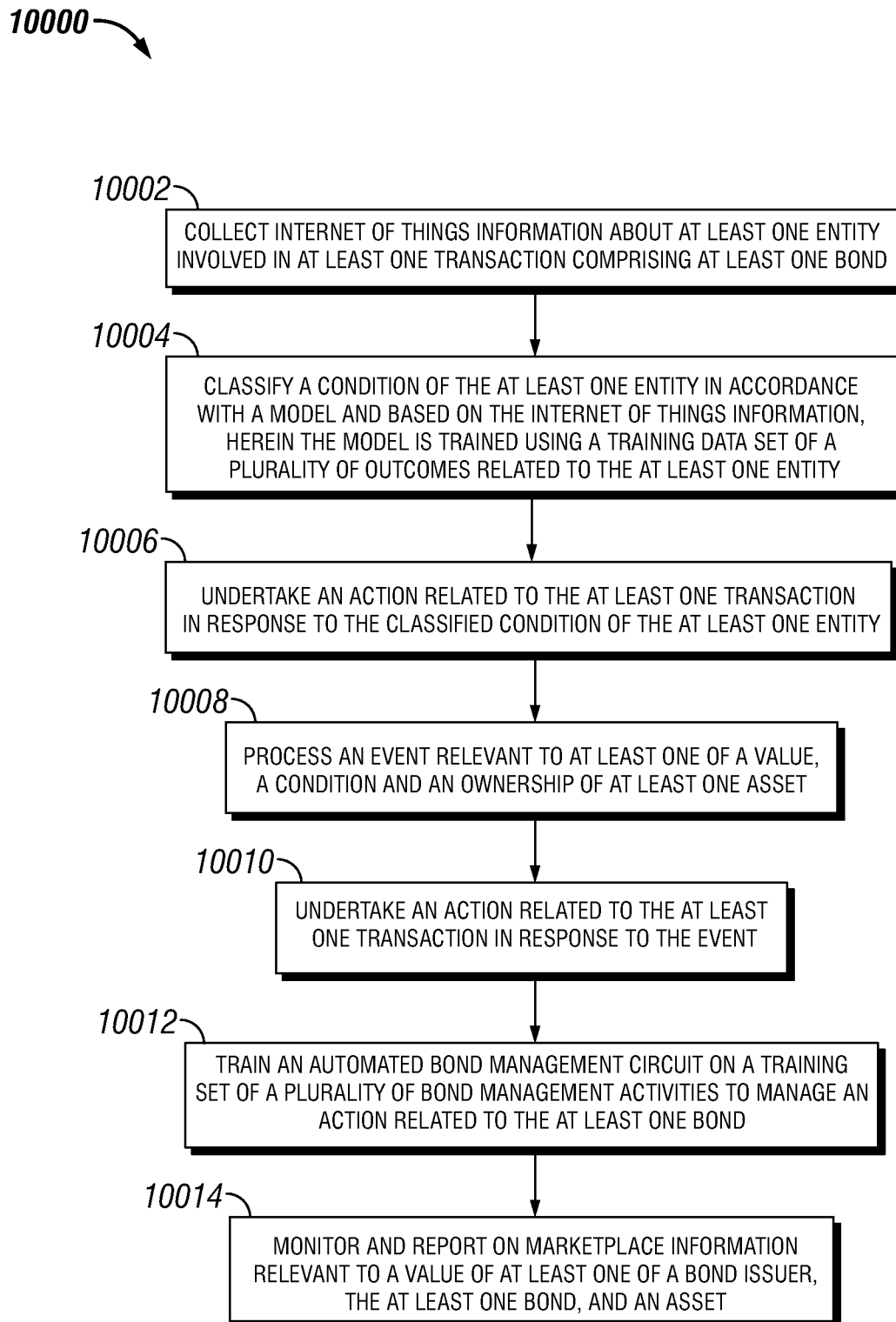
FIG. 100 depicts a method of a lending platform.

Referring now to FIG. 100, an illustrative and non-limiting example method for monitoring a condition of an issuer for a bond 10000 is depicted. An example method may include collecting Internet of Things information about at least one entity involved in at least one transaction comprising at least one bond 10002; and classifying a condition of the at least one entity in accordance with a model and based on the Internet of Things information, wherein the model is trained using a training data set of a plurality of outcomes related to the at least one entity 10004; and undertaking an action related to the at least one transaction in response to the classified condition of the at least one entity 10006.

An event relevant to at least one of a value, a condition and an ownership of at least one asset may be processed 10008. An action related to the at least one transaction may be undertaken in response to the event 10010. An automated bond management circuit may be trained on a training set of a plurality of bond management activities to manage an action related to the at least one bond 10012. An example method may further include monitoring and reporting on marketplace information relevant to a value of at least one of a bond issuer, the at least one bond, or an asset 10014.

Figure 101:
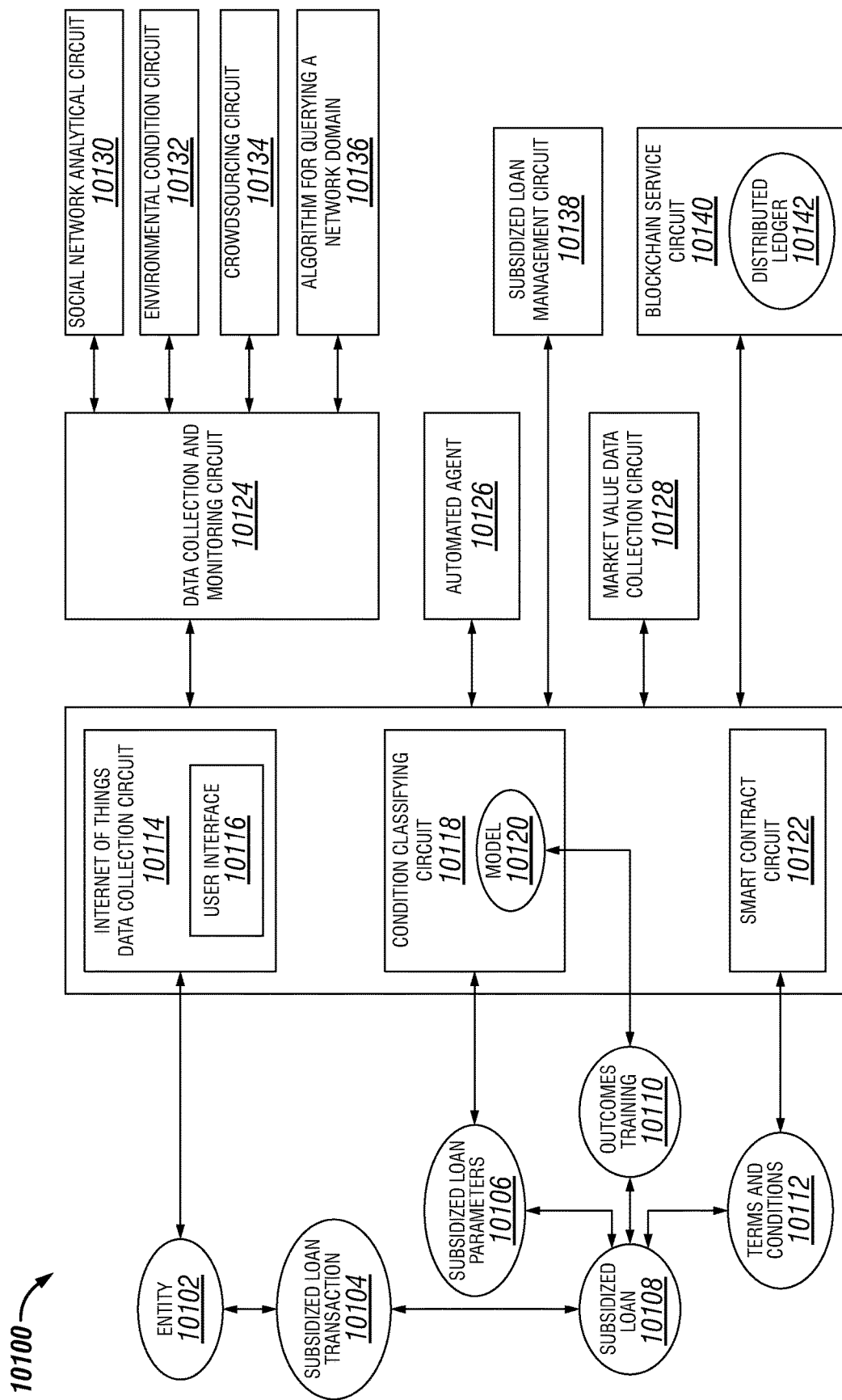
FIG. 101 depicts components and interactions of a lending platform.

FIG. 101 depicts a system 10100 including an Internet of Things data collection circuit 10114 structured to collect information about an entity 10102 (e.g., where an entity may be a subsidized loan, a party, a subsidy, a guarantor, a subsidizing party, a collateral, and the like, where a party may be least one of a municipality, a corporation, a contractor, a government entity, a non-governmental entity, and a non-profit entity) involved in a subsidized loan transaction 10104. In embodiments, the Internet of Things data collection circuit may include a user interface 10116 structured to enable a user to configure a query for information about the at least one entity. The system may include a condition classifying circuit 10118 that may include a model 10120 structured to classify a parameter 10106 of a subsidized loan 10108 (e.g., municipal subsidized loan, a government subsidized loan, a student loan, an asset-backed subsidized loan, or a corporate subsidized loan) involved in a subsidized loan transaction, such as based on the information from the Internet of Things data collection circuit. In embodiments, the condition classifying circuit may include a machine learning system, a model-based system, a rule-based system, a deep learning system, a hybrid system, a neural network, a convolutional neural network, a feed forward neural network, a feedback neural network, a self-organizing map, a fuzzy logic system, a random walk system, a random forest system, a probabilistic system, a Bayesian system, a simulation system, and the like. The subsidized loan may be backed by an asset, such as a municipal asset, a vehicle, a ship, a plane, a building, a home, real estate property, undeveloped land, a farm, a crop, a municipal facility, a warehouse, a set of inventory, a commodity, a security, a currency, a token of value, a ticket, a cryptocurrency, a consumable item, an edible item, a beverage, a precious metal, an item of jewelry, a gemstone, intellectual property, an intellectual property right, a contractual right, an antique, a fixture, an item of furniture, an item of equipment, a tool, an item of machinery, an item of personal property, and the like. The condition classified by the condition classifying circuit may be a default condition, a foreclosure condition, a condition indicating violation of a covenant, a financial risk condition, a behavioral risk condition, a contractual performance condition, a policy risk condition, a financial health condition, a physical defect condition, a physical health condition, an entity risk condition, an entity health condition, and the like. The model may be trained using a training data set of a plurality of outcomes 10110 related to the subsidized loan. For instance, the subsidized loan may be a student loan and the condition classifying circuit may classify a progress of a student toward a degree, a participation of a student in a non-profit activity, a participation of a student in a public interest activity, and the like. The system may include a smart contract circuit 10122 structured to automatically modify terms and conditions 10112 of the subsidized loan, such as based on the classified parameter from the condition classifying circuit. The system may include a configurable data collection and circuit 10124 structured to monitor the entity, such as further including a social network analytic circuit 10130, an environmental condition circuit 10132, a crowdsourcing circuit 10134, and an algorithm for querying a network domain 10136, where the configurable data collection and circuit may monitor an environment selected from an environment, such as a municipal environment, an educational environment, a corporate environment, a securities trading environment, a real property environment, a commercial facility, a warehousing facility, a transportation environment, a manufacturing environment, a storage environment, a home, a vehicle, and the like. The system may include an automated agent 10126 structured to process an event relevant to a value, a condition and an ownership of the asset and undertake an action related to the subsidized loan transaction to which the asset is related, wherein the action may be a subsidized loan transaction, underwriting a subsidized loan transaction, setting an interest rate, deferring a payment requirement, modifying an interest rate, validating a title, managing an inspection, recording a change in a title, assessing the value of an asset, calling a loan, closing a transaction, setting terms and conditions for a transaction, providing notices required to be provided, foreclosing on a set of assets, modifying terms and conditions, setting a rating for an entity, syndicating a subsidized loan, consolidating a subsidized loan, and the like. The system may include an automated subsidized loan management circuit 10138 structured to manage an action related to the at least one subsidized loan, wherein the automated subsidized loan management circuit is trained on a training set of subsidized loan management activities. For instance, the automated subsidized loan management circuit may be trained on a plurality of interactions of parties with a plurality of user interfaces involved in a plurality of subsidized loan transaction activities, where the plurality of subsidized loan transaction activities may be selected from the activities consisting of offering a subsidized loan transaction, underwriting a subsidized loan transaction, setting an interest rate, deferring a payment requirement, modifying an interest rate, validating a title, managing an inspection, recording a change in a title, assessing a value of an asset, calling a loan, closing a transaction, setting terms and conditions for a transaction, providing notices required to be provided, foreclosing on a set of assets, modifying terms and conditions, setting a rating for an entity, syndicating a subsidized loan, and consolidating a subsidized loan. The system may include a blockchain service circuit 10140 structured to record the modified set of terms and conditions for a subsidized loan, such as in a distributed ledger 10142. The system may include a market value data collection circuit 10128 structured to monitor and report on marketplace information relevant to a value of an issuer, a subsidized loan, an asset, and the like, where reporting may be on an asset selected from the assets consisting of a municipal asset, a vehicle, a ship, a plane, a building, a home, real estate property, undeveloped land, a farm, a crop, a municipal facility, a warehouse, a set of inventory, a commodity, a security, a currency, a token of value, a ticket, a cryptocurrency, a consumable item, an edible item, a beverage, a precious metal, an item of jewelry, a gemstone, intellectual property, an intellectual property right, a contractual right, an antique, a fixture, an item of furniture, an item of equipment, a tool, an item of machinery, and an item of personal property. The market value data collection circuit may be further structured to monitor pricing or financial data for an offset asset item in a public marketplace. A set of offset asset items for valuing the asset may be constructed using a clustering circuit based on an attribute of the asset, where the attribute may be a category, an asset age, an asset condition, an asset history, an asset storage, a geolocation, and the like. The smart contract circuit may be structured to manage a smart contract for a subsidized loan transaction, where the smart contract circuit may set terms and conditions for the subsidized loan, where the terms and conditions for the subsidized loan that are specified and managed by the smart contract circuit may include a principal amount of debt, a balance of debt, a fixed interest rate, a variable interest rate, a payment amount, a payment schedule, a balloon payment schedule, a specification of assets that back the at least one subsidized loan, a specification of substitutability of assets, a party, an issuer, a purchaser, a guarantee, a guarantor, a security, a personal guarantee, a lien, a duration, a covenant, a foreclose condition, a default condition, a consequence of default, and the like.

Figure 102:
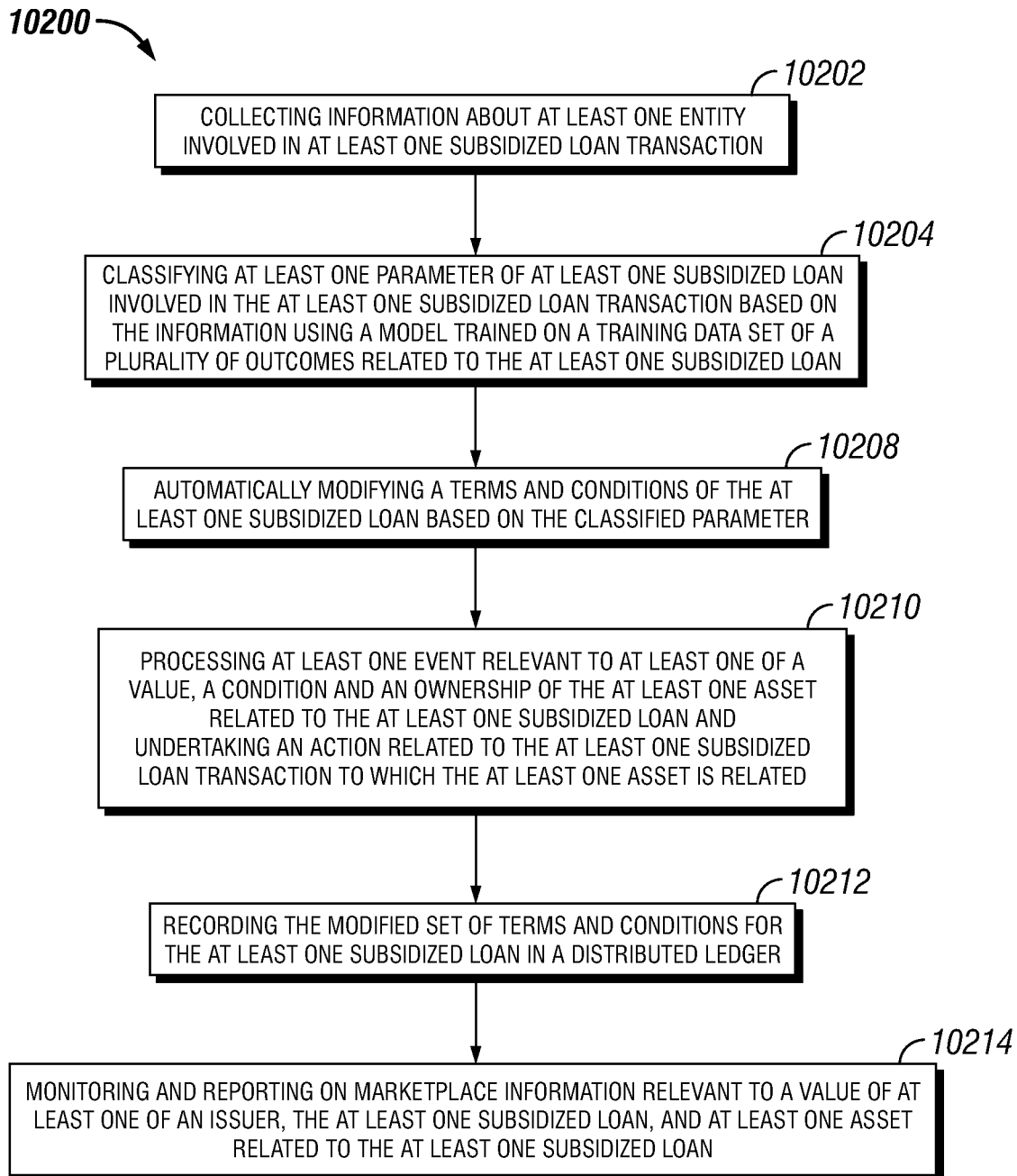
FIG. 102 depicts a method of a lending platform.

FIG. 102 depicts a method 10200 including collecting information about an entity involved in a subsidized loan transaction 10202. The method may include classifying a parameter of a subsidized loan involved in the subsidized loan transaction based on the information using a model trained on a training data set of a plurality of outcomes related to the at least one subsidized loan 10204. The method may include automatically modifying terms and conditions of the subsidized loan based on the classified parameter 10208. The method may include processing an event 10210 relevant to a value, a condition and an ownership of an asset related to the at least one subsidized loan and undertaking an action related to the subsidized loan transaction to which the asset is related. The method may include recording the modified set of terms and conditions for the subsidized loan in a distributed ledger 10212. The method may include monitoring and reporting on marketplace information 10214 relevant to a value of an issuer, the subsidized loan, the asset related to the at least one subsidized loan, and the like.

Figure 103:
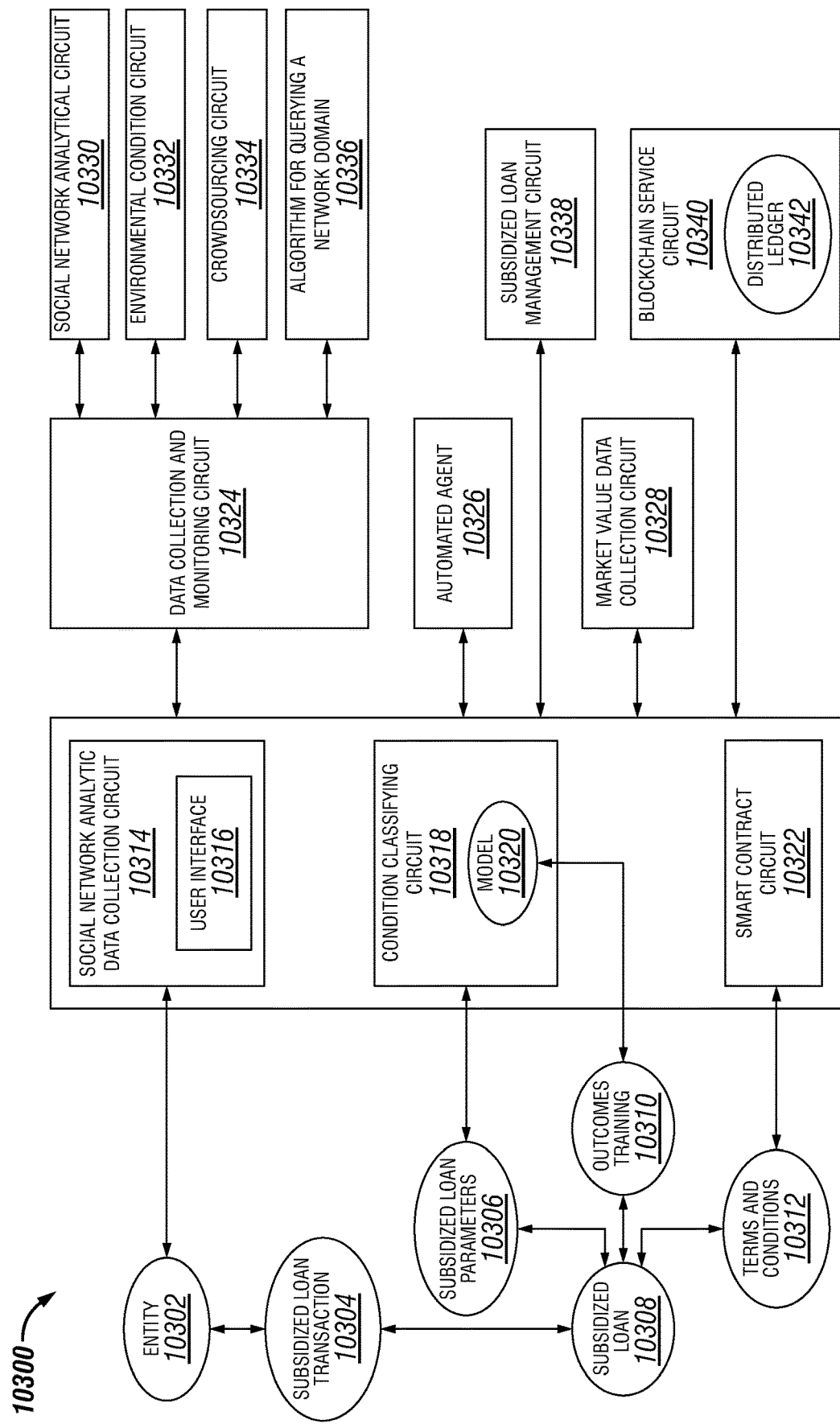
FIG. 103 depicts components and interactions of a lending platform.

FIG. 103 depicts a system 10300 including a social network analytic data collection circuit 10314 structured to collect social network information about an entity 10302 (e.g., where an entity may be a subsidized loan, a party, a subsidy, a guarantor, a subsidizing party, a collateral, and the like, where a party may be least one of a municipality, a corporation, a contractor, a government entity, a non-governmental entity, and a non-profit entity) involved in a subsidized loan transaction 10304. In embodiments, the social network analytic data collection circuit may include a user interface 10316 structured to enable a user to configure a query for information about the at least one entity, wherein, in response to the query, the social network analytic data collection circuit may initiate at least one algorithm that searches and retrieves data from at least one social network based on the query. The system may include a condition classifying circuit 10318 that may include a model 10320 structured to classify a parameter 10306 of a subsidized loan 10308 (e.g., municipal subsidized loan, a government subsidized loan, a student loan, an asset-backed subsidized loan, or a corporate subsidized loan) involved in a subsidized loan transaction, such as based on the social network information from the social network analytic data collection circuit. In embodiments, the condition classifying circuit may include a machine learning system, a model-based system, a rule-based system, a deep learning system, a hybrid system, a neural network, a convolutional neural network, a feed forward neural network, a feedback neural network, a self-organizing map, a fuzzy logic system, a random walk system, a random forest system, a probabilistic system, a Bayesian system, a simulation system, and the like. The subsidized loan may be backed by an asset, such as a municipal asset, a vehicle, a ship, a plane, a building, a home, real estate property, undeveloped land, a farm, a crop, a municipal facility, a warehouse, a set of inventory, a commodity, a security, a currency, a token of value, a ticket, a cryptocurrency, a consumable item, an edible item, a beverage, a precious metal, an item of jewelry, a gemstone, intellectual property, an intellectual property right, a contractual right, an antique, a fixture, an item of furniture, an item of equipment, a tool, an item of machinery, an item of personal property, and the like. The parameter classified by the condition classifying circuit may be a default condition, a foreclosure condition, a condition indicating violation of a covenant, a financial risk condition, a behavioral risk condition, a contractual performance condition, a policy risk condition, a financial health condition, a physical defect condition, a physical health condition, an entity risk condition, an entity health condition, and the like. The model may be trained using a training data set of a plurality of outcomes 10310 related to the subsidized loan. For instance, the subsidized loan may be a student loan and the condition classifying circuit may classify a progress of a student toward a degree, a participation of a student in a non-profit activity, a participation of a student in a public interest activity, and the like. The system may include a smart contract circuit 10322 structured to automatically modify terms and conditions 10312 of the subsidized loan, such as based on the classified parameter. The system may include a configurable data collection and circuit 10324 structured to monitor the entity, such as further including a social network analytic circuit 10330, an environmental condition circuit 10332, a crowdsourcing circuit 10334, and an algorithm for querying a network domain 10336, where the configurable data collection and circuit may monitor an environment selected from an environment, such as a municipal environment, an educational environment, a corporate environment, a securities trading environment, a real property environment, a commercial facility, a warehousing facility, a transportation environment, a manufacturing environment, a storage environment, a home, a vehicle, and the like. The system may include an automated agent 10326 structured to process an event relevant to a value, a condition and an ownership of the asset and undertake an action related to the subsidized loan transaction to which the asset is related, wherein the action may be a subsidized loan transaction, underwriting a subsidized loan transaction, setting an interest rate, deferring a payment requirement, modifying an interest rate, validating a title, managing an inspection, recording a change in a title, assessing the value of an asset, calling a loan, closing a transaction, setting terms and conditions for a transaction, providing notices required to be provided, foreclosing on a set of assets, modifying terms and conditions, setting a rating for an entity, syndicating a subsidized loan, consolidating a subsidized loan, and the like. The system may include an automated subsidized loan management circuit 10338 structured to manage an action related to the at least one subsidized loan, wherein the automated subsidized loan management circuit is trained on a training set of subsidized loan management activities. For instance, the automated subsidized loan management circuit may be trained on a plurality of interactions of parties with a plurality of user interfaces involved in a plurality of subsidized loan transaction activities, where the plurality of subsidized loan transaction activities may be selected from the activities consisting of offering a subsidized loan transaction, underwriting a subsidized loan transaction, setting an interest rate, deferring a payment requirement, modifying an interest rate, validating a title, managing an inspection, recording a change in a title, assessing a value of an asset, calling a loan, closing a transaction, setting terms and conditions for a transaction, providing notices required to be provided, foreclosing on a set of assets, modifying terms and conditions, setting a rating for an entity, syndicating a subsidized loan, and consolidating a subsidized loan. The system may include a blockchain service circuit 10340 structured to record the modified set of terms and conditions for a subsidized loan, such as in a distributed ledger 10342. The system may include a market value data collection circuit 10328 structured to monitor and report on marketplace information relevant to a value of an issuer, a subsidized loan, an asset, and the like, where reporting may be on an asset selected from the assets consisting of a municipal asset, a vehicle, a ship, a plane, a building, a home, real estate property, undeveloped land, a farm, a crop, a municipal facility, a warehouse, a set of inventory, a commodity, a security, a currency, a token of value, a ticket, a cryptocurrency, a consumable item, an edible item, a beverage, a precious metal, an item of jewelry, a gemstone, intellectual property, an intellectual property right, a contractual right, an antique, a fixture, an item of furniture, an item of equipment, a tool, an item of machinery, and an item of personal property. The market value data collection circuit may be further structured to monitor pricing or financial data for an offset asset item in a public marketplace. A set of offset asset items for valuing the asset may be constructed using a clustering circuit based on an attribute of the asset, where the attribute may be a category, an asset age, an asset condition, an asset history, an asset storage, a geolocation, and the like. The smart contract circuit may be structured to manage a smart contract for a subsidized loan transaction, where the smart contract circuit may set terms and conditions for the subsidized loan, where the terms and conditions for the subsidized loan that are specified and managed by the smart contract circuit may include a principal amount of debt, a balance of debt, a fixed interest rate, a variable interest rate, a payment amount, a payment schedule, a balloon payment schedule, a specification of assets that back the at least one subsidized loan, a specification of substitutability of assets, a party, an issuer, a purchaser, a guarantee, a guarantor, a security, a personal guarantee, a lien, a duration, a covenant, a foreclose condition, a default condition, a consequence of default, and the like.

Figure 104:
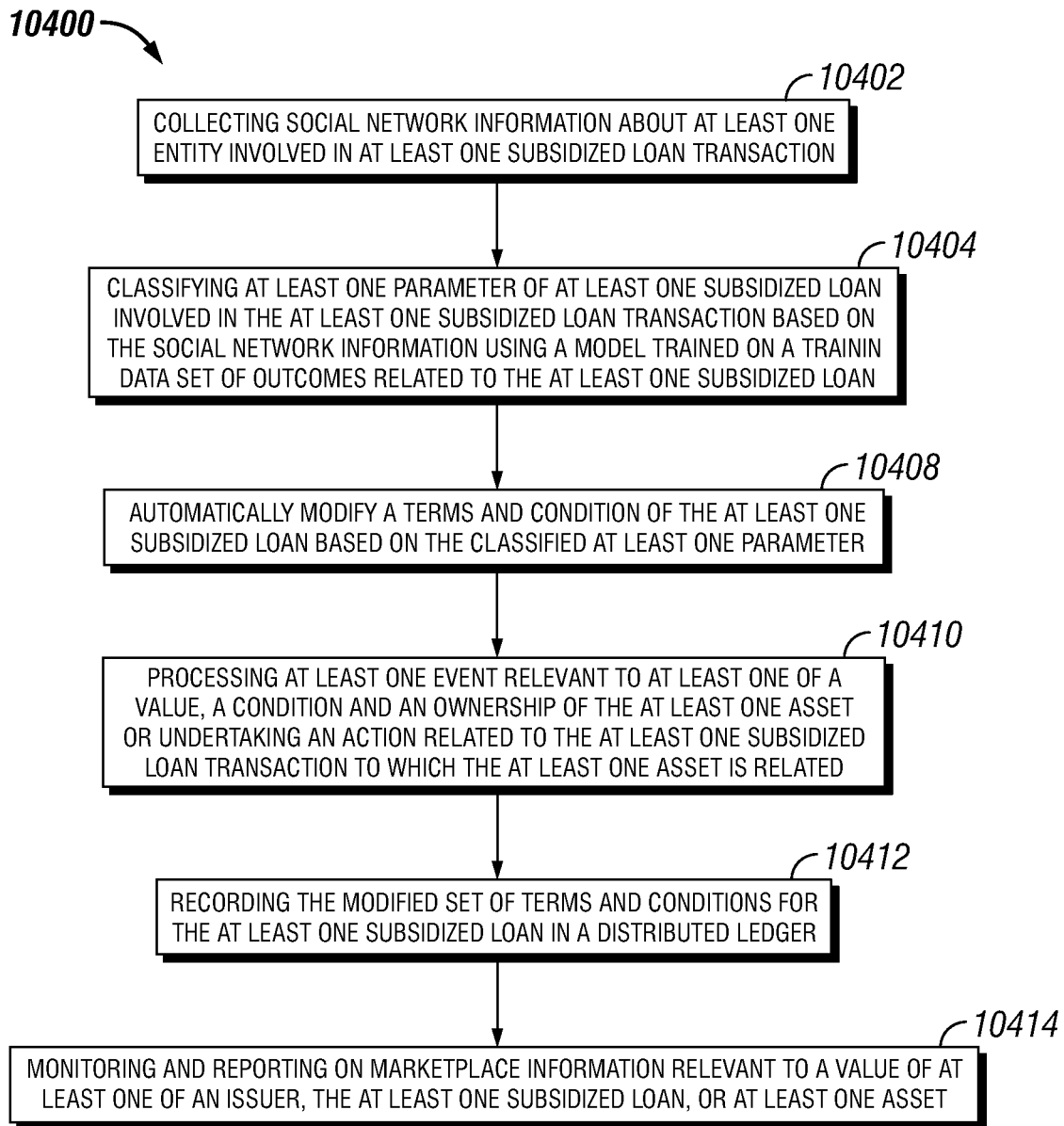
FIG. 104 depicts a method of a lending platform.

FIG. 104 depicts a method 10400 including collecting social network information about an entity involved in a subsidized loan transaction 10402. The method may include classifying a parameter of a subsidized loan involved in the subsidized loan transaction based on the social network information using a model trained on a training data set of a plurality of outcomes related to the at least one subsidized loan 10404. The method may include automatically modifying terms and conditions of the subsidized loan based on the classified parameter 10408. The method may include processing an event 10410 relevant to a value, a condition and an ownership of an asset and undertaking an action related to the subsidized loan transaction to which the asset is related. The method may include recording the modified set of terms and conditions for the subsidized loan in a distributed ledger 10412. The method may include monitoring and reporting on marketplace information 10414 relevant to a value of an issuer, the subsidized loan, the asset, and the like.

Figure 105:
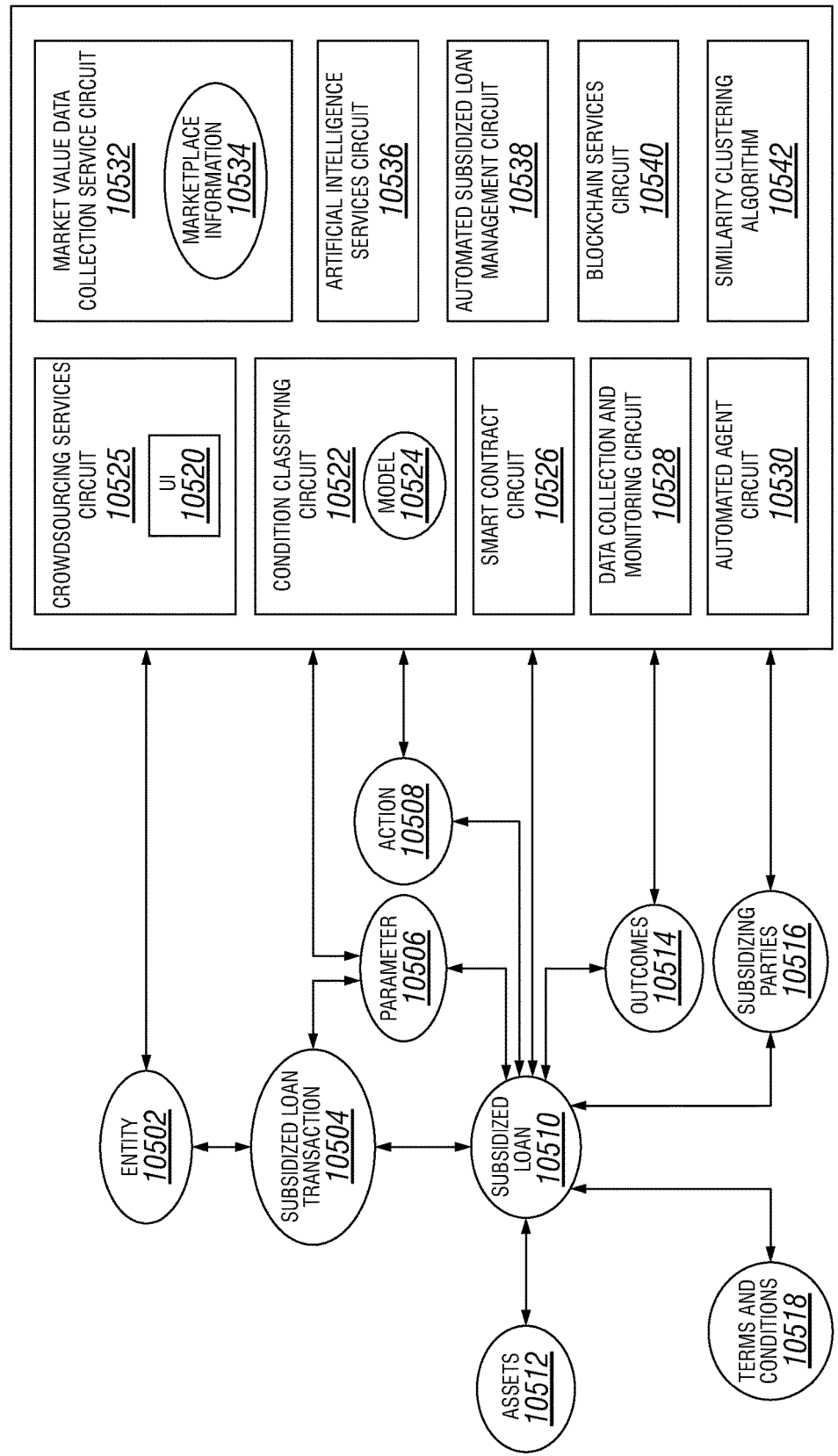
FIG. 105 depicts components and interactions of a lending platform.

FIG. 105 depicts a system 10500 for automating handling of a subsidized loan including a crowdsourcing services circuit 10525 structured to collect information related to a set of entities 10502 involved in a set of subsidized loan transactions 10504. The set of entities may include entities such as a subsidized loan from a set of subsidized loans corresponding to the set of subsidized loan transactions, a party related to at least one of the set of subsidized loan transactions, a subsidy corresponding to a subsidized loan from a set of subsidized loans corresponding to the set of subsidized loan transactions, a guarantor related to at least one of the set of subsidized loan transactions, a subsidy corresponding to a subsidized loan from a set of subsidized loans corresponding to the set of subsidized loan transactions, a subsidized party related to at least one of the set of subsidized loan transactions, a subsidizing party related to at least one of the set of subsidized loan transactions, a subsidy corresponding to a subsidized loan from a set of subsidized loans corresponding to the set of subsidized loan transactions, and an item of collateral related to at least one of the set of subsidized loan transactions, a subsidy corresponding to a subsidized loan from a set of subsidized loans corresponding to the set of subsided loan transactions. A set of subsidizing parties may include a municipality, a corporation, a contractor, a government entity, a non-governmental entity, and a non-profit entity, and the like. The loan may be a student loan and the condition classifying circuit classifies at least one of the progress of a student toward a degree, the participation of a student in a non-profit activity, the participation of the student in a public interest activity, and the like. The crowdsourcing services circuit may be further structured with a user interface 10520 by which a user may configure a query for information about the set of entities and the crowdsourcing services circuit automatically configures a crowdsourcing request based on the query. The set of subsidized loans may be backed by a set of assets 10512, such as a municipal asset, a vehicle, a ship, a plane, a building, a home, real estate property, undeveloped land, a farm, a crop, a municipal facility, a warehouse, a set of inventory, a commodity, a security, a currency, a token of value, a ticket, a cryptocurrency, a consumable item, an edible item, a beverage, a precious metal, an item of jewelry, a gemstone, intellectual property, an intellectual property right, a contractual right, an antique, a fixture, an item of furniture, an item of equipment, a tool, an item of machinery, an item of personal property, and the like. An example system may include a condition classifying circuit 10522 including a model 10524 and an artificial intelligence services circuit 10536 structured to classify a set of parameters 10506 of the set of subsidized loans 10510 involved in the transactions based on information from crowdsourcing services circuit, where the model may be trained using a training data set of outcomes 10514 related to subsidized loans. The set of subsidized loans may include at least one of a municipal subsidized loan, a government subsidized loan, a student loan, an asset-backed subsidized loan, and a corporate subsidized loan. The condition classified by the condition classifying circuit may be a default condition, a foreclosure condition, a condition indicating violation of a covenant, a financial risk condition, a behavioral risk condition, a contractual performance condition, a policy risk condition, a financial health condition, a physical defect condition, a physical health condition, an entity risk condition, an entity health condition, and the like. The artificial intelligence services circuit may a machine learning system, a model-based system, a rule-based system, a deep learning system, a hybrid system, a neural network, a convolutional neural network, a feed forward neural network, a feedback neural network, a self-organizing map, a fuzzy logic system, a random walk system, a random forest system, a probabilistic system, a Bayesian system, a simulation system, and the like. An example system may include a smart contract circuit 10526 for automatically modifying the terms and conditions 10518 of a subsidized loan based on the classified set of parameters from the condition classifying circuit. The smart contract services circuit may be utilized for managing a smart contract for the subsidized loan transaction, set terms and conditions for the subsidized loan, and the like. In embodiments, the set of terms and conditions for the debt transaction that are specified and managed by the smart contract services circuit may be selected from among a principal amount of debt, a balance of debt, a fixed interest rate, a variable interest rate, a payment amount, a payment schedule, a balloon payment schedule, a specification of assets that back the subsidized loan, a specification of substitutability of assets, a party, an issuer, a purchaser, a guarantee, a guarantor, a security, a personal guarantee, a lien, a duration, a covenant, a foreclose condition, a default condition, and a consequence of default. An example system may include a configurable data collection and monitoring services circuit 10528 for monitoring the entities such as a set of Internet of Things services, a set of environmental condition sensors, a set of social network analytic services, a set of algorithms for querying network domains, and the like. The configurable data collection and monitoring services circuit may be further structured to monitor an environment such as a municipal environment, an educational environment, a corporate environment, a securities trading environment, a real property environment, a commercial facility, a warehousing facility, a transportation environment, a manufacturing environment, a storage environment, a home, a vehicle, and the like. An example system may include an automated agent circuit 10530 structured to process events relevant to at least one of the value, the condition, and the ownership of the assets and undertakes an action 10508 related to a subsidized loan transaction to which the asset is related, such as where the action 10508 may be a subsidized loan transaction, underwriting a subsidized loan transaction, setting an interest rate, deferring a payment requirement, modifying an interest rate, validating title, managing inspection, recording a change in title, assessing the value of an asset, calling a loan, closing a transaction, setting terms and conditions for a transaction, providing notices required to be provided, foreclosing on a set of assets, modifying terms and conditions, setting a rating for an entity, syndicating subsidized loans, consolidating subsidized loans, and the like. An example system may include an automated subsidized loan management circuit 10538 structured to manage an action related to the subsidized loan, where the automated subsidized loan management circuit may be trained on a training set of subsidized loan management activities. The automated subsidized loan management circuit may be trained on a set of interactions of parties with a set of user interfaces involved in a set of subsidized loan transaction activities, such as offering a subsidized loan transaction, underwriting a subsidized loan transaction, setting an interest rate, deferring a payment requirement, modifying an interest rate, validating title, managing inspection, recording a change in title, assessing the value of an asset, calling a loan, closing a transaction, setting terms and conditions for a transaction providing notices required to be provided, foreclosing on a set of assets, modifying terms and conditions, setting a rating for an entity, syndicating subsidized loans, consolidating subsidized loans, and the like. An example system may include a blockchain services circuit 10540 structured to record the modified set of terms and conditions for the set of subsidized loans in a distributed ledger. An example system may include a market value data collection service circuit 10532 structured to monitor and report on marketplace information 10534 relevant to the value of at least one of a party, a set of subsidized loans, and a set of assets, where reporting may be on a set of assets such as one of a municipal asset, a vehicle, a ship, a plane, a building, a home, real estate property, undeveloped land, a farm, a crop, a municipal facility, a warehouse, a set of inventory, a commodity, a security, a currency, a token of value, a ticket, a cryptocurrency, a consumable item, an edible item, a beverage, a precious metal, an item of jewelry, a gemstone, intellectual property, an intellectual property right, a contractual right, an antique, a fixture, an item of furniture, an item of equipment, a tool, an item of machinery, and an item of personal property. The market value data collection service circuit may be further structured to monitor pricing or financial data for items that are similar to the assets in at least one public marketplace. In embodiments, a set of similar items for valuing the assets may be constructed using a similarity clustering algorithm 10542 based on the attributes of the assets, such as from among a category of the assets, asset age, asset condition, asset history, asset storage, geolocation of assets, and the like.

Figure 106:
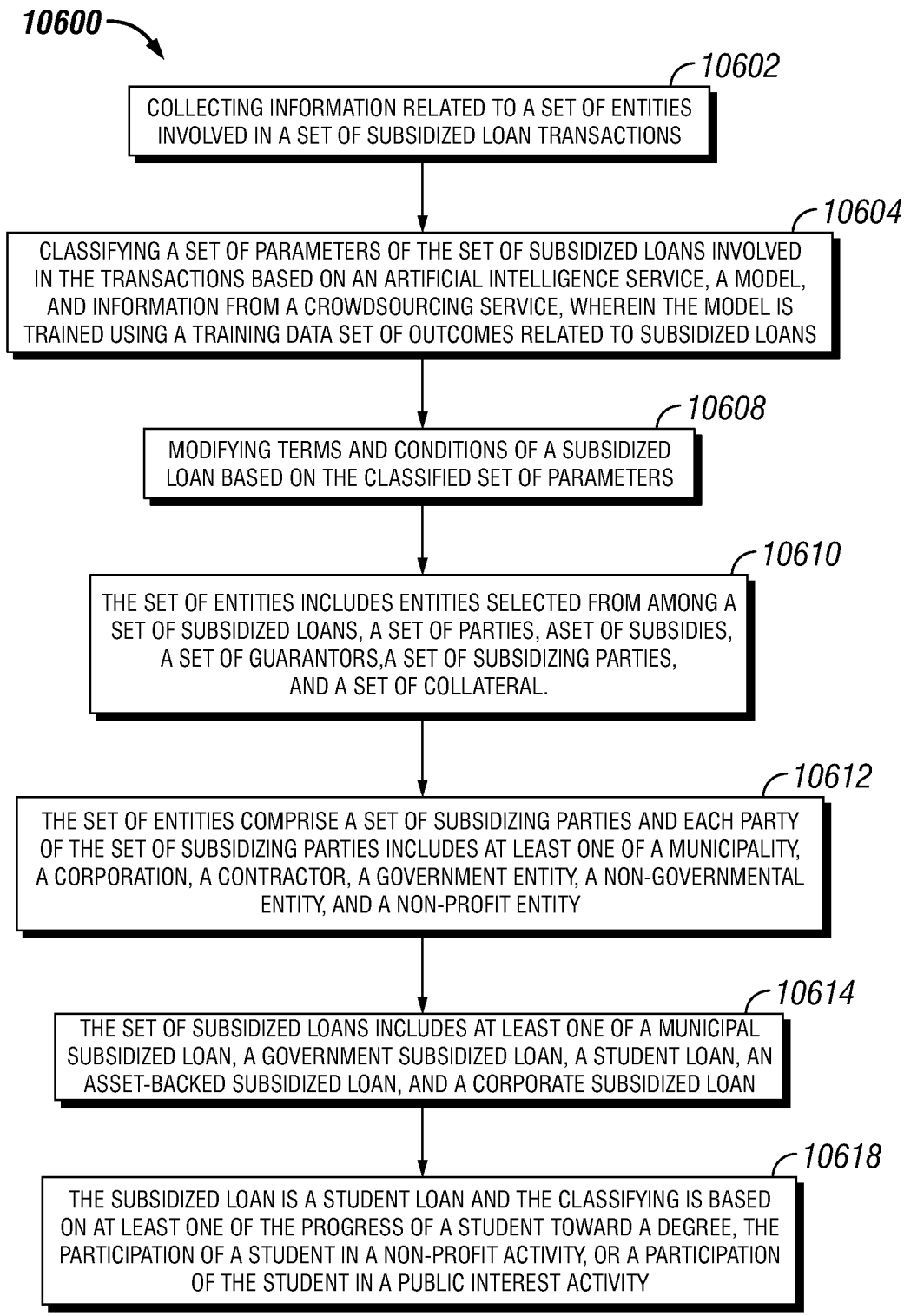
FIG. 106 depicts a method of a lending platform.

FIG. 106 depicts a method 10600 for automating handling of a subsidized loan including collecting information related to a set of entities involved in a set of subsidized loan transactions 10602, classifying a set of parameters of the set of subsidized loans involved in the transactions based on an artificial intelligence service, a model, and information from a crowdsourcing service, where the model is trained using a training data set of outcomes related to subsidized loans 10604; and modifying terms and conditions of a subsidized loan based on the classified set of parameters 10608. The set of entities may include entities among a set of subsidized loans, a set of parties, a set of subsidies, a set of guarantors, a set of subsidizing parties, and a set of collateral 10610. The set of entities comprise a set of subsidizing parties 10516 and each party of the set of subsidizing parties may include a municipality, a corporation, a contractor, a government entity, a non-governmental entity, and a non-profit entity 10612. The set of subsidized loans may include a municipal subsidized loan, a government subsidized loan, a student loan, an asset-backed subsidized loan, and a corporate subsidized loan 10614. The subsidized loan may be a student loan where the condition classifying system classifies at least one of the progress of a student toward a degree, the participation of a student in a non-profit activity, or a participation of the student in a public interest activity 10618.

Figure 107:
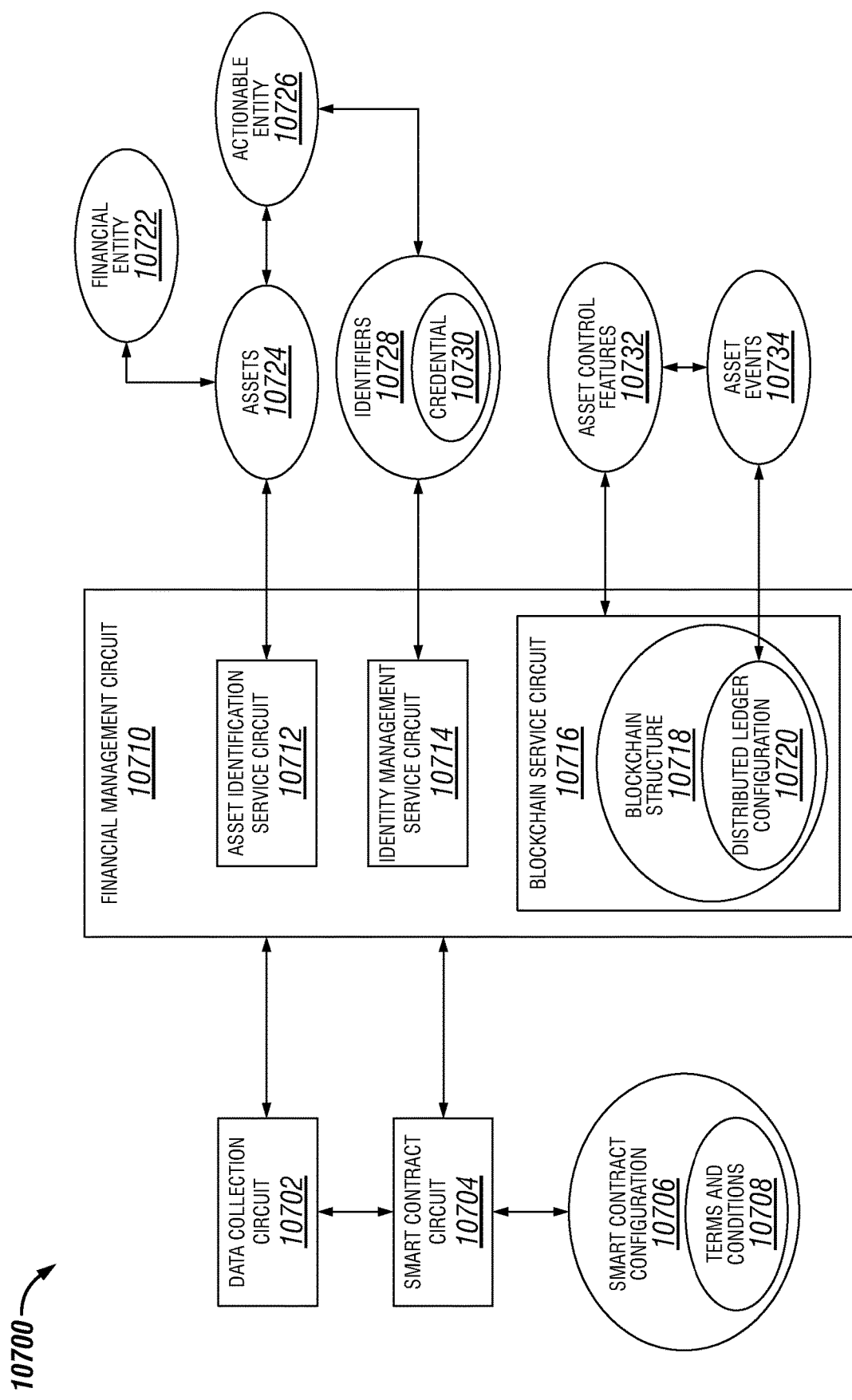
FIG. 107 depicts components and interactions of a lending platform.

FIG. 107 depicts a system 10700 including an asset identification service circuit 10712 structured to interpret assets 10724 corresponding to a financial entity 10722 configured to take custody of the assets (e.g., identifying assets for which a bank may take custody), where an identity management service circuit 10714 may be structured to authenticate identifiers 10728 (e.g., including a credential 10730) corresponding to actionable entities 10726 (e.g., an owner, a beneficiary, an agent, a trustee, a custodian, and the like) entitled to take action with respect to the assets. For example, a group of financial entities may have permissions with respect to actions to be taken with respect to an asset. A blockchain service circuit 10716 may be structured to store a plurality of asset control features 10732 in a blockchain structure 10718, where the blockchain structure may include a distributed ledger configuration 10720. For instance, transactional events may be stored in a distributed ledger in the blockchain structure where the financial entity and actionable entities may have distributed access through the blockchain structure to share and distribute the asset events. A financial management circuit 10710 may be structured to communicate the interpreted assets and authenticated identifiers to the blockchain service circuit for storage in the blockchain structure as asset control features, wherein the asset control features are recorded in the distributed ledger configuration as asset events 10734 (e.g., a transfer of title, death of an owner, disability of an owner, bankruptcy of an owner, foreclosure, placement of a lien, use of assets as collateral, designation of a beneficiary, undertaking a loan against assets, providing a notice with respect to assets, inspection of assets, assessment of assets, reporting on assets for taxation purposes, allocation of ownership of assets, disposal of assets, sale of assets, purchase of assets, a designation of an ownership status, and the like). A data collection circuit 10702 may be structured to monitor the interpretation of the plurality of assets, authentication of the plurality of identifiers, and the recording of asset events, where t data collection circuit may be communicatively coupled with an Internet of Things system, a camera system, a networked monitoring system, an internet monitoring system, a mobile device system, a wearable device system, a user interface system, and an interactive crowdsourcing system. A smart contract circuit 10704 may be structured to manage the custody of the assets, where an asset event related to the plurality of assets may be managed by the smart contract circuit based on terms and conditions 10708 embodied in a smart contract configuration 10706 and based on data collected by the data collection service circuit. In embodiments, the asset identification service circuit, identity management service circuit, blockchain service circuit, and the financial management circuit may include a corresponding application programming interface (API) component structured to facilitate communication among the circuits of the system, such as where the corresponding API components of the circuits further include user interfaces structured to interact with users of the system.

Figure 108:
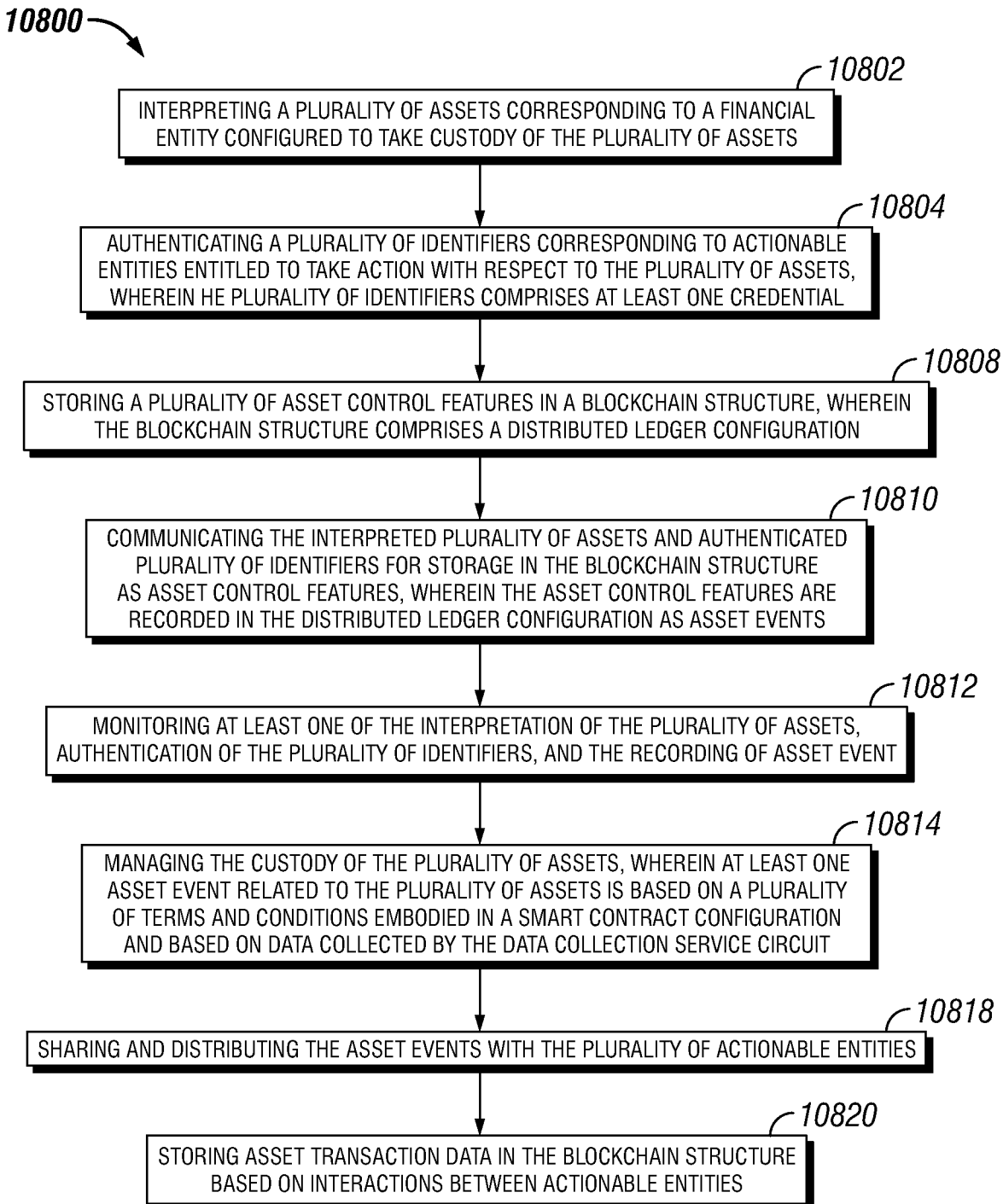
FIG. 108 depicts a method of a lending platform.

FIG. 108 depicts a method 10800 including interpreting assets corresponding to a financial entity configured to take custody of the plurality of assets 10802, such as where the interpreting of the assets may include identifying the plurality of assets for which a financial entity is responsible for taking custody. The method may include authenticating identifiers (e.g., including a credential) corresponding to actionable entities (e.g., owner, a beneficiary, an agent, a trustee, and a custodian) entitled to take action with respect to the plurality of assets 10804, such as where authenticating the identifiers includes verifying the identifiers corresponding to actionable entities are entitled to take action with respect to the assets. The method may include storing a plurality of asset control features in a blockchain structure 10808 (e.g., including a distributed ledger configuration) The blockchain structure may be provided in conjunction with a block-chain marketplace, utilize an automated blockchain-based transaction application, the blockchain structure may be a distributed blockchain structure across a plurality of asset nodes, and the like. The method may include communicating the interpreted assets and authenticated identifiers for storage in the blockchain structure as asset control features, where the asset control features may be recorded in the distributed ledger configuration as asset events 10810. The method may include monitoring the interpretation of the assets, authentication of the identifiers, and the recording of asset events 10812, such as where asset events may include transfer of title, death of an owner, disability of an owner, bankruptcy of an owner, foreclosure, placement of a lien, use of assets as collateral, designation of a beneficiary, undertaking a loan against assets, providing a notice with respect to assets, inspection of assets, assessment of assets, reporting on assets for taxation purposes, allocation of ownership of assets, disposal of assets, sale of assets, purchase of assets, and designation of an ownership status. In embodiments, monitoring may be executed by an Internet of Things system, a camera system, a networked monitoring system, an internet monitoring system, a mobile device system, a wearable device system, a user interface system, an interactive crowdsourcing system, and the like. The method may include managing the custody of the assets, where an asset event related to the plurality of assets may be based on terms and conditions embodied in a smart contract configuration and based on data collected by a data collection service circuit 10814. The method may include sharing and distributing the asset events with the plurality of actionable entities 10818. The method may include storing asset transaction data in the blockchain structure based on interactions between actionable entities 10820. An asset may include a virtual asset tag where interpreting the assets comprises identifying the virtual asset tag (e.g., storing of the asset control features may include storing virtual asset tag data, such as where the virtual asset tag data is location data, tracking data, and the like. For instance, an identifier corresponding to the financial entity or actionable entities may be stored as virtual asset tag data.

Figure 109:
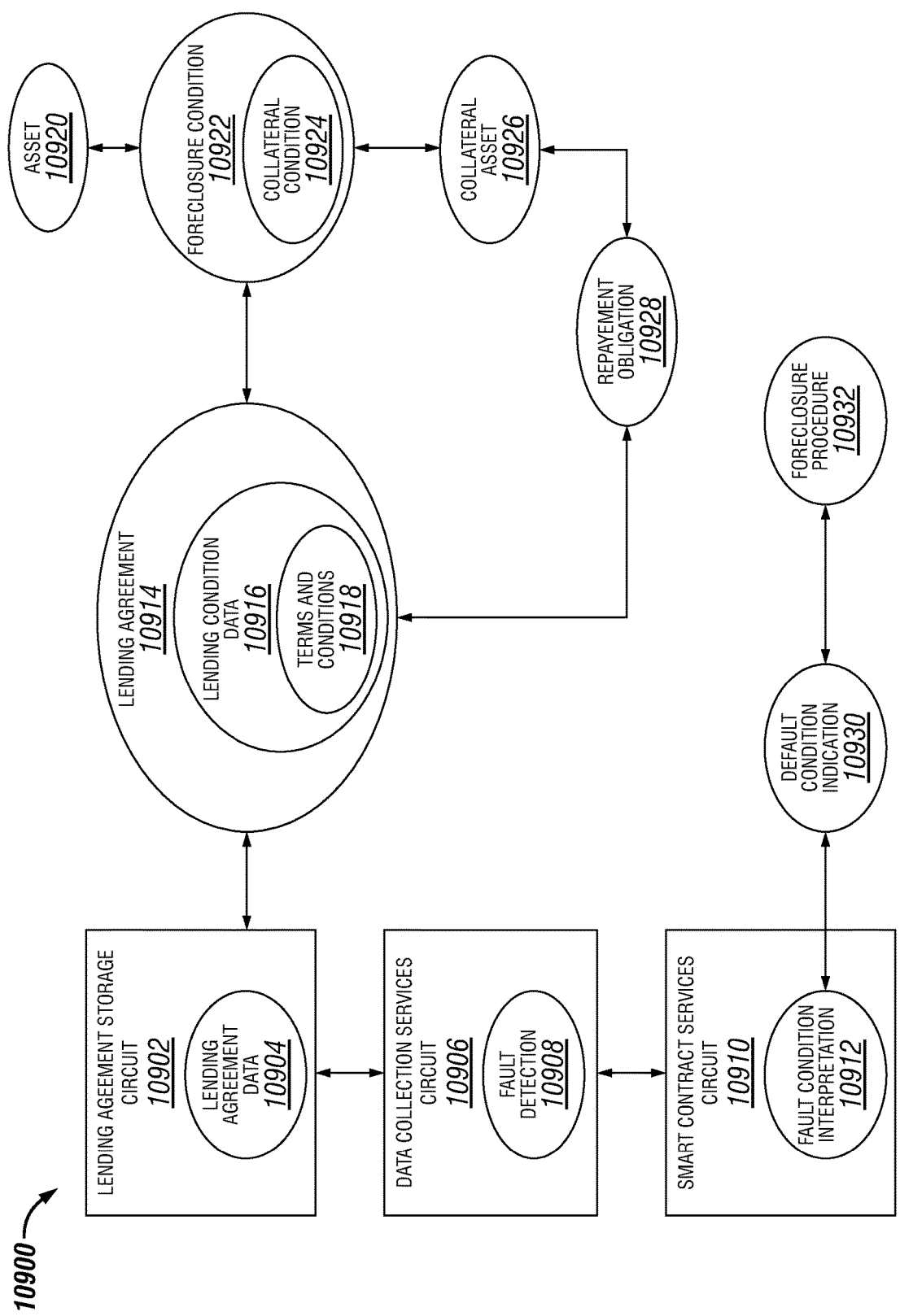
FIG. 109 depicts components and interactions of a lending platform.

FIG. 109 depicts a system 10900 including a lending agreement storage circuit 10902 structured to store a lending agreement data 10904 including a lending agreement 10914, wherein the lending agreement may include a lending condition data 10916. In embodiments, the lending condition data may include a terms and condition data 10918 of the at least one lending agreement related to a foreclosure condition 10922 on an asset 10920 that provides a collateral condition 10924 related to a collateral asset 10926, such as for securing a repayment obligation 10928 of the lending agreement. The system may include a data collection services circuit 10906 structured to monitor the lending condition data and to detect a default condition 10908 based on a change to the lending condition data. Further, the data collection services circuit may include an Internet of Things system, a camera system, a networked monitoring system, an internet monitoring system, a mobile device system, a wearable device system, a user interface system, and an interactive crowdsourcing system. The system may include a smart contract services circuit 10910 structured to, when the default condition is detected by the data collection services circuit, interpret the default condition 10912 and communicate a default condition indication 10930, such as to initiate a foreclosure procedure 10932 based on the collateral condition. For instance, the foreclosure procedure may configure and initiate a listing of the collateral asset on a public auction site, configure and deliver a set of transport instructions for the collateral asset, configure a set of instructions for a drone to transport the collateral asset, configure a set of instructions for a robotic device to transport the collateral asset, initiate a process for automatically substituting a set of substitute collateral, initiate a collateral tracking procedure, initiates a collateral valuation process, initiates a message to a borrower initiating a negotiation regarding the foreclosure, and the like. The default condition indication may be communicated to a smart lock and a smart container to lock the collateral asset. The negotiation may be managed by a robotic process automation system trained on a training set of foreclosure negotiations, and may relate to modification of interest rate, payment terms, collateral for the lending agreement, and the like. In embodiments, each of the lending agreement storage circuit, data collection services circuit, and smart contract services circuit may further include a corresponding application programming interface (API) component structured to facilitate communication among the circuits of the system, where the corresponding API components of the circuits may include user interfaces structured to interact with a plurality of users of the system.

Figure 110:
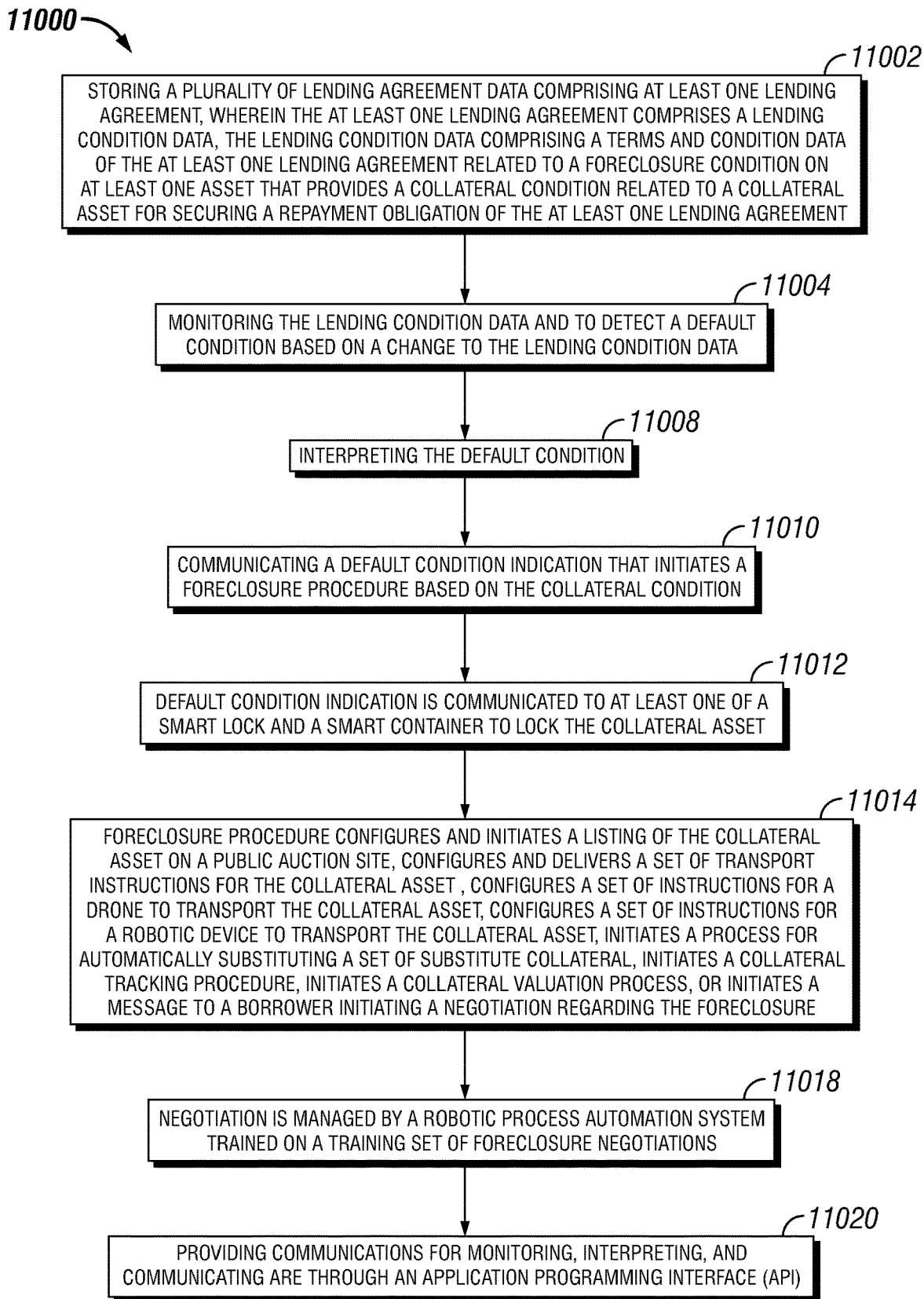
FIG. 110 depicts a method of a lending platform.

FIG. 110 depicts a method 11000 for facilitating foreclosure on collateral, the method including storing a lending agreement data including a lending agreement, where the lending agreement may include a lending condition data, such as where the lending condition data includes a terms and condition data of the lending agreement related to a foreclosure condition on an asset that provides a collateral condition related to a collateral asset for securing a repayment obligation of the at least one lending agreement 11002. The method may include monitoring the lending condition data and to detect a default condition based on a change to the lending condition data 11004. The method may include interpreting the default condition 11008 and communicating a default condition indication that initiates a foreclosure procedure based on the collateral condition 11010. For instance, the foreclosure procedure may configure and initiate a listing of the collateral asset on a public auction site, configure and deliver a set of transport instructions for the collateral asset, configure a set of instructions for a drone to transport the collateral asset, configure a set of instructions for a robotic device to transport the collateral asset, initiate a process for automatically substituting a set of substitute collateral, initiate a collateral tracking procedure, initiates a collateral valuation process, initiates a message to a borrower initiating a negotiation regarding the foreclosure, and the like 11014. The default condition indication may be communicated to a smart lock and a smart container to lock the collateral asset 11012. The negotiation may be managed by a robotic process automation system trained on a training set of foreclosure negotiations 11018, and may relate to modification of interest rate, payment terms, collateral for the lending agreement, and the like. In embodiments, communications may be provided by a corresponding application programming interface (API) 11020, where the corresponding API may include user interfaces structured to interact with a plurality of users.

In embodiments, provided herein is a system for adaptive intelligence and robotic process automation capabilities of a transactional, financial and marketplace enablement. An example platform or system may include a blockchain service circuit structured to interpret a plurality of access control features corresponding to a plurality of parties associated with a loan; a data collection circuit structured to interpret entity information corresponding to a plurality of entities related to a lending transaction corresponding to the loan; a smart contract circuit structured to specify loan terms and conditions relating to the loan; and a loan management circuit structured to: interpret loan related events in response to the entity information, the plurality of access control features, and the loan terms and conditions, wherein the loan related events are associated with the loan; implement loan related activities in response to the entity information, the plurality of access control features, and the loan terms and conditions, wherein the loan related activities are associated with the loan; and wherein each of the blockchain service circuit, the data collection circuit, the smart contract circuit, and the loan management circuit further comprise a corresponding application programming interface (API) component structured to facilitate communication among the circuits of the system.

Certain further aspects of an example system are described following, any one or more of which may be present in certain embodiments. An example system may include wherein the plurality of entities each comprise at least one entity selected from the entities consisting of: a lender, a borrower, a guarantor, equipment related to the loan, goods related to the loan, a system related to the loan, a fixture related to the loan, a building, a storage facility, and an item of collateral.

An example system may include at least one of the plurality of entities comprises an item of collateral, and wherein the data collection circuit is further structured to interpret a condition of the item of collateral, wherein the item of collateral comprises at least one item selected from the items consisting of: a vehicle, a ship, a plane, a building, a home, a real estate property, an undeveloped land property, a farm, a crop, a municipal facility, a warehouse, a set of inventory, a commodity, a security, a currency, a token of value, a ticket, a cryptocurrency, a consumable item, an edible item, a beverage, a precious metal, an item of jewelry, a gemstone, an item of intellectual property, an intellectual property right, a contractual right, an antique, a fixture, an item of furniture, a tool, an item of machinery, and an item of personal property.

An example system may include wherein the data collection circuit further comprises at least one system selected from the systems consisting of: an Internet of Things system, a camera system, a networked monitoring system, an internet monitoring system, a mobile device system, a wearable device system, a user interface system, and an interactive crowdsourcing system.

An example system may include wherein the loan related events each comprise at least one event selected from the events consisting of: a loan request, a loan offer, a loan acceptance, a provision of underwriting information for a loan, a provision of a credit report, a deferral of a payment, a requested deferral of a payment, an identification of collateral, a validation of title for collateral, a validation of title for a security, an inspection of property, a change in condition for at least one of the plurality of entities, a change in value of an entity, a change in value for collateral, a change in value for a security, a change in a job status of at least one of the parties, a change in a financial rating of a lender, a provision of insurance for the loan, a provision of evidence of insurance for a property, a provision of eligibility for a loan, an identification of security for the loan, an execution of underwriting the loan, a payment of the loan, a default of the loan, a calling of the loan, a closing of the loan, a change in the specified loan terms and conditions, an initial specification of the loan terms and conditions, and a foreclosure of a property subject to the loan.

An example system may include wherein the loan terms and conditions each comprise at least one member selected from the group consisting of: a principal amount of the loan, a balance of the loan, a fixed interest rate, a variable interest rate description, a payment amount, a payment schedule, a balloon payment schedule, a collateral specification, a collateral substitution description, a description of at least one of the parties, a guarantee description, a guarantor description, a security description, a personal guarantee, a lien, a foreclosure condition, a default condition, a consequence of default, a covenant related to any one of the foregoing, and a duration of any one of the foregoing.

An example system may include wherein at least one of the parties comprises at least one party selected from the parties consisting of: a primary lender, a secondary lender, a lending syndicate, a corporate lender, a government lender, a bank lender, a secured lender, bond issuer, a bond purchaser, an unsecured lender, a guarantor, a provider of security, a borrower, a debtor, an underwriter, an inspector, an assessor, an auditor, a valuation professional, a government official, a government agency, and an accountant.

An example system may include wherein loan related activities each comprise at least one activity selected from the activities consisting of: finding at least one of the parties interested in participating in a loan transaction, an application for the loan, underwriting the loan, forming a legal contract for the loan, monitoring performance of the loan, making payments on the loan, restructuring or amending the loan, settling the loan, monitoring collateral for the loan, forming a syndicate for the loan, foreclosing on the loan, and closing a loan transaction and wherein the loan comprises at least one loan type selected from the loan types consisting of: an auto loan, an inventory loan, a capital equipment loan, a bond for performance, a capital improvement loan, a building loan, a loan backed by an account receivable, an invoice finance arrangement, a factoring arrangement, a pay day loan, a refund anticipation loan, a student loan, a syndicated loan, a title loan, a home loan, a venture debt loan, a loan of intellectual property, a loan of a contractual claim, a working capital loan, a small business loan, a farm loan, a municipal bond, and a subsidized loan.

An example system may include wherein the smart contract circuit is further structured to perform a contract related loan action in response to the entity information.

An example system may include wherein the contract related loan action comprises at least one action selected from the actions consisting of: offering the loan, accepting the loan, underwriting the loan, setting an interest rate for the loan, deferring a payment requirement for the loan, modifying an interest rate for the loan, validating title for collateral of the loan, recording a change in title, assessing the value of collateral, initiating inspection of collateral, calling the loan, closing the loan, modifying the terms and conditions for the loan, providing a notice to one of the parties, providing a required notice to a borrower of the loan, and foreclosing on a property subject to the loan.

An example system may further include an automated agent circuit structured to interpret an event relevant to the loan, and to perform an action related to the loan in response to the event relevant to the loan, wherein the event relevant to the loan comprises an event relevant to at least one of: the value of the loan, a condition of collateral of the loan, or an ownership of collateral of the loan and wherein the action related to the loan comprises at least one of: modifying the terms and conditions for the loan, providing a notice to one of the parties, providing a required notice to a borrower of the loan, and foreclosing on a property subject to the loan.

An example system may include wherein the corresponding API components of the circuits further comprise user interfaces structured to interact with a plurality of users of the system.

An example system may include wherein the plurality of users each comprise one of the plurality of parties or one of the plurality of entities and wherein at least one of the plurality of users comprises one of a prospective party or a prospective entity.

An example system may include wherein each of the user interfaces is configured to be responsive to the plurality of access control features.

In embodiments, provided herein is a method for providing access control for loan terms and conditions on a distributed ledger. An example method may include interpreting a plurality of access control features corresponding to a plurality of parties associated with a loan from a distributed ledger; interpreting entity information corresponding to a plurality of entities related to a lending transaction corresponding to the loan; specifying loan terms and conditions relating to the loan; interpreting loan related events in response to the entity information, the plurality of access control features, and the loan terms and conditions, wherein the loan related events are associated with the loan.

Certain further aspects of an example system are described following, any one or more of which may be present in certain embodiments. An example method can include wherein at least one of the plurality of entities comprises an item of collateral, the method further comprising interpreting a condition of the item of collateral.

An example method can further include performing a contract related loan action in response to the entity information.

An example method can include wherein performing the contract related loan action comprises at least one action selected from the actions consisting of: offering the loan, accepting the loan, underwriting the loan, setting an interest rate for the loan, deferring a payment requirement for the loan, modifying an interest rate for the loan, validating title for collateral of the loan, recording a change in title, assessing the value of collateral, initiating inspection of collateral, calling the loan, closing the loan, modifying the terms and conditions for the loan, providing a notice to one of the parties, providing a required notice to a borrower of the loan, and foreclosing on a property subject to the loan.

An example method can further include interpreting an event relevant to the loan, and performing an action related to the loan in response to the event relevant to the loan, wherein the event relevant to the loan comprises an event relevant to at least one of: the value of the loan, a condition of collateral of the loan, or an ownership of collateral of the loan and wherein performing the action related to the loan comprises at least one of: modifying the terms and conditions for the loan, providing a notice to one of the parties, providing a required notice to a borrower of the loan, and foreclosing on a property subject to the loan.

An example method can further include providing a user interface to a user, wherein the user comprises at least one of: one of the plurality of parties, one of the plurality of entities, a prospective party, or a prospective entity, wherein the providing the user interface is further responsive to the plurality of access control features.

An example method can further include creating a smart lending contract for the loan and recording the smart lending contract as blockchain data.

In embodiments, provided herein is a system for adaptive intelligence and robotic process automation capabilities of a transactional, financial and marketplace enablement. An example platform or system may include a blockchain service circuit structured to interpret a plurality of access control features corresponding to a plurality of parties associated with a secured loan, and a data collection circuit structured to receive first collateral data from at least one sensor associated with an item of collateral used to secure the loan, receive second collateral data regarding an environment of the item of collateral from an Internet of Things circuit, and associate the collateral data with a unique identifier associated with the item of collateral, wherein the blockchain service circuit is further structured to store the unique identifier and associated collateral data as blockchain data. The example platform or system may further include a smart contract circuit structured to create a smart lending contract, and a secure access control circuit structured to receive access control instructions from a lender of the secured loan via an access control interface, wherein the secure access control circuit is further structured to provide instructions to the blockchain service circuit regarding access to the blockchain data associated with the item of collateral, wherein each of the blockchain service circuit, the data collection circuit, the secure access control circuit, and the Internet of Things circuit further comprise a corresponding application programming interface (API) component structured to facilitate communication among the circuits of the system.

Certain further aspects of an example system are described following, any one or more of which may be present in certain embodiments. An example system may include wherein the sensor associated with the item of collateral is positioned on in a location selected from the list consisting of on the item of collateral, on a container for the item of collateral, and on a package of the item of collateral.

An example system may include wherein the data collection circuit is further structured to interpret a condition of the item of collateral in response to a subset of the received collateral data.

An example system may include wherein the item of collateral is selected from among the list of items consisting of: a vehicle, a ship, a plane, a building, a home, a real estate property, an undeveloped land property, a farm, a crop, a municipal facility, a warehouse, a set of inventory, a commodity, a security, a currency, a token of value, a ticket, a cryptocurrency, a consumable item, an edible item, a beverage, a precious metal, an item of jewelry, a gemstone, an item of intellectual property, an intellectual property right, a contractual right, an antique, a fixture, an item of furniture, a tool, an item of machinery, and an item of personal property.

An example system may include wherein the secured loan is at least one of an auto loan, an inventory loan, a capital equipment loan, a bond for performance, a capital improvement loan, a building loan, a loan backed by an account receivable, an invoice finance arrangement, a factoring arrangement, a pay day loan, a refund anticipation loan, a student loan, a syndicated loan, a title loan, a home loan, a venture debt loan, a loan of intellectual property, a loan of a contractual claim, a working capital loan, a small business loan, a farm loan, a municipal bond, and a subsidized loan.

An example system may include wherein the environment of the item of collateral is selected from, the list of environments consisting of a real property environment, a commercial facility, a warehousing facility, a transportation environment, a manufacturing environment, a storage environment, a home, and a vehicle.

An example system may include wherein the at least one sensor is selected from the group consisting of an image capture device, a thermometer, a pressure gauge, a humidity sensor, a velocity sensor, an acceleration sensor, a rotational sensor, a torque sensor, a scale, chemical, magnetic field, electrical field, and position sensors.

An example system may further include a reporting circuit structured to report a collateral event related to an aspect of the collateral selected from the list of aspects consisting of: a value of the item of collateral, a condition of the item of collateral, and an ownership of the item of collateral.

An example system may further include an automated agent circuit structured to interpret the collateral event and to perform a loan-related action in response to the collateral event.

An example system may include wherein the loan-related action is selected from among the actions consisting of: offering a loan, accepting a loan, underwriting a loan, setting an interest rate for a loan, deferring a payment requirement, modifying an interest rate for a loan, validating title for collateral, recording a change in title, assessing the value of collateral, initiating inspection of collateral, calling a loan, closing a loan, setting terms and conditions for a loan, providing notices required to be provided to a borrower, foreclosing on property subject to a loan, and modifying terms and conditions for a loan.

An example system may further include a collateral classification circuit structured to identify a group of offset items of collateral, wherein each member of the group of offset items of collateral and the item of collateral share a common attribute.

An example system may include wherein the common attribute is selected from a list of attributes consisting of: a category of the item of collateral, an age of the item of collateral, a condition of the item of collateral, a history of the item of collateral, an ownership of the item of collateral, a caretaker of the item of collateral, a security of the item of collateral, a condition of an owner of the item of collateral, a lien on the item of collateral, a storage condition of the item of collateral, a geolocation of the item of collateral, and a jurisdictional location of the item of collateral.

An example system may further include a market value data collection circuit structured to monitor and report on marketplace information relevant to a value of the item of collateral or at least one of the group of offset items of collateral.

An example system may include wherein the market value data collection circuit is further structured to monitor a price or financial data the item of collateral or at least one of the group of offset items of collateral in at least one public marketplace.

An example system may include wherein the market value data collection circuit is further structured to report the monitored one of the price or the financial data.

An example system may include wherein the smart contract circuit is further structured to modify a term or condition of the loan based on the marketplace information for offset items of collateral relevant to the value of the item of collateral.

An example system may further include a smart contract services circuit structured to manage a smart contract for the secured loan.

An example system may include wherein the smart contract services circuit is further structured to set terms and conditions related to the item of collateral securing the loan.

An example system may include wherein the terms and conditions are selected from a list consisting of: a specification of the item of collateral, a specification of substitutability of the item of collateral, a specification of condition of the item of collateral, a specification related to liens on the item of collateral, a specification related to the security of the item of collateral, and a specification related to the environment of the item of collateral.

In embodiments, provided herein is a method for automated smart contract creation and collateral assignment. An example method may include receiving first collateral data from a sensor associated with an item of collateral used to secure a loan, receiving second collateral data regarding an environment of the item of collateral, associating the collateral data with a unique identifier associated with the item of collateral, creating a smart lending contract, storing the unique identifier and the collateral data in a blockchain structure, receiving access control instructions from a lender of the secured loan, interpreting a plurality of access control features, and providing access to the data regarding the item of collateral.

Certain further aspects of an example method are described following, any one or more of which may be present in certain embodiments. An example method may further include interpreting a condition of the item of collateral in response to a subset of the received collateral data.

An example method may further include identifying a collateral event from the condition of the item of collateral and reporting the collateral event, wherein the collateral event is relevant to a collateral characteristic selected from the list consisting of: a value of the item of collateral, a condition of the item of collateral, and an ownership of the item of collateral.

An example method may further include determining a value for the item of collateral.

An example method may further include interpreting the collateral event; and performing a loan-related action in response to the collateral event.

An example method may further include identifying a group of offset collateral, wherein each member of the group of offset items of collateral and the item of collateral share a common attribute.

An example method may further include monitoring a marketplace for information relevant to a value of the item of collateral or at least one of the group of offset items of collateral and modifying a term of condition of the loan based on the marketplace information.

An example method may further include creating a smart lending contract for the loan.

An example method may further include receiving access control instructions, interpreting a plurality of access control features, and providing access to the collateral data.

In embodiments, provided herein is a system for handling a loan. An example platform, system, or apparatus may include a blockchain service circuit structured to interface with a distributed ledger; a data collection circuit structured to receive data related to a plurality of items of collateral or data related to environments of the plurality of items of collateral; a valuation circuit structured to determine a value for each of the plurality of items of collateral based on a valuation model and the received data; a smart contract circuit structured to interpret a smart lending contract for a loan, and to modify the smart lending contract by assigning, based on the determined value for each of the plurality of items of collateral, at least a portion of the plurality of items of collateral as security for the loan such that the determined value of the of the plurality of items of collateral is sufficient to provide security for the loan. The blockchain service circuit may be further structured to record the assigned at least a portion of items of collateral to an entry in the distributed ledger, wherein the entry is used to record events relevant to the loan. Each of the blockchain service circuit, the data collection circuit, the valuation circuit and the smart contract circuit may further include a corresponding application programming interface (API) component structured to facilitate communication among the circuits of the system.

Certain further aspects of an example system are described following, any one or more of which may be present in certain embodiments. An example system may include wherein modifying the smart lending contract further comprises specifying terms and conditions that govern an item selected from the list consisting of a loan term, a loan condition, a loan-related event, and a loan-related activity.

An example system may include wherein the terms and conditions each comprise at least one member selected from the group consisting of: a principal amount of the loan, a balance of the loan, a fixed interest rate, a variable interest rate description, a payment amount, a payment schedule, a balloon payment schedule, a collateral specification, a collateral substitution description, a description of at least one of the parties, a guarantee description, a guarantor description, a security description, a personal guarantee, a lien, a foreclosure condition, a default condition, a consequence of default, a covenant related to any one of the foregoing, and a duration of any one of the foregoing.

An example system may include wherein the loan comprises at least one loan type selected from the loan types consisting of: an auto loan, an inventory loan, a capital equipment loan, a bond for performance, a capital improvement loan, a building loan, a loan backed by an account receivable, an invoice finance arrangement, a factoring arrangement, a pay day loan, a refund anticipation loan, a student loan, a syndicated loan, a title loan, a home loan, a venture debt loan, a loan of intellectual property, a loan of a contractual claim, a working capital loan, a small business loan, a farm loan, a municipal bond, and a subsidized loan.

An example system may include wherein the item of collateral comprises at least one item selected from the items consisting of: a vehicle, a ship, a plane, a building, a home, a real estate property, an undeveloped land property, a farm, a crop, a municipal facility, a warehouse, a set of inventory, a commodity, a security, a currency, a token of value, a ticket, a cryptocurrency, a consumable item, an edible item, a beverage, a precious metal, an item of jewelry, a gemstone, an item of intellectual property, an intellectual property right, a contractual right, an antique, a fixture, an item of furniture, a tool, an item of machinery, and an item of personal property.

An example system may include wherein the data collection circuit is further structured to receive outcome data related to the loan and a corresponding item of collateral, and wherein the valuation circuit comprises an artificial intelligent circuit structured to iteratively improve the valuation model based on the outcome data.

An example system may include wherein the valuation circuit further comprises a market value data collection circuit structured to monitor and report marketplace information relevant to the value of at least one of the plurality of items of collateral.

An example system may include wherein the market value monitoring circuit is further structured to monitor pricing or financial data for items that are similar to the item of collateral in at least one public marketplace.

An example system may further include a clustering circuit structured to identify a set of similar items for use in valuing the item of collateral based on similarity to an attribute of the collateral.

An example system may include wherein the attribute of the collateral is selected from among a list of attributes consisting of: a category of the collateral, an age of the collateral, a condition of the collateral, a history of the collateral, a storage condition of the collateral, and a geo-location of the collateral.

An example system may include wherein the data collection circuit is further structured to interpret a condition of the item of collateral.

An example system may include wherein the data collection circuit further comprises at least one system selected from the systems consisting of: an Internet of Things system, a camera system, a networked monitoring system, an internet monitoring system, a mobile device system, a wearable device system, a user interface system, and an interactive crowdsourcing system.

An example system may include wherein the loan comprises at least one loan type selected from the loan types consisting of: an auto loan, an inventory loan, a capital equipment loan, a bond for performance, a capital improvement loan, a building loan, a loan backed by an account receivable, an invoice finance arrangement, a factoring arrangement, a pay day loan, a refund anticipation loan, a student loan, a syndicated loan, a title loan, a home loan, a venture debt loan, a loan of intellectual property, a loan of a contractual claim, a working capital loan, a small business loan, a farm loan, a municipal bond, and a subsidized loan.

An example system may further include a loan management circuit structured to interpret an event relevant to the loan, and to perform an action related to the loan in response to the event relevant to the loan.

An example system may include wherein the event relevant to the loan comprises an event relevant to at least one of: a value of the loan, a condition of collateral of the loan, or an ownership of collateral of the loan.

An example system may include wherein the action related to the loan comprises at least one of: modifying the terms and conditions for the loan, providing a notice to one of the parties, providing a required notice to a borrower of the loan, and foreclosing on a property subject to the loan.

An example system may include wherein the corresponding API components of the circuits further comprise user interfaces structured to interact with a plurality of users of the system.

An example system may include wherein the plurality of users each comprise: one of the plurality of parties, one of the plurality of entities, or a representative of any one of the foregoing.

An example system may include wherein at least one of the plurality of users comprises: a prospective party, a prospective entity, or a representative of any one of the foregoing.

In embodiments, provided herein is a method for handling a loan. An example method may include receiving data related to a plurality of items of collateral; setting a value for each of the plurality of items of collateral; assigning at least a portion of the plurality of items of collateral as security for a loan; and recording the assigned at least a portion of the plurality of items of collateral to an entry in a distributed ledger, wherein the entry is used to record events relevant to the loan.

Certain further aspects of an example method are described following, any one or more of which may be present in certain embodiments. An example method may further include modifying a smart lending contract for the loan.

An example method may further include modifying a smart lending contract comprises adjusting or specifying terms and conditions for the loan.

An example method may include wherein the terms and conditions are each selected from the list consisting of: a principal amount of debt, a balance of debt, a fixed interest rate, a variable interest rate, a payment amount, a payment schedule, a balloon payment schedule, a party, a guarantee, a guarantor, a security, a personal guarantee, a lien, a duration, a covenant, a foreclose condition, a default condition, and a consequence of default.

An example method may further include receiving outcome data related to the loan; and iteratively improving a valuation model based on the outcome data and corresponding collateral.

An example method may further include monitoring marketplace information relevant to the value of at least one of the plurality of items of collateral.

An example method may further include identifying a set of items similar to one of the plurality of items of collateral based on similarity to an attribute of the one of the plurality of items of collateral.

An example method may further include interpreting a condition of the one of the plurality of items of collateral.

An example method may further include reporting events related to a value of the one of the plurality of items of collateral, a condition of the one of the plurality of items of collateral, or an ownership of the one of the items of collateral.

An example method may further include interpreting an event relevant to: a value of one of the plurality of items of collateral, a condition of one of the plurality of items of collateral, or an ownership of one of the plurality of items of collateral; and performing an action related to the secured loan in response to the event relevant to the one of the plurality of items of collateral for said secured loan.

An example method may further include wherein the loan-related action is selected from among the actions consisting of: offering a loan, accepting a loan, underwriting a loan, setting an interest rate for a loan, deferring a payment requirement, modifying an interest rate for a loan, validating title for collateral, recording a change in title, assessing the value of collateral, initiating inspection of collateral, calling a loan, closing a loan, setting terms and conditions for a loan, providing notices required to be provided to a borrower, foreclosing on property subject to a loan, and modifying terms and conditions for a loan.

In embodiments, provided herein is a system for adaptive intelligence and robotic process automation capabilities of a transactional, financial and marketplace enablement. An example platform or system may include a blockchain service circuit structured to interface with a distributed ledger; a data collection circuit structured to receive data related to a set of items of collateral that provide security for a loan: a smart contract circuit structured to create a smart lending contract for the loan and assign at least a portion of the set of items of collateral to the loan, thereby creating an assigned set of items of collateral; wherein the blockchain service circuit is further structured to record the assigned set of items of collateral to a loan-entry in the distributed ledger, and wherein each of the blockchain service circuit, the data collection circuit, and the smart contract circuit further comprise a corresponding application programming interface (API) component structured to facilitate communication among the circuits of the system.

Certain further aspects of an example system are described following, any one or more of which may be present in certain embodiments. An example system may include wherein the data collection circuit is further structured to receive data related to an environment of the assigned set of items of collateral.

An example system may include wherein the smart contract circuit is further structured to specify a term or condition of the loan that governs an item selected from the list consisting of: a loan term, a loan condition, a loan-related event, and a loan-related activity, wherein the terms and conditions of the loan each comprise at least one member selected from the group consisting of: a principal amount of the loan, a balance of the loan, a fixed interest rate, a variable interest rate description, a payment amount, a payment schedule, a balloon payment schedule, a collateral specification, a collateral substitution description, a description of at least one party to the loan, a guarantee description, a guarantor description, a security description, a personal guarantee, a lien, a foreclosure condition, a default condition, a consequence of default, a covenant related to any one of the foregoing, and a duration of any one of the foregoing.

An example system may include wherein the loan comprises at least one loan type selected from the loan types consisting of: an auto loan, an inventory loan, a capital equipment loan, a bond for performance, a capital improvement loan, a building loan, a loan backed by an account receivable, an invoice finance arrangement, a factoring arrangement, a pay day loan, a refund anticipation loan, a student loan, a syndicated loan, a title loan, a home loan, a venture debt loan, a loan of intellectual property, a loan of a contractual claim, a working capital loan, a small business loan, a farm loan, a municipal bond, and a subsidized loan.

An example system may include wherein the assigned set of items of collateral comprises at least one item selected from the items consisting of: a vehicle, a ship, a plane, a building, a home, a real estate property, an undeveloped land property, a farm, a crop, a municipal facility, a warehouse, a set of inventory, a commodity, a security, a currency, a token of value, a ticket, a cryptocurrency, a consumable item, an edible item, a beverage, a precious metal, an item of jewelry, a gemstone, an item of intellectual property, an intellectual property right, a contractual right, an antique, a fixture, an item of furniture, a tool, an item of machinery, and an item of personal property.

An example system may further include a valuation circuit structured to determine a value for each of the set of items of collateral or the assigned set of items of collateral, based on a valuation model and the received data, wherein the valuation circuit comprises a valuation model improvement circuit, wherein the valuation model improvement circuit modifies the valuation model based on a first set of valuation determinations for a first set of items of collateral and a corresponding set of loan outcomes having the first set of items of collateral as security.

An example system may further include wherein the valuation model improvement circuit comprises at least one system from the list of systems consisting of: a machine learning system, a model-based system, a rule-based system, a deep learning system, a neural network, a convolutional neural network, a feed forward neural network, a feedback neural network, a self-organizing map, a fuzzy logic system, a random walk system, a random forest system, a probabilistic system, a Bayesian system, a simulation system, a hybrid system, and a hybrid system including at least two of any of the foregoing.

An example system may further include a collateral classification circuit structured to identify a group of offset items of collateral, wherein each member of the group of offset items of collateral and at least one of the assigned set of items of collateral share a common attribute, wherein the common attribute is selected from a list of attributes consisting of: a category of the items, an age of the items, a condition of the items, a history of the items, an ownership of the items, a caretaker of the items, a security of the items, a condition of an owner of the items, a lien on the items, a storage condition of the items, a geolocation of the items, and a jurisdictional location of the items.

An example system may further include, wherein the valuation circuit further includes a market value data collection circuit structured to monitor and report marketplace information for offset items of collateral relevant to the value of at least one of the assigned set of items of collateral. An example system may further include wherein the smart contract circuit is further structured to apportion, among a set of lenders, the value for one of the assigned set of items of collateral.

An example system may include wherein the loan-entry in the distributed ledger further comprises priority information related to a lender, and wherein an apportionment of value is based on the priority information for the lender, wherein the lender is selected from a list consisting of: a primary lender, a secondary lender, a lending syndicate, a corporate lender, a government lender, a bank lender, a secured lender, a bond issuer, and an unsecured lender.

An example system may further include, wherein the data collection circuit comprises at least one system selected from systems consisting of: an Internet of Things system, a camera system, a networked monitoring system, an internet monitoring system, a mobile device system, a wearable device system, a user interface system, and an interactive crowdsourcing system.

An example system may further include wherein the data collection circuit is further structured to identify a collateral event based on the received data, wherein the collateral event is related to a value of one of the assigned set of items of collateral, a condition of one of the assigned set of items of collateral, or an ownership of one of the assigned set of items of collateral and further including an automated agent circuit structured to perform a collateral-related action in response to the collateral event, wherein the collateral-related action is selected from among the actions consisting of: validating title for the one of the assigned set of items of collateral, recording a change in title for the one of the assigned set of items of collateral, assessing the value of the one of the assigned set of items of collateral, initiating inspection of the one of the assigned set of items of collateral, initiating maintenance of the one of the assigned set of items of collateral, initiating security for the one of the assigned set of items of collateral, and modifying terms and conditions for the one of the assigned set of items of collateral.

An example system may include wherein the automated agent circuit is further structured to perform a loan-related action in response to the collateral event, wherein the loan-related action is selected from the list of actions consisting of: offering the loan, accepting the loan, underwriting the loan, setting an interest rate for a loan, deferring a payment requirement, modifying the interest rate for the loan, calling the loan, closing the loan, setting terms and conditions for the loan, providing notices required to be provided to a borrower, foreclosing on property subject to the loan, and modifying terms and conditions for the loan.

In embodiments, provided herein is a method for adaptive intelligence and robotic process automation capabilities of a transactional, financial and marketplace enablement. An example method may include receiving data related to a set of items of collateral that provide security for a loan; creating a smart lending contract for the loan; recording the set of items of collateral in the smart lending contract; and recording a loan-entry in a distributed ledger, wherein the loan-entry comprises one of the smart lending contract or a reference to the smart lending contract.

Certain further aspects of an example system are described following, any one or more of which may be present in certain embodiments. An example method may further include receiving data related to an environment of one of the set of items of collateral.

An example method may further include determining a value for each of the set of items of collateral based on a valuation model and the received data and modifying the valuation model based on a first set of valuation determinations for a first set of items of collateral and a corresponding set of loan outcomes having the first set of items of collateral as security.

An example method may further include apportioning, among a set of lenders, the value of one of the set of items of collateral.

An example method may further include determining a collateral event based on at least one of the value of one of the set of items of collateral and the received data and performing a loan-related action in response to the collateral event, wherein the loan-related action is selected from the list of actions consisting of: offering the loan, accepting the loan, underwriting the loan, setting an interest rate for a loan, deferring a payment requirement, modifying the interest rate for the loan, calling the loan, closing the loan, setting terms and conditions for the loan, providing notices required to be provided to a borrower, foreclosing on property subject to the loan, and modifying terms and conditions for the loan.

An example method may further include performing a collateral-related action in response to the collateral event, wherein the collateral-related action is selected from the list of actions consisting of: validating title for the one of the set of items of collateral, recording a change in title for the one of the set of items of collateral, assessing the value of the one of the set of items of collateral, initiating inspection of the one of the set of items of collateral, initiating maintenance of the one of the set of items of collateral, initiating security for the one of the set of items of collateral, and modifying terms and conditions for the one of the set of items of collateral.

An example method may further include identifying a group of offset items of collateral, wherein the group of offset items of collateral and at least one of the set of items of collateral share a common attribute; monitoring marketplace information for data related to the group of offset items of collateral; updating the value of the at least one of the set of items based on the monitored data; and updating the loan-entry in the distributed ledger with the updated value.

In embodiments, provided herein is a system for adaptive intelligence and robotic process automation capabilities of a transactional, financial and marketplace enablement. An example platform or system may include a data collection circuit structured to receive data related to an item of collateral that provides security for a loan; a valuation circuit structured to determine a value for the item of collateral based on the received data and a valuation model; a smart contract circuit structured to create a smart lending contract, wherein the smart lending contract specifies a covenant defining a required value of the item of collateral; and a loan management circuit including: a value comparison circuit structured to compare the value of the item and the specified covenant and determine a collateral satisfaction value; an automated agent circuit structured to automatically implement loan related activities in response to the collateral satisfaction value, wherein the loan related activities comprise: issuing a notice of default or a foreclosure action.

Certain further aspects of an example system are described following, any one or more of which may be present in certain embodiments. An example system may include wherein the smart contract circuit is further structured to: determine at least one of a term or a condition for the smart lending contract in response to the collateral satisfaction value; and modify the smart lending contract to include the at least one of the term or the condition, wherein the at least one of the term or the condition is related to a loan component selected from the loan components consisting of: a loan party, a loan collateral, a loan-related event, and a loan-related activity.

An example system may include wherein the at least one of a term or condition is selected from the list consisting of: a principal amount of the loan, a balance of the loan, a fixed interest rate, a variable interest rate description, a payment amount, a payment schedule, a balloon payment schedule, a collateral specification, a collateral substitution description, a description of a party, a guarantee description, a guarantor description, a security description, a personal guarantee, a lien, a foreclosure condition, a default condition, a consequence of default, a principal amount of debt, a balance of debt, a fixed interest rate, a variable interest rate, a payment amount, a payment schedule, a balloon payment schedule, a party, a guarantee, a guarantor, a security, a personal guarantee, a lien, a duration, a covenant, a foreclose condition, a default condition, and a consequence of default, a covenant related to any one of the foregoing, and a duration of any one of the foregoing.

An example system may include wherein the valuation circuit comprises a valuation model improvement circuit, wherein the valuation model improvement circuit modifies the valuation model based on a first set of valuation determinations for a first set of items of collateral and a corresponding set of loan outcomes having the first set of items of collateral as security, and wherein the valuation model improvement circuit comprises at least one system from the list of systems consisting of: a machine learning system, a model-based system, a rule-based system, a deep learning system, a neural network, a convolutional neural network, a feed forward neural network, a feedback neural network, a self-organizing map, a fuzzy logic system, a random walk system, a random forest system, a probabilistic system, a Bayesian system, a simulation system, and a hybrid system of at least two of any of the foregoing.

An example system may include wherein the data collection circuit comprises at least one system selected from systems consisting of: an Internet of Things system, a camera system, a networked monitoring system, an internet monitoring system, a mobile device system, a wearable device system, a user interface system, and an interactive crowdsourcing system.

An example system may include wherein the valuation circuit further comprises a collateral classification circuit structured to identify a group of offset items of collateral, wherein each member of the group of offset items of collateral and the item of collateral share a common attribute, wherein the common attribute is selected from a list of attributes consisting of: a category of the item of collateral, an age of the item of collateral, a condition of the item of collateral, a history of the item of collateral, an ownership of the item of collateral, a caretaker of the item of collateral, a security of the item of collateral, a condition of an owner of the item of collateral, a lien on the item of collateral, a storage condition of the item of collateral, a geolocation of the item of collateral, and a jurisdictional location of the item of collateral.

An example system may include wherein the valuation circuit further comprises a market value data collection circuit structured to monitor and report marketplace information for offset items of collateral relevant to the value of the item of collateral, wherein the market value data collection circuit is further structured to: monitor one of pricing or financial data for the offset items of collateral in at least one public marketplace; and report the monitored one of pricing or financial data.

An example system may include wherein the loan comprises at least one loan type selected from the loan types consisting of: an auto loan, an inventory loan, a capital equipment loan, a bond for performance, a capital improvement loan, a building loan, a loan backed by an account receivable, an invoice finance arrangement, a factoring arrangement, a pay day loan, a refund anticipation loan, a student loan, a syndicated loan, a title loan, a home loan, a venture debt loan, a loan of intellectual property, a loan of a contractual claim, a working capital loan, a small business loan, a farm loan, a municipal bond, and a subsidized loan.

An example system may include wherein the item of collateral is selected from the list of items consisting of: a vehicle, a ship, a plane, a building, a home, a real estate property, an undeveloped land property, a farm, a crop, a municipal facility, a warehouse, a set of inventory, a commodity, a security, a currency, a token of value, a ticket, a cryptocurrency, a consumable item, an edible item, a beverage, a precious metal, an item of jewelry, a gemstone, an item of intellectual property, an intellectual property right, a contractual right, an antique, a fixture, an item of furniture, a tool, an item of machinery, and an item of personal property.

An example system may further include a blockchain service circuit structured to store at least one of the smart lending contract or a reference to the smart lending contract as blockchain data and a reporting circuit structured to report a collateral event based on the received data, wherein the collateral event is related to a value of the item of collateral, a condition of the item of collateral, or an ownership of the item of collateral.

An example system may further include an automated agent circuit structured to perform a collateral-related action in response to the collateral event, wherein the collateral-related action is selected from among the actions consisting of: validating title for the item of collateral, recording a change in title for the item of collateral, assessing the value of the item of collateral, initiating inspection of the item of collateral, initiating maintenance of the item of collateral, initiating security for the item of collateral, and modifying terms and conditions for the item of collateral.

An example system may include wherein the automated agent circuit is further structured to perform a loan-related action in response to the collateral event, wherein the loan-related action is selected from the list of actions consisting of: offering the loan, accepting the loan, underwriting the loan, setting an interest rate for a loan, deferring a payment requirement, modifying the interest rate for the loan, calling the loan, closing the loan, setting terms and conditions for the loan, providing notices required to be provided to a borrower, foreclosing on property subject to the loan, and modifying terms and conditions for the loan. In embodiments, provided herein is a method for robotic process automation of transactional, financial and marketplace activities. An example method may include receiving data related to an item of collateral that provides security for a loan; determining a value for the item of collateral based on the received data and a valuation model; creating a smart lending contract, wherein the smart lending contract specifies a covenant having a required value of collateral; comparing the value of the item of collateral to the value of collateral specified in the covenant; determining a collateral satisfaction value; and implementing a loan related activity in response to the collateral satisfaction value.

An example method may further include determining at least one of a term or a condition for the smart lending contract in response to the collateral satisfaction value; and modifying the smart lending contract to include the at least one of the term or the condition.

An example method may further include modifying the valuation model based on a first set of valuation determinations for a first set of items of collateral and a corresponding set of loan outcomes having the first set of items of collateral as security.

An example method may further include identifying a group of offset items of collateral, wherein each member of the group of offset items of collateral and the item of collateral share a common attribute, wherein the common attribute is selected from a list of attributes consisting of: a category of the item of collateral, an age of the item of collateral, a condition of the item of collateral, a history of the item of collateral, an ownership of the item of collateral, a caretaker of the item of collateral, a security of the item of collateral, a condition of an owner of the item of collateral, a lien on the item of collateral, a storage condition of the item of collateral, a geolocation of the item of collateral, and a jurisdictional location of the item of collateral.

An example method may further include monitoring and reporting marketplace information for data relevant to a member of the group of offset items of collateral and modifying the smart lending contract in response to the marketplace information, wherein monitoring marketplace information comprises monitoring at least one public marketplace for pricing data or financial data related to the member of the group of offset items of collateral.

An example method may further include automatic initiation of a loan related action in response to one of the pricing data or the financial data, wherein the loan-related action includes an action selected from a list of actions consisting of: modifying a term of the loan, issuing a notice of default, initiating a foreclosure action modifying a conditions of the loan, providing a notice to a party of the loan, providing a required notice to a borrower of the loan, and foreclosing on a property subject to the loan.

In embodiments, provided herein is a system for adaptive intelligence and robotic process automation capabilities of a transactional, financial and marketplace enablement. An example platform or system may include a data collection circuit structured to receive data related to a plurality of items of collateral; a collateral classification circuit structured to identify, among the plurality of items of collateral, at least one group of related items of collateral, wherein each member of the at least one group shares a common attribute; and a smart contract circuit structured to create a smart lending contract, wherein the smart lending contract defines a subset of items of collateral as security for a set of loans, wherein the subset of items of collateral is selected from the at least one group of related items of collateral.

Certain further aspects of an example system are described following, any one or more of which may be present in certain embodiments. An example system may include wherein the collateral classification circuit is further structured to select the common attribute from the received data, wherein the common attribute is a type of the item of collateral, a category of the item of collateral, a value of the item of collateral, a price of a type of the item of collateral, a value of a type of the item of collateral, a specification of the item of collateral, a product feature set of the item of collateral, a liquidity of the item of collateral, a shelf-life of the item of collateral, a useful life of the item of collateral, a model of the item of collateral, a brand of the item of collateral, a manufacturer of the item of collateral, an age of the item of collateral, a condition of the item of collateral, a valuation of the item of collateral, a status of the item of collateral, a context of the item of collateral, a state of the item of collateral, a storage location of the item of collateral, a history of the item of collateral, an ownership of the item of collateral, a caretaker of the item of collateral, a security of the item of collateral, a condition of an owner of the item of collateral, a lien on the item of collateral, a storage condition of the item of collateral, a maintenance history of the item of collateral, a usage history of the item of collateral, an accident history of the item of collateral, a fault history of the item of collateral, a history of ownership of the item of collateral, an assessment of the item of collateral, a geolocation of the item of collateral, a jurisdictional location of the item of collateral, and the like.

An example system may include wherein the smart lending contract is further structured to identify the subset of items of collateral in real-time, and wherein the common attribute is similarity of status of the items of collateral.

An example system may include wherein the similarity of status is based on each of the subset of items of collateral being in transit during a defined time period.

An example system may include wherein the data collection circuit comprises at least one system selected from systems consisting of: an Internet of Things system, a camera system, a networked monitoring system, an internet monitoring system, a mobile device system, a wearable device system, a user interface system, and an interactive crowdsourcing system.

An example system may include wherein the set of loans comprises a plurality of loans distributed among a plurality of borrowers.

An example system may include wherein a valuation circuit structured to determine, based on the received data and a valuation model, a value for each item of collateral in the subset of items of collateral; and wherein the smart contract circuit is further structured to redefine the subset based on the value for each item of collateral.

An example system may include wherein the smart contract circuit is further structured to determine at least one of a term or a condition for the smart lending contract based on the value of at least one of the subset of items of collateral; and modify the smart lending contract to include the determined term or condition, wherein the term or the condition is related to a loan component selected from the loan components consisting of: a loan party, a loan collateral, a loan-related event, and a loan-related activity and wherein the determined term or condition is a principal amount of the loan, a balance of the loan, a fixed interest rate, a variable interest rate description, a payment amount, a payment schedule, a balloon payment schedule, a collateral specification, a collateral substitution description, a description of a party, a guarantee description, a guarantor description, a security description, a personal guarantee, a lien, a foreclosure condition, a default condition, a consequence of default, a covenant related to any one of the foregoing, a duration of any one of the foregoing, and the like.

An example system may include wherein the valuation circuit comprises a valuation model improvement circuit, wherein the valuation model improvement circuit is structured to modify the valuation model based on a first set of valuation determinations for a first set of items of collateral and a corresponding set of loan outcomes having the first set of items of collateral as security, wherein the valuation model improvement circuit comprises at least one system from the list of systems consisting of: a machine learning system, a model-based system, a rule-based system, a deep learning system, a neural network, a convolutional neural network, a feed forward neural network, a feedback neural network, a self-organizing map, a fuzzy logic system, a random walk system, a random forest system, a probabilistic system, a Bayesian system, a simulation system, and a hybrid system including at least two of the foregoing.

An example system may include wherein the collateral classification circuit is further structured to identify a group of offset items of collateral, wherein each member of the group of offset items of collateral and the subset of items of collateral share a common attribute.

An example system may include wherein the valuation circuit further comprises a market value data collection circuit structured to monitor and report marketplace information, such as pricing data and financial data in at least one public marketplace, for at least one of the group of offset items of collateral and report the monitored one of pricing or financial data.

An example system may include wherein at least one of the set of loans is of a type selected from among the loan types consisting of: an auto loan, an inventory loan, a capital equipment loan, a bond for performance, a capital improvement loan, a building loan, a loan backed by an account receivable, an invoice finance arrangement, a factoring arrangement, a pay day loan, a refund anticipation loan, a student loan, a syndicated loan, a title loan, a home loan, a venture debt loan, a loan of intellectual property, a loan of a contractual claim, a working capital loan, a small business loan, a farm loan, a municipal bond, and a subsidized loan.

An example system may include wherein, wherein at least one of the plurality of items of collateral is selected from among the list of items consisting of: a vehicle, a ship, a plane, a building, a home, a real estate property, an undeveloped land property, a farm, a crop, a municipal facility, a warehouse, a set of inventory, a commodity, a security, a currency, a token of value, a ticket, a cryptocurrency, a consumable item, an edible item, a beverage, a precious metal, an item of jewelry, a gemstone, an item of intellectual property, an intellectual property right, a contractual right, an antique, a fixture, an item of furniture, a tool, an item of machinery, and an item of personal property.

An example system may further include a blockchain service circuit to store a smart lending contract or a reference to the smart lending contract as blockchain data.

An example system may further include a reporting circuit structured to report a collateral event based on the received data, wherein the collateral event is related to a value of one of the plurality of items of collateral, a condition of one of the plurality of items of collateral, or an ownership of one of the plurality of items of collateral.

An example system may further include an automated agent circuit structured to perform a collateral-related action in response to the collateral event, wherein the collateral-related action is selected from among the actions consisting of: validating title for one of the plurality of items of collateral, recording a change in title for one of the plurality of items of collateral, assessing the value of one of the plurality of items of collateral, initiating inspection of one of the plurality of items of collateral, initiating maintenance of the one of the plurality of items of collateral, initiating security for one of the plurality of items of collateral, and modifying terms and conditions for one of the plurality of items of collateral.

In embodiments, provided herein is a method for transactional, financial and marketplace enablement. An example method may include receiving data related to at least one of a plurality of items of collateral; identifying a group of the plurality of items of collateral, wherein each member of the group share a common attribute; identifying a subset of the group as security of a set of loans; and creating a set of smart lending contracts for the set of loans.

Certain further aspects of an example method are described following, any one or more of which may be present in certain embodiments. An example method may further include determining a value for each item of collateral in the subset of the group using received data and a valuation model.

An example method may further include redefining, based on the value for each item of collateral in the subset of items of collateral, the subset of items of collateral used as security for the set of loan, of the group.

An example method may further include determining at least one of a term or a condition for at least one of the smart lending contracts based on the value for at least one of the items of collateral in the subset of the group.

An example method may further include modifying the smart lending contract to include the at least one of the term and the condition.

An example method may further include modifying the valuation model based on a first set of valuation determinations for a first set of items of collateral and a corresponding set of loan outcomes having the first set of items of collateral as security.

An example method may further include identifying a group of offset items of collateral, wherein each member of the group of offset items of collateral and the group of the plurality of items of collateral share a common attribute.

An example method may further include monitoring and reporting marketplace information for the group of offset items of collateral.

In embodiments, an example platform or system may include a data collection circuit structured to receive data related to at least one of a set of parties to a loan; a smart contract circuit structured to create a smart lending contract for the loan; and an automated agent circuit structured to automatically perform a loan-related action in response to the received data, wherein the loan-related action is a change in an interest rate for the loan, and wherein the smart contract circuit is further structured to update the smart lending contract with the changed interest rate.

Certain further aspects of an example system are described following, any one or more of which may be present in certain embodiments. An example system may include wherein the data collection circuit is further structured to receive collateral-related data related to a set of items of collateral acting as security for the loan and determine a condition of at least one of the set of items of collateral, wherein the change in the interest rate is further based on a condition of the at least one of the set of items of collateral.

An example system may include where in the received data comprises an attribute of the at least one of the set of parties to the loan, and where in the change in the interest rate is based in part on the attribute.

An example system may include wherein the smart contract circuit is further structured to: determine at least one of a term or a condition for the smart lending contract based on the attribute; and modify the smart lending contract to include the at least one of the term or the condition.

An example system may include wherein the at least one of the term or the condition is related to a loan component selected from the loan components consisting of: a loan party, a loan collateral, a loan-related event, and a loan-related activity.

An example system may include wherein the at least one of the term or the condition is selected from the list consisting of: a principal amount of the loan, a balance of the loan, a fixed interest rate, a variable interest rate description, a payment amount, a payment schedule, a balloon payment schedule, a collateral specification, a collateral substitution description, a description of a party, a guarantee description, a guarantor description, a security description, a personal guarantee, a lien, a foreclosure condition, a default condition, a consequence of default, a covenant related to any one of the foregoing, and a duration of any one of the foregoing.

An example system may include wherein the data collection circuit comprises at least one system selected from systems consisting of: an Internet of Things circuit, an image capture device, a networked monitoring circuit, an internet monitoring circuit, a mobile device, a wearable device, a user interface circuit, and an interactive crowdsourcing circuit.

An example system may include wherein the data collection circuit comprises an Internet of Things circuit structured to monitor attributes of at least one of the set of parties to the loan.

An example system may include wherein the data collection circuit comprises a wearable device associated with at least one of the set of parties, and wherein the wearable device is structured to acquire human-related data, and wherein the received data includes at least a portion of the human-related data.

An example system may include wherein the data collection circuit comprises a user interface circuit structured to receive data from at least one of the parties of the loan and provide the data from at least one of the parties of the loan as a portion of the received data.

An example system may include wherein the data collection circuit comprises an interactive crowdsourcing circuit structured to: solicit data regarding at least one of the set of parties of the loan; receive solicited data; and provide at least a subset of the solicited data as a portion of the received data.

An example system may include wherein the data collection circuit further comprises an internet monitoring circuit structured to retrieve data related to at least one of the parties of the loan from at least one publicly available information site.

An example system may include further comprising a valuation circuit structured to determine, based on the received data and a valuation model, a value for the at least one of the set of items of collateral.

An example system may include wherein the smart contract circuit is further structured to: determine at least one of a term or a condition for the smart lending contract based on the value for the at least one of the set of items of collateral; and modify the smart lending contract to include the at least one of the term or the condition.

An example system may include wherein the at least one of the term or the condition is related to a loan component selected from the loan components consisting of: a loan party, a loan collateral, a loan-related event, and a loan-related activity.

An example system may include wherein the at least one of the term or the condition is selected from the list consisting of: a principal amount of the loan, a balance of the loan, a fixed interest rate, a variable interest rate description, a payment amount, a payment schedule, a balloon payment schedule, a collateral specification, a collateral substitution description, a description of a party, a guarantee description, a guarantor description, a security description, a personal guarantee, a lien, a foreclosure condition, a default condition, a consequence of default, a covenant related to any one of the foregoing, and a duration of any one of the foregoing.

An example system may include wherein the valuation circuit comprises a valuation model improvement circuit, wherein the valuation model improvement circuit modifies the valuation model based on a first set of valuation determinations for a first set of items of collateral and a corresponding set of loan outcomes having the first set of items of collateral as security.

An example system may include wherein the valuation model improvement circuit comprises at least one system from the list of systems consisting of: a machine learning system, a model-based system, a rule-based system, a deep learning system, a neural network, a convolutional neural network, a feed forward neural network, a feedback neural network, a self-organizing map, a fuzzy logic system, a random walk system, a random forest system, a probabilistic system, a Bayesian system, a simulation system, and a hybrid system including at least two of the foregoing.

An example system may include wherein the change in the interest rate is further based on the value for the at least one of the set of items of collateral.

An example system may include further comprising a collateral classification circuit structured to identify a group of offset items of collateral, wherein each member of the group of offset items of collateral and at least one of the set of items of collateral share a common attribute.

An example system may include wherein the common attribute is selected from a list of attributes consisting of: a category of the item, an age of the item, a condition of the item, a history of the item, an ownership of the item, a caretaker of the item, a security of the item, a condition of an owner of the item, a lien on the item, a storage condition of the item, a geolocation of the item, and a jurisdictional location of the item.

An example system may include wherein the valuation circuit further comprises a market value data collection circuit structured to monitor and report marketplace information for offset items of collateral relevant to the value of the item of collateral.

An example system may include wherein the market value data collection circuit is further structured to: monitor one of pricing or financial data for the offset items of collateral in at least one public marketplace; and report the monitored one of pricing or financial data.

An example system may include wherein the item of collateral is selected from the list of items consisting of: a vehicle, a ship, a plane, a building, a home, a real estate property, an undeveloped land property, a farm, a crop, a municipal facility, a warehouse, a set of inventory, a commodity, a security, a currency, a token of value, a ticket, a cryptocurrency, a consumable item, an edible item, a beverage, a precious metal, an item of jewelry, a gemstone, an item of intellectual property, an intellectual property right, a contractual right, an antique, a fixture, an item of furniture, a tool, an item of machinery, and an item of personal property.

An example system may include wherein the loan is of a type selected from among the loan types consisting of: an auto loan, an inventory loan, a capital equipment loan, a bond for performance, a capital improvement loan, a building loan, a loan backed by an account receivable, an invoice finance arrangement, a factoring arrangement, a pay day loan, a refund anticipation loan, a student loan, a syndicated loan, a title loan, a home loan, a venture debt loan, a loan of intellectual property, a loan of a contractual claim, a working capital loan, a small business loan, a farm loan, a municipal bond, and a subsidized loan.

In embodiments, an example method may include receiving data related to at least one of a set of parties to a loan; creating a smart lending contract for the loan; performing a loan-related action in response to the received data, wherein the loan-related action is a change in an interest rate for the loan; and updating the smart lending contract with the changed interest rate.

Certain further aspects of an example method are described following, any one or more of which may be present in certain embodiments. An example method may include further comprising: receiving data related to a set of items of collateral acting as security for the loan; determining a condition of at least one of the set of items of collateral;

and performing a loan-related action in response to the condition of the at least one of the set of items of collateral, wherein the loan-related action is a change in interest rate for the loan.

An example method may include receiving data related to a set of items of collateral acting as security for the loan; determining a condition of at least one of the set of items of collateral; determining at least one of a term or a condition for the smart lending contract based on the condition of the at least one of the set of items of collateral; and modifying the smart lending contract to include the at least one of the term or the condition.

An example method may include identifying a group of offset items of collateral wherein each member of the group of offset items of collateral and at least one of the set of items of collateral share a common attribute; monitoring the group of offset items of collateral in at least one public marketplace; and reporting monitored data.

An example method may include further comprising changing, based at least in part on the monitored group of offset items of collateral, the interest rate of the loan secured by at least one of the set of items of collateral.

In embodiments, an example platform or system may include a data collection circuit structured to acquire data, from public sources of information, related to at least one party of a set of parties to a loan; a smart contract circuit structured to create a smart lending contract for the loan; and an automated agent circuit structured to automatically perform a loan-related action in response to the acquired data, wherein the loan-related action is a change in an interest rate for the loan, and wherein the smart contract circuit is further structured to update the smart lending contract with the changed interest rate.

Certain further aspects of an example system are described following, any one or more of which may be present in certain embodiments. An example system may include wherein the public sources of information include at least one information source selected from the sources consisting of: a website, a news article, a social network, and crowdsourced information.

An example system may include wherein the acquired data comprises a financial condition of the at least one party of the set of parties to the loan.

An example system may include wherein the financial condition is determined based on at least one attribute of the at least one party of the set of parties to the loan, the attribute selected from among the list of attributes consisting of: a publicly stated valuation of the party, a set of property owned by the party as indicated by public records, a valuation of a set of property owned by the party, a bankruptcy condition of the party, a foreclosure status of the party, a contractual default status of the party, a regulatory violation status of the party, a criminal status of the party, an export controls status of the party, an embargo status of the party, a tariff status of the party, a tax status of the party, a credit report of the party, a credit rating of the party, a website rating of the party, a set of customer reviews for a product of the party, a social network rating of the party, a set of credentials of the party, a set of referrals of the party, a set of testimonials for the party, a set of behavior of the party, a location of the party, a geolocation of the party, and a judicial location of the party.

An example system may include wherein the at least one party is selected from a list of parties consisting of: a primary lender, a secondary lender, a lending syndicate, a corporate lender, a government lender, a bank lender, a secured lender, bond issuer, a bond purchaser, an unsecured lender, a guarantor, a provider of security, a borrower, a debtor, an underwriter, an inspector, an assessor, an auditor, a valuation professional, a government official, and an accountant.

An example system may include wherein the data collection circuit is further structured to receive collateral-related data related to a set of items of collateral acting as security for the loan and to determine a condition of at least one of the set of items of collateral, wherein the change in the interest rate is further based on the condition of the at least one of the set of items of collateral.

An example system may include further comprising an automated agent circuit structured to identify an event relevant to the loan, based, at least in part, on the received data.

An example system may include wherein the event relevant to the loan comprises an event relevant to at least one of: a value of the loan, a condition of collateral of the loan, or an ownership of collateral of the loan.

An example system may include wherein the automated agent circuit is further structured to perform, in response to the event relevant to the loan, an action selected from the list of actions consisting of: offering the loan, accepting the loan, underwriting the loan, setting an interest rate for the loan, deferring a payment requirement, modifying an interest rate for the loan, validating title for at least one of the set of items of collateral, assessing the value of at least one of the set of items of collateral, initiating inspection of at least one of the set of items of collateral, setting or modifying terms and conditions for the loan, providing a notice to one of the parties, providing a required notice to a borrower of the loan, and foreclosing on a property subject to the loan.

An example system may include wherein the smart contract circuit is further structured to specify terms and conditions in the smart lending contract, wherein one of a term or a condition in the smart lending contract governs one of loan-related events or loan-related activities.

An example system may include wherein the terms and conditions are each selected from the list consisting of: a principal amount of debt, a balance of debt, a fixed interest rate, a variable interest rate, a payment amount, a payment schedule, a balloon payment schedule, a party, a guarantee, a guarantor, a security, a personal guarantee, a lien, a duration, a covenant, a foreclose condition, a default condition, and a consequence of default.

An example system may include wherein the loan comprises a loan type selected from the loan types consisting of: an auto loan, an inventory loan, a capital equipment loan, a bond for performance, a capital improvement loan, a building loan, a loan backed by an account receivable, an invoice finance arrangement, a factoring arrangement, a pay day loan, a refund anticipation loan, a student loan, a syndicated loan, a title loan, a home loan, a venture debt loan, a loan of intellectual property, a loan of a contractual claim, a working capital loan, a small business loan, a farm loan, a municipal bond, and a subsidized loan.

An example system may include wherein the acquired data is related to one of the set of items of collateral selected from the list consisting of: a vehicle, a ship, a plane, a building, a home, a real estate property, an undeveloped land property, a farm, a crop, a municipal facility, a warehouse, a set of inventory, a commodity, a security, a currency, a token of value, a ticket, a cryptocurrency, a consumable item, an edible item, a beverage, a precious metal, an item of jewelry, a gemstone, an item of intellectual property, an intellectual property right, a contractual right, an antique, a fixture, an item of furniture, a tool, an item of machinery, and an item of personal property.

An example system may include further comprising a valuation circuit structured to determine, based on the acquired data and a valuation model, a value for at least one of the set of items of collateral.

An example system may include wherein the smart contract circuit is further structured to: determine at least one of a term or a condition for the smart lending contract based on the value for the at least one of the set of items of collateral; and modify the smart lending contract to include the at least one of the term or the condition.

An example system may include wherein the valuation circuit comprises a valuation model improvement circuit, wherein the valuation model improvement circuit modifies the valuation model based on a first set of valuation determinations for a first set of items of collateral and a corresponding set of loan outcomes having the first set of items of collateral as security.

An example system may include wherein the valuation model improvement circuit comprises at least one system from the list of systems consisting of: a machine learning system, a model-based system, a rule-based system, a deep learning system, a neural network, a convolutional neural network, a feed forward neural network, a feedback neural network, a self-organizing map, a fuzzy logic system, a random walk system, a random forest system, a probabilistic system, a Bayesian system, a simulation system, and a hybrid system including at least two of the foregoing.

An example system may include further comprising a collateral classification circuit structured to identify a group of offset items of collateral, wherein each member of the group of offset items of collateral and at least one of the set of items of collateral share a common attribute.

An example system may include wherein the common attribute is selected from a list of attributes consisting of: a category of the item, an age of the item, a condition of the item, a history of the item, an ownership of the item, a caretaker of the item, a security of the item, a condition of an owner of the item, a lien on the item, a storage condition of the item, a geolocation of the item o, and a jurisdictional location of the item.

An example system may include wherein the valuation circuit further comprises a market value data collection circuit structured to monitor and report marketplace information for offset items of collateral relevant to the value of the item of collateral.

An example system may include wherein the market value data collection circuit is further structured to: monitor one of pricing or financial data for the offset items of collateral in at least one public marketplace; and report the monitored one of pricing or financial data.

An example system may include wherein the smart contract circuit is further structured to modify a term or condition of the loan based on the marketplace information for offset items of collateral relevant to the value of the item of collateral.

In embodiments, an example method may include acquiring data, from public sources, related to at least one of a set of parties to a loan, wherein the public sources of information are selected from the list of information sources consisting of: a website, a news article, a social network, and crowdsourced information; creating a smart lending contract; performing a loan-related action in response to the acquired data, wherein the loan-related action is a change in an interest rate for the loan; and updating the smart lending contract with the changed interest rate.

Certain further aspects of an example method are described following, any one or more of which may be present in certain embodiments. An example method may include receiving collateral-related data related to a set of items of collateral acting as security for the loan; and determining a condition of at least one of the set of items of collateral, wherein the change in the interest rate is further based on the condition of the at least one of the set of items of collateral.

An example method may include identifying an event relevant to the loan based, at least in part, on the collateral-related data; and performing, in response the event relevant to the loan, an action selected from the list of actions consisting of: offering the loan, accepting the loan, underwriting the loan, setting an interest rate for the loan, deferring a payment requirement, modifying an interest rate for the loan, validating title for at least one of the set of items of collateral, assessing a value of at least one of the set of items of collateral, initiating inspection of at least one of the set of items of collateral, setting or modifying terms and conditions for the loan, providing a notice to one of the parties, providing a required notice to a borrower of the loan, and foreclosing on a property subject to the loan.

An example method may include further comprising determining, based on at least one of the collateral-related data or the acquired data, and a valuation model, a value for at least one of the set of items of collateral.

An example method may include further comprising determining at least one of a term or a condition for the smart lending contract based on the value for the at least one of the set of items of collateral.

An example method may include further comprising modifying the smart lending contract to include the at least one of the term or the condition.

An example method may include further comprising modifying the valuation model based on a first set of valuation determinations for a first set of items of collateral and a corresponding set of loan outcomes having the first set of items of collateral as security.

An example method may include identifying a group of offset items of collateral, wherein each member of the group of offset items of collateral and at least one of the set of items of collateral share a common attribute; monitoring one of pricing data or financial data for least one of the group offset items of collateral in at least one public marketplace; reporting the monitored data for the at least one of the group offset items of collateral; and modifying a term or condition of the loan based the reported monitored data.

In embodiments, an example platform or system may include a data collection circuit structured to receive data relating to a status of a loan and data relating to a set of items of collateral acting as security for the loan; a blockchain service circuit structured to maintain a secure historical ledger of events related to the loan, the block chain circuit further structured to interpret a plurality of access control features corresponding to a plurality of parties associated with the loan; a loan evaluation circuit structured to determine a loan status based on the received data; a smart contract circuit structured to create a smart lending contract for the loan; and an automated agent circuit structured to perform a loan-action based on the loan status; wherein the blockchain service circuit is further structured to update the historical ledger of events with the loan action.

Certain further aspects of an example system are described following, any one or more of which may be present in certain embodiments. An example system may include wherein the data collection circuit is further structured to receive data related to one or more loan entities, and wherein the loan evaluation circuit is further structured to determine compliance with a covenant based on the data related to the one or more of the loan entities.

An example system may include wherein the data collection circuit further comprises at least one system for monitoring one or more of the loan entities, the system selected from the systems consisting of: an Internet of Things system, a camera system, a networked monitoring system, an internet monitoring system, a mobile device system, a wearable device system, a user interface system, and an interactive crowdsourcing system.

An example system may include wherein the interactive crowdsourcing system comprises a user interface, the user interface configured to solicit information related to one or more of the loan entities from a crowdsourcing site.

An example system may include wherein the user interface is structured to allow one or more of the loan entities to input information one or more of the loan entities.

An example system may include wherein the networked monitoring system comprises a network search circuit structured to search publicly available information sites for information related one or more of the loan entities.

An example system may include wherein the loan evaluation circuit is further structured to determine a state of performance for a condition of the loan based on the received data and a status of the one or more of the loan entities, and wherein the determination of the loan status is determined based in part on the status of the at least one or more of the loan entities and the state of performance of the condition for the loan.

An example system may include wherein the condition of the loan relates to at least one of a payment performance and a satisfaction on a covenant.

An example system may include wherein the data collection circuit further comprises a market data collection circuit structured to receive financial data regarding at least one of the plurality of parties associated with the loan.

An example system may include wherein the loan evaluation circuit is further structured to determine a financial condition of the least one of the plurality of parties associated with the loan based on the received financial data.

An example system may include wherein the at least one of the plurality of parties is selected from a list of parties consisting of: a primary lender, a secondary lender, a lending syndicate, a corporate lender, a government lender, a bank lender, a secured lender, bond issuer, a bond purchaser, an unsecured lender, a guarantor, a provider of security, a borrower, a debtor, an underwriter, an inspector, an assessor, an auditor, a valuation professional, a government official, and an accountant.

An example system may include wherein the received financial data relates to an attribute of the entity at least one of the plurality of parties selected from the list of attributes consisting of: a publicly stated valuation of the party, a set of property owned by the party as indicated by public records, a valuation of a set of property owned by the party, a bankruptcy condition of the party, a foreclosure status of the entity, a contractual default status of the entity, a regulatory violation status of the entity, a criminal status of the entity, an export controls status of the entity, an embargo status of the entity, a tariff status of the entity, a tax status of the entity, a credit report of the entity, a credit rating of the entity, a website rating of the entity, a set of customer reviews for a product of the entity, a social network rating of the entity, a set of credentials of the entity, a set of referrals of the entity, a set of testimonials for the entity, a set of behavior of the entity, a location of the entity, and a geolocation of the entity.

An example system may include further comprising a valuation circuit structured to determine, based on the received data and a valuation model, a value for at least one of the set of items of collateral.

An example system may include wherein the smart contract circuit is further structured to determine at least one of a term or a condition for the smart lending contract based on the value for the at least one of the set of items of collateral; and modify the smart lending contract to include the at least one of the term or the condition.

An example system may include wherein the terms and conditions are each selected from the list consisting of: a principal amount of debt, a balance of debt, a fixed interest rate, a variable interest rate, a payment amount, a payment schedule, a balloon payment schedule, a party, a guarantee, a guarantor, a security, a personal guarantee, a lien, a duration, a covenant, a foreclose condition, a default condition, and a consequence of default.

An example system may include wherein the valuation circuit comprises a valuation model improvement circuit, wherein the valuation model improvement circuit modifies the valuation model based on a first set of valuation determinations for a first set of items of collateral and a corresponding set of loan outcomes having the first set of items of collateral as security.

An example system may include wherein the valuation model improvement circuit comprises at least one system from the list of systems consisting of: a machine learning system, a model-based system, a rule-based system, a deep learning system, a hybrid system, a neural network, a convolutional neural network, a feed forward neural network, a feedback neural network, a self-organizing map, a fuzzy logic system, a random walk system, a random forest system, a probabilistic system, a Bayesian system, and a simulation system.

An example system may include further comprising a collateral classification circuit structured to identify a group of offset items of collateral, wherein each member of the group of offset items of collateral and at least one of the set of items of collateral share a common attribute.

An example system may include wherein the common attribute is selected from a list of attributes consisting of: a category of the item of collateral, an age of the item of collateral, a condition of the item of collateral, a history of the item of collateral, an ownership of the item of collateral, a caretaker of the item of collateral, a security of the item of collateral, a condition of an owner of the item of collateral, a lien on the item of collateral, a storage condition of the item of collateral, a geolocation of the item of collateral, and a jurisdictional location of the item of collateral.

An example system may include wherein the valuation circuit further comprises a market value data collection circuit structured to monitor and report marketplace information for offset items of collateral relevant to the value of the item of collateral.

An example system may include wherein the market value data collection circuit is further structured to monitor one of pricing or financial data for the offset items of collateral in at least one public marketplace; and report the monitored one of pricing or financial data.

An example system may include wherein the smart contract circuit is further structured to modify a term or condition of the loan based on the marketplace information for offset items of collateral relevant to the value of the item of collateral.

In embodiments, an example method may include maintaining a secure historical ledger of events related to a loan; receiving data relating to a status of the loan; receiving data related to a set of items of collateral acting as security of the loan; determining a status of the loan; performing a loan-action based on the loan status; and updating the historical ledger of events related to the loan.

Certain further aspects of an example method are described following, any one or more of which may be present in certain embodiments. An example method may include receiving data related to one or more loan entities; and determining compliance with a covenant of the loan based on the data received.

An example method may include determining a state of performance for a condition of the loan, wherein the determination of the loan status is based on part on the state of performance of the condition of the loan.

An example method may include receiving financial data related to at least one party to the loan.

An example method may include determining a financial condition of the at least one party to the loan based on the financial data.

An example method may include determining a value for at least one set of items of collateral based on the received data and a valuation model.

An example method may include determining at least one of a term or a condition for the loan based on the value of the at least one of the items of collateral; and modifying a smart lending contract to include the at least one of the term or the condition.

An example method may include identifying a group of offset items of collateral, wherein each member of the group of offset items of collateral and at least one of the set of items of collateral share a common attribute; receiving data related to the group of offset items of collateral, wherein the determination of the value for the at least one set of items of collateral is partially based on the received data related to the group of offset items of collateral.

In embodiments, provided herein is a smart contract system for managing collateral for a loan. An example platform, system, or apparatus may include a data collection circuit structured to monitor a status of a loan and of a collateral for the loan; a smart contract circuit structured to process information from the data collection circuit and automatically initiate at least one of a substitution, a removal, or an addition of one or items from the collateral for the loan based on the information and a smart lending contract in response to at least one of the status of the loan or the status of the collateral for the loan; and a blockchain service circuit structured to interpret a plurality of access control features corresponding to at least one party associated with the loan and record the at least one substitution, removal, or addition in a distributed ledger for the loan.

Certain further aspects of an example system are described following, any one or more of which may be present in certain embodiments. An example system may include wherein the data collection circuit further includes at least one system selected from the systems consisting of: an Internet of Things system, a camera system, a networked monitoring system, an internet monitoring system, a mobile device system, a wearable device system, a user interface system, and an interactive crowdsourcing system.

An example system may include wherein the loan comprises at least one loan type selected from the loan types consisting of: an auto loan, an inventory loan, a capital equipment loan, a bond for performance, a capital improvement loan, a building loan, a loan backed by an account receivable, an invoice finance arrangement, a factoring arrangement, a pay day loan, a refund anticipation loan, a student loan, a syndicated loan, a title loan, a home loan, a venture debt loan, a loan of intellectual property, a loan of a contractual claim, a working capital loan, a small business loan, a farm loan, a municipal bond, and a subsidized loan.

An example system may include wherein a status of the loan is determined based on the status of at least one of an entity related to the loan and a state of a performance of a condition for the loan.

An example system may include wherein the state of the performance of the condition relates to at least one of a payment performance or a satisfaction of a covenant for the loan.

An example system may include wherein the status of the loan is determined based on a status of at least one entity related to the loan and a state of performance of a condition for the loan; wherein the performance of the condition relates to at least one of a payment performance or a satisfaction of a covenant for the loan; and wherein the data collection circuit is further structured to determine compliance with the covenant by monitoring the at least one entity.

An example system may include wherein the at least one entity is a party to the loan, and wherein the data collection circuit is further structured to monitor a financial condition of the at least one entity.

An example system may include wherein the condition for the loan comprises a financial condition for the loan, and wherein the state of performance of the financial condition is determined based on an attribute selected from the attributes consisting of: a publicly stated valuation of the at least one entity, a property owned by the at least one entity as indicated by public records, a valuation of a property owned by the at least one entity, a bankruptcy condition of the at least one entity, a foreclosure status of the at least one entity, a contractual default status of the at least one entity, a regulatory violation status of the at least one entity, a criminal status of the at least one entity, an export controls status of the at least one entity, an embargo status of the at least one entity, a tariff status of the at least one entity, a tax status of the at least one entity, a credit report of the at least one entity, a credit rating of the at least one entity, a website rating of the at least one entity, a plurality of customer reviews for a product of the at least one entity, a social network rating of the at least one entity, a plurality of credentials of the at least one entity, a plurality of referrals of the at least one entity, a plurality of testimonials for the at least one entity, a behavior of the at least one entity, a location of the at least one entity, a geolocation of the at least one entity, and a relevant jurisdiction for the at least one entity.

An example system may include wherein the party to the loan comprises at least one party selected from the parties consisting of: a primary lender, a secondary lender, a lending syndicate, a corporate lender, a government lender, a bank lender, a secured lender, bond issuer, a bond purchaser, an unsecured lender, a guarantor, a provider of security, a borrower, a debtor, an underwriter, an inspector, an assessor, an auditor, a valuation professional, a government official, and an accountant.

An example system may include wherein the data monitoring circuit is further structured to monitor the status of the collateral of the loan based on at least one attribute of the collateral selected from the attributes consisting of: a category of the collateral, an age of the collateral, a condition of the collateral, a history of the collateral, a storage condition of the collateral, and a geolocation of the collateral.

An example system may include wherein the collateral comprises at least one item selected from the items consisting of: a vehicle, a ship, a plane, a building, a home, real estate property, undeveloped land, a farm, a crop, a municipal facility, a warehouse, a set of inventory, a commodity, a security, a currency, a token of value, a ticket, a cryptocurrency, a consumable item, an edible item, a beverage, a precious metal, an item of jewelry, a gemstone, an item of intellectual property, an intellectual property right, a contractual right, an antique, a fixture, an item of furniture, an item of equipment, a tool, an item of machinery, and an item of personal property.

An example system may further include a valuation circuit structured use a valuation model to determine a value for the collateral based on the status of the collateral for the loan.

An example system may include wherein the smart contract circuit is further structured to initiate the at least one substitution, removal, or addition of one or more items from the collateral for the loan to maintain a value of the collateral within a predetermined range.

An example system may include wherein the valuation circuit further comprises a transactions outcome processing circuit structured to interpret outcome data relating to a transaction in collateral and iteratively improve the valuation model in response to the outcome data.

An example system may include wherein the valuation circuit further comprises a market value data collection circuit structured to monitor and report on marketplace information relevant to a value of the collateral.

An example system may include wherein the market value data collection circuit is further structured to monitor at least one of pricing data or financial data for an offset collateral item in at least one public marketplace.

An example system may include wherein the market value data collection circuit is further structured to construct a set of offset collateral items for valuing the item of collateral using a clustering circuit based on an attribute of the collateral.

An example system may include wherein the attribute comprises at least one attribute selected from among: a category of the collateral, an age of the collateral, a condition of the collateral, a history of the collateral, a storage condition of the collateral, and a geolocation of the collateral.

An example system may include wherein the smart lending contract comprises terms and conditions for the loan, wherein each of the terms and conditions comprise at least one member selected from the group consisting of: a principal amount of debt, a balance of debt, a fixed interest rate, a variable interest rate, a payment amount, a payment schedule, a balloon payment schedule, a specification of collateral, a specification of substitutability of collateral, a party, a guarantee, a guarantor, a security, a personal guarantee, a lien, a duration, a covenant, a foreclose condition, a default condition, and a consequence of default.

An example system may include wherein the smart contract circuit further comprises a loan management circuit structured to specify terms and conditions of the smart lending contract that governs at least one of: terms and conditions of the loan, a loan-related event, or a loan-related activity.

In embodiments, provided herein is a smart contract method for managing collateral for a loan. An example method may include monitoring a status of a loan and of a collateral for the loan; processing information from the monitoring and automatically initiating at least one of a substitution, a removal, or an addition of one or more items from the collateral for the loan based on the at least one of the status of the loan or the collateral for the loan; and interpreting a plurality of access control features corresponding to at least one party associated with the loan and recording the at least one substitution, removal, or addition in a distributed ledger for the loan.

Certain further aspects of an example method are described following, any one or more of which may be present in certain embodiments.

An example method may include wherein the status of the loan is determined based on a status of at least one of an entity related to the loan or a state of a performance of a condition for the loan.

An example method may include determining a value with a valuation model for a set of collateral based on at least one of the status of the loan or the collateral for the loan.

An example method may include wherein the at least one substitution, removal, or addition is initiated to maintain a value of the collateral within a predetermined range.

An example method may include interpreting outcome data relating to a transaction of one of the collateral or an offset collateral and iteratively improving the valuation model in response to the outcome data.

An example method may include monitoring and reporting on marketplace information relevant to a value of the collateral.

An example method may include monitoring at least one of pricing data or financial data for an offset collateral item in at least one public marketplace.

An example method may include specifying terms and conditions of a smart contract that governs at least one of terms and conditions for the loan, a loan-related event, or a loan-related activity.

An example apparatus may include a data collection circuit structured to monitor at least one of a status of a loan or a status of a collateral for the loan; a smart contract circuit structured interpret a smart contract for the loan, and to adjust at least one term or condition of the smart contract for the loan in response to the at least one of the status of the loan or the status of the collateral for the loan; and a blockchain service circuit structured to interpret a plurality of access control features corresponding to a plurality of parties associated with the loan and record the adjusted at least one term or condition of the smart contract for the loan in a distributed ledger for the loan. The data collection circuit may monitor the status of the collateral for the loan, the apparatus further including a valuation circuit structured use a valuation model to determine a value for the collateral based on the status of the collateral for the loan, and wherein the smart contract circuit is further structured to adjust at least one term or condition of the smart contract for the loan in response to the value for the collateral.

In embodiments, provided herein is a crowdsourcing system for validating conditions of collateral for a loan. An example platform, system, or apparatus may include a crowdsourcing request circuit structured to configure at least one parameter of a crowdsourcing request related to obtaining information on a condition of a collateral for a loan; a crowdsourcing publishing circuit configured to publish the crowdsourcing request to a group of information suppliers; and a crowdsourcing communications circuit structured to collect and process at least one response from the group of information suppliers, and to provide a reward to at least one of the group of information suppliers in response to a successful information supply event. A successful information supply event may be the receipt of information identified to relate to a collateral that is the subject of the crowdsourcing request and wherein the information relates to a condition of the collateral. Information regarding identifying features of the collateral, such as a serial number or a model number, may not be a successful information supply event.

Certain further aspects of an example system are described following, any one or more of which may be present in certain embodiments. An example system may include wherein the crowdsourcing publishing circuit is further configured to publish a reward description to at least a portion of the group of information suppliers in response to the successful information supply event. The reward description may include a kind or type of reward, a value of the reward, an amount of the reward, information regarding valid dates of use of the reward or information for using the reward, and the like.

An example system may include wherein the crowdsourcing communications circuit further includes or is in communication with a smart contract circuit structured to manage the reward by determining the successful information supply event in response to the at least one parameter configured for the crowdsourcing request, and to automatically allocate the reward to the at least one of the group of information suppliers in response to the successful information supply event.

An example system may include wherein the loan comprises at least one loan type selected from the loan types consisting of: an auto loan, an inventory loan, a capital equipment loan, a bond for performance, a capital improvement loan, a building loan, a loan backed by an account receivable, an invoice finance arrangement, a factoring arrangement, a pay day loan, a refund anticipation loan, a student loan, a syndicated loan, a title loan, a home loan, a venture debt loan, a loan of intellectual property, a loan of a contractual claim, a working capital loan, a small business loan, a farm loan, a municipal bond, and a subsidized loan.

An example system may include wherein the collateral comprises at least one item selected from the items consisting of: a vehicle, a ship, a plane, a building, a home, real estate property, undeveloped land, a farm, a crop, a municipal facility, a warehouse, a set of inventory, a commodity, a security, a currency, a token of value, a ticket, a cryptocurrency, a consumable item, an edible item, a beverage, a precious metal, an item of jewelry, a gemstone, an item of intellectual property, an intellectual property right, a contractual right, an antique, a fixture, an item of furniture, an item of equipment, a tool, an item of machinery, and an item of personal property.

An example system may include wherein the condition of collateral is determined based on an attribute selected from the attributes consisting of: a quality of the collateral, a condition of the collateral, a status of a title to the collateral, a status of a possession of the collateral, and a status of a lien on the collateral.

An example system may include wherein the condition of the collateral, wherein the collateral is an item, is determined based on an attribute selected from the attributes consisting of: a new or used status of the item, a type of the item, a category of the item, a specification of the item, a product feature set of the item, a model of the item, a brand of the item, a manufacturer of the item, a status of the item, a context of the item, a state of the item, a value of the item, a storage location of the item, a geolocation of the item, an age of the item, a maintenance history of the item, a usage history of the item, an accident history of the item, a fault history of the item, an ownership of the item, an ownership history of the item, a price of a type of the item, a value of a type of the item, an assessment of the item, and a valuation of the item.

An example system may further include a blockchain service circuit structured to record identifying information and the at least one parameter of the crowdsourcing request, the at least one response to the crowdsourcing request, and a reward description in a distributed ledger for the crowdsourcing request.

An example system may include wherein the crowdsourcing request circuit is further structured to enable a workflow by which a human user enters the at least one parameter to establish the crowdsourcing request.

An example system may include wherein the at least one parameter comprises a type of requested information, a reward description, and a condition for receiving the reward.

An example system may include wherein the reward is selected from selected from the rewards consisting of: a financial reward, a token, a ticket, a contractual right, a cryptocurrency amount, a plurality of reward points, a currency amount, a discount on a product or service, and an access right.

An example system may further include a smart contract circuit structured to process the at least one response and, in response, automatically undertake an action related to the loan.

An example system may include wherein the action is at least one of a foreclosure action, a lien administration action, an interest-rate setting action, a default initiation action, a substitution of collateral, or a calling of the loan.

An example system may further include a robotic process automation circuit structured to, based on training on a training data set comprising human user interactions with at least one of the crowdsourcing request circuit or the crowdsourcing communications circuit, configure the crowdsourcing request based on at least one attribute of the loan.

An example system may include wherein the at least one attribute of the loan is obtained from a smart contract circuit that manages the loan.

An example system may include wherein the training data set further comprises outcomes from a plurality of crowdsourcing requests.

An example system may include wherein the robotic process automation circuit is further structured to determine the reward.

An example system may include wherein the robotic process automation circuit is further structured to determine at least one domain to which the crowdsourcing publishing circuit publishes the crowdsourcing request.

In embodiments, provided herein is a crowdsourcing method for validating conditions of collateral for a loan. An example method may include configuring at least one parameter of a crowdsourcing request related to obtaining information on a condition of a collateral for a loan; publishing the crowdsourcing request to a group of information suppliers; collecting and processing at least one response to the crowdsourcing request; and providing a reward in response to a successful information supply event.

Certain further aspects of an example method are described following, any one or more of which may be present in certain embodiments.

An example method may further include publishing a reward description to at least a portion of the group of information suppliers in response to the successful information supply event.

An example method may further include wherein the reward is automatically allocated to at least one of the group of information suppliers in response to the successful information supply event.

An example method may further include recording identifying information and the at least one parameter of the crowdsourcing request, the at least one response to the crowdsourcing request, and a reward description, in a distributed ledger for the crowdsourcing request.

An example method may further include configuring a graphical user interface to enable a workflow by which a human user enters the at least one parameter to establish the crowdsourcing request.

An example method may further include automatically undertaking an action related to the loan in response to the successful information supply event.

An example method may further include training a robotic process automation circuit on a training data set comprising a plurality of outcomes corresponding to a plurality of the crowdsourcing requests, and operating the robotic process automation circuit to iteratively improve the crowdsourcing request.

An example method may further include providing at least one attribute of the loan to the robotic process automation circuit to configure the crowdsourcing request.

An example method may further include configuring the crowdsourcing request comprises determining the reward.

An example method may further include inputting at least one attribute of the loan to the robotic process automation circuit to determine at least one domain to which to publish the crowdsourcing request.

An example apparatus may include a crowdsourcing request circuit structured to provide an interface to enable configuration of at least one parameter of a crowdsourcing request related to obtaining information on a condition of a collateral for a loan; a crowdsourcing publishing circuit configured to publish the crowdsourcing request to a group of information suppliers in response to the crowdsourcing request; and a crowdsourcing communications circuit structured to provide an interface to collect at least one response to the crowdsourcing request from members of the group of information suppliers, and to provide a reward to at least one of the group of information suppliers in response to a successful information supply event.

The apparatus may further include a smart contract circuit structured to manage the reward by determining the successful information supply event in response to the at least one parameter configured for the crowdsourcing request, and to automatically allocate the reward to the at least one of the group of information suppliers in response to the successful information supply event.

In embodiments, provided herein is a crowdsourcing system for validating conditions of a guarantor for a loan. An example platform, system, or apparatus may include a crowdsourcing request circuit structured to configure at least one parameter of a crowdsourcing request related to obtaining information on a condition of a guarantor for a loan; a crowdsourcing publishing circuit configured to publish the crowdsourcing request to a group of information suppliers; and a crowdsourcing communications circuit structured to collect and process at least one response from the group of information suppliers, and to provide a reward to at least one of the group of information suppliers in response to a successful information supply event.

Certain further aspects of an example system are described following, any one or more of which may be present in certain embodiments. An example system may include wherein the condition is a financial condition of an entity that is the guarantor for the loan. An example system may include wherein the financial condition is determined at least in part based on information about the entity selected from the information consisting of: a publicly stated valuation of the entity, a property owned by the entity as indicated by a public record, a valuation of a property owned by the entity, a bankruptcy condition of the entity, a foreclosure status of the entity, a contractual default status of the entity, a regulatory violation status of the entity, a criminal status of the entity, an export controls status of the entity, an embargo status of the entity, a tariff status of the entity, a tax status of the entity, a credit report of the entity, a credit rating of the entity, a web site rating of the entity, a plurality of customer reviews for a product of the entity, a social network rating of the entity, a plurality of credentials of the entity, a plurality of referrals of the entity, a plurality of testimonials for the entity, a plurality of behaviors of the entity, a location of the entity, a geolocation of the entity, and a jurisdiction of the entity.

The crowdsourcing communications circuit may further include a smart contract circuit structured to manage the reward by determining the successful information supply event in response to the at least one parameter configured for the crowdsourcing request, and to automatically allocate the reward to the at least one of the group of information suppliers in response to the successful information supply event.

An example system may include wherein the loan comprises at least one loan type selected from the loan types consisting of: an auto loan, an inventory loan, a capital equipment loan, a bond for performance, a capital improvement loan, a building loan, a loan backed by an account receivable, an invoice finance arrangement, a factoring arrangement, a pay day loan, a refund anticipation loan, a student loan, a syndicated loan, a title loan, a home loan, a venture debt loan, a loan of intellectual property, a loan of a contractual claim, a working capital loan, a small business loan, a farm loan, a municipal bond, and a subsidized loan.

An example system may include wherein the crowdsourcing request circuit is further structured to configure at least one further parameter of the crowdsourcing request to obtain information on a condition of a collateral for the loan.

An example system may include wherein the collateral comprises at least one item selected from the items consisting of: a vehicle, a ship, a plane, a building, a home, real estate property, undeveloped land, a farm, a crop, a municipal facility, a warehouse, a set of inventory, a commodity, a security, a currency, a token of value, a ticket, a cryptocurrency, a consumable item, an edible item, a beverage, a precious metal, an item of jewelry, a gemstone, an item of intellectual property, an intellectual property right, a contractual right, an antique, a fixture, an item of furniture, an item of equipment, a tool, an item of machinery, and an item of personal property.

An example system may include wherein the condition of the collateral, wherein the collateral is an item, and wherein the condition of the collateral is determined based on an attribute selected from the attributes consisting of: a new or used status of the item, a type of the item, a category of the item, a specification of the item, a product feature set of the item, a model of the item, a brand of the item, a manufacturer of the item, a status of the item, a context of the item, a state of the item, a value of the item, a storage location of the item, a geolocation of the item, an age of the item, a maintenance history of the item, a usage history of the item, an accident history of the item, a fault history of the item, an ownership of the item, an ownership history of the item, a price of a type of the item, a value of a type of the item, an assessment of the item, and a valuation of the item.

An example system may further include a blockchain service circuit structured to record identifying information and the at least one parameter of the crowdsourcing request, the at least one response to the crowdsourcing request, and a reward description in a distributed ledger for the crowdsourcing request.

An example system may include wherein the crowdsourcing request circuit is further structured to enable a workflow by which a human user enters the at least one parameter to establish the crowdsourcing request.

An example system may include wherein the at least one parameter comprises a type of requested information, a reward description, and a condition for receiving the reward.

An example system may include wherein the reward is selected from selected from the rewards consisting of: a financial reward, a token, a ticket, a contractual right, a cryptocurrency amount, a plurality of reward points, a currency amount, a discount on a product or service, and an access right.

An example system may further include a smart contract circuit structured to process the at least one response and, in response, automatically undertake an action related to the loan.

An example system may include a smart contract circuit structured to process the at least one response and, in response, automatically undertake an action related to the loan, wherein the action is at least one of a foreclosure action, a lien administration action, an interest-rate setting action, a default initiation action, a substitution of collateral, and a calling of the loan.

An example system may further include a robotic process automation circuit structured to, based on training on a training data set comprising human user interactions with at least one of the crowdsourcing request circuit or the crowdsourcing communications circuit, to configure a crowdsourcing request based on at least one attribute of a loan.

An example system may include wherein the at least one attribute of the loan is obtained from a smart contract circuit that manages the loan An example system may include wherein the training data set further comprises outcomes from a plurality of crowdsourcing requests.

An example system may include wherein the robotic process automation circuit is further structured to determine a reward.

An example system may include wherein the robotic process automation circuit is further structured to determine at least one domain to which the crowdsourcing publishing circuit publishes the crowdsourcing request.

In embodiments, provided herein is a crowdsourcing method for validating conditions of collateral for a loan. An example method may include configuring at least one parameter of a crowdsourcing request related to obtaining information on a condition of a guarantor for a loan; publishing the crowdsourcing request to a group of information suppliers; collecting and processing at least one response to the crowdsourcing request; and providing a reward to at least one supplier of the group of information suppliers in response to a successful information supply event.

Certain further aspects of an example method are described following, any one or more of which may be present in certain embodiments. An example method may further include publishing a reward description to at least a portion of the group of information suppliers in response to the successful information supply event.

An example method may further include wherein the reward is automatically allocated to at least one of the group of information suppliers in response to the successful information supply event.

An example method may further include recording identifying information and the at least one parameter of the crowdsourcing request, the at least one response to the crowdsourcing request, and a reward description, in a distributed ledger for the crowdsourcing request.

An example method may further include configuring a graphical user interface to enable a workflow by which a human user enters the at least one parameter to establish the crowdsourcing request.

An example method may further include automatically undertaking an action related to the loan in response to the successful information supply event.

An example method may further include training a robotic process automation circuit on a training data set comprising a plurality of outcomes corresponding to a plurality of the crowdsourcing requests, and operating the robotic process automation circuit to iteratively improve the crowdsourcing request.

An example method may further include providing at least one attribute of the loan to the robotic process automation circuit in order to configure the crowdsourcing request.

An example method may further include configuring the crowdsourcing request comprises determining the reward.

An example method may further include inputting at least one attribute of the loan to the robotic process automation circuit to determine at least one domain to which to publish the crowdsourcing request.

In embodiments, provided herein is a smart contract system for modifying a loan having a set of computational services. An example platform, system, or apparatus may include a data collection circuit structured to determine location information corresponding to each one of a plurality of entities involved in a loan; a jurisdiction definition circuit structured to determine a jurisdiction for at least one of the plurality of entities in response to the location information; and a smart contract circuit structured to automatically undertake a loan-related action for the loan based at least in part on the jurisdiction for at least one of the plurality of entities.

Certain further aspects of an example system are described following, any one or more of which may be present in certain embodiments. An example system may include wherein the smart contract circuit is further structured to automatically undertake the loan-related action in response to a first one of the plurality of entities being in a first jurisdiction, and a second one of the plurality of entities being in a second jurisdiction.

An example system may include wherein the smart contract circuit is further structured to automatically undertake the loan-related action in response to one of the plurality of entities moving from a first jurisdiction to a second jurisdiction.

An example system may include wherein the loan-related action comprises at least one loan-related action selected from the loan-related actions consisting of: offering the loan, accepting the loan, underwriting the loan, setting an interest rate for the loan, deferring a payment requirement, modifying an interest rate for the loan, validating title for collateral, recording a change in title, assessing a value of collateral, initiating inspection of collateral, calling the loan, closing the loan, setting terms and conditions for the loan, providing notices required to be provided to a borrower, foreclosing on property subject to the loan, and modifying terms and conditions for the loan.

An example system may include wherein the smart contract circuit is further structured to process a plurality of jurisdiction-specific regulatory notice requirements and to provide an appropriate notice to a borrower based on a jurisdiction corresponding to at least one entity selected from the entities consisting of: a lender, a borrower, funds provided via the loan, a repayment of the loan, or a collateral for the loan.

An example system may include wherein the smart contract circuit is further structured to process a plurality of jurisdiction-specific regulatory foreclosure requirements and to provide an appropriate foreclosure notice to a borrower based on a jurisdiction corresponding to at least one entity selected from the entities consisting of: a lender, a borrower, funds provided via the loan, a repayment of the loan, or a collateral for the loan.

An example system may include wherein the smart contract circuit is further structured to process a plurality of jurisdiction-specific rules for setting terms and conditions of the loan and to configure a smart contract based on a jurisdiction corresponding to at least one entity selected from the entities consisting of: a borrower, funds provided via the loan, a repayment of the loan, and a collateral for the loan.

An example system may include wherein the smart contract circuit is further structured to determine an interest rate for the loan to cause the loan to comply with a maximum interest rate limitation applicable in a jurisdiction corresponding to a selected one of the plurality of entities.

An example system may include wherein the data collection circuit is further structured to monitor a condition of a collateral for the loan, and wherein the smart contract circuit is further structured to determine the interest rate for the loan in response to the condition of the collateral for the loan.

An example system may include wherein the data collection circuit is further structured to monitor an attribute of at least one of the plurality of entities that are party to the loan, and wherein the smart contract circuit is further structured to determine the interest rate for the loan in response to the attribute.

An example system may include wherein the smart contract circuit further comprises a loan management circuit for specifying terms and conditions of smart contracts that govern at least one of loan terms and conditions, loan-related events, or loan-related activities.

An example system may include wherein the loan comprises at least one loan type selected from the loan types consisting of: an auto loan, an inventory loan, a capital equipment loan, a bond for performance, a capital improvement loan, a building loan, a loan backed by an account receivable, an invoice finance arrangement, a factoring management, a pay day loan, a refund anticipation loan, a student loan, a syndicated loan, a title loan, a home loan, a venture debt loan, a loan of intellectual property, a loan of a contractual claim, a working capital loan, a small business loan, a farm loan, a municipal bond, and a subsidized loan.

An example system may include wherein a terms and conditions for the loan each comprise at least one member selected from the group consisting of: a principal amount of debt, a balance of debt, a fixed interest rate, a variable interest rate, a payment amount, a payment schedule, a balloon payment schedule, a specification of collateral, a specification of substitutability of collateral, a party, a guarantee, a guarantor, a security, a personal guarantee, a lien, a duration, a covenant, a foreclose condition, a default condition, and a consequence of default.

An example system may include wherein the data collection circuit further comprises at least one system selected from the systems consisting of: an Internet of Things system, a camera system, a networked monitoring system, an internet monitoring system, a mobile device system, a wearable device system, a user interface system, and an interactive crowdsourcing system.

An example system may include a valuation circuit is structured to use a valuation model to determine a value for a collateral for the loan based on the jurisdiction corresponding to at least one of the plurality of entities.

An example system may include wherein the valuation model is a jurisdiction-specific valuation model, and wherein the jurisdiction corresponding to at least one of the plurality of entities comprises a jurisdiction corresponding to at least one entity selected from the entities consisting of: a lender, a borrower, funds provided pursuant to the loan, a delivery location of funds provided pursuant to the loan, a payment of the loan, and a collateral for the loan.

An example system may include wherein at least one of the terms and conditions for the loan is based on the value of the collateral for the loan.

An example system may include wherein the collateral comprises at least one item selected from the items consisting of: a vehicle, a ship, a plane, a building, a home, real estate property, undeveloped land, a farm, a crop, a municipal facility, a warehouse, a set of inventory, a commodity, a security, a currency, a token of value, a ticket, a cryptocurrency, a consumable item, an edible item, a beverage, a precious metal, an item of jewelry, a gemstone, an item of intellectual property, an intellectual property right, a contractual right, an antique, a fixture, an item of furniture, an item of equipment, a tool, an item of machinery, and an item of personal property.

An example system may include wherein the valuation circuit further comprises a transactions outcome processing circuit structured to interpret outcome data relating to a transaction in collateral and iteratively improve the valuation model in response to the outcome data.

An example system may include wherein the valuation circuit further comprises a market value data collection circuit structured to monitor and report on marketplace information relevant to the value of the collateral.

An example system may include wherein the market value data collection circuit monitors pricing data or financial data for an offset collateral item in at least one public marketplace.

An example system may include wherein the clustering circuit constructs a set of offset collateral items for valuing an item of collateral based on an attribute of the collateral.

An example system may include wherein the attribute is selected from among: a category of the collateral, an age of the collateral, a condition of the collateral, a history of the collateral, a storage condition of the collateral, and a geo-location of the collateral.

In embodiments, provided herein is a smart contract method for modifying a loan having a set of computational services. An example method may include monitoring location information corresponding to each one of a plurality of entities involved in a loan; determining a jurisdiction for at least one of the plurality of entities in response to the location information; and automatically undertaking a loan-related action for the loan based at least in part on the jurisdiction for at least one of the plurality of entities.

Certain further aspects of an example method are described following, any one or more of which may be present in certain embodiments. An example method may include automatically undertaking the loan-related action in response to a first one of the plurality of entities being in a first jurisdiction, and a second one of the plurality of entities being in a second jurisdiction.

An example method may include automatically undertaking the loan-related action in response to one of the plurality of entities moving from a first jurisdiction to a second jurisdiction.

An example method may include processing a plurality of jurisdiction-specific requirements based on a jurisdiction of a relevant one of the plurality of entities, and performing at least one operation selected from the operations consisting of: providing an appropriate notice to a borrower in response to the plurality of jurisdiction-specific requirements comprising regulatory notice requirements; setting specific rules for setting terms and conditions of the loan in response to the plurality of jurisdiction-specific requirements comprising jurisdiction-specific rules for terms and conditions of the loan; determining an interest rate for the loan to cause the loan to comply with a maximum interest rate limitation in response to the plurality of jurisdiction-specific requirements comprising a maximum interest rate limitation; and wherein the relevant one of the plurality of entities comprises at least one entity selected from the entities consisting of: a lender, a borrower, funds provided pursuant to the loan, a repayment of the loan, and a collateral for the loan.

An example method may include monitoring at least one of a condition of a plurality of collateral for the loan or an attribute of at least one of the plurality of entities that are party to the loan, wherein the condition or the attribute is used to determine an interest rate.

An example method may include operating a valuation model to determine a value for a collateral for the loan based on the jurisdiction for at least one of the plurality of entities.

An example method may include interpreting outcome data relating to a transaction in collateral and iteratively improving the valuation model in response to the outcome data.

In embodiments, provided herein is a smart contract system for modifying a loan. An example platform, system, or apparatus may include a data collection circuit structured to monitor and collect information about at least one entity involved in a loan; and a smart contract circuit structured to automatically restructure a debt related to the loan based on the monitored and collected information about the at least one entity involved in the loan.

Certain further aspects of an example system are described following, any one or more of which may be present in certain embodiments. An example system may include wherein the monitored and collected information comprises a condition of a collateral for the loan.

An example system may include wherein the smart contract circuit may be further structured to determine the occurrence of an event based on a covenant of the loan and the monitored and collected information about the at least one entity involved in the loan, and to automatically restructure the debt in response to the occurrence of the event.

An example system may include wherein the event is a failure of collateral for the loan to exceed a required fractional value of a remaining balance of the loan.

An example system may include wherein the event is a default of a buyer with respect to the covenant.

An example system may include wherein the monitored and collected information comprises an attribute of the at least one entity involved in the loan.

An example system may include wherein the smart contract circuit further comprises a loan management circuit structured to specify terms and conditions of a smart contract that governs at least one of loan terms and conditions, a loan-related event or a loan-related activity.

An example system may include wherein the loan comprises at least one loan type selected from the loan types consisting of: an auto loan, an inventory loan, a capital equipment loan, a bond for performance, a capital improvement loan, a building loan, a loan backed by an account receivable, an invoice finance arrangement, a factoring arrangement, a pay day loan, a refund anticipation loan, a student loan, a syndicated loan, a title loan, a home loan, a venture debt loan, a loan of intellectual property, a loan of a contractual claim, a working capital loan, a small business loan, a farm loan, a municipal bond, and a subsidized loan.

An example system may include wherein a terms and conditions for the loan each comprise at least one member selected from the group consisting of: a principal amount of debt, a balance of debt, a fixed interest rate, a variable interest rate, a payment amount, a payment schedule, a balloon payment schedule, a specification of collateral, a specification of substitutability of collateral, a party, a guarantee, a guarantor, a security, a personal guarantee, a lien, a duration, a covenant, a foreclose condition, a default condition, and a consequence of default.

An example system may include wherein the data collection circuit further comprises at least one system selected from the systems consisting of: an Internet of Things system, a camera system, a networked monitoring system, an internet monitoring system, a mobile device system, a wearable device system, a user interface system, and an interactive crowdsourcing system.

An example system may further include a valuation circuit structured to use a valuation model to determine a value for a collateral based on monitored and collected information about the at least one entity involved in the loan.

An example system may include wherein the restructuring of the debt is based on a valuation of the collateral for the loan that is monitored by the data collection circuit.

An example system may include wherein the collateral comprises at least one item selected from the items consisting of: a vehicle, a ship, a plane, a building, a home, real estate property, undeveloped land, a farm, a crop, a municipal facility, a warehouse, a set of inventory, a commodity, a security, a currency, a token of value, a ticket, a cryptocurrency, a consumable item, an edible item, a beverage, a precious metal, an item of jewelry, a gemstone, an item of intellectual property, an intellectual property right, a contractual right, an antique, a fixture, an item of furniture, an item of equipment, a tool, an item of machinery, and an item of personal property.

An example system may include wherein the valuation circuit further comprises a transactions outcome processing circuit structured to interpret outcome data relating to a transaction in collateral and to iteratively improve the valuation model in response to the outcome data.

An example system may include wherein the valuation circuit further comprises a market value data collection circuit structured to monitor and report on marketplace information relevant to a value of collateral.

An example system may include wherein the market value data collection circuit monitors pricing or financial data for an offset collateral item in at least one public marketplace.

An example system may include wherein a set of offset collateral items for valuing an item of collateral is constructed using a clustering circuit based on an attribute of the collateral.

An example system may include wherein the attribute is selected from among a category of the collateral, an age of the collateral, a condition of the collateral, a history of the collateral, a storage condition of the collateral, and a geo-location of the collateral.

In embodiments, provided herein is a smart contract method for modifying a loan. An example method may include monitoring and collecting information about at least one entity involved in a loan; and automatically restructuring a debt related to the loan based on the monitored and collected information about the at least one entity.

Certain further aspects of an example method are described following, any one or more of which may be present in certain embodiments.

An example method may include determining the occurrence of an event based on a covenant of the loan and the monitored and collected information about the at least one entity involved in the loan, and automatically restructuring the debt in response to the occurrence of the event.

An example method may include specifying terms and conditions of a smart contract that governs at least one of loan terms and conditions, a loan-related event, or a loan-related activity.

An example method may include operating a valuation model to determine a value for a collateral based on the monitored and collected information about the at least one entity involved in the loan.

An example method may further include interpreting outcome data relating to a transaction in collateral and iteratively improving the valuation model in response to the outcome data.

An example method may further include monitoring and reporting on marketplace information relevant to the value for the collateral.

An example method may further include monitoring pricing or financial data for an offset collateral item in at least one public marketplace.

An example method may further include constructing a set of offset collateral items for valuing the collateral using a similarity clustering algorithm based on an attribute of the collateral.

An apparatus may include a data collection circuit structured to monitor and collect information about at least one of a borrower or a collateral for the loan; and a smart contract circuit structured to automatically restructure a debt related to the loan based on the monitored and collected information about the at least one of the borrower or the collateral for the loan.

The data collection circuit may be structured to monitor and collect information about the collateral for the loan, and wherein the monitored and collected information comprises a condition of the collateral for the loan.

The apparatus may further include a valuation circuit structured to and use a valuation model to determine a value for the collateral for the loan based at least in part on the condition of the collateral for the loan.

The valuation circuit may further include a transactions outcome processing circuit structured to interpret outcome data relating to a transaction in collateral and iteratively improve the valuation model in response to the outcome data.

In embodiments, provided herein is a social network monitoring system for validating conditions of a guarantee for a loan. An example platform, system, or apparatus may include a social networking input circuit structured to interpret a loan guarantee parameter; a social network data collection circuit structured to collect data using a plurality of algorithms that are configured to monitor social network information about an entity involved in a loan in response to the loan guarantee parameter; and a guarantee validation circuit structured to validate a guarantee for the loan in response to the monitored social network information.

Certain further aspects of an example system are described following, any one or more of which may be present in certain embodiments. An example system may include wherein the loan guarantee parameter comprises a financial condition of the entity, wherein the entity is a guarantor for the loan.

An example system may include wherein the guarantee validation circuit is further structured to determine the financial condition based on at least one attribute selected from the attributes consisting of: a publicly stated valuation of the entity, a property owned by the entity as indicated by public records, a valuation of a property owned by the entity, a bankruptcy condition of the entity, a foreclosure status of the entity, a contractual default status of the entity, a regulatory violation status of the entity, a criminal status of the entity, an export controls status of the entity, an embargo status of the entity, a tariff status of the entity, a tax status of the entity, a credit report of the entity, a credit rating of the entity, a web site rating of the entity, a plurality of customer reviews for a product of the entity, a social network rating of the entity, a plurality of credentials of the entity, a plurality of referrals of the entity, a plurality of testimonials for the entity, a plurality of behaviors of the entity, a location of the entity, a jurisdiction of the entity, and a geolocation of the entity.

An example system may include wherein the loan comprises at least one loan type selected from the loan types consisting of: an auto loan, an inventory loan, a capital equipment loan, a bond for performance, a capital improvement loan, a building loan, a loan backed by an account receivable, an invoice finance arrangement, a factoring arrangement, a pay day loan, a refund anticipation loan, a student loan, a syndicated loan, a title loan, a home loan, a venture debt loan, a loan of intellectual property, a loan of a contractual claim, a working capital loan, a small business loan, a farm loan, a municipal bond, and a subsidized loan.

An example system may include a data collection circuit structured to obtain information about a condition of a collateral for the loan, wherein the collateral comprises at least one item selected from the items consisting of: a vehicle, a ship, a plane, a building, a home, real estate property, undeveloped land, a farm, a crop, a municipal facility, a warehouse, a set of inventory, a commodity, a security, a currency, a token of value, a ticket, a cryptocurrency, a consumable item, an edible item, a beverage, a precious metal, an item of jewelry, a gemstone, an item of intellectual property, an intellectual property right, a contractual right, an antique, a fixture, an item of furniture, an item of equipment, a tool, an item of machinery, and an item of personal property; and wherein the guarantee validation circuit is further structured to validate the guarantee of the loan in response to the condition of the collateral for the loan.

An example system may include wherein the condition of the collateral comprises a condition attribute selected from the group consisting of: a quality of the collateral, a status of title to the collateral, a status of possession of the collateral, a status of a lien on the collateral, a new or used status, a type, a category, a specification, a product feature set, a model, a brand, a manufacturer, a status, a context, a state, a value, a storage location, a geolocation, an age, a maintenance history, a usage history, an accident history, a fault history, an ownership, an ownership history, a price, an assessment, and a valuation.

An example system may include wherein the social networking input circuit is further structured to enable a workflow by which a human user enters the loan guarantee parameter to establish a social network data collection and monitoring request.

An example system may include a smart contract circuit structured to automatically undertake an action related to the loan in response to the validation of the loan.

An example system may include wherein the action related to the loan is in response to the loan guarantee not being validated, and wherein the action comprises at least one action selected from the actions consisting of: a foreclosure action, a lien administration action, an interest-rate adjustment action, a default initiation action, a substitution of collateral, a calling of the loan, and providing an alert to a second entity involved in the loan.

An example system may include a robotic process automation circuit structured to, based on iteratively training on a training data set comprising human user interactions with the social network data collection circuit, configure the loan guarantee parameter based on at least one attribute of the loan.

An example system may include wherein the at least one attribute of the loan is obtained from a smart contract circuit that manages the loan.

An example system may include wherein the training data set further comprises outcomes from a plurality of social network data collection and monitoring requests performed by the social network data collection circuit.

An example system may include wherein the robotic process automation circuit is further structured to determine at least one domain to which the social network data collection circuit will apply.

An example system may include wherein training comprises training the robotic process automation circuit to configure the plurality of algorithms.

In embodiments, provided herein is a social network monitoring method for validating conditions of a guarantee for a loan. An example method may include interpreting a loan guarantee parameter; collecting data using a plurality of algorithms that are configured to monitor social network information about an entity involved in a loan in response to the loan guarantee parameter; and validating a guarantee for the loan in response to the monitored social network information.

Certain further aspects of an example method are described following, any one or more of which may be present in certain embodiments. An example method may further include enabling a workflow by which a human user enters the loan guarantee parameter to establish a social network data collection and monitoring request.

An example method may further include automatically undertaking an action related to the loan in response to the validation of the loan.

An example method may further include wherein the action related to the loan is in response to the loan guarantee not being validated, and wherein the action comprises a foreclosure action.

An example method may further include wherein the action related to the loan is in response to the loan guarantee not being validated, and wherein the action comprises a lien administration action.

An example method may further include wherein the action related to the loan is in response to the loan guarantee not being validated, and wherein the action comprises an interest-rate adjustment action.

An example method may further include wherein the action related to the loan is in response to the loan guarantee not being validated, and wherein the action comprises a default initiation action.

An example method may further include wherein the action related to the loan is in response to the loan guarantee not being validated, and wherein the action comprises a substitution of collateral.

An example method may further include wherein the action related to the loan is in response to the loan guarantee not being validated, and wherein the action comprises a calling of the loan.

An example method may further include wherein the action related to the loan is in response to the loan guarantee not being validated, and wherein the action comprises providing an alert to a second entity involved in the loan.

An example method may further include iteratively training a robotic process automation circuit to configure a data collection and monitoring action based on at least one attribute of the loan, wherein the robotic process automation circuit is trained on a training data set comprising at least one of outcomes from or human user interactions with the plurality of algorithms.

An example method may further include determining at least one domain to which the plurality of algorithms will apply. For example, the algorithm may query a plurality of domains in determining.

An example apparatus may include a social networking input circuit structured to interpret a loan guarantee parameter; a social network data collection circuit structured to collect data using a plurality of algorithms that are configured to monitor social network information about a guarantor of the loan in response to the loan guarantee parameter; and a guarantee validation circuit structured to validate a guarantee for the loan in response to the monitored social network information.

The loan guarantee parameter may include a financial condition of the guarantor of the loan, and wherein the guarantee validation circuit is further structured to determine the financial condition of the guarantor of the loan based on at least one attribute selected from the attributes consisting of: a publicly stated valuation of the entity, a set of property owned by the entity as indicated by public records, a valuation of a set of property owned by the entity, a bankruptcy condition of the entity, a foreclosure status of the entity, a contractual default status of the entity, a regulatory violation status of the entity, a criminal status of an entity, an export controls status of the entity, an embargo status of the entity, a tariff status of the entity, a tax status of the entity, a credit report of the entity, a credit rating of the entity, a web site rating of the entity, a set of customer reviews for a product of the entity, a social network rating of the entity, a set of credentials of the entity, a set of referrals of the entity, a set of testimonials for the entity, a set of behavior of the entity, a location of the entity, and a geolocation of the entity.

In embodiments, provided herein is a monitoring system for validating conditions of a guarantee for a loan. An example platform, system, or apparatus may include an Internet of Things (IoT) data input circuit structured to interpret a loan guarantee parameter; an IoT data collection circuit structured to collect data using at least one algorithm that is configured to monitor IoT information collected from and about an entity involved in a loan in response to the loan guarantee parameter; and a guarantee validation circuit structured to validate a guarantee for the loan in response to the monitored IoT information.

Certain further aspects of an example system are described following, any one or more of which may be present in certain embodiments. An example system may include wherein the loan guarantee parameter comprises a financial condition of the entity, wherein the entity is a guarantor for the loan.

An example system may include wherein the monitored IoT information comprises at least one of: a publicly stated valuation of the entity, a property owned by the entity as indicated by public records, a valuation of a property owned by the entity, a bankruptcy condition of the entity, a foreclosure status of the entity, a contractual default status of the entity, a regulatory violation status of the entity, a criminal status of the entity, an export controls status of the entity, an embargo status of the entity, a tariff status of the entity, a tax status of the entity, a credit report of the entity, a credit rating of the entity, a web site rating of the entity, a plurality of customer reviews for a product of the entity, a social network rating of the entity, a plurality of credentials of the entity, a plurality of referrals of the entity, a plurality of testimonials for the entity, a plurality of behaviors of the entity, a location of the entity, a jurisdiction of the entity, and a geolocation of the entity.

An example system may include wherein the loan comprises at least one loan type selected from the loan types consisting of: an auto loan, an inventory loan, a capital equipment loan, a bond for performance, a capital improvement loan, a building loan, a loan backed by an account receivable, an invoice finance arrangement, a factoring arrangement, a pay day loan, a refund anticipation loan, a student loan, a syndicated loan, a title loan, a home loan, a venture debt loan, a loan of intellectual property, a loan of a contractual claim, a working capital loan, a small business loan, a farm loan, a municipal bond, and a subsidized loan.

An example system may include wherein the IoT data collection circuit is further structured to obtain information about a condition of a collateral for the loan, wherein the collateral comprises at least one item selected from the items consisting of a vehicle, a ship, a plane, a building, a home, a real estate property, an undeveloped land, a farm, a crop, a municipal facility, a warehouse, a set of inventory, a commodity, a security, a currency, a token of value, a ticket, a cryptocurrency, a consumable item, an edible item, a beverage, a precious metal, an item of jewelry, a gemstone, an item of intellectual property, an intellectual property right, a contractual right, an antique, a fixture, an item of furniture, an item of equipment, a tool, an item of machinery, and an item of personal property; and wherein the guarantee validation circuit is further structured to validate the guarantee of the loan in response to the condition of the collateral for the loan.

An example system may include wherein the condition of the collateral comprises a condition attribute selected from the group consisting of a quality of the collateral, a status of title to the collateral, a status of possession of the collateral, a status of a lien on the collateral, a new or used status, a type, a category, a specification, a product feature set, a model, a brand, a manufacturer, a status, a context, a state, a value, a storage location, a geolocation, an age, a maintenance history, a usage history, an accident history, a fault history, an ownership, an ownership history, a price, an assessment, and a valuation.

An example system may include wherein the IoT data collection input circuit is further structured to enable a workflow by which a human user enters the loan guarantee parameter to establish an Internet of Things data collection request.

An example system may include a smart contract circuit structured to automatically undertake an action related to the loan in response to the validation of the loan.

An example system may include wherein the action related to the loan is in response to the loan guarantee not being validated, and wherein the action comprises at least one action selected from the actions consisting of: a foreclosure action, a lien administration action, an interest-rate adjustment action, a default initiation action, a substitution of collateral, a calling of the loan, and providing an alert to second entity involved in the loan.

An example system may include a robotic process automation circuit structured to, based on iteratively training on a training data set comprising human user interactions with the IoT data collection circuit, configure the loan guarantee parameter based on at least one attribute of the loan.

An example system may include wherein the at least one attribute of the loan is obtained from a smart contract circuit that manages the loan.

An example system may include wherein the training data set further comprises outcomes from a plurality of IoT data collection and monitoring requests performed by the IoT data collection circuit.

An example system may include wherein the robotic process automation circuit is further structured to determine at least one domain to which the IoT data collection circuit will apply.

An example system may include wherein the training comprises training the robotic process automation circuit to configure the at least one algorithm.

In embodiments, provided herein is a monitoring method for validating conditions of a guarantee for a loan. An example method may include interpreting a loan guarantee parameter; collecting data using a plurality of algorithms that are configured to monitor Internet of Things (IoT) information collected from and about an entity involved in a loan in response to the loan guarantee parameter; and validating a guarantee for the loan in response to the monitored IoT information.

Certain further aspects of an example method are described following, any one or more of which may be present in certain embodiments. An example method may further include configuring the loan guarantee parameter to obtain information about a financial condition of the entity, wherein the entity is a guarantor for the loan.

An example method may further include configuring the at least one algorithm to obtain information about a condition of a collateral for the loan, wherein the collateral comprises at least one item selected from the items consisting of a vehicle, a ship, a plane, a building, a home, a real estate property, an undeveloped land, a farm, a crop, a municipal facility, a warehouse, a set of inventory, a commodity, a security, a currency, a token of value, a ticket, a cryptocurrency, a consumable item, an edible item, a beverage, a precious metal, an item of jewelry, a gemstone, an item of intellectual property, an intellectual property right, a contractual right, an antique, a fixture, an item of furniture, an item of equipment, a tool, an item of machinery, and an item of personal property; and validating the guarantee for the loan further in response to the condition of the collateral for the loan.

An example method may further include enabling a workflow by which a human user enters the loan guarantee parameter to establish an IoT data collection request.

An example method may further include automatically undertaking an action related to the loan in response to the validation of the loan.

An example method may further include wherein the action related to the loan is in response to the loan guarantee not being validated, and wherein the action comprises a foreclosure action.

An example method may further include wherein the action related to the loan is in response to the loan guarantee not being validated, and wherein the action comprises a lien administration action.

An example method may further include wherein the action related to the loan is in response to the loan guarantee not being validated, and wherein the action comprises an interest-rate adjustment action.

An example method may further include wherein the action related to the loan is in response to the loan guarantee not being validated, and wherein the action comprises a default initiation action.

An example method may further include wherein the action related to the loan is in response to the loan guarantee not being validated, and wherein the action comprises a substitution of collateral.

An example method may further include wherein the action related to the loan is in response to the loan guarantee not being validated, and wherein the action comprises a calling of the loan.

An example method may further include wherein the action related to the loan is in response to the loan guarantee not being validated, and wherein the action comprises providing an alert to a second entity involved in the loan.

An example method may further include iteratively training a robotic process automation circuit to configure an IoT data collection and monitoring action based on at least one attribute of the loan, wherein the robotic process automation circuit is trained on a training data set comprising at least one of outcomes from or human user interactions with the plurality of algorithms.

An example method may further include determining at least one domain to which the plurality of algorithms will apply.

An example method may further include wherein training comprises training the robotic process automation circuit to configure plurality of algorithms.

An example method may further include wherein the training data set further comprises outcomes from a set of IoT data collection and monitoring requests.

In embodiments, provided herein is a robotic process automation system for negotiating a loan. An example platform, system, or apparatus may include a data collection circuit structured to collect a training set of interactions from at least one entity related to at least one loan transaction; an automated loan classification circuit trained on the training set of interactions to classify a at least one loan negotiation action; and a robotic process automation circuit trained on a training set of a plurality of loan negotiation actions classified by the automated loan classification circuit and a plurality of loan transaction outcomes to negotiate a terms and conditions of a new loan on behalf of a party to the new loan.

Certain further aspects of an example system are described following, any one or more of which may be present in certain embodiments. An example system may include wherein the data collection circuit further comprises at least one system selected from the systems consisting of: an Internet of Things system, a camera system, a networked monitoring system, an internet monitoring system, a mobile device system, a wearable device system, a user interface system, and an interactive crowdsourcing system.

An example system may include wherein the at least one entity is a party to the at least one loan transaction.

An example system may include wherein the at least one entity is selected from the entities consisting of: a primary lender, a secondary lender, a lending syndicate, a corporate lender, a government lender, a bank lender, a secured lender, bond issuer, a bond purchaser, an unsecured lender, a guarantor, a provider of security, a borrower, a debtor, an underwriter, an inspector, an assessor, an auditor, a valuation professional, a government official, and an accountant.

An example system may include wherein the automated loan classification circuit comprises a system selected from the systems consisting of: a machine learning system, a model-based system, a rule-based system, a deep learning system, a hybrid system, a neural network, a convolutional neural network, a feed forward neural network, a feedback neural network, a self-organizing map, a fuzzy logic system, a random walk system, a random forest system, a probabilistic system, a Bayesian system, and a simulation system.

An example system may include wherein the robotic process automation circuit is further trained on a plurality of interactions of parties with a plurality of user interfaces involved in a plurality of lending processes.

An example system may further include a smart contract circuit structured to automatically configure a smart contract for the new loan based on an outcome of the negotiation.

An example system may further include a distributed ledger associated with the new loan, wherein the distributed ledger is structured to record at least one of an outcome and a negotiating event of the negotiation.

An example system may include wherein the new loan comprises at least one loan type selected from the loan types consisting of: an auto loan, an inventory loan, a capital equipment loan, a bond for performance, a capital improvement loan, a building loan, a loan backed by an account receivable, an invoice finance arrangement, a factoring arrangement, a pay day loan, a refund anticipation loan, a student loan, a syndicated loan, a title loan, a home loan, a venture debt loan, a loan of intellectual property, a loan of a contractual claim, a working capital loan, a small business loan, a farm loan, a municipal bond, and a subsidized loan.

An example system may further include a valuation circuit structured to use a valuation model to determine a value for a collateral for the new loan.

An example system may include wherein the collateral comprises at least one item selected from the items consisting of: a vehicle, a ship, a plane, a building, a home, real estate property, undeveloped land, a farm, a crop, a municipal facility, a warehouse, a set of inventory, a commodity, a security, a currency, a token of value, a ticket, a cryptocurrency, a consumable item, an edible item, a beverage, a precious metal, an item of jewelry, a gemstone, an item of intellectual property, an intellectual property right, a contractual right, an antique, a fixture, an item of furniture, an item of equipment, a tool, an item of machinery, and an item of personal property.

An example system may include wherein the valuation circuit further comprises a market value data collection circuit structured to monitor and report on marketplace information relevant to a value of the collateral.

An example system may include wherein the market value data collection circuit monitors pricing or financial data for an offset collateral item in at least one public marketplace.

An example system may include wherein a set of offset collateral items for valuing the collateral is constructed using a clustering circuit based on an attribute of the collateral.

An example system may include wherein the attribute is selected from among a category of the collateral, an age of the collateral, a condition of the collateral, a history of the collateral, a storage condition of the collateral, and a geo-location of the collateral.

An example system may include wherein the terms and conditions for the new loan comprise at least one member selected from the group consisting of: a principal amount of debt, a balance of debt, a fixed interest rate, a variable interest rate, a payment amount, a payment schedule, a balloon payment schedule, a specification of collateral, a specification of substitutability of collateral, a party, a guarantee, a guarantor, a security, a personal guarantee, a lien, a duration, a covenant, a foreclose condition, a default condition, and a consequence of default.

In embodiments, provided herein is a robotic process automation method for negotiating a loan. An example method may include collecting a training set of interactions from at least one entity related to at least one loan transaction; training an automated loan classification circuit on the training set of interactions to classify a at least one loan negotiation action; and training a robotic process automation circuit on a training set of a plurality of loan negotiation actions classified by the automated loan classification circuit and a plurality of loan transaction outcomes to negotiate a terms and conditions of a new loan on behalf of a party to the new loan.

Certain further aspects of an example method are described following, any one or more of which may be present in certain embodiments. An example method may further include An example method may further include training the robotic process automation circuit on a plurality of interactions of parties with a plurality of user interfaces involved in a plurality of lending processes.

An example method may further include configuring a smart contract for the new loan based on an outcome of the negotiation.

An example method may further include recording at least one of an outcome and a negotiating event of the negotiation in a distributed ledger associated with the new loan.

An example method may further include determining a value for a collateral for the new loan using a valuation model.

An example method may further include monitoring and reporting on marketplace information relevant to a value of the collateral.

An example method may further include constructing a set of offset collateral items for valuing the collateral using a similarity clustering algorithm based on an attribute of the collateral.

In embodiments, provided herein is a system for adaptive intelligence and robotic process automation capabilities of a transactional, financial and marketplace enablement.

An example apparatus or system may include a data collection circuit structured to interpret interactions among entities corresponding to a plurality of entities related to at least one transaction of a first set of loans, wherein the at least one transaction involves a first collection action of a set of payments corresponding to the first set of loans; an artificial intelligence circuit structured to classify the first collection action, wherein the artificial intelligence circuit is trained on the interactions corresponding to the first set of loans; and a robotic process automation circuit that is trained on the interactions and a set of loan collection outcomes corresponding to the first set of loans to implement a second loan collection action on behalf of a party to a second loan.

Certain further aspects of an example system or apparatus are described following, any one or more of which may be present in certain embodiments.

An example apparatus or system may include wherein the second loan collection action is selected from actions consisting of: initiation of a collection process, referral of a loan to an agent for collection, configuration of a collection communication, scheduling of a collection communication, configuration of content for a collection communication, configuration of an offer to settle a loan, termination of a collection action, deferral of a collection action, configuration of an offer for an alternative payment schedule, initiation of a litigation, initiation of a foreclosure, initiation of a bankruptcy process, initiation of a repossession process, and placement of a lien on collateral.

An example apparatus or system may include wherein the set of loan collection outcomes is selected from outcomes consisting of: a response to a collection contact event, a payment of a loan, a default of a borrower on a loan, a bankruptcy of a borrower of a loan, an outcome of a collection litigation, a financial yield of a set of collection actions, a return on investment on collection, and a measure of reputation of a party involved in collection.

An example apparatus or system may include wherein the data collection circuit comprises at least one system selected from systems consisting of: an Internet of Things system, a camera system, a networked monitoring system, an internet monitoring system, a mobile device system, a wearable device system, a user interface system, and an interactive crowdsourcing system.

An example apparatus or system may include wherein the entities are a set of parties to a loan transaction.

An example apparatus or system may include wherein the set of parties is selected from parties consisting of: a primary lender, a secondary lender, a lending syndicate, a corporate lender, a government lender, a bank lender, a secured lender, bond issuer, a bond purchaser, an unsecured lender, a guarantor, a provider of security, a borrower, a debtor, an underwriter, an inspector, an assessor, an auditor, a valuation professional, a government official, and an accountant.

An example apparatus or system may include wherein the artificial intelligence circuit comprises at least one system selected from systems consisting of: a machine learning system, a model-based system, a rule-based system, a deep learning system, a hybrid system, a neural network, a convolutional neural network, a feed forward neural network, a feedback neural network a self-organizing map, a fuzzy logic system, a random walk system, a random forest system, a probabilistic system, a Bayesian system, and a simulation system.

An example apparatus or system may include wherein the robotic process automation circuit is trained on a set of interactions of parties, the system further comprising at least one user interface configured to interact with at least one party involved in a set of lending processes.

An example apparatus or system may include wherein upon completion of negotiation of a collection process a smart contract for a loan is automatically configured by a smart contract circuit based on the outcome of the negotiation.

An example apparatus or system may include wherein robotic process automation circuit is structured to record the set of loan collection outcomes and the first collection action in a distributed ledger associated with the first set of loans.

An example apparatus or system may include wherein the second loan comprises at least one loan selected from a set of loans consisting of: auto loan, an inventory loan, a capital equipment loan, a bond for performance, a capital improvement loan, a building loan, a loan backed by an account receivable, an invoice finance arrangement, a factoring arrangement, a pay day loan, a refund anticipation loan, a student loan, a syndicated loan, a title loan, a home loan, a venture debt loan, a loan of intellectual property, a loan of a contractual claim, a working capital loan, a small business loan, a farm loan, a municipal bond, and a subsidized loan.

An example apparatus or system may include wherein the artificial intelligence circuit includes at least one system from systems consisting of: a machine learning system, a model-based system, a rule-based system, a deep learning system, a hybrid system, a neural network, a convolutional neural network, a feed forward neural network, a feedback neural network, a self-organizing map, a fuzzy logic system, a random walk system, a random forest system, a probabilistic system, a Bayesian system, and a simulation system.

An example apparatus or system may include wherein the entities each comprise at least one entity selected from the entities consisting of: a lender, a borrower, a guarantor, equipment related to the first set of loans, goods related to the first set of loans, a system related to the first set of loans, a fixture related to the first set of loans, a building, a storage facility, and an item of collateral.

An example apparatus or system may include wherein robotic process automation circuit is structured to record the second loan collection action in a distributed ledger associated with the second loan.

An example apparatus or system may include wherein the first collection action is selected from the actions consisting of: an initiation of a collection process, a referral of a loan to an agent for collection, a configuration of a collection communication, a scheduling of a collection communication, a configuration of content for a collection communication, a configuration of an offer to settle a loan, a termination of a collection action, a deferral of a collection action, a configuration of an offer for an alternative payment schedule, an initiation of a litigation, an initiation of a foreclosure, an initiation of a bankruptcy process, an initiation of a repossession process, and a placement of a lien on collateral.

In embodiments, provided herein is a method for adaptive intelligence and robotic process automation capabilities of a transactional, financial and marketplace enablement. An example method may include interpreting a plurality of interactions among entities corresponding to a plurality of entities related to at least one transaction of a first set of loans, wherein the at least one transaction involves a first collection action of a set of payments corresponding to the first set of loans; classifying the first collection action based at least in part on the plurality of interactions; and specifying, based at least in part on the plurality of interactions and a set of loan collection outcomes corresponding to the first set of loans, a second loan collection action on behalf of a party to a second loan.

Certain further aspects of an example system are described following, any one or more of which may be present in certain embodiments. An example method may further include wherein the second loan collection action comprises at least one of initiation of a collection process, configuration of a collection communication, or scheduling of a collection action.

An example method may further include wherein the second loan collection action comprises at least one of referral of a loan to an agent for collection, configuration of an offer to settle the second loan, or configuration of content for a collection communication.

An example method may further include wherein the second loan collection action comprises at least one of termination of a collection action, deferral of a collection action, or configuration of an offer for an alternative payment schedule.

An example method may further include wherein the second loan collection action comprises at least one of initiation of a litigation, initiation of a foreclosure, or initiation of a bankruptcy process.

An example method may further include wherein the second loan collection action comprises at least one of initiation of a repossession process or placement of a lien on collateral of the second loan.

An example method may further include wherein the set of loan collection outcomes is selected from outcomes consisting of: a response to a collection contact event, a payment of a loan, a default of a borrower on a loan, a bankruptcy of a borrower of a loan, an outcome of a collection litigation, a financial yield of a set of collection actions, a return on investment on collection, and a measure of reputation of a party involved in collection.

An example method may further include wherein upon completion of negotiation of a collection process a smart contract for a loan is automatically configured by a set of smart contract services based on the outcome of the negotiation.

An example method may further include further comprising recording at least one of the set of loan collection outcomes in a distributed ledger associated with the first set of loans.

An example method may further include further comprising providing a user interface to a party of the second loan, and notifying the party of the second loan of the specified second collection action.

An example method may further include further comprising initiating the specified second collection action in response to an input from the party of the second loan to the user interface.

An example method may further include further comprising recording the second loan collection action in a distributed ledger associated with the second loan.

An example method may further include wherein the first loan collection action comprises at least one of initiation of a collection process, configuration of a collection communication, or scheduling of a collection action, referral of a loan to an agent for collection, configuration of an offer to settle the second loan, or configuration of content for a collection communication.

An example method may further include wherein the first loan collection action comprises at least one of termination of a collection action, deferral of a collection action, or configuration of an offer for an alternative payment schedule.

An example method may further include wherein the first loan collection action comprises at least one of initiation of a litigation, initiation of a foreclosure, or initiation of a bankruptcy process, initiation of a repossession process, or placement of a lien on collateral of the second loan.

In embodiments, provided herein is a system for adaptive intelligence and robotic process automation capabilities of a transactional, financial and marketplace enablement.

In embodiments, provided herein is a system for adaptive intelligence and robotic process automation capabilities of a transactional, financial and marketplace enablement.

An example apparatus or system may include a data collection circuit structured to collect a training set of loan interactions between entities, wherein the training set of loan interactions comprises a set of loan refinancing activities and a set of loan refinancing outcomes; an artificial intelligence circuit structured to classify the set of loan refinancing activities, wherein the artificial intelligence circuit is trained on the training set of loan interactions; and a robotic process automation circuit structured to perform a second loan refinancing activity on behalf of a party to a second loan, wherein the robotic process automation circuit is trained on the set of loan refinancing activities and the set of loan refinancing outcomes.

Certain further aspects of an example system or apparatus are described following, any one or more of which may be present in certain embodiments.

An example apparatus or system may include wherein at least one loan refinancing activity of the set of loan refinancing activities is selected from a group consisting of: initiating an offer to refinance, initiating a request to refinance, configuring a refinancing interest rate, configuring a refinancing payment schedule, configuring a refinancing balance, configuring collateral for a refinancing, managing use of proceeds of a refinancing, removing or placing a lien associated with a refinancing, verifying title for a refinancing, managing an inspection process, populating an application, negotiating terms and conditions for a refinancing, or closing a refinancing.

An example apparatus or system may include wherein the data collection circuit comprises at least one system selected from systems consisting of: Internet of Things systems that monitor the entities, a set of cameras that monitor the entities, a set of software services that pull information related to the entities from publicly available information sites, a set of mobile devices that report on information related to the entities, a set of wearable devices worn by human entities, a set of user interfaces by which entities provide information about the entities and a set of crowdsourcing services configured to solicit and report information related to the entities.

An example apparatus or system may include wherein at least one entity of the entities is a party to at least one loan refinancing activity of the set of loan refinancing activities.

An example apparatus or system may include wherein the party is at least one party selected from a group consisting of: a primary lender, a secondary lender, a lending syndicate, a corporate lender, a government lender, a bank lender, a secured lender, bond issuer, a bond purchaser, an unsecured lender, a guarantor, a provider of security, a borrower, a debtor, an underwriter, an inspector, an assessor, an auditor, a valuation professional, a government official, or an accountant.

An example apparatus or system may include wherein the artificial intelligence circuit comprises at least one system selected from systems consisting of: a machine learning system, a model-based system, a rule-based system, a deep learning system, a hybrid system, a neural network, a convolutional neural network, a feed forward neural network, a feedback neural network, a self-organizing map, a fuzzy logic system, a random walk system, a random forest system, a probabilistic system, a Bayesian system, or a simulation system.

An example apparatus or system may include further comprising an interface circuit structured to receive interactions from at least one of the entities and wherein the robotic process automation circuit is further trained on the interactions.

An example apparatus or system may include a smart contract circuit structured to determine completion of the second loan refinancing activity, and to modify a smart refinance contract based on an outcome of the second loan refinancing activity.

An example apparatus or system may include a distributed ledger circuit structured to determine an event associated with the second loan refinancing activity, and to record, in a distributed ledger associated with the second loan, the event associated with the second loan refinancing activity.

An example apparatus or system may include wherein the second loan comprises at least one loan selected from a group consisting of: an auto loan, an inventory loan, a capital equipment loan, a bond for performance, a capital improvement loan, a building loan, a loan backed by an account receivable, an invoice finance arrangement, a factoring arrangement, a pay day loan, a refund anticipation loan, a student loan, a syndicated loan, a title loan, a home loan, a venture debt loan, a loan of intellectual property, a loan of a contractual claim, a working capital loan, a small business loan, a farm loan, a municipal bond, or a subsidized loan.

An example apparatus or system may include wherein the artificial intelligence circuit includes at least one system from systems consisting of: a machine learning system, a model-based system, a rule-based system, a deep learning system, a hybrid system, a neural network, a convolutional neural network, a feed forward neural network, a feedback neural network, a self-organizing map, a fuzzy logic system, a random walk system, a random forest system, a probabilistic system, a Bayesian system, and a simulation system.

In embodiments, provided herein is a method for adaptive intelligence and robotic process automation capabilities of a transactional, financial and marketplace enablement. An example method may include collecting a training set of loan interactions between entities, wherein the training set of loan interactions comprises a set of loan refinancing activities and a set of loan refinancing outcomes; classifying the set of loan refinancing activities based at least in part on the training set of loan interactions; and specifying a second loan refinancing activity on behalf of a party to a second loan based at least in part on the set of loan refinancing activities and the set of loan refinancing outcomes.

Certain further aspects of an example system are described following, any one or more of which may be present in certain embodiments. An example method may further include An example method may further include wherein at least one loan refinancing activity of the set of loan refinancing activities includes initiating an offer to refinance, initiating a request to refinance, configuring a refinancing interest rate, configuring a refinancing payment schedule, configuring a refinancing balance, configuring collateral for a refinancing, managing use of proceeds of a refinancing, removing or placing a lien associated with a refinancing, verifying title for a refinancing, managing an inspection process, populating an application, negotiating terms and conditions for a refinancing, and the like.

An example method may further include wherein at least one entity of the entities is a party to at least one loan refinancing activity of the set of loan refinancing activities. receiving interactions from at least one of the entities, and wherein the classifying is further trained on the interactions.

An example method may further include wherein the party is at least one party selected from a group consisting of: a primary lender, a secondary lender, a lending syndicate, a corporate lender, a government lender, a bank lender, a secured lender, bond issuer, a bond purchaser, an unsecured lender, a guarantor, a provider of security, a borrower, a debtor, an underwriter, an inspector, an assessor, an auditor, a valuation professional, a government official, or an accountant.

An example method may further include determining completion of the second loan refinancing activity; and modifying a smart refinance contract based on an outcome of the second loan refinancing activity.

An example method may further include recording, in a distributed ledger associated with the second loan, one of the modified smart refinance contract or a reference to the modified smart refinance contract.

An example method may further include determining an event associated with the second loan refinancing activity; and recording, in a distributed ledger associated with the second loan, the event associated with the second loan refinancing activity.

In embodiments, provided herein is a system for adaptive intelligence and robotic process automation capabilities of a transactional, financial and marketplace enablement.

In embodiments, provided herein is a system for adaptive intelligence and robotic process automation capabilities of a transactional, financial and marketplace enablement.

An example apparatus or system may include a data collection circuit structured to collect a training set of loan interactions between entities. The training set of loan interactions comprises a set of loan consolidation transactions. The apparatus or system may further include an artificial intelligence circuit structured to classify a set of loans as candidates for consolidation, wherein the artificial intelligence circuit is trained on training set of interactions; a robotic process automation circuit structured to manage a consolidation of at least a subset of the set of loans on behalf of a party to the consolidation, wherein the robotic process automation circuit is trained on the set of loan consolidation transactions.

Certain further aspects of an example system or apparatus are described following, any one or more of which may be present in certain embodiments.

An example apparatus or system may include wherein the data collection circuit comprises at least one system selected from systems consisting of: Internet of Things systems that monitor the entities, a set of cameras that monitor the entities, a set of software services that pull information related to the entities from publicly available information sites, a set of mobile devices that report on information related to the entities, a set of wearable devices worn by human entities, a set of user interfaces by which entities provide information about the entities and a set of crowd-sourcing services configured to solicit and report information related to the entities.

An example apparatus or system may include wherein the set of loans that are classified as candidates for consolidation are determined based on a model that processes attributes of the entities; and wherein at least one attribute selected from a group consisting of: identity of a party, interest rate, payment balance, payment terms, payment schedule, type of loan, type of collateral, financial condition of party, payment status, condition of collateral, or value of collateral.

An example apparatus or system may include wherein at least one managing the consolidation includes managing selected from a group consisting of: identification of loans from a set of candidate loans, preparation of a consolidation offer, preparation of a consolidation plan, preparation of content communicating a consolidation offer, scheduling a consolidation offer, communicating a consolidation offer, negotiating a modification of a consolidation offer, preparing a consolidation agreement, executing a consolidation agreement, modifying collateral for a set of loans, handling an application workflow for consolidation, managing an inspection, managing an assessment, setting an interest rate, deferring a payment requirement, setting a payment schedule, or closing a consolidation agreement.

An example apparatus or system may include wherein at least one entity of the entities is a party to at least one loan consolidation transaction of the set of loan consolidation transactions.

An example apparatus or system may include wherein the party is at least one party selected from a group consisting of: a primary lender, a secondary lender, a lending syndicate, a corporate lender, a government lender, a bank lender, a secured lender, bond issuer, a bond purchaser, an unsecured lender, a guarantor, a provider of security, a borrower, a debtor, an underwriter, an inspector, an assessor, an auditor, a valuation professional, a government official, or an accountant.

An example apparatus or system may include wherein the artificial intelligence circuit comprises at least one system selected from systems consisting of: a machine learning system, a model-based system, a rule-based system, a deep learning system, a hybrid system, a neural network, a convolutional neural network, a feed forward neural network, a feedback neural network, a self-organizing map, a fuzzy logic system, a random walk system, a random forest system, a probabilistic system, a Bayesian system, or a simulation system.

An example apparatus or system may further include an interface circuit structured to receive interactions from at least one of the entities and wherein the robotic process automation circuit is further trained on the interactions.

An example apparatus or system may further include a smart contract circuit structured to determine completion of a negotiation of the consolidation of at least one loan from the subset of the set of loans; and modify a smart consolidation contract based on an outcome of the negotiation.

An example apparatus or system may further include a distributed ledger circuit structured to determine at least one of an outcome and a negotiation event associated with the consolidation of at least the subset of the set of loans; and record, in a distributed ledger associated with the subset of the set of loans, at least one of the outcome and the negotiation event associated with the consolidation.

An example apparatus or system may include wherein at least one loan from the subset of the set of loans is selected from a group consisting of: an auto loan, an inventory loan, a capital equipment loan, a bond for performance, a capital improvement loan, a building loan, a loan backed by an account receivable, an invoice finance arrangement, a factoring arrangement, a pay day loan, a refund anticipation loan, a student loan, a syndicated loan, a title loan, a home loan, a venture debt loan, a loan of intellectual property, a loan of a contractual claim, a working capital loan, a small business loan, a farm loan, a municipal bond, or a subsidized loan.

In embodiments, provided herein is a method for adaptive intelligence and robotic process automation capabilities of a transactional, financial and marketplace enablement. An example method may include collecting a training set of loan interactions between entities, wherein the training set of loan interactions comprises a set of loan consolidation transactions; classifying a set of loans as candidates for consolidation based at least in part on the training set of loan interactions; and managing a consolidation of at least a subset of the set of loans on behalf of a party to the consolidation based at least in part on the set of loan consolidation transactions.

Certain further aspects of an example system are described following, any one or more of which may be present in certain embodiments. An example method may further include classifying the set of loans as candidates for consolidation is based on a model that processes attributes of the entities; and wherein at least one attribute selected from a group consisting of: identity of a party, interest rate, payment balance, payment terms, payment schedule, type of loan, type of collateral, financial condition of party, payment status, condition of collateral, or value of collateral.

An example method may further include at least one entity of the entities is a party to at least one loan consolidation transaction of the set of loan consolidation transactions.

An example method may further include that at least one managing the consolidation includes managing selected from a group consisting of: identification of loans from a set of candidate loans, preparation of a consolidation offer, preparation of a consolidation plan, preparation of content communicating a consolidation offer, scheduling a consolidation offer, communicating a consolidation offer, negotiating a modification of a consolidation offer, preparing a consolidation agreement, executing a consolidation agreement, modifying collateral for a set of loans, handling an application workflow for consolidation, managing an inspection, managing an assessment, setting an interest rate, deferring a payment requirement, setting a payment schedule, or closing a consolidation agreement.

An example method may further include that at least one entity of the entities is a party to at least one loan consolidation transaction of the set of loan consolidation transactions.

An example method may further include that the party is at least one party selected from a group consisting of: a primary lender, a secondary lender, a lending syndicate, a corporate lender, a government lender, a bank lender, a secured lender, bond issuer, a bond purchaser, an unsecured lender, a guarantor, a provider of security, a borrower, a debtor, an underwriter, an inspector, an assessor, an auditor, a valuation professional, a government official, or an accountant.

An example method may further include determining completion of a negotiation of the consolidation of at least one loan from the subset of the set of loans; and modifying a smart consolidation contract based on an outcome of the negotiation.

An example method may further include determining at least one of an outcome and a negotiation event associated with the consolidation of at least the subset of the set of loans; and recording, in a distributed ledger associated with the subset of the set of loans, at least one of the outcome and the negotiation event associated with the consolidation.

In embodiments, provided herein is a system for adaptive intelligence and robotic process automation capabilities of a transactional, financial and marketplace enablement.

An example apparatus or system may include a data collection circuit structured to collect information about entities involved in a set of factoring loans and a training set of interactions between entities for a set of factoring loan transactions. The apparatus or system may further include an artificial intelligence circuit structured to classify the entities involved in the set of factoring loans, wherein the artificial intelligence circuit is trained on the training set of interactions; and a robotic process automation circuit structured to manage a factoring loan, wherein the robotic process automation circuit is trained on the set of factoring loan interactions.

Certain further aspects of an example system or apparatus are described following, any one or more of which may be present in certain embodiments.

An example apparatus or system may include wherein the data collection circuit comprises at least one system selected from systems consisting of: Internet of Things systems that monitor the entities, a set of cameras that monitor the entities, a set of software services that pull information related to the entities from publicly available information sites, a set of mobile devices that report on information related to the entities, a set of wearable devices worn by human entities, a set of user interfaces by which entities provide information about the entities and a set of crowd-sourcing services configured to solicit and report information related to the entities.

An example apparatus or system may include wherein the artificial intelligence circuit is further structured to use a model that processes attributes of entities involved in the set of factoring loans; and wherein at least one attribute selected from a group consisting of: assets used for factoring, identity of a party, interest rate, payment balance, payment terms, payment schedule, type of loan, type of collateral, financial condition of party, payment status, condition of collateral, or value of collateral.

An example apparatus or system may include wherein at least one managing the factoring loan includes managing selected from a group consisting of: managing at least one of a set of assets for factoring, identification of loans for factoring from a set of candidate loans, preparation of a factoring offer, preparation of a factoring plan, preparation of content communicating a factoring offer, scheduling a factoring offer, communicating a factoring offer, negotiating a modification of a factoring offer, preparing a factoring agreement, executing a factoring agreement, modifying collateral for a set of factoring loans, handing transfer of a set of accounts receivable, handling an application workflow for factoring, managing an inspection, managing an assessment of a set of assets to be factored, setting an interest rate, deferring a payment requirement, setting a payment schedule, or dosing a factoring agreement.

An example apparatus or system may include wherein the assets used for factoring include a set of accounts receivable.

An example apparatus or system may include wherein at least one managing the factoring loan includes managing selected from a group consisting of: managing at least one of a set of assets for factoring, identification of loans for factoring from a set of candidate loans, preparation of a factoring offer, preparation of a factoring plan, preparation of content communicating a factoring offer, scheduling a factoring offer, communicating a factoring offer, negotiating a modification of a factoring offer, preparing a factoring agreement, executing a factoring agreement, modifying collateral for a set of factoring loans, handing transfer of a set of accounts receivable, handling an application workflow for factoring, managing an inspection, managing an assessment of a set of assets to be factored, setting an interest rate, deferring a payment requirement, setting a payment schedule, or dosing a factoring agreement.

An example apparatus or system may include wherein at least one entity of the entities is a party to at least one factoring loan transactions of the set of factoring loan transactions.

An example apparatus or system may include wherein the party is at least one party selected from parties consisting of: a primary lender, a secondary lender, a lending syndicate, a corporate lender, a government lender, a bank lender, a secured lender, bond issuer, a bond purchaser, an unsecured lender, a guarantor, a provider of security, a borrower, a debtor, an underwriter, an inspector, an assessor, an auditor, a valuation professional, a government official, and an accountant.

An example apparatus or system may include wherein the artificial intelligence circuit comprises at least one system selected from systems consisting of: a machine learning system, a model-based system, a rule-based system, a deep learning system, a hybrid system, a neural network, a convolutional neural network, a feed forward neural network, a feedback neural network, a self-organizing map, a fuzzy logic system, a random walk system, a random forest system, a probabilistic system, a Bayesian system, or a simulation system.

An example apparatus or system may further include interface circuit structured to receive interactions from at least one of the entities and wherein the robotic process automation circuit is further trained on the interactions.

An example apparatus or system may further include a smart contract circuit structured to determine completion of a negotiation of the factoring loan; and modify a smart factoring loan contract based on an outcome of the negotiation.

An example apparatus or system may further include a distributed ledger circuit structured to determine at least one of an outcome and a negotiation event associated with the negotiation of the factoring loan; and record, in a distributed ledger associated with the factoring loan, at least one of the outcome and the negotiation event associated with the factoring loan.

In embodiments, provided herein is a method for adaptive intelligence and robotic process automation capabilities of a transactional, financial and marketplace enablement. An example method may include collecting information about entities involved in a set of factoring loans and a training set of interactions between entities for a set of factoring loan transactions; classifying the entities involved in the set of factoring loans based at least in part on the training set of interactions; and managing a factoring loan based at least in part on the set of factoring loan interactions.

Certain further aspects of an example system are described following, any one or more of which may be present in certain embodiments. An example method may further include that at least one managing the factoring loan includes managing selected from a group consisting of: managing at least one of a set of assets for factoring, identification of loans for factoring from a set of candidate loans, preparation of a factoring offer, preparation of a factoring plan, preparation of content communicating a factoring offer, scheduling a factoring offer, communicating a factoring offer, negotiating a modification of a factoring offer, preparing a factoring agreement, executing a factoring agreement, modifying collateral for a set of factoring loans, handing transfer of a set of accounts receivable, handling an application workflow for factoring, managing an inspection, managing an assessment of a set of assets to be factored, setting an interest rate, deferring a payment requirement, setting a payment schedule, or dosing a factoring agreement.

An example method may further include that at least one entity of the entities is a party to at least one factoring loan transactions of the set of factoring loan transactions.

An example method may include that the party is at least one party selected from a group consisting of: a primary lender, a secondary lender, a lending syndicate, a corporate lender, a government lender, a bank lender, a secured lender, bond issuer, a bond purchaser, an unsecured lender, a guarantor, a provider of security, a borrower, a debtor, an underwriter, an inspector, an assessor, an auditor, a valuation professional, a government official, or an accountant.

An example method may further include determining completion of a negotiation of the factoring loan; and modifying a smart factoring loan contract based on an outcome of the negotiation.

An example method may further include determining at least one of an outcome and a negotiation event associated with the negotiation of the factoring loan; and recording, in a distributed ledger associated with the factoring loan, at least one of the outcome and the negotiation event associated with the factoring loan.

In embodiments, provided herein is a system for adaptive intelligence and robotic process automation capabilities of a transactional, financial and marketplace enablement.

An example apparatus or system may include a data collection circuit structured to collect information about entities involved in a set of mortgage loan activities and a training set of interactions between entities for a set of mortgage loan transactions. The apparatus or system may further include an artificial intelligence circuit structured to classify the entities involved in the set of mortgage loan activities, wherein the artificial intelligence circuit is trained on the training set of interactions; and a robotic process automation circuit is structured broker a mortgage loan, wherein the robotic process automation circuit is trained on at least one of the set of mortgage loan activities and the training set of interactions.

Certain further aspects of an example system or apparatus are described following, any one or more of which may be present in certain embodiments. An example apparatus or system may include wherein at least one of the set of mortgage loan activities and the set of mortgage loan transactions includes activities selected from a group consisting of: among marketing activity, identification of a set of prospective borrowers, identification of property, identification of collateral, qualification of borrower, title search, title verification, property assessment, property inspection, property valuation, income verification, borrower demographic analysis, identification of capital providers, determination of available interest rates, determination of available payment terms and conditions, analysis of existing mortgage, comparative analysis of existing and new mortgage terms, completion of application workflow, population of fields of application, preparation of mortgage agreement, completion of schedule to mortgage agreement, negotiation of mortgage terms and conditions with capital provider, negotiation of mortgage terms and conditions with borrower, transfer of title, placement of lien, or closing of mortgage agreement.

An example apparatus or system may include wherein the data collection circuit comprises at least one system selected from systems consisting of: Internet of Things systems that monitor the entities, a set of cameras that monitor the entities, a set of software services that pull information related to the entities from publicly available information sites, a set of mobile devices that report on information related to the entities, a set of wearable devices worn by human entities, a set of user interfaces by which entities provide information about the entities and a set of crowd-sourcing services configured to solicit and report information related to the entities.

An example apparatus or system may include wherein the artificial intelligence circuit is further structured to use a model that processes attributes of entities involved in the set of mortgage loan activities; and wherein at least one attribute selected from a group consisting of: properties that are subject to mortgages, assets used for collateral, identity of a party, interest rate, payment balance, payment terms, payment schedule, type of mortgage, type of property, financial condition of party, payment status, condition of property, or value of property.

An example apparatus or system may include wherein brokering the mortgage loan comprises at least one activity selected from a group consisting of: managing at least one of a property that is subject to a mortgage, identification of candidate mortgages from a set of borrower situations, preparation of a mortgage offer, preparation of content communicating a mortgage offer, scheduling a mortgage offer, communicating a mortgage offer, negotiating a modification of a mortgage offer, preparing a mortgage agreement, executing a mortgage agreement, modifying collateral for a set of mortgage loans, handing transfer of a lien, handling an application workflow, managing an inspection, managing an assessment of a set of assets to be subject to a mortgage, setting an interest rate, deferring a payment requirement, setting a payment schedule, or closing a mortgage agreement.

An example apparatus or system may include wherein at least one entity of the entities is a party to at least one mortgage loan transactions of the set of mortgage loan transactions.

An example apparatus or system may include wherein the party is at least one party selected from parties consisting of: a primary lender, a secondary lender, a lending syndicate, a corporate lender, a government lender, a bank lender, a secured lender, bond issuer, a bond purchaser, an unsecured lender, a guarantor, a provider of security, a borrower, a debtor, an underwriter, an inspector, an assessor, an auditor, a valuation professional, a government official, and an accountant.

An example apparatus or system may include wherein the artificial intelligence circuit comprises at least one system selected from systems consisting of: a machine learning system, a model-based system, a rule-based system, a deep learning system, a hybrid system, a neural network, a convolutional neural network, a feed forward neural network, a feedback neural network, a self-organizing map, a fuzzy logic system, a random walk system, a random forest system, a probabilistic system, a Bayesian system, or a simulation system.

An example apparatus or system may further include an interface circuit structured to receive interactions from at least one of the entities and wherein the robotic process automation circuit is further trained on the interactions.

An example apparatus or system may further include a smart contract circuit structured to determine completion of a negotiation of the mortgage loan; and modify a smart factoring loan contract based on an outcome of the negotiation.

An example apparatus or system may further include a distributed ledger circuit structured to determine at least one of an outcome and a negotiation event associated with the negotiation of the mortgage loan; and record, in a distributed ledger associated with the mortgage loan, at least one of the outcome and the negotiation event associated with the mortgage loan.

In embodiments, provided herein is a method for adaptive intelligence and robotic process automation capabilities of a transactional, financial and marketplace enablement. An example method may include collecting information about entities involved in a set of mortgage loan activities and a training set of interactions between entities for a set of mortgage loan transactions; classifying the entities involved in the set of mortgage loan activities based at least in part on the training set of interactions; and brokering a mortgage loan based at least in part on at least one of the set of mortgage loan activities and the training set of interactions.

Certain further aspects of an example system are described following, any one or more of which may be present in certain embodiments. An example method may further include classifying the entities involved in the set of mortgage loan activities is based on a model that processes attributes of entities involved in the set of mortgage loan activities; and wherein at least one attribute selected from a group consisting of: properties that are subject to mortgages, assets used for collateral, identity of a party, interest rate, payment balance, payment terms, payment schedule, type of mortgage, type of property, financial condition of party, payment status, condition of property, or value of property.

An example method may further include that at least one brokering the mortgage loan includes an activity selected from a group consisting of: managing at least one of a property that is subject to a mortgage, identification of candidate mortgages from a set of borrower situations, preparation of a mortgage offer, preparation of content communicating a mortgage offer, scheduling a mortgage offer, communicating a mortgage offer, negotiating a modification of a mortgage offer, preparing a mortgage agreement, executing a mortgage agreement, modifying collateral for a set of mortgage loans, handing transfer of a lien, handling an application workflow, managing an inspection, managing an assessment of a set of assets to be subject to a mortgage, setting an interest rate, deferring a payment requirement, setting a payment schedule, or closing a mortgage agreement.

An example method may include that the at least one entity of the entities is a party to at least one mortgage loan transactions of the set of mortgage loan transactions.

An example method may include that the party is at least one party selected from a group consisting of: a primary lender, a secondary lender, a lending syndicate, a corporate lender, a government lender, a bank lender, a secured lender, bond issuer, a bond purchaser, an unsecured lender, a guarantor, a provider of security, a borrower, a debtor, an underwriter, an inspector, an assessor, an auditor, a valuation professional, a government official, or an accountant.

An example method may further include determining completion of a negotiation of the mortgage loan; and modifying a smart factoring loan contract based on an outcome of the negotiation.

An example method may further include determining at least one of an outcome and a negotiation event associated with the negotiation of the mortgage loan; and recording, in a distributed ledger associated with the mortgage loan, at least one of the outcome and the negotiation event associated with the mortgage loan.

In embodiments, provided herein is a system for adaptive intelligence and robotic process automation capabilities of a transactional, financial and marketplace enablement.

An example system may include a data collection circuit structured to collect information about entities involved in a set of debt transactions, training data set of outcomes related to the entities, and a training set of debt management activities. The system may further include a condition classifying circuit structured to classify a condition of at least one entity of the entities, wherein the condition classifying circuit comprises a model and a set of artificial intelligence circuits, and wherein the model is trained using the training data set of outcomes related to the entities; and an automated debt management circuit structured to manage an action related to a debt, wherein the automated debt management circuit is trained on the training set of debt management activities.

Certain further aspects of an example system are described following, any one or more of which may be present in certain embodiments. An example system may include wherein the data collection circuit comprises at least one system selected from a group consisting of: Internet of Things devices, a set of environmental condition sensors, a set of crowdsourcing services, a set of social network analytic services, or a set of algorithms for querying network domains.

An example system may include wherein at least one debt transaction of the set of debt transactions is selected from a group consisting of: an auto loan, an inventory loan, a capital equipment loan, a bond for performance, a capital improvement loan, a building loan, a loan backed by an account receivable, an invoice finance arrangement, a factoring arrangement, a pay day loan, a refund anticipation loan, a student loan, a syndicated loan, a title loan, a home loan, a venture debt loan, a loan of intellectual property, a loan of a contractual claim, a working capital loan, a small business loan, a farm loan, a municipal bond, or a subsidized loan.

An example system may include wherein the entities involved in the set of debt transactions include at least one of set of parties and a set of assets.

An example system may include wherein at least one asset from the set of assets includes an asset selected from a group consisting of: municipal asset, a vehicle, a ship, a plane, a building, a home, real estate property, undeveloped land, a farm, a crop, a municipal facility, a warehouse, a set of inventory, a commodity, a security, a currency, a token of value, a ticket, a cryptocurrency, a consumable item, an edible item, a beverage, a precious metal, an item of jewelry, a gemstone, intellectual property, an intellectual property right, a contractual right, an antique, a fixture, an item of furniture, an item of equipment, a tool, an item of machinery, or an item of personal property.

An example system may further include a set of sensors positioned on at least one asset from the set of assets, on a container for least one asset from the set of assets, and on a package for at least one asset from the set of assets, wherein the set of sensors configured to associate sensor information sensed by the set of sensors with a unique identifier for the at least one asset from the set of assets; and a set of block chain circuits structured to receive information from the data collection circuit and the set of sensors and storing the information in a blockchain, wherein access to the blockchain is provided via a secure access control interface circuit for a party for a debt transaction involving the at least one asset from the set of assets.

An example system may include wherein at least one sensor from the set of sensors is selected from a group consisting of: image, temperature, pressure, humidity, velocity, acceleration, rotational, torque, weight, chemical, magnetic field, electrical field, or position sensors.

An example system may include an automated agent circuit structured to process events relevant to at least one of a value, a condition, and an ownership of at least one asset of the set of assets and further structured to undertake a set of actions related to a debt transaction to which the asset is related.

An example system may further include wherein at least one action of the set of actions is selected from a group consisting of: offering a debt transaction, underwriting a debt transaction, setting an interest rate, deferring a payment requirement, modifying an interest rate, validating title, managing inspection, recording a change in title, assessing the value of an asset, calling a loan, closing a transaction, setting terms and conditions for a transaction, providing notices required to be provided, foreclosing on a set of assets, modifying terms and conditions, setting a rating for an entity, syndicating debt, or consolidating debt.

An example system may further include wherein at least one artificial intelligence circuit from the set of artificial intelligence circuits includes at least one system selected from a group consisting of: a machine learning system, a model-based system, a rule-based system, a deep learning system, a hybrid system, a neural network, a convolutional neural network, a feed forward neural network, a feedback neural network, a self-organizing map, a fuzzy logic system, a random walk system, a random forest system, a probabilistic system, a Bayesian system, or a simulation system.

An example system may further include an interface circuit structured to receive interactions from at least one of the entities and wherein the automated debt management circuit is further trained on the interactions.

An example system may further include wherein at least one debt management activity from the training set of debt management activities includes activities selected from a group consisting of: offering a debt transaction, underwriting a debt transaction, setting an interest rate, deferring a payment requirement, modifying an interest rate, validating title, managing inspection, recording a change in title, assessing a value of an asset, calling a loan, closing a transaction, setting terms and conditions for a transaction, providing notices required to be provided, foreclosing on a set of assets, modifying terms and conditions, setting a rating for an entity, syndicating debt, or consolidating debt.

An example system may further include a market value data collection circuit structured to monitor and report marketplace information relevant to a value of a of at least one asset of a set of assets.

An example system may further include wherein at least one asset from the set of assets is selected from group consisting of: a municipal asset, a vehicle, a ship, a plane, a building, a home, real estate property, undeveloped land, a farm, a crop, a municipal facility, a warehouse, a set of inventory, a commodity, a security, a currency, a token of value, a ticket, a cryptocurrency, a consumable item, an edible item, a beverage, a precious metal, an item of jewelry, a gemstone, intellectual property, an intellectual property right, a contractual right, an antique, a fixture, an item of furniture, an item of equipment, a tool, an item of machinery, or an item of personal property.

An example system may further include wherein the market value data collection circuit is further structured to monitor at least one pricing and financial data for items that are similar to at least one asset in the set of assets in at least one public marketplace.

An example system may further include wherein a set of similar items for valuing at least one asset from the set of assets is constructed using a similarity clustering algorithm based on attributes of the assets.

An example system may further include wherein at least one attribute of the attributes of the assets is selected from a group consisting of: a category of assets, asset age, asset condition, asset history, asset storage, or geolocation of assets.

An example system may further include a smart contract circuit structured to manage a smart contract for a debt transaction.

An example system may further include wherein the smart contract circuit is further structured to establish a set of terms and conditions for the debt transaction.

An example system may further include wherein at least one of the terms and conditions of the set of terms and conditions for the debt transaction is selected from a group consisting of: a principal amount of debt, a balance of debt, a fixed interest rate, a variable interest rate, a payment amount, a payment schedule, a balloon payment schedule, a specification of collateral, a specification of substitutability of collateral, a party, a guarantee, a guarantor, a security, a personal guarantee, a lien, a duration, a covenant, a foreclose condition, a default condition, or a consequence of default.

In embodiments, provided herein is a method for adaptive intelligence and robotic process automation capabilities of a transactional, financial and marketplace enablement. An example method may include collecting information about entities involved in a set of debt transactions, training data set of outcomes related to the entities, and a training set of debt management activities; classifying a condition of at least one entity of the entities based at least in part the training data set of outcomes related to the entities; and managing an action related to a debt based at least in part on the training set of debt management activities.

Certain further aspects of an example system are described following, any one or more of which may be present in certain embodiments. An example method may further include that the entities involved in the set of debt transactions include a set of parties and a set of assets.

An example method may further include receiving information from a set of sensors positioned on at least one asset, wherein the set of sensors configured to associate sensor information sensed by the set of sensors with a unique identifier for the at least one asset from the set of assets, and wherein the set of sensors is positioned on at least one asset from the set of assets, on a container for least one asset from the set of assets, and on a package for at least one asset from the set of assets; and storing the information in a blockchain, wherein access to the blockchain is provided via a secure access control interface for a party for a debt transaction involving the at least one asset from the set of assets.

An example method may include processing events relevant to at least one of a value, a condition, and an ownership of at least one asset of the set of assets; and processing a set of actions related to a debt transaction to which the asset is related.

An example method may include receiving interactions from at least one of the entities.

An example method may further include monitoring and reporting marketplace information relevant to a value of a of at least one asset of a set of assets.

An example method may further include that monitoring further comprises monitoring at least one pricing and financial data for items that are similar to at least one asset in the set of assets in at least one public marketplace.

An example method may further include constructing using a similarity clustering algorithm based on attributes of the assets a set of similar items for valuing at least one asset from the set of assets.

An example method may further include managing a smart contract for a debt transaction.

An example method may further include establishing a set of terms and conditions for the smart contract for the debt transaction.

In embodiments, provided herein is a system for adaptive intelligence and robotic process automation capabilities of a transactional, financial and marketplace enablement.

An example system may include a crowdsourcing data collection circuit structured to collect information about entities involved in a set of bond transactions and a training data set of outcomes related to the entities. The system may further include a condition classifying circuit structured to classify a condition of a set of issuers using the information from the crowdsourcing data collection circuit and a model, wherein the model is trained using the training data set of outcomes related to the set of issuers.

Certain further aspects of an example system are described following, any one or more of which may be present in certain embodiments. An example system may include wherein at least one entity from the entities is selected from a group consisting of: a set of entities includes entities among a set of issuers, a set of bonds, a set of parties, or a set of assets.

An example system may include wherein at least one issuer from the set of issuers is selected from a group consisting of: a municipality, a corporation, a contractor, a government entity, a non-governmental entity, or a non-profit entity.

An example system may include wherein at least one bond from the set of bonds is selected from a group consisting of: a municipal bond, a government bond, a treasury bond, an asset-backed bond, or a corporate bond.

An example system may include wherein the condition classified by the condition classifying circuit is selected from a group consisting of: a default condition, a foreclosure condition, a condition indicating violation of a covenant, a financial risk condition, a behavioral risk condition, a policy risk condition, a financial health condition, a physical defect condition, a physical health condition, an entity risk condition, or an entity health condition.

An example system may include wherein the crowdsourcing data collection circuit is structured to enable a user interface by which a user may configure a crowdsourcing request for information relevant to the condition about the set of issuers.

An example system may further include a configurable data collection and monitoring circuit structured to monitor at least one issuer from the set of issuers, wherein the configurable data collection and monitoring circuit includes a system selected from a group consisting of: Internet of Things devices, a set of environmental condition sensors, a set of social network analytic services, or a set of algorithms for querying network domains.

An example system may include wherein the configurable data collection and monitoring circuit is structured to monitor an at least one environment selected from the group consisting of: a municipal environment, a corporate environment, a securities trading environment, a real property environment, a commercial facility, a warehousing facility, a transportation environment, a manufacturing environment, a storage environment, a home, or a vehicle.

An example system may include wherein a set of bonds associated with the set of bond transactions is backed by a set of assets.

An example system may include wherein at least one asset from the set of assets includes assets selected from the group consisting of: municipal asset, a vehicle, a ship, a plane, a building, a home, real estate property, undeveloped land, a farm, a crop, a municipal facility, a warehouse, a set of inventory, a commodity, a security, a currency, a token of value, a ticket, a cryptocurrency, a consumable item, an edible item, a beverage, a precious metal, an item of jewelry, a gemstone, intellectual property, an intellectual property right, a contractual right, an antique, a fixture, an item of furniture, an item of equipment, a tool, an item of machinery, or an item of personal property.

An example system may include an automated agent circuit structured to processes events relevant to at least one of a value, a condition, and an ownership of at least one asset of the set of assets, and wherein the automated agent circuit is further structured to perform an action related to a debt transaction to which the asset is related.

An example system may include wherein the action is selected from a group consisting of: offering a debt transaction, underwriting a debt transaction, setting an interest rate, deferring a payment requirement, modifying an interest rate, validating title, managing inspection, recording a change in title, assessing the value of an asset, calling a loan, closing a transaction, setting terms and conditions for a transaction, providing notices required to be provided, foreclosing on a set of assets, modifying terms and conditions, setting a rating for an entity, syndicating debt, or consolidating debt.

An example system may include wherein the condition classifying circuit includes a system selected from a group consisting of: a machine learning system, a model-based system, a rule-based system, a deep learning system, a hybrid system, a neural network, a convolutional neural network, a feed forward neural network, a feedback neural network, a self-organizing map, a fuzzy logic system, a random walk system, a random forest system, a probabilistic system, a Bayesian system, or a simulation system.

An example system may further include an automated bond management circuit configured to manage an action related to the bond, wherein the automated bond management circuit is trained on a training set of bond management activities.

An example system may include wherein the automated bond management circuit is trained on a set of interactions of parties with a set of user interfaces involved in a set of bond transaction activities.

An example system may include wherein at least one bond transaction from the set of bond transaction includes activities selected from a group consisting of: a debt transaction, underwriting a debt transaction, setting an interest rate, deferring a payment requirement, modifying an interest rate, validating title, managing inspection, recording a change in title, assessing the value of an asset, calling a loan, closing a transaction, setting terms and conditions for a transaction, providing notices required to be provided, foreclosing on a set of assets, modifying terms and conditions, setting a rating for an entity, syndicating debt, or consolidating debt.

An example system may further include a market value data collection circuit structured to monitor and reports on marketplace information relevant to a value of at least one of the issuer and a set of assets.

An example system may include wherein reporting is on a at least one asset from the set of assets selected from a group consisting of: a municipal asset, a vehicle, a ship, a plane, a building, a home, real estate property, undeveloped land, a farm, a crop, a municipal facility, a warehouse, a set of inventory, a commodity, a security, a currency, a token of value, a ticket, a cryptocurrency, a consumable item, an edible item, a beverage, a precious metal, an item of jewelry, a gemstone, intellectual property, an intellectual property right, a contractual right, an antique, a fixture, an item of furniture, an item of equipment, a tool, an item of machinery, or an item of personal property.

An example system may include wherein the market value data collection circuit is structured to monitor pricing or financial data for items that are similar to the assets in at least one public marketplace.

An example system may include wherein a set of similar items for valuing the assets is constructed using a similarity clustering algorithm based on attributes of the assets.

An example system may include wherein at least one attribute from the attributes is selected from a group consisting of: a category of the assets, asset age, asset condition, asset history, asset storage, or geolocation of assets.

An example system may further include a smart contract circuit structured for managing a smart contract for a bond transaction.

An example system may include wherein the smart contract circuit is structured to determine terms and conditions for the bond.

An example system may include wherein at least one term and condition from the set of terms and conditions for the debt transaction that is specified and managed by the set of smart contract circuits is selected from a group consisting of: a principal amount of debt, a balance of debt, a fixed interest rate, a variable interest rate, a payment amount, a payment schedule, a balloon payment schedule, a specification of assets that back the bond, a specification of substitutability of assets, a party, an issuer, a purchaser, a guarantee, a guarantor, a security, a personal guarantee, a lien, a duration, a covenant, a foreclose condition, a default condition, or a consequence of default.

In embodiments, provided herein is a method for adaptive intelligence and robotic process automation capabilities of a transactional, financial and marketplace enablement. An example method may include collecting information about entities involved in a set of bond transactions of a set of bonds and a training data set of outcomes related to the entities; classifying a condition of a set of issuers using the collected information and a model, wherein the model is trained using the training data set of outcomes related to the set of issuers.

Certain further aspects of an example system are described following, any one or more of which may be present in certain embodiments. An example method may further include processing events relevant to at least one of a value, a condition, and an ownership of at least one asset of the set of assets; and performing an action related to a debt transaction to which the asset is related.

An example method may further include managing an action related to the bond based at least in part a training set of bond management activities.

An example method may further include monitoring and reporting on marketplace information relevant to a value of at least one of the issuer and a set of assets.

An example method may further include managing a smart contract for a bond transaction.

An example method may further include determining terms and conditions for the smart contract for at least one bond.

In embodiments, provided herein is a system for monitoring a condition of an issuer for a bond. An example platform, system, or apparatus may include a social network data collection circuit structured to collect information about at least one entity involved in at least one transaction comprising at least one bond; a condition classifying circuit structured to classify a condition of the at least one entity in accordance with a model and based on information from the social network data collection circuit, wherein the model is trained using a training data set of a plurality of outcomes related to the at least one entity; and an automated bond management circuit structured to manage an action related to the at least one bond in response to the classified condition of the at least one entity.

Certain further aspects of an example system are described following, any one or more of which may be present in certain embodiments. An example system may include wherein the at least one entity is selected from the entities consisting of: a bond issuer, a bond, a party, and an asset.

An example system may include wherein the at least one entity comprises a bond issuer selected from the bond issuers consisting of: a municipality, a corporation, a contractor, a government entity, a non-governmental entity, and a non-profit entity.

An example system may include wherein the bond is selected from the entities consisting of: a municipal bond, a government bond, a treasury bond, an asset-backed bond, and a corporate bond.

An example system may include wherein the condition classified by the condition classifying circuit comprises at least one condition selected from the conditions consisting of: a default condition, a foreclosure condition, a condition indicating violation of a covenant, a financial risk condition, a behavioral risk condition, a policy risk condition, a financial health condition, a physical defect condition, a physical health condition, an entity risk condition or an entity health condition.

An example system may include wherein the social network data collection circuit further comprises a social networking input circuit structured to receive input from a user used to configure a query for information about the at least one entity in response to the received input.

An example system may further include a data collection circuit structured to monitor at least one of an Internet of Things device, an environmental condition sensor, a crowdsourcing request circuit, a crowdsourcing communication circuit, a crowdsourcing publishing circuit, and an algorithm for querying network domains.

An example system may further include wherein the condition classifying circuit is further structured to classify the condition in response to the information from the data collection circuit.

An example system may include wherein the data collection circuit is further structured to monitor an environment selected from the group consisting of: a municipal environment, a corporate environment, a securities trading environment, a real property environment, a commercial facility, a warehousing facility, a transportation environment, a manufacturing environment, a storage environment, a home, and a vehicle.

An example system may further include wherein the condition classifying circuit is further structured to classify the condition in response to the monitored environment.

An example system may include wherein the at least one bond is backed by at least one asset.

An example system may include wherein the at least one asset is selected from the assets consisting of: a municipal asset, a vehicle, a ship, a plane, a building, a home, real estate property, undeveloped land, a farm, a crop, a municipal facility, a warehouse, a set of inventory, a commodity, a security, a currency, a token of value, a ticket, a cryptocurrency, a consumable item, an edible item, a beverage, a precious metal, an item of jewelry, a gemstone, intellectual property, an intellectual property right, a contractual right, an antique, a fixture, an item of furniture, an item of equipment, a tool, an item of machinery, and an item of personal property.

An example system may further include an event processing circuit structured to process an event relevant to at least one of a value, a condition and an ownership of the at least one asset and to undertake an action related to the at least one transaction in response to the event.

An example system may include wherein the action is selected from the actions consisting of: a bond transaction, underwriting a bond transaction, setting an interest rate, deferring a payment requirement, modifying an interest rate, validating title, managing inspection, recording a change in title, assessing the value of an asset, calling a loan, closing a transaction, setting terms and conditions for a transaction, providing notices required to be provided, foreclosing on a set of assets, modifying terms and conditions, setting a rating for an entity, syndicating bonds, and consolidating bonds.

An example system may include wherein the condition classifying circuit comprises a system selected from the systems consisting of: a machine learning system, a model-based system, a rule-based system, a deep learning system, a hybrid system, a neural network, a convolutional neural network, a feed forward neural network, a feedback neural network, a self-organizing map, a fuzzy logic system, a random walk system, a random forest system, a probabilistic system, a Bayesian system, and a simulation system.

An example system may further include an automated bond management circuit structured to manage an action related to the at least one bond, wherein the automated bond management circuit is trained on a training data set of a plurality of bond management activities.

An example system may include wherein the automated bond management circuit is trained on a plurality of interactions of parties with a plurality of user interfaces involved in a plurality of bond transaction activities.

An example system may include wherein the plurality of bond transaction activities is selected from the bond transaction activities consisting of: offering a bond transaction, underwriting a bond transaction, setting an interest rate, deferring a payment requirement, modifying an interest rate, validating title, managing inspection, recording a change in title, assessing a value of an asset, calling a loan, closing a transaction, setting terms and conditions for a transaction, providing notices required to be provided, foreclosing on a set of assets, modifying terms and conditions, setting a rating for an entity, syndicating bonds, and consolidating bonds.

An example system may further include a market value data collection circuit structured to monitor and report on marketplace information relevant to a value of at least one of a bond issuer, the at least one bond, and an asset related to the at least one bond.

An example system may include wherein the asset is selected from the assets consisting of: a municipal asset, a vehicle, a ship, a plane, a building, a home, real estate property, undeveloped land, a farm, a crop, a municipal facility, a warehouse, a set of inventory, a commodity, a security, a currency, a token of value, a ticket, a cryptocurrency, a consumable item, an edible item, a beverage, a precious metal, an item of jewelry, a gemstone, intellectual property, an intellectual property right, a contractual right, an antique, a fixture, an item of furniture, an item of equipment, a tool, an item of machinery, and an item of personal property.

An example system may include wherein the market value data collection circuit is further structured to monitor pricing or financial data for an offset asset item in at least one public marketplace.

An example system may further include wherein comprising a clustering circuit structured to construct a set of offset asset items for valuing the asset is constructed using a clustering circuit based on an attribute of the asset.

An example system may include wherein the attribute is selected from the attributes consisting of: a category, an asset age, an asset condition, an asset history, an asset storage, and a geolocation.

An example system may further include a smart contract circuit structured to manage a smart contract for the at least one transaction.

An example system may include wherein the smart contract circuit is further structured to determine a terms and conditions for the at least one bond.

An example system may include wherein the terms and conditions are selected from the group consisting of: a principal amount of debt, a balance of debt, a fixed interest rate, a variable interest rate, a payment amount, a payment schedule, a balloon payment schedule, a specification of assets that back the at least one bond, a specification of substitutability of assets, a party, an issuer, a purchaser, a guarantee, a guarantor, a security, a personal guarantee, a lien, a duration, a covenant, a foreclose condition, a default condition, and a consequence of default. In embodiments, provided herein is a method for monitoring a condition of an issuer for a bond. An example method may include collecting social network information about at least one entity involved in at least one transaction comprising at least one bond; and classifying a condition of the at least one entity in accordance with a model and based on the social network information, wherein the model is trained using a training data set of a plurality of outcomes related to the at least one entity, and managing an action related to the at least one bond in response to the classified condition of the at least one entity.

Certain further aspects of an example method are described following, any one or more of which may be present in certain embodiments. An example method may further include processing an event relevant to at least one of a value, a condition, and an ownership of at least one asset related to the at least one bond and undertaking an action related to the at least one transaction in response to the event.

An example method may further include training an automated bond management circuit on a training set of a plurality of bond management activities to manage an action related to the at least one bond, and wherein managing the action comprises operating the automated bond management circuit. An example method may further include monitoring and reporting on marketplace information relevant to a value of at least one of a bond issuer, the at least one bond, and an asset.

In embodiments, provided herein is a system for monitoring a condition of an issuer for a bond. An example platform, system, or apparatus may include an Internet of Things data collection circuit structured to collect information about at least one entity involved in at least one transaction comprising at least one bond; and a condition classifying circuit structured to classify a condition of the at least one entity in accordance with a model and based on information from the Internet of Things data collection circuit, wherein the model is trained using a training data set of a plurality of outcomes related to the at least one entity, and an event processing circuit structured undertake an action related to the at least one transaction in response to the classified condition of the at least one entity.

Certain further aspects of an example system are described following, any one or more of which may be present in certain embodiments. An example system may include wherein the at least one entity is selected from the entities consisting of: a bond issuer, a bond, a party, and an asset.

An example system may include wherein the bond issuer is selected from the bond issuers consisting of: a municipality, a corporation, a contractor, a government entity, a non-governmental entity, and a non-profit entity.

An example system may include wherein the bond is selected from the entities consisting of: a municipal bond, a government bond, a treasury bond, an asset-backed bond, and a corporate bond.

An example system may include wherein the condition classified by the condition classifying circuit at least one of a default condition, a foreclosure condition, a condition indicating violation of a covenant, a financial risk condition, a behavioral risk condition, a policy risk condition, a financial health condition, a physical defect condition, a physical health condition, an entity risk condition, or an entity health condition.

An example system may include wherein the Internet of Things data collection circuit further comprises an Internet of Things input circuit structured to receive input from a user used to configure a query for information about the at least one entity.

An example system may further include a data collection circuit structured to monitor at least one of an Internet of Things device, an environmental condition sensor, a crowdsourcing request circuit, a crowdsourcing communication circuit, a crowdsourcing publishing circuit, and an algorithm for querying network domains.

An example system may further include wherein the condition classifying circuit is further structured to classify the condition in response to the information from the data collection circuit.

An example system may include wherein the data collection circuit is further structured to monitor an environment selected from the group consisting of: a municipal environment, a corporate environment, a securities trading environment, a real property environment, a commercial facility, a warehousing facility, a transportation environment, a manufacturing environment, a storage environment, a home, and a vehicle.

An example system may include wherein the condition classifying circuit is further structured to classify the condition in response to the monitored environment.

An example system may include wherein the at least one bond is backed by at least one asset.

An example system may include wherein the at least one asset is selected from the assets consisting of: a municipal asset, a vehicle, a ship, a plane, a building, a home, real estate property, undeveloped land, a farm, a crop, a municipal facility, a warehouse, a set of inventory, a commodity, a security, a currency, a token of value, a ticket, a cryptocurrency, a consumable item, an edible item, a beverage, a precious metal, an item of jewelry, a gemstone, intellectual property, an intellectual property right, a contractual right, an antique, a fixture, an item of furniture, an item of equipment, a tool, an item of machinery, and an item of personal property.

An example system may further include an event processing circuit structured to process an event relevant to at least one of a value, a condition, and an ownership of the at least one asset and undertake an action related to the at least one transaction further in response to the event.

An example system may include wherein the action is selected from the actions consisting of: a bond transaction, underwriting a bond transaction, setting an interest rate, deferring a payment requirement, modifying an interest rate, validating title, managing inspection, recording a change in title, assessing the value of an asset, calling a loan, closing a transaction, setting terms and conditions for a transaction, providing notices required to be provided, foreclosing on a set of assets, modifying terms and conditions, setting a rating for an entity, syndicating bonds, and consolidating bonds.

An example system may include wherein the condition classifying circuit comprises a system selected from the systems consisting of: a machine learning system, a model-based system, a rule-based system, a deep learning system, a hybrid system, a neural network, a convolutional neural network, a feed forward neural network, a feedback neural network, a self-organizing map, a fuzzy logic system, a random walk system, a random forest system, a probabilistic system, a Bayesian system, and a simulation system.

An example system may further include an automated bond management circuit structured to manage an action related to the at least one bond, wherein the automated bond management circuit is trained on a training data set of a plurality of bond management activities.

An example system may include wherein the automated bond management circuit is trained on a plurality of interactions of parties with a plurality of user interfaces involved in a plurality of bond transaction activities.

An example system may include wherein the plurality of bond transaction activities is selected from the bond transaction activities consisting of: offering a bond transaction, underwriting a bond transaction, setting an interest rate, deferring a payment requirement, modifying an interest rate, validating title, managing inspection, recording a change in title, assessing a value of an asset, calling a loan, closing a transaction, setting terms and conditions for a transaction, providing notices required to be provided, foreclosing on a set of assets, modifying terms and conditions, setting a rating for an entity, syndicating bonds, and consolidating bonds.

An example system may further include a market value data collection circuit structured to monitor and report on marketplace information relevant to a value of at least one of a bond issuer, the at least one bond, and an asset related to the at least one bond.

An example system may include wherein the asset is selected from the assets consisting of: a municipal asset, a vehicle, a ship, a plane, a building, a home, real estate property, undeveloped land, a farm, a crop, a municipal facility, a warehouse, a set of inventory, a commodity, a security, a currency, a token of value, a ticket, a cryptocurrency, a consumable item, an edible item, a beverage, a precious metal, an item of jewelry, a gemstone, intellectual property, an intellectual property right, a contractual right, an antique, a fixture, an item of furniture, an item of equipment, a tool, an item of machinery, and an item of personal property.

An example system may include wherein the market value data collection circuit is further structured to monitor pricing or financial data for an offset asset item in at least one public marketplace.

An example system may further include a clustering circuit structured to construct wherein a set of offset asset items for valuing the asset is constructed using a clustering circuit based on an attribute of the asset.

An example system may include wherein the attribute is selected from the attributes consisting of: a category, an asset age, an asset condition, an asset history, an asset storage, and a geolocation.

An example system may further include a smart contract circuit structured to manage a smart contract for the at least one transaction.

An example system may include wherein the smart contract circuit is further structured to determine a terms and conditions for the at least one bond.

An example system may include wherein the terms and conditions are selected from the group consisting of: a principal amount of debt, a balance of debt, a fixed interest rate, a variable interest rate, a payment amount, a payment schedule, a balloon payment schedule, a specification of assets that back the at least one bond, a specification of substitutability of assets, a party, an issuer, a purchaser, a guarantee, a guarantor, a security, a personal guarantee, a lien, a duration, a covenant, a foreclose condition, a default condition, and a consequence of default.

In embodiments, provided herein is a method for monitoring a condition of an issuer for a bond. An example method may include collecting Internet of Things information about at least one entity involved in at least one transaction comprising at least one bond; and classifying a condition of the at least one entity in accordance with a model and based on the Internet of Things information, wherein the model is trained using a training data set of a plurality of outcomes related to the at least one entity and undertaking an action related to the at least one transaction in response to the classified condition of the at least one entity.

Certain further aspects of an example method are described following, any one or more of which may be present in certain embodiments. An example method may further include processing an event relevant to at least one of a value, a condition, and an ownership of at least one asset and undertaking an action related to the at least one transaction in response to the event. An example method may further include training an automated bond management circuit on a training set of a plurality of bond management activities to manage an action related to the at least one bond. An example method may further include monitoring and reporting on marketplace information relevant to a value of at least one of a bond issuer, the at least one bond, and an asset.

In embodiments, an example platform or system may include an Internet of Things data collection circuit structured to collect information about at least one entity involved in at least one subsidized loan transaction; a condition classifying circuit comprising a model structured to classify at least one parameter of at least one subsidized loan involved in the at least one subsidized loan transaction based on the information from the Internet of Things data collection circuit, wherein the model is trained using a training data set of a plurality of outcomes related to the at least one subsidized loan: and a smart contract circuit structured to automatically modify a terms and conditions of the at least one subsidized loan based on the classified parameter from the condition classifying circuit.

Certain further aspects of an example system are described following, any one or more of which may be present in certain embodiments. An example system may include wherein the at least one entity is selected from the entities consisting of: the at least one subsidized loan, a distinct at least one subsidized loan involved in the at least one subsidized loan transaction, a party, a subsidy, a guarantor, a subsidizing party, and a collateral.

An example system may include wherein the at least one entity comprises a party is selected from the parties consisting of: at least one of a municipality, a corporation, a contractor, a government entity, a non-governmental entity, and a non-profit entity.

An example system may include wherein the at least one subsidized loan comprises at least one of a municipal subsidized loan, a government subsidized loan, a student loan, an asset-backed subsidized loan, or a corporate subsidized loan.

An example system may include wherein the condition classified by the condition classifying circuit is selected from the conditions consisting of: a default condition, a foreclosure condition, a condition indicating violation of a covenant, a financial risk condition, a behavioral risk condition, a contractual performance condition, a policy risk condition, a financial health condition, a physical defect condition, a physical health condition, an entity risk condition and an entity health condition.

An example system may include wherein the at least one subsidized loan is a student loan and the condition classifying circuit classifies at least one of a progress of a student toward a degree, a participation of a student in a non-profit activity, and a participation of a student in a public interest activity.

An example system may include wherein further comprising a user interface of the Internet of Things data collection circuit structured to enable a user to configure a query for information about the at least one entity.

An example system may include wherein further comprising at least one configurable data collection and circuit structured to monitor the at least one entity selected from the group consisting of: a social network analytic circuit, an environmental condition circuit, a crowdsourcing circuit, and an algorithm for querying a network domain.

An example system may include wherein the at least one configurable data collection and circuit monitors an environment selected from the environments consisting of: a municipal environment, an educational environment, a corporate environment, a securities trading environment, a real property environment, a commercial facility, a warehousing facility, a transportation environment, a manufacturing environment, a storage environment, a home, and a vehicle.

An example system may include wherein the at least one subsidized loan is backed by at least one asset.

An example system may include wherein the at least one asset is selected from the assets consisting of: a municipal asset, a vehicle, a ship, a plane, a building, a home, real estate property, undeveloped land, a farm, a crop, a municipal facility, a warehouse, a set of inventory, a commodity, a security, a currency, a token of value, a ticket, a cryptocurrency, a consumable item, an edible item, a beverage, a precious metal, an item of jewelry, a gemstone, intellectual property, an intellectual property right, a contractual right, an antique, a fixture, an item of furniture, an item of equipment, a tool, an item of machinery, and an item of personal property.

An example system may include wherein further comprising an automated agent structured to process at least one event relevant to at least one of a value, a condition, and an ownership of the at least one asset and undertake an action related to the at least one subsidized loan transaction to which the at least one asset is related.

An example system may include wherein the action is selected from the actions consisting of: a subsidized loan transaction, underwriting a subsidized loan transaction, setting an interest rate, deferring a payment requirement, modifying an interest rate, validating a title, managing an inspection, recording a change in a title, assessing the value of an asset, calling a loan, closing a transaction, setting terms and conditions for a transaction, providing notices required to be provided, foreclosing on a set of assets, modifying terms and conditions, setting a rating for an entity, syndicating a subsidized loan, and consolidating a subsidized loan.

An example system may include wherein the condition classifying circuit comprises a system selected from the systems consisting of: a machine learning system, a model-based system, a rule-based system, a deep learning system, a hybrid system, a neural network, a convolutional neural network, a feed forward neural network, a feedback neural network, a self-organizing map, a fuzzy logic system, a random walk system, a random forest system, a probabilistic system, a Bayesian system, and a simulation system.

An example system may include wherein further comprising an automated subsidized loan management circuit structured to manage an action related to the at least one subsidized loan, wherein the automated subsidized loan management circuit is trained on a training set of subsidized loan management activities.

An example system may include wherein the automated subsidized loan management circuit is trained on a plurality of interactions of parties with a plurality of user interfaces involved in a plurality of subsidized loan transaction activities.

An example system may include wherein the plurality of subsidized loan transaction activities are selected from the activities consisting of: offering a subsidized loan transaction, underwriting a subsidized loan transaction, setting an interest rate, deferring a payment requirement, modifying an interest rate, validating a title, managing an inspection, recording a change in a title, assessing a value of an asset, calling a loan, closing a transaction, setting terms and conditions for a transaction, providing notices required to be provided, foreclosing on a set of assets, modifying terms and conditions, setting a rating for an entity, syndicating a subsidized loan, and consolidating a subsidized loan.

An example system may include wherein further comprising a blockchain service circuit structured to record the modified set of terms and conditions for the at least one subsidized loan in a distributed ledger.

An example system may include wherein further comprising a market value data collection circuit structured to monitor and report on marketplace information relevant to a value of at least one of an issuer, at least one subsidized loan, and at least one asset.

An example system may include wherein reporting is on at least one asset selected from the assets consisting of: a municipal asset, a vehicle, a ship, a plane, a building, a home, real estate property, undeveloped land, a farm, a crop, a municipal facility, a warehouse, a set of inventory, a commodity, a security, a currency, a token of value, a ticket, a cryptocurrency, a consumable item, an edible item, a beverage, a precious metal, an item of jewelry, a gemstone, intellectual property, an intellectual property right, a contractual right, an antique, a fixture, an item of furniture, an item of equipment, a tool, an item of machinery, and an item of personal property.

An example system may include wherein the market value data collection circuit is further structured to monitor pricing or financial data for an offset asset item in at least one public marketplace.

An example system may include a clustering circuit structured to construct a set of offset asset items for valuing the at least one asset is constructed using a clustering circuit based on an attribute of the at least one asset.

An example system may include wherein the attribute is selected from the attributes consisting of a category, an asset age, an asset condition, an asset history, an asset storage, and a geolocation.

An example system may include wherein further comprising a smart contract circuit structured to manage a smart contract for the at least one subsidized loan transaction.

An example system may include wherein the smart contract is further structured to modify the smart contract in response to the classified parameter of the at least one subsidized loan.

An example system may include wherein the terms and conditions for the at least one subsidized loan that are automatically modified by the smart contract circuit are selected from the group consisting of: a principal amount of debt, a balance of debt, a fixed interest rate, a variable interest rate, a payment amount, a payment schedule, a balloon payment schedule, a specification of assets that back the at least one subsidized loan, a specification of substitutability of assets, a party, an issuer, a purchaser, a guarantee, a guarantor, a security, a personal guarantee, a lien, a duration, a covenant, a foreclose condition, a default condition, and a consequence of default.

In embodiments, an example method may include collecting information about at least one entity involved in at least one subsidized loan transaction; classifying at least one parameter of at least one subsidized loan involved in the at least one subsidized loan transaction based on the information using a model trained on a training data set of a plurality of outcomes related to the at least one subsidized loan; and automatically modifying a terms and conditions of the at least one subsidized loan based on the classified parameter.

Certain further aspects of an example method are described following, any one or more of which may be present in certain embodiments. An example method may include wherein further comprising processing at least one event relevant to at least one of a value, a condition, or an ownership of the at least one asset related to the at least one subsidized loan and undertaking an action related to the at least one subsidized loan transaction to which the at least one asset is related.

An example method may include wherein further comprising recording the modified set of terms and conditions for the at least one subsidized loan in a distributed ledger.

An example method may include wherein further comprising monitoring and reporting on marketplace information relevant to a value of at least one of an issuer, the at least one subsidized loan, or at least one asset related to the at least one subsidized loan.

In embodiments, an example platform or system may include a social network analytic data collection circuit structured to collect social network information about at least one entity involved in at least one subsidized loan transaction; a condition classifying circuit comprising a model structured to classify at least one parameter of at least one subsidized loan involved in the at least one subsidized loan transaction based on the social network information from the social network analytic data collection circuit, wherein the model is trained using a training data set of outcomes related to the at least one subsidized loan; and a smart contract circuit structured to automatically modify a terms and conditions of the at least one subsidized loan based on the classified at least one parameter.

Certain further aspects of an example system are described following, any one or more of which may be present in certain embodiments. An example system may include wherein the at least one entity is selected from the entities consisting of: the at least one subsidized loan, a distinct at least one subsidized loan involved in the at least one subsidized loan transaction, a party, a subsidy, a guarantor, a subsidizing party, and a collateral.

An example system may include wherein a party subsidizing the at least one subsidized loan is selected from the parties consisting of: a municipality, a corporation, a contractor, a government entity, a non-governmental entity, and a non-profit entity.

An example system may include wherein the at least one subsidized loan comprises at least one of a municipal subsidized loan, a government subsidized loan, a student loan, an asset-backed subsidized loan, or a corporate subsidized loan.

An example system may include wherein the at least one parameter classified by the condition classifying circuit is selected from the conditions consisting of: a default condition, a foreclosure condition, a condition indicating violation of a covenant, a financial risk condition, a behavioral risk condition, a contractual performance condition, a policy risk condition, a financial health condition, a physical defect condition, a physical health condition, an entity risk condition and an entity health condition.

An example system may include wherein the at least one subsidized loan is a student loan and the condition classifying circuit classifies at least one of a progress of a student toward a degree, a participation of a student in a non-profit activity, or a participation of a student in a public interest activity.

An example system may include wherein further comprising a user interface of the social network analytic data collection circuit structured to enable a user to configure a query for information about the at least one entity, wherein, in response to the query, wherein the social network analytic data collection circuit initiates at least one algorithm that searches and retrieves data from at least one social network in response to the query.

An example system may include wherein further comprising at least one configurable data collection and circuit structured to monitor the at least one entity, and selected from the group consisting of: a social network analytic circuit, an environmental condition circuit, a crowdsourcing circuit, and an algorithm for querying a network domain.

An example system may include wherein the at least one configurable data collection and circuit monitors an environment selected from the environments consisting of: a municipal environment, an educational environment, a corporate environment, a securities trading environment, a real property environment, a commercial facility, a warehousing facility, a transportation environment, a manufacturing environment, a storage environment, a home, and a vehicle.

An example system may include wherein the at least one subsidized loan is backed by at least one asset.

An example system may include wherein the at least one asset is selected from the assets consisting of: a municipal asset, a vehicle, a ship, a plane, a building, a home, real estate property, undeveloped land, a farm, a crop, a municipal facility, a warehouse, a set of inventory, a commodity, a security, a currency, a token of value, a ticket, a cryptocurrency, a consumable item, an edible item, a beverage, a precious metal, an item of jewelry, a gemstone, intellectual property, an intellectual property right, a contractual right, an antique, a fixture, an item of furniture, an item of equipment, a tool, an item of machinery, and an item of personal property.

An example system may include wherein further comprising an automated agent structured to process at least one event relevant to at least one of a value, a condition, or an ownership of the at least one asset and undertake an action related to the at least one subsidized loan transaction to which the at least one asset is related.

An example system may include wherein the action is selected from the actions consisting of: a subsidized loan transaction, underwriting a subsidized loan transaction, setting an interest rate, deferring a payment requirement, modifying an interest rate, validating a title, managing an inspection, recording a change in a title, assessing the value of an asset, calling a loan, closing a transaction, setting terms and conditions for a transaction, providing notices required to be provided, foreclosing on a set of assets, modifying terms and conditions, setting a rating for an entity, syndicating a subsidized loan, and consolidating a subsidized loan.

An example system may include wherein the condition classifying circuit comprises a system selected from the systems consisting of: a machine learning system, a model-based system, a rule-based system, a deep learning system, a hybrid system, a neural network, a convolutional neural network, a feed forward neural network, a feedback neural network, a self-organizing map, a fuzzy logic system, a random walk system, a random forest system, a probabilistic system, a Bayesian system, and a simulation system.

An example system may include wherein further comprising an automated subsidized loan management circuit structured to manage an action related to the at least one subsidized loan, and wherein the automated subsidized loan management circuit is trained on a training set of subsidized loan management activities.

An example system may include wherein the automated subsidized loan management circuit is trained on a plurality of interactions of parties with a plurality of user interfaces involved in a plurality of subsidized loan transaction activities.

An example system may include wherein the plurality of subsidized loan transaction activities are selected from the activities consisting of: offering a subsidized loan transaction, underwriting a subsidized loan transaction, setting an interest rate, deferring a payment requirement, modifying an interest rate, validating a title, managing an inspection, recording a change in a title, assessing a value of an asset, calling a loan, closing a transaction, setting terms and conditions for a transaction, providing notices required to be provided, foreclosing on a set of assets, modifying terms and conditions, setting a rating for an entity, syndicating a subsidized loan, and consolidating a subsidized loan.

An example system may include wherein further comprising a blockchain service circuit structured to record the modified set of terms and conditions for the at least one subsidized loan in a distributed ledger.

An example system may include wherein further comprising a market value data collection circuit structured to monitor and report on marketplace information relevant to a value of at least one of an issuer, at least one subsidized loan, or at least one asset.

An example system may include wherein reporting is on at least one asset selected from the assets consisting of: a municipal asset, a vehicle, a ship, a plane, a building, a home, real estate property, undeveloped land, a farm, a crop, a municipal facility, a warehouse, a set of inventory, a commodity, a security, a currency, a token of value, a ticket, a cryptocurrency, a consumable item, an edible item, a beverage, a precious metal, an item of jewelry, a gemstone, intellectual property, an intellectual property right, a contractual right, an antique, a fixture, an item of furniture, an item of equipment, a tool, an item of machinery, and an item of personal property.

An example system may include wherein the market value data collection circuit is further structured to monitor pricing or financial data for an offset asset item in at least one public marketplace.

An example system may further include a clustering circuit structured to construct a set of offset asset items for valuing the at least one asset is constructed using a clustering circuit based on an attribute of the at least one asset.

An example system may include wherein the attribute is selected from the attributes consisting of: a category, an asset age, an asset condition, an asset history, an asset storage, and a geolocation.

An example system may include wherein further comprising a smart contract circuit structured to manage a smart contract for the at least one subsidized loan transaction.

An example system may include wherein the smart contract circuit sets a terms and conditions for the at least one subsidized loan.

An example system may include wherein the terms and conditions for the at least one subsidized loan that are specified and managed by the smart contract circuit are selected from the group consisting of: a principal amount of debt, a balance of debt, a fixed interest rate, a variable interest rate, a payment amount, a payment schedule, a balloon payment schedule, a specification of assets that back the at least one subsidized loan, a specification of substitutability of assets, a party, an issuer, a purchaser, a guarantee, a guarantor, a security, a personal guarantee, a lien, a duration, a covenant, a foreclose condition, a default condition, and a consequence of default.

In embodiments, an example method may include collecting social network information about at least one entity involved in at least one subsidized loan transaction; classifying at least one parameter of at least one subsidized loan involved in the at least one subsidized loan transaction based on the social network information using a model trained on a training data set of outcomes related to the at least one subsidized loan; automatically modifying a terms and conditions of the at least one subsidized loan based on the classified at least one parameter.

Certain further aspects of an example method are described following, any one or more of which may be present in certain embodiments. An example method may include wherein further comprising processing at least one event relevant to at least one of a value, a condition, and an ownership of the at least one asset and undertaking an action related to the at least one subsidized loan transaction to which the at least one asset is related.

An example method may include wherein further comprising recording the modified set of terms and conditions for the at least one subsidized loan in a distributed ledger.

An example method may include wherein further comprising monitoring and reporting on marketplace information relevant to a value of at least one of an issuer, the at least one subsidized loan, or at least one asset.

In embodiments, provided herein is a system for automating handling of a subsidized loan. An example platform or system may include a crowdsourcing services circuit structured to collect information related to a set of entities involved in a set of subsidized loan transactions; a condition classifying circuit comprising a model and an artificial intelligence services circuit structured to classify a set of parameters of the set of subsidized loans involved in the transactions based on information from the crowdsourcing services circuit, wherein the model is trained using a training data set of outcomes related to subsidized loans; and a smart contract circuit for automatically modifying the terms and conditions of a subsidized loan based on the classified set of parameters from the condition classifying circuit.

Certain further aspects of an example system are described following, any one or more of which may be present in certain embodiments. An example system may include wherein the set of entities includes entities among a set of subsidized loans, a set of parties, a set of subsidies, a set of guarantors, a set of subsidizing parties, and a set of collateral.

An example system may include wherein each entity of the set of entities includes entities selected from the list consisting of: a subsidized loan from a set of subsidized loans corresponding to the set of subsidized loan transactions, a party related to at least one of the set of subsidized loan transactions, a subsidy corresponding to a subsidized loan from a set of subsidized loans corresponding to the set of subsidized loan transactions, a guarantor related to at least one of the set of subsidized loan transactions, a subsidy corresponding to a subsidized loan from a set of subsidized loans corresponding to the set of subsidized loan transactions, a subsidized party related to at least one of the set of subsidized loan transactions, a subsidizing party related to at least one of the set of subsidized loan transactions, a subsidy corresponding to a subsidized loan from a set of subsidized loans corresponding to the set of subsidized loan transactions, and an item of collateral related to at least one of the set of subsidized loan transactions, a subsidy corresponding to a subsidized loan from a set of subsidized loans corresponding to the set of subsidized loan transactions.

An example system may at least one entity of the set of entities includes a subsidizing party related to at least one of the set of subsidized loan transactions, wherein the subsidizing party includes at least one of a municipality, a corporation, a contractor, a government entity, a non-governmental entity, or a non-profit entity.

An example system may include wherein each loan of a set of subsidized loans corresponding to the set of loan transactions includes at least one of a municipal subsidized loan, a government subsidized loan, a student loan, an asset-backed subsidized loan, or a corporate subsidized loan.

An example system may include wherein the condition classified by the condition classifying circuit is among a default condition, a foreclosure condition, a condition indicating violation of a covenant, a financial risk condition, a behavioral risk condition, a contractual performance condition, a policy risk condition, a financial health condition, a physical defect condition, a physical health condition, an entity risk condition, and an entity health condition.

An example system may include wherein the subsidized loan is a student loan and the condition classifying circuit classifies at least one of the progress of a student toward a degree, the participation of a student in a non-profit activity, and a participation of the student in a public interest activity.

An example system may include wherein the crowdsourcing services circuit is further structured with a user interface by which a user may configure a query for information about the set of entities and the crowdsourcing services circuit automatically configures a crowdsourcing request based on the query.

An example system may include further comprising a configurable data collection and monitoring services circuit for monitoring the entities wherein the configurable data collection and monitoring services circuit includes at least one of a set of: Internet of Things services, a set of environmental condition sensors, a set of social network analytic services, and a set of algorithms for querying network domains.

An example system may include wherein the configurable data collection and monitoring services circuit is further structured to monitor an environment selected from among a municipal environment, an educational environment, a corporate environment, a securities trading environment, a real property environment, a commercial facility, a warehousing facility, a transportation environment, a manufacturing environment, a storage environment, a home, and a vehicle.

An example system may include wherein the set of subsidized loans is backed by a set of assets.

An example system may include wherein the set of assets, each selected from among: a municipal asset, a vehicle, a ship, a plane, a building, a home, real estate property, undeveloped land, a farm, a crop, a municipal facility, a warehouse, a set of inventory, a commodity, a security, a currency, a token of value, a ticket, a cryptocurrency, a consumable item, an edible item, a beverage, a precious metal, an item of jewelry, a gemstone, intellectual property, an intellectual property right, a contractual right, an antique, a fixture, an item of furniture, an item of equipment, a tool, an item of machinery, and an item of personal property.

An example system may include further comprising an automated agent circuit structured to process events relevant to at least one of a value, a condition, or an ownership of at least one asset of the set of assets and undertakes an action related to a subsidized loan transaction to which the at least one asset is related.

An example system may include wherein the action is selected from among offering a subsidized loan transaction, underwriting a subsidized loan transaction, setting an interest rate, deferring a payment requirement, modifying an interest rate, validating title, managing inspection, recording a change in title, assessing the value of an asset, calling a loan, closing a transaction, setting terms and conditions for a transaction, providing notices required to be provided, foreclosing on a set of assets, modifying terms and conditions, setting a rating for an entity, syndicating subsidized loans, or consolidating subsidized loans.

An example system may include wherein the artificial intelligence services circuit comprises at least one of a machine learning system, a model-based system, a rule-based system, a deep learning system, a hybrid system, a neural network, a convolutional neural network, a feed forward neural network, a feedback neural network, a self-organizing map, a fuzzy logic system, a random walk system, a random forest system, a probabilistic system, a Bayesian system, and a simulation system.

An example system may include further comprising an automated subsidized loan management circuit structured to manage an action related to the subsidized loan, wherein the automated subsidized loan management circuit is trained on a training set of subsidized loan management activities.

An example system may include wherein the automated subsidized loan management circuit is further trained on a set of interactions of parties with a set of user interfaces, wherein the parties are involved in a set of subsidized loan transaction activities.

An example system may include wherein the set of subsidized loan transaction activities includes activities each selected from among offering a subsidized loan transaction, underwriting a subsidized loan transaction, setting an interest rate, deferring a payment requirement, modifying an interest rate, validating title, managing inspection, recording a change in title, assessing the value of an asset, calling a loan, closing a transaction, setting terms and conditions for a transaction providing notices required to be provided, foreclosing on a set of assets, modifying terms and conditions, setting a rating for an entity, syndicating subsidized loans, or consolidating subsidized loans.

An example system may include further comprising a blockchain services circuit structured to record the modified set of terms and conditions for a set of subsidized loans corresponding to the set of subsidized loan transactions in a distributed ledger.

An example system may include further comprising a market value data collection service circuit structured to monitor and report on marketplace information relevant to the value of at least one of a party related to the subsidized loan, a set of subsidized loans corresponding to the set of subsidized loan transactions, and a set of assets.

An example system may include wherein reporting is on a set of assets that includes at least one of a municipal asset, a vehicle, a ship, a plane, a building, a home, real estate property, undeveloped land, a farm, a crop, a municipal facility, a warehouse, a set of inventory, a commodity, a security, a currency, a token of value, a ticket, a cryptocurrency, a consumable item, an edible item, a beverage, a precious metal, an item of jewelry, a gemstone, intellectual property, an intellectual property right, a contractual right, an antique, a fixture, an item of furniture, an item of equipment, a tool, an item of machinery, or an item of personal property.

An example system may include wherein the market value data collection service circuit is further structured to monitor pricing or financial data for items that are similar to the assets of the set of assets in at least one public marketplace.

An example system may include wherein a set of similar items for valuing the assets of the set of assets is constructed using a similarity clustering algorithm based on the attributes of the assets.

An example system may include wherein the attributes are selected from among a category of the assets, asset age, asset condition, asset history, asset storage, or geolocation of assets.

An example system may include further comprising a smart contract services circuit for managing a smart contract for the subsidized loan.

An example system may include wherein the smart contract services circuit is further structured to set terms and conditions for the subsidized loan.

An example system may include wherein the terms and conditions for the debt transaction that are specified and managed by the smart contract services circuit is selected from among a principal amount of debt, a balance of debt, a fixed interest rate, a variable interest rate, a payment amount, a payment schedule, a balloon payment schedule, a specification of assets that back the subsidized loan, a specification of substitutability of assets, a party, an issuer, a purchaser, a guarantee, a guarantor, a security, a personal guarantee, a lien, a duration, a covenant, a foreclose condition, a default condition, or a consequence of default.

In embodiments, provided herein is a method for facilitating automating handling of a subsidized loan. An example method may include collecting information related to a set of entities involved in a set of subsidized loan transactions; classifying a set of parameters of the set of subsidized loans involved in the subsidized loan transactions based on an artificial intelligence service, a model, and information from a crowdsourcing service, wherein the model is trained using a training data set of outcomes related to subsidized loans; and modifying terms and conditions of a subsidized loan based on the classified set of parameters.

Certain further aspects of an example method are described following, any one or more of which may be present in certain embodiments. An example method may include wherein the set of entities includes entities selected from among a set of subsidized loans, a set of parties, a set of subsidies, a set of guarantors, a set of subsidizing parties, or a set of collateral.

An example method may include wherein the set of entities comprise a set of subsidizing parties, and wherein each party of the set of subsidizing parties includes at least one of a municipality, a corporation, a contractor, a government entity, a non-governmental entity, or a non-profit entity.

An example method may include wherein the set of subsidized loans includes at least one of a municipal subsidized loan, a government subsidized loan, a student loan, an asset-backed subsidized loan, and a corporate subsidized loan.

An example method may include wherein the subsidized loan is a student loan wherein the classifying is based on at least one of the progress of a student toward a degree, the participation of a student in a non-profit activity, and the participation of the student in a public interest activity.

In embodiments, an example platform or system may include an asset identification service circuit structured to interpret a plurality of assets corresponding to a financial entity configured to take custody of the plurality of assets; an identity management service circuit structured to authenticate a plurality of identifiers corresponding to actionable entities entitled to take action with respect to the plurality of assets, wherein the plurality of identifiers comprises at least one credential; a blockchain service circuit structured to store a plurality of asset control features in a blockchain structure, wherein the blockchain structure comprises a distributed ledger configuration; and a financial management circuit structured to communicate the interpreted plurality of assets and authenticated plurality of identifiers to the blockchain service circuit for storage in the blockchain structure as asset control features, and wherein the blockchain service circuit is further structured to record the asset control features in the distributed ledger configuration as asset events Certain further aspects of an example system are described following, any one or more of which may be present in certain embodiments. An example system may include wherein the at least one credential comprises an owner credential, an agent credential, a beneficiary credential, a trustee credential, or a custodian credential.

An example system may include wherein the asset events include events selected from among: transfer of title, death of an owner, disability of an owner, bankruptcy of an owner, foreclosure, placement of a lien, use of assets as collateral, designation of a beneficiary, undertaking a loan against assets, providing a notice with respect to assets, inspection of assets, assessment of assets, reporting on assets for taxation purposes, allocation of ownership of assets, disposal of assets, sale of assets, purchase of assets, or designation of an ownership status.

An example system may include a data collection circuit structured to monitor at least one of the interpretation of the plurality of assets, the authentication of the plurality of identifiers, and the recording of asset events.

An example system may include wherein the actionable entities each include at least one of an owner, a beneficiary, an agent, a trustee, or a custodian.

An example system may include a smart contract circuit structured to manage the custody of the plurality of assets, and wherein at least one asset event related to the plurality of assets is managed by the smart contract circuit based on a plurality of terms and conditions embodied in a smart contract configuration and based on data collected by the data collection service circuit.

An example system may include wherein the at least one asset event related to the plurality of assets comprises at least one event selected from among a transfer of title, death of an owner, disability of an owner, bankruptcy of an owner, foreclosure, placement of a lien, use of assets as collateral, designation of a beneficiary, undertaking a loan against assets, providing a notice with respect to assets, inspection of assets, assessment of assets, reporting on assets for taxation purposes, allocation of ownership of assets, disposal of assets, sale of assets, purchase of assets, and designation of an ownership status.

An example system may include wherein the data collection circuit further includes at least one system selected from the systems consisting of: an Internet of Things system, a camera system, a networked monitoring system, an internet monitoring system, a mobile device system, a wearable device system, a user interface system, and an interactive crowdsourcing system.

An example system may include wherein each of the asset identification service circuit, identity management service circuit, blockchain service circuit, and the financial management circuit further comprise a corresponding application programming interface (API) component structured to facilitate communication among the circuits of the system. The corresponding API components of the circuits further include user interfaces structured to interact with a plurality of users of the system.

An example system may include the blockchain service circuit further structured to share and distribute the asset events with the plurality of actionable entities.

In embodiments, an example method may include interpreting a plurality of assets corresponding to a financial entity configured to take custody of the plurality of assets; authenticating a plurality of identifiers corresponding to actionable entities entitled to take action with respect to the plurality of assets, wherein the plurality of identifiers comprises at least one credential; storing a plurality of asset control features in a blockchain structure, wherein the blockchain structure comprises a distributed ledger configuration; and communicating the interpreted plurality of assets and authenticated plurality of identifiers for storage in the blockchain structure as asset control features, wherein the asset control features are recorded in the distributed ledger configuration as asset events.

An example method may include wherein the at least one credential comprises an owner credential, an agent credential, a beneficiary credential, a trustee credential, or a custodian credential.

An example method may include wherein the asset events each include at least on event selected from among transfer of title, death of an owner, disability of an owner, bankruptcy of an owner, foreclosure, placement of a lien, use of assets as collateral, designation of a beneficiary, undertaking a loan against assets, providing a notice with respect to assets, inspection of assets, assessment of assets, reporting on assets for taxation purposes, allocation of ownership of assets, disposal of assets, sale of assets, purchase of assets, or designation of an ownership status.

An example method may include monitoring at least one of the interpretation of the plurality of assets, the authentication of the plurality of identifiers, or the recording of asset events.

An example method may include wherein the actionable entities each comprise at least one of an owner, a beneficiary, an agent, a trustee, or a custodian.

An example method may include managing the custody of the plurality of assets, wherein at least one asset event related to the plurality of assets is based on a plurality of terms and conditions embodied in a smart contract configuration and based on data collected by the data about the plurality of assets.

An example method may include wherein each asset event related to the plurality of assets comprises at least one event selected from among a transfer of title, death of an owner, disability of an owner, bankruptcy of an owner, foreclosure, placement of a lien, use of assets as collateral, designation of a beneficiary, undertaking a loan against assets, providing a notice with respect to assets, inspection of assets, assessment of assets, reporting on assets for taxation purposes, allocation of ownership of assets, disposal of assets, sale of assets, purchase of assets, or designation of an ownership status.

An example method may include wherein the monitoring is executed by at least one of an Internet of Things system, a camera system, a networked monitoring system, an internet monitoring system, a mobile device system, a wearable device system, a user interface system, or an interactive crowdsourcing system.

An example method may include comprising sharing and distributing the asset events with the plurality of actionable entities.

An example method may include wherein interpreting the plurality of assets comprises identifying the plurality of assets for which a financial entity is responsible for taking custody.

An example method may include wherein authenticating the plurality of identifiers comprises verifying the plurality of identifiers corresponding to actionable entities are entitled to take action with respect to the plurality of assets.

An example method may include wherein the blockchain structure is provided in conjunction with a block-chain marketplace.

An example method may include wherein the block-chain marketplace utilizes an automated blockchain-based transaction application.

An example method may include comprising storing asset transaction data in the blockchain structure based on interactions between actionable entities.

An example method may include wherein the blockchain structure is a distributed blockchain structure across a plurality of asset nodes.

An example method may include wherein at least one of the plurality of assets is a virtual asset tag and interpreting the plurality of assets comprises identifying the virtual asset tag.

An example method may include wherein the storing of the plurality of asset control features comprising storing virtual asset tag data.

An example method may include wherein the virtual asset tag data is at least one of location data or tracking data.

An example method may include wherein an identifier corresponding to at least one of the financial entity or actionable entities is stored as virtual asset tag data.

In embodiments, provided herein is a system for facilitating foreclosure on collateral. An example platform or system may include a lending agreement storage circuit structured to store a plurality of lending agreement data comprising at least one lending agreement, wherein the at least one lending agreement comprises a lending condition data, the lending condition data comprising a terms and condition data of the at least one lending agreement related to a foreclosure condition on at least one asset that provides a collateral condition related to a collateral asset for securing a repayment obligation of the at least one lending agreement; a data collection services circuit structured to monitor the lending condition data and to detect a default condition based on a change to the lending condition data; and a smart contract services circuit structured to, when the default condition is detected by the data collection services circuit, interpret the default condition and communicate a default condition indication that initiates a foreclosure procedure based on the collateral condition and the default condition.

Certain further aspects of an example system are described following, any one or more of which may be present in certain embodiments. An example system may include wherein the smart contract services circuit is further structured to communicate the detected default condition indication is communicated to at least one of a smart lock and a smart container to lock the collateral asset.

An example system may include wherein the foreclosure procedure configures and initiates a listing of the collateral asset on a public auction site.

An example system may include wherein the foreclosure procedure configures and delivers a set of transport instructions for the collateral asset.

An example system may include wherein the foreclosure procedure configures a set of instructions for a drone to transport the collateral asset.

An example system may include wherein the foreclosure procedure configures a set of instructions for a robotic device to transport the collateral asset.

An example system may include wherein the foreclosure procedure initiates a process for automatically substituting a set of substitute collateral.

An example system may include wherein the foreclosure procedure initiates a collateral tracking procedure.

An example system may include wherein the foreclosure procedure initiates a collateral valuation process.

An example system may include wherein the foreclosure procedure initiates a message to a borrower initiating a negotiation regarding the foreclosure.

An example system may include wherein the negotiation is managed by a robotic process automation system trained on a training set of foreclosure negotiations.

An example system may include wherein the negotiation relates to modification of at least one of interest rate, payment terms, and collateral for the at least one lending agreement.

An example system may include wherein the data collection services circuit further comprises at least one system selected from the systems consisting of: an Internet of Things system, a camera system, a networked monitoring system, an internet monitoring system, a mobile device system, a wearable device system, a user interface system, and an interactive crowdsourcing system.

An example system may include wherein each of the lending agreement storage circuit, data collection services circuit, and smart contract services circuit further comprise a corresponding application programming interface (API) component structured to facilitate communication among the circuits of the system.

An example system may include wherein the corresponding API components of the circuits further comprise user interfaces structured to interact with a plurality of users of the system.

In embodiments, provided herein is a method for facilitating foreclosure on collateral. An example method may include storing a plurality of lending agreement data comprising at least one lending agreement, wherein the at least one lending agreement comprises a lending condition data, the lending condition data comprising a terms and condition data of the at least one lending agreement related to a foreclosure condition on at least one asset that provides a collateral condition related to a collateral asset for securing a repayment obligation of the at least one lending agreement; monitoring the lending condition data and to detect a default condition based on a change to the lending condition data; interpreting the default condition; and communicating a default condition indication that initiates a foreclosure procedure based on the collateral condition.

Certain further aspects of an example method are described following, any one or more of which may be present in certain embodiments. An example method may include wherein the detected default condition indication is communicated to at least one of a smart lock and a smart container to lock the collateral asset.

An example method may include wherein the foreclosure procedure configures and initiates a listing of the collateral asset on a public auction site.

An example method may include wherein the foreclosure procedure configures and delivers a set of transport instructions for the collateral asset.

An example method may include wherein the foreclosure procedure configures a set of instructions for a drone to transport the collateral asset.

An example method may include wherein the foreclosure procedure configures a set of instructions for a robotic device to transport the collateral asset.

An example method may include wherein the foreclosure procedure initiates a process for automatically substituting a set of substitute collateral.

An example method may include wherein the foreclosure procedure initiates a collateral tracking procedure.

An example method may include wherein the foreclosure procedure initiates a collateral valuation process.

An example method may include wherein the foreclosure procedure initiates a message to a borrower initiating a negotiation regarding the foreclosure.

An example method may include wherein the negotiation is managed by a robotic process automation system trained on a training set of foreclosure negotiations.

An example method may include wherein the negotiation relates to modification of at least one of interest rate, payment terms, or collateral for the at least one lending agreement.

An example method may include wherein the monitoring is provided by at least one of an Internet of Things system, a camera system, a networked monitoring system, an internet monitoring system, a mobile device system, a wearable device system, a user interface system, or an interactive crowdsourcing system.

An example method may include wherein providing communications for monitoring, interpreting, and communicating are through an application programming interface (API).

An example method may include wherein providing a user interface incorporating the API to interact with a plurality of users.

Figure 111:
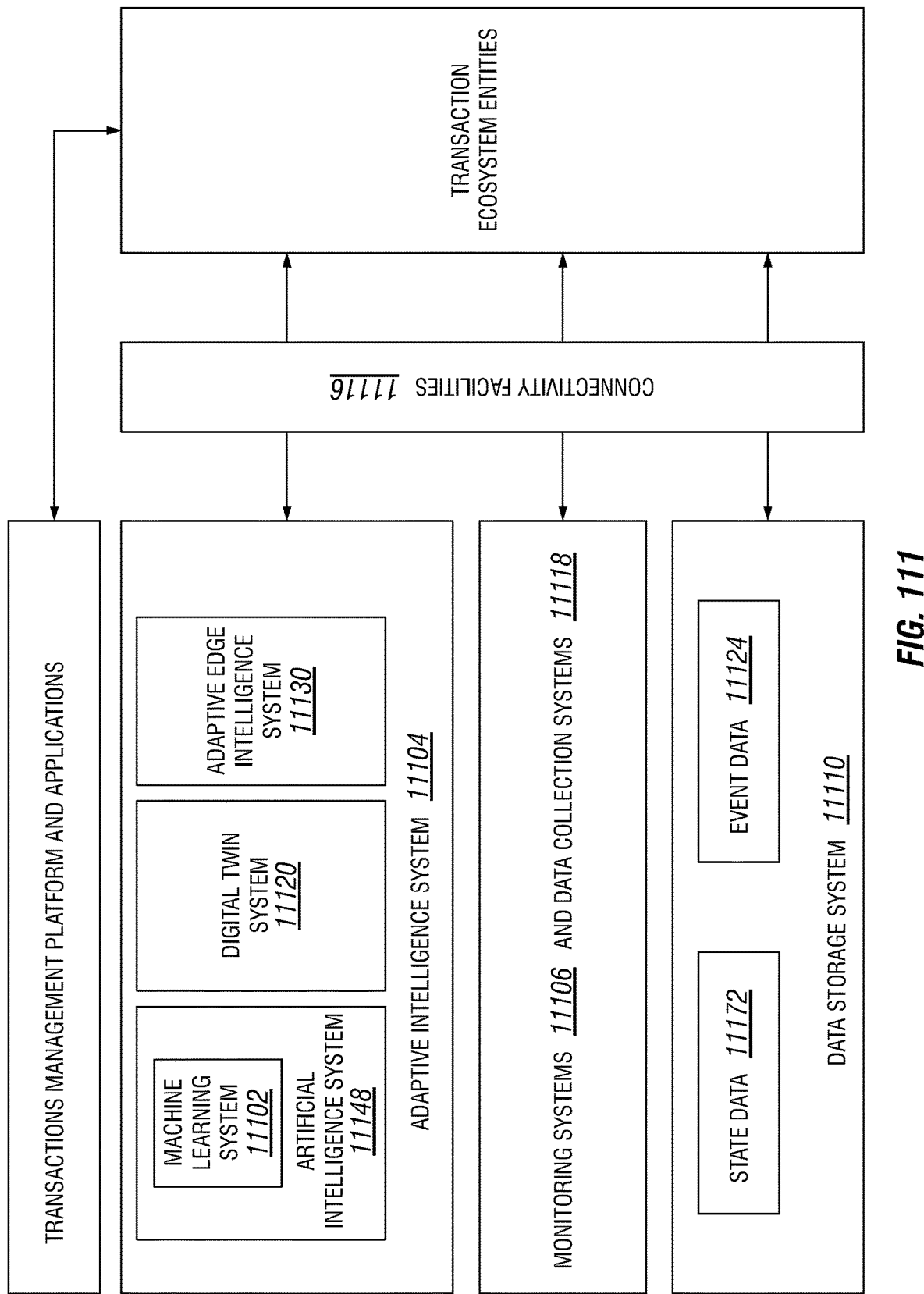
FIG. 111 depicts a schematic illustrating an example of a portion of an information technology system for transaction artificial intelligence leveraging digital twins according to some embodiments of the present disclosure.

Referring to FIG. 111, an adaptive intelligence system 11104 may include an artificial intelligence system 11148, a digital twin system 11120, and an adaptive device (or edge) intelligence system 11130. The artificial intelligence system 11148 may define a machine learning model 11102 for performing analytics, simulation, decision making, and prediction making related to data processing, data analysis, simulation creation, and simulation analysis of one or more of the transaction entities. The machine learning model 11102 is an algorithm and/or statistical model that performs specific tasks without using explicit instructions, relying instead on patterns and inference. The machine learning model 11102 builds one or more mathematical models based on training data to make predictions and/or decisions without being explicitly programmed to perform the specific tasks. The machine learning model 11102 may receive inputs of sensor data as training data, including event data 11124 and state data 11172 related to one or more of the transaction entities through data collection systems 11118 and monitoring systems 11106 and connectivity facilities 11116. The event data 11124 and state data 11172 may be stored in a data storage system 11110 The sensor data input to the machine learning model 11102 may be used to train the machine learning model 11102 to perform the analytics, simulation, decision making, and prediction making relating to the data processing, data analysis, simulation creation, and simulation analysis of the one or more of the transaction entities. The machine learning model 11102 may also use input data from a user or users of the information technology system. The machine learning model 11102 may include an artificial neural network, a decision tree, a support vector machine, a Bayesian network, a genetic algorithm, any other suitable form of machine learning model, or a combination thereof. The machine learning model 11102 may be configured to learn through supervised learning, unsupervised learning, reinforcement learning, self learning, feature learning, sparse dictionary learning, anomaly detection, association rules, a combination thereof, or any other suitable algorithm for learning.

The artificial intelligence system 11148 may also define the digital twin system 11120 to create a digital replica of one or more of the transaction entities. The digital replica of the one or more of the transaction entities may use substantially real-time sensor data to provide for substantially real-time virtual representation of the transaction entity and provides for simulation of one or more possible future states of the one or more transaction entities. The digital replica exists simultaneously with the one or more transaction entities being replicated. The digital replica provides one or more simulations of both physical elements and properties of the one or more transaction entities being replicated and the dynamics thereof, in embodiments, throughout the lifestyle of the one or more transaction entities being replicated. The digital replica may provide a hypothetical simulation of the one or more transaction entities, for example during a design phase before the one or more transaction entities are constructed or fabricated, or during or after construction or fabrication of the one or more transaction entities by allowing for hypothetical extrapolation of sensor data to simulate a state of the one or more transaction entities, such as during high stress, after a period of time has passed during which component wear may be an issue, during maximum throughput operation, after one or more hypothetical or planned improvements have been made to the one or more transaction entities, or any other suitable hypothetical situation. In some embodiments, the machine learning model 11102 may automatically predict hypothetical situations for simulation with the digital replica, such as by predicting possible improvements to the one or more transaction entities, predicting when one or more components of the one or more transaction entities may fail, and/or suggesting possible improvements to the one or more transaction entities, such as changes to timing settings, arrangement, components, or any other suitable change to the transaction entities. The digital replica allows for simulation of the one or more transaction entities during both design and operation phases of the one or more transaction entities, as well as simulation of hypothetical operation conditions and configurations of the one or more transaction entities. The digital replica allows for invaluable analysis and simulation of the one or more transaction entities, by facilitating observation and measurement of nearly any type of metric, including temperature, wear, light, vibration, etc. not only in, on, and around each component of the one or more transaction entities, but in some embodiments within the one or more transaction entities. In some embodiments, the machine learning model 11102 may process the sensor data including the event data 11124 and the state data 11172 to define simulation data for use by the digital twin system 11120. The machine learning model 11102 may, for example, receive state data 11172 and event data 11124 related to a particular transaction entity of the plurality of transaction entities and perform a series of operations on the state data 11172 and the event data 11124 to format the state data 11172 and the event data 11124 into a format suitable for use by the digital twin system 11120 in creation of a digital replica of the transaction entity. For example, one or more transaction entities may include a robot configured to augment products on an adjacent assembly line. The machine learning model 11102 may collect data from one or more sensors positioned on, near, in, and/or around the robot. The machine learning model 11102 may perform operations on the sensor data to process the sensor data into simulation data and output the simulation data to the digital twin system 11120. The digital twin system 11120 simulation may use the simulation data to create one or more digital replicas of the robot, the simulation including for example metrics including temperature, wear, speed, rotation, and vibration of the robot and components thereof. The simulation may be a substantially real-time simulation, allowing for a human user of the information technology to view the simulation of the robot, metrics related thereto, and metrics related to components thereof, in substantially real time. The simulation may be a predictive or hypothetical situation, allowing for a human user of the information technology to view a predictive or hypothetical simulation of the robot, metrics related thereto, and metrics related to components thereof.

In some embodiments, the machine learning model 11102 and the digital twin system 11120 may process sensor data and create a digital replica of a set of transaction entities of the plurality of transaction entities to facilitate design, real-time simulation, predictive simulation, and/or hypothetical simulation of a related group of transaction entities. The digital replica of the set of transaction entities may use substantially real-time sensor data to provide for substantially real-time virtual representation of the set of transaction entities and provide for simulation of one or more possible future states of the set of transaction entities. The digital replica exists simultaneously with the set of transaction entities being replicated. The digital replica provides one or more simulations of both physical elements and properties of the set of transaction entities being replicated and the dynamics thereof, in embodiments throughout the lifestyle of the set of transaction entities being replicated. The one or more simulations may include a visual simulation, such as a wire-frame virtual representation of the one or more transaction entities that may be viewable on a monitor, using an augmented reality (AR) apparatus, or using a virtual reality (VR) apparatus. The visual simulation may be able to be manipulated by a human user of the information technology system, such as zooming or highlighting components of the simulation and/or providing an exploded view of the one or more transaction entities. The digital replica may provide a hypothetical simulation of the set of transaction entities, for example during a design phase before the one or more transaction entities are constructed or fabricated, or during or after construction or fabrication of the one or more transaction entities by allowing for hypothetical extrapolation of sensor data to simulate a state of the set of transaction entities, such as during high stress, after a period of time has passed during which component wear may be an issue, during maximum throughput operation, after one or more hypothetical or planned improvements have been made to the set of transaction entities, or any other suitable hypothetical situation. In some embodiments, the machine learning model 11102 may automatically predict hypothetical situations for simulation with the digital replica, such as by predicting possible improvements to the set of transaction entities, predicting when one or more components of the set of transaction entities may fail, and/or suggesting possible improvements to the set of transaction entities, such as changes to timing settings, arrangement, components, or any other suitable change to the transaction entities. The digital replica allows for simulation of the set of transaction entities during both design and operation phases of the set of transaction entities, as well as simulation of hypothetical operation conditions and configurations of the set of transaction entities. The digital replica allows for invaluable analysis and simulation of the one or more transaction entities, by facilitating observation and measurement of nearly any type of metric, including temperature, wear, light, vibration, etc. not only in, on, and around each component of the set of transaction entities, but in some embodiments within the set of transaction entities. In some embodiments, the machine learning model 11102 may process the sensor data including the event data 11124 and the state data 11172 to define simulation data for use by the digital twin system 11120. The machine learning model 11102 may, for example, receive state data 11172 and event data 11124 related to a particular transaction entity of the plurality of transaction entities and perform a series of operations on the state data 11172 and the event data 11124 to format the state data 11172 and the event data 11124 into a format suitable for use by the digital twin system 11120 in the creation of a digital replica of the set of transaction entities. For example, a set of transaction entities may include a die machine configured to place products on a conveyor belt, the conveyor belt on which the die machine is configured to place the products, and a plurality of robots configured to add parts to the products as they move along the assembly line. The machine learning model 11102 may collect data from one or more sensors positioned on, near, in, and/or around each of the die machines, the conveyor belt, and the plurality of robots. The machine learning model 11102 may perform operations on the sensor data to process the sensor data into simulation data and output the simulation data to the digital twin system 11120. The digital twin system 11120 simulation may use the simulation data to create one or more digital replicas of the die machine, the conveyor belt, and the plurality of robots, the simulation including for example metrics including temperature, wear, speed, rotation, and vibration of the die machine, the conveyor belt, and the plurality of robots and components thereof. The simulation may be a substantially real-time simulation, allowing for a human user of the information technology to view the simulation of the die machine, the conveyor belt, and the plurality of robots, metrics related thereto, and metrics related to components thereof, in substantially real time. The simulation may be a predictive or hypothetical situation, allowing for a human user of the information technology to view a predictive or hypothetical simulation of the die machine, the conveyor belt, and the plurality of robots, metrics related thereto, and metrics related to components thereof.

In some embodiments, the machine learning model 11102 may prioritize collection of sensor data for use in digital replica simulations of one or more of the transaction entities. The machine learning model 11102 may use sensor data and user inputs to train, thereby learning which types of sensor data are most effective for creation of digital replicate simulations of one or more of the transaction entities. For example, the machine learning model 11102 may find that a particular transaction entity has dynamic properties such as component wear and throughput affected by temperature, humidity, and load. The machine learning model 11102 may, through machine learning, prioritize collection of sensor data related to temperature, humidity, and load, and may prioritize processing sensor data of the prioritized type into simulation data for output to the digital twin system 11120. In some embodiments, the machine learning model 11102 may suggest to a user of the information technology system that more and/or different sensors of the prioritized type be implemented in the information technology near and around the transaction entity being simulation such that more and/or better data of the prioritized type may be used in simulation of the transaction entity via the digital replica thereof.

In some embodiments, the machine learning model 11102 may be configured to learn to determine which types of sensor data are to be processed into simulation data for transmission to the digital twin system 11120 based on one or both of a modeling goal and a quality or type of sensor data. A modeling goal may be an objective set by a user of the information technology system or may be predicted or learned by the machine learning model 11102. Examples of modeling goals include creating a digital replica capable of showing dynamics of throughput on an assembly line, which may include collection, simulation, and modeling of, e.g., thermal, electrical power, component wear, and other metrics of a conveyor belt, an assembly machine, one or more products, and other components of the transaction ecosystem. The machine learning model 111102 may be configured to learn to determine which types of sensor data are necessary to be processed into simulation data for transmission to the digital twin system 11120 to achieve such a model. In some embodiments, the machine learning model 11102 may analyze which types of sensor data are being collected, the quality and quantity of the sensor data being collected, and what the sensor data being collected represents, and may make decisions, predictions, analyses, and/or determinations related to which types of sensor data are and/or are not relevant to achieving the modeling goal and may make decisions, predictions, analyses, and/or determinations to prioritize, improve, and/or achieve the quality and quantity of sensor data being processed into simulation data for use by the digital twin system 11120 in achieving the modeling goal.

In some embodiments, a user of the information technology system may input a modeling goal into the machine learning model 11102. The machine learning model 11102 may learn to analyze training data to output suggestions to the user of the information technology system regarding which types of sensor data are most relevant to achieving the modeling goal, such as one or more types of sensors positioned in, on, or near a transaction entity or a plurality of transaction entities that is relevant to the achievement of the modeling goal is and/or are not sufficient for achieving the modeling goal, and how a different configuration of the types of sensors, such as by adding, removing, or repositioning sensors, may better facilitate achievement of the modeling goal by the machine learning model 11102 and the digital twin system 11120. In some embodiments, the machine learning model 11102 may automatically increase or decrease collection rates, processing, storage, sampling rates, bandwidth allocation, bitrates, and other attributes of sensor data collection to achieve or better achieve the modeling goal. In some embodiments, the machine learning model 11102 may make suggestions or predictions to a user of the information technology system related to increasing or decreasing collection rates, processing, storage, sampling rates, bandwidth allocation, bitrates, and other attributes of sensor data collection to achieve or better achieve the modeling goal. In some embodiments, the machine learning model 11102 may use sensor data, simulation data, previous, current, and/or future digital replica simulations of one or more transaction entities of the plurality of transaction entities to automatically create and/or propose modeling goals. In some embodiments, modeling goals automatically created by the machine learning model 11102 may be automatically implemented by the machine learning model 11102. In some embodiments, modeling goals automatically created by the machine learning model 11102 may be proposed to a user of the information technology system, and implemented only after acceptance and/or partial acceptance by the user, such as after modifications are made to the proposed modeling goal by the user.

In some embodiments, the user may input the one or more modeling goals, for example, by inputting one or more modeling commands to the information technology system. The one or more modeling commands may include, for example, a command for the machine learning model 11102 and the digital twin system 11120 to create a digital replica simulation of one transaction entity or a set of transaction entities, may include a command for the digital replica simulation to be one or more of a real-time simulation, and a hypothetical simulation. The modeling command may also include, for example, parameters for what types of sensor data should be used, sampling rates for the sensor data, and other parameters for the sensor data used in the one or more digital replica simulations. In some embodiments, the machine learning model 11102 may be configured to predict modeling commands, such as by using previous modeling commands as training data. The machine learning model 11102 may propose predicted modeling commands to a user of the information technology system, for example, to facilitate simulation of one or more of the transaction entities that may be useful for the management of the transaction entities and/or to allow the user to easily identify potential issues with or possible improvements to the transaction entities. The system of FIG. 111 may include a transactions management platform and applications.

In some embodiments, the machine learning model 11102 may be configured to evaluate a set of hypothetical simulations of one or more of the transaction entities. The set of hypothetical simulations may be created by the machine learning model 11102 and the digital twin system 11120 as a result of one or more modeling commands, as a result of one or more modeling goals, one or more modeling commands, by prediction by the machine learning model 11102, or a combination thereof. The machine learning model 11102 may evaluate the set of hypothetical simulations based on one or more metrics defined by the user, one or more metrics defined by the machine learning model 11102, or a combination thereof. In some embodiments, the machine learning model 11102 may evaluate each of the hypothetical simulations of the set of hypothetical simulations independently of one another. In some embodiments, the machine learning model 11102 may evaluate one or more of the hypothetical simulations of the set of hypothetical simulations in relation to one another, for example by ranking the hypothetical simulations or creating tiers of the hypothetical simulations based on one or more metrics.

In some embodiments, the machine learning model 11102 may include one or more model interpretability systems to facilitate human understanding of outputs of the machine learning model 11102, as well as information and insight related to cognition and processes of the machine learning model 11102, i.e., the one or more model interpretability systems allow for human understanding of not only "what" the machine learning model 11102 is outputting, but also "why" the machine learning model 11102 is outputting the outputs thereof, and what process led to the machine learning models 11102 formulating the outputs. The one or more model interpretability systems may also be used by a human user to improve and guide training of the machine learning model 11102, to help debug the machine learning model 11102, to help recognize bias in the machine learning model 11102. The one or more model interpretability systems may include one or more of linear regression, logistic regression, a generalized linear model (GLM), a generalized additive model (GAM), a decision tree, a decision rule, RuleFit, Naive Bayes Classifier, a K-nearest neighbors algorithm, a partial dependence plot, individual conditional expectation (ICE), an accumulated local effects (ALE) plot, feature interaction, permutation feature importance, a global surrogate model, a local surrogate (LIME) model, scoped rules, i.e. anchors, Shapley values, Shapley additive explanations (SHAP), feature visualization, network dissection, or any other suitable machine learning interpretability implementation. In some embodiments, the one or more model interpretability systems may include a model dataset visualization system. The model dataset visualization system is configured to automatically provide to a human user of the information technology system visual analysis related to distribution of values of the sensor data, the simulation data, and data nodes of the machine learning model 11102.

In some embodiments, the machine learning model 11102 may include and/or implement an embedded model interpretability system, such as a Bayesian case model (BCM) or glass box. The Bayesian case model uses Bayesian case-based reasoning, prototype classification, and clustering to facilitate human understanding of data such as the sensor data, the simulation data, and data nodes of the machine learning model 11102. In some embodiments, the model interpretability system may include and/or implement a glass box interpretability method, such as a Gaussian process, to facilitate human understanding of data such as the sensor data, the simulation data, and data nodes of the machine learning model 11102.

In some embodiments, the machine learning model 11102 may include and/or implement testing with concept activation vectors (TCAV). The TCAV allows the machine learning model 11102 to learn human-interpretable concepts, such as "running," "not running," "powered," "not powered," "robot," "human," "truck," or "ship" from examples by a process including defining the concept, determining concept activation vectors, and calculating directional derivatives. By learning human-interpretable concepts, objects, states, etc., TCAV may allow the machine learning model 11102 to output useful information related to the transaction entities and data collected therefrom in a format that is readily understood by a human user of the information technology system.

In some embodiments, the machine learning model 11102 may be and/or include an artificial neural network, e.g. a connectionist system configured to "learn" to perform tasks by considering examples and without being explicitly programmed with task-specific rules. The machine learning model 11102 may be based on a collection of connected units and/or nodes that may act like artificial neurons that may in some ways emulate neurons in a biological brain. The units and/or nodes may each have one or more connections to other units and/or nodes. The units and/or nodes may be configured to transmit information, e.g. one or more signals, to other units and/or nodes, process signals received from other units and/or nodes, and forward processed signals to other units and/or nodes. One or more of the units and/or nodes and connections therebetween may have one or more numerical "weights" assigned. The assigned weights may be configured to facilitate learning, i.e. training, of the machine learning model 11102. The weights assigned weights may increase and/or decrease one or more signals between one or more units and/or nodes, and in some embodiments may have one or more thresholds associated with one or more of the weights. The one or more thresholds may be configured such that a signal is only sent between one or more units and/or nodes if a signal and/or aggregate signal crosses the threshold. In some embodiments, the units and/or nodes may be assigned to a plurality of layers, each of the layers having one or both of inputs and outputs. A first layer may be configured to receive training data, transform at least a portion of the training data, and transmit signals related to the training data and transformation thereof to a second layer. A final layer may be configured to output an estimate, conclusion, product, or other consequence of processing of one or more inputs by the machine learning model 11102. Each of the layers may perform one or more types of transformations, and one or more signals may pass through one or more of the layers one or more times. In some embodiments, the machine learning model 11102 may employ deep learning and being at least partially modeled and/or configured as a deep neural network, a deep belief network, a recurrent neural network, and/or a convolutional neural network, such as by being configured to include one or more hidden layers.

In some embodiments, the machine learning model 11102 may be and/or include a decision tree, e.g. a tree-based predictive model configured to identify one or more observations and determine one or more conclusions based on an input. The observations may be modeled as one or more "branches" of the decision tree, and the conclusions may be modeled as one or more "leaves" of the decision tree. In some embodiments, the decision tree may be a classification tree. the classification tree may include one or more leaves representing one or more class labels, and one or more branches representing one or more conjunctions of features configured to lead to the class labels. In some embodiments, the decision tree may be a regression tree. The regression tree may be configured such that one or more target variables may take continuous values.

In some embodiments, the machine learning model 11102 may be and/or include a support vector machine, e.g. a set of related supervised learning methods configured for use in one or both of classification and regression-based modeling of data. The support vector machine may be configured to predict whether a new example falls into one or more categories, the one or more categories being configured during training of the support vector machine.

In some embodiments, the machine learning model 11102 may be configured to perform regression analysis to determine and/or estimate a relationship between one or more inputs and one or more features of the one or more inputs. Regression analysis may include linear regression, wherein the machine learning model 11102 may calculate a single line to best fit input data according to one or more mathematical criteria.

In embodiments, inputs to the machine learning model 11102 (such as a regression model, Bayesian network, supervised model, or other type of model) may be tested, such as by using a set of testing data that is independent from the data set used for the creation and/or training of the machine learning model, such as to test the impact of various inputs to the accuracy of the model 11102. For example, inputs to the regression model may be removed, including single inputs, pairs of inputs, triplets, and the like, to determine whether the absence of inputs creates a material degradation of the success of the model 11102. This may assist with recognition of inputs that are in fact correlated (e.g., are linear combinations of the same underlying data), that are overlapping, or the like. Comparison of model success may help select among alternative input data sets that provide similar information, such as to identify the inputs (among several similar ones) that generate the least "noise" in the model, that provide the most impact on model effectiveness for the lowest cost, or the like. Thus, input variation and testing of the impact of input variation on model effectiveness may be used to prune or enhance model performance for any of the machine learning systems described throughout this disclosure.

In some embodiments, the machine learning model 11102 may be and/or include a Bayesian network. The Bayesian network may be a probabilistic graphical model configured to represent a set of random variables and conditional independence of the set of random variables. The Bayesian network may be configured to represent the random variables and conditional independence via a directed acyclic graph. The Bayesian network may include one or both of a dynamic Bayesian network and an influence diagram.

In some embodiments, the machine learning model 11102 may be defined via supervised learning, i.e. one or more algorithms configured to build a mathematical model of a set of training data containing one or more inputs and desired outputs. The training data may consist of a set of training examples, each of the training examples having one or more inputs and desired outputs, i.e. a supervisory signal. Each of the training examples may be represented in the machine learning model 11102 by an array and/or a vector, i.e. a feature vector. The training data may be represented in the machine learning model 11102 by a matrix. The machine learning model 11102 may learn one or more functions via iterative optimization of an objective function, thereby learning to predict an output associated with new inputs. Once optimized, the objective function may provide the machine learning model 11102 with the ability to accurately determine an output for inputs other than inputs included in the training data. In some embodiments, the machine learning model 11102 may be defined via one or more supervised learning algorithms such as active learning, statistical classification, regression analysis, and similarity learning. Active learning may include interactively querying, by the machine learning model 11102, a user and/or an information source to label new data points with desired outputs. Statistical classification may include identifying, by the machine learning model 11102, to which a set of subcategories, i.e. subpopulations, a new observation belongs based on a training set of data containing observations having known categories. Regression analysis may include estimating, by the machine learning model 11102 relationships between a dependent variable, i.e. an outcome variable, and one or more independent variables, i.e. predictors, covariates, and/or features. Similarity learning may include learning, by the machine learning model 11102, from examples using a similarity function, the similarity function being designed to measure how similar or related two objects are.

In some embodiments, the machine learning model 11102 may be defined via unsupervised learning, i.e. one or more algorithms configured to build a mathematical model of a set of data containing only inputs by finding structure in the data such as grouping or clustering of data points. In some embodiments, the machine learning model 11102 may learn from test data, i.e. training data, that has not been labeled, classified, or categorized. The unsupervised learning algorithm may include identifying, by the machine learning model 11102, commonalities in the training data and learning by reacting based on the presence or absence of the identified commonalities in new pieces of data. In some embodiments, the machine learning model 11102 may generate one or more probability density functions. In some embodiments, the machine learning model 11102 may learn by performing cluster analysis, such as by assigning a set of observations into subsets, i.e. clusters, according to one or more predesignated criteria, such as according to a similarity metric of which internal compactness, separation, estimated density, and/or graph connectivity are factors.

In some embodiments, the machine learning model 11102 may be defined via semi-supervised learning, i.e. one or more algorithms using training data wherein some training examples may be missing training labels. The semi-supervised learning may be weakly supervised learning, wherein the training labels may be noisy, limited, and/or imprecise. The noisy, limited, and/or imprecise training labels may be cheaper and/or less labor intensive to produce, thus allowing the machine learning model 11102 to train on a larger set of training data for less cost and/or labor.

In some embodiments, the machine learning model 11102 may be defined via reinforcement learning, such as one or more algorithms using dynamic programming techniques such that the machine learning model 11102 may train by taking actions in an environment in order to maximize a cumulative reward. In some embodiments, the training data is represented as a Markov Decision Process.

In some embodiments, the machine learning model 11102 may be defined via self-learning, wherein the machine learning model 11102 is configured to train using training data with no external rewards and no external teaching, such as by employing a Crossbar Adaptive Array (CAA). The CAA may compute decisions about actions and/or emotions about consequence situations in a crossbar fashion, thereby driving teaching of the machine learning model 11102 by interactions between cognition and emotion.

In some embodiments, the machine learning model 11102 may be defined via feature learning, i.e. one or more algorithms designed to discover increasingly accurate and/or apt representations of one or more inputs provided during training, e.g. training data. Feature learning may include training via principal component analysis and/or cluster analysis. Feature learning algorithms may include attempting, by the machine learning model 11102, to preserve input training data while also transforming the input training data such that the transformed input training data is useful. In some embodiments, the machine learning model 11102 may be configured to transform the input training data prior to performing one or more classifications and/or predictions of the input training data. Thus, the machine learning model 11102 may be configured to reconstruct input training data from one or more unknown data-generating distributions without necessarily conforming to implausible configurations of the input training data according to the distributions. In some embodiments, the feature learning algorithm may be performed by the machine learning model 11102 in a supervised, unsupervised, or semi-supervised manner.

In some embodiments, the machine learning model 11102 may be defined via anomaly detection, i.e. by identifying rare and/or outlier instances of one or more items, events and/or observations. The rare and/or outlier instances may be identified by the instances differing significantly from patterns and/or properties of a majority of the training data. Unsupervised anomaly detection may include detecting of anomalies, by the machine learning model 11102, in an unlabeled training data set under an assumption that a majority of the training data is "normal." Supervised anomaly detection may include training on a data set wherein at least a portion of the training data has been labeled as "normal" and/or "abnormal."

In some embodiments, the machine learning model 11102 may be defined via robot learning. Robot learning may include generation, by the machine learning model 11102, of one or more curricula, the curricula being sequences of learning experiences, and cumulatively acquiring new skills via exploration guided by the machine learning model 11102 and social interaction with humans by the machine learning model 11102. Acquisition of new skills may be facilitated by one or more guidance mechanisms such as active learning, maturation, motor synergies, and/or imitation.

In some embodiments, the machine learning model 11102 can be defined via association rule learning. Association rule learning may include discovering relationships, by the machine learning model 11102, between variables in databases, in order to identify strong rules using some measure of "interestingness." Association rule learning may include identifying, learning, and/or evolving rules to store, manipulate and/or apply knowledge. The machine learning model 11102 may be configured to learn by identifying and/or utilizing a set of relational rules, the relational rules collectively representing knowledge captured by the machine learning model 11102. Association rule learning may include one or more of learning classifier systems, inductive logic programming, and artificial immune systems. Learning classifier systems are algorithms that may combine a discovery component, such as one or more genetic algorithms, with a learning component, such as one or more algorithms for supervised learning, reinforcement learning, or unsupervised learning. Inductive logic programming may include rule-learning, by the machine learning model 11102, using logic programming to represent one or more of input examples, background knowledge, and hypothesis determined by the machine learning model 11102 during training. The machine learning model 11102 may be configured to derive a hypothesized logic program entailing all positive examples given an encoding of known background knowledge and a set of examples represented as a logical database of facts.

Figure 112:
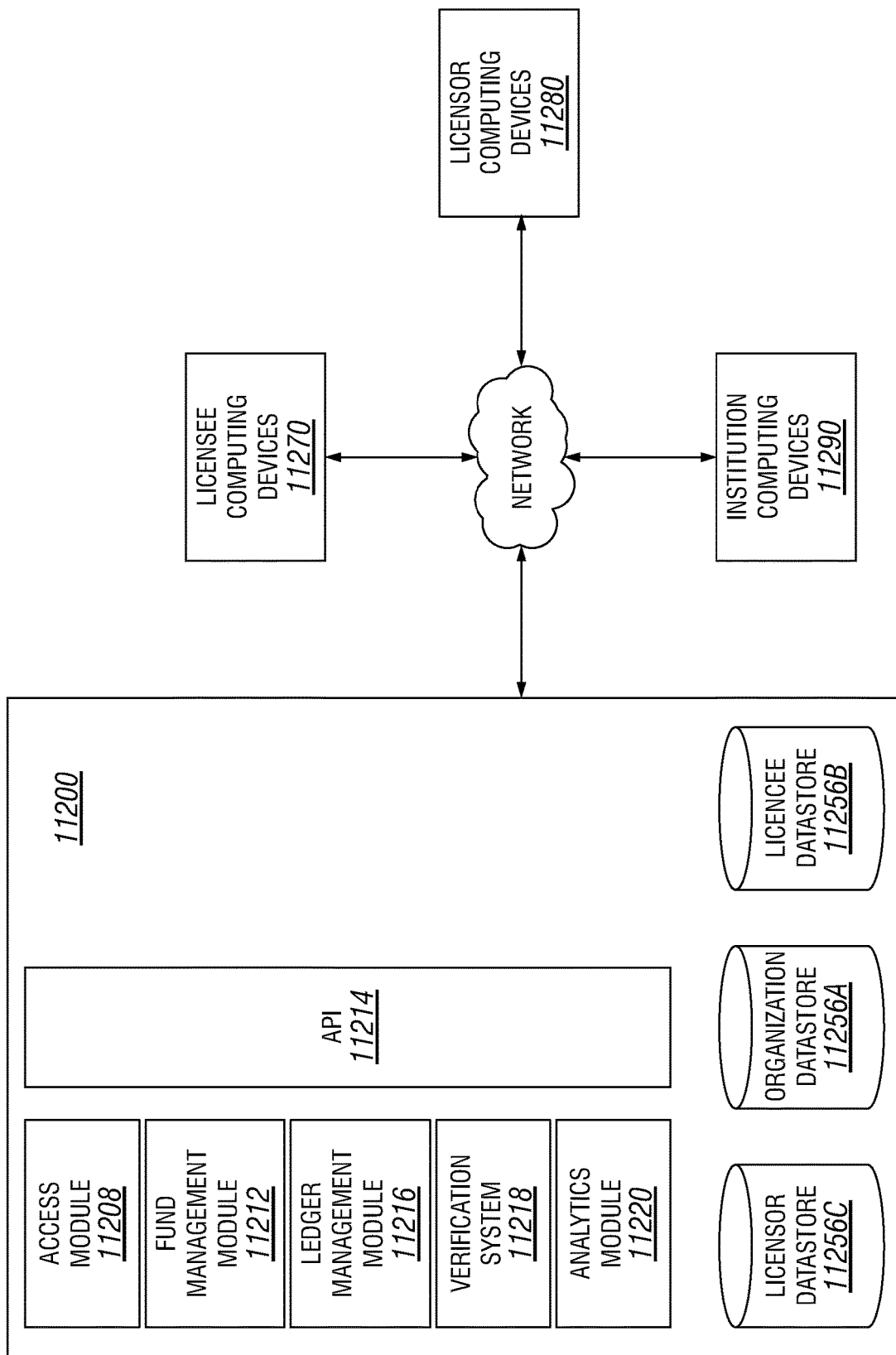
FIG. 112 depicts a schematic illustrating a compliance system that facilitates the licensing of personality rights according to some embodiments of the present disclosure.

Referring to FIG. 112, a compliance system 11200 that facilitates the licensing of personality rights using a distributed ledger and cryptocurrency is depicted. As used herein, personality rights may refer to an entity's ability to control the use of his, her, or its identity for commercial purposes. The term entity, as used herein, may refer to an individual or an organization (e.g., a university, a school, a team, a corporation, or the like) that agrees to license its personality rights, unless context suggests otherwise. This may include an entity's ability to control the use of its name, image, likeness, voice, or the like. For example, an individual exercising their personality rights for commercial purposes may include appearing in a commercial, television show, or movie, making a sponsored social media post (e.g., Instagram post, Facebook post, Twitter tweet, or the like), having their name appear on clothing (e.g., a jersey, t-shirts, sweatshirts, or the like) or other goods, appearing in a video game, or the like. In embodiments, individuals may refer to student athletes or professional athletes, but may include other classes of individuals as well. While the current description makes reference to the NCAA, the system may be used to monitor and facilitate transactions relating to other individuals and organizations. For example, the system may be used in the context of professional sports, where organizations may use sponsorships and other licensing deals to circumvent salary caps or other league rules (e.g., FIFA fair play rules).

In embodiments, the compliance system 11200 maintains one or more digital ledgers that record transactions relating to the licensing of personality rights of entities. In embodiments, a digital ledger may be a distributed ledger that is distributed amongst a set of computing devices 11270, 11280, 11290 (also referred to as nodes) and/or may be encrypted. Put another way, each participating node may store a copy of the distributed ledger. An example of the digital ledger is a Blockchain ledger. In some embodiments, a distributed ledger is stored across a set of public nodes. In other embodiments, a distributed ledger is stored across a set of whitelisted participant nodes (e.g., on the servers of participating universities or teams). In some embodiments, the digital ledger is privately maintained by the compliance system 11200. The latter configuration provides a more energy efficient means of maintaining a digital ledger; while the former configurations (e.g., distributed ledgers) provide a more secure/verifiable means of maintaining a digital ledger.

In embodiments, a distributed ledger may store tokens. The tokens may be cryptocurrency tokens that are transferrable to licensors and licensees. In some embodiments, a distributed ledger may store the ownership data of each token. A token (or a portion thereof) may be owned by the compliance system, the governing organization (e.g., the NCAA), a licensor, a licensee, a team, an institution, an individual or the like. In embodiments, the distributed ledger may store event records. Event records may store information relating to events associated with the entities involved with the compliance system. For example, an event record may record an agreement entered into by two parties, the completion of an obligation by a licensor, the distribution of funds to a licensor from a license, the non-completion of an obligation by a licensor, the distribution of funds to entities associated with the licensee (e.g., teammates, institution, team, etc.), and the like.

In embodiments, the digital ledger may store smart contracts that govern agreements between licensors and licensees. As used herein, a licensee may be an organization or person that wishes to enter an agreement to license a licensor's personality rights. Examples of licensees may include, but are not limited to, a car dealership that wants a star student athlete to appear in a print ad, a company that wants the likeness of a licensor (e.g., an athlete and/or a team) to appear in a commercial, a video game maker that wants to use team names, team apparel, player names and/or numbers in a video game, a shoe maker that wants an athlete to endorse a sneaker, a television show producer that wants an athlete to appear in the television show, or the like. In embodiments, the compliance system 11200 generates a smart contract that memorializes an agreement between the individual and a licensee and facilitates the transfer of consideration (e.g., money) when the parties agree that the individual has performed his or her requirements as put forth in the agreement. For example, an athlete may agree to appear in a commercial on behalf of a local car dealership. The smart contract in this example may include an identifier of the athlete (e.g., an individual ID and/or an individual account ID), an identifier of the organization (e.g., an organization ID and/or an organization account ID), the requirements of the individual (e.g., to appear in a commercial, to make a sponsored social media post, to appear at an autograph signing, or the like), and the consideration (e.g., a monetary amount). In embodiments, the smart contract may include additional terms. In embodiments, the additional terms may include an allocation rule that defines a manner by which the consideration is allocated to the athlete and one or more other parties (e.g., agent, manager, university, team, teammates, or the like). For example, in the context of a student athlete, a smart contract may define a split between the licensing athlete, the athletic department of the student athlete's university, and the student athlete's teammates. In a specific example, a university may have a policy that requires a player appearing in any advertisement to split the funds according to a 60/20/20 split, whereby 60% of the funds are allocated to the student athlete appearing in the commercial, 20% of the funds are allocated to the athletic department, and 20% of the funds are allocated to the student athlete's teammates. When a smart contract verifies that the athlete has performed his or her duties with respect to the smart contract (e.g., appeared for the commercial), the smart contract can transfer the agreed upon amount from an account of the licensee to an account of the athlete and accounts of any other entities that may be allocated a percentage of the funds in the smart contract (e.g., athletic department and teammates).

In embodiments, the compliance system 11200 utilizes cryptocurrency to facilitate the transfer of funds. In embodiments, the cryptocurrency is mined by participant nodes and/or generated by the compliance system. The cryptocurrency can be an established type of cryptocurrency (e.g., Bitcoin, Ethereum, Litecoin, or the like) or may be a proprietary cryptocurrency. In some embodiments, the cryptocurrency is a pegged cryptocurrency that is pegged to a particular fiat currency (e.g., pegged to the US dollar, British Pound, Euro, or the like). For example, a single unit of cryptocurrency (also referred to as a "coin") may be pegged to a single unit of fiat currency (e.g., a US dollar). In embodiments, a licensee may exchange fiat currency for a corresponding amount of cryptocurrency. For example, if the cryptocurrency is pegged to the dollar, the licensee may exchange an amount of US dollars for a corresponding amount of cryptocurrency. In embodiments, the compliance system 11200 may keep a percentage of the real-world currency as a transaction fee (e.g., 5%). For example, in exchanging $10,000, the compliance system 11200 may distribute $9,500 dollars' worth of cryptocurrency to an account of the licensee and may keep the $5,000 dollars as a transaction fee. Once the cryptocurrency is deposited in an account of a licensee, the licensee may enter into transactions with individuals.

In embodiments, the compliance system 11200 may allow organizations to create smart contract templates that define one or more conditions/restrictions on the contract. For example, an organization may predefine the allocation between the licensee, the organization, and any other individuals (e.g., coaches, teammates, representatives). Additionally or alternatively, the organization may place minimum and/or maximum amounts of agreements. Additionally or alternatively, the organization may place restrictions on when an agreement can be entered into and/or performed. For example, players may be restricted from appearing in commercials or advertisements during the season and/or during exam periods. These details may be stored in an organization datastore 11256A Organizations may place other conditions/restrictions in a smart contract. In these embodiments, an individual and licensee wishing to enter to an agreement must use a smart contract template provided by the organization to which the individual belongs. In other words, the compliance system 11200 may only allow an individual that has an active relationship with an organization (e.g., plays on a team of a university) to participate in a smart contract if the smart contract is defined by or otherwise approved by the organization.

In embodiments, the compliance system 11200 manages a clearinghouse process that approves potential licensees. Before a licensee can participate in agreements facilitated by the compliance system 11200, the licensee can provide information relating to the licensee. This may include a tax ID number, an entity name, incorporation information (e.g., state and type), a list of key personnel (e.g., directors, executives, board members, approved decision makers, and/or the like), and any other suitable information. In embodiments, the potential licensee may be required to sign (e.g., eSign or wet ink signature) a document indicating that the organization will not willingly use the compliance system 11200 to circumvent any rules, laws, or regulations (e.g., they will not circumvent NCAA regulations). In embodiments, the compliance system 11200 or another entity (e.g., the NCAA) may verify the licensee. Once verified, the information is stored in a licensee datastore 11256B and the licensee may participate in transactions.

In embodiments, the compliance system 11200 may create accounts for licensors once they have joined an organization (e.g., signed an athletic scholarship with a university). Once a licensor is verified as being affiliated with the organization, the compliance system 11200 may create an account for the licensor and may create a relationship between the individual and the organization, whereby the licensor may be required to use smart contracts that are approved or provided by the organization. Should the licensor join another organization (e.g., transfers to another school), the compliance system 11200 may sever the relationship with the previous organization and may create a new relationship with the other organization. Similarly, once a licensor is no longer affiliated with any organization (e.g., the player graduates, enters a professional league, retires, or the like), the compliance system 11200 may prevent the licensor from participating in transactions on the compliance system 11200.

In embodiments, the compliance system 11200 may provide a graphical user interface that allows users to create smart contracts governing personality rights licenses. In these embodiments, the compliance system allows a user (e.g., a licensor) to select a smart contract template. In some embodiments, the compliance system 11200 may restrict the user to only select a smart contract template that is associated with an institution of the licensor. In embodiments, the graphical user interface allows a user to define certain terms (e.g., the type or types of obligations placed on the licensor, an amount of funds to paid, a date by which the obligations of the licensor must be completed by, a location at which the obligation is completed, and/or other suitable terms). Upon a user providing input for parameterizing a smart contract template, the compliance system 11200 may generate a smart contract by parameterizing one or more variables in the smart contract with the provided input. Upon parameterizing an instance of a smart contract, the compliance system 11200 may deploy the smart contract. In some embodiments, the compliance system 11200 may deploy the smart contract by broadcasting the parameterized smart contract to the participant nodes, which in turn may update each respective instance of the distributed ledger with the new smart contract. In some embodiments, an institution of the licensor must approve the parameterized smart contract before the parameterized smart contract may be deployed to the distributed ledger.

In embodiments, the compliance system 11200 may provide a graphical user interface to verify performance of an obligation by a licensor. In some of these embodiments, the compliance system 11200 may include an application that is accessed by licensors, that allows a licensor to prove that he or she performed an obligation. In some of these embodiments, the application may allow a user to record locations that the licensor went to (e.g., locations of film or photo shoots), to upload records (e.g., screen shots of social media posts) or to provide other corroborating evidence that the licensor has performed his or her obligations with respect to a licensing transaction. In this way, the licensor can prove that he or she performed the tasks required by the licensing deal. In some embodiments, the application may interact with a wearable device or may capture other digital exhaust, such as social media posts of the user (e.g., licensor) to collect evidence that supports or disproves a licensor's claim that he or she performed the obligations under the transaction agreement. In embodiments, the corroborating evidence collected by the application may be recorded by the application and stored on the distributed ledger as a licensor datastore 11256C.

In embodiments, the compliance system 11200 (or a smart contract issued in connection with the compliance system 11200) may complete transactions pertaining to a smart contract governing the licensing of the personality rights of a licensor upon verification that licensor has performed his or her obligations defined in the agreement. As mentioned, the licensor may use an application to provide evidence of satisfaction of the obligations of the agreement. Additionally or alternatively, the licensee may provide verification that the licensor has performed his or her obligations (e.g., using an application). In embodiments, the smart contract governing the agreement may receive verification that the licensor has performed his or her obligations defined by the agreement. In response the smart contract may release (or initiate the release of) the cryptocurrency amount defined in the smart contract. The cryptocurrency amount may be distributed to the accounts of the licensor and any other parties defined in the agreement (e.g., teammates of the licensor, the program of the licensor, the regulating body, or the like).

In embodiments, the compliance system 11200 is configured to perform analytics and provide reports to a regulatory body and/or other entities (e.g., the other organizations). In these embodiments, the analytics may be used to identify individuals that are potentially circumventing the rules and regulations of the regulatory body. Furthermore, in some embodiments, transaction records may be maintained on a distributed ledger, whereby different organizations may be able to view agreements entered into by individuals affiliated with other organizations such that added levels of transparency and oversight may disincentivize individuals, organizations, and/or licensees from circumventing rules and regulations.

In embodiments, the compliance system 11200 may train and/or leverage machine-learned models to identify potential instances of circumvention of rules or regulations. In these embodiments, the compliance system 11200 may train machine-learned models using outcome data. Examples of outcome data may include data relating to a set of transactions where an organization (e.g., a team or university), licensee (e.g., a company), and/or licensor (e.g., an athlete) were determined to be circumventing rules or regulations and data relating to a set of transactions where an organization, licensee, and/or licensor were found to be in compliance with the rules and regulations. Examples of machine-learned models include neural networks, regression-based models, decisions trees, random forests, Hidden Markov Models, Bayesian Models, and the like. In embodiments, the compliance system 11200 may leverage a machine-learned model by obtaining a set of records relating to transactions a licensee, a licensor, and/or an organization (e.g., a team or university) from the distributed ledger. The compliance system may extract relevant features, such as the amount paid to a particular licensor by a licensee, amounts paid to other licensors on other teams, affiliations of the licensor, amounts paid to a licensor by other licensees, and the like, and may feed the features to the machine-learned model. The machine-learned model may issue a score that indicates a likelihood that the transaction was legitimate (or illegitimate) based on the extracted features. In embodiments, the compliance system 11200 may provide notifications to relevant parties (e.g., regulators) when the output of a machine-learned model indicates that a transaction was likely illegitimate.

Figure 113:
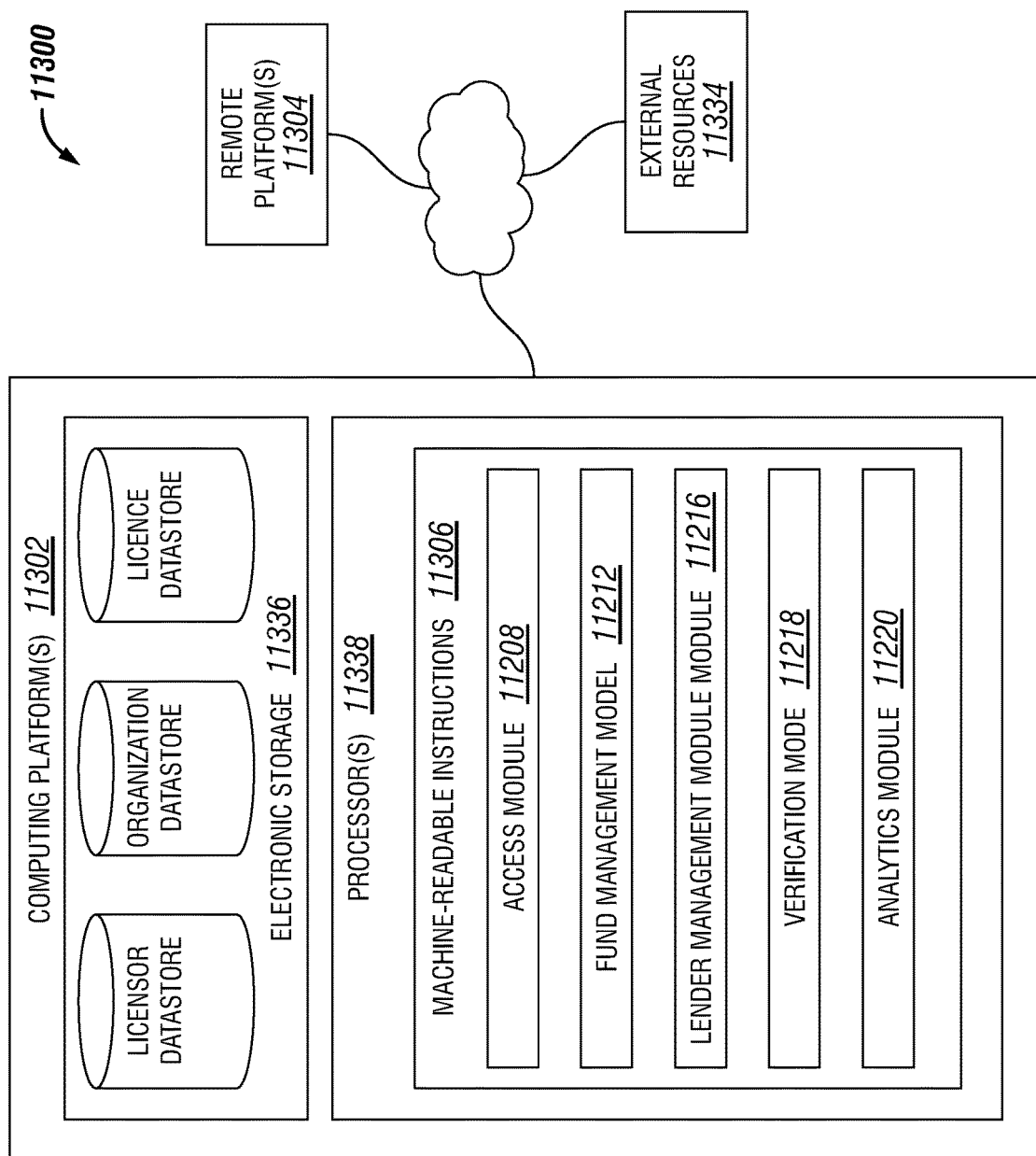
FIG. 113 depicts a schematic illustrating an example set of components of a compliance system according to some embodiments of the present disclosure.

FIG. 113 illustrates an example system 11300 configured for electronically facilitating licensing of one or more personality rights of a licensor, in accordance with some embodiments of the present disclosure. In some embodiments, the system 11300 may include one or more computing platforms 11302. Computing platform(s) 11302 may be configured to communicate with one or more remote platforms 11304 according to a client/server architecture, a peer-to-peer architecture, and/or other architectures. Remote platform(s) 11304 may be configured to communicate with other remote platforms via computing platform(s) 11302 and/or according to a client/server architecture, a peer-to-peer architecture, and/or other architectures. Users may access system 11300 via remote platform(s) 11304.

In embodiments, computing platform(s) 11302 may be configured by machine-readable instructions 11306. Machine-readable instructions 11306 may include one or more instruction modules. The instruction modules may include computer program modules. The instruction modules may include one or more of an access module 11208, a fund management module 11212, a ledger management module 11216, a verification module 11218, an analytics module 11220, and/or other instruction modules.

In embodiments, the access module 11208 may be configured to receive an access request from a licensee to obtain approval to license personality rights from a set of available licensors. In embodiments, the access module 11208 may be configured to selectively grant access to the licensee based on the access request. For example, the access module 11208 may receive a name of a potential licensee (e.g., corporate name), a list of principals (e.g., executives and/or owners) of the potential licensee, a location of the licensee, affiliations of the licensee and the principals thereof, and the like. In embodiments, the access module 11208 may provide this information to a human that grants access and/or may feed this information into an artificial intelligence system that vets potential licensees. In embodiments, the access module 11208 is configured to selectively grant access to a licensor by verifying that the licensee is permitted to engage with a set of licensors including the licensor based on the set of affiliations. Selectively granting access to the licensor may include, in response to verifying that the licensee is permitted to engage with the set of licensors, granting the licensee approval to engage with the set of licensees. The set of affiliations of the licensee may include organizations to which the licensee or a principal associated with the licensee donates to or owns.

In embodiments, the fund management module 11212 may be configured to receive confirmation of a deposit of an amount of funds from the licensee. In some embodiments, the fund management module 11212 may be configured to issue an amount of cryptocurrency corresponding to the amount of funds deposited by the licensee to an account of the licensee. In embodiments, the fund management system 11212 may be configured to escrow the consideration amount of cryptocurrency from the account of the licensee until the funds are released by a smart contract.

In embodiments, the ledger management module 11216 may be configured to receive a smart contract request to create a smart contract governing the licensing of the one or more personality rights of the licensor by the licensee. In embodiments, the ledger management module 11216 may be configured to generate the smart contract based on the smart contract request. The smart contract may be generated using a smart contract template provided by an interested third party (e.g., a university, a governing body, or the like) and by one or more parameters provided by a user (e.g., the licensor, the team of the licensor, an institution, and/or licensee) By way of non-limiting example, the interested third party may be one of a university, a sports team, or a collegiate athletics governance organization. The smart contract request may indicate one or more terms including a consideration amount of cryptocurrency to be paid to the licensor in exchange for one or more obligations on the licensor. In embodiments, the ledger management module 11216 may be configured to deploy the smart contract to a distributed ledger. The distributed ledger may be auditable by a set of third parties, including the interested third party. The distributed ledger may be a public ledger. The distributed ledger may be a private ledger that is only hosted on computing devices associated with interested third parties. In embodiments, the distributed ledger may be a blockchain.

In embodiments, the verification module 11218 may be configured to verify that the licensor has performed the one or more obligation. In some embodiments, verifying that a licensor has performed the one or more obligations may include receiving location data from a wearable device associated with the licensor and verifying that the licensor has performed the one or more obligations based on the location data, whereby the location may be used to show that the licensor was at a particular location at a particular time (e.g., a photoshoot or a filming). In embodiments, verifying that the licensor may have performed the one or more obligations includes receiving social media data from a social media website and verifying that the licensor has performed the one or more obligations based on the social media data, whereby the social media data may be used to show that the licensor has made a required social media posting. In embodiments, verifying that the licensor may have performed the one or more obligations includes receiving media content from an external data source and verifying that the licensor has performed the one or more obligations based on the media content, whereby a licensor and/or licensee may upload the media content to prove that the licensor has appeared in the media content. By way of non-limiting example, the media content may be one of a video, a photograph, or an audio recording. In embodiments, the verification module 11218 may generate and output an event record to the participating nodes upon verifying that a licensor has performed its obligations. In embodiments, the verification module 11218 may generate and output an event record to the participating nodes that indicates that the compliance system 11200 has received corroborating evidence (e.g., social media data, location data, and/or media contents) that show that the licensor has performed his or her obligations. In embodiments, the verification module 11218 may be configured to output an event record indicating completion of a licensing transaction defined by the smart contract to the distributed ledger.

In embodiments, the verification module 11218 may be configured to verify, by the smart contract, that the licensor has performed the one or more obligations. In embodiments, the verification module 11218 and/or a smart contract may be configured to, in response to receiving verification that the licensor has performed the one or more obligations, release at least a portion of the consideration amount of cryptocurrency into a licensor account of the licensor. Releasing the at least a portion of the consideration amount of cryptocurrency into a licensee account of the licensee may include identifying an allocation smart contract associated with the licensee and distributing the consideration amount of the cryptocurrency in accordance with the allocation rules. By way of non-limiting example, the additional entities may include one or more of teammates of the licensor, coaches of the licensor, a team of the licensor, a university of the licensee, and a governing body (e.g., the NCAA).

In embodiments, an analytics module 11220 may be configured to obtain a set of records indicating completion of a set of respective transactions from the distributed ledger. The set of records may include the record indicating the completion of the transaction defined by the smart contract. In embodiments, the analytics module 11220 may be configured to determine whether an organization associated with the licensor is likely in violation of one or more regulations based on the set of records and a fraud detection model. The fraud detection model may be trained using training data that indicates permissible transactions and fraudulent transactions.

In some implementations, the allocation smart contract may define allocation rules governing a manner by which funds resulting from licensing the one or more personality rights are to be distributed amongst the licensor and one or more additional entities.

In some implementations, by way of non-limiting example, the regulations may be provided by one of NCAA, FIFA, NBA, MLB, NFL, MLS, NHL, and the like.

In some implementations, computing platform(s) 11302, remote platform(s) 11304, and/or external resources 11334 may be operatively linked via one or more electronic communication links. For example, such electronic communication links may be established, at least in part, via a network such as the Internet and/or other networks. It will be appreciated that this is not intended to be limiting, and that the scope of this disclosure includes implementations in which computing platform(s) 11302, remote platform(s) 11304, and/or external resources 11334 may be operatively linked via some other communication media.

A given remote platform 11304 may include one or more processors configured to execute computer program modules. The computer program modules may be configured to enable an expert or user associated with the given remote platform 11304 to interface with compliance system 11200 and/or external resources 11334, and/or provide other functionality attributed herein to remote platform(s). 11304. By way of non-limiting example, a given remote platform 11304 and/or a given computing platform 11302 may include one or more of a server, a desktop computer, a laptop computer, a handheld computer, a tablet computing platform, a Netbook, a Smartphone, a gaming console, and/or other computing platforms.

External resources 11334 may include sources of information outside of compliance system 11200, external entities participating with compliance system 11200, and/or other resources. In some implementations, some or all of the functionality attributed herein to external resources 11334 may be provided by resources included in compliance system 11200.

Computing platform(s) 202 may include electronic storage 11336, one or more processors 11338, and/or other components. Computing platform(s) 1202 may include communication lines, or ports to enable the exchange of information with a network and/or other computing platforms.

Illustration of computing platform(s) 11302 in FIG. 113 is not intended to be limiting. Computing platform(s) 11302 may include a plurality of hardware, software, and/or firmware components operating together to provide the functionality attributed herein to computing platform(s) 11302. For example, computing platform(s) 11302 may be implemented by a cloud of computing platforms operating together as computing platform(s) 11302.

Electronic storage 11336 may comprise non-transitory storage media that electronically stores information. The electronic storage media of electronic storage 11336 may include one or both of system storage that is provided integrally (i.e., substantially non-removable) with computing platform(s) 11302 and/or removable storage that is removably connectable to computing platform(s) 11302 via, for example, a port (e.g., a USB port, a firewire port, etc.) or a drive (e.g., a disk drive, etc.). Electronic storage 11336 may include one or more of optically readable storage media (e.g., optical disks, etc.), magnetically readable storage media (e.g., magnetic tape, magnetic hard drive, floppy drive, etc.), electrical charge-based storage media (e.g., EEPROM, RAM, etc.), solid-state storage media (e.g., flash drive, etc.), and/or other electronically readable storage media. Electronic storage 11336 may include one or more virtual storage resources (e.g., cloud storage, a virtual private network, and/or other virtual storage resources). Electronic storage 11336 may store software algorithms, information determined by processor(s) 11338, information received from computing platform(s) 11302, information received from remote platform(s) 11304, and/or other information that enables computing platform(s) 11302 to function as described herein.

Processor(s) 11338 may be configured to provide information processing capabilities in computing platform(s) 11302. As such, processor(s) 11338 may include one or more of a digital processor, an analog processor, a digital circuit designed to process information, an analog circuit designed to process information, a state machine, and/or other mechanisms for electronically processing information. Although processor(s) 11338 is shown in FIG. 113 as a single entity, this is for illustrative purposes only. In some implementations, processor(s) 11338 may include a plurality of processing units. These processing units may be physically located within the same device, or processor(s) 11338 may represent processing functionality of a plurality of devices operating in coordination. Processor(s) 11338 may be configured to execute modules 11208, 11212, 11216, 11218, 11220, and/or other modules. Processor(s) 11338 may be configured to execute modules 11208, 11212, 11216, 11218, 11220, and/or other modules by software; hardware; firmware; some combination of software, hardware, and/or firmware; and/or other mechanisms for configuring processing capabilities on processor(s) 11338. As used herein, the term "module" may refer to any component or set of components that perform the functionality attributed to the module. This may include one or more physical processors during execution of processor readable instructions, the processor readable instructions, circuitry, hardware, storage media, or any other components.

It should be appreciated that although modules 11208, 11212, 11216, 11218, and 11220 are illustrated in FIG. 113 as being implemented within a single processing unit, in implementations in which processor(s) 11338 includes multiple processing units, one or more of modules 11208, 11212, 11216, 11218, and 11220 may be implemented remotely from the other modules. The description of the functionality provided by the different modules 11208, 11212, 11216, 11218, and 11220 described below is for illustrative purposes, and is not intended to be limiting, as any of modules 11208, 11212, 11216, 11218, and/or 11220 may provide more or less functionality than is described. For example, one or more of modules 11208, 11212, 11216, 11218, and/or 11220 may be eliminated, and some or all of its functionality may be provided by other ones of modules 11208, 11212, 11216, 11218, and/or 11220. As another example, processor(s) 11338 may be configured to execute one or more additional modules that may perform some or all of the functionality attributed below to one of modules 11208, 11212, 11216, 11218, and/or 11220.

Figure 114:
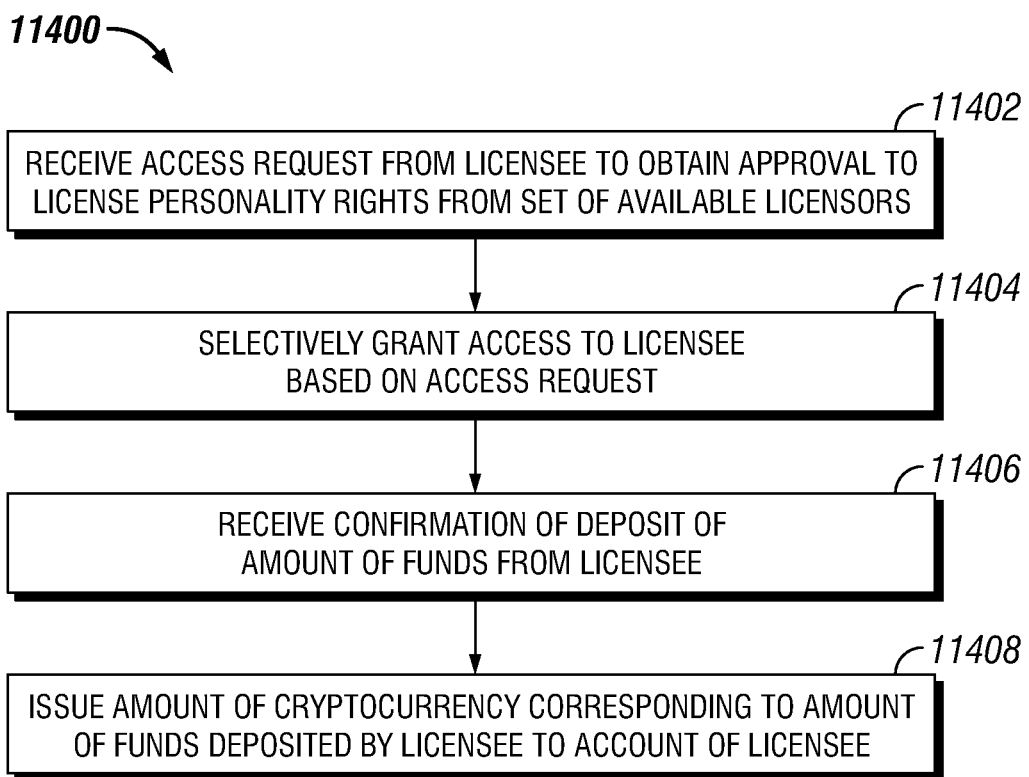
FIG. 114 depicts a set of operations of a method for vetting a potential licensee for purposes of licensing personality rights of a licensor according to some embodiments of the present disclosure.

FIGS. 114 and/or 115 illustrates an example method 11400 for electronically facilitating licensing of one or more personality rights of a licensor, in accordance with some embodiments of the present disclosure. The operations of method 11400 presented below are intended to be illustrative. In some embodiments, method 11400 may be accomplished with one or more additional operations not described, and/or without one or more of the operations discussed. Additionally, the order in which the operations of method 11400 are illustrated in FIGS. 114 and/or 115 and described below is not intended to be limiting.

In some implementations, method 11400 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 11400 in response to instructions stored electronically on an electronic storage medium. The one or more processing devices may include one or more devices configured through hardware, firmware, and/or software to be specifically designed for execution of one or more of the operations of method 11400.

FIG. 114 illustrates method 11400, in accordance with one or more implementations of the present disclosure.

At 11402, the method includes receiving an access request from a licensee to obtain approval to license personality rights from a set of available licensors. Operation 11402 may be performed by one or more hardware processors configured by machine-readable instructions including a module that is the same as or similar to access module 11208, in accordance with one or more implementations.

At 11404, the method includes selectively granting access to the licensee based on the access request. Operation 11404 may be performed by one or more hardware processors configured by machine-readable instructions including a module that is the same as or similar to access module 11208, in accordance with one or more implementations.

At 11406, the method includes receiving confirmation of a deposit of an amount of funds from the licensee. Operation 11406 may be performed by one or more hardware processors configured by machine-readable instructions including a module that is the same as or similar to fund management module 11212, in accordance with one or more implementations.

At 11408, the method includes issuing an amount of cryptocurrency corresponding to the amount of funds deposited by the licensee to an account of the licensee. Operation 11408 may be performed by one or more hardware processors configured by machine-readable instructions including a module that is the same as or similar to fund management module 11212, in accordance with one or more implementations.

Figure 115:
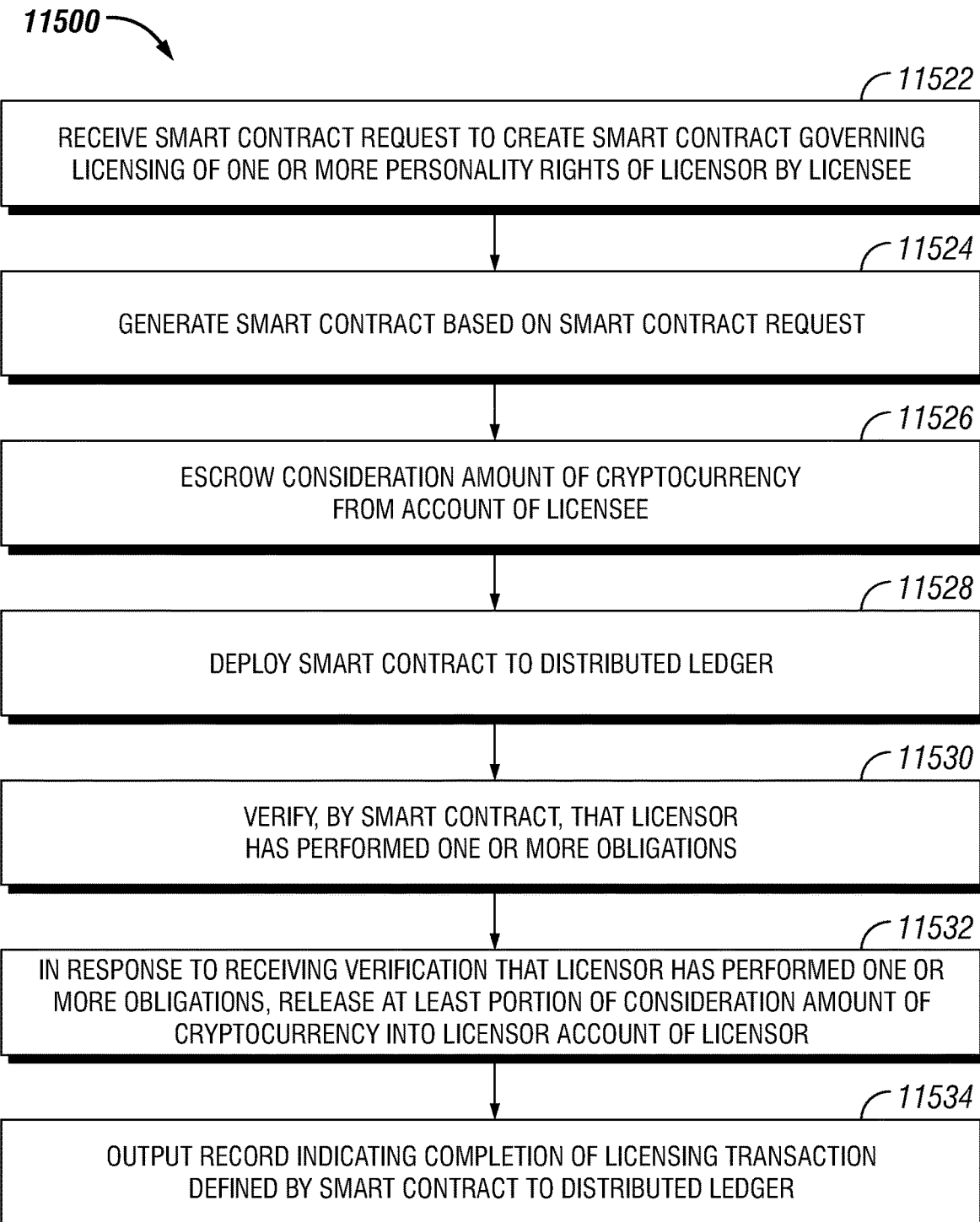
FIG. 115 depicts a set of operations of a method for facilitating the licensing of personality rights of a licensor by a licensee according to some embodiments of the present disclosure.

FIG. 115 illustrates method 11500, in accordance with one or more implementations of the present disclosure.

At 11522, the method includes receiving a smart contract request to create a smart contract governing the licensing of the one or more personality rights of the licensor by the licensee. The smart contract request may indicate one or more terms including a consideration amount of cryptocurrency to be paid to the licensor in exchange for one or more obligations on the licensor. Operation 11522 may be performed by one or more hardware processors configured by machine-readable instructions including a module that is the same as or similar to the ledger management module 11216, in accordance with one or more implementations.

At 11524, the method includes generating the smart contract based on the smart contract request. Operation 11524 may be performed by one or more hardware processors configured by machine-readable instructions including a module that is the same as or similar to ledger management module 11216, in accordance with one or more implementations.

At 11526, the method includes escrowing the consideration amount of cryptocurrency from the account of the licensee. Operation 11526 may be performed by one or more hardware processors configured by machine-readable instructions including a module that is the same as or similar to fund management module 11212, in accordance with one or more implementations.

At 11528, the method includes deploying the smart contract to a distributed ledger. Operation 11528 may be performed by one or more hardware processors configured by machine-readable instructions including a module that is the same as or similar to ledger management module 11216, in accordance with one or more implementations.

At 11530, the method includes verifying, by the smart contract, that the licensor has performed the one or more obligations. Operation 11530 may be performed by one or more hardware processors configured by machine-readable instructions including a module that is the same as or similar to verification module 11218, in accordance with one or more implementations.

At 11532, the method includes in response to receiving verification that the licensor has performed the one or more obligations, releasing at least a portion of the consideration amount of cryptocurrency into a licensor account of the licensor. Operation 11532 may be performed by one or more hardware processors configured by machine-readable instructions including a module that is the same as or similar to the verification module 11218, in accordance with one or more implementations.

At 11534, the method includes outputting a record indicating a completion of a licensing transaction defined by the smart contract to the distributed ledger. Operation 11534 may be performed by one or more hardware processors configured by machine-readable instructions including a module that is the same as or similar to the verification module 11218 and/or the ledger management module 11216, in accordance with one or more implementations.

Figure 116:
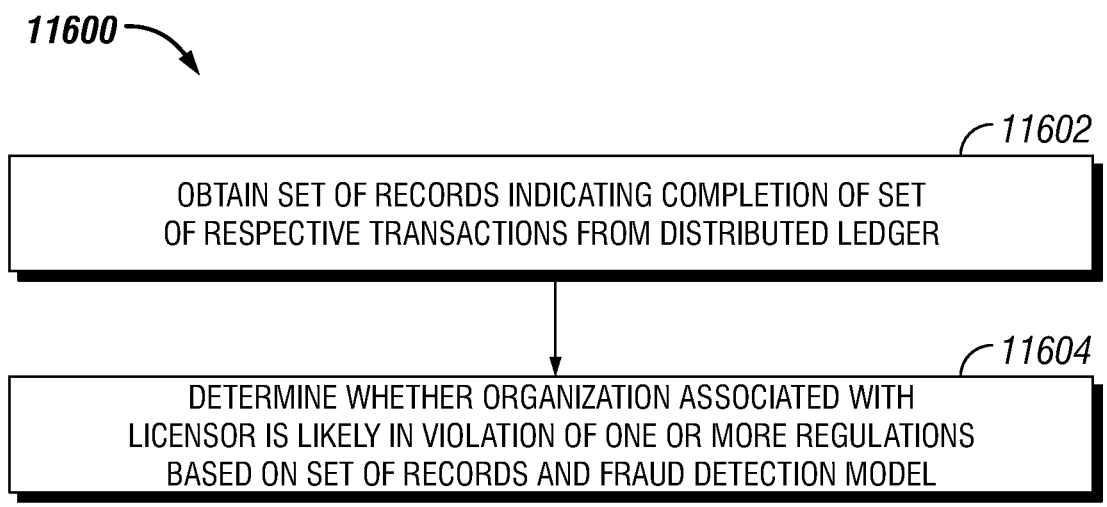
FIG. 116 depicts a set of operations of a method for detecting potential circumvention of rules or regulations by a licensor and/or licensee according to some embodiments of the present disclosure.

FIG. 116 illustrates method 11600, in accordance with one or more implementations.

At 11602, the method includes obtaining a set of records indicating completion of a set of respective transactions from the distributed ledger. The set of records may include the record indicating the completion of the transaction defined by the smart contract. Operation 11602 may be performed by one or more hardware processors configured by machine-readable instructions including a module that is the same as or similar to the analytics module 11220, in accordance with one or more implementations.

At 11604, the method includes determining whether an organization associated with the licensor is likely in violation of one or more regulations based on the set of records and a fraud detection model. Operation 11604 may be performed by one or more hardware processors configured by machine-readable instructions including a module that is the same as or similar to the analytics module 11220, in accordance with one or more implementations.

Figure 117:
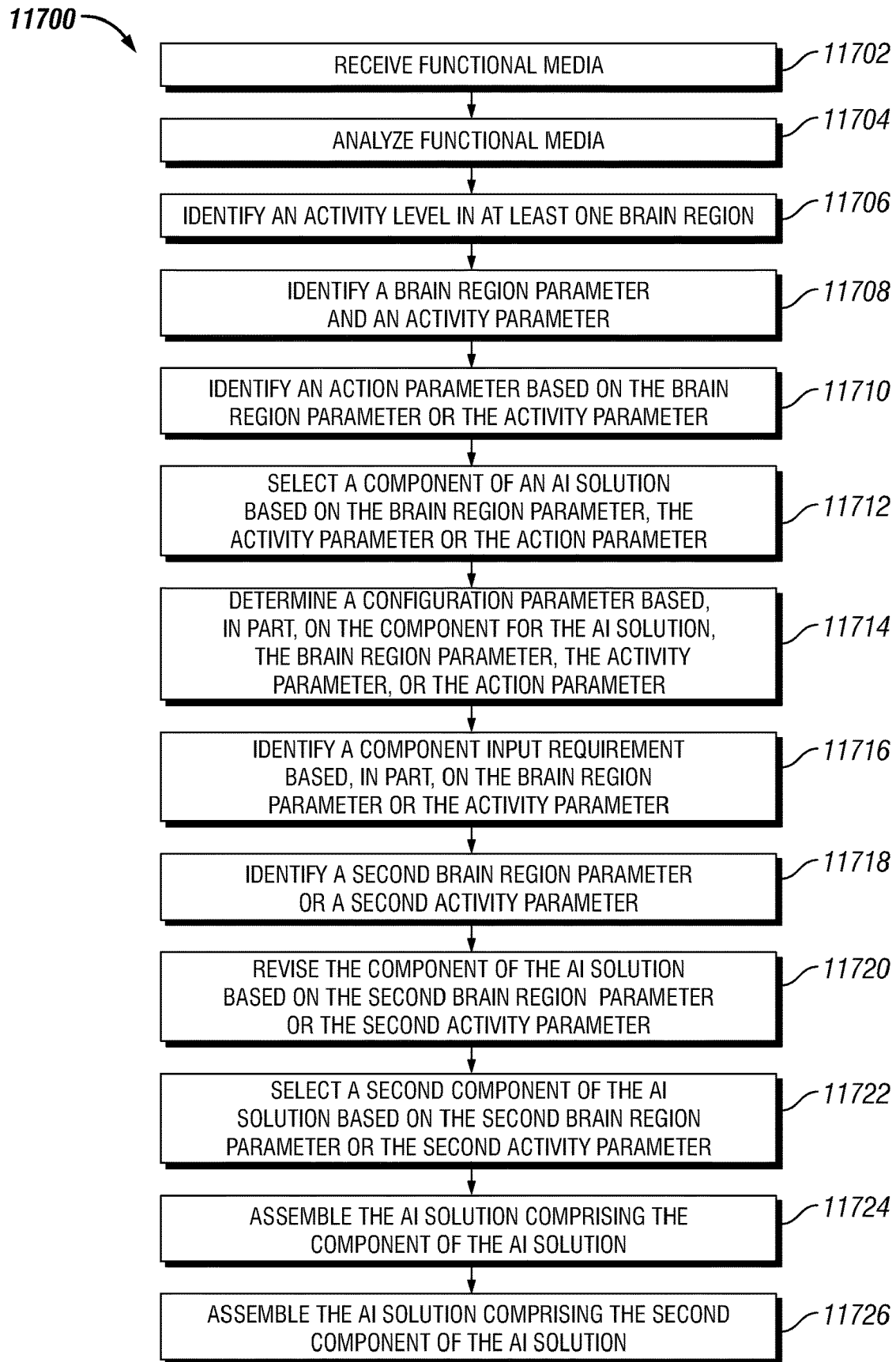
FIG. 117 depicts a method for selecting an AI solution.

Referring to FIG. 117, a computer-implemented method 11700 for selecting an AI solution for use in a robotic or automated process is depicted. The computer-implemented method may include receiving one or more functional media 11702. The functional media may include information indicative of brain activity of a worker engaged in a task to be automated. The functional media may be functional imaging, such an MRI, an FMRI, and the like from which an area of neocortex activity may be identified. The functional media may be an image, a video stream, an audio stream, and the like, from which a type of brain activity may be inferred. The functional media may be acquired while the worker is performing the work or while performing a simulation of the work, for example in an augmented reality, a virtual reality environment, or on a model of the equipment and/or environment. After being received, the functional media(s) are analyzed 11704 to identify an activity level in at least one brain region 11706. Based on the activity level, a brain region parameter and/or an activity parameter are identified 11708. The brain region parameter may represent a specific region of the neocortex such as frontal, parietal, occipital, and temporal lobes of the neocortex, including primary visual cortex and the primary auditory cortex, or subdivisions of the neocortex, including ventrolateral prefrontal cortex (Broca's area), and orbitofrontal cortex. The activity parameter may represent functional areas of the brain, such as visual processing, inductive reasoning, audio processing, olfactory processing, muscle control, and the like. An activity parameter may be representative of a type of activity in which the worker is engaged such as visual processing (looking) audio processing (listening), olfactory processing (smelling), motion activity, listening to the sound of the equipment, watching another negotiator, and the like. An activity level may be representative of a strength or level of activity, such as an extent of the brain region involved, a signal strength, whether a brain region is engaged or unengaged, and the like.

Based on one or more of the brain region parameter, the activity parameter, or the activity level, an action parameter may be identified 11710. An action parameter may provide additional information regarding the activity parameter. For example, activity parameter is indicative of motion, an action parameter may describe a range of motion, a speed of motion, a repetition of motion, a use of muscle memory, a smoothness of motion, a flow of motion, a timing of motion, and the like. Based on one or more of the brain region parameter, the activity parameter, or the activity level, a component to be incorporated in the final AI solution may be selected 11712. The component may include one or more of a model, an expert system, a neural network, and the like. After the component for the AI solution has been selected, configuration parameters may be determined 11714. The configuration parameters may be based, in part, on the type of component selected, the brain region parameter, the activity parameter, the activity level, or the action parameter. Configuring and configuration parameters may include selecting an input for a machine learning process, identifying an output to be provided by the machine learning process, identifying an input for an operational solution process 11716, identifying an output an operational solution process, tuning a learning parameter, identifying a change rates, identifying a weighting factor, identifying a parameter for inclusion, identifying a parameter for exclusion of a parameter, setting a threshold for input data, setting an output threshold for the operational robotic process, or setting a parameter threshold. Additionally, analysis of the functional media 11704 may include identifying a second brain region parameter or a second activity parameter 11718. The component of the AI solution may be revised 11720 based on the second brain region parameter or the second activity parameter. A second component of the AI solution may be selected 11722 based on the second brain region parameter or the second activity parameter. The final AI solution may be assembled from the component 11724 or the second component 11726. In embodiments, the final AI solution may be assembled from the component and the second components, optionally along with any standard or mandatory components that enable operation.

Figure 118:
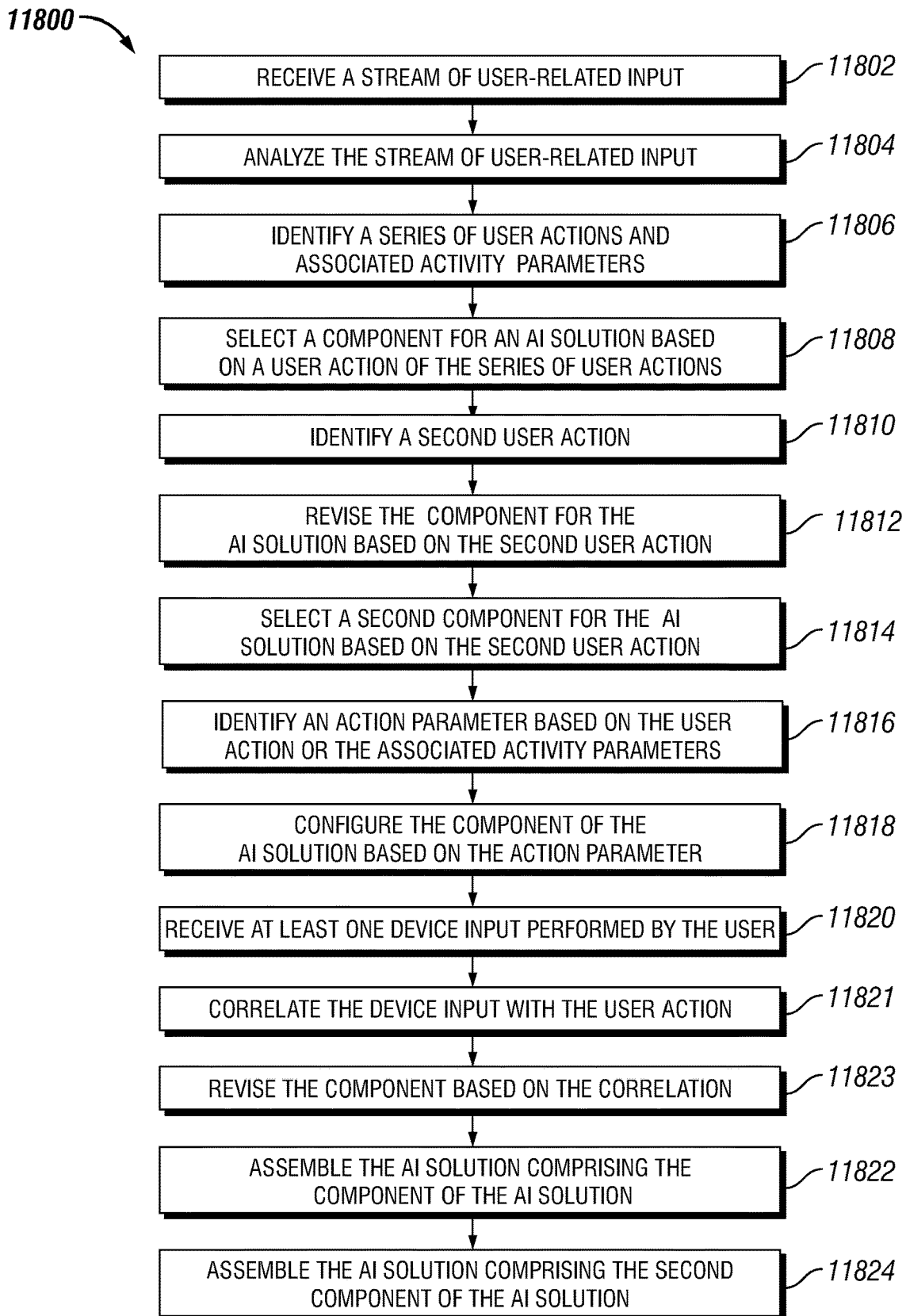
FIG. 118 depicts a method for selecting an AI solution.

Referring to FIG. 118, a computer-implemented method 11800 for selecting an AI solution for use in a robotic or automated process is depicted. The method may include receiving a user-related input 11802 comprising a timestamp and analyzing the user-related input 11804. The user-related input may include an audio feed, a motion sensor, a video feed, a heartbeat monitor, an eye tracker, a biosensor (e.g. galvanic skin response), and the like. The analysis may enable the identification of a series of user actions and associated activity parameters 11806. A component for an AI solution may be selected based on a user action of the series of user actions 11808. The analysis may enable the identification of a second user action of the series of user actions 11810. Based on the second user action, the selected component for the AI solution may be revised 11812. A second component for the AI solution may be selected 11814 based on the second user action. An action parameter may be identified 11816 based on the user action and/or the associated activity parameters. For example, if the user action is motion, an action parameter may include a range of motion, a speed of motion, a repetition of motion, a use of muscle memory, a smoothness of motion, a flow of motion, a timing of motion, and the like. The selected component of the AI solution may be configured 11818 based on the action parameter. In embodiments, at least one device input performed by the user may be received (11820). The device input may be synchronized with the user actions based on the timestamp and a correlation between the device input and the user action determined 11819. The component may be revised 11823 based on the correlation. The selection of the component of the AI solution may be partially based on the correlation between the device input and the user-related input 11821. The AI solution may be assembled 11822 from the component. The AI solution may be assembled from the second component 11824. In embodiments, the AI may be assembled from both the component and the second component, optionally along with any standard or mandatory components that enable operation.

Figure 119:
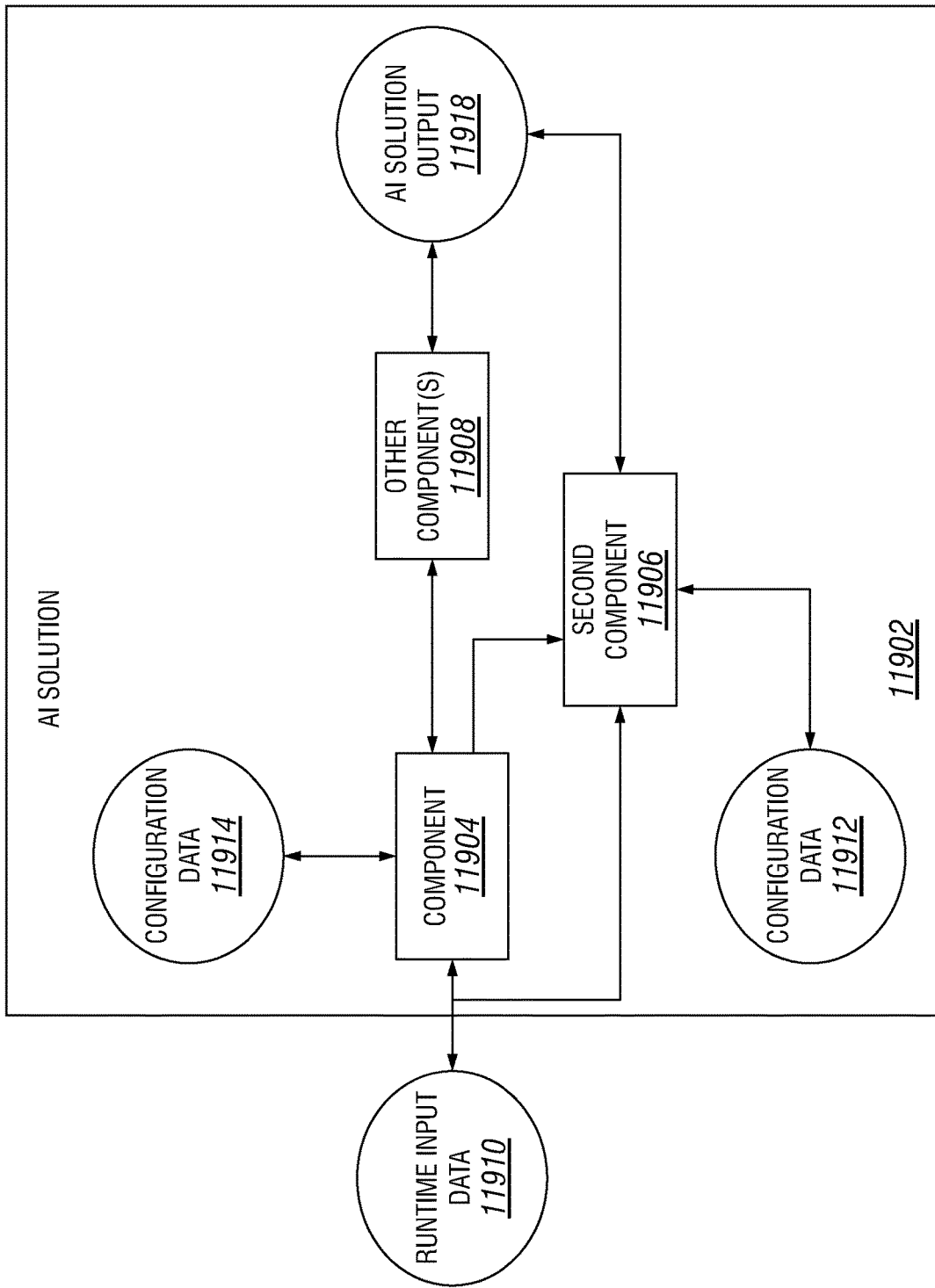
FIG. 119 depicts an example of an assembled AI solution.

Referring to FIG. 119, an illustrative and non-limiting example of an assembled AI solution 11902 is shown. The assembled AI solution 11902 may include the selected component 11904 and a second selected component 11906, as well as other components 11908. Configuration data 11914 for the first selected component and configuration data 11912 for the second selected component may be provided. Runtime input data 11910 may be specified as part of the component configuration process. Components may be structured to run serially (such as the selected component 11904 and the second selected component 11906 which received input from the selected component 11904) or in parallel (such as the second component 11906 and the other component(s) 11908). Some of the components may provide input for other components (such as the selected component 11904 providing input to the second selected component 11906). Multiple components may provide various portions of the overall AI solution output 11918 (such as the second selected component 11906 and the other components 11908). This depiction is not meant to be limiting and the final solution may include a varying number of components, configuration data and input, as well as other components (e.g. sensors, voice modulators, and the like) and may be interconnected in a variety of configurations.

Figure 120:
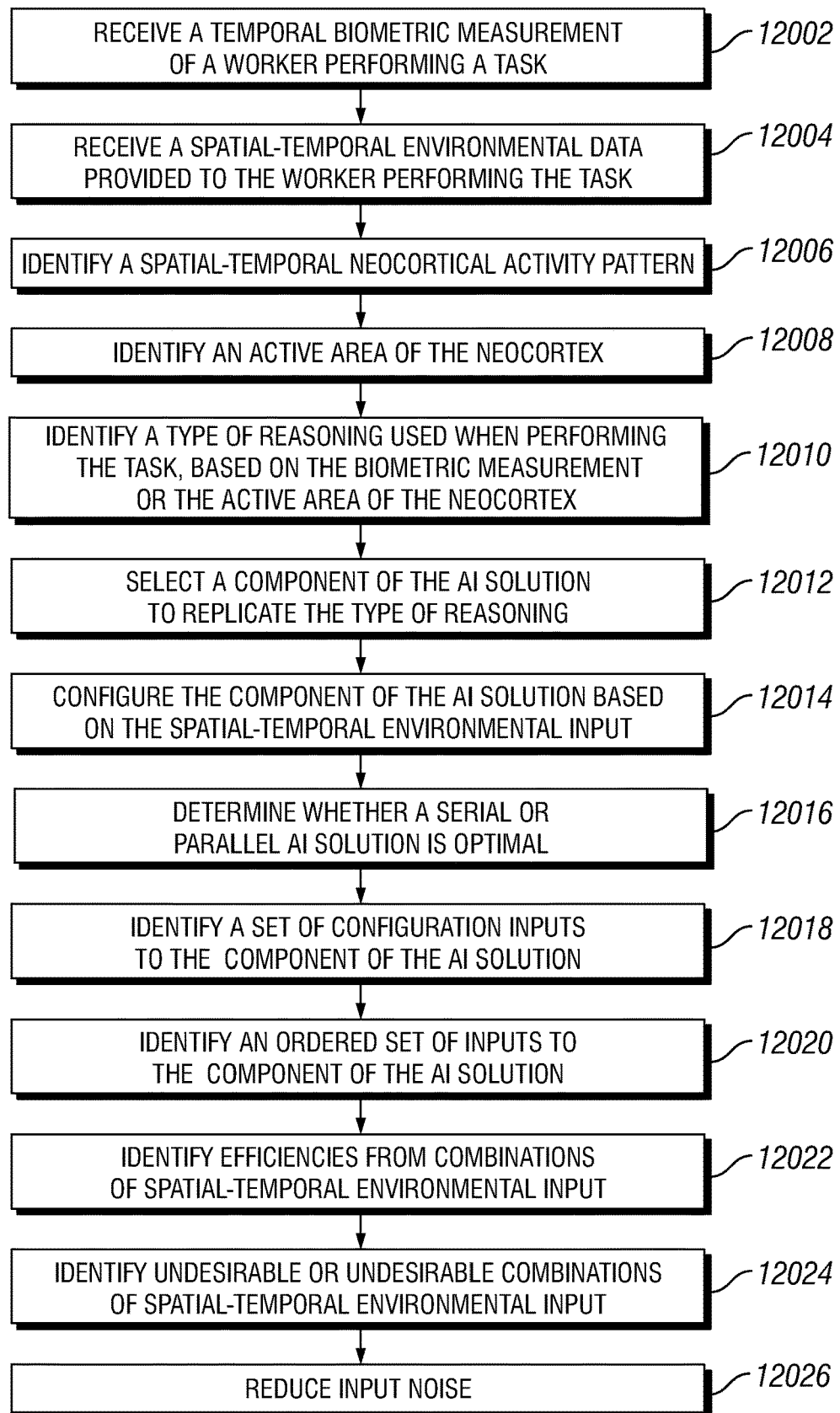
FIG. 120 depicts a method for selecting an AI solution.
Figure 121:
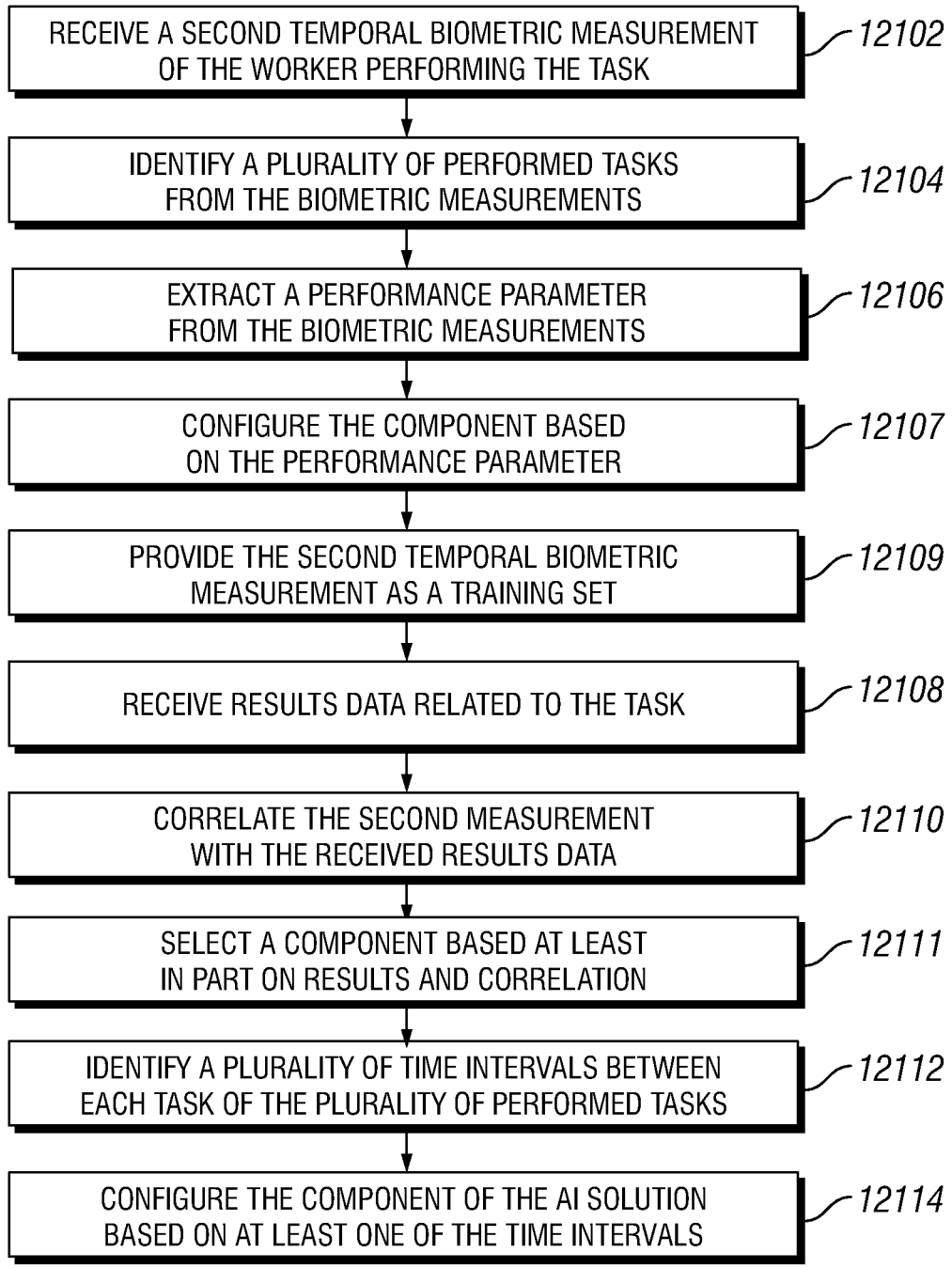
FIG. 121 depicts a method for selecting an AI solution.

Referring to FIGS. 120-121, a computer-implemented method for selecting an AI solution for use in a robotic or automated process is depicted. The method may include receiving temporal biometric measurement data 12002 of a worker performing a task and receiving spatial-temporal environmental data 12004 experienced by the worker performing the task. Using the received data, a spatial-temporal activity pattern may be identified 12006. Based on the spatial-temporal activity pattern, an active area of the worker's neocortex may be identified 12008. A type of reasoning used when performing the task may be identified 12010 based on the active area of the neocortex and/or the biometric measurement data, or the spatial-temporal environmental data. A component may be selected 12012 for use in the AI solution to replicate the type of reasoning. The component of the AI solution may be configured 12014 based on the spatial-temporal environmental input. A determination may be made as to whether a serial or parallel AI solution is optimal 12016. A set of configuration inputs to the component may be identified 12018 and an ordered set of inputs to the component of the AI solution may be identified 12020. Training the machine may include providing various subsets of the spatial-temporal environmental input to determine appropriate input weightings and identify efficiencies from combinations of spatial-temporal environmental input 12022. Desirable or undesirable combinations of the spatial-temporal environmental data may also be identified 12024. Based on the identified required input, input environmental data may be processed to reduce input noise 12026 (e.g. improve signal to noise for a signal of interest), filtered to provide the appropriate input signals to the component, and the like.

Continuing with reference to FIG. 121, a second temporal biometric measurement data of the same worker performing the task may be received 12102 and a plurality of performed tasks identified from the biometric measurements 12104. A performance parameter may be extracted from the biometric measurements 12106 (e.g. worker heartrate, galvanic skin response, and the like). In some embodiments, the component may be configured based on the performance parameter 12107. In some embodiments, the second temporal biometric measurements may be provided to the configuration module as a training set 12109. Results data related to the task may be received 12108 and the second temporal biometric measurement data may be correlated with the received results data 12110. In some embodiments, the component may be selected based, at least in part, on the correlation 12111. A series of time intervals between each of the plurality of performed tasks may be identified 12112 and the component of the AI solution configured based on at least one of the time intervals 12114. For example, if the worker inspects an object for a long period of time before moving on to the next action, this may indicate complex visual processing as well as mental processing and may indicate that the corresponding component for the task be configured for in-depth, fine detail processing and the like.

Figure 122:
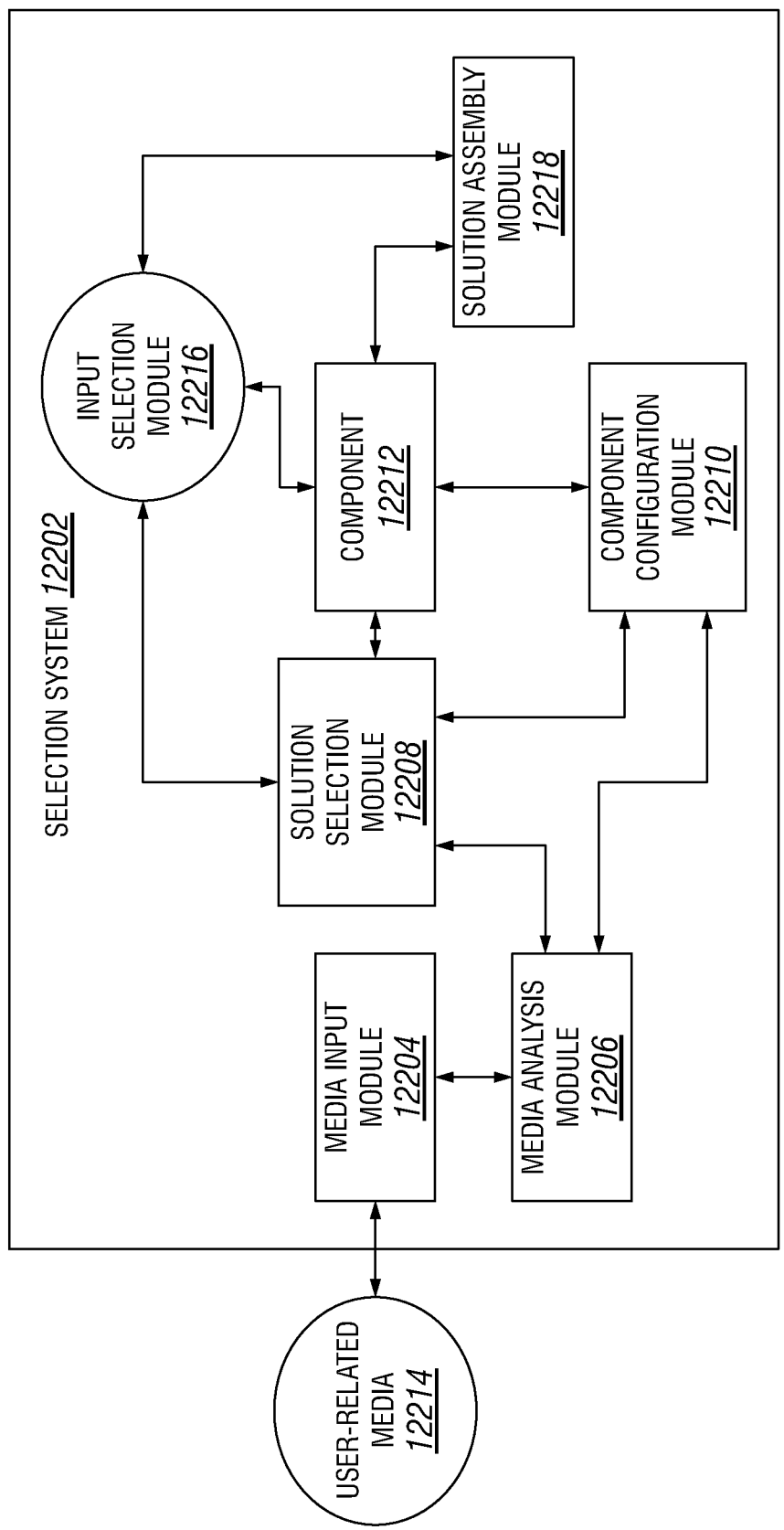
FIG. 122 depicts an AI solution selection and configuration system.

Referring to FIG. 122, an AI solution selection and configuration system 12202 is depicted. An example selection and configuration system 12202 may include a media input module 12204 structured to receive user-related functional media 12214. The user-related functional media 12214 may include images of a person engaged in a task to be automated, audio recordings, video feeds, biometric data (e.g. heartbeat data, galvanic skin response data, and the like), motion data, and the like. A media analysis module 12206 may analyze the received media and identify an action parameter. The action parameter may be representative of a type of activity in which the person appears to be engaged such as watching, listening, moving, thinking, and the like. In some embodiments, the functional media is indicative of a type of brain activity of a human engaged in the task to be automated and the media analysis module 122206 identifies an activity level in at least one brain region and provide a brain region parameter corresponding with the activity level in the identified brain region. The media analysis module may also identify an activity parameter indicative of a level of engagement such as engaged, unengaged, level of activity, type of activity, and the like. A solution selection module 12208 may be structured to select at least one component of the AI solution for use in the automated process based, at least in part, on the action parameter, the brain region parameter, or the activity parameter. The brain region parameter or the action parameter may suggest a type of component to select and the activity parameter may suggest a level of processing required for that component. For example, an action parameter of watching would suggest selecting a component suited to visual processing. If the activity parameter was representative of olfactory procession, the input specification module may identify at least one chemical sensor as an input. If the activity parameter is representative of visual processing the input specification module 11216 may identify at least one visual sensor as a robotic input. In some embodiments, the visual sensor may be selected to be sensitive to a portion of the visible spectrum with wavelengths between about 380 to 700 nanometers. If the activity parameter is representative of auditory processing, the input specification module 11216 may identify at least one microphone as a robotic input. If the activity parameter was representative of a very high level of concentration, the solution selection module 12208 may suggest a level of processing that will be required, where the processing might occur, and the like. A component configuration module 12210 may configure the component 12212. Configuring the component may include: selecting an input for a machine learning process for the selected component, identifying an output to be provided by the machine learning process, identifying an input for an operational solution process, identifying an output an operational solution process, tuning a learning parameter, identifying a change rates, identifying a weighting factor, identifying a parameter for inclusion, identifying a parameter for exclusion of a parameter, setting a threshold for input data, setting an output threshold for the operational robotic process, setting a parameter threshold, and the like. A solution assembly module 12218 may assemble the final AI solution based on one or more selected components, configuration components, and required runtime. An input specification module 12216 may suggest input sources based on the selected component, the action parameter, brain region parameter, activity parameter, or the like.

Figure 123:
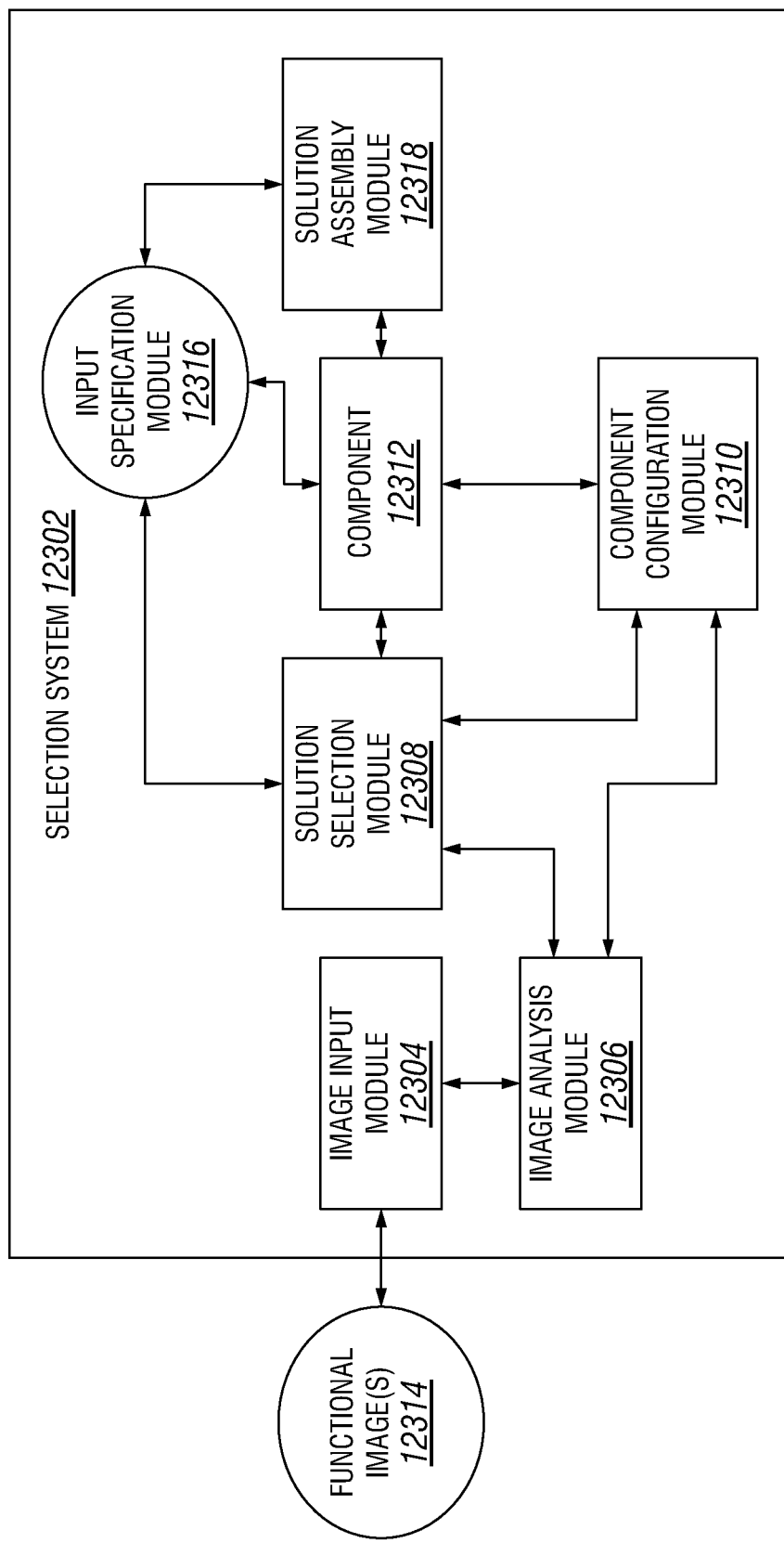
FIG. 123 depicts an AI solution selection and configuration system.
Figure 124:
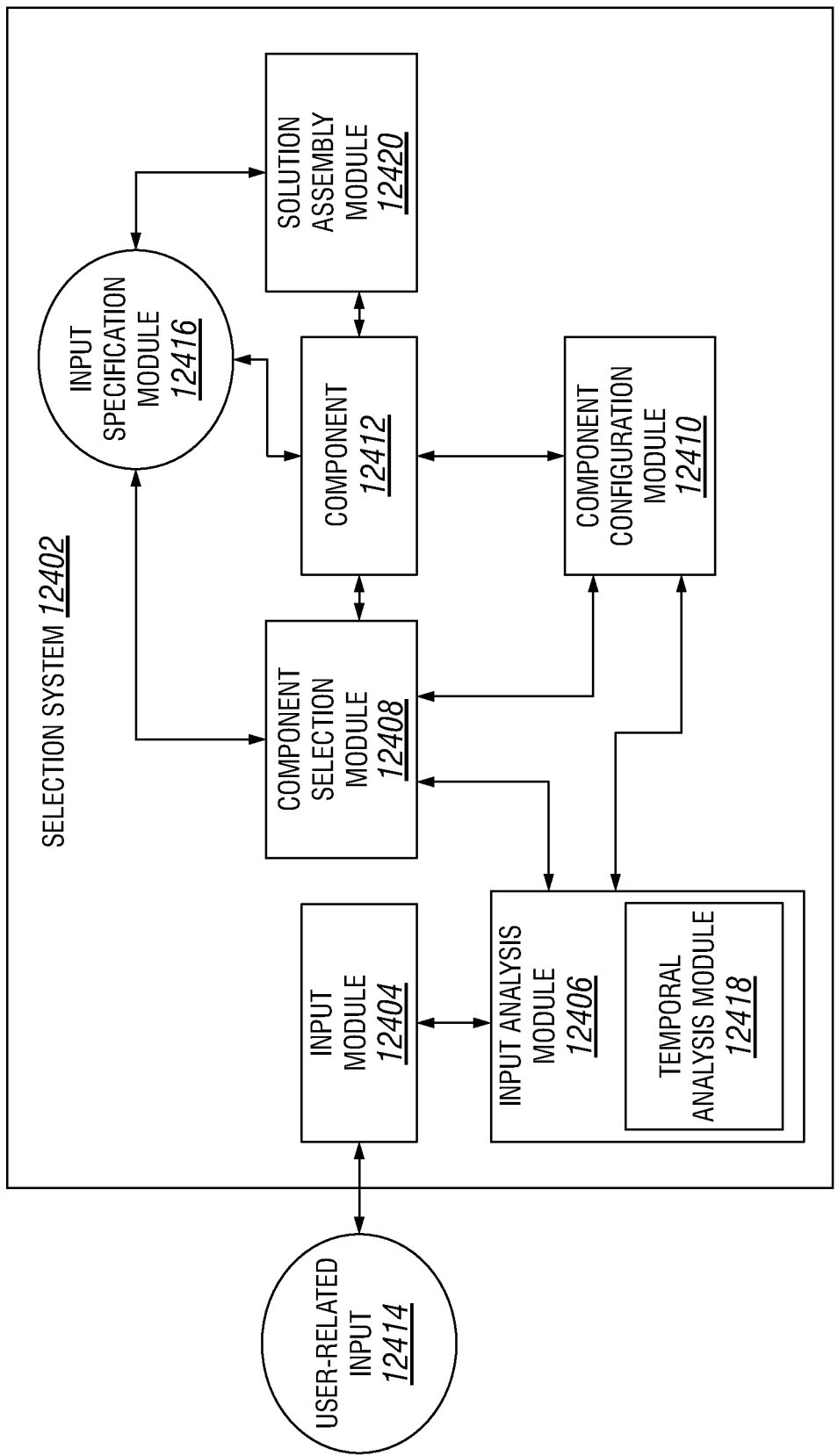
FIG. 124 depicts an AI solution selection and configuration system.
Figure 125:
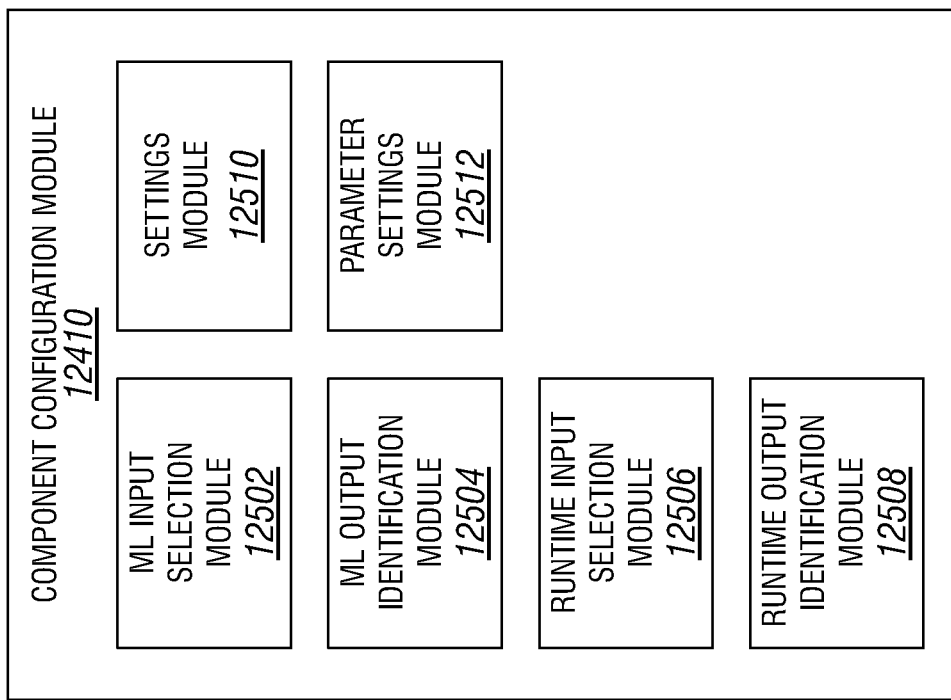
FIG. 125 depicts a component configuration circuit.

Referring to FIG. 123, an AI solution selection and configuration system 12302 is depicted. An example selection system 12302 may include an image input module 12304 structured to receive functional images 12314 of the brain such as, such as functional MM or other magnetic imaging, electroencephalogram (EEG), or other imaging, such as by identifying broad brain activity (e.g., wave bands of activity, such as delta, theta, alpha and gamma waves), by identifying a set of brain regions that are activated and/or inactive while the worker is performing one of the tasks to be automated. The image input module 12304 may provide a subset of the functional images 12314 to the image analysis module 12306. In some embodiments the image input module 12304 may perform some preprocessing for the subset of functional images 12314, such as noise reduction, histogram adjustment, filtering, and the like, prior to providing the subset of functional images 12314 to the image analysis module 12306. The image analysis module 12306, may identify an activity level in at least one brain region and provide a brain region parameter based on the subset of functional images. The brain region parameter may represent a specific region of the neocortex such as frontal, parietal, occipital, and temporal lobes of the neocortex, including primary visual cortex and the primary auditory cortex, or subdivisions of the neocortex, including ventrolateral prefrontal cortex (Broca's area), and orbitofrontal cortex. The brain region parameter may represent functional areas of the brain, such as visual processing, inductive reasoning, audio processing, olfactory processing, muscle control, and the like. A solution selection module 12308 may select a component for use in an AI solution based on the brain region parameter, and provide input into a component configuration module (such as selecting an input for a machine learning process, identifying an output to be provided by the machine learning process, identifying an input for an operational solution process, identifying an output an operational solution process, tuning a learning parameter, identifying a change rates, identifying a weighting factor, identifying a parameter for inclusion, identifying a parameter for exclusion of a parameter, setting a threshold for input data, setting an output threshold for the operational robotic process, and setting a parameter threshold, and the like. The component configuration module 12310, may use the input to configure the component 12312. The solution selection module 12308 may also supply data to the input specification module 12316. A solution assembly module 12318 may combine the component, and other components, to create the AI solution. The AI solution may be set up to receive inputs as specified by the input specification module 12316. Although one iteration of selecting a component is shown in this figure, it is envisioned, that multiple components may be selected, configured and assembled as part of the AI solution Referring to FIGS. 124-125, an AI solution selection and configuration system 12402 is depicted. An example AI solution selection and configuration system 12402 may include an input module 12404 structured to receive a variety of user-related input such as videos, audio recording, heartbeat monitors, galvanic skin response data, motion data, and the like. There may be temporal data associated with the user-related input. The input module 12404 may provide a subset of the user-related input data 12414 to the input analysis module 12406. The analysis module 12406 may include a temporal analysis module 12418 to identify timing of user-related actions. The temporal analysis module 12418 may enable identification of timing of user actions. In some embodiments the input module 12404 may perform some preprocessing for the subset of the user-related input data 12414, such as noise reduction, correlation between types of input data, and the like, prior to providing the subset of user-related input data 12414 to the input analysis module 12406. The input analysis module 12406, may identify a type of brain activity being engaged in (e.g. visual processing, auditory processing, olfactory processing, motion control, and the like) and a level of intensity of activity based on data such as heartbeat data, galvanic skin response data and the like. A component selection module 12408 may select a component for use in an AI solution based on the type of brain activity and provide input into a component configuration module 12410 which may include an ML input selection module 12502 for selecting an input for a machine learning process, an MP output identification module 12504 for identifying an output to be provided by the machine learning process, a runtime input selection module 12506 for identifying an input for an operational solution process, a runtime output identification module 12508 for identifying an output of the component, a settings module 12510 for identifying a change rate, identifying a weighting factor, setting a threshold for input data, setting an output threshold for the operational robotic process, and the like, a parameter settings module 12512 for tuning a learning parameter, identifying a parameter for inclusion, identifying a parameter for exclusion, setting a parameter threshold, and the like. The component configuration module 12410 may configure the selected component 12412. The component selection module 12408 may also supply data to the input specification module 12416. An AI solution assembly module 12420 may combine the configured component with other components, along with any standard or mandatory components, as necessary, to create the AI solution. The AI solution may be set up to receive inputs as specified by the input specification module 12416. Although one iteration of selecting a component is shown in this figure, it is envisioned, that multiple components may be selected, configured and assembled as part of the AI solution.

Figure 126:
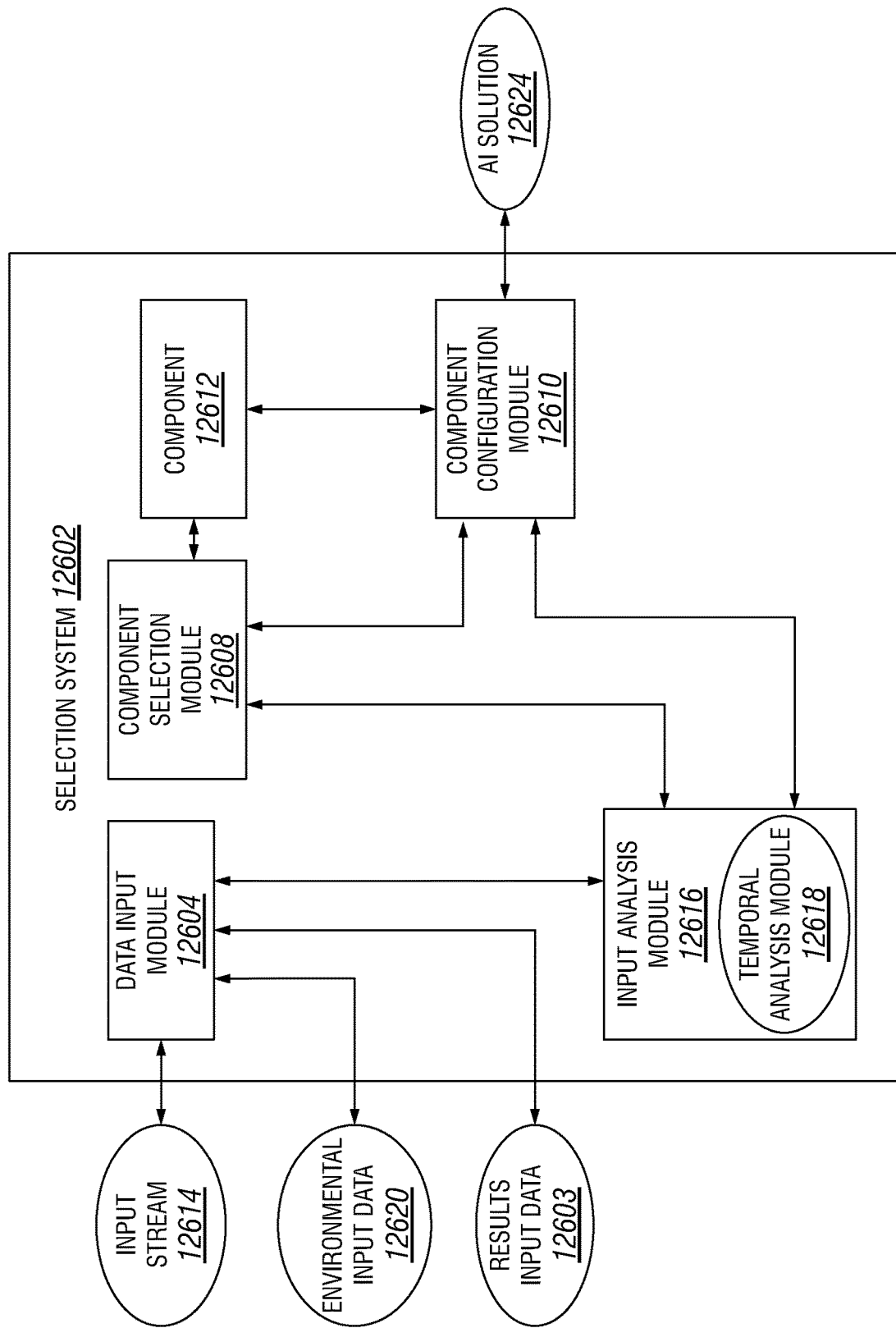
FIG. 126 depicts an AI solution selection and configuration system.

In embodiments, referring to FIG. 126, an AI solution selection and configuration system 12602 is depicted. An example AI solution selection and configuration system 12602 may include a data input module 12604 to receive an input stream including temporal user-related data 12614 which may include video streams, audio streams, equipment interactions (e.g. mouse clicks, mouse motion, physical input to a machine) user biometrics such as heartbeat, galvanic skin response, eye tracking, and the like. The data input module 12604 may also receive temporal environmental input data 12620 representative of environmental input the user is receiving such as a visual environment, an auditory environment, olfactory environment, equipment displays, a device user interface, and the like. The data input module 12604 may also receive temporal results input data 12603. The data input module 12604 may provide a subset of the received data 12614, 12620, 12603 to an input analysis module 12616. The data input module 12604 may process the received data 12614, 12620 12603 to reduce noise, compress the data, correlate some of the data, and the like. The analysis module 12616 may identify a plurality of user actions to provide to the component selection module 12608. The image analysis module 12616 may include a temporal analysis module 12618 to identify timing of user actions. The temporal analysis module 12618 may allow for the correlation between temporal user-related data 12614, environmental data 12620, and results data 12603. Based on the user actions, the component selection module 12608 may select a component that would simulate one or more mental processes of the user needed to perform at least one of the plurality of user actions. Factors in identifying the selected component may include the level of computational intensity needed, time sensitivity, and the like. This may dictate a type of component, a location of component (on-board, in the cloud, edge-computing, and the like. The input analysis module 12616 may also provide information regarding the user's actions and environmental data to the component configuration module 12610. This data may be used by the component configuration module as input to a machine learning algorithm, in conjunction with the results data to identify which inputs are beneficial and which are detrimental to enabling the component to reach desired results, and identify appropriate weighting of inputs, parameter settings, and the like. The component configuration module 12610 configures the component 12612 which is provided to the overall AI solution 12624 together with configuration information.

As described elsewhere herein, this disclosure concerns systems and methods for the discovery of opportunities for increased automation and intelligence, including solutions to domain-specific problems. Further, this disclosure also concerns selection and configuration of an artificial intelligence solution (e.g. neural networks, machine learning systems, expert systems, etc.) once opportunities are discovered.

Figure 127:
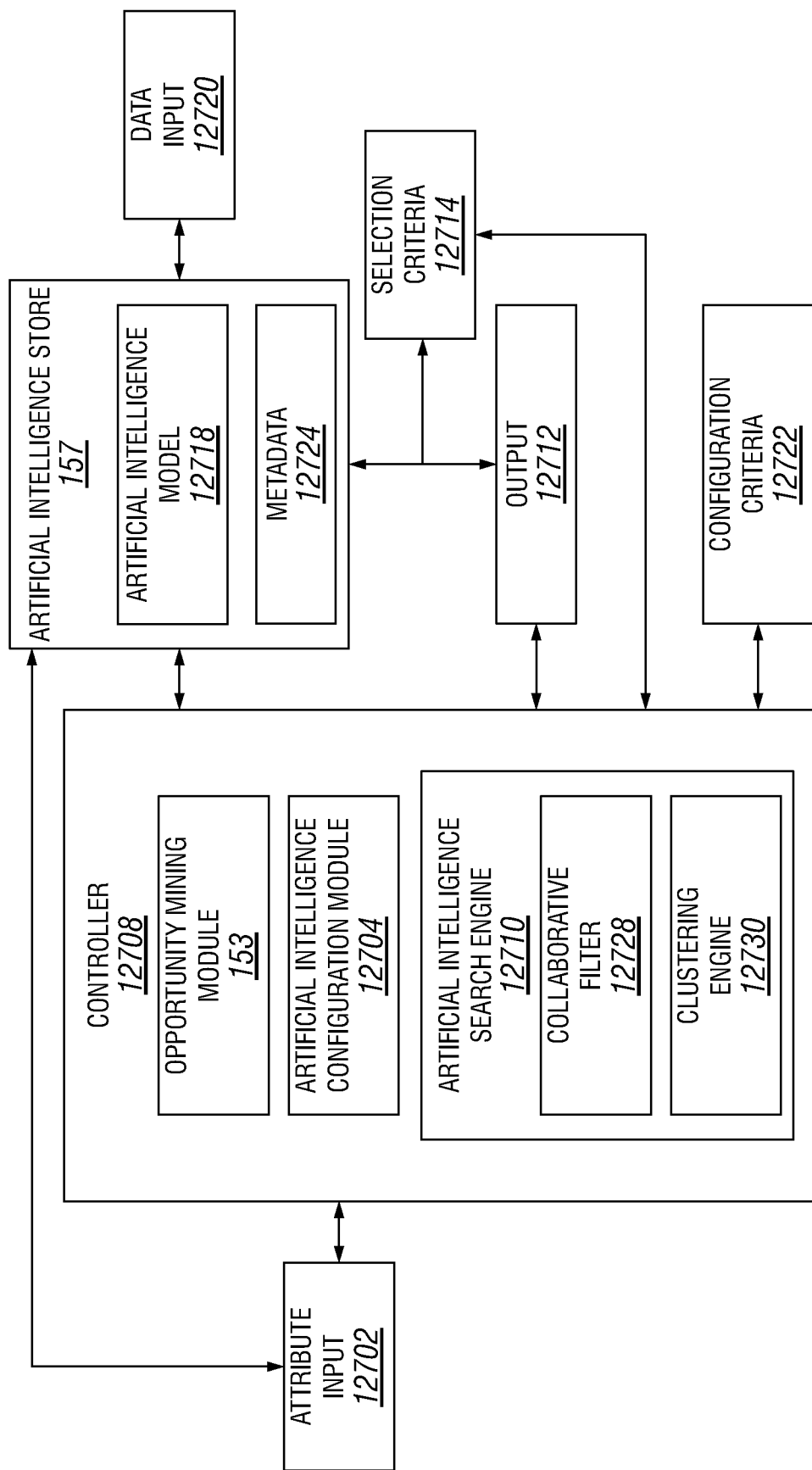
FIG. 127 depicts a system for selecting and configuring an artificial intelligence model.

Referring now to FIG. 127, a controller 12708 includes an opportunity mining module 153, an artificial intelligence configuration module 12704, and an artificial intelligence search engine 12710, optionally having a collaborative filter 12728 and a clustering engine 12730. The opportunity mining module 153 receives input 12702, such as attribute input regarding an attribute of a task, a domain, or a domain-related problem.

The input 12702 may be processed by the opportunity mining module 153 to determine whether an artificial intelligence system can be applied to the task or the domain. For example, the attribute input 12702 may include an attribute of a task, domain or problem, such as a negotiating task, a drafting task, a data entry task, an email response task, a data analysis task, a document review task, an equipment operation task, a forecasting task, an NLP task, an image recognition task, a pattern recognition task, a motion detection task, a route optimization task, and the like. The opportunity mining module 153 may determine if one or more attributes of the task are similar to other tasks that have been automated or to which an intelligence has been applied, or based on the attribute of the task, if the task is potentially automatable or suitable to have an intelligence applied to it regardless of whether it has been done previously. For example, attributes of a drafting task may include articulating a first idea, articulating a second idea, articulating a plurality of ideas, combining the plurality of ideas in a pairwise fashion, and combining the ideas in a triplicate fashion. Articulating ideas may not be suitable for automation, but the task of combining ideas pairwise or in triplicate form may be suitable for automation or to have an intelligence applied to the task.

If a determination is made that an artificial intelligence system can be applied to the task or the domain, the output 12712 regarding that determination may be used to trigger an artificial intelligence search engine 12710 to perform a search of an artificial intelligence store 157. The artificial intelligence store 157 may include a plurality of domain-specific and general artificial intelligence models 12718, and components of domain-specific and general artificial intelligence models 12718. The artificial intelligence store 157 may be organized by a category. The category may be at least one of an artificial intelligence model component type, a domain, an input type, a processing type, an output type, a computational requirement, a computational capability, a cost, a training status, or an energy usage. The artificial intelligence store may include at least one e-commerce feature. The at least one e-commerce feature may include at least one of a rating, a review, a link to relevant content, a mechanism for provisioning, a mechanism for licensing, a mechanism for delivery, or a mechanism for payment. Models 12718 may be pre-trained, or may be available for training. Components of domain-specific and general artificial intelligence models 12718 may include artificial intelligence building blocks, such as a component that detects and translates between languages, or a component that delivers highly personalized customer recommendations. One or more models 12718 and/or components of a model 12718 may be identified in a search of the artificial intelligence store 157. Components of a model 12718 may be identified either as a stand-alone element to be used in the assembly of a custom AI model 12718 or as a component of a complete, optionally pre-trained, model 12718.

The artificial intelligence store 157 may include metadata 12724 or other descriptive material indicating a suitability of an artificial intelligence system for at least one of solving a particular type of problem or operating on domain-specific inputs, data, or other entities. The metadata 12724, or other descriptive material, category, or e-commerce feature may be searched using the attribute input 12702 and/or other selection criteria 12714. For example, attributes of a task involving 2D object classification may be searched in the artificial intelligence store 157 and its metadata 12724 to reveal that an artificial intelligence model 12718 suitable for a task involving 2D object classification may be a convolutional neural network. Continuing with the example, there may be model diversity even within the class of convolutional neural networks (CNN) in the artificial intelligence store 157, such as a CNN calibrated to a certain type of 2D object recognition (e.g., straight edges) and another CNN calibrated to another kind of 2D object recognition (e.g., combo of curved and straight edges). In this example, if the further edge vs. curved attribute of the type of 2D object is searched, the artificial intelligence store 157 would present the CNN best suited to the 2D object to be classified.

In embodiments, in addition to the input 12702, at least one selection criteria 12714 may be used by the artificial intelligence search engine 12710 to search the artificial intelligence store 157 for artificial intelligence models 12718 and/or components thereof. Selection criteria used in the recommendation of an artificial intelligence model 12718 or model component may include at least one of if the model is pre-trained or not, an availability of the at least one artificial intelligence model 12718 or component thereof to execute in a user environment, an availability of the at least one artificial intelligence model 12718 or component thereof to a user, a governance principle, a governance policy, a computational factor, a network factor, a data availability, a task-specific factor, a performance factor, a quality of service factor, a model deployment consideration, a security consideration, or a human interface, which may be elsewhere described herein. For example, a governance principle, such as a requirement for an anti-bias review of pedestrian accident-avoidance systems, may be used to search an artificial intelligence store 157 for artificial intelligence models to apply to an autonomous driving task. In another example, a selection criteria for an artificial intelligence solution to be used with air traffic control system may be a requirement for having been trained on adversarial attacks and deceptive input. In yet another example, a selection criteria for an artificial intelligence solution to be used with an equities trading task may be the requirement for human oversight, and particularly, human-based final decisions.

The artificial intelligence search engine 12710 may rank one or more results of the search according to a strength or a weakness of the at least one artificial intelligence model 12718 or model component relative to the at least one selection criteria 12714. The ranked search results may be presented to a user for evaluation and consideration, and ultimately, selection. In embodiments, the artificial intelligence search engine 12710 may further include a collaborative filter 12728 that receives an indication of an element of the at least one artificial intelligence model 12718 or model component from a user that is used to filter the search results. In embodiments, the artificial intelligence search engine 12710 may further include a clustering engine 12730 structured to cluster search results comprising the at least one artificial intelligence model 12718 or model component. The clustering engine 12730 may be at least one of a similarity matrix or a k-means clustering. The clustering engine 12730 may associate at least one of similar developers, similar domain-specific problems, or similar artificial intelligence solutions in the search results.

Once an artificial intelligence model 12718 or components thereof are identified by the artificial intelligence search engine 12710, either by searching with the input 12702 alone or with both the input 12702 and a selection criteria 12714, an artificial intelligence configuration module 12704 may configure one or more data inputs 12720 to use with the at least one artificial intelligence model 12718 or model component. The artificial intelligence configuration module 12704 may, in certain embodiments, be operative in discovering and selecting what inputs 12720 may enable effective and efficient use of artificial intelligence for a given problem. In embodiments, the artificial intelligence configuration module 12704 may further configure the at least one artificial intelligence model 12718 or model component(s) in accordance with at least one configuration criteria 12722. In embodiments, individual data inputs and model components may be configured via one or more configuration criteria, while in other embodiments, a single configuration criteria governs configuration of data input, AI component assembly, and the like.

In embodiments, the at least one configuration criteria 12722 may include at least one of an availability of the at least one artificial intelligence model 12718 or model component to execute in a user environment, an availability of the at least one artificial intelligence model 12718 or model component to a user, a governance principle, a governance policy, a computational factor, a network factor, a data availability, a task-specific factor, a performance factor, a quality of service factor, a model deployment consideration, a security consideration, or a human interface. In embodiments, the at least one configuration criteria may include at least one of identifying a desired output, identifying training data, identifying parameters for exclusion or inclusion in training or operation of the model, an input data threshold, an output data threshold, a selection of a neural network type, a selection of an input model type, a setting of initial model weights, a setting of model size, a selection of computational deployment environment, a selection of input data sources for training, a selection of input data sources for operation, a selection of feedback function/outcome measures, a selection of data integration language(s) for inputs and outputs, a configuration of APIs for model training, a configuration of APIs 11214 for model inputs, a configuration of APIs 11214 for outputs, a configuration of access controls, a configuration of security parameters, a configuration of network protocols, a configuration of storage parameters, a configuration of economic factors, a configuration of data flows, a configuration of high availability, one or more fault tolerance environments, a price-based data acquisition strategy, a heuristic method, a decision to make a decision model, or a coordination of massively parallel decision making environments. In embodiments, the at least one configuration criteria may include parameters for assembly of an AI solution from a plurality of identified model components, optionally along with other standard or mandatory model components. For example, the model components may be configured to run in parallel, to run serially, or in a combination of serial and parallel.

For example, the artificial intelligence configuration module 12704 may configure an artificial intelligence model 12718 to weight one data input 12720 more heavily than another. For example, in the rain, an autonomous driving solution may weight input from a traction control system and a forward radar system more heavily than sensors targeted to increasing fuel efficiency, such as sensors measuring road slope and vehicle speed. After the rain, the weighting may be reversed.

In another example, the artificial intelligence configuration module 12704 may configure an artificial intelligence model 12718 to operate within certain thresholds of data input 12720. For example, an artificial intelligence model 12718 may be used in a combinatorial drafting task. When only two articulated ideas are provided to the model 12718, the model 12718 may not be triggered to operate. However, once the model 12718 receives a third articulated idea, its combinatorial processing of articulated ideas may commence.

The artificial intelligence configuration module 12704 may configure which sensors to use as data input 12720, how frequently to sample data, how frequently to transmit output, the weighting of various data inputs 12720, thresholds to apply to data from data inputs 12720, whether an output of one component of the model 12718 is used as input to another component of the model 12718, an order of operation of the components of the model 12718, a positioning of a model component within a workflow of a model, and the like.

The artificial intelligence configuration module 12704 may configure an artificial intelligence model 12718 from one or more model components identified by the artificial intelligence search engine 12710. For example, if the search result consisted solely of model components, the AI configuration module 12704 may configure where to place the identified 127
components in relation to one another, such as in a workflow or data flow, as well as in relation to other components that may be required for the model 12718 to function.

In embodiments, an artificial intelligence store 157 may include a set of interfaces to artificial intelligence systems, such as enabling the download of relevant artificial intelligence applications, establishment of links or other connections to artificial intelligence systems (such as links to cloud-deployed artificial intelligence systems via APIs, ports, connectors, or other interfaces) and the like.

Figure 128:
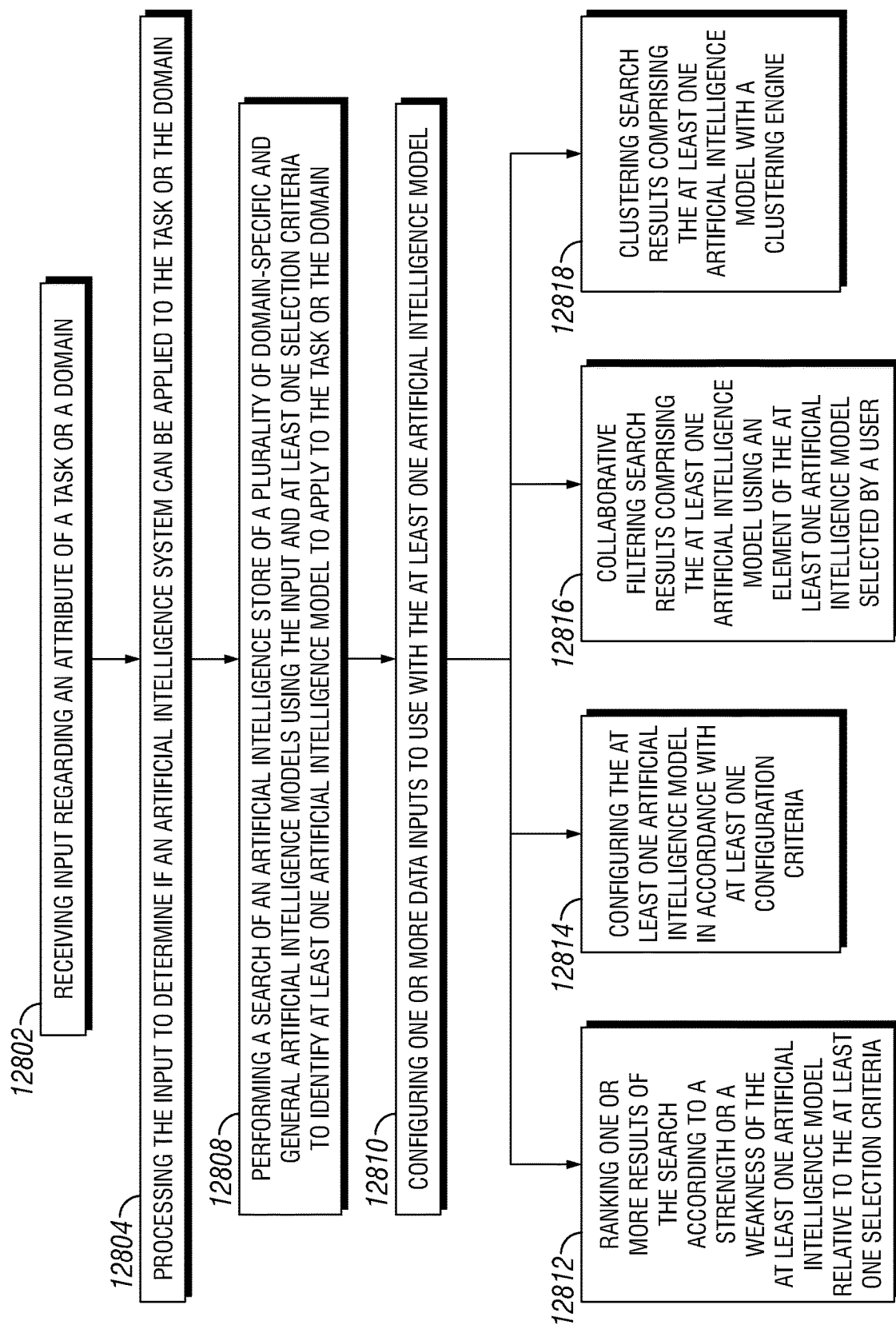
FIG. 128 depicts a method of selecting and configuring an artificial intelligence model.

Referring now to FIG. 128, a method of artificial intelligence model identification and selection may include receiving input regarding an attribute of a task or a domain 12802, and processing the input to determine whether an artificial intelligence system can be applied to the task or the domain 12804, performing a search of an artificial intelligence store of a plurality of domain-specific and general artificial intelligence models and model components using the input and/or at least one selection criteria to identify at least one artificial intelligence model or model component to apply to the task or the domain 12808, and configuring one or more data inputs to use with the at least one artificial intelligence model 12810 or model component. The artificial intelligence store may include metadata or other descriptive material indicating a suitability of an artificial intelligence system for at least one of solving a particular type of problem or operating on domain-specific inputs, data, or other entities.

The method may further include ranking one or more results of the search according to a strength or a weakness of the at least one artificial intelligence model relative to the at least one selection criteria 12812. The method may further include configuring the at least one artificial intelligence model or model component in accordance with at least one configuration criteria 12814. The method may further include collaborative filtering search results comprising the at least one artificial intelligence model using an element of the at least one artificial intelligence model selected or model component by a user 12816. The method may further include clustering search results comprising the at least one artificial intelligence model or model component with a clustering engine 12818.

In embodiments, one or more of the controllers, circuits, systems, data collectors, storage systems, network elements, or the like as described throughout this disclosure may be embodied in or on an integrated circuit, such as an analog, digital, or mixed signal circuit, such as a microprocessor, a programmable logic controller, an application-specific integrated circuit, a field programmable gate array, or other circuit, such as embodied on one or more chips disposed on one or more circuit boards, such as to provide in hardware (with potentially accelerated speed, energy performance, input-output performance, or the like) one or more of the functions described herein. This may include setting up circuits with up to billions of logic gates, flip-flops, multiplexers, and other circuits in a small space, facilitating high speed processing, low power dissipation, and reduced manufacturing cost compared with board-level integration. In embodiments, a digital IC, typically a microprocessor, digital signal processor, microcontroller, or the like may use Boolean algebra to process digital signals to embody complex logic, such as involved in the circuits, controllers, and other systems described herein. In embodiments, a data collector, an expert system, a storage system, or the like may be embodied as a digital integrated circuit, such as a logic IC, memory chip, interface IC (e.g., a level shifter, a serializer, a deserializer, and the like), a power management IC and/or a programmable device; an analog integrated circuit, such as a linear IC, RF IC, or the like, or a mixed signal IC, such as a data acquisition IC (including A/D converters, D/A converter, digital potentiometers) and/or a clock/timing IC.

While only a few embodiments of the present disclosure have been shown and described, it will be obvious to those skilled in the art that many changes and modifications may be made thereunto without departing from the spirit and scope of the present disclosure as described in the following claims. All patent applications and patents, both foreign and domestic, and all other publications referenced herein are incorporated herein in their entireties to the full extent permitted by law.

The present disclosure references one or more elements such as controllers, circuits, modules, engines, processors, or the like ("control elements"), which are structured to and/or configured to perform certain operations and/or procedures to illustrate embodiments of the disclosure. A given control element may be described as a single device for clarity of the description, but a control element may be a single device, or distributed across more than one device, where aspects of the control element are embodied as all or part of the given device(s). Without limitation to any aspect of the present disclosure, a control element may be embodied as, and/or may be communicatively or operatively coupled to, any one or more of: a sensor; an actuator; a user interface; a computing resource (e.g., a processor, a network, and/or a memory storage); and/or as executable instructions on a computer readable medium.

The methods and systems described herein may be deployed in part or in whole through a machine that executes computer software, program codes, and/or instructions on a processor. The present disclosure may be implemented as a method on the machine, as a system or apparatus as part of or in relation to the machine, or as a computer program product embodied in a computer readable medium executing on one or more of the machines. In embodiments, the processor may be part of a server, cloud server, client, network infrastructure, mobile computing platform, stationary computing platform, or other computing platform. A processor may be any kind of computational or processing device capable of executing program instructions, codes, binary instructions, and the like. The processor may be or may include a signal processor, digital processor, embedded processor, microprocessor, or any variant such as a co-processor (math co-processor, graphic co-processor, communication co-processor and the like) and the like that may directly or indirectly facilitate execution of program code or program instructions stored thereon. In addition, the processor may enable execution of multiple programs, threads, and codes. The threads may be executed simultaneously to enhance the performance of the processor and to facilitate simultaneous operations of the application. By way of implementation, methods, program codes, program instructions and the like described herein may be implemented in one or more thread. The thread may spawn other threads that may have assigned priorities associated with them; the processor may execute these threads based on priority or any other order based on instructions provided in the program code. The processor, or any machine utilizing one, may include non-transitory memory that stores methods, codes, instructions, and programs as described herein and elsewhere. The processor may access a non-transitory storage medium through an interface that may store methods, codes, and instructions as described herein and elsewhere. The storage medium associated with the processor for storing methods, programs, codes, program instructions or other type of instructions capable of being executed by the computing or processing device may include but may not be limited to one or more of a CD-ROM, DVD, memory, hard disk, flash drive, RAM, ROM, cache, and the like.

A processor may include one or more cores that may enhance speed and performance of a multiprocessor. In embodiments, the process may be a dual core processor, quad core processors, other chip-level multiprocessor and the like that combine two or more independent cores (called a die).

The methods and systems described herein may be deployed in part or in whole through a machine that executes computer software on a server, client, firewall, gateway, hub, router, or other such computer and/or networking hardware. The software program may be associated with a server that may include a file server, print server, domain server, internet server, intranet server, cloud server, and other variants such as secondary server, host server, distributed server, and the like. The server may include one or more of memories, processors, computer readable media, storage media, ports (physical and virtual), communication devices, and interfaces capable of accessing other servers, clients, machines, and devices through a wired or a wireless medium, and the like. The methods, programs, or codes as described herein and elsewhere may be executed by the server. In addition, other devices required for execution of methods as described in this application may be considered as a part of the infrastructure associated with the server.

The server may provide an interface to other devices including, without limitation, clients, other servers, printers, database servers, print servers, file servers, communication servers, distributed servers, social networks, and the like. Additionally, this coupling and/or connection may facilitate remote execution of program across the network. The networking of some or all of these devices may facilitate parallel processing of a program or method at one or more location without deviating from the scope of the disclosure. In addition, any of the devices attached to the server through an interface may include at least one storage medium capable of storing methods, programs, code and/or instructions. A central repository may provide program instructions to be executed on different devices. In this implementation, the remote repository may act as a storage medium for program code, instructions, and programs.

The software program may be associated with a client that may include a file client, print client, domain client, internet client, intranet client and other variants such as secondary client, host client, distributed client, and the like. The client may include one or more of memories, processors, computer readable media, storage media, ports (physical and virtual), communication devices, and interfaces capable of accessing other clients, servers, machines, and devices through a wired or a wireless medium, and the like. The methods, programs, or codes as described herein and elsewhere may be executed by the client. In addition, other devices required for execution of methods as described in this application may be considered as a part of the infrastructure associated with the client.

The client may provide an interface to other devices including, without limitation, servers, other clients, printers, database servers, print servers, file servers, communication servers, distributed servers, and the like. Additionally, this coupling and/or connection may facilitate remote execution of program across the network. The networking of some or all of these devices may facilitate parallel processing of a program or method at one or more location without deviating from the scope of the disclosure. In addition, any of the devices attached to the client through an interface may include at least one storage medium capable of storing methods, programs, applications, code and/or instructions. A central repository may provide program instructions to be executed on different devices. In this implementation, the remote repository may act as a storage medium for program code, instructions, and programs.

The methods and systems described herein may be deployed in part or in whole through network infrastructures. The network infrastructure may include elements such as computing devices, servers, routers, hubs, firewalls, clients, personal computers, communication devices, routing devices and other active and passive devices, modules and/or components as known in the art. The computing and/or non-computing device(s) associated with the network infrastructure may include, apart from other components, a storage medium such as flash memory, buffer, stack, RAM, ROM, and the like. The processes, methods, program codes, instructions described herein and elsewhere may be executed by one or more of the network infrastructural elements. The methods and systems described herein may be adapted for use with any kind of private, community, or hybrid cloud computing network or cloud computing environment, including those which involve features of software as a service (SaaS), platform as a service (PaaS), and/or infrastructure as a service (IaaS).

The methods, program codes, and instructions described herein and elsewhere may be implemented on a cellular network having multiple cells. The cellular network may either be frequency division multiple access (FDMA) network or code division multiple access (CDMA) network. The cellular network may include mobile devices, cell sites, base stations, repeaters, antennas, towers, and the like. The cell network may be a GSM, GPRS, 3G, EVDO, mesh, or other network types.

The methods, program codes, and instructions described herein and elsewhere may be implemented on or through mobile devices. The mobile devices may include navigation devices, cell phones, mobile phones, mobile personal digital assistants, laptops, palmtops, netbooks, pagers, electronic books readers, music players and the like. These devices may include, apart from other components, a storage medium such as a flash memory, buffer, RAM, ROM and one or more computing devices. The computing devices associated with mobile devices may be enabled to execute program codes, methods, and instructions stored thereon. Alternatively, the mobile devices may be configured to execute instructions in collaboration with other devices. The mobile devices may communicate with base stations interfaced with servers and configured to execute program codes. The mobile devices may communicate on a peer-to-peer network, mesh network, or other communications network. The program code may be stored on the storage medium associated with the server and executed by a computing device embedded within the server. The base station may include a computing device and a storage medium. The storage device may store program codes and instructions executed by the computing devices associated with the base station.

The computer software, program codes, and/or instructions may be stored and/or accessed on machine readable media that may include: computer components, devices, and recording media that retain digital data used for computing for some interval of time; semiconductor storage known as random access memory (RAM); mass storage typically for more permanent storage, such as optical discs, forms of magnetic storage like hard disks, tapes, drums, cards and other types; processor registers, cache memory, volatile memory, non-volatile memory; optical storage such as CD, DVD; removable media such as flash memory (e.g. USB sticks or keys), floppy disks, magnetic tape, paper tape, punch cards, standalone RAM disks, Zip drives, removable mass storage, off-line, and the like; other computer memory such as dynamic memory, static memory, read/write storage, mutable storage, read only, random access, sequential access, location addressable, file addressable, content addressable, network attached storage, storage area network, bar codes, magnetic ink, and the like.

The methods and systems described herein may transform physical and/or or intangible items from one state to another. The methods and systems described herein may also transform data representing physical and/or intangible items from one state to another.

The elements described and depicted herein, including in flow charts and block diagrams throughout the figures, imply logical boundaries between the elements. However, according to software or hardware engineering practices, the depicted elements and the functions thereof may be implemented on machines through computer executable media having a processor capable of executing program instructions stored thereon as a monolithic software structure, as standalone software modules, or as modules that employ external routines, code, services, and so forth, or any combination of these, and all such implementations may be within the scope of the present disclosure. Examples of such machines may include, but may not be limited to, personal digital assistants, laptops, personal computers, mobile phones, other handheld computing devices, medical equipment, wired or wireless communication devices, transducers, chips, calculators, satellites, tablet PCs, electronic books, gadgets, electronic devices, devices having artificial intelligence, computing devices, networking equipment, servers, routers, and the like. Furthermore, the elements depicted in the flow chart and block diagrams or any other logical component may be implemented on a machine capable of executing program instructions. Thus, while the foregoing drawings and descriptions set forth functional aspects of the disclosed systems, no particular arrangement of software for implementing these functional aspects should be inferred from these descriptions unless explicitly stated or otherwise clear from the context. Similarly, it will be appreciated that the various steps identified and described above may be varied, and that the order of steps may be adapted to particular applications of the techniques disclosed herein. All such variations and modifications are intended to fall within the scope of this disclosure. As such, the depiction and/or description of an order for various steps should not be understood to require a particular order of execution for those steps, unless required by a particular application, or explicitly stated or otherwise clear from the context.

The methods and/or processes described above, and steps associated therewith, may be realized in hardware, software or any combination of hardware and software suitable for a particular application. The hardware may include a general-purpose computer and/or dedicated computing device or specific computing device or particular aspect or component of a specific computing device. The processes may be realized in one or more microprocessors, microcontrollers, embedded microcontrollers, programmable digital signal processors or other programmable device, along with internal and/or external memory. The processes may also, or instead, be embodied in an application specific integrated circuit, a programmable gate array, programmable array logic, or any other device or combination of devices that may be configured to process electronic signals. It will further be appreciated that one or more of the processes may be realized as a computer executable code capable of being executed on a machine-readable medium.

The computer executable code may be created using a structured programming language such as C, an object oriented programming language such as C++, or any other high-level or low-level programming language (including assembly languages, hardware description languages, and database programming languages and technologies) that may be stored, compiled or interpreted to run on one of the above devices, as well as heterogeneous combinations of processors, processor architectures, or combinations of different hardware and software, or any other machine capable of executing program instructions.

Thus, in one aspect, methods described above and combinations thereof may be embodied in computer executable code that, when executing on one or more computing devices, performs the steps thereof. In another aspect, the methods may be embodied in systems that perform the steps thereof, and may be distributed across devices in a number of ways, or all of the functionality may be integrated into a dedicated, standalone device or other hardware. In another aspect, the means for performing the steps associated with the processes described above may include any of the hardware and/or software described above. All such permutations and combinations are intended to fall within the scope of the present disclosure.

While the disclosure has been disclosed in connection with the preferred embodiments shown and described in detail, various modifications and improvements thereon will become readily apparent to those skilled in the art. Accordingly, the spirit and scope of the present disclosure is not to be limited by the foregoing examples, but is to be understood in the broadest sense allowable by law.

The use of the terms "a" and "an" and "the" and similar referents in the context of describing the disclosure (especially in the context of the following claims) is to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the disclosure, and does not pose a limitation on the scope of the disclosure unless otherwise claimed. The term "set" may include a set with a single member. No language in the specification should be construed as indicating any non-claimed element as essential to the practice of the disclosure.

While the foregoing written description enables one of ordinary skill to make and use what is considered presently to be the best mode thereof, those of ordinary skill will understand and appreciate the existence of variations, combinations, and equivalents of the specific embodiment, method, and examples herein. The disclosure should therefore not be limited by the above described embodiment, method, and examples, but by all embodiments and methods within the scope and spirit of the disclosure.

All documents referenced herein are hereby incorporated by reference as if fully set forth herein.

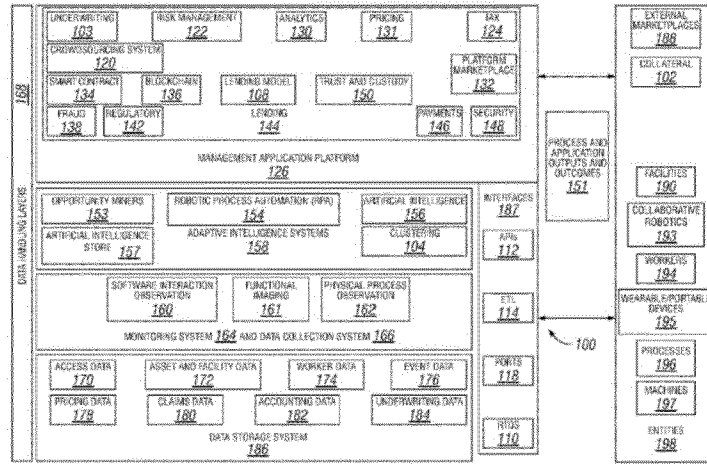

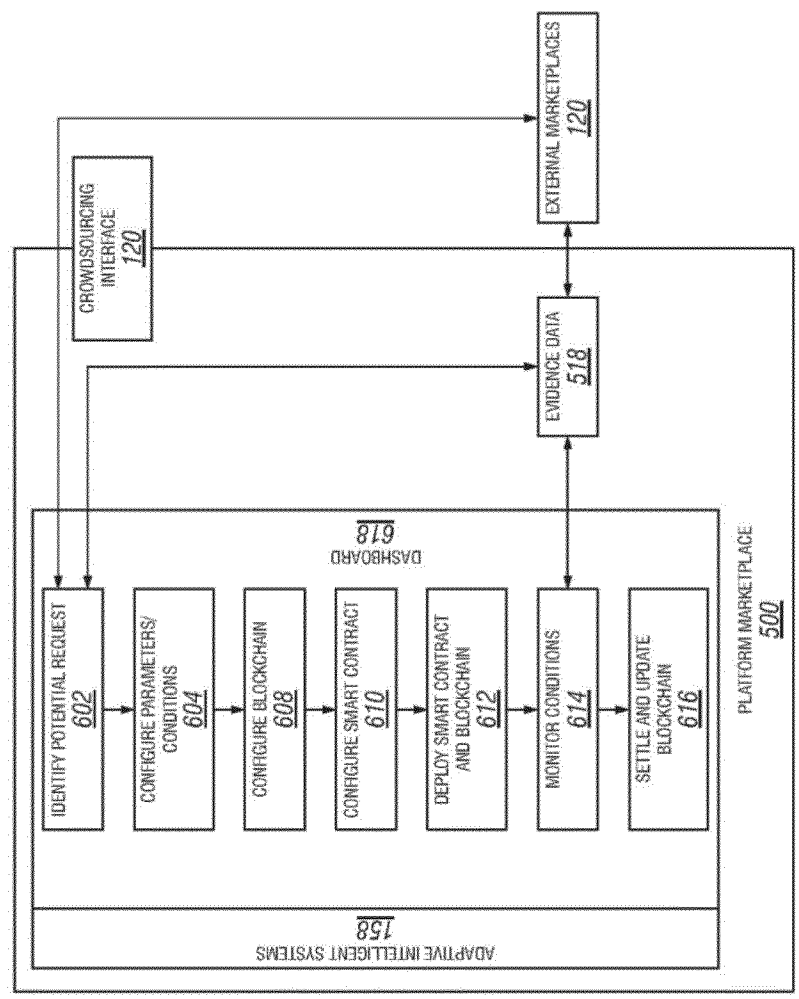

What is claimed is:

1. A computer-implemented method for selection and configuration of an automated robotic process, the method comprising:
receiving a temporal biometric measurement of a worker performing a task;
receiving a spatial-temporal environmental input provided to the worker;
identifying a type of reasoning used when performing the task based, at least in part, on the temporal biometric measurement of the worker, the identifying the type of reasoning comprising:
identifying a set of spatial-temporal neocortical activity patterns of the worker; and
identifying an active area of a neocortex of the worker;
selecting a component of an AI solution to replicate the type of reasoning, the selecting the component of the AI solution is based, at least in part, on the identified active area of the neocortex, the types of reasoning comprising at least one of visual processing, inductive reasoning, audio processing, olfactory processing, muscle control, looking, listening, smelling, motion activity, listening to sound of equipment, or watching another negotiator; and
configuring the component of the AI solution based on the spatial-temporal environmental input,
wherein the temporal biometric measurement comprises a set of spatial-temporal imaging data of a brain of the worker.

2. The method of claim 1, wherein:
the identified active area of the neocortex comprises a O1 neocortex region; and
the selected AI component is improved for visual processing.

3. The method of claim 2, wherein the configuring the component of the AI solution further comprises identifying a visual input for the component based on the spatial-temporal environmental input.

4. The method of claim 1, wherein:
the identified active area of the neocortex comprises a C3 neocortex region; and
the selected component is improved for at least one of data storage or retrieval.

5. The method of claim 1, wherein the selected component comprises a block-chain based distributed ledger.

6. The method of claim 1, further comprising identifying whether a serial or a parallel processing AI component is improved based, at least in part, on the spatial-temporal neocortical activity patterns.

7. The method of claim 1, wherein the configuring the selected component of the AI solution further comprises identifying an ordered set of inputs to the component of the AI solution.

8. The method of claim 1, wherein the configuring the selected component of the AI solution further comprises identifying efficiencies from combinations of the spatial-temporal environmental input.

9. The method of claim 1, wherein the configuring the selected component of the AI solution further comprises:
identifying undesirable portions of the spatial-temporal environmental input that do not improve the selected component; and
configuring an input to a portion of the AI solution to limit undesirable input to the AI solution.

10. The method of claim 9, wherein limiting undesirable input to the AI solution further comprises removing input noise.

11. The method of claim 1, wherein the spatial-temporal environmental comprises at least one of: an auditory environment, a visual environment, an olfactory environment, or a device user interface.

12. The method of claim 1, further comprising receiving a second temporal biometric measurement of the worker performing a task, the second temporal biometric measurement comprising at least one of: an image of the worker, a video feed of the worker, an audio feed from the worker, a movement of the worker, a heartbeat of the worker, a galvanic skin response of the worker, or eye movements of the worker.

13. The method of claim 1, further comprising:
identifying a plurality of performed tasks from the biometric measurements; and
extracting a performance parameter from the biometric measurements,
wherein the configuring the selected component of the AI solution is based, at least in part, on the performance parameter.

14. The method of claim 12, wherein the second temporal biometric measurement is provided in a training set for the component of the AI solution.

15. The method of claim 12, further comprising:
receiving results data related to the task; and
correlating the second temporal biometric measurement with the received results data;
wherein the selecting the component of the AI solution is further based on, at least in part, at least one of the results data or the correlation.

16. The method of claim 1, further comprising:
identifying a plurality of time intervals between each task of a plurality of performed tasks; and
configuring the selected component of the AI solution based on at least one of the time intervals.

* * * * *

UNITED STATES PATENT AND TRADEMARK OFFICE
CERTIFICATE OF CORRECTION

PATENT NO. : 11,567,478 B2
APPLICATION NO. : 17/333491
DATED : January 31, 2023
INVENTOR(S) : Charles Howard Cella et al.

It is certified that error appears in the above-identified patent and that said Letters Patent is hereby corrected as shown below:

On the Title Page

Replace the Title Page with the attached Title Page showing the corrected number of drawing sheets.

In the Drawings

After sheet 5 of 106, insert figure 6 as shown on the attached drawing sheet.

In the Claims

Column 434, Line 18, in Claim 1, delete "negotiator;" and insert -- worker; --.

Signed and Sealed this
Eighth Day of October, 2024

*Katherine Kelly Vidal*
Katherine Kelly Vidal
*Director of the United States Patent and Trademark Office*

CERTIFICATE OF CORRECTION (continued)

Page 2 of 3

(12) United States Patent
Cella et al.

(10) Patent No.: US 11,567,478 B2
(45) Date of Patent: Jan. 31, 2023

(54) SELECTION AND CONFIGURATION OF AN AUTOMATED ROBOTIC PROCESS

(71) Applicant: Strong Force TX Portfolio 2018, LLC, Fort Lauderdale, FL (US)

(72) Inventors: Charles Howard Cella, Pembroke, MA (US); Jenna Lynn Parenti, Boulder, CO (US); Taylor D. Charon, Troy, MI (US)

(73) Assignee: Strong Force TX Portfolio 2018, LLC, Fort Lauderdale, FL (US)

( * ) Notice: Subject to any disclaimer, the term of this patent is extended or adjusted under 35 U.S.C. 154(b) by 0 days.

(21) Appl. No.: 17/333,491

(22) Filed: May 28, 2021

(65) Prior Publication Data
US 2021/0356941 A1 Nov. 18, 2021

Related U.S. Application Data

(63) Continuation of application No. 17/332,700, filed on May 27, 2021, which is a continuation of application
(Continued)

(51) Int. Cl.
*G05B 19/41* (2006.01)
*G05B 19/4155* (2006.01)
(Continued)

(52) U.S. Cl.
CPC ........ *G05B 19/4155* (2013.01); *B25J 9/161* (2013.01); *B25J 9/163* (2013.01); *B25J 9/1656* (2013.01);
(Continued)

(58) Field of Classification Search
CPC ........ G05B 19/4155; B25J 9/163; G06N 5/04
See application file for complete search history.

(56) References Cited

U.S. PATENT DOCUMENTS 5,126,028 A 6/1992 Hurwitt et al.
5,812,422 A 9/1998 Lyons
(Continued)

FOREIGN PATENT DOCUMENTS

AU 2017352545 A1 8/2018
CA 3064604 A1 * 12/2018 ............ G06N 5/04
(Continued)

OTHER PUBLICATIONS

U.S. Appl. No. 17/332,700, filed May 27, 2021, Pending, Charles Howard Cella.
(Continued)

*Primary Examiner* — Scott C Anderson
(74) *Attorney, Agent, or Firm* — GTC Law Group PC & Affiliates

(57) ABSTRACT

A method for selection and configuration of an automated robotic process includes receiving a temporal biometric measurement of a worker performing a task, receiving a spatial-temporal environmental input provided to the worker, identifying a type of reasoning used when performing the task partially based on the temporal biometric measurement of the worker, selecting a component of an AI solution to replicate the type of reasoning, and configuring the component of the AI solution based on the spatial-temporal environmental input. The temporal biometric measurement includes a set of spatial-temporal imaging data of a brain of the worker and identifying the type of reasoning includes identifying a set of spatial-temporal neocortical activity patterns of the worker, identifying an active area of a neocortex of the worker; and selecting the component of the AI solution partially based on the identified active area of the neocortex.

16 Claims, 107 Drawing Sheets